US008895745B2

(12) United States Patent
Berdini et al.

(10) Patent No.: US 8,895,745 B2
(45) Date of Patent: *Nov. 25, 2014

(54) BICYCLIC HETEROCYCLIC COMPOUNDS AS FGFR INHIBITORS

(75) Inventors: Valerio Berdini, Cambridge (GB);
Gilbert Ebai Besong, Cambridge (GB);
Owen Callaghan, Den Bosch (NL);
Maria Grazia Carr, Luton (GB); Miles Stuart Congreve, Royston (GB);
Adrian Liam Gill, Macclesfield (GB);
Charlotte Mary Griffiths-Jones, Cambridge (GB); Andrew Madin, Cambridge (GB); Christopher William Murray, Cambridge (GB); Rajdeep Kaur Nijjar, Uxbridge (GB); Michael Alistair O'Brien, Hitchin (GB);
Andrew Pike, Bishop's Stortford (GB);
Gordon Saxty, Cambridge (GB);
Richard David Taylor, Maidenhead (GB); Emma Vickerstaffe, Baldock (GB)

(73) Assignee: Astex Therapeutics Limited, Cambridge (GB)

( * ) Notice: Subject to any disclaimer, the term of this patent is extended or adjusted under 35 U.S.C. 154(b) by 693 days.

This patent is subject to a terminal disclaimer.

(21) Appl. No.: 12/520,481

(22) PCT Filed: Dec. 21, 2007

(86) PCT No.: PCT/GB2007/004934
§ 371 (c)(1),
(2), (4) Date: Dec. 9, 2009

(87) PCT Pub. No.: WO2008/078091
PCT Pub. Date: Jul. 3, 2008

(65) Prior Publication Data
US 2010/0120761 A1   May 13, 2010

Related U.S. Application Data

(60) Provisional application No. 60/981,039, filed on Oct. 18, 2007, provisional application No. 60/979,587, filed on Oct. 12, 2007, provisional application No. 60/871,543, filed on Dec. 22, 2006.

(30) Foreign Application Priority Data

Dec. 22, 2006   (GB) .................................. 0625826.3
Oct. 12, 2007   (GB) .................................. 0720000.9

(51) Int. Cl.
*C07D 471/04*   (2006.01)
*A61K 31/437*   (2006.01)
*C07D 487/04*   (2006.01)

(52) U.S. Cl.
CPC ............ *C07D 487/04* (2013.01); *A61K 31/437* (2013.01); *C07D 471/04* (2013.01)

USPC .......................................... 546/121; 514/300

(58) Field of Classification Search
CPC ........................... C07D 471/04; A61K 31/437
USPC .......................................... 546/121; 514/300
See application file for complete search history.

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson et al. | |
| 5,554,630 A | 9/1996 | Teuber et al. | |
| 5,882,864 A | 3/1999 | An et al. | |
| 5,990,146 A | 11/1999 | Boschelli et al. | |
| 6,218,529 B1 | 4/2001 | An et al. | |
| 6,465,484 B1 | 10/2002 | Bilodeau et al. | |
| 6,498,165 B1 | 12/2002 | Armstrong et al. | |
| 6,855,719 B1 | 2/2005 | Thomas et al. | |
| 7,074,801 B1 | 7/2006 | Yoshida et al. | |
| 8,071,614 B2 | 12/2011 | Saxty et al. | |
| 8,076,354 B2 * | 12/2011 | Saxty et al. ................. | 514/300 |
| 8,131,527 B1 | 3/2012 | Saxty et al. | |
| 8,481,531 B2 | 7/2013 | Saxty et al. | |
| 8,513,276 B2 * | 8/2013 | Berdini et al. ............... | 514/300 |
| 2002/0041880 A1 | 4/2002 | DeFeo-Jones et al. | |
| 2003/0203897 A1 | 10/2003 | Love et al. | |
| 2004/0019210 A1 | 1/2004 | Chivikas Connolly et al. | |
| 2004/0067948 A1 | 4/2004 | Hallett | |

(Continued)

FOREIGN PATENT DOCUMENTS

| | | |
|---|---|---|
| EP | 1382603 A1 | 1/2004 |
| EP | 1724258 A1 | 11/2006 |
| EP | 1748048 A1 | 1/2007 |
| EP | 1790650 A1 | 5/2007 |
| EP | 1882475 A1 | 1/2008 |
| EP | 2116543 A1 | 11/2009 |
| JP | 2001-057292 | 2/2001 |
| JP | 2004-002826 | 1/2004 |
| WO | 95/35296 A1 | 12/1995 |
| WO | 96/34866 A1 | 11/1996 |

(Continued)

OTHER PUBLICATIONS

West, Anthony R., Solid State Chemistry and its Applications, Wiley, New York, 1988, pp. 358 & 365.*

(Continued)

*Primary Examiner* — David K O Dell
(74) *Attorney, Agent, or Firm* — Heslin Rothenberg Farley & Mesiti P.C.

(57) ABSTRACT

The invention relates to new bicyclic heterocyclic derivative compounds, to pharmaceutical compositions comprising said compounds and to the use of said compounds in the treatment of diseases, e.g. cancer.

20 Claims, No Drawings

(56) References Cited

U.S. PATENT DOCUMENTS

| | | |
|---|---|---|
| 2004/0220189 A1 | 11/2004 | Sun et al. |
| 2004/0267510 A1 | 12/2004 | Bemis et al. |
| 2006/0035921 A1 | 2/2006 | Castelhano et al. |
| 2006/0089362 A1 | 4/2006 | Seno et al. |
| 2006/0116402 A1 | 6/2006 | Crew et al. |
| 2006/0189629 A1 | 8/2006 | Bolger et al. |
| 2007/0185140 A1 | 8/2007 | Bordon-Pallier et al. |
| 2008/0139606 A1 | 6/2008 | Tabart et al. |
| 2008/0167314 A1* | 7/2008 | Uchikawa et al. ............ 514/248 |
| 2012/0035152 A1* | 2/2012 | Saxty et al. ............. 514/210.18 |
| 2012/0035153 A1* | 2/2012 | Saxty et al. ............. 514/210.18 |

FOREIGN PATENT DOCUMENTS

| | | |
|---|---|---|
| WO | 97/12613 A1 | 4/1997 |
| WO | 98/03510 A1 | 1/1998 |
| WO | 98/54093 A1 | 12/1998 |
| WO | 99/38868 A1 | 8/1999 |
| WO | 00/12089 A1 | 3/2000 |
| WO | 00/53605 A1 | 9/2000 |
| WO | 01/00207 A1 | 1/2001 |
| WO | 01/00213 A1 | 1/2001 |
| WO | 01/00214 A1 | 1/2001 |
| WO | 01/14375 A1 | 3/2001 |
| WO | 01/18000 A1 | 3/2001 |
| WO | 01/21634 A1 | 3/2001 |
| WO | 01/38326 A2 | 5/2001 |
| WO | 01/66098 A2 | 9/2001 |
| WO | 02/12238 A2 | 2/2002 |
| WO | 02/34748 A1 | 5/2002 |
| WO | 02/38569 A1 | 5/2002 |
| WO | 02/46168 A1 | 6/2002 |
| WO | 02/066477 A2 | 8/2002 |
| WO | 02/066478 A1 | 8/2002 |
| WO | 02/066480 A2 | 8/2002 |
| WO | 02/066481 A1 | 8/2002 |
| WO | 02/074773 A1 | 9/2002 |
| WO | 02/080914 A2 | 10/2002 |
| WO | 03/007955 A2 | 1/2003 |
| WO | 03/048132 A1 | 6/2003 |
| WO | 03/050117 A1 | 6/2003 |
| WO | 03/050119 A2 | 6/2003 |
| WO | WO 03082208 A2 * | 10/2003 |
| WO | 03/092595 A2 | 11/2003 |
| WO | 03/099811 A1 | 12/2003 |
| WO | 03/099816 A1 | 12/2003 |
| WO | 03/099817 A1 | 12/2003 |
| WO | 03/101993 A1 | 12/2003 |
| WO | 2004/026867 A2 | 4/2004 |
| WO | 2004/035579 A1 | 4/2004 |
| WO | 2004/052286 A2 | 6/2004 |
| WO | 2004/052315 A2 | 6/2004 |
| WO | 2004/087153 A2 | 10/2004 |
| WO | 2005/021531 A1 | 3/2005 |
| WO | 2005/021544 A2 | 3/2005 |
| WO | 2005/054230 A1 | 6/2005 |
| WO | 2005/075470 A1 | 8/2005 |
| WO | 2006/000420 A1 | 1/2006 |
| WO | 2006/034402 A2 | 3/2006 |
| WO | 2006/038001 A1 | 4/2006 |
| WO | 2006/070198 A1 | 7/2006 |
| WO | WO 2006070943 A1 * | 7/2006 |
| WO | 2006/091671 A1 | 8/2006 |
| WO | WO 2006091671 A1 * | 8/2006 |
| WO | 2006/094235 A1 | 9/2006 |
| WO | 2006/108103 A1 | 10/2006 |
| WO | 2006/135667 A1 | 12/2006 |
| WO | 2007/036732 A1 | 4/2007 |
| WO | 2007/109362 A2 | 9/2007 |
| WO | 2007/112093 A2 | 10/2007 |
| WO | 2008/003511 A1 | 1/2008 |
| WO | 2008/008747 A1 | 1/2008 |
| WO | 2008/075068 A2 | 6/2008 |
| WO | 2008/078091 A1 | 7/2008 |
| WO | 2008/078100 A2 | 7/2008 |
| WO | 2008/081910 A1 | 7/2008 |
| WO | 2008/124323 A1 | 10/2008 |
| WO | 2008/154642 A2 | 12/2008 |
| WO | 2009/002534 A1 | 12/2008 |
| WO | 2009/047506 A1 | 4/2009 |
| WO | 2009/047522 A1 | 4/2009 |
| WO | 2009/150240 A1 | 12/2009 |
| WO | 2010/119284 A1 | 10/2010 |
| WO | 2010/119285 A1 | 10/2010 |

OTHER PUBLICATIONS

Search Report for GB0625827.1 dated Apr. 25, 2007.
Search Report for GB0719998.7 dated Nov. 12, 2007.
Search Report for PCT/GB2007/004960 dated Sep. 22, 2008.
Search Report for GB0625826.3 dated Apr. 25, 2007.
Search Report for GB0720000.9 dated Nov. 12, 2007.
Search Report for PCT/GB2007/004934 dated May 6, 2008.
Search Report for GB0810902.7 dated Sep. 17, 2008.
Search Report for PCT/EP2009/057318 dated Oct. 12, 2009.
Search Report for GB0720038.9 dated Apr. 17, 2008.
Search Report for PCT/GB2008/003439 dated Jan. 29, 2009.
Search Report for GB0720041.3 dated Apr. 17, 2008.
Search Report for PCT/GB2008/003418 dated Jan. 29, 2009.
Search Report for GB0906472.6 dated Jul. 7, 2009.
Search Report for PCT/GB2010/050617 dated Jul. 20, 2010.
Search Report for GB0906470.0 dated Jul. 8, 2009.
Search Report for PCT/GB2010/050618 dated Jul. 23, 2010.
Bilodeau, Mark T. et al., Design and Synthesis of 1,5-Dairylbenzimidazoles as Inhibitors of the VEGF-Receptor KDR, Bioorganic & Medicinal Chemistry Letters 13, 2003, pp. 2485-2488.
Clark, Michael P. et al., Development of new pyrrolopyrimidine-based inhibitors of Janus kinase 3 (JAK3), Bioorganic & Medicinal Chemistry Letters 17 (5), 2007, pp. 1250-1253.
Wermuth, Camille G., Molecular Variations Based on Isosteric Replacements, The Practice of Medicinal Chemistry, 1996, pp. 203-237.
Fraley, Mark E. et al., Synthesis and Initial SAR Studies of 3,6-Disubstituted Pyrazolo[1,5-α]pyrimidines: A New Class of KDR Kinase Inhibitors, Bioorganic & Medicinal Chemistry Letters 12, 2002, pp. 2767-2770.
Wu, Zhicai et al., Design and Synthesis of 3,7-diarylimidazopyridines as inhibitors of the VEGF-receptor KDR, Bioorganic & Medicinal Chemistry Letters 14, 2004, pp. 909-912.
Fraley, Mark E. et al., Optimization of a Pyrazolo[1,5-α]pyrimidine Class of KDR Kinase Inhibitors: Improvements in Physical Properties Enhance Cellular Activity and Pharmacokinetics, Bioorganic & Medicinal Chemistry Letters 12, 2002, pp. 3537-3541.
Skaper, Stephen D. et al., The FGFR1 Inhibitor PD 173074 Selectively and Potently Antagonizes FGF-2 Neurotrophic and Neurotropic Effects, Journal of Neurochemistry, 2000, pp. 1520-1527.
Mohammadi, Moosa et al., Crystal structure of an angiogenesis inhibitor bound to the FGR receptor tyrosine kinase domain, The EMBO Journal, vol. 17, No. 20, 1998, pp. 5896-5904.
Connolly, Cleo J.C. et al., Discovery and Structure-Activity Studies of a Novel Series of Pyrido[2,3-d]Pyrimidine Tyrosine Kinase Inhibitors, Bioorganic & Medicinal Chemistry Letters, vol. 7, No. 18, 1997, pp. 2415-2420.
Hamby, James M. et al., Structure-Activity Relationships for a Novel Series of Pyrido[2,3-d]pyrimidine Tyrosine Kinase Inhibitors, J. Med. Chem, 40, 1997, pp. 2296-2303.
Scribner, Andrew et al., Synthesis and biological activity of imidazopyridine anticoccidial agents: Part I, European Journal of Medicinal Chemistry 42, 2007, pp. 1334-1357.
Anderson, Malcolm et al., Imidazo[1,2-a]pyridines: A Potent and Selective Class of Cyclin-Dependent Kinase Inhibitors Identified Through Structure-Based Hybridisation, Bioorganic & Medicinal Chemistry Letters 13, 2003, pp. 3021-3026.
Mohammadi, Moosa et al., Structures of the Tyrosine Kinase Domain of Fibroblast Growth Factor Receptor in Complex with Inhibitors, Science, 276, 1997, pp. 955-960.

(56) References Cited

OTHER PUBLICATIONS

Dorwald, F. Zaragoza, Side Reactions in Organic Synthesis, 2005, Wiley: VCH, Weinheim p. IX of Preface.

Vippagunta, Sudha R., et al., Crystalline solids, Advanced Drug Delivery Reviews 48, 2001, pp. 3-26.

Berge, Stephen M. et al. "Pharmaceutical Salts", *Journal of Pharmaceutical Sciences*, vol. 66, No. 1, 1977, pp. 1-19.

Deady, Leslie W. "Ring Nitrogen Oxidation of Amino Substituted Nitrogen Heterocycles with m-Chloroperbenzoic Acid", *Synthetic Communications*, vol. 7(8), 1977, pp. 509-514.

Angerer, Lynne M. et al. "Demonstration of Tissue-Specific Gene Expression by in Situ Hybridization", *Methods in Enzymology*, vol. 152, 1987, pp. 649-661.

Deprimo, Samuel E. et al. "Expression profiling of blood samples from an SU5416 Phase III metastatic colorectal cancer clinical trial: a novel strategy for biomarker identification", *BMC Cancer*, vol. 3, 2003; pp. 1-12.

Orre, Maxine and Rogers, Peter A.W. "VEGF, VEGFR-1, VEGFR-2, Microvessel Density and Endothelial Cell Proliferation in Tumours of the Ovary", *Int. J. Cancer (Pred. Oncol.)*, vol. 84(2), 1999, pp. 101-108.

Palmer, Brian D., et al.,"Structure-Activity Relationships for 1-Phenylbenzimidazoles as Selective ATP Site Inhibitors of the Platelet-Derived Growth Factor Receptor" *Journal of Medicinal Chemistry*, 1998, 41 (27), pp. 5457-5465.

Ellis, Lee M. et al., "VEGF-Targeted Therapy: Mechanisms of Anti-Tumour Activity" *Nature Reviews/Cancer*, Aug. 2008, vol. 8, pp. 579-591.

Hamdi et al. "Solvates of Indomethacin"; *Journal of Thermal Analysis and Calorimetry*; 2004; pp. 985-1001; vol. 76.

Morissette et al. "High-throughput crystallization: polymorphs, salts, co-crystals and solvates of pharmaceutical solids"; *Advanced Drug Delivery Reviews*; 2004; pp. 275-300; vol. 56.

\* cited by examiner

BICYCLIC HETEROCYCLIC COMPOUNDS AS FGFR INHIBITORS

CROSS REFERENCE TO RELATED APPLICATIONS

This application is a national phase filing under 35 U.S.C. §371 of PCT International Application No. PCT/GB2007/004934 filed Dec. 21, 2007, and published under PCT Article 21(2) in English as WO2008/078091 on Jul. 3, 2008. PCT/GB2007/004934 claimed priority from U.S. provisional patent application No. 60/871,543 filed on Dec. 22, 2006, British application No. 0625826.3 filed on Dec. 22, 2006, British application No. 0720000.9 filed on Oct. 12, 2007, U.S. provisional patent application No. 60/979,587 filed Oct. 12, 2007, and U.S. provisional patent application No. 60/981,039 filed on Oct. 18, 2007. The entire contents of each of the prior applications are incorporated herein by reference.

FIELD OF THE INVENTION

The invention relates to new bicyclic heterocyclic derivative compounds, to pharmaceutical compositions comprising said compounds and to the use of said compounds in the treatment of diseases, e.g. cancer.

SUMMARY OF THE INVENTION

According to a first aspect of the invention there is provided a compound of formula (I):

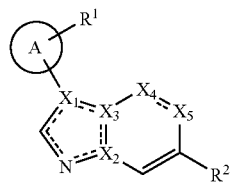

(I)

wherein $X_1$, $X_2$ and $X_3$ are each independently selected from carbon or nitrogen, such that at least one of $X_1$-$X_3$ represents nitrogen;

$X_4$ represents $CR^3$ or nitrogen;

$X_5$ represents $CR^6$, nitrogen or C=O;

provided that no more than three of $X_1$-$X_5$ represent nitrogen;

----- represents a single or double bond, such that at least one bond within the 5 membered ring system is a double bond;

$R^3$ represents hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkenyl, cyano, halo$C_{1-6}$ alkyl, halo$C_{1-6}$ alkoxy or =O;

A represents an aromatic or non-aromatic carbocyclic or heterocyclic group which may be optionally substituted by one or more (e.g. 1, 2 or 3) $R^a$ groups;

$R^1$ represents —NHCONR$^4$R$^5$, —NHCOOR$^4$, —NH—CO—(CH$_2$)$_n$—NR$^4$R$^5$, —NH—(CH$_2$)$_n$—CONR$^4$R$^5$, —NH—CO—(CH$_2$)$_n$—COOR$^4$, —NH—CO—(CH$_2$)$_n$—CSOR$^4$, —NHSO$_2$R$^4$, NHSO$_2$NR$^4$R$^5$, —NHCSNR$^4$R$^5$, —NHCOR$^4$, —NHCSR$^4$, —NHCSSR$^4$, —NHC(=NR$^4$)NR$^5$, NHC(=NR$^4$)R$^5$, —NH—C(=NH$_2$)—NH—CO—R$^4$, —NHCSOR$^4$ or —NHCOSR$^4$;

$R^4$ and $R^5$ independently represent hydrogen, $C_{1-6}$ alkyl, $C_{2-6}$ alkenyl, $C_{2-6}$ alkynyl, $C_{3-8}$ cycloalkyl, $C_{3-8}$ cycloalkenyl, $C_{1-6}$ alkanol, halo$C_{1-6}$ alkyl, —(CH$_2$)$_n$—NR$^x$R$^y$, —(CH$_2$)$_s$—COOR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O—heterocyclyl wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more (e.g. 1, 2 or 3) $R^a$ groups;

$R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, —COOC$_{1-6}$ alkyl, hydroxy, $C_{1-6}$ alkoxy, halo$C_{1-6}$ alkyl, —CO—(CH$_2$)$_n$—$C_{1-6}$ alkoxy, $C_{1-6}$ alkylamino, $C_{3-8}$ cycloalkyl or $C_{3-8}$ cycloalkenyl;

$R^2$ and $R^6$ independently represent halogen, hydrogen, $C_{1-6}$ alkyl, $C_{1-6}$ alkoxy, $C_{2-6}$ alkenyl, $C_{2-6}$ alkynyl, —C≡N, $C_{3-8}$ cycloalkyl, $C_{3-8}$ cycloalkenyl, —NHSO$_2$R$^w$, —CH=N—OR$^w$, an aryl or heterocyclyl group wherein said $C_{1-6}$ alkyl, $C_{2-6}$ alkenyl, $C_{2-6}$ alkynyl, aryl and heterocyclyl groups may be optionally substituted by one or more $R^b$ groups provided that $R^2$ and $R^6$ do not both represent hydrogen;

$R^w$ represents hydrogen or $C_{1-6}$ alkyl;

$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^x$, —(CH$_2$)$_n$—O—$C_{1-6}$ alkyl, —O—(CH$_2$)$_n$—OR$^x$, halo$C_{1-6}$ alkyl, halo$C_{1-6}$ alkoxy, $C_{1-6}$ alkanol, =O, =S, nitro, Si(R$^x$)$_4$, —(CH$_2$)$_s$—CN, —S—R$^x$, —SO—R$^x$, —SO$_2$—R$^x$, —COR$^x$, —(CR$^x$R$^y$)$_s$—COOR$^z$, —(CH$_2$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$SO$_2$—R$^y$, —(CH$_2$)$_s$—NH—SO$_2$—NR$^x$R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$ or —(CH$_2$)$_s$—SO$_2$NR$^x$R$^y$ groups;

$R^b$ represents an $R^a$ group or a —Y-carbocyclyl or —Z-heterocyclyl group wherein said carbocyclyl and heterocyclyl groups may be optionally substituted by one or more (e.g. 1, 2 or 3) $R^a$ groups;

Y and Z independently represent a bond, —CO—(CH$_2$)$_s$—, —COO—, —(CH$_2$)$_n$—, —NR$^x$—(CH$_2$)$_n$—, —(CH$_2$)$_n$—NR$^x$—, —CONR$^x$—, —NR$^x$CO—, —SO$_2$NR$^x$—, —NR$^x$SO$_2$—, —NR$^x$CONR$^y$—, —NR$^x$CS-NR$^y$—, —O—(CH$_2$)$_s$—, —(CH$_2$)$_s$—O—, S—, —SO— or —(CH$_2$)$_s$—SO$_2$—;

m and n independently represent an integer from 1-4;

s and t independently represent an integer from 0-4;

or a pharmaceutically acceptable salt, solvate or derivative thereof, with the proviso that the compound of formula (I) is not:

3-(3-acetamidophenyl)-6-(4-methylphenyl)pyrazolo(1,5a)pyrimidine;

3-(3-acetamidophenyl)-6-(4-methoxyphenyl)pyrazolo(1,5a)pyrimidine;

N-(4-{6-[3-(4-fluorophenyl)-1H-4-pyrazolyl]imidazo[1,2-a]-pyridin-3-yl}phenyl)methane sulfonamide;

N-(4-{6-[3-(4-fluorophenyl)-1-trityl-1H-4-pyrazolyl]-imidazo[1,2-a]pyridin-3-yl}phenyl)methane sulfonamide;

N-cyclohexyl-N'-{2-fluoro-4-[6-(1-trityl-1H-4-pyrazolyl)imidazo[1,2-a]pyridin-3-yl]phenyl}urea;

N-{2-fluoro-4-[6-(1-trityl-1H-4-pyrazolyl)imidazo[1,2-a]pyridine-3-yl]phenyl}-N'-isopropyl urea;

N-cyclohexyl-N'-{2-fluoro-4-[6-(1H-4-pyrazolyl)imidazo[1,2-a]pyridin-3-yl]phenyl}urea;

N-12-fluoro-4-[6-(1H-4-pyrazolyl)imidazo[1,2-a]pyridin-3-yl]phenyl}-N'-isopropylurea; or N1-{2-fluoro-4-[6-(1H-4-pyrazolyl)imidazo[1,2-a]pyridin-3-yl]phenyl}-4-fluorobenzamide.

U.S. Pat. No. 7,074,801 (Eisai), US 2002/0041880 (Merck), WO 98/54093 (Merck), WO 2006/091671 (Eli Lilly), WO 2003/048132 (Merck), WO 2004/052286

(Merck), WO 00/53605 (Merck), WO 03/101993 (Neogenesis), WO 2006/135667 (BMS), WO 2002/46168 (Astra Zeneca), WO 2005/080330 (Chugai), WO 2006/094235 (Sirtris Pharmaceuticals), WO 2006/034402 (Synta Pharmaceuticals), WO 01/18000 (Merck), U.S. Pat. No. 5,990,146 (Warner Lambert) and WO 00/12089 (Merck) each disclose a series of heterocyclic derivatives.

DETAILED DESCRIPTION OF THE INVENTION

According to a first aspect of the invention there is provided a compound of formula (I):

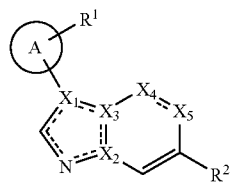

wherein $X_1$, $X_2$ and $X_3$ are each independently selected from carbon or nitrogen, such that at least one of $X_1$-$X_3$ represents nitrogen;

$X_4$ represents $CR^3$ or nitrogen;

$X_5$ represents $CR^6$, nitrogen or C=O;

provided that no more than three of $X_1$-$X_5$ represent nitrogen;

------ represents a single or double bond, such that at least one bond within the 5 membered ring system is a double bond;

$R^3$ represents hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkenyl, cyano, halo$C_{1-6}$ alkyl, halo$C_{1-6}$ alkoxy or =O;

A represents an aromatic or non-aromatic carbocyclic or heterocyclic group which may be optionally substituted by one or more (e.g. 1, 2 or 3) $R^a$ groups;

$R^1$ represents —NHCONR$^4$R$^5$, —NHCOOR$^4$, —NH—CO—(CH$_2$)$_n$—NR$^4$R$^5$, —NH—(CH$_2$)$_n$—CONR$^4$R$^5$, —NH—CO—(CH$_2$)$_n$—COOR$^4$, —NH—CO—(CH$_2$)$_n$—CSOR$^4$, —NHSO$_2$R$^4$, NHSO$_2$NR$^4$R$^5$, —NHCSNR$^4$R$^5$, —NHCOR$^4$, —NHCSR$^4$, —NHCSSR$^4$, —NHC(=NR$^4$)NR$^5$, NHC(=NR$^4$)R$^5$, —NH—C(=NH$_2$)—NH—CO—R$^4$, —NHCSOR$^4$ or —NHCOSR$^4$;

$R^4$ and $R^5$ independently represent hydrogen, $C_{1-6}$ alkyl, $C_{2-6}$ alkenyl, $C_{2-6}$ alkynyl, $C_{3-8}$ cycloalkyl, $C_{3-8}$ cycloalkenyl, $C_{1-6}$ alkanol, halo$C_{1-6}$ alkyl, —(CH$_2$)$_n$—NR$^x$R$^y$, —(CH$_2$)$_s$—COOR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more (e.g. 1, 2 or 3) $R^a$ groups;

$R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, —COOC$_{1-6}$ alkyl, hydroxy, $C_{1-6}$ alkoxy, halo$C_{1-6}$ alkyl, —CO—(CH$_2$)$_n$—$C_{1-6}$ alkoxy, $C_{1-6}$ alkylamino, $C_{3-8}$ cycloalkyl or $C_{3-8}$ cycloalkenyl;

$R^2$ and $R^6$ independently represent halogen, hydrogen, $C_{1-6}$ alkyl, $C_{1-6}$ alkoxy, $C_{2-6}$ alkenyl, $C_{2-6}$ alkynyl, $C_{3-8}$ cycloalkyl, $C_{3-8}$ cycloalkenyl, —NHSO$_2$R$^w$, —CH=N—OR$^w$, an aryl or heterocyclyl group wherein said $C_{1-6}$ alkyl, $C_{2-6}$ alkenyl, $C_{2-6}$ alkynyl, aryl and heterocyclyl groups may be optionally substituted by one or more $R^b$ groups provided that $R^2$ and $R^6$ do not both represent hydrogen;

$R^w$ represents hydrogen or $C_{1-6}$ alkyl;

$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^x$, —(CH$_2$)$_n$—O—$C_{1-6}$ alkyl, —O—(CH$_2$)$_n$—OR$^x$, halo$C_{1-6}$ alkyl, halo$C_{1-6}$ alkanol, =O, =S, nitro, Si(R$^x$)$_4$, —(CH$_2$)$_s$—CN, —S—R$^x$, —SO—R$^x$, —SO$_2$—R$^x$, —COR$^x$, —(CR$^x$R$^y$)$_s$—COOR$^z$, —(CH$_2$)$_s$—CONR$^x$R$^y$, —(CH$_2$)$_s$—NR$^x$R$^y$, —(CH$_2$)$_s$—NR$^x$-COR$^y$, —(CH$_2$)$_s$—NR$^x$SO$_2$—R$^y$, —(CH$_2$)$_s$—NH—SO$_2$—NR$^x$R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$ or —(CH$_2$)$_s$—SO$_2$NR$^x$R$^y$ groups;

$R^b$ represents an $R^a$ group or a —Y-carbocyclyl or —Z-heterocyclyl group wherein said carbocyclyl and heterocyclyl groups may be optionally substituted by one or more (e.g. 1, 2 or 3) $R^a$ groups;

Y and Z independently represent a bond, —CO—(CH$_2$)$_s$—, —COO—, —(CH$_2$)$_n$—, —NR$^x$—(CH$_2$)$_n$—, —(CH$_2$)$_n$—NR$^x$—, —CONR$^x$—, —NR$^x$CO—, —SO$_2$NR$^x$—, —NR$^x$SO$_2$—, —NR$^x$CONR$^y$—, —NR$^x$CS-NR$^y$—, —O—(CH$_2$)$_s$—, —(CH$_2$)$_s$—O—, S—, —SO— or —(CH$_2$)$_s$—SO$_2$—;

m and n independently represent an integer from 1-4;

s and t independently represent an integer from 0-4;

or a pharmaceutically acceptable salt, solvate or derivative thereof, with the proviso that the compound of formula (I) is not:

3-(3-acetamidophenyl)-6-(4-methylphenyl)pyrazolo(1,5a)pyrimidine;

3-(3-acetamidophenyl)-6-(4-methoxyphenyl)pyrazolo(1,5a)pyrimidine;

N-(4-{6-[3-(4-fluorophenyl)-1H-4-pyrazolyl]imidazo[1,2-a]-pyridin-3-yl}phenyl)methane sulfonamide;

N-(4-{6-[3-(4-fluorophenyl)-1-trityl-1H-4-pyrazolyl]-imidazo[1,2-a]pyridin-3-yl}phenyl)methane sulfonamide;

N-cyclohexyl-N'-{2-fluoro-4-[6-(1-trityl-1H-4-pyrazolyl)imidazo[1,2-a]pyridin-3-yl]phenyl}urea;

N-{2-fluoro-4-[6-(1-trityl-1H-4-pyrazolyl)imidazo[1,2-a]pyridine-3-yl]phenyl}-N'-isopropyl urea;

N-cyclohexyl-N'-{2-fluoro-4-[6-(1H-4-pyrazolyl)imidazo[1,2-a]pyridin-3-yl]phenyl}urea;

N-12-fluoro-4-[6-(1H-4-pyrazolyl)imidazo[1,2-a]pyridin-3-yl]phenyl}-N'-isopropylurea; or N1-{2-fluoro-4-[6-(1H-4-pyrazolyl)imidazo[1,2-a]pyridin-3-yl]phenyl}-4-fluorobenzamide.

In one embodiment, there is provided a compound of formula (I):

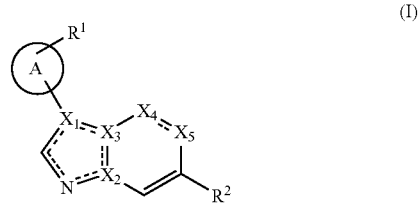

wherein $X_1$, $X_2$ and $X_3$ are each independently selected from carbon or nitrogen, such that at least one of $X_1$-$X_3$ represents nitrogen;

$X_4$ represents $CR^3$ or nitrogen;

$X_5$ represents $CR^6$, nitrogen or C=O;

provided that no more than three of $X_1$-$X_5$ represent nitrogen;

----- represents a single or double bond, such that when $X_5$ represents C=O, $X_4$ and $X_5$ are joined by a single bond and such that at least one bond within the 5 membered ring system is a double bond;

$R^3$ represents hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkenyl, cyano, halo$C_{1-6}$ alkyl, halo$C_{1-6}$ alkoxy or =O;

A represents an aromatic or non-aromatic carbocyclic or heterocyclic group which may be optionally substituted by one or more (e.g. 1, 2 or 3) $R^a$ groups;

$R^1$ represents —NHCONR$^4$R$^5$, —NHCOOR$^4$, —NH—CO—(CH$_2$)$_n$—NR$^4$R$^5$, —NH—(CH$_2$)$_n$—CONR$^4$R$^5$, —NH—CO—(CH$_2$)$_n$—COOR$^4$, —NH—CO—(CH$_2$)$_n$—CSOR$^4$, —NHSO$_2$R$^4$, NHSO$_2$NR$^4$R$^5$, —NHCSNR$^4$R$^5$, —NHCOR$^4$, —NHCSR$^4$, —NHCSSR$^4$, —NHC(=NR$^4$)NR$^5$, NHC(=NR$^4$)R$^5$, —NH—C(=NH$_2$)—NH—CO—R$^4$, —NHCSOR$^4$ or —NHCOSR$^4$;

$R^4$ and $R^5$ independently represent hydrogen, $C_{1-6}$ alkyl, $C_{2-6}$ alkenyl, $C_{2-6}$ alkynyl, $C_{3-8}$ cycloalkyl, $C_{3-8}$ cycloalkenyl, $C_{1-6}$ alkanol, halo$C_{1-6}$ alkyl, —(CH$_2$)$_n$—NR$^x$R$^y$, —(CH$_2$)$_s$—COOR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more (e.g. 1, 2 or 3) $R^a$ groups;

$R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, —COOC$_{1-6}$ alkyl, hydroxy, $C_{1-6}$ alkoxy, halo$C_{1-6}$ alkyl, —CO—(CH$_2$)$_n$—C$_{1-6}$ alkoxy, $C_{1-6}$ alkylamino, $C_{3-8}$ cycloalkyl or $C_{3-8}$ cycloalkenyl;

$R^2$ and $R^6$ independently represent halogen, hydrogen, $C_{1-6}$ alkyl, $C_{1-6}$ alkoxy, $C_{2-6}$ alkenyl, $C_{2-6}$ alkynyl, —C≡N, $C_{3-8}$ cycloalkyl, $C_{3-8}$ cycloalkenyl, —NHSO$_2$R$^w$, —CH=N—OR$^w$, an aryl or heterocyclyl group wherein said $C_{1-6}$ alkyl, $C_{2-6}$ alkenyl, $C_{2-6}$ alkynyl, aryl and heterocyclyl groups may be optionally substituted by one or more $R^b$ groups provided that $R^2$ and $R^6$ do not both represent hydrogen;

$R^w$ represents hydrogen or $C_{1-6}$ alkyl;

$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^x$, —O—(CH$_2$)$_n$—OR$^x$, halo$C_{1-6}$ alkyl, halo$C_{1-6}$ alkoxy, $C_{1-6}$ alkanol, =O, =S, nitro, Si(R$^x$)$_4$, —(CH$_2$)$_s$—CN, —S—R$^x$, —SO—R$^x$, —SO$_2$—R$^x$, —COR$^x$, —(CR$^x$R$^y$)$_s$—COOR$^z$, —(CH$_2$)$_s$—CONR$^x$R$^y$, —(CH$_2$)$_2$—NR$^x$R$^y$, —(CH$_2$)$_s$—NR$^x$COR$^y$, —(CH$_2$)$_s$—NR$^x$SO$_2$—R$^y$, —(CH$_2$)$_s$—NH—SO$_2$—NR$^x$R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$ or —(CH$_2$)$_s$—SO$_2$NR$^x$R$^y$ groups;

$R^b$ represents an $R^a$ group or a —Y-aryl or —Z-heterocyclyl group wherein said aryl and heterocyclyl groups may be optionally substituted by one or more (e.g. 1, 2 or 3) $R^a$ groups;

Y and Z independently represent a bond, —CO—(CH$_2$)$_s$—, —COO—, —(CH$_2$)$_n$—, —NR$^x$—(CH$_2$)$_n$—, —(CH$_2$)$_n$—NR$^x$—, —CONR$^x$—, —NR$^x$CO—, —SO$_2$NR$^x$—, —NR$^x$SO$_2$—, —NR$^x$CONR$^y$—, —NR$^x$CS-NR$^y$, —O—(CH$_2$)$_s$—, —(CH$_2$)$_s$—O—, S—, —SO— or —(CH$_2$)$_s$—SO$_2$—;

m and n independently represent an integer from 1-4;
s and t independently represent an integer from 0-4;
aryl represents a carbocyclic ring;
heterocyclyl represents a heterocyclic ring;
or a pharmaceutically acceptable salt, solvate or derivative thereof, with the proviso that the compound of formula (I) is not:
3-(3-acetamidophenyl)-6-(4-methylphenyl)pyrazolo(1,5a)pyrimidine;
3-(3-acetamidophenyl)-6-(4-methoxyphenyl)pyrazolo(1,5a)pyrimidine;
N-(4-{6-[3-(4-fluorophenyl)-1H-4-pyrazolyl]imidazo[1,2-a]-pyridin-3-yl}phenyl)methane sulfonamide;
N-(4-{6-[3-(4-fluorophenyl)-1-trityl-1H-4-pyrazolyl]-imidazo[1,2-a]pyridin-3-yl}phenyl)methane sulfonamide;
N-cyclohexyl-N'-{2-fluoro-4-[6-(1-trityl-1H-4-pyrazolyl)imidazo[1,2-a]pyridin-3-yl]phenyl}urea;
N-{2-fluoro-4-[6-(1-trityl-1H-4-pyrazolyl)imidazo[1,2-a]pyridine-3-yl]phenyl}-N'-isopropyl urea;
N-cyclohexyl-N'-{2-fluoro-4-[6-(1H-4-pyrazolyl)imidazo[1,2-a]pyridin-3-yl]phenyl}urea;
N-12-fluoro-4-[6-(1H-4-pyrazolyl)imidazo[1,2-a]pyridin-3-yl]phenyl}-N'-isopropylurea; or
N1-{2-fluoro-4-[6-(1H-4-pyrazolyl)imidazo[1,2-a]pyridin-3-yl]phenyl}-4-fluorobenzamide.

In one embodiment, there is provided a compound of formula (I):

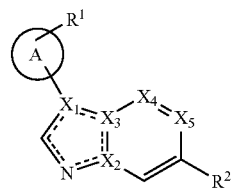

(I)

wherein
$X_1$, $X_2$ and $X_3$ are each independently selected from carbon or nitrogen, such that at least one of $X_1$-$X_3$ represents nitrogen;
$X_4$ represents CR$^3$ or nitrogen;
$X_5$ represents CR$^6$, nitrogen or C=O;
provided that no more than three of $X_1$-$X_5$ represent nitrogen;

----- represents a single or double bond;

$R^3$ represents hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkenyl, cyano, halo$C_{1-6}$ alkyl, halo$C_{1-6}$ alkoxy or =O;

A represents an aromatic or non-aromatic carbocyclic or heterocyclic group which may be optionally substituted by one or more (e.g. 1, 2 or 3) $R^a$ groups;

$R^1$ represents —NHCONR$^4$R$^5$, —NHCOOR$^4$, —NH—CO—(CH$_2$)$_n$—NR$^4$R$^5$, —NH—CO—(CH$_2$)$_n$—COOR$^4$, —NH—CO—(CH$_2$)$_n$—CSOR$^4$, —NHSO$_2$R$^4$, NHSO$_2$NR$^4$R$^5$, —NHCSNR$^4$R$^5$, —NHCOR$^4$, —NHCSR$^4$, —NHCSSR$^4$, —NHC(=NR$^4$)NR$^5$, NHC(=NR$^4$)R$^5$, —NH—C(=NH$_2$)—NH—CO—R$^4$, —NHCSOR$^4$ or —NHCOSR$^4$;

$R^4$ and $R^5$ independently represent hydrogen, $C_{1-6}$ alkyl, $C_{2-6}$ alkenyl, $C_{2-6}$ alkynyl, $C_{3-8}$ cycloalkyl, $C_{3-8}$ cycloalkenyl, $C_{1-6}$ alkanol, halo$C_{1-6}$ alkyl, —(CH$_2$)$_n$—NR$^x$R$^y$, —(CH$_2$)$_s$—COOR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more (e.g. 1, 2 or 3) $R^a$ groups;

$R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, hydroxy, $C_{1-6}$ alkoxy, haloC$_{1-6}$ alkyl, —CO—(CH$_2$)$_n$—C$_{1-6}$ alkoxy, C$_{3-8}$ cycloalkyl or C$_{3-8}$ cycloalkenyl;

R$^2$ and R$^6$ independently represent hydrogen, C$_{1-6}$ alkyl, C$_{2-6}$ alkenyl, C$_{2-6}$ alkynyl, C$_{3-8}$ cycloalkyl, C$_{3-8}$ cycloalkenyl, an aryl or heterocyclyl group wherein said aryl and heterocyclyl group may be optionally substituted by one or more R$^b$ groups with the proviso that when R$^6$ represents a heterocyclyl group, said heterocyclyl group is not pyrazolyl;

R$^a$ represents halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^x$, —O—(CH$_2$)$_n$—OR$^x$, haloC$_{1-6}$ alkyl, haloC$_{1-6}$ alkoxy, C$_{1-6}$ alkanol, =O, =S, nitro, —(CH$_2$)$_s$—CN, —S—R$^x$, —SO—R$^x$, —SO$_2$—R$^x$, —COR$^x$, —(CR$^x$R$^y$)$_s$—COOR$^z$, —(CH$_2$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$SO$_2$—R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$ or —(CH$_2$)$_s$—SO$_2$NR$^x$R$^y$ groups;

R$^b$ represents an R$^a$ group or a —Y-aryl or —Z-heterocyclyl group wherein said aryl and heterocyclyl groups may be optionally substituted by one or more (e.g. 1, 2 or 3) R$^a$ groups;

provided that when R$^2$ represents a group other than hydrogen, X$_5$ represents CH or C=O and when R$^2$ represents hydrogen, R$^6$ represents a group other than hydrogen;

Y and Z independently represent a bond, —CO—(CH$_2$)$_s$—, —COO—, —NR$^x$—(CH$_2$)$_n$—, —(CH$_2$)$_n$—NR$^x$—, —CONR$^x$—, —NR$^x$CO—, —SO$_2$NR$^x$—, —NR$^x$SO$_2$—, —NR$^x$CONR$^y$—, —NR$^x$CSNR$^y$—, —O—(CH$_2$)$_s$—, —(CH$_2$)$_s$—O—, S—, —SO— or —(CH$_2$)$_s$—SO$_2$—;

m and n independently represent an integer from 1-4;
s and t independently represent an integer from 0-4;
aryl represents a carbocyclic ring;
heterocyclyl represents a heterocyclic ring;
or a pharmaceutically acceptable salt, solvate or derivative thereof, with the proviso that the compound of formula (I) is not 3-(3-acetamidophenyl)-6-(4-methylphenyl)pyrazolo(1,5A)pyrimidine or 3-(3-acetamidophenyl)-6-(4-methoxyphenyl)pyrazolo(1,5A)pyrimidine.

In one embodiment, there is provided a compound of formula (I) wherein:

X$_1$, X$_2$ and X$_3$ are each independently selected from carbon or nitrogen, such that at least one of X$_1$-X$_3$ represents nitrogen;

X$_4$ represents CR$^3$ or nitrogen;
X$_5$ represents CH, nitrogen or C=O;
provided that no more than three of X$_1$-X$_5$ represent nitrogen;

------ represents a single or double bond;

R$^3$ represents hydrogen or =O;

A represents an aromatic or non-aromatic carbocyclic or heterocyclic group which may be optionally substituted by one or more (e.g. 1, 2 or 3) R$^a$ groups;

R$^1$ represents —NHCONR$^4$R$^5$, —NHCOOR$^4$, —NH—CO—(CH$_2$)$_n$—NR$^4$R$^5$, —NH—CO—(CH$_2$)$_n$—COOR$^4$, —NHSO$_2$R$^4$, or —NHCSNR$^4$R$^5$;

R$^4$ and R$^5$ independently represent hydrogen, C$_{1-6}$ alkyl, C$_{1-6}$ alkanol, —(CH$_2$)$_n$—NR$^x$R$^y$, —(CH$_2$)$_n$-aryl or haloC$_{1-6}$ alkyl;

R$^x$, R$^y$ and R$^z$ independently represent hydrogen, C$_{1-6}$ alkyl, C$_{1-6}$ alkanol, hydroxy, C$_{1-6}$ alkoxy, haloC$_{1-6}$ alkyl or —CO—(CH$_2$)$_n$—C$_{1-6}$ alkoxy;

R$^2$ represents an aryl or heterocyclyl group optionally substituted by one or more R$^b$ groups;

R$^a$ represents halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^x$, —O—(CH$_2$)$_n$—OR$^x$, haloC$_{1-6}$ alkyl, haloC$_{1-6}$ alkoxy, C$_{1-6}$ alkanol, =O, =S, nitro, —(CH$_2$)$_s$—CN, —S—R$^x$, —SO—R$^x$, —SO$_2$—R$^x$, —COR$^x$, —(CR$^x$R$^y$)$_s$—COOR$^z$, —(CH$_2$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$SO$_2$—R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$ or —(CH$_2$)$_s$—SO$_2$NR$^x$R$^y$ groups;

R$^b$ represents a —Y-aryl or —Z-heterocyclyl group wherein said aryl and heterocyclyl groups may be optionally substituted by one or more (e.g. 1, 2 or 3) R$^a$ groups;

provided that when R$^2$ represents a group other than hydrogen, X$_5$ represents CH or C=O;

Y and Z independently represent a bond, CO, —(CH$_2$)$_n$—, —NR$^x$—(CH$_2$)$_n$—, —O— or —O—(CH$_2$)$_s$—;

m and n independently represent an integer from 1-4;
s and t independently represent an integer from 0-4;
aryl represents a carbocyclic ring; and
heterocyclyl represents a heterocyclic ring.

The term 'C$_{1-6}$ alkyl' as used herein as a group or a part of the group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like.

The term 'C$_{1-6}$ alkoxy' as used herein refers to an —O—C$_{1-6}$ alkyl group wherein C$_{1-6}$ alkyl is as defined herein. Examples of such groups include methoxy, ethoxy, propoxy, butoxy, pentoxy or hexoxy and the like.

The term 'C$_{1-6}$ alkanol' as used herein refers to a C$_{1-6}$ alkyl group substituted by one or more hydroxy groups. Examples of such groups include hydroxymethyl, hydroxyethyl, hydroxypropyl and the like.

The term 'C$_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term 'C$_{3-6}$ cycloalkyl' as used herein refers to a saturated monocyclic hydrocarbon ring of 3 to 6 carbon atoms. Examples of such groups include cyclopropyl, cyclobutyl, cyclopentyl, cyclohexyl, and the like.

The term 'halogen' as used herein refers to a fluorine, chlorine, bromine or iodine atom.

The term 'haloC$_{1-6}$ alkyl' as used herein refers to a C$_{1-6}$ alkyl group as defined herein wherein at least one hydrogen atom is replaced with halogen. Examples of such groups include fluoroethyl, trifluoromethyl or trifluoroethyl and the like.

The term 'haloC$_{1-6}$ alkoxy' as used herein refers to a C$_{1-6}$ alkoxy group as herein defined wherein at least one hydrogen atom is replaced with halogen. Examples of such groups include difluoromethoxy or trifluoromethoxy and the like.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members. Where reference is made herein to carbocyclic and heterocyclic groups, the carbocyclic or heterocyclic ring can, unless the context indicates otherwise, be unsubstituted or substituted by one or more substituents for example molecular fragments, a molecular scaffolds or functional groups as discussed herein. It will be appreciated that references to "carbocyclic" and "heterocyclic" groups include reference to carbocyclic and heterocyclic groups which may be optionally substituted by one or more (e.g. 1, 2 or 3) $R^a$ or $R^b$ groups.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring.

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cyclohexenyl, cycloheptenyl and cyclooctenyl. Saturated heterocyclic groups include piperidine, morpholine, thiomorpholine. Partially saturated heterocyclic groups include pyrazolines, for example 2-pyrazoline and 3-pyrazoline.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. One further example of a five membered heteroaryl group includes thiadiazole.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) an imidazole ring fused to a 5- or 6-membered ring containing 1 or 2 ring heteroatoms;
g) an oxazole ring fused to a 5- or 6-membered ring containing 1 or 2 ring heteroatoms;
h) an isoxazole ring fused to a 5- or 6-membered ring containing 1 or 2 ring heteroatoms;
i) a thiazole ring fused to a 5- or 6-membered ring containing 1 or 2 ring heteroatoms;
j) an isothiazole ring fused to a 5- or 6-membered ring containing 1 or 2 ring heteroatoms;
k) a thiophene ring fused to a 5- or 6-membered ring containing 1, 2 or 3 ring heteroatoms;
l) a furan ring fused to a 5- or 6-membered ring containing 1, 2 or 3 ring heteroatoms;
m) an oxazole ring fused to a 5- or 6-membered ring containing 1 or 2 ring heteroatoms;
n) an isoxazole ring fused to a 5- or 6-membered ring containing 1 or 2 ring heteroatoms;
o) a cyclohexyl ring fused to a 5- or 6-membered ring containing 1, 2 or 3 ring heteroatoms; and
p) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups. One further example of a bicyclic heteroaryl group containing a six membered ring fused to a five membered ring includes imidazopyridine.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups. One further example of a polycyclic heteroaryl group containing an aromatic ring and a non-aromatic ring includes tetrahydrotriazolopyrazine (e.g. 5,6,7,8-tetrahydro-[1,2,4]triazolo[4,3-a]pyrazine).

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

Examples of carbocyclic aryl groups include phenyl, naphthyl, indenyl, and tetrahydronaphthyl groups.

Examples of non-aromatic heterocyclic groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclic groups include saturated groups such as piperidine, pyrrolidine, azetidine, morpholine, piperazine and N-alkyl piperazines.

In a nitrogen-containing non-aromatic heterocyclic ring the ring must contain at least one ring nitrogen atom. The heterocyclic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof.

Particular examples of nitrogen-containing non-aromatic heterocyclic groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The heterocyclic groups can be polycyclic fused ring systems or bridged ring systems such as bicycloalkanes, tricycloalkanes and their oxa- and aza analogues (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

The heterocyclic groups can each be unsubstituted or substituted by one or more substituent groups. For example, heterocyclic groups can be unsubstituted or substituted by 1, 2, 3 or 4 substituents. Where the heterocyclic group is monocyclic or bicyclic, typically it is unsubstituted or has 1, 2 or 3 substituents.

As mentioned above, ------ represents a single or double bond. It will be clear to the skilled person that when $X_5$ represents C=O or $R^3$ represents =O, $X_4$ and $X_5$ are joined by a single bond.

Particular Embodiments of the Invention

Examples of ring systems encompassed by the definitions of $X_1$-$X_5$ are shown in the following formulae (I)a-(I)t:

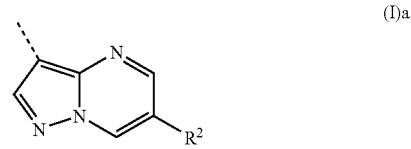

(I)a

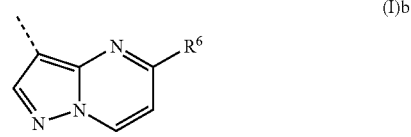

(I)b

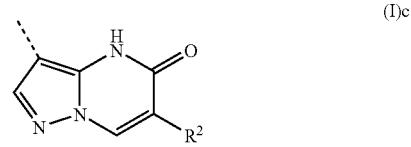

(I)c

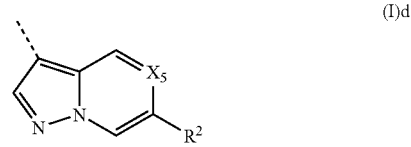

(I)d

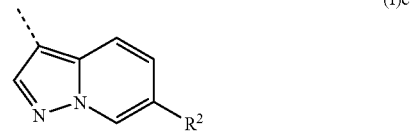

(I)e

-continued

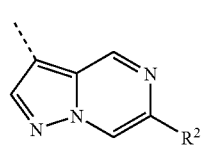
(I)f

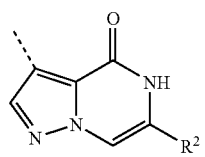
(I)g

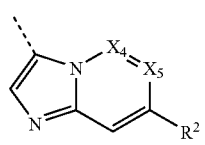
(I)h

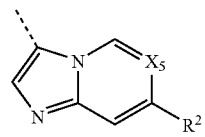
(I)i

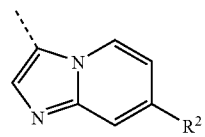
(I)j

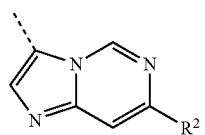
(I)k

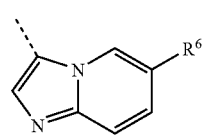
(I)l

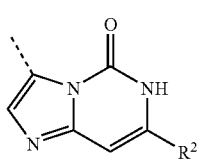
(I)m

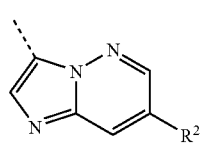
(I)n

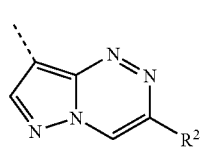
(I)o

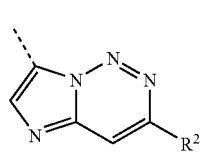
(I)p (I)q (I)r (I)s (I)t

Further examples of ring systems encompassed by the definitions of $X_1$-$X_5$ are shown in the following formulae (I)u-(I)v:

(I)u (I)v

In one embodiment, two bonds within the 5 membered ring system are double bonds.

In one embodiment, $X_1$ represents C.

In one embodiment, $X_1$, $X_3$ and $X_5$ represent C and $X_2$ and $X_4$ represent nitrogen (i.e. a ring system of formula (I)a).

In an alternative embodiment, $X_1$, $X_3$, $X_4$ and $X_5$ represent C and $X_2$ represents nitrogen (i.e. a ring system of formula (I)e).

In an alternative embodiment, $X_1$, $X_3$ and $X_4$ represent C and $X_2$ and $X_5$ represent nitrogen (i.e. a ring system of formula (I)f).

In an alternative embodiment, $X_1$ and $X_2$ represent C, $X_3$ represents nitrogen, $X_4$ represents $CR^3$ (e.g. CH) and $X_5$ represents $CR^6$ (e.g. C-Me) (i.e. a ring system of formula (I)h).

In an alternative embodiment, $X_1$, $X_2$, $X_4$ and $X_5$ represent C and $X_3$ represents nitrogen (i.e. a ring system of formula (I)j).

In an alternative embodiment, $X_1$, $X_2$ and $X_4$ represent C and $X_3$ and $X_5$ represent nitrogen (i.e. a ring system of formula (I)k). In an alternative embodiment, $X_2$, $X_3$, $X_4$ and $X_5$ represent C and $X_1$ represents nitrogen (i.e. a ring system of formula (I)q).

In an alternative embodiment, $X_2$, $X_3$ and $X_5$ represent C and $X_1$ and $X_4$ represent nitrogen (i.e. a ring system of formula (I)r).

In one embodiment, $X_1$-$X_5$ represent a ring system of formulae (I)a, (I)e, (I)f, (I)j, (I)k, (I)q or (I)r. In a further embodiment, $X_1$-$X_5$ represent a ring system of formula (I)a or (I)j. In a further embodiment, $X_1$-$X_5$ represent a ring system of formula (I)j.

In one embodiment, when $X_1$, $X_3$ and $X_5$ represent C and $X_2$ and $X_4$ represent nitrogen, $R^1$ represents a group other than —NHCOR$^4$.

In one embodiment, when $X_1$, $X_2$, $X_4$ and $X_5$ represent C and $X_3$ represents nitrogen, $R^1$ represents a group other than —NHCO(CH$_2$)$_n$NR$^4$R$^5$ or —NHCONR$^4$R$^5$.

In one embodiment, when $X_3$ represents nitrogen and A represents phenyl, $R^1$ represents a group other than —NHCOR$^4$.

In one embodiment, when $X_1$, $X_3$ and $X_5$ represent C and $X_2$ and $X_4$ represent nitrogen, $R^a$ is a group other than =O.

In one embodiment, when $X_2$, $X_3$, $X_4$ and $X_5$ represent C and $X_1$ represents nitrogen, $R^1$ represents a group other than —NHCOR$^4$ or —NHSO$_2$R$^4$.

In one embodiment, when $X_5$ represents CR$^6$ and $R^6$ represents a heterocyclyl group, said heterocyclyl group is other than pyrazole (e.g. optionally substituted pyrazole).

In one embodiment, when $X_2$, $X_3$ and $X_5$ represent C, $X_1$ and $X_4$ represent nitrogen, and $R^1$ represents —NHCONR$^4$R$^5$, A represents a group other than phenyl.

Examples of ring systems encompassed by the definition A are shown in the following formulae (I)A-(I)O:

(I)A
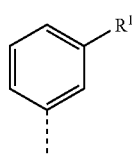

(I)B
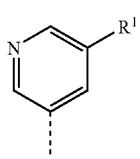

(I)C
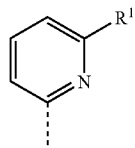

(I)D
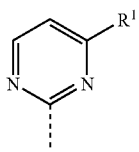

(I)E
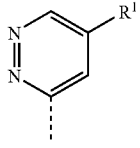

-continued (I)F
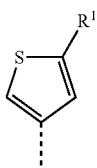

(I)G
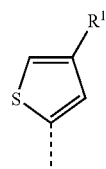

(I)H
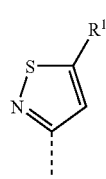

(I)I
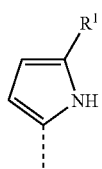

(I)J
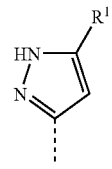

(I)K
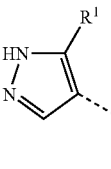

(I)L
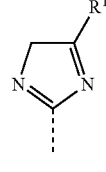

(I)M
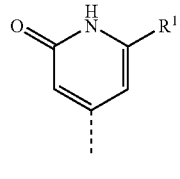

(I)N
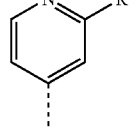

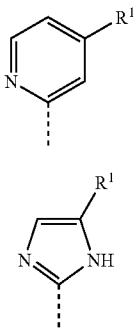

The group (I)L can be any tautomer of imidazole e.g. (I)L2.

In one embodiment, A represents a group selected from any one of formulae (I)A to (I)J and (I)L-(I)O.

In one embodiment, A is a group other than pyrazolyl.

In one embodiment, A is selected from (I)B, (I)N and (I)O.

In one embodiment, A is the group (I)A which can be optionally substituted by one or more (e.g. 1, 2 or 3) $R^a$ groups.

It will be appreciated that in the embodiment wherein $X_1$ represents nitrogen, ring A will be attached to said $X_1$ group via a carbon atom.

In one embodiment, A represents a monocyclic aromatic carbocyclic or heterocyclic ring system having for example a 5, 6 or 7 membered ring. In a further embodiment, A represents a 6 membered carbocyclic ring. In a yet further embodiment, A represents a phenyl group (i.e. a ring system of formula (I)A) optionally substituted by one or more (e.g. 1, 2 or 3) $R^a$ groups. In one embodiment, A represents unsubstituted phenyl or phenyl substituted with an —$(CH_2)_s$—CON-$R^xR^y$ (e.g. —$CONH_2$), —$(CH_2)_s$—CN (e.g. —CN), $C_{1-6}$ alkyl (e.g. methyl) or —$OR^x$ (e.g. methoxy) group.

In one embodiment, A represents a monocyclic aromatic carbocyclic or heterocyclic ring system having for example a 5, 6 or 7 membered ring. In a further embodiment, A represents a 6 membered carbocyclic ring. In a yet further embodiment, A represents a phenyl group (i.e. a ring system of formula (I)A) or a pyridyl group (i.e. a ring system of formula (IB) or (IC)) optionally substituted by one or more (e.g. 1, 2 or 3) $R^a$ groups.

In one embodiment, A represents a 6 membered monocyclic aromatic carbocyclic or heterocyclic ring system (e.g. phenyl or pyridyl), substituted by $R^1$ at the 3-position or 5-position. When A represents phenyl, in one embodiment $R^1$ is present at the 3-position of the phenyl with respect to the position of attachment to $X_1$.

In one embodiment, A represents a 6 membered monocyclic aromatic carbocyclic or heterocyclic ring system (e.g. phenyl or pyridyl), substituted by $R^1$ at the 5-position and further optionally substituted by a single $R^a$ group at the 3-position.

In one embodiment, A represents unsubstituted phenyl or phenyl substituted with an —$(CH_2)_s$—$CONR^xR^y$ (e.g. —$CONH_2$), —$(CH_2)_s$—CN (e.g. —CN), halogen (e.g. fluorine), $C_{1-6}$ alkyl (e.g. methyl), $C_{1-6}$ alkanol (e.g. —$CH_2OH$) or —$OR^x$ (e.g. methoxy or —$OCH(Me)_2$) group.

In a further embodiment, A represents unsubstituted phenyl.

In one embodiment, $R^1$ represents —$NHCONR^4R^5$, —NH—CO—$(CH_2)_n$—$NR^4R^5$, —NH—$(CH_2)_n$—$CONR^4R^5$, —NH—CO—$(CH_2)_n$—$COOR^4$, —NH—CO—$(CH_2)_n$—$CSOR^4$, —$NHSO_2R^4$, $NHSO_2NR^4R^5$, —$NHCSNR^4R^5$, —$NHCOR^4$, —$NHCSR^4$, —$NHCSSR^4$, —NHC(=$NR^4$)$NR^5$, NHC(=$NR^4$)$R^5$, —NH—C(=$NH_2$)—NH—CO—$R^4$, —$NHCSOR^4$ or —$NHCOSR^4$;

In one embodiment, $R^1$ represents —$NHCONR^4R^5$, —$NHCOOR^4$, —NH—CO—$(CH_2)_n$—$NR^4R^5$, —NH—CO—$(CH_2)_n$—$COOR^4$, —$NHSO_2R^4$, or —$NHCSNR^4R^5$.

In one embodiment, $R^1$ represents —$NHCONR^4R^5$, —$NHCOOR^4$, $NHSO_2NR^4R^5$, —NH—$(CH_2)_n$—$CONR^4R^5$, —NH—$CH_2$-aryl, —NH—CO—$(CH_2)_n$—$NR^4R^5$, —NH—CO—$(CH_2)_n$—$COOR^4$, —$NHSO_2R^4$, or —$NHCSNR^4R^5$.

In one embodiment, $R^1$ represents —$NHCONR^4R^5$. In a further embodiment, $R^4$ represents hydrogen or $C_{1-6}$ alkyl (e.g. methyl) and $R^5$ represents hydrogen, $C_{1-6}$ alkyl (e.g. methyl, ethyl or butyl), —$(CH_2)_n$—$NR^xR^y$ (e.g. —$(CH_2)_2NH_2$ or —$(CH_2)_3NH_2$), —$(CH_2)_n$-aryl (e.g. benzyl optionally substituted by a halogen atom, such as a fluorine atom), or halo$C_{1-6}$ alkyl (e.g. —$CH_2$—$CF_3$).

In one embodiment, $R^1$ represents —$NHCONR^4R^5$. In a further embodiment, $R^4$ represents hydrogen or $C_{1-6}$ alkyl (e.g. methyl) and $R^5$ represents hydrogen, $C_{1-6}$ alkyl (e.g. methyl, ethyl, butyl, —$CH(Me)_2$, —$CH_2CH(Me)_2$ or —$C(Me)_3$), $C_{1-6}$ alkyl substituted by one or more $R^a$ groups (e.g. —$CH_2$—C(Me)$_2$-$CH_2$—$NH_2$, —$CH_2$—CH(Me)-OMe or —$CH_2$—$C(F)_2$—$CH_2NH_2$), $C_{1-6}$ alkanol (e.g. —$CH_2$—CH(OH)—$CH_2OH$), —$(CH_2)_n$—$NR^xR^y$ (e.g. —$(CH_2)_2NH$-COOt-Bu, —$(CH_2)_2NH_2$ or —$(CH_2)_3NH_2$), —$(CH_2)_n$-aryl (e.g. benzyl optionally substituted by a halogen atom, such as a fluorine atom), —$(CH_2)_n$-heterocyclyl (e.g. —$CH_2$-dioxaolanyl (optionally substituted by one or more $C_{1-6}$ alkyl (e.g. methyl) groups), —$CH_2$-tetrahydrofuranyl or —$CH_2$-piperidinyl) or halo$C_{1-6}$ alkyl (e.g. —$(CH_2)_2$—F, —$CH_2$—CH—$F_2$—CH(Me)—$CF_3$ or —$CH_2$—$CF_3$).

In one embodiment, when A represents phenyl and $R^1$ represents —$NHCONR^4R^5$, $R^4$ and $R^5$ represent a group other than phenyl.

In one embodiment, $R^1$ represents —$NHCOOR^4$. In a further embodiment, $R^4$ represents $C_{1-6}$ alkyl (e.g. methyl) or halo$C_{1-6}$ alkyl. In a further embodiment, $R^4$ represents $C_{1-6}$ alkyl (e.g. methyl) or halo$C_{1-6}$ alkyl (e.g. —$CH_2$—$CF_3$). In a yet further embodiment, $R^4$ represents $C_{1-6}$ alkyl (e.g. methyl).

In one embodiment, $R^1$ represents —NH—CO—$(CH_2)_n$—$NR^4R^5$. In a further embodiment, n represents 1 and $R^4$ and $R^5$ both represent hydrogen.

In one embodiment, $R^1$ represents —NH—CO—$(CH_2)_n$—$COOR^4$. In a further embodiment, n represents 2 and $R^4$ represents hydrogen.

In one embodiment, $R^1$ represents —$NHSO_2R^4$. In a further embodiment, $R^4$ represents $C_{1-6}$ alkyl (e.g. methyl) or —$(CH_2)_n$—$NR^xR^y$ (e.g. $NH_2$ or $NMe_2$).

In one embodiment, $R^1$ represents —$NHCSNR^4R^5$. In a further embodiment, one of $R^4$ and $R^5$ represents hydrogen and the other represents $C_{1-6}$ alkyl (e.g. ethyl).

In one embodiment, $R^1$ represents —$NHCOR^4$. In a further embodiment, $R^4$ represents $C_{1-6}$ alkyl (e.g. methyl, ethyl or propyl) or $C_{1-6}$ alkanol (e.g. —$CH_2OH$).

In a further embodiment, $R^1$ represents —$NHCONR^4R^5$ (e.g. —NHCONHEt or —$NHCONHCH_2CF_3$) or —$NHCSNR^4R^5$ (e.g. —NHCSNHEt). In a yet further embodiment, $R^1$ represents —$NHCONR^4R^5$ (e.g. —NHCONHEt or —$NHCONHCH_2CF_3$). In a yet further embodiment, $R^1$ represents —$NHCONHCH_2CF_3$.

In a one embodiment, $R^1$ represents $NHSO_2NR^4R^5$. In a further embodiment, $R^4$ represents hydrogen and $R^5$ represents halo$C_{1-6}$ alkyl (e.g. —$CH_2$—$CF_3$).

In one embodiment, $R^1$ represents —NH—$(CH_2)_n$—CONR$^4$R$^5$. In a further embodiment, n represents 1, $R^4$ represents hydrogen and $R^5$ represents hydrogen or $C_{1-6}$ alkyl (e.g. methyl).

When $R^2$ or $R^6$ represents a heterocyclyl group, in one embodiment the heterocyclyl group is other than pyrazolyl (e.g. optionally substituted pyrazolyl).

In one embodiment, when $R^2$ represents hydrogen, $X_5$ represents CR$^6$ wherein $R^6$ represents a group other than hydrogen.

In one embodiment, when $X_5$ represents CH or nitrogen, $R^2$ represents a group other than hydrogen.

In one embodiment, when $R^2$ represents a group other than hydrogen, $X_5$ represents CH, nitrogen or C═O.

In one embodiment, when $X_5$ represents CR$^6$ wherein $R^6$ represents a group other than hydrogen, $R^2$ represents hydrogen.

In one embodiment, $R^2$ represents an aryl or heterocyclyl group optionally substituted by one or more $R^a$ groups.

In one embodiment, $R^2$ represents an aryl or heterocyclyl group optionally substituted by one or more $R^b$ groups.

In one embodiment, $R^2$ represents phenyl optionally substituted by an $R^b$ group.

In one embodiment, $R^2$ represents an aryl (e.g. phenyl) group optionally substituted by one or more (e.g. 1, 2 or 3) $R^b$ groups selected from halogen (e.g. fluorine), haloC$_{1-6}$ alkoxy (e.g. —OCF$_3$), —OR$^x$ (e.g. methoxy or —OCH$_2$OHCH$_2$OH), C$_{1-6}$ alkanol (e.g. —CH$_2$OH), —(CR$^x$R$^y$)$_s$—COOR$^z$ (e.g. —COOH, —COOMe, —C(Me)$_2$-COOH, —CH$_2$—COOH or —C(Me)$_2$-COOMe), —(CH$_2$)$_s$—CN (e.g —CH$_2$CN), —(CH$_2$)$_s$—NR$^x$R$^y$ (e.g. —NMe$_2$, —(CH$_2$)$_2$—NH$_2$, —(CH$_2$)$_2$—NMe$_2$ or —NH—CO—CH$_2$-methoxy) or —O—(CH$_2$)$_n$—OR$^x$ (e.g. —O—(CH$_2$)$_2$-ethoxy).

In one embodiment, $R^2$ represents an aryl (e.g. phenyl) group optionally substituted by one or more (e.g. 1, 2 or 3) $R^b$ groups selected from halogen (e.g. fluorine or chlorine), deuterium (e.g. D$_5$), haloC$_{1-6}$ alkyl (e.g. —CF$_3$), haloC$_{1-6}$ alkoxy (e.g. —OCF$_3$), —OR$^x$ (e.g. methoxy or —OCH$_2$OHCH$_2$OH), C$_{1-6}$ alkyl (e.g. i-Pr), C$_{1-6}$ alkanol (e.g. —CH$_2$OH), —(CR$^x$R$^y$)$_s$—COOR$^z$ (e.g. —COOH, —COOMe, —C(Me)$_2$-COOH, —CH$_2$—COOH or —C(Me)$_2$-COOMe), —(CH$_2$)$_s$—CN (e.g. —CN or —CH$_2$CN), —(CH$_2$)$_s$—NR$^x$R$^y$ (e.g. —NMe$_2$, —(CH$_2$)$_2$—NH$_2$, —(CH$_2$)$_2$—NMe$_2$ or —NH—CO—CH$_2$-methoxy), —O—(CH$_2$)$_n$—OR$^x$ (e.g. —O—(CH$_2$)$_2$-ethoxy), —(CH$_2$)$_s$—CONR$^x$R$^y$ (e.g. —CONH$_2$, —CONHMe, —CONHEt, —CONH-iPr, —CH$_2$—CONHMe, —CONH—(CH$_2$)$_2$—OMe or —CONH—(CH$_2$)$_2$—NH$_2$), —SO$_2$—R$^x$ (e.g. —SO$_2$Me), —(CH$_2$)$_s$—SO$_2$NR$^x$R$^y$ (e.g. —SO$_2$NH$_2$), —(CH$_2$)$_s$—NR$^x$—SO$_2$—R$^y$ (e.g. —NHSO$_2$Me or —CH$_2$—NHSO$_2$Me), —(CH$_2$)$_s$—NH—SO$_2$—NR$^x$R$^y$ (e.g. —NH—SO$_2$—NMe$_2$).

In a further embodiment, $R^2$ represents an aryl (e.g. phenyl) group optionally substituted by a halogen (e.g. fluorine), —Z-heterocyclyl group (e.g. —CH$_2$-morpholinyl, —CH$_2$-piperazinyl, —CH$_2$-piperidinyl, —CH$_2$-azetidinyl), —(CR$^x$R$^y$)$_s$—COOR$^z$ (e.g. —COOH or —C(Me)$_2$-COOH), wherein said heterocyclyl group may be optionally substituted by a C$_{1-6}$ alkyl (e.g. methyl), or —(CR$^x$R$^y$)$_s$—COOR$^z$ (e.g. —COOH) group.

In one embodiment, $R^2$ represents an aryl (e.g. phenyl) group optionally substituted by a —Y-aryl (e.g. —Y-phenyl) group.

In one embodiment, Y represents —O—(CH$_2$)$_s$— (e.g. —O—CH$_2$—).

In one embodiment, $R^2$ represents an aryl (e.g. phenyl) group optionally substituted by a —Z-heterocyclyl group (e.g. —Z-morpholinyl, —Z-azetidinyl, —Z-pyrrolidinyl, —Z-tetrazolyl, —Z-piperidinyl, —Z-piperazinyl) wherein said heterocyclyl group may be optionally substituted by one or more (e.g. 1, 2 or 3) $R^a$ groups selected from C$_{1-6}$ alkyl (e.g. methyl) or —(CR$^x$R$^y$)$_s$—COOR$^z$ (e.g. —COOH, —COOMe or —COOtBu) groups.

In one embodiment, $R^2$ represents an aryl (e.g. phenyl) group optionally substituted by a —Z-heterocyclyl group (e.g. —Z-morpholinyl, —Z-azetidinyl, —Z-pyrrolidinyl, —Z-pyrazolyl, —Z-tetrazolyl, —Z-piperidinyl, —Z-piperazinyl, —Z-diazepanyl or —Z-tetrahydropyranyl) wherein said heterocyclyl group may be optionally substituted by one or more (e.g. 1, 2 or 3) $R^a$ groups selected from C$_{1-6}$ alkyl (e.g. methyl or ethyl), ═O, —COR$^x$ (e.g. —COMe) or —(CR$^x$R$^y$)$_s$—COOR$^z$ (e.g. —COOH, —COOMe or —COOtBu) groups.

In a further embodiment, $R^2$ represents an aryl (e.g. phenyl) group optionally substituted by a halogen (e.g. fluorine), —Z-heterocyclyl group (e.g. —CH$_2$-morpholinyl, —CH$_2$-piperazinyl, —CH$_2$-piperidinyl, —CH$_2$-azetidinyl), —(CR$^x$R$^y$)$_s$—COOR$^z$ (e.g. —COOH or —C(Me)$_2$-COOH), wherein said heterocyclyl group may be optionally substituted by a C$_{1-6}$ alkyl (e.g. methyl), or —(CR$^x$R$^y$)$_s$—COOR$^z$ (e.g. —COOH) group. In a yet further embodiment, $R^2$ represents an aryl (e.g. phenyl) group optionally substituted by a —Z-heterocyclyl group (e.g. oxetanyl) wherein said heterocyclyl group may be optionally substituted by a C$_{1-6}$ alkyl (e.g. methyl) group.

In a yet further embodiment, $R^2$ represents an aryl (e.g. phenyl) group optionally substituted by a halogen (e.g. fluorine) atom or a —Z-heterocyclyl group (e.g. —CH$_2$-morpholinyl or —CH$_2$-piperazinyl) wherein said heterocyclyl group may be optionally substituted by a C$_{1-6}$ alkyl (e.g. methyl) group.

In a yet further embodiment, $R^2$ represents an aryl (e.g. phenyl) group optionally substituted by a halogen (e.g. fluorine) atom. In a still yet further embodiment, $R^2$ represents 4-fluorophenyl.

In one embodiment, $R^2$ represents a 5 membered heterocyclyl group optionally substituted by one or more $R^a$ groups.

In one embodiment, $R^2$ represents a 5 membered heteroaryl group optionally substituted by one or more $R^a$ groups.

In one embodiment, $R^2$ represents a heterocyclyl group optionally substituted by an $R^b$ group.

In one embodiment, $R^2$ represents a heterocyclyl group optionally substituted by a —Z-heterocyclyl or —(CH$_2$)$_s$—NR$^x$R$^y$ group.

In one embodiment, $R^2$ represents a heterocyclyl group (e.g. morpholinyl, piperazinyl, pyridyl, thienyl, pyrazinyl, benzothienyl, furanyl or pyrimidinyl) optionally substituted by one or more (e.g. 1, 2 or 3) $R^b$ groups selected from ═O (e.g. pyridinone), C$_{1-6}$ alkyl (e.g. methyl), —(CH$_2$)$_s$—NR$^x$R$^y$ (e.g. —NH$_2$), —OR$^x$ (e.g. methoxy), —COR$^x$ (e.g. —COMe) or C$_{1-6}$ alkanol (e.g. —CH$_2$OH) groups.

In one embodiment, $R^2$ represents a heterocyclyl group (e.g. morpholinyl, piperazinyl, pyridyl, thienyl, pyrazinyl, pyridazinyl, benzothienyl, furanyl, imidazolyl, pyrazolyl, benzodioxolyl, pyrrolidinyl, azetidinyl, piperidinyl, oxazolyl, thiazolyl, isothiazolyl, thiadiazolyl, triazolyl, tetrazolyl, oxadiazolyl, isoxazolyl, benzodioxolyl, tetrahydrotriazolopyrazinyl or pyrimidinyl) optionally substituted by one or more (e.g. 1, 2 or 3) $R^b$ groups selected from ═O (e.g. pyridinone or 5-oxo-4,5-dihydro-[1,3,4]oxadiazolyl), ═S (e.g. thioxo-4,5-dihydro-[1,3,4]oxadiazole), halogen (e.g.

fluorine), $C_{1-6}$ alkyl (e.g. methyl, ethyl, propyl, i-Pr or t-Bu), halo$C_{1-6}$ alkyl (e.g. —$CH_2$—F, —$CF_3$ or —$CH_2CF_3$), $C_{3-8}$ cycloalkyl (e.g. cyclopropyl), —$(CH_2)_s$—$NR^xR^y$ (e.g. —$NH_2$ or —$(CH_2)_2$—$NH_2$), —$OR^x$ (e.g. hydroxy, methoxy or —O-i-Pr), —$(CH_2)_n$—O—$C_{1-6}$ alkyl (e.g. —$CH_2$—O-Me), —$COR^x$ (e.g. —COMe), —$(CR^xR^y)_s$—$COOR^z$ (e.g. —COOH, —COOEt or —COOt-Bu), —S—$R^x$ (e.g. —S-Me), —$SO_2$—$R^x$ (e.g. —$SO_2$-Et), —$(CH_2)_s$—$NR^xR^y$ (e.g. —$NH_2$), —$(CH_2)_s$—$SO_2NR^xR^y$ (e.g. —$SO_2$—$NMe_2$) or $C_{1-6}$ alkanol (e.g. —C(OH)(Me)$_2$ or —$CH_2OH$) groups.

In one embodiment, $R^2$ represents a heterocyclyl group (e.g. morpholinyl, piperazinyl, pyridyl, thienyl, pyrazinyl, benzothienyl, furanyl, imidazolyl, pyrazolyl, benzodioxolyl, pyrrolidinyl, azetidinyl, piperidinyl, oxazolyl, thiazolyl, isothiazolyl, thiadiazolyl, triazolyl, tetrazolyl, oxadiazolyl, isoxazolyl, benzodioxolyl, tetrahydrotriazolopyrazinyl or pyrimidinyl) optionally substituted by one or more (e.g. 1, 2 or 3) $R^b$ groups selected from =O (e.g. pyridinone or 5-oxo-4,5-dihydro-[1,3,4]oxadiazolyl), =S (e.g. thioxo-4,5-dihydro-[1,3,4]oxadiazole), halogen (e.g. fluorine), $C_{1-6}$ alkyl (e.g. methyl, ethyl, propyl, i-Pr or t-Bu), halo$C_{1-6}$ alkyl (e.g. —$CH_2$—F, —$CF_3$ or —$CH_2CF_3$), $C_{3-8}$ cycloalkyl (e.g. cyclopropyl), —$(CH_2)_s$—$NR^xR^y$ (e.g. —$NH_2$), —$OR^x$ (e.g. hydroxy, methoxy or —O-i-Pr), —$(CH_2)_n$—O—$C_{1-6}$ alkyl (e.g. —$CH_2$—O-Me), —$COR^x$ (e.g. —COMe), —$(CR^xR^y)_s$—$COOR^z$ (e.g. —COOH, —COOEt or —COOt-Bu), —S—$R^x$ (e.g. —S-Me), —$SO_2$—$R^x$ (e.g. —$SO_2$-Et), —$(CH_2)_s$—$NR^xR^y$ (e.g. —$NH_2$), —$(CH_2)_s$—$SO_2NR^xR^y$ (e.g. —$SO_2$—$NMe_2$) or $C_{1-6}$ alkanol (e.g. —C(OH)(Me)$_2$ or —$CH_2OH$) groups.

In one embodiment, $R^2$ represents a heterocyclyl group (e.g. morpholinyl, piperazinyl, pyridyl, thienyl, pyrazinyl, benzothienyl, furanyl, imidazolyl, pyrazolyl, benzodioxolyl, pyrrolidinyl, azetidinyl, piperidinyl, oxazolyl, thiazolyl, isothiazolyl, thiadiazolyl, triazolyl, tetrazolyl, oxadiazolyl, isoxazolyl, benzodioxolyl, tetrahydrotriazolopyrazinyl or pyrimidinyl) optionally substituted by one or more (e.g. 1, 2 or 3) $R^b$ groups selected from =O (e.g. pyridinone or 5-oxo-4,5-dihydro-[1,3,4]oxadiazolyl), =S (e.g. thioxo-4,5-dihydro-[1,3,4]oxadiazole), halogen (e.g. fluorine), $C_{1-6}$ alkyl (e.g. methyl, ethyl, propyl, i-Pr or t-Bu), halo$C_{1-6}$ alkyl (e.g. —$CH_2$—F or —$CF_3$), $C_{3-8}$ cycloalkyl (e.g. cyclopropyl), —$(CH_2)_s$—$NR^xR^y$ (e.g. —$NH_2$), —$OR^x$ (e.g. hydroxy, methoxy or —O-i-Pr), —$COR^x$ (e.g. —COMe), —$(CR^xR^y)_s$—$COOR^z$ (e.g. —COOH, —COOEt or —COOt-Bu), —S—$R^x$ (e.g. —S-Me), —$SO_2$—$R^x$ (e.g. —$SO_2$-Et), —$(CH_2)_s$—$NR^xR^y$ (e.g. —$NH_2$), —$(CH_2)_s$—$SO_2NR^xR^y$ (e.g. —$SO_2$—$NMe_2$) or $C_{1-6}$ alkanol (e.g. —C(OH)(Me)$_2$ or —$CH_2OH$) groups.

In one embodiment, $R^2$ represents an aromatic heterocyclyl group optionally substituted by one or more $R^a$ groups.

In a further embodiment, $R^2$ represents oxazole, oxadiazole, triazole, tetrazole, pyrazole, thiadiazole, thiazole, imidazole or oxathiadiazole optionally substituted by one or more $R^a$ groups.

In a further embodiment, $R^2$ represents oxazole, oxadiazole, triazole, tetrazole, thiadiazole or oxathiadiazole optionally substituted by one or more $R^a$ groups.

In a further embodiment, $R^2$ represents thiadiazole, thiazole, or imidazole optionally substituted by one or more $R^a$ groups.

In a further embodiment, $R^2$ represents a 5 membered heterocyclyl group (e.g. oxazole, oxadiazole, triazole (e.g. 1,2,3-triazole or 1,2,4-triazole), tetrazole, thiadiazole or oxathiadiazole) optionally substituted by a $C_{1-6}$ alkyl (e.g. methyl or ethyl) or —S—$R^x$ (e.g. —S-Me) group.

In a further embodiment, $R^2$ represents oxadiazole (e.g. 1,3,4-oxadiazole), tetrazole or thiadiazole (e.g. 1,3,4-thiadiazole) optionally substituted by a $C_{1-6}$ alkyl (e.g. methyl or ethyl) or —S—$R^x$ (e.g. —S-Me) group. In a further embodiment, $R^2$ represents thiadiazole (e.g. 1,3,4-thiadiazole) optionally substituted by a $C_{1-6}$ alkyl (e.g. methyl or ethyl) or —S—$R^x$ (e.g. —S-Me) group. In a yet further embodiment, $R^2$ represents unsubstituted thiadiazole (e.g. 1,3,4-thiadiazole).

In a further embodiment, $R^2$ represents pyrazole optionally substituted by one or more $R^a$ groups, for example one or two optionally substituted $C_{1-4}$ alkyl groups (e.g. $CH_3$, $CH_2OH$, $(CH_2)_2OH$ or $(CH_2)_2NH_2$).

In a further embodiment, $R^2$ represents pyrazole optionally substituted by one or more $R^a$ groups, for example one or two $C_{1-4}$ alkyl groups (e.g. methyl groups). In a yet further embodiment, $R^2$ represents pyrazole optionally substituted by one or two optionally substituted $C_{1-4}$ alkyl groups (e.g. $CH_3$, $(CH_2)_2OH$).

In a further embodiment, $R^2$ represents oxazole, oxadiazole, triazole, tetrazole, imidazole, thiadiazole or oxathiadiazole substituted with one or two optionally substituted $C_{1-4}$ alkyl groups (e.g. $CH_3$, $CH_2OH$) or an =O group.

In a further embodiment, $R^2$ represents oxazole, oxadiazole, triazole, tetrazole, thiadiazole or oxathiadiazole substituted with one or two optionally substituted $C_{1-4}$ alkyl groups (e.g. $CH_3$, $CH_2OH$).

In a further embodiment, $R^2$ represents an aryl (e.g. phenyl) group optionally substituted by a halogen (e.g. fluorine) atom or $R^2$ represents a 5 membered heterocyclyl group (e.g. oxadiazole, tetrazole or thiadiazole) optionally substituted by a $C_{1-6}$ alkyl (e.g. methyl or ethyl) or —S—$R^x$ (e.g. —S-Me) group.

In a further embodiment, $R^2$ represents a heterocyclyl (e.g. pyridyl or pyrimidinyl) group optionally substituted by a —Z-heterocyclyl group (e.g. —Z-azetidinyl, —Z-piperazinyl, —Z-morpholinyl or —Z-piperidinyl).

In a further embodiment, $R^2$ represents a heterocyclyl (e.g. pyridyl) group optionally substituted by a —Z-heterocyclyl group (e.g. —Z-piperazinyl, —Z-morpholinyl or —Z-piperidinyl).

In a further embodiment, $R^2$ represents a heterocyclyl (e.g. pyridyl) group optionally substituted by a —Z-heterocyclyl group (e.g. —Z-piperazinyl, —Z-morpholinyl, Z-tetrahydropyranyl or —Z-piperidinyl).

In a yet further embodiment, $R^2$ represents a heterocyclyl (e.g. pyridyl) group optionally substituted by a —$(CH_2)_s$—$NR^xR^y$ (e.g. —$NH_2$) group.

In a yet further embodiment, $R^2$ represents a 6 membered aromatic ring (e.g. phenyl, pyridyl, pyrimindinyl or pyridazinyl optionally substituted by one or more (e.g. 1 or 2) $C_{1-6}$ alkyl (e.g. methyl) or halogen (e.g. fluorine) groups.

In one embodiment, $R^2$ represents halogen (e.g. fluorine or chlorine). In one embodiment, $R^2$ represents chlorine.

In one embodiment, $R^2$ represents $C_{1-6}$ alkyl (e.g. methyl or ethyl) optionally substituted by one or more $R^b$ groups (e.g. —$CH_2OH$, —C(OH)(Me)$_2$ or —$CF_3$).

In one embodiment, $R^2$ represents $C_{3-8}$ cycloalkyl (e.g. cyclopropyl).

In one embodiment, $R^2$ represents —CH=N—$OR^w$ (e.g. —CH=N—OH or —CH=N—OMe).

In one embodiment, $R^2$ represents —$NHSO_2R^w$ (e.g. —$NHSO_2Me$).

In one embodiment, $R^2$ represents $C_{1-6}$ alkoxy (e.g. methoxy or ethoxy).

In one embodiment, $R^2$ represents $C_{2-6}$ alkynyl (e.g. ethynyl or propynyl) optionally substituted by an $R^b$ group (e.g.

—C≡C—Si(Me)$_4$). In a further embodiment, R$^2$ represents C$_{2-6}$ alkynyl (e.g. ethynyl) optionally substituted by an R$^b$ group (e.g. —C≡C—Si(Me)$_4$). In a further embodiment, R$^2$ represents C$_{2-6}$ alkynyl (e.g. ethynyl) optionally substituted by an R$^b$ group (e.g. cyclopropyl).

In one embodiment, R$^2$ represents —C≡N.

In one embodiment, R$^2$ represents C$_{2-6}$ alkenyl optionally substituted by an R$^b$ group (e.g. —CH═CH—COOEt or —CH═CHCONHMe).

In one embodiment R$^6$ represents halogen, hydrogen, C$_{1-6}$ alkyl, C$_{1-6}$ alkoxy, C$_{2-6}$ alkenyl, C$_{2-6}$ alkynyl, —C≡N, C$_{3-8}$ cycloalkyl, C$_{3-8}$ cycloalkenyl, —NHSO$_2$R$^w$, —CH═N—OR$^w$, or a 3-6 membered monocyclic heterocyclyl group wherein said C$_{1-6}$ alkyl, C$_{2-6}$ alkenyl, C$_{2-6}$ alkynyl and heterocyclyl groups may be optionally substituted by one or more R$^a$ groups.

In one embodiment R$^2$ and R$^6$ may be optionally substituted by an R$^b$ group. In a further embodiment R$^b$ includes a group R$^a$ or —Y-aryl or —Z-heterocyclyl.

In one embodiment, Y and Z independently represent —CO—, —O—(CH$_2$)$_s$— or —NH—(CH$_2$)$_n$—.

In one embodiment, Y and Z independently represent a bond, CO, —CH$_2$—, —(CH$_2$)$_2$, —(CH$_2$)$_3$ or —O—.

In one embodiment, Z represents a bond, CO, —(CH$_2$)$_n$— (e.g. —CH$_2$—, —(CH$_2$)$_2$ or —(CH$_2$)$_3$) or —O—. In a further embodiment, Z represents —(CH$_2$)$_n$— (e.g. —CH$_2$—).

In one embodiment, Z represents a bond, CO, —(CH$_2$)$_n$— (e.g. —CH$_2$—, —(CH$_2$)$_2$ or —(CH$_2$)$_3$), —NH—(CH$_2$)$_n$— (e.g. —NH—) or —O—. In a further embodiment, Z represents —(CH$_2$)$_n$— (e.g. —CH$_2$—).

In one embodiment, Z represents a bond, CO, —(CH$_2$)$_n$— (e.g. —CH$_2$—, —(CH$_2$)$_2$ or —(CH$_2$)$_3$) or —O—.

In one embodiment, Z represents a bond or —CH$_2$—.

In one embodiment, R$^b$ represents an R$^a$ group or a —Y-aryl or —Z-heterocyclyl group wherein said aryl and heterocyclyl groups may be optionally substituted by one or more (e.g. 1, 2 or 3) R$^a$ groups.

In one embodiment the compound of formula (I) is a compound of formula (Ia) or (Ib):

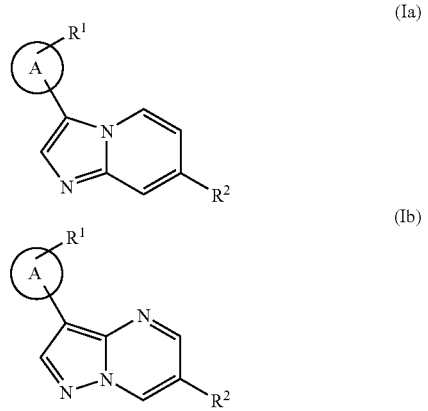

wherein

A represents an aromatic carbocyclic or heterocyclic group which may be optionally substituted by one or more (e.g. 1, 2 or 3) R$^a$ groups;

R$^1$ represents —NHCONR$^4$R$^5$, —NHCOOR$^4$, —NH—CO—(CH$_2$)$_n$—NR$^4$R$^5$, —NH—CO—(CH$_2$)$_n$—COOR$^4$, —NH—CO—(CH$_2$)$_n$—CSOR$^4$, —NHSO$_2$R$^4$, —NHSO$_2$NR$^4$R$^5$, —NHCOR$^4$;

R$^4$ and R$^5$ independently represent hydrogen, C$_{1-6}$ alkyl, C$_{2-6}$ alkenyl, C$_{2-6}$ alkynyl, C$_{3-8}$ cycloalkyl, C$_{3-8}$ cycloalkenyl, C$_{1-6}$ alkanol, haloC$_{1-6}$ alkyl, —(CH$_2$)$_n$—NR$^x$R$^y$, —(CH$_2$)$_s$—COOR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said C$_{1-6}$ alkyl, C$_{2-6}$ alkenyl, C$_{2-6}$ alkynyl, C$_{3-8}$ cycloalkyl, C$_{3-8}$ cycloalkenyl, aryl and heterocyclyl groups may be optionally substituted by one or more (e.g. 1, 2 or 3) R$^a$ groups;

R$^x$, R$^y$ and R$^z$ independently represent hydrogen, C$_{1-6}$ alkyl, C$_{2-6}$ alkenyl, C$_{2-6}$ alkynyl, C$_{1-6}$ alkanol, hydroxy, C$_{1-6}$ alkoxy, haloC$_{1-6}$ alkyl, —CO—(CH$_2$)$_n$—C$_{1-6}$ alkoxy, C$_{3-8}$ cycloalkyl or C$_{3-8}$ cycloalkenyl;

R$^2$ independently represent hydrogen, an aryl or heterocyclyl group wherein said aryl and heterocyclyl group may be optionally substituted by one or more R$^b$ groups;

R$^a$ represents halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^x$, —(CH$_2$)$_n$—O—C$_{1-6}$ alkyl, —O—(CH$_2$)$_n$—OR$^x$, haloC$_{1-6}$ alkyl, haloC$_{1-6}$ alkoxy, C$_{1-6}$ alkanol, ═O, ═S, nitro, —(CH$_2$)$_s$—CN, —S—R$^x$, —SO—R$^x$, —SO$_2$—R$^x$, —COR$^x$, —(CR$^x$R$^y$)$_s$—COOR$^z$, —(CH$_2$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$SO$_2$—R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$ or —(CH$_2$)$_s$—SO$_2$NR$^x$R$^y$ groups;

R$^b$ represents an R$^a$ group or a —Y-aryl or —Z-heterocyclyl group wherein said aryl and heterocyclyl groups may be optionally substituted by one or more (e.g. 1, 2 or 3) R$^a$ groups;

Y and Z independently represent a bond, —CO—(CH$_2$)$_s$—, —COO—, —NR$^x$—(CH$_2$)$_n$—, —(CH$_2$)$_n$—NR$^x$—, —CONR$^x$—, —NR$^x$CO—, —SO$_2$NR$^x$—, —NR$^x$SO$_2$—, —NR$^x$CONR$^y$—, —NR$^x$CSNR$^y$—, —O—(CH$_2$)$_s$—, —(CH$_2$)$_s$—O—, S—, —SO— or —(CH$_2$)$_s$—SO$_2$—;

m and n independently represent an integer from 1-4;

s and t independently represent an integer from 0-4;

aryl represents a carbocyclic ring;

heterocyclyl represents a heterocyclic ring;

or a pharmaceutically acceptable salt, solvate or derivative thereof.

It will be appreciated that specific embodiments of A, R$^1$ and R$^2$ groups in formula (Ia) and (Ib) above are as outlined hereinbefore for formula (I).

In one embodiment the compound of formula (I) is a compound of formula (Ia) as defined hereinbefore.

In one embodiment the compound of formula (I) is a compound of formula (Ia) wherein:

R$^1$ is —NHCONHCH$_2$CF$_3$;

A is phenyl or pyridine (e.g. pyridin-3-yl);

R$^2$ is optionally substituted phenyl; optionally substituted oxadiazole; optionally substituted thiadiazole; optionally substituted tetrazole; optionally substituted imidazole; optionally substituted triazole, optionally substituted pyrazole, optionally substituted pyridazine or optionally substituted C$_{2-4}$ alkynyl e.g. prop-1-ynyl, wherein the optional substituents are selected from halogen (e.g. fluorine), with one or two or three C$_{1-4}$ alkyl groups (e.g. methyl), C$_{1-4}$ alkylsulfanyl (e.g. methylsulfanyl) or C$_{1-4}$ alkanol (e.g. hydroxylethyl).

In a further embodiment the compound of formula (I) is a compound of formula (Ia) wherein:

R$^1$ is —NHCONHCH$_2$CF$_3$;

A is phenyl or pyridine (e.g. pyridin-3-yl);

R$^2$ is phenyl optionally substituted with halogen (e.g. fluorine), such as 4-fluorophenyl; oxadiazole optionally substituted with methyl or S-Me (e.g. 5-methyl-[1,3,4]oxadiazol-2-yl or 5-methylsulfanyl-[1,3,4]oxadiazol-2-yl); tetrazole optionally substituted by methyl (e.g. 2-methyl-2H-tetrazol-5-yl); imidazole e.g. imidazol-4-yl or imidazol-1-y optionally substituted with one or two or three methyl groups (e.g. 1,5-dimethyl-1H-imidazol-4-yl or 1-methyl-1H-imidazol-4-yl or 4-methyl-imidazol-1-yl or 1,2,5-trimethyl-1H-imidazol-4-yl); triazole optionally substituted by methyl (e.g. 1,5-dimethyl-1H-[1,2,3]triazol-4-yl); thiadiazole e.g. [1,3,4]thiadiazol-2-yl or [1,2,4]thiadiazol-5-yl, optionally substituted by methyl (e.g. [1,3,4]thiadiazol-2-yl or 3-methyl-[1,2,4]thiadiazol-5-yl or [1,2,4]thiadiazol-5-yl or 5-methyl-[1,3,4]thiadiazol-2-yl); pyrazole optionally substituted by hydroxylethyl (e.g. 2-hydroxyethyl)-1H-pyrazol-4-yl; or pyridazine optionally substituted by methyl (e.g. 6-Methylpyridazin-3-yl or $C_{2-4}$ alkynyl e.g. prop-1-ynyl.

In one embodiment, the compound of formula (I) is a sub-formula of (Ia) and is defined by a compound of formula (Ic):

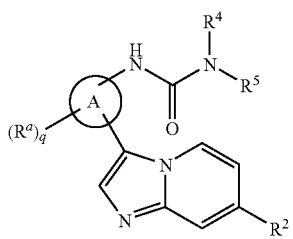

(Ic)

wherein $R^a$, $R^2$, $R^4$ and $R^5$ are as defined herein and q represents an integer from 0 to 3.

Particular preferences of variables $R^a$, $R^2$, $R^4$ and $R^5$ are defined herein.

In one embodiment, the compound of formula (I) is a sub-formula of (Ia) and is defined by a compound of formula (Id):

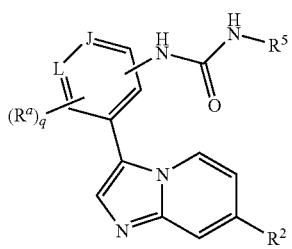

(Id)

wherein in $R^a$, $R^2$, $R^5$ and q are as defined herein and J and L are independently selected from carbon or nitrogen.

Particular preferences of variables $R^a$, $R^2$ and $R^5$ are defined herein

In particular, one of J or L is carbon and the other is nitrogen. In one embodiment J and L are both carbon.

In particular $R^5$ is alkyl optionally substituted with a group $R^a$. In particular $R^5$ is optionally substituted ethyl. Preferably $R^5$ is trifluoroethyl.

In particular $R^2$ is optionally substituted phenyl or a 5-6 membered monocyclic heterocycle. Particular preferences of $R^2$ are as outlined herein.

In one embodiment, the compound of formula (I) is a sub-formula of (Ia) and is defined by a compound of formula (Ie):

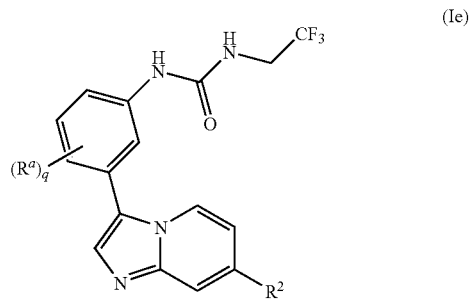

(Ie)

wherein $R^a$, q and $R^2$ and preferences thereof are outlined herein.

In one embodiment $R^2$ is phenyl optionally substituted by $R^b$. In another embodiment $R^2$ is phenyl optionally substituted by $R^a$. In one embodiment the $R^a$ or $R^b$ group is at the 3- or 4-position of the phenyl ring. In one embodiment where the phenyl ring is substituted by $R^a$, the $R^a$ group is at the 4-position of the phenyl ring. In one embodiment where the phenyl ring is substituted by $R^b$, where $R^b$ group is —Y-carbocycle (e.g. Y-aryl) group or —Z-heterocyclyl group the $R^b$ group is at the 3-position of the phenyl ring.

In one embodiment the $R^b$ groups are selected from halogen (e.g. fluorine or chlorine), deuterium (e.g. $D_5$), halo$C_{1-6}$ alkyl (e.g. —$CF_3$), halo$C_{1-6}$ alkoxy (e.g. —$OCF_3$), —$OR^x$ (e.g. methoxy or —$OCH_2OHCH_2OH$), $C_{1-6}$ alkyl (e.g. i-Pr), $C_{1-6}$ alkanol (e.g. —$CH_2OH$), —$(CR^xR^y)_s$—$COOR^z$ (e.g. —COOH, —COOMe, —C(Me)$_2$-COOH, —CH$_2$—COOH or —C(Me)$_2$-COOMe), —(CH$_2$)$_s$—CN (e.g. —CN or —CH$_2$CN), —(CH$_2$)$_s$—NR$^x$R$^y$ (e.g. —NMe$_2$, —(CH$_2$)$_2$—NH$_2$, —(CH$_2$)$_2$—NMe$_2$ or —NH—CO—CH$_2$-methoxy), —O—(CH$_2$)$_n$—OR$^x$ (e.g. —O—(CH$_2$)$_2$-ethoxy), —(CH$_2$)$_s$—CONR$^x$R$^y$ (e.g. —CONH$_2$, —CONHMe, —CONHEt, —CONH-iPr, —CH$_2$—CONHMe, —CONH—(CH$_2$)$_2$—OMe or —CONH—(CH$_2$)$_2$—NH$_2$), —SO$_2$—R$^x$ (e.g. —SO$_2$Me), —(CH$_2$)$_s$—SO$_2$NR$^x$R$^y$ (e.g. —SO$_2$NH$_2$), —(CH$_2$)$_s$—NR$^x$—SO$_2$—R$^y$ (e.g. —NHSO$_2$Me or —CH$_2$—NHSO$_2$Me), —(CH$_2$)$_s$—NH—SO$_2$—NR$^x$R$^y$ (e.g. —NH—SO$_2$—NMe$_2$).

In one embodiment the $R^b$ groups are selected from halogen (e.g. fluorine), halo$C_{1-6}$ alkoxy (e.g. —OCF$_3$), —OR$^x$ (e.g. methoxy or —OCH$_2$OHCH$_2$OH), $C_{1-6}$ alkanol (e.g. —CH$_2$OH), —(CR$^x$R$^y$)$_s$—COOR$^z$ (e.g. —COOH, —COOMe, —C(Me)$_2$-COOH, —CH$_2$—COOH or —C(Me)$_2$-COOMe), —(CH$_2$)$_s$—CN (e.g —CH$_2$CN), —(CH$_2$)$_s$—NR$^x$R$^y$ (e.g. —NMe$_2$, —(CH$_2$)$_2$—NH$_2$, —(CH$_2$)$_2$—NMe$_2$ or —NH—CO—CH$_2$-methoxy) or —O—(CH$_2$)$_n$—OR$^x$ (e.g. —O—(CH$_2$)$_2$-ethoxy).

In one embodiment the $R^b$ groups are selected from halogen (e.g. fluorine), —Y-aryl (e.g. —Y-phenyl) group or —Z-heterocyclyl group (e.g. —Z-morpholinyl, —Z-azetidinyl, —Z-pyrrolidinyl, —Z-tetrazolyl, —Z-piperidinyl, —Z-piperazinyl) wherein said heterocyclyl group may be optionally substituted by one or more (e.g. 1, 2 or 3) $R^a$ groups selected from $C_{1-6}$ alkyl (e.g. methyl) or —(CR$^x$R$^y$)$_s$—COOR$^z$ (e.g. —COOH, —COOMe or —COOtBu) groups and where Z is CO, CH$_2$ or a bond.

In one embodiment the $R^b$ groups are selected from —Z-heterocyclyl group (e.g. —Z-morpholinyl, —Z-azetidinyl, —Z-pyrrolidinyl, —Z-pyrazolyl, —Z-tetrazolyl, —Z-piperidinyl, —Z-piperazinyl, —Z-diazepanyl or —Z-tetrahydropyranyl) wherein said heterocyclyl group may be optionally substituted by one or more (e.g. 1, 2 or 3) $R^a$ groups selected from $C_{1-6}$ alkyl (e.g. methyl or ethyl), =O, —COR$^x$ (e.g. —COMe) or —(CR$^x$R$^y$)$_s$—COOR$^z$ (e.g. —COOH, —COOMe or —COOtBu) groups and where Z is CH$_2$ or a bond.

In a yet further embodiment, R$^2$ represents an aryl (e.g. phenyl) group optionally substituted by a halogen (e.g. fluorine) atom. In a still yet further embodiment, R$^2$ represents 4-fluorophenyl.

In one embodiment, the compound of formula (I) is a sub-formula of (Ia) and is defined by a compound of formula (If):

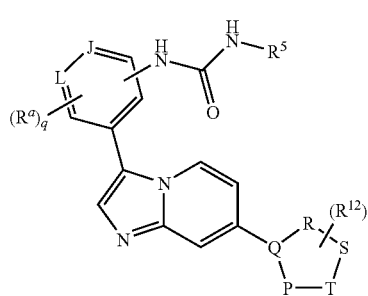

(If)

wherein R$^a$, q and R$^5$ are as defined herein and:

J and L are independently selected from carbon or nitrogen;

Q is carbon or nitrogen;

P, R, S, T can be carbon, nitrogen, oxygen or sulfur such that there are no more than 4 heteroatoms in the ring;

R$^{12}$ is selected from hydrogen, halogen, amino, hydroxyl, C$_{1-4}$ alkyl (e.g. methyl, ethyl, n-propyl, isopropyl and t-butyl), C$_{1-3}$ alkyl substituted with hydroxyl, C$_{1-3}$alkoxy or halogen (e.g. hydroxymethyl, trifluoromethyl, monofluoroethyl, trifluoroethyl, methoxymethyl), C$_{1-3}$alkylsulfanyl (e.g. methylsulfanyl), C$_{2-4}$ cycloalkyl (e.g. cyclopropyl) and C$_{1-3}$ alkoxy (e.g. methoxy); and r is 0, 1, 2 or 3

In particular, one of J or L is carbon and the other is nitrogen. In one embodiment J and L are carbon.

In particular R$^5$ is alkyl optionally substituted with a group R$^a$. In particular R$^5$ is optionally substituted ethyl. Preferably R$^5$ is trifluoroethyl.

In one embodiment Q is nitrogen and P, R, S, T are all carbon.

Preferably P, Q, R, S and T form an aromatic ring.

Preferably Q is carbon.

In one embodiment if P is carbon substituted with anything other than hydrogen, then R is preferably N, O, or S.

Preferably two of P, R, S, T are nitrogen and the other is carbon, oxygen or sulfur.

Preferably r is 0 or 1.

In one embodiment R$^{12}$ is selected from hydrogen, amino, SO$_2$NMe$_2$, C$_{1-3}$ alkyl (e.g. methyl, ethyl, n-propyl, isopropyl), C$_{1-3}$ alkyl substituted with hydroxyl, C$_{1-3}$alkoxy or halogen (e.g. hydroxymethyl, trifluoromethyl, monofluoroethyl, trifluoroethyl, methoxymethyl), and C$_{1-3}$ alkoxy (e.g. methoxy).

Preferably R$^{12}$ is selected from hydrogen, or C$_{1-3}$ alkyl (e.g. methyl, ethyl, n-propyl or isopropyl).

Preferably R$^{12}$ is methyl.

In one embodiment, the compound of formula (I) is a sub-formula of (Ia) and is defined by a compound of formula (Ig):

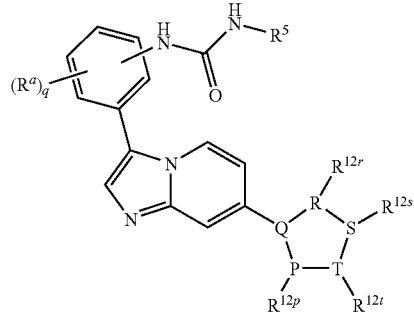

(Ig)

wherein R$^a$, q, R$^5$, P, Q, R, S and T are as defined herein and R$^{12r}$, R$^{12p}$, R$^{12s}$ and R$^{12t}$ can be R$^{12}$ as outlined above.

In one embodiment Q is nitrogen. In another embodiment Q is nitrogen and one or two of P, R, S, T are also nitrogen. In a further embodiment Q is carbon, R is sulphur, S is carbon, P and T are nitrogen.

In one embodiment R$^{12r}$ and R$^{12p}$ are independently selected from hydrogen, amino, methyl, trifluoromethyl, and methoxy.

In one embodiment when one of R$^{12r}$ or R$^{12p}$ a group other than hydrogen and the other is hydrogen.

In one embodiment P—R$^{12p}$ is C—H.

In one embodiment, the compound of formula (I) is a compound selected from Examples 2-17, 19, 24, 26-62, 64-67, 75, 77-97, 100-109, 111-115, 117, 119-131, 133-156, 158-166, 168-234 and 236-422.

In one embodiment, the compound of formula (I) is a compound selected from Examples 2-17, 19, 24, 26-62, 64-67, 75, 77-97, 100-109, 111-115, 117, 119-131, 133-156, 158-166, 168-234 and 236-402, 407-408, 412, 414, 416 and 421-422.

In one embodiment, the compound of formula (I) is a compound selected from Examples 2-17, 19, 24, 26-62, 64-67, 75, 77-97, 100-109, 111-115, 117, 119-131, 133-156, 158-166, 168-234 and 236-381.

In one embodiment, the compound of formula (I) is a compound selected from Examples 2-17, 19, 24, 26-62, 64-67, 75, 77-97, 100-109, 111-115, 117 and 119-126.

In one embodiment, the compound of formula (I) is a compound selected from Examples 1-74, 76-191, 193-401, 407, 412, 414, and 416.

In one embodiment, the compound of formula (I) is a compound selected from Examples 1-25, 27-29, 31-67, 70, 72-74, 77-97, 100, 101, 103-105, 107-109, 111-115, 117-131, 133-156, 158-166, 168-172, 174-191, 193-254, 256-342, 344-402, 407, 412, 414, 416 and 421-422.

In one embodiment, the compound of formula (I) is a compound selected from Examples 2, 5, 6, 7, 8, 9, 10, 11, 15, 16, 28, 29, 35, 36, 39, 43, 45, 49, 51, 56, 57, 58, 59, 62, 64, 65, 66, 67, 78, 79, 80, 81, 82, 83, 94, 95, 103, 104, 107, 108, 109, 111, 113, 114, 115, 123, 127, 128, 134, 135, 137, 140, 141, 142, 143, 144, 149, 150, 151, 155, 158, 159, 164, 165, 169, 174, 175, 177, 179, 180, 183, 184, 189, 193, 197, 200, 201, 202, 203, 204, 206, 208, 211, 212, 214, 216, 217, 218, 219, 220, 221, 225, 227, 228, 229, 230, 233, 234, 238, 239, 240, 243, 244, 245, 246, 247, 249, 250, 251, 252, 253, 254, 256, 257, 258, 260, 261, 262, 263, 264, 266, 267, 268, 269, 270, 271, 273, 274, 276, 278, 279, 280, 281, 283, 284, 285-294, 296, 298-305, 307, 309-312, 315-320, 322-327, 329, 330, 331, 332, 334, 336, 337, 340, 341, 344, 345, 346, 348, 349, 351, 352, 354-375, 378-381, 383-394, 396-402, 412, 414, 416 and 421.

In one embodiment, the compound of formula (I) is a compound selected from Examples 59, 310, 329, 354, 359, 374, 375, 378, 384, 396, 399, 401, 402, 407, 412, 416 and 421-422.

In one embodiment, the compound of formula (I) is a compound other than N-{4-[7-(4-fluoro-phenyl)-imidazo[1,2-a]pyridin-3-yl]-phenyl}-acetamide (E75) and {3-[7-(4-fluoro-phenyl)-imidazo[1,2-a]pyridin-3-yl]-phenyl}-carbamic acid 2,2,2-trifluoro-ethyl ester (E192).

In one embodiment, the compound of formula (I) is a compound other than a compound of any one or more of Examples 401-418.

In a further embodiment, the compound of formula (I) is 1-{3-[7-(4-fluoro-phenyl)-imidazo[1,2-a]pyridin-3-yl]-phenyl}-3-(2,2,2-trifluoro-ethyl)-urea (Example 59) or a pharmaceutically acceptable salt, solvate or derivative thereof (e.g. 1-{3-[7-(4-fluoro-phenyl)-imidazo[1,2-a]pyridin-3-yl]-phenyl}-3-(2,2,2-trifluoro-ethyl)-urea hydrochloride.

In a further embodiment, the compound of formula (I) is 1-[3-(7-[1,3,4]Thiadiazol-2-yl-imidazo[1,2-a]pyridin-3-yl)-phenyl]-3-(2,2,2-trifluoro-ethyl)-urea (Example 384) or a pharmaceutically acceptable salt, solvate or derivative thereof (e.g. 1-[3-(7-[1,3,4]Thiadiazol-2-yl-imidazo[1,2-a]pyridin-3-yl)-phenyl]-3-(2,2,2-trifluoro-ethyl)-urea hydrochloride (Example 384A)).

In a second aspect of the invention there is provided the use of a compound of formula (II):

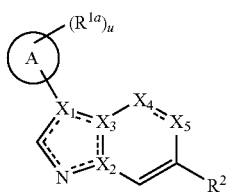

(II)

wherein $X_1$-$X_5$ and A are as defined for compounds of formula (I):

u represents an integer from 0 to 2;

$R^{1a}$ represents —NHCONR$^4$R$^5$, —NHCOOR$^4$, —NH—CO—(CH$_2$)$_n$—NR$^4$R$^5$, —NH—(CH$_2$)$_n$—CONR$^4$R$^5$, —NH—CO—(CH$_2$)$_n$—COOR$^4$, —NH—CO—(CH$_2$)$_n$—CSOR$^4$, —NHSO$_2$R$^4$, —NHSO$_2$SR$^4$, —NHSO$_2$NR$^4$R$^5$, —NHCSNR$^4$R$^5$, —NHCOR$^4$, —NHCSR$^4$, —NHCSSR$^4$, —NR$^4$R$^5$,—C(=NR$^4$)NR$^5$, halogen, C$_{1-6}$ alkyl, aryl, —CO-aryl, heterocyclyl, —CO-heterocyclyl, —CONR$^4$R$^5$, —(CH$_2$)$_n$—NR$^4$COR$^5$, —(CH$_2$)$_s$—CN, —OR$^4$ or —COOR$^4$, wherein said aryl and heterocyclyl groups may be optionally substituted with one or more (e.g. 1, 2 or 3) R$^a$ groups as defined for compounds of formula (I);

R$^4$ and R$^5$ are as defined for compounds of formula (I), with the proviso that when one of R$^4$ and R$^5$ represents hydrogen the other represents a group other than -aryl or -heterocyclyl;

R$^2$ is as defined for compounds of formula (I);

in the manufacture of a medicament for the treatment of a disease mediated by FGFR kinases.

In one embodiment, there is provided the use of a compound of formula (II):

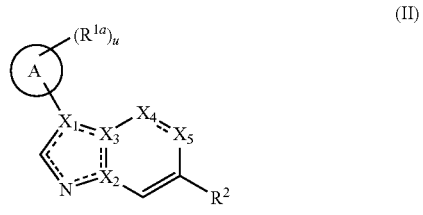

(II)

wherein $X_1$-$X_5$ and A are as defined for compounds of formula (I):

u represents an integer from 0 to 2;

$R^{1a}$ represents —NHCONR$^4$R$^5$, —NHCOOR$^4$, —NH—CO—(CH$_2$)$_n$—NR$^4$R$^5$, —NH—CO—(CH$_2$)$_n$—COOR$^4$, —NH—CO—(CH$_2$)$_n$—CSOR$^4$, —NHSO$_2$R$^4$, —NHSO$_2$SR$^4$, —NHSO$_2$NR$^4$R$^5$, —NHCSNR$^4$R$^5$, —NH—COR$^4$, —NHCSR$^4$, —NHCSSR$^4$, —NR$^4$R$^5$, —C(=NR$^4$) NR$^5$, C$_{1-6}$ alkyl, aryl, —CO-aryl, heterocyclyl, —CO-heterocyclyl, —CONR$^4$R$^5$, —(CH$_2$)$_n$—NR$^4$COR$^5$, —(CH$_2$)$_s$—CN, —OR$^4$ or —COOR$^4$, wherein said aryl and heterocyclyl groups may be optionally substituted with one or more (e.g. 1, 2 or 3) R$^a$ groups as defined for compounds of formula (I);

R$^4$ and R$^5$ are as defined for compounds of formula (I);

R$^2$ is as defined for compounds of formula (I) without the proviso;

in the manufacture of a medicament for the treatment of disease mediated by FGFR kinases.

In one embodiment, $R^{1a}$ represents heterocyclyl optionally substituted by one or more R$^a$ groups selected from =S; —COOR$^4$; —CO-heterocyclyl; —(CH$_2$)$_s$—CN; —(CH$_2$)$_n$—NR$^4$COR$^5$, —CONR$^4$R$^5$ or —NR$^4$R$^5$.

In one embodiment, $R^{1a}$ represents heterocyclyl (e.g. pyridyl, pyrazolyl, indazolyl, indolyl or dihydrotriazolyl) optionally substituted by one or more R$^a$ groups selected from halogen (e.g. chlorine) or =S (e.g. dihydrotriazolethione).

In one embodiment, $R^{1a}$ represents heterocyclyl (e.g. pyrazolyl or triazolyl) optionally substituted by one or more R$^a$ groups selected from =S (e.g. dihydrotriazolethione).

In one embodiment, $R^{1a}$ represents —COOR$^4$ (e.g. —COOMe).

In one embodiment, $R^{1a}$ represents —CO-heterocyclyl (e.g. —CO-morpholinyl).

In one embodiment, $R^{1a}$ represents —(CH$_2$)$_s$—CN (e.g. —CH$_2$—CN).

In one embodiment, $R^{1a}$ represents —(CH$_2$)$_n$—NR$^4$COR$^5$ (e.g. —CH$_2$—NHCOMe).

In one embodiment, $R^{1a}$ represents —NR$^4$R$^5$. In a further embodiment, R$^4$ and R$^5$ both represent hydrogen or one of R$^4$ and R$^5$ represents hydrogen and the other represents C$_{1-6}$ alkyl (e.g. ethyl).

In one embodiment, $R^{1a}$ represents —CONR$^4$R$^5$ (e.g. —CONHMe).

In one embodiment, u represents 0 or 1.

In one embodiment, A represents an aromatic carbocyclic group (e.g. phenyl) optionally substituted by one or more R$^a$ groups selected from C$_{1-6}$ alkyl (e.g. methyl).

In one embodiment, A represents an aromatic heterocyclic group (e.g. pyridyl, pyrazolyl, indolyl or indazolyl) optionally substituted by one or more R$^a$ groups selected from halogen (e.g. chlorine).

In one embodiment, when A represents unsubstituted phenyl, unsubstituted thienyl or phenyl substituted by an —OH, —OMe or —NH$_2$ group, R$^2$ represents an optionally substituted aryl or heterocyclyl group.

In one embodiment, when A represents unsubstituted phenyl, unsubstituted thiazolyl, phenyl substituted by a CN group, unsubstituted pyridinyl or unsubstituted thienyl, $R^2$ represents a group other than 4-methoxyphenyl or an aryl or heterocyclyl group substituted by a —$(CH_2)_s$—$NR^xR^y$, —Y-aryl or —Z-heterocyclyl group.

It will be appreciated that specific embodiments for formula (II) above are as outlined hereinbefore for formula (I).

In one embodiment, the compound of formula (II) is a compound selected from Examples 1, 18, 20-23, 25, 63, 68-74, 76, 98-99, 110, 116, 118, 132, 157, 167 and 235.

In one embodiment, the compound of formula (II) is a compound selected from Examples 1, 18, 20-23, 25, 63, 68-74, 76, 98-99, 110, 116 and 118.

In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

In the specification, references to Formula (I) include sub-formulas such as (Ia), (Ib), (Ic), (Id), (Ie), (If), (Ig) and Formula (II), and sub-groups, examples or embodiments of formulae (I), (Ia), (Ib), (Ic), (Id), (Ie), (If) and (Ig) unless the context indicates otherwise.

Thus for example, references to inter alia therapeutic uses, pharmaceutical formulations and processes for making compounds, where they refer to formula (I), are also to be taken as referring to formulae (I), (Ia), (Ib), (Ic), (Id), (Ie), (If), (Ig), (II), and sub-groups, examples or embodiments of formulae (I), (Ia), (Ib), (Ic), (Id), (Ie), (If), (Ig), and (II).

Similarly, where preferences, embodiments and examples are given for compounds of the formula (I), they are also applicable to formulae (I), (Ia), (Ib), (Ic), (Id), (Ie), (If), (Ig), (II), and sub-groups, examples or embodiments of formulae (I), (Ia), (Ib), (Ic), (Id), (Ie) (If), (Ig) and (II) unless the context requires otherwise.

Methods for the Preparation of Compounds of Formula (I)

In this section, as in all other sections of this application unless the context indicates otherwise, references to formula (I) also include formulae (II), and all other sub-groups and examples thereof as defined herein.

Compounds of the formula (I) can be prepared in accordance with synthetic methods well known to the skilled person. In particular, compounds of formula (I) are readily prepared by palladium mediated coupling chemistries between aromatic chloro, bromo, iodo, or pseudo-halogens such as a trifluoromethanesulphonate (triflate) or tosylate compounds, and aromatic boronic acids or stannane derivatives. In particular, Suzuki coupling chemistry is broadly applicable to synthesis of these compounds. The Suzuki reaction can be carried out under typical conditions in the presence of a palladium catalyst such as bis(tri-t-butylphosphine)palladium, tetrakis(triphenyl-phosphine)-palladium or a palladacycle catalyst (e.g. the palladacycle catalyst described in Bedford, R. B. and Cazin, C. S. J. (2001) Chem. Commun., 1540-1541 and a base (e.g. a carbonate such as potassium carbonate) as discussed in more detail below. The reaction may be carried out in polar solvent for example an aqueous solvent system, including aqueous ethanol, or an ether such as dimethoxyethane or dioxane, and the reaction mixture is typically subjected to heating, for example to a temperature of 80° C. or more, e.g. a temperature in excess of 100° C.

As illustrated in Scheme 1, the imidazo[1,2-a]pyridine core can be synthesised from commercially available starting materials using Route A (to give a 3,7 disubstituted ring) or C (to give a 3,6 disubstituted ring).

4-Chloro-pyridin-2-ylamine or 4-bromo-pyridin-2-ylamine in an appropriate solvent and base can be cyclised under reflux with chloroacetaldehyde to give the imidazopyridine ring. The 7-chloro-imidazo[1,2-a]pyridine in an appropriate solvent can then be iodinated, for example using N-iodosuccinimide at RT.

Appropriate functionality can then be added at the halogenated positions, for example using a range of metal-catalysed reactions. In particular, appropriately functionalised boronic acids or their boronate esters may react with the aryl halide. This transformation, commonly known as the Suzuki reaction, has been reviewed by Rossi et al (2004) Synthesis, 15, 2419.

The Suzuki reaction is often carried out in mixtures of water and organic solvents. Examples of suitable organic solvents include toluene, tetrahydrofuran, 1,4-dioxane, 1,2-dimethoxyethane, acetonitrile, N-methyl pyrrolidinone, ethanol, methanol and dimethylformamide. The reaction mixture is typically subjected to heating, for example to a temperature in excess of 100° C. The reaction is carried out in the presence of a base. Examples of suitable bases include sodium carbonate, potassium carbonate, cesium carbonate and potassium phosphate. Examples of suitable catalysts include bis(tri-t-butylphosphine)palladium(0), tris(dibenzylideneacetone)dipalladium(0), bis(triphenylphosphine)palladium(II) chloride, palladium(II) acetate, tetrakis(triphenylphosphine)palladium(0), bis(tricyclohexylphosphine)palladium(0), [1,1'-bis(diphenylphosphino)ferrocene]-dichloropalladium (II), dichlorobis(tri-o-tolylphosphine)palladium(II), 2'-(dimethylamino)-2-biphenylyl-palladium(II) chloride dinorbornylphosphine complex and 2-(dimethylamino)ferrocen-1-yl-palladium(II) chloride dinorbornylphosphine complex. In some cases additional ligands may be added to facilitate the coupling reaction. Examples of suitable ligands include tri-t-butylphosphine, 2,2-bis(diphenylphosphino)-1,1-binaphthyl, triphenylphosphine, 1,2-bis(diphenylphosphino)ethane, 1,1'-bis(diphenylphosphino)ferrocene, tricyclohexylphosphine, 9,9-dimethyl-4,5-bis(diphenylphosphino)xanthene, 1,3-bis(diphenylphosphino)propane, 2-(di-t-butylphosphino)biphenyl, 2-dicyclohexylphosphino-2'-(n,n-dimethylamino)biphenyl, tri-o-tolylphosphine, 2-(dicyclohexylphosphino)biphenyl, 2-dicyclohexylphosphino-2',4',6'-triisopropylbiphenyl, tri(2-furyl)phosphine, 2-dicyclohexylphosphino-2',6'-dimethoxybiphenyl and 2-di-tert-butylphosphino-2',4',6'-triisopropylbiphenyl.

Scheme 1

General Route A

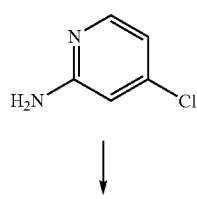

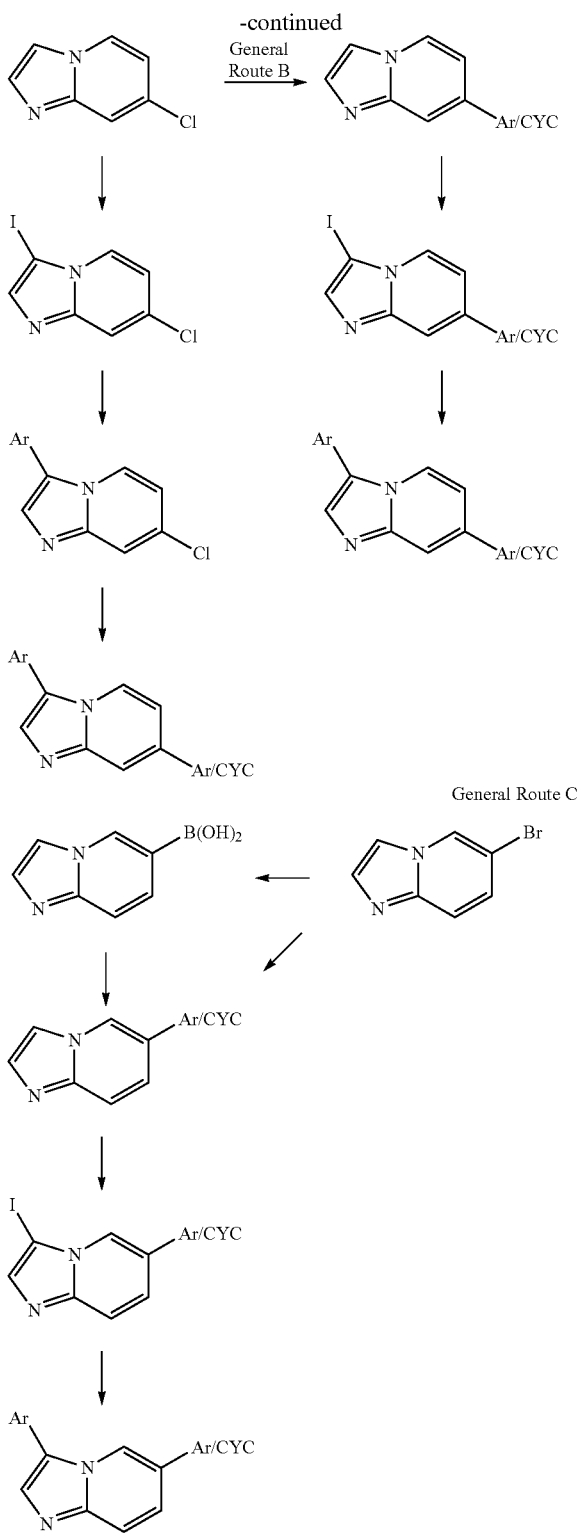

-continued
General Route B istry for Organic Synthesis [Volume 1, Edited by Ei-ichi Negishi, Wiley, ISBN 0-471-31506-0].

In particular, one reaction which can be utilised is the Buchwald-Hartwig type reaction (see *Review*: Hartwig, J. F. (1998) *Angew. Chem. Int. Ed.* 37, 2046-2067) which provides a means for palladium-catalyzed synthesis of aryl amines. The starting materials are aryl halides or pseudohalides (for example triflates) and primary or secondary amines, in the presence of a strong base such as sodium tert-butoxide and a palladium catalyst such as tris-(dibenzylideneacetone)-dipalladium ($Pd_2(dba)_3$), or 2,2'-bis(diphenylphosphino)-1'1-binaphthyl (BINAP).

In particular for synthesis compounds of formula (II) the aryl halide can be reacted with 3-aminobenzeneboronic acid using an appropriate metal catalyst e.g. bis(triphenylphosphine)palladium(II) chloride, to form the amino precursor for urea, amide and secondary amine bond formations.

This sequence of reactions outlined in Route A can be alternated as outlined in Route B. Alternatively the halogen functionality at the 7-position of the imidazo[1,2-a]pyridine can be converted to a boronic acid or ester and used to synthesise alternative motifs as outlined in Scheme 2. This can then be used directly in any of the metal catalysed reactions outlined herein. For example, for conversion of a halide to a boronate, the halide is reacted with a palladium catalyst and a phosphine ligand in an appropriate solvent e.g. dioxane and base e.g. KOAc, and the appropriate substituted boron compound.

Scheme 2

General Route E

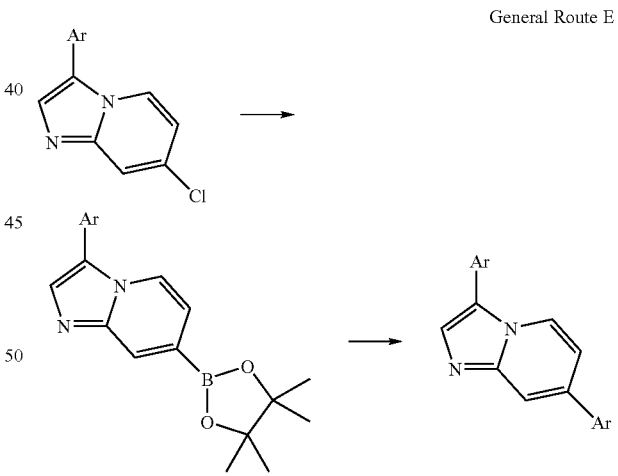

Other examples of possible metal catalysed functionalisations of the halide are reactions with organo-tin reagents (the Stille reaction), with Grignard reagents and reaction with nitrogen nucleophiles. A general overview, and further leading references, of these transformations is presented in 'Palladium Reagents and Catalysts' [Jiro Tsuji, Wiley, ISBN 0-470-85032-9] and Handbook of OrganoPalladium Chem- Once synthesised, a range of functional group conversions can be employed on di-aryl substituted imidazopyridine compounds to produce further compounds of formula (I) and in particular compounds of formula (II). For example, some of the following reactions can be used hydrogenation e.g. using Raney nickel catalyst, hydrolysis, deprotection, and oxidation.

In particular, as outlined Scheme 3, the amine functionality introduced can be used to synthesise sulfonyl ureas, sulphonamides, ureas, amides, secondary amines and carbamates.

Scheme 3

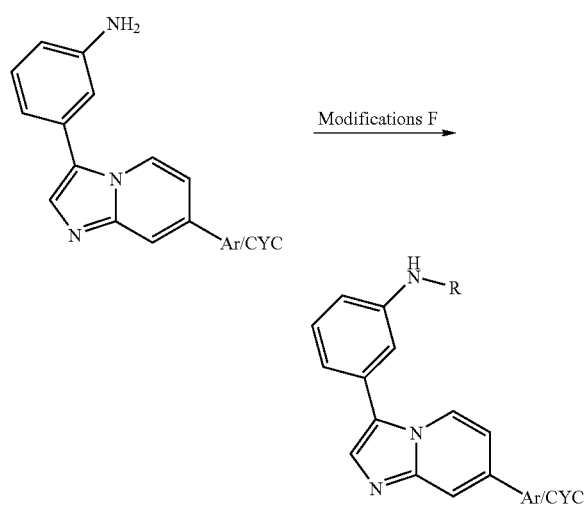

An amide bond can be prepared by the reaction of a carboxylic acid or a reactive derivative thereof and an amine under standard amide forming conditions.

The coupling reaction between the carboxylic acid and the amine can be carried out in the presence of a reagent of the type commonly used in the formation of peptide linkages. Examples of such reagents include 1,3-dicyclohexylcarbodiimide (DCC) (Sheehan et al (1955) *J. Amer. Chem Soc.* 77, 1067), 1-ethyl-3-(3'-dimethylaminopropyl)-carbodiimide (EDC) (Sheehan et al (1961) *J. Org. Chem.*, 26, 2525), uronium-based coupling agents such as O-(7-azabenzotriazol-1-yl)-N,N,N',N'-tetramethyluronium hexafluorophosphate (HATU) (Carpino, L. A. (1993) *J. Amer. Chem. Soc.*, 115, 4397) and phosphonium-based coupling agents such as 1-benzo-triazolyloxytris(pyrrolidino)phosphonium hexafluorophosphate (PyBOP) (Castro et al (1990) *Tetrahedron Letters*, 31, 205). Carbodiimide-based coupling agents are advantageously used in combination with 1-hydroxyazabenzotriazole (HOAt) or 1-hydroxybenzotriazole (HOBt) (Konig et al, *Chem. Ber.*, 103, 708, 2024-2034). Preferred coupling reagents include EDC and DCC in combination with HOAt or HOBt.

The coupling reaction is typically carried out in a non-aqueous, non-protic solvent such as acetonitrile, dioxane, dimethylsulphoxide, dichloromethane, dimethylformamide or N-methylpyrrolidone, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine.

Amines can be prepared by reduction of the corresponding nitro-compound under standard conditions. The reduction may be effected, for example by catalytic hydrogenation in the presence of a catalyst, such as palladium on carbon, in a polar solvent, such as ethanol or dimethylformamide, at room temperature.

Ureas can also be prepared using standard methods. For example, such compounds can be prepared by reacting an amino compound with a suitably substituted isocyanate in a polar solvent such as DMF. The reaction is conveniently carried out at room temperature.

Alternatively, ureas of the formula (I) can be prepared by reacting an amine with an appropriately substituted amine in the presence of carbonyl diimidazole (CDI). The reaction is typically carried out in a polar solvent such as THF with heating (for example using a microwave heater) to a temperature of up to about 150° C. Instead of using CDI, the coupling of the two amines to form the urea can be effected using triphosgene (bis(trichloromethyl)carbonate) in the presence of a non-interfering base such as triethylamine, in a solvent such as dichloromethane at room temperature or below. As a further alternative to CDI, phosgene may be used instead of triphosgene.

Compounds of the formula (I) containing a carbamate can be made using standard methods for the synthesis of carbamates, for example by reaction of an amino compound with a chloroformate derivative of the formula $R^1$—O—C(O)—Cl under conditions well known to the skilled person.

Compounds of the formula (I) containing a sulfonamide can be prepared from amino-compounds by standard methods for the formation of sulphonamides. For example, an amine compound can be reacted with sulphonyl chlorides of the formula $R^1SO_2Cl$ or anhydrides of the formula $(R^1SO_2)_2O$. The reaction is typically carried out in an aprotic solvent such as acetonitrile or a chlorinated hydrocarbon (for example dichloromethane) in the presence of a non-interfering base such as a tertiary amine (e.g. triethylamine or diisopropylethyl amine or pyridine). Alternatively, where the base is a liquid, for example pyridine, the base itself may be used as the solvent for the reaction.

Sulfonyl ureas can be prepared from the amine compound by reaction in an appropriate aprotic solvent, such as THF, with a base e.g. triethylamine, and the appropriately substituted sulfamoyl chloride.

Compounds of the formula (I) in which $R_{1a}$ is a secondary amine group, can be prepared from the amino compounds by a number of methods. Reductive amination with an appropriately substituted aldehyde or ketone can be carried out in the presence of variety of reducing agents (see *Advanced Organic Chemistry* by Jerry March, $4^{th}$ Edition, John Wiley & Sons, 1992, pp 898-900). For example, reductive amination can be carried out in the presence of sodium triacetoxyborohydride in the presence of an aprotic solvent, such as dichloromethane, at or near ambient temperatures. They can also be prepared by the reaction of the amino compound in a nucleophilic displacement reaction where the reagent contains a leaving group such as a halogen.

In addition the amide or urea compounds can be synthesised by use of the appropriate substituted boronic acid in the Suzuki reaction e.g. 1-Methyl-3-[3-(4,4,5,5-tetramethyl-[1, 3,2]dioxaborolan-2-yl)-phenyl]-urea or 3-Methoxy-5-nitrophenyl boronic acid pinacol ester. These can be synthesised as described herein.

Alternatively the secondary amine can be formed by cyclisation of an appropriate group to form a ring as described in Scheme 4

Scheme 4

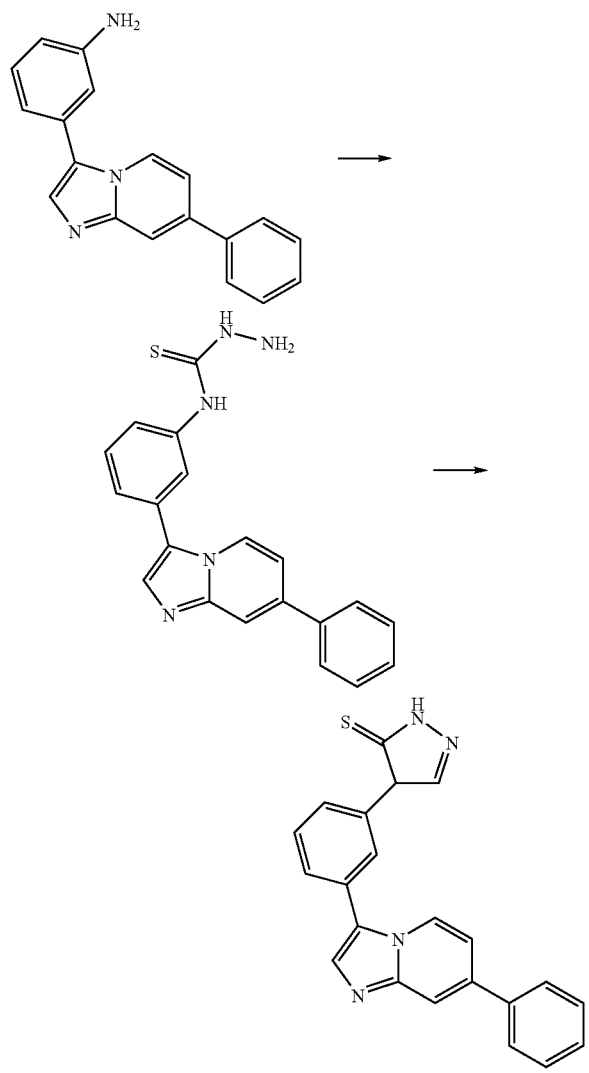

This involves reacting the amino compound in anhydrous solvent e.g. toluene with 1,1'-thiocarbonyldi-2(1H)-pyridone. Typical reaction conditions are heating for 1 hour, work up and then treatment with hydrazine hydrate to form the thiosemicarbazide. This is then cyclised under conditions such as through the addition of diethyl chlorophosphate dropwise. This may also generate the alternate cyclisation product and hence separation may be required.

Other compounds of formula (I) including other examples of $R^1$ such as thioureas, thioamides, thiocarbamates e.g. O-substituted thiocarbamates or S-substituted thiocarbamates, dithiocarbamates, amidines, and guanidines, can be synthesised from the amine intermediate using a range of well known functional group interconversions as described in *Advanced Organic Chemistry* by Jerry March, 4$^{th}$ Edition, John Wiley & Sons, 1992.

Appropriate starting material and reagents for these reactions can be obtained commercially or by any of a large number of standard synthetic methods well known those skilled in the art, for example see *Advanced Organic Chemistry* by Jerry March, 4$^{th}$ Edition, John Wiley & Sons, 1992, and *Organic Syntheses*, Volumes 1-8, John Wiley, edited by Jeremiah P. Freeman (ISBN: 0-471-31192-8), 1995, and see also the methods described in the experimental section below. For example, a range of appropriate functionalized aniline and amino pyridine starting materials, and metal catalysts are commercially available.

Many boronates, for example boronic acids or esters or trifluoroborates, suitable for use in preparing compounds of the invention are commercially available, for example from Boron Molecular Limited of Noble Park, Australia, or from Combi-Blocks Inc. of San Diego, USA. Where the appropriately substituted boronate is not commercially available, they can be prepared by methods known in the art, for example as described in the review article by Miyaura, N. and Suzuki, A. (1995) *Chem. Rev.*, 95, 2457. Thus, boronates can be prepared by reacting the corresponding bromo-compound with an alkyl lithium such as butyl lithium and then reacting with a borate ester e.g. ($^i$PrO)$_3$B. The reaction is typically carried out in a dry polar solvent such as tetrahydrofuran at a reduced temperature (for example −78° C.). Boronate esters (for example a pinacolatoboronate) can also be prepared from a bromo-compound by reaction with a diboronate ester such as bis(pinacolato)diboron in the presence of a phosphine such as tricyclohexyl-phosphine and a palladium (0) reagent such as tris(dibenzylideneacetone)-dipalladium (0). The formation of the boronate ester is typically carried out in a dry polar aprotic solvent such as dioxane or DMSO with heating to a temperature of up to about 100° C., for example around 80° C. The resulting boronate ester derivative can, if desired, be hydrolysed to give the corresponding boronic acid or converted into the trifluoroborate.

All of the reactions described above can be used to functionalise alternative heterocyclic templates of formula I, whose synthesis is outline below.

Pyrazolo[1,5-a]pyrimidines

The pyrazolo[1,5-a]pyrimidine template can be synthesised from the appropriately substituted aminopyrazole (VI) and fragments (VII) as shown in Scheme 5A, where $R_a$ can be hydrogen or $R_1$. This may occur by one step or two step process, where $X_1$ and $X_2$ are electrophilic carbons (i.e. carbonyl, masked carbonyl i.e. acetal, enamine, conjugated alkenes or alkynes) (Perkin I, J. C. S. (1979), 3085-3094). $X_3$ is an appropriate substituent either a group $R_2$ or groups such as halogen or pseudo halogens which will allow reaction to introduce $R_2$ as described herein. Cyclisation of the pyrazole (VI) with an appropriately substituted free or masked 1,3-dicarbonyl derivative can be used to prepare substituted pyrazolo[1,5-a]pyrimidines. Cyclisation occurs typically in an alcohol solvent or in toluene or in acetic acid, and may have additives such as piperidine, sodium ethoxide, HCl, AcOH, pTsOH, or ZnCl$_2$ present (J. Med. Chem. (2001), 44 (3), 350-361; Bull. Korean Chem. Soc. (2002), 23 (4), 610-612; Australian Journal of Chemistry (1985), 38(1), 221-30).

Scheme 5A

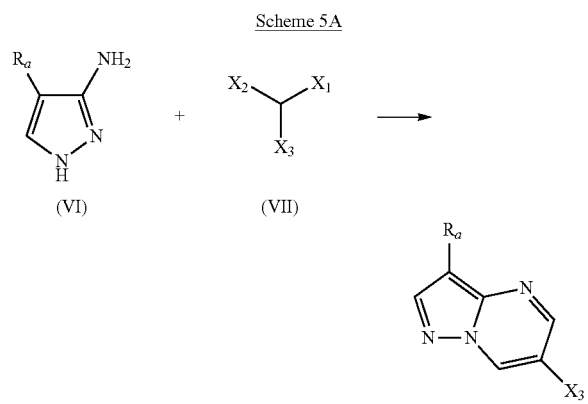

A particular synthetic scheme for the preparation of 3,7-disubstituted pyrazolo[1,5-a]pyrimidines is outlined in Scheme 5B. The pyrazolopyrimidine ring is formed by reaction of a substituted malonaldehyde as fragment VII with aminopyrazole. The substituted malonaldehyde can be substituted with the desired cyclic functionality e.g. 2-(4-fluorophenyl)-malonaldehyde, or with a latent functionality e.g. a halogen as in 2-bromo-malonaldehyde, which allows further derivatisation at this position as in the scheme shown below using the reactions outlined herein.

In the cyclisation reaction, the malonaldehyde in solvent is added to 3-aminopyrazole followed by acid e.g. glacial acetic acid. The reagents are then cyclised upon heating under reflux. The compound of formula (I) can then be synthesised using the halogenation and metal-catalysed reactions outlined herein.

Scheme 5B

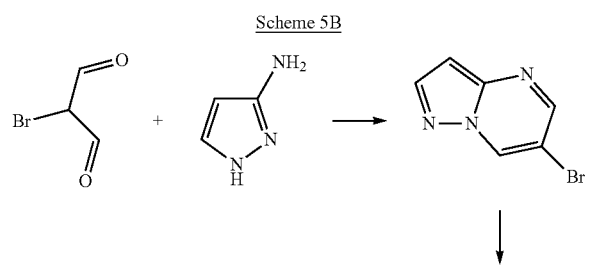

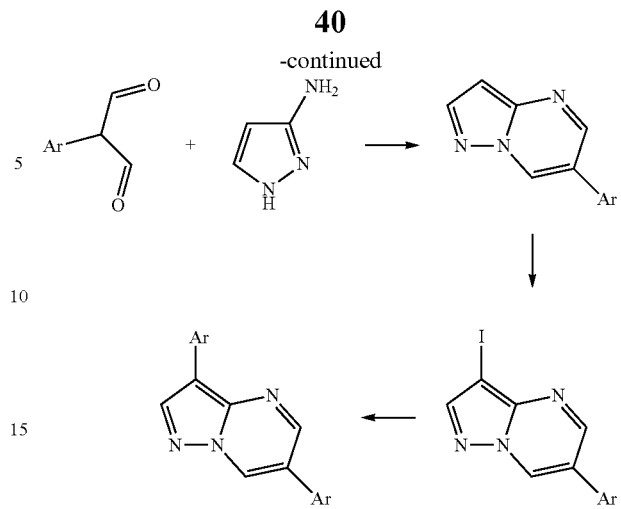

Compounds of formula (VI) and (VII) are known compounds or can be prepared by analogy to known methods. Many pyrazoles of formula (VI) are commercially available. Alternatively they can be obtained from known methods e.g. from ketones in a process described in EP308020 (Merck), or the methods discussed by Schmidt in Helv. Chim. Ada. (1956), 39, 986-991 and Helv. Chim. Acta. (1958), 41, 1052-1060 or by conversion of the pyrazoles of formula (VI) or the compound of formula (I) where $R_a$ is hydrogen, halogen, nitro, ester, or amide to the desired $R^1$ functionality by standard methods known to a person skilled in the art. For example, where $R^1$ is halogen, coupling reactions with tin or palladium chemistry could be performed as described herein.

Pyrazolo[1,5-a]pyrazines

Reaction of a mixture of 2-bromo-5-iodo-pyrazine and copper (I) iodide under inert conditions in an appropriate solvent and base e.g. DMF/Et$_3$N with ethynyl-trimethyl-silane using a palladium catalyst e.g. Pd(PPh$_3$)$_4$ at room temperature gives 2-Bromo-5-trimethylsilanylethynyl-pyrazine. This material can be used without further purification and reacted to form 6-bromo-2-trimethylsilanyl-pyrazolo[1,5-a]pyrazine using O-(mesitylenesulfonyl)hydroxylamine to form the N-amino adduct. This can then be cyclised by reacting with base e.g. K$_2$CO$_3$ to form pyrazolopyrazine core (Scheme 6).

Scheme 6

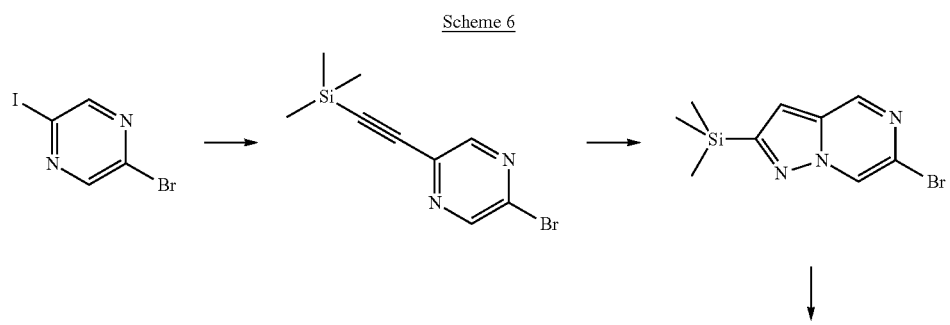

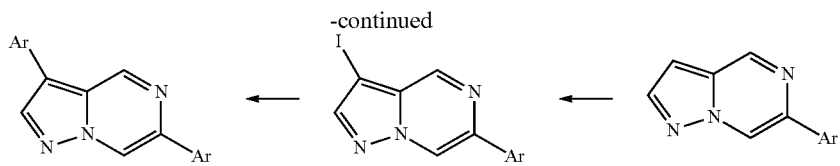

Appropriate groups at positions 3 and 7 can then be introduced by halogenation and reaction of the latent functionality at the 3 and 7 positions in the metal catalysed reactions outlined herein.

Pyrazolo[1,5-a]pyridines 3-bromopyridine is reacted with the appropriately substituted boronic acid in a solvent such as in DME under inert conditions with base ($Na_2CO_3$) and a palladium catalyst to form 3-substituted pyridine (Scheme 7). O-(Mesitylenesulfonyl)hydroxylamine is then reacted with 3-substituted-pyridine under inert conditions to form the N-aminopyridine which can be used without further purification. Cyclisation of the N-adduct using base ($K_2CO_3$) and 2-benzenesulfonyl-3-dimethylamino-acrylic acid methyl ester in an inert atmosphere give the 3-carboxylic acid ester pyrazolo[1,5-a]pyridine. The carboxylic ester can be removed, for example by saponification using sodium hydroxide to form the acid and then decarboxylation in polyphosphoric acid.

Scheme 7

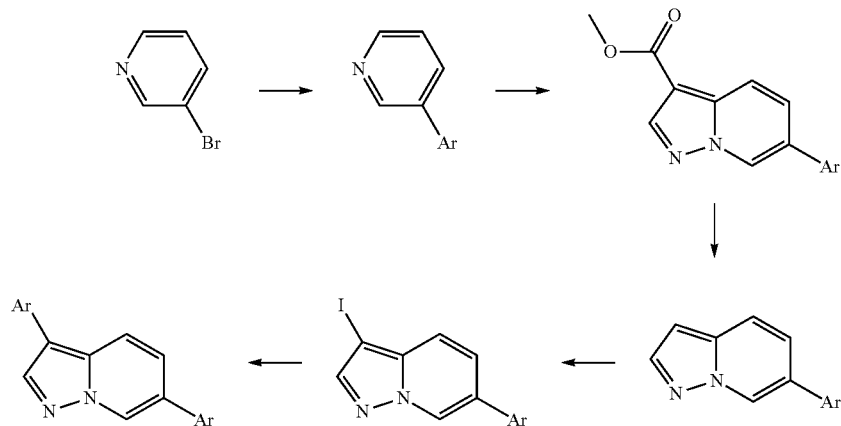

Iodination with N-iodosuccinimide and metal catalysed reaction of aryl halides, can be used to introduced the required functionality at the 3 position as outlined herein.

Imidazo[4,5-b]pyridines

An imidazo[4,5-b]pyridine ring system may be constructed by reaction of an aniline with 2-chloro-3-amino pyridine as described in J. Heterocyclic Chemistry (1983), 20(5), 1339 (Scheme 8).

Scheme 8

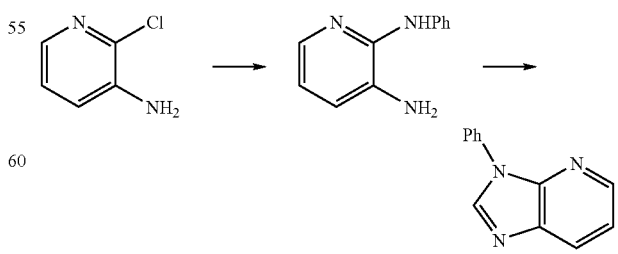

An alternative synthesis of a more functionalized intermediate has been described in U.S. Pat. No. 6,723,735 (Scheme 9).

Scheme 9

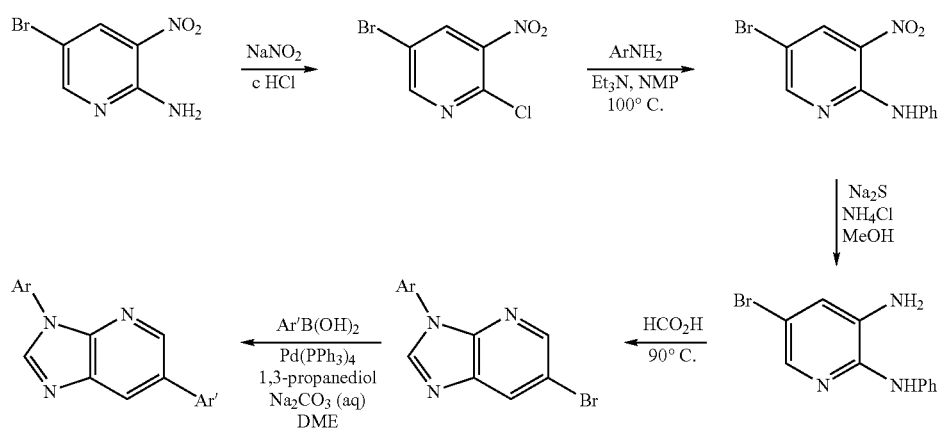

As described herein the aryl halides similar to that shown above may undergo a range of metal catalysed reactions to generate the required compounds of formula (I).

Imidazo[4,5-c]pyridines

A 3-aryl-3H-imidazo[4,5-c]pyridine ring system may be constructed by reaction of 3H-imidazo[4,5-c]pyridine with an aryl iodide as discussed in Biorg. Med. Chem. Lett. (2004), 14, 5263 (Scheme 10).

Scheme 10

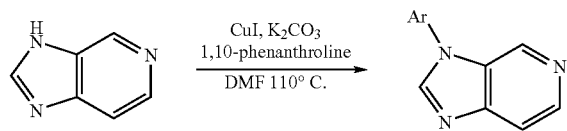

It is reported that the regioisomeric products may be separated by chromatography. A possible way to further elaborate this material to give the desired substitution pattern is illustrated below (Scheme 11).

Scheme 11

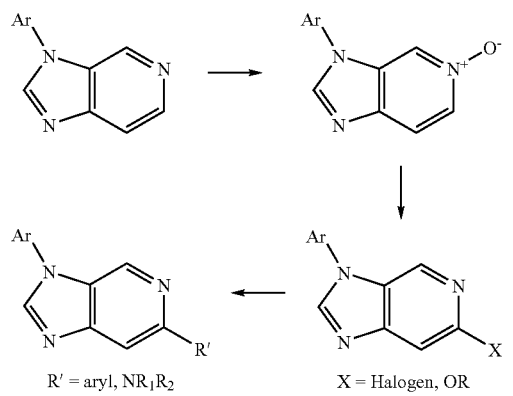

Reaction with an oxidizing agent, such as 3-chloro perbenzoic acid, could be used to prepare the N-oxide which may be rearranged to the disubstituted 3H-imidazo[4,5-c]pyridine with several reagents e.g. $POCl_3$, $SOCl_2$. The regioisomeric products could then be separated by chromatography. Displacement of X to give aryl and amino substituted products could be achieved by reaction of a suitable nucleophile in the presence of a metal catalyst e.g. palladium.

An alternative strategy is shown in Scheme 12. The synthesis of 6-chloro-3H-imidazo[4,5-c]pyridine is described in J. Heterocyclic Chem (1965), 2(2), 196-201. The chloro group may be displaced with a nucleophile in the presence of a metal catalyst (e.g. palladium) to give aryl and amino substituted products. A protecting group can be used in this conversion such as a carbamate or benzyl group. Subsequent elaboration to the N-aryl compounds could then be achieved according to the conditions shown in Scheme 10.

Scheme 12

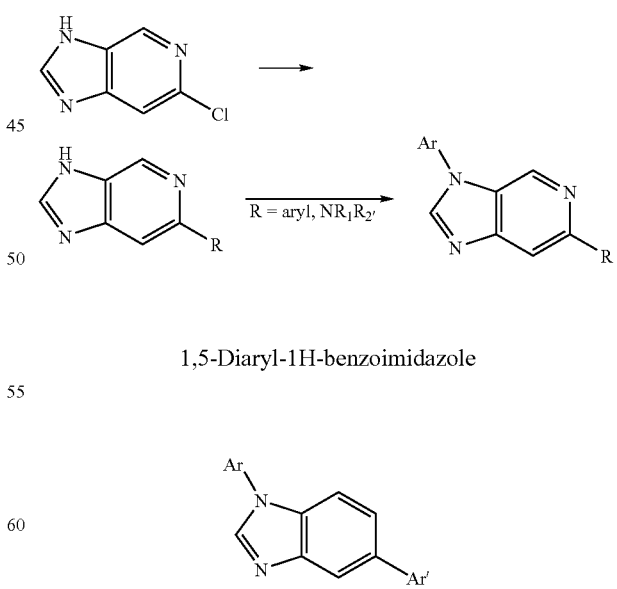

1,5-Diaryl-1H-benzoimidazole

A synthesis of 1,5-diaryl-1H-benzoimidazoles is reported in Biorg. Med. Chem. Lett (2003), 13, 2485-2488 (Scheme 13).

Scheme 13

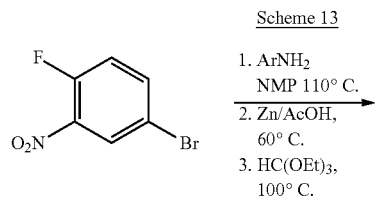

1. ArNH₂
   NMP 110° C.
2. Zn/AcOH,
   60° C.
3. HC(OEt)₃,
   100° C.

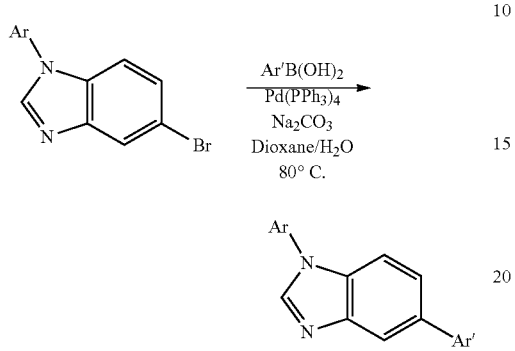

Ar'B(OH)₂
Pd(PPh₃)₄
Na₂CO₃
Dioxane/H₂O
80° C.

Displacement of fluorine from 4-bromo-1-fluoro-2-nitrobenzene with an appropriate aniline followed by reduction and cyclisation with triethyl orthoformate gives the bromobenzoimidazole with the desired substitution pattern. The product may be further elaborated by metal catalysed reaction of the bromide to give 1,5-disubstituted benzoimidazoles.

Imidazo[1,2-c]pyrimidines

Di-substituted imidazo[1,2-c]pyrimidines can be prepared as outlined in Scheme 14.

Scheme 14

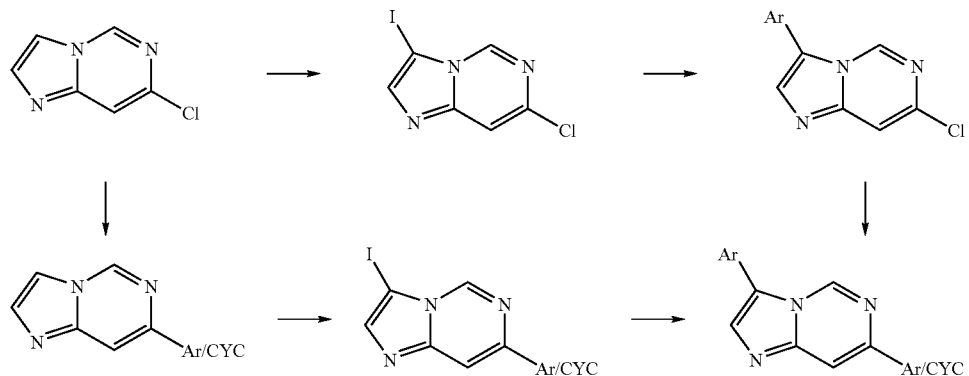

This starts from 7-chloro-imidazo[1,2-c]pyrimidine, whose synthesis has been described in Yanai et al, Heterocyclic compounds. XVIII. Synthesis of imidazo[1,2-c]- and pyrimido[1,2-c]pyrimidine derivatives, Yakugaku Zasshi (1974), 94(12), 1503-14. This material can then be further elaborated using any of the reactions described above.

Alternatively, where the 7-position is a N-linked saturated heterocycle, for example morpholine, a S$_N$Ar reaction (for examples of S$_N$Ar reaction see "*Advanced Organic Chemistry*" by Jerry March, 4$^{th}$ edition, pages 641-644) could be performed, for example as described in U.S. Pat. No. 4,503,050 (Scheme 15).

Scheme 15

[Structures shown]

-continued

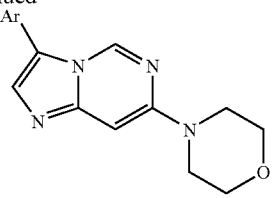

Where the 7-position is an aryl or heteroaryl group the S$_N$Ar group can be replaced with a standard palladium cross coupling reaction using similar chemistries as described herein (Scheme 16).

Scheme 16

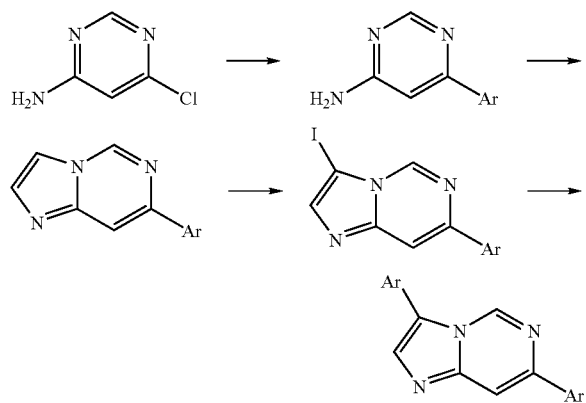

3,7 disubstituted imidazo[1,2-c]pyrimidin-5-ones can be prepared from the 7-Chloro-6H-imidazo[1,2-c]pyrimidin-5-one (CAS number 56817-09-5) whose synthesis is described in Maggiali et al (1982) Acta Naturalia de l'Ateneo Parmense, 18(3), 93-101 and Bartholomew et al (1975) Journal of Organic Chemistry, 40(25), 3708-13.

7-Chloro-6H-imidazo[1,2-c]pyrimidin-5-one can be derivatised using nucleophilic substitution reactions such as $S_NAr$ or subject to a Suzuki reaction to add functionality at the 7 position (Scheme 17). This compound can then be iodinated as described above before further functionalisation using the Suzuki reaction.

Scheme 17

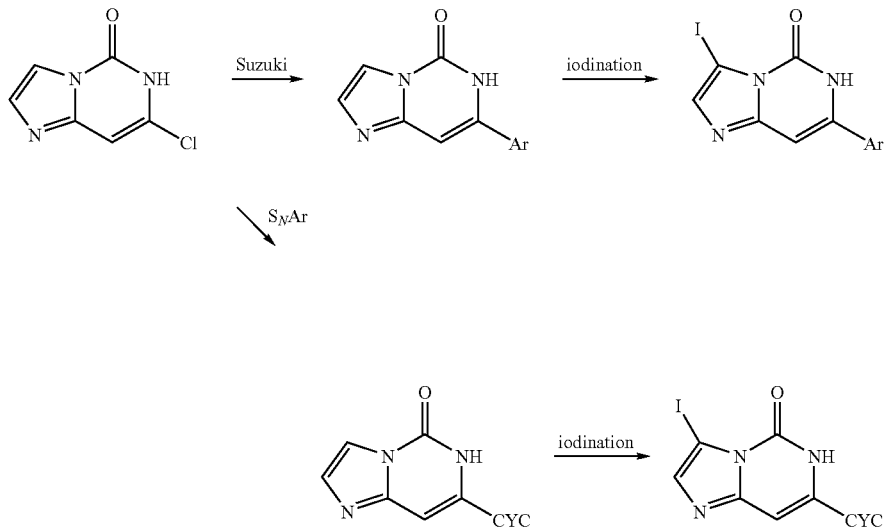

Alternatively 7-Chloro-6H-imidazo[1,2-c]pyrimidin-5-one could be directly iodinated to the intermediate below for use in the reactions described herein (Scheme 18).

Scheme 18

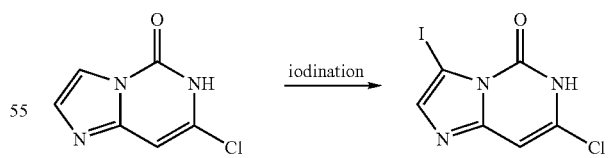

In addition, other oxo-heterocycles could be synthesized from the appropriate chloro derivative by hydrolysis. The protected compound would be subjected to base hydrolysis to afford the pyridone. This could be performed with NaOH (or NaOH/$H_2O_2$) in $H_2O$/MeOH or $H_2O$/dioxane following procedures described in the literature for the hydrolysis of chloropyridines (e.g. Australian J. Chem. (1984), 37(12), 2469-2477).

Imidazo[1,2-b]pyridazine

Scheme 19

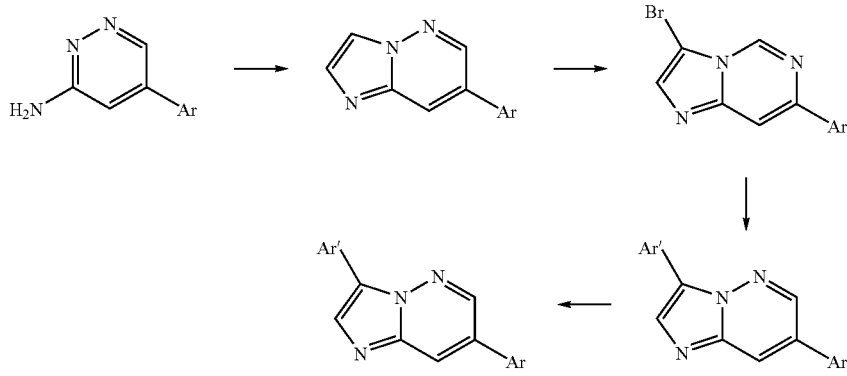

The synthesis of the Imidazo[1,2-b]pyridazine core can be performed as described in Scheme 19 using a pyridazin-3-ylamine derivative as reported in J. Heterocyclic Chem. (2002), 39 (4), p 737-742. Introduction of substituents at the 3 position is exemplified in J. Med. Chem (2006), 49 (4), p 1235-1238 to give the 3,7 substituent compounds.

Other heterocycles can be synthesised using well known reactions for example as described in Comprehensive Heterocyclic Chemistry I (Edited by A. R. Katritzky, C. W. Rees, Elsevier, 1982) and Comprehensive Heterocyclic Chemistry II (Edited by A. R. Katritzky, C. W. Rees, E. F. V. Scriven, Elsevier, 1996, ISBN 0-08-042072-9).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc). An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

Key intermediates in the preparation of the compounds of formula (I) are the compounds of formula (XX). Novel chemical intermediates of the formula (XX) form a further aspect of the invention.

A further aspect of the invention is a process for the preparation of a compound of formula (I) as defined herein, which process comprises:

(i) the reaction of a compound of the formula (XX) or (XXI):

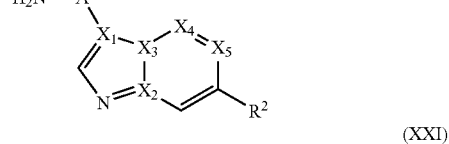
(XX)

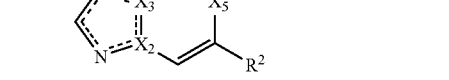
(XXI)

or a protected form thereof, with an appropriately substituted isocyanate or an appropriately substituted amine in the presence of carbonyl diimidazole (CDI); or (ii) the reaction of a compound of the formula (XX) or (XXI):

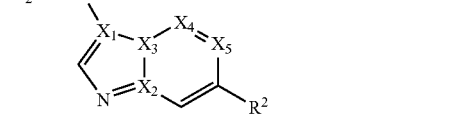
(XX)

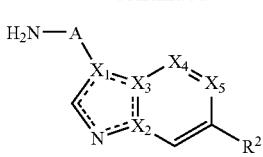
(XXI)

or a protected form thereof, with an appropriately substituted aldehyde or ketone; or (iii) the reaction of a compound of the formula (XX) or (XXI):

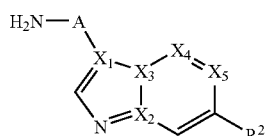
(XX)

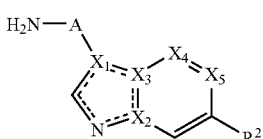
(XXI)

wherein $X_{1-5}$, A and $R_2$ are as defined herein; or a protected form thereof, with an appropriately substituted carboxylic acid or a reactive derivative and thereafter removing any protecting group present;

and optionally thereafter converting one compound of the formula (I) into another compound of the formula (I).

In one embodiment, the process for the preparation of a compound of formula (I) as defined herein, additionally comprises:

(iv) reacting a compound of formula (V) and (VI):

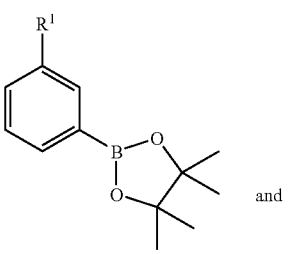
(V)

and

(VI)

wherein $R^1$ and $R^2$ are as defined above for compounds of formula (I).

In one embodiment, $R^1$ represents —NHCON(H)($C_{1-6}$ alkyl) or —NHCON(H)($CH_2CF_3$) and $R^2$ represents 4-fluorophenyl.

According to a further aspect of the invention there is provided a novel intermediate as defined herein. In one embodiment, the novel intermediate is selected from:

1-(3-Bromo-phenyl)-3-(2,2,2-trifluoro-ethyl)-urea;
7-(4-Fluoro-phenyl)-imidazo[1,2-a]pyridine; and
7-(4-Fluoro-phenyl)-3-iodo-imidazo[1,2-a]pyridine.

Pharmaceutically Acceptable Salts, Solvates or Derivatives Thereof

In this section, as in all other sections of this application, unless the context indicates otherwise, references to formula (I) include references to all other sub-groups, preferences and examples thereof as defined herein.

Unless otherwise specified, a reference to a particular compound also includes ionic forms, salts, solvates, isomers, tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or tautomers or solvates or protected forms thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphorsulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids.

Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

The compounds of the invention may exist as mono- or di-salts depending upon the pKa of the acid from which the salt is formed.

If the compound is anionic, or has a functional group which may be anionic (e.g., —COOH may be —COO), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane. Particular examples of N-oxides include morpholine N-oxides and pyridine N-oxides.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

Other examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

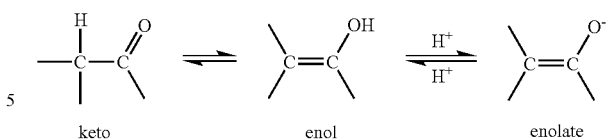

keto     enol     enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl.*, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(═O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(═O)OCH$_3$, —C(═O)OCH$_2$CH$_3$, —C(═O)OC(CH$_3$)$_3$, and —C(═O)OPh. Examples of acyloxy (reverse ester) groups are represented by —OC(═O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(═O)CH$_3$ (acetoxy), —OC(═O)CH$_2$CH$_3$, —OC(═O)C(CH$_3$)$_3$, —OC(═O)Ph, and —OC(═O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and prodrugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Examples of such metabolically labile esters include those of the formula —C(═O)OR wherein R is:

$C_{1-7}$alkyl (e.g., -Me, -Et, -nPr, -iPr, -nBu, -sBu, -iBu, -tBu);
$C_{1-7}$aminoalkyl (e.g., aminoethyl; 2-(N,N-diethylamino)ethyl; 2-(4-morpholino)ethyl); and acyloxy-$C_{1-7}$alkyl (e.g., acyloxymethyl; acyloxyethyl; pivaloyloxymethyl; acetoxymethyl;

1-acetoxyethyl; 1-(1-methoxy-1-methyl)ethyl-carbonyloxyethyl; 1-(benzoyloxy)ethyl; isopropoxy-carbonyloxymethyl;

1-isopropoxy-carbonyloxyethyl; cyclohexyl-carbonyloxymethyl; 1-cyclohexyl-carbonyloxyethyl; cyclohexyloxy-carbonyloxymethyl;

1-cyclohexyloxy-carbonyloxyethyl; (4-tetrahydropyranyloxy)carbonyloxymethyl; 1-(4-tetrahydropyranyloxy)carbonyloxyethyl;

(4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, tautomer, N-oxide or solvate thereof.

According to a further aspect of the invention there is provided a compound as defined herein or a salt or solvate thereof.

References to compounds of the formula (I), (Ia), (Ib), (Ic), (Id), (Ie), (If), (Ig) and (II) and sub-groups thereof as defined herein include within their scope the salts or solvates or tautomers or N-oxides of the compounds.

Protein Tyrosine Kinases (PTK)

The compounds of the invention described herein inhibit or modulate the activity of certain tyrosine kinases, and thus the compounds will be useful in the treatment or prophylaxis of disease states or conditions mediated by those tyrosine kinases in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signaling molecules which act as autocrine as well as paracrine factors. Autocrine FGF signaling may be particularly important in the progression of steroid hormone-dependent cancers to a hormone independent state (Powers, et al. (2000) Endocr. Relat. Cancer, 7, 165-197).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Ozawa, et al. (2001), Teratog. Carcinog. Mutagen., 21, 27-44).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4). Upon ligand binding, the receptors dimerize and auto- or trans-phosphorylate specific cytoplasmic tyrosine residues to transmit an intracellular signal that ultimately regulates nuclear transcription factor effectors.

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signaling in intramembranous bone formation. For example, in Apert (AP) syndrome, characterized by premature cranial suture ossification, most cases are associated with point mutations engendering gain-of-function in fibroblast growth factor receptor 2 (Lemonnier, et al. (2001), J. Bone Miner. Res., 16, 832-845). In addition, mutation screening in patients with syndromic craniosynostoses indicates that a number of recurrent FGFR2 mutations accounts for severe forms of Pfeiffer syndrome (Lajeunie et al, *Euro-* pean *Journal of Human Genetics* (2006) 14, 289-298). Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene (Meyers, et al. (1996) Am. J. Hum. Genet., 58, 491-498; Plomp, et al. (1998) Am. J. Med. Genet., 75, 245-251), and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of fibroblast growth factor receptor 2 (Yu, et al. (2000), Proc. Natl. Acad. Sci. U.S.A., 97, 14536-14541).

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas (Powers, C. J. (2000), et al., Endocr. Rel. Cancer, 7, 165; Qiu, W. et. al. (2005), World Journal Gastroenterol, 11(34)). Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC) (Journal of Pathology (2007), 213 (1), 91-98). Increased expression was associated with mutation (85% of mutant tumors showed high-level expression) but also 42% of tumors with no detectable mutation showed over-expression, including many muscle-invasive tumors.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Over expression of FGFR4 has been linked to poor prognosis in both prostate and thyroid carcinomas (Ezzat, S., et al. (2002) The Journal of Clinical Investigation, 109, 1; Wang et al. (2004) Clinical Cancer Research, 10). In addition a germline polymorphism (Gly388Arg) is associated with increased incidence of lung, breast, colon and prostate cancers (Wang et al. (2004) Clinical Cancer Research, 10). In addition, a truncated form of FGFR4 (including the kinase domain) has also been found to present in 40% of pituitary tumours but not present in normal tissue.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signaling pathway (Reis-Filho et al. (2006) Clin Cancer Res. 12(22): 6652-6662.

Rhabdomyosarcoma (RMS), the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes (Genes, Chromosomes & Cancer (2007), 46(11), 1028-1038).

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis (Inoue, et al. (1997 & 2002); Barrios, et al. (1997)). TGFβ1 and PDGF have been reported to be involved in the fibrogenic process (reviewed by Atamas & White, 2003) and further published work suggests the elevation of FGF's and consequent increase in fibroblast proliferation, may be in response to elevated TGFβ1 (Khalil, et al., 2005). The potential therapeutic relevance of this pathway in fibrotic conditions is suggested by the reported clinical effect of Pirfenidone (Arata, et al., 2005) in idiopathic pulmonary fibrosis (IPF).

Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels. (Folkman (1997), 79, 1-81; Folkman (1995), *Nature Medicine*, 1, 27-31; Folkman and Shing (1992) *J. Biol. Chem.*, 267, 10931).

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott (1992), *Ann. Rhum. Dis.*, 51, 919). In diabetes (and in many different eye diseases), new vessels invade the macula or retina or other ocular structures, and may cause blindness (Brooks, et al. (1994) *Cell*, 79, 1157). The process of atherosclerosis has been linked to angiogenesis (Kahlon, et al. (1992) *Can. J. Cardiol.*, 8, 60). Tumor growth and metastasis have been found to be angiogenesis-dependent (Folkman (1992), *Cancer Biol*, 3, 65; Denekamp, (1993) *Br. J. Rad.*, 66, 181; Fidler and Ellis (1994), *Cell*, 79, 185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly, et al. (1994) *Cell*, 79, 315; Ingber, et al. (1990) *Nature*, 348, 555), ocular diseases (Friedlander, et al. (1995) *Science*, 270, 1500), arthritis (Peacock, et al. (1992), *J. Exp. Med.*, 175, 1135; Peacock et al. (1995), *Cell. Immun.*, 160, 178) and hemangioma (Taraboletti, et al. (1995) *J. Natl. Cancer Inst.*, 87, 293).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al. (2000), *The Oncologist*, 5(90001), 1-2). VEGFR(s) are protein tyrosine kinases (PTKs). PTKs catalyze the phosphorylation of specific tyrosine residues in proteins involved in cell function thus regulating cell growth, survival and differentiation. (Wilks, A. F. (1990), *Progress in Growth Factor Research*, 2, 97-111; Courtneidge, S. A. (1993) *Dev. Supp. I*, 57-64; Cooper, J. A. (1994), *Semin. Cell Biol.*, 5(6), 377-387; Paulson, R. F. (1995), *Semin. Immunol.*, 7(4), 267-277; Chan, A. C. (1996), *Curr. Opin. Immunol.*, 8(3), 394-401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. (1995), et al., *J. Cell Biol.*, 129, 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G. (2000), *The Oncologist*, 5(90001), 3-10).

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition. Inhibition of VEGFR2 but not VEGFR1 markedly disrupted angiogenic switching, persistent angiogenesis, and initial tumor growth. In late-stage tumours, phenotypic resistance to VEGFR2 blockade emerged, as tumours regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

A FGF-trap adenovirus has been previously reported to bind and block various ligands of the FGF family, including FGF1, FGF3, FGF7, and FGF10, thereby effectively inhibiting angiogenesis in vitro and in vivo. Indeed, adding the FGF-trap treatment in the regrowth phase of a mouse model produced a significant decrease in tumor growth compared to anti-VEGFR2 alone. This decrease in tumor burden was accompanied by a decrease in angiogenesis that was observed as decreased intratumoral vessel density.

Batchelor et al. (Batchelor et al., 2007, *Cancer Cell,* 11(1), 83-95) provide evidence for normalization of glioblastoma blood vessels in patients treated with a pan-VEGF receptor tyrosine kinase inhibitor, AZD2171, in a phase 2 study. The rationale for using AZD2171 was based partially on results showing a decrease in perfusion and vessel density in an in vivo breast cancer model (Miller et al., 2006, *Clin. Cancer Res.* 12, 281-288). Furthermore, using an orthotopic glioma model, it had previously been identified that the optimal window of time to deliver anti-VEGFR2 antibody to achieve a synergistic effect with radiation. During the window of normalization, there was improved oxygenation, increased pericyte coverage, and upregulation of angiopoietin-1 leading to a decrease in interstitial pressure and permeability within the tumour (Winkler et al., 2004, *Cancer Cell* 6, 553-563). The window of normalization can be quantified using magnetic resonance imaging (MRI) using MRI gradient echo, spin echo, and contrast enhancement to measure blood volume, relative vessel size, and vascular permeability.

The authors showed that progression on treatment with AZD2171 was associated with an increase in CECs, SDF1, and FGF2, while progression after drug interruptions correlated with increases in circulating progenitor cells (CPCs) and plasma FGF2 levels. The increase in plasma levels of SDF1 and FGF2 correlated with MRI measurements, demonstrated an increase in the relative vessel density and size. Thus, MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment of chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. In addition, sorafenib (BAY 43-9006) which has the chemical name 4-(4-(3-(4-chloro-3 (trifluoromethyl)phenyl)ureido)phenoxy)-N2-methylpyridine-2-carboxamide, targets both the Raf signaling pathway to inhibit cell proliferation and the VEGFR/PDGFR signaling cascades to inhibit tumour angiogenesis. Sorafenib is being investigated for the treatment of a number of cancers including liver and kidney cancer.

There are conditions which are dependent on activation of PDGFR such as hypereosinophilic syndrome. PDGFR activation is also associated with other malignancies, which include chronic myelomonocytic leukemia (CMML). In another disorder, dermatofibrosarcoma protuberans, an infiltrative skin tumor, a reciprocal translocation involving the gene encoding the PDGF-B ligand results in constitutive secretion of the chimeric ligand and receptor activation. Imatinib has which is a known inhibitor of PDGFR has activity against all three of these diseases.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, it is envisaged that the compounds of the invention will be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3.

Preferred compounds are compounds that inhibit one or more FGFR selected from FGFR1, FGFR2 and FGFR3, and also FGFR4. Preferred compounds of the invention are those having $IC_{50}$ values of less than 0.1 μM.

Compounds of the invention also have activity against VEGFR.

Compounds of the invention also have activity against PDGFR kinases. In particular, the compounds are inhibitors of PDGFR and, for example, inhibit PDGFR A and/or PDGFR B.

In addition many of the compounds of the invention exhibit selectivity for the FGFR 1, 2, and/or 3 kinase, and/or FGFR4 compared to VEGFR (in particular VEGFR2) and/or PDGFR and such compounds represent one preferred embodiment of the invention. In particular, the compounds exhibit selectivity for VEGFR2. For example, many compounds of the invention have $IC_{50}$ values against FGFR1, 2 and/or 3 and/or FGFR4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, VEGFR and/or PDGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukemia, acute lymphocytic leukemia, chronic lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, myeloproliferative syndrome, myelodysplastic syndrome, or promyelocytic leukemia; multiple myeloma; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis.

Thus, in the pharmaceutical compositions, uses or methods of this invention for treating a disease or condition comprising abnormal cell growth, the disease or condition comprising abnormal cell growth in one embodiment is a cancer.

Further T-cell lymphoproliferative diseases include those derived from natural Killer cells. The term B-cell lymphoma includes diffuse large B-cell lymphoma.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

A further example of a tumour of mesenchymal origin is Ewing's sarcoma.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

It is further envisaged that the compound of the invention having FGFR such as FGFR1 inhibitory activity, will be particularly useful in the treatment or prevention of breast cancer in particular Classic Lobular Carcinomas (CLC).

As the compounds of the invention have FGFR4 activity they will also be useful in the treatment of prostate or pituitary cancers.

In particular the compounds of the invention as FGFR inhibitors, are useful in the treatment of multiple myeloma, myeloproliferative disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are in the treatment of multiple myeloma (in particular multiple myeloma with t(4;14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the compounds are useful for the treatment of lobular carcinomas such as CLC (Classic lobular carcinoma).

As the compounds have activity against FGFR3 they will be useful in the treatment of multiple myeloma and bladder.

In particular the compounds are useful for the treatment of t(4;14) translocation positive multiple myeloma.

As the compounds have activity against FGFR2 they will be useful in the treatment of endometrial, ovarian, gastric and colorectal cancers. FGFR2 is also overexpressed in epithelial ovarian cancer, therefore the compounds of the invention may be specifically useful in treating ovarian cancer such as epithelial ovarian cancer.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR, VEGFR or PDGFR signaling may be determined by means of a cell growth assay as set out in Examples 79 and 80 below or by a method as set out in the section headed "Methods of Diagnosis".

It is further envisaged that the compounds of the invention, and in particular those compounds having FGFR, VEGFR or PDGFR inhibitory activity, will be particularly useful in the treatment or prevention of cancers of a type associated with or characterised by the presence of elevated levels of FGFR, VEGFR or PDGFR, for example the cancers referred to in this context in the introductory section of this application.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

It is also envisaged that the compounds of the invention will be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions where it is envisaged that the compounds of the invention will be useful consists of inflammatory diseases, cardiovascular diseases and wound healing.

FGFR, VEGFR and PDGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, hematological diseases, for example, chronic anemia and aplastic anemia; degenerative diseases of the musculoskeletal system, for example, osteoporosis and arthritis, aspirinsensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

It is further envisaged that the compound of the invention having FGFR such as FGFR2 or FGFR3 inhibitory activity, will be particularly useful in the treatment or prevention of the skeletal diseases. Particular skeletal diseases are achondroplasia or thanatophoric dwarfism (also known as thanatophoric dysplasia).

It is further envisaged that the compound of the invention having FGFR such as FGFR1, FGFR2 or FGFR3 inhibitory activity, will be particularly useful in the treatment or prevention in pathologies in which progressive fibrosis is a symptom. Fibrotic conditions in which the compounds of the inventions may be useful in the treatment of in include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

Since compounds of the invention inhibit PDGFR they may also be useful in the treatment of a number of tumour and leukemia types including glioblastomas such as glioblastoma multiforme, prostate carcinomas, gastrointestinal stromal tumours, liver cancer, kidney cancer, chronic myeloid leukemia, chronic myelomonocytic leukemia (CMML) as well as hypereosinophilic syndrome, a rare proliferative hematological disorder and dermatofibrosarcoma protuberans, an infiltrative skin tumour.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value. Preferred compounds of the present invention are compounds having an $IC_{50}$ value of less than 1 μM, more preferably less than 0.1 μM.

The invention provides compounds that have FGFR inhibiting or modulating activity, and which it is envisaged will be useful in preventing or treating disease states or conditions mediated by FGFR kinases.

In one embodiment, there is provided a compound as defined herein for use in therapy. In a further embodiment, there is provided a compound as defined herein for use in the prophylaxis or treatment of a disease state or condition mediated by a FGFR kinase.

Thus, for example, it is envisaged that the compounds of the invention will be useful in alleviating or reducing the incidence of cancer.

Accordingly, in one aspect, the invention provides the use of a compound for the manufacture of a medicament for the prophylaxis or treatment of a disease state or condition mediated by a FGFR kinase, the compound having the formula (I) as defined herein.

In one embodiment, there is provided the use of a compound as defined herein for the manufacture of a medicament for the prophylaxis or treatment of a disease state or condition as described herein.

In a further embodiment, there is provided the use of a compound as defined herein for the manufacture of a medicament for the prophylaxis or treatment of cancer.

Accordingly, the invention provides inter alia:

A method for the prophylaxis or treatment of a disease state or condition mediated by a FGFR kinase, which method comprises administering to a subject in need thereof a compound of the formula (I) as defined herein.

In one embodiment, there is provided a method for the prophylaxis or treatment of a disease state or condition as described herein, which method comprises administering to a subject in need thereof a compound of the formula (I) as defined herein.

In a further embodiment, there is provided a method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use as a modulator (e.g. inhibitor) of FGFR.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of FGFR kinase, thereafter administering to the patient a compound of the formula (I) as defined herein having FGFR kinase inhibiting activity.

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme (Carter et al (2005), PNAS, 102(31), 11011-110116).

There are mutations that have been observed in PDGFR in imatinib-treated patients, in particular the T674I mutation. The clinical importance of these mutations may grow considerably, as to date it appears to represent the primary mechanism of resistance to src/Abl inhibitors in patients.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR or PDGFR including PDGFR-beta and PDGFR-alpha in particular the T674I mutation of PDGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

Accordingly, in a further aspect, the invention provides compounds of the formula (I) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly (2004), Solubilizing Excipients in oral and injectable formulations, Pharmaceutical Research, Vol 21(2), p 201-230).

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman (1971), J. Pharm. Sci., 60, 1281-1300) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. A tablet can contain the solid solution blended with at least one disintegrant, a lubricant, a surfactant, and a glidant. The chewable tablet can contain the solid solution blended with a bulking agent, a lubricant, and if desired an additional sweetening agent (such as an artificial sweetener), and suitable flavours.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Examples of Pharmaceutical Formulations (i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

Methods of Treatment

It is envisaged that the compounds of the formula (I) and sub-groups thereof as defined herein will be useful in the prophylaxis or treatment of a range of disease states or conditions mediated by FGFR. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic.

However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently, i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compounds as defined herein can be administered as the sole therapeutic agent or they can be administered in combination therapy with one of more other compounds for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and,
Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromoembolic episodes.

Each of the compounds present in the combinations of the invention may be given in individually varying dose schedules and via different routes.

Where the compound of the formula (I) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against FGFR, VEGFR and/or PDGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, VEGFR and/or PDGFR or to sensitisation of a pathway to normal FGFR, VEGFR and/or PDGFR activity, or to upregulation of these growth factor signaling pathways such as growth factor ligand levels or growth factor ligand activity or to upregulation of a biochemical pathway downstream of FGFR, VEGFR and/or PDGFR activation.

Examples of such abnormalities that result in activation or sensitisation of the FGFR, VEGFR and/or PDGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions (Lemonnier, et al. (2001), J. Bone Miner. Res., 16, 832-845). In particular activating mutations in FGFR2 have been identified in 10% of endometrial tumours (Pollock et al, Oncogene, 2007, 26, 7158-7162).

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas (Powers, C. J., et al. (2000), Endocr. Rel. Cancer, 7, 165). A particular mutation T674I of the PDGF receptor has been identified in imatinib-treated patients.

In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signaling pathway (Reis-Filho et al. (2006), Clin Cancer Res. 12(22), 6652-6662).

Alternatively, a biological sample taken from a patient may be analysed for loss of a negative regulator or suppressor of FGFR, VEGFR or PDGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, VEGFR and/or PDGFR. The term diagnosis includes screening. By marker we include genetic markers including, for example, the measurement of DNA composition to identify mutations of FGFR, VEGFR and/or PDGFR. The term marker also includes markers which are characteristic of up regulation of FGFR, VEGFR and/or PDGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, VEGFR and/or PDGFR may mean that the patient would be particularly suitable for treatment with a FGFR, VEGFR and/or PDGFR inhibitor. Tumours may preferentially be screened for presence of a FGFR, VEGFR and/or PDGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, VEGFR and/or PDGFR, or detection of FGFR, VEGFR and/or PDGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105 (Mineo et al. (2004) J Clin Pathol. 57(6), 591-7).

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcinomas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung and breast cancer.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect of the inventions includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

EXPERIMENTAL

Analytical LC-MS System and Method Description

In the examples, the compounds prepared were characterised by liquid chromatography and mass spectroscopy using commercially available systems (Waters Platform LC-MS system, Waters Fractionlynx LC-MS system), standard operating conditions and commercially available columns (Phenomenex, Waters etc) but a person skilled in the art will appreciate that alternative systems and methods could be used. Where atoms with different isotopes are present and a single mass quoted, the mass quoted for the compound is the monoisotopic mass (i.e. 35Cl; 79Br etc.).

Mass Directed Purification LC-MS System

Preparative LC-MS (or HPLC) is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; J Comb Chem.; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; J Comb Chem.; 2003; 5(3); 322-9.

Two such systems for purifying compounds via preparative LC-MS are the Waters Fractionlynx system or the Agilent 1100 LC-MS preparative system although a person skilled in the art will appreciate that alternative systems and methods could be used. In particular, reverse phase methods were used for preparative HPLC for the compounds described herein, but normal phase preparative LC based methods might be used in place of the reverse phase methods. Most preparative LC-MS systems utilise reverse phase LC and volatile acidic modifiers, since the approach is very effective for the purification of small molecules and because the eluents are compatible with positive ion electrospray mass spectrometry. According to the analytical trace obtained the most appropriate preparative chromatography type is chosen. A typical routine is to run an analytical LC-MS using the type of chromatography (low or high pH) most suited for compound structure. Once the analytical trace showed good chromatography a suitable preparative method of the same type is chosen. A range of chromatographic solutions e.g. normal or reverse phase LC; acidic, basic, polar, or lipophilic buffered mobile phase; basic modifiers could be used to purify the compounds. From the information provided someone skilled in the art could purify the compounds described herein by preparative LC-MS.

All compounds were usually dissolved in 100% MeOH or 100% DMSO.

General Synthetic Routes

General Route A

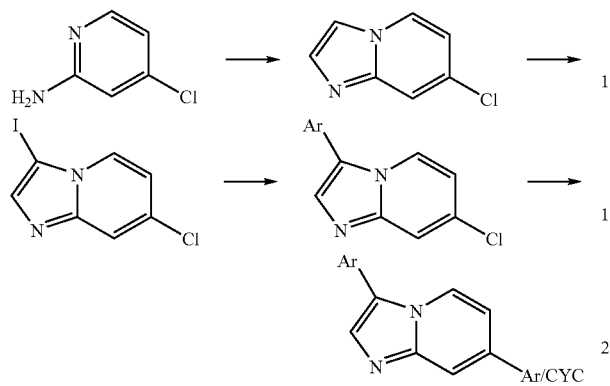

Procedure A1—General Imidazopyridine Ring Formation

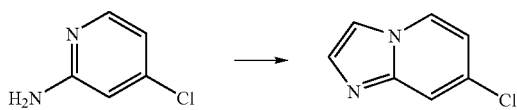 [SMILES: Nc1cc(Cl)ccn1 ; Clc1ccn2ccnc2c1]

To a solution of 4-Chloro-pyridin-2-ylamine (12.8 g, 100 mmol, 1.0 equiv) in EtOH (170 ml) was added NaHCO$_3$ (16.8 g, 200 mmol, 2.0 equiv) followed by chloroacetaldehyde (19.0 ml, 150 mmol, 1.5 equiv). The mixture was refluxed for 6 h. Solvents removed under reduced pressure and the crude mixture was partitioned between water and EtOAc. The organic layer was washed with brine, dried (MgSO$_4$), filtered and concentrated under reduced pressure. The product was purified by column chromatography (SiO$_2$, eluted with 50% EtOAC-petrol) to afford 13.2 g of product.

Procedure A2—General Iodination

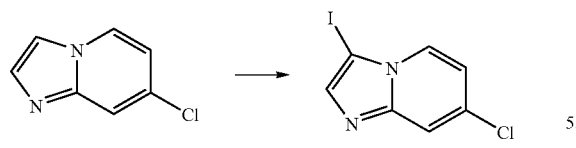

To a solution of 7-Chloro-imidazo[1,2-a]pyridine (30.9 g, 186 mmol, 1.0 equiv) in DMF (280 ml) was added N-iodosuccinimide (43.6 g, 194 mmol, 1.05 equiv) and the resulting mixture was stirred overnight at RT. The thin brown slurry was diluted with water (840 ml), brine (280 ml) and extracted with EtOAc (560 ml). The aqueous layer was further extracted with EtOAc (3×280 ml). The combined organic phases were washed with water (2×280 ml), 10% w/v sodium thiosulfate (280 ml), brine (280 ml), dried (MgSO$_4$), filtered and concentrated in vacuo to give a brown residue. The residue was triturated with ether (200 ml), filtered and the solid was washed with ether (2×50 ml) and dried on the filter to give 39 g of product.

Procedure A3 General Suzuki at the 3-Position

Procedure A3a—Suzuki

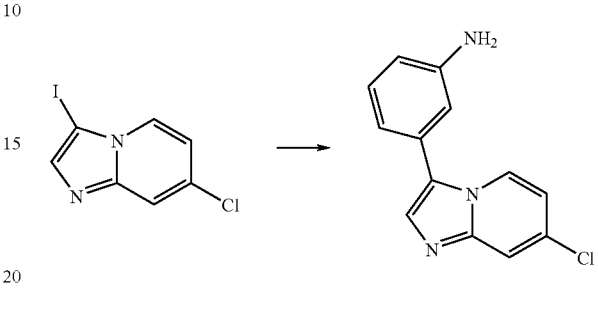

To a solution of 7-Chloro-3-iodo-imidazo[1,2-a]pyridine (2.8 g, 10 mmol) in acetonitrile (100 ml) was added 3-aminobenzeneboronic acid (2.5 g, 10.57 mmol), 2M Na$_2$CO$_3$ (21.6 ml) [reaction degassed by bubbling N$_2$ through] followed by bis(triphenylphosphine)palladium(II)chloride (0.35 g, 0.49 mmol). The mixture was heated at 70° C. overnight, then diluted with water and extracted with EtOAc. The organic layer was washed with brine, dried (MgSO$_4$), filtered and concentrated under reduced pressure and purified by column chromatography on the Biotage (SiO$_2$, eluted with 80% EtOAC-petrol to 100% EtOAC) to give 1.9 g of product. MS: [M+H]$^+$ 244

Procedure A3b—Suzuki

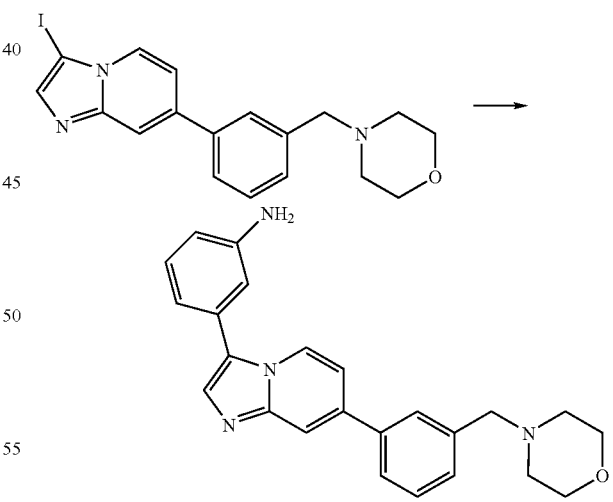

To a solution of 3-Iodo-7-(3-morpholin-4-ylmethyl-phenyl)-imidazo[1,2-a]pyridine (1.55 g, 3.72 mmol) in DME (20 ml) was added 3-aminobenzeneboronic acid (0.69 g, 4.8 mmol) and 2M Na$_2$CO$_3$ (6.93 ml) [reaction degassed by bubbling N$_2$ through] followed by tetrakis(triphenylphosphine) palladium(0) (0.139 g, 0.12 mmol). The mixture was heated at 75° C. overnight, then diluted with water and extracted with EtOAc. The organic layer was washed with brine, dried (MgSO$_4$), filtered and concentrated under reduced pressure and purified by column chromatography on the Biotage (SiO$_2$, eluted with EtOAC-20% MeOH/EtOAC) to give 0.56 g of product. MS: [M+H]$^+$ 385

Procedure A4 General Palladium Mediated Addition of Cycle at the 7-Position

Procedure A4a—Suzuki

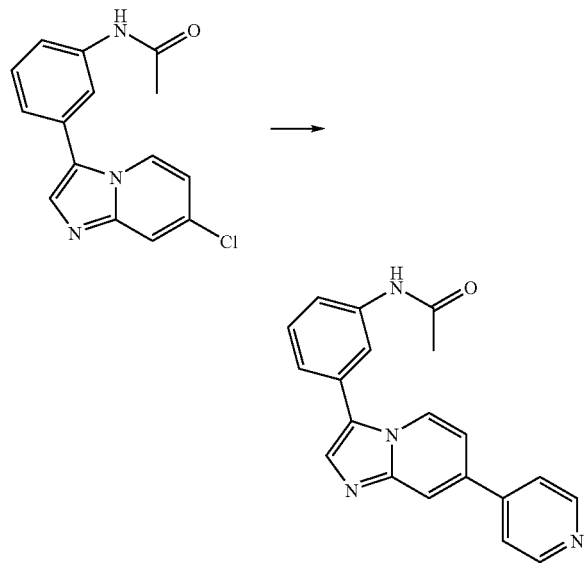

To a suspension of N-[3-(7-Chloro-imidazo[1,2-a]pyridin-3-yl)-phenyl]-acetamide (0.090 g, 0.3 mmol) in toluene (0.5 ml) was added 4-(4,4,5,5-Tetramethyl-[1,3,2]dioxaborolan-2-yl)-pyridine (0.078 g, 0.36 mmol), K$_2$CO$_3$ (0.25 g, 1.8 mmol), MeOH (0.5 ml), EtOH (0.5 ml), H$_2$O (0.75 ml) [reaction degassed by bubbling N$_2$ through] followed by bis(tri-t-butylphosphine)palladium(0) (0.003 g, 0.0058 mmol). The mixture was heated using microwave radiation in a CEM discover microwave synthesizer (50 W) at 140° C. until the reaction was complete. The reaction was diluted with water and extracted with EtOAc. The organic layer was washed with brine, dried (MgSO$_4$), filtered and concentrated under reduced pressure and purified by preparative HPLC to give 0.007 g of product. MS: [M+H]$^+$ 329

Procedure A4b—Suzuki

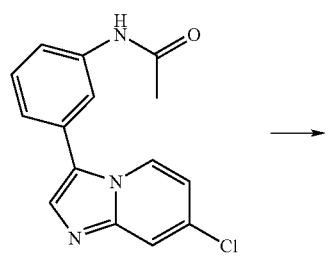

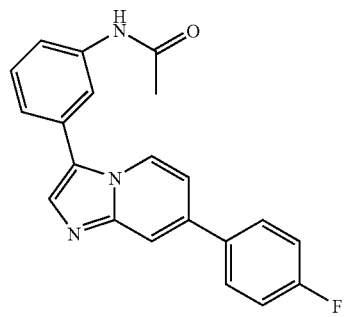

To a solution of N-[3-(7-Chloro-imidazo[1,2-a]pyridin-3-yl)-phenyl]-acetamide (0.1 g, 0.35 mmol) in DME (4 ml) was added 4-fluorophenylboronic acid (0.059 g, 4.2 mmol) and 2M Na$_2$CO$_3$ (1.2 ml) [reaction degassed by bubbling N$_2$ through] followed by tetrakis(triphenylphosphine)palladium (0) (0.018 g, 0.015 mmol). The mixture was heated at 80° C. overnight, then diluted with water and extracted with EtOAc. The organic layer was washed with brine, dried (MgSO$_4$) and concentrated under reduced pressure and purified by preparative HPLC to give 0.045 g of product. MS: [M+H]$^+$ 346

Procedure A4c—Buchwald

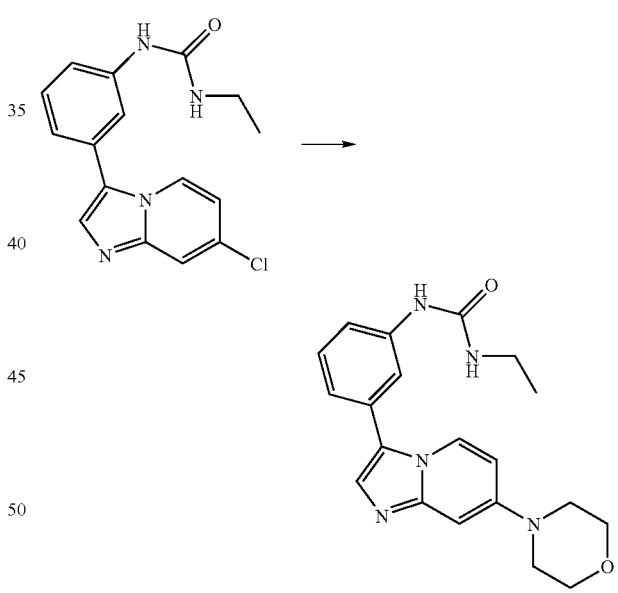

To a solution of 1-[3-(7-Chloro-imidazo[1,2-a]pyridin-3-yl)-phenyl]-3-ethyl-urea (0.1 g, 0.32 mmol) in anhydrous dioxane (4 ml) was added morpholine (0.03 ml, 0.35 mmol), NaO$^t$Bu (0.096 g, 0.96 mmol) [reaction degassed by bubbling N$_2$ through] followed by BINAP (0.021 g, 0.033 mmol) and Pd$_2$(dba)$_3$ (tris-(dibenzylideneacetone)dipalladium(0)) (0.016 g, 0.017 mmol). The mixture was heated at 80° C. overnight, then diluted with water and extracted with EtOAc. The organic layer was washed with brine, dried (MgSO$_4$), filtered and concentrated under reduced pressure and purified by preparative HPLC to give 0.015 g of product. MS: [M+H]$^+$ 366

Procedure A4d—Suzuki Coupling

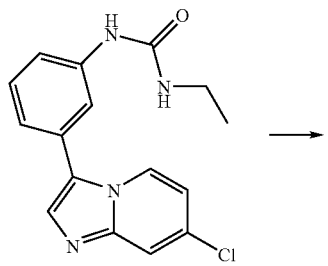

A solution of 1-[3-(7-chloro-imidazo[1,2-a]pyridin-3-yl)-phenyl]-3-ethyl urea (200 mg, 0.636 mmol, 1 equivalent, made using procedure F1a), 1-methylpyrazole-4-boronic acid pinacol ester (commercially available, 265 mg, 1.272 mmol, 2 equivalents), potassium carbonate (527 mg, 3.816 mmol, 6 equivalents), and bis(tri-t-butylphosphine)palladium(0) (16 mg, 0.032 mmol, 0.05 equivalents) in ethanol (10 ml), toluene (10 ml) and water (10 ml) was heated at 70° C. for 24 h. The reaction mixture was partitioned between ethyl acetate and water. The organic layer was washed with a saturated brine solution, dried (MgSO$_4$), filtered and the solvent evaporated in vacuo. The residue was purified by column chromatography (Biotage SP4, 25S, flow rate 25 ml/min, gradient 0% to 20% methanol in ethyl acetate) to give 1-ethyl-3-{3-[7-(1-methyl-1H-pyrazol-4-yl)-imidazo[1,2-a]pyridin-3-yl]-phenyl}-urea as a white solid (35 mg). MS: [M+H]$^+$ 361.

Procedure A4e—Using Microwave Conditions

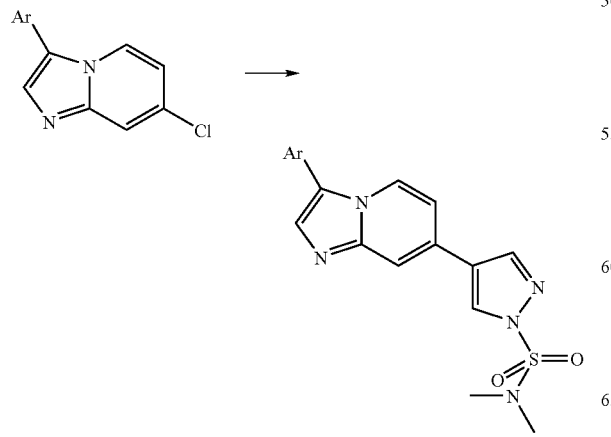

To a solution of 1-[3-(7-Chloro-imidazo[1,2-a]pyridin-3-yl)-phenyl]-3-(2,2,2-trifluoro-ethyl)-urea (370 mg, 1.0 mmol) and I40, 1-Dimethylsulfamoyl-1H-pyrazole-4-boronic acid (440 mg, 2.0 mmol) was added a solution of K$_3$PO$_4$ (636 mg, 3 mmol) in H$_2$O (1 ml). S-Phos (41 mg, 0.1 mmol) and Pd$_2$(dba)$_3$ (45 mg, 0.05 mmol) were added and the reaction mixture deoxygenated, then heated at 130° C. for 30 min using microwave irradiation. The reaction mixture was partitioned between H$_2$O and CH$_2$Cl$_2$, the resulting precipitate was collected by filtration and dried under vacuum to give a grey solid (350 mg). MS: [M+H]$^+$ 508

General Route B

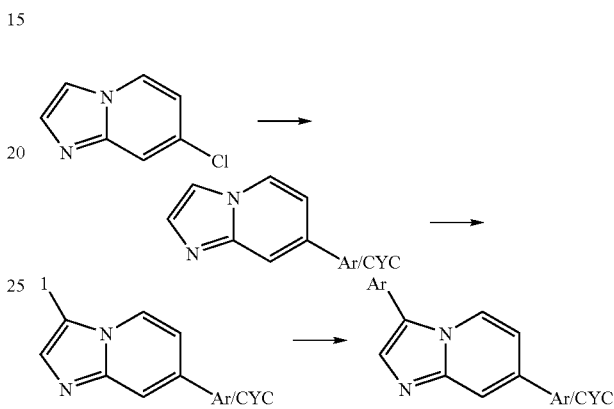

Procedure B1—General Palladium Mediated Addition of Cycle at the 7-Position

Procedure B1a—Suzuki for Aryl Cycles

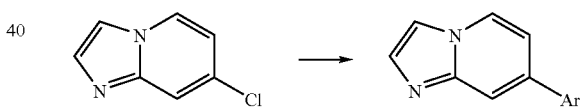

Method as described in General Route A Procedure 4a or 4b

Procedure B1b—Buchwald for Saturated Cycles

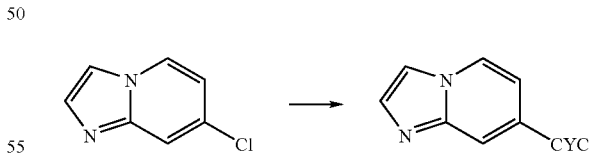

Method as described in General Route A Procedure 4c

Procedure B1c—Suzuki Coupling for Heterocycles

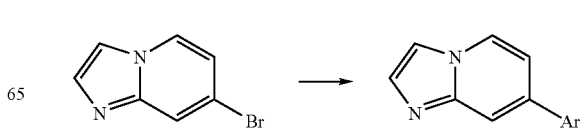

A solution of 7-Bromo-imidazol[1,2-a]pyridine (0.5 g, 2.54 mmol, 1 equivalent, made according to general procedure A1 using 4-bromo-pyridin-2-ylamine instead of 4-chloro-pyridin-2-ylamine), 1-methyl-5-(4,4,5,5-tetramethyl-[1,3,2]dioxaborolan-2-yl)-1H-pyrazole (1.1 g, 5.08 mmol, 2 equivalents), bis(tri-t-butylphosphine)palladium(0) (66 mg, 0.13 mmol, 0.05 equivalents) and potassium carbonate (2.1 g, 15.24 mmol, 6 equivalents) in ethanol (10 ml), toluene (10 ml) and water (10 ml) was heated at 75° C. for 2 hours. The reaction mixture was partitioned between ethyl acetate and water. The organic layer was then washed with a saturated brine solution, dried (MgSO$_4$), filtered and the solvent removed by evaporation in vacuo. The residue was purified by column chromatography (Biotage SP4, 25S, flow rate 25 ml/min, gradient 0% to 20% methanol in ethyl acetate) to give 7-(2-methyl-2H-pyrazol-3-yl)-imidazo[1,2,a]pyridine as a colourless oil (350 mg, 70%). MS: [M+H]$^{30}$ 199.

Procedure B1d

Synthesis of 7-[3-(4-Methyl-piperazin-1-ylmethyl)-phenyl]-imidazo[1,2-a]pyridine

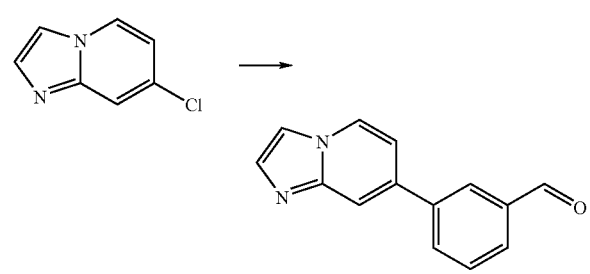

Method as described in General Route A Procedure A4a using 3-formylphenylboronic acid

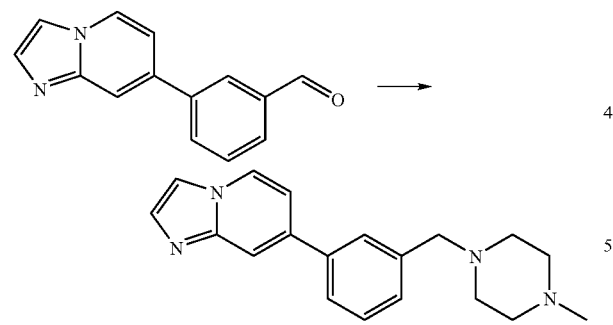

To a solution of 3-Imidazo[1,2-a]pyridin-7-yl-benzaldehyde (1.889 g, 8.5 mmol, 1.0 equiv) in toluene (30 ml) and methanol (10 ml) was added was added N-methylpiperazine (1.1 ml, 10.2 mmol, 1.2 equiv). The reaction mixture was stirred at room temperature for 3 h and the solvents were removed under reduced pressure. The resultant crude imine was dissolved in ethanol and methanol (1:1, 30 ml) and sodium borohydride (483 mg, 12.75 mmol, 1.5 equiv) was added portion-wise. The reaction mixture was stirred overnight and solvents were removed in vacuo. The reaction was quenched very slowly by the addition of aqueous 2N NaOH (20 ml). Ethyl acetate was added and the layers were separated. The organic layer was washed with brine, dried (MgSO$_4$), and concentrated under reduced pressure. The compound was purified by column chromatography (eluted with 5% methanol:dichloromethane) to afford desired compound.

Procedure B2—Iodination

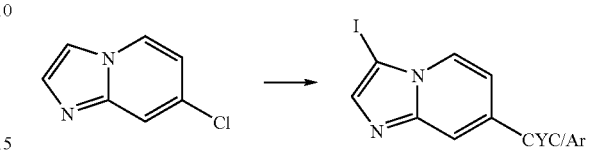

Method as described in General Route A Procedure A2

Procedure B3a—General Suzuki at the 3-Position

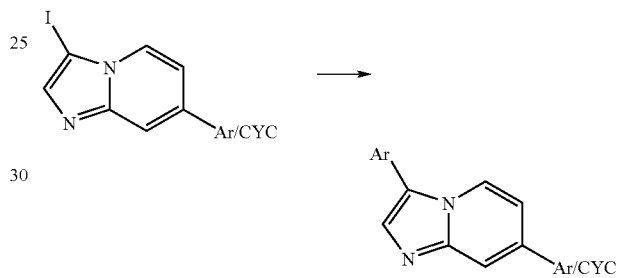

Method as described in General Route A Procedure A3a or A3b

Procedure B3b—General Suzuki at the 3-Position

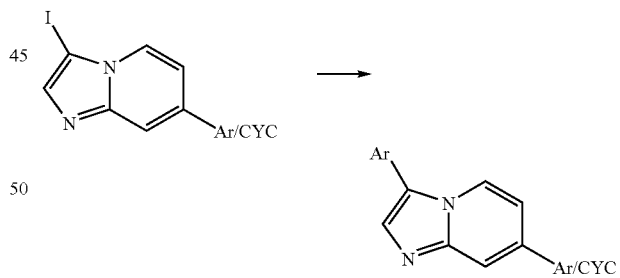

Method as described in General route B procedure B1c

General Route C—Synthesis of 3,6-Disubstituted Compounds

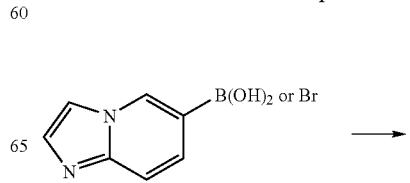

-continued

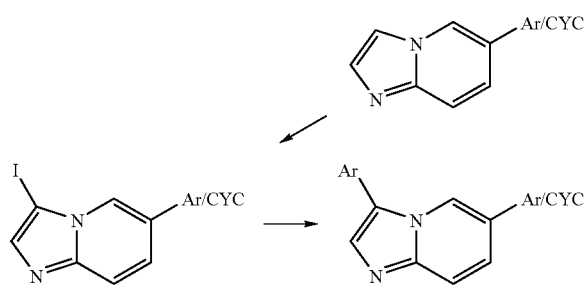

Procedure C1—General Palladium Mediated Addition of Cycle at 6 Position

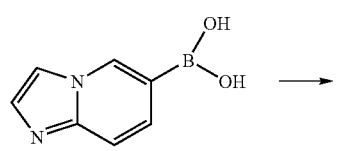

To a solution of imidazo[1,2-a]pyridin-6-ylboronic acid (0.162 g, 1 mmol) in EtOH (2.7 ml), toluene (2.7 ml) was added 3-bromoanisole (0.24 g, 1.3 mmol), 2M $Na_2CO_3$ (1.5 ml) [reaction degassed by bubbling $N_2$ through] followed by tetrakis (triphenylphosphine) palladium(O) (0.059 g, 0.05 mmol). The mixture was heated at 70° C. overnight, then diluted with water and extracted with EtOAc. The organic layer was washed with brine, dried ($MgSO_4$) and concentrated under reduced pressure. Residue then dried to afford (0.3 g) of the product MS: $[M+H]^+$ 225

Procedure C1 (b)—General Palladium Mediated Addition of Cycle at 6 Position

To a solution of 6-bromoimidazo[1,2a]pyridine (0.197 g, 1 mmol) in a mixture of EtOH (2.7 ml), and toluene (2.7 ml) was added 2-[3-methoxyphenyl]-4,4,5,5,-tetramethyl-[1,3,2]-dioxaborolane (0.304 g, 1.3 mmol), 2M $Na_2CO_3$ (1.5 ml) [reaction degassed by bubbling $N_2$ through] followed by tetrakis (triphenylphosphine) palladium(O) (0.059 g, 0.05 mmol). The mixture was heated at 70° C. for 2 hours, then diluted with water and extracted with EtOAc. The organic layer was washed with brine, dried ($MgSO_4$), filtered and concentrated under reduced pressure to afford (0.3 g) of the product MS: $[M+H]^+$225

Procedure C2—Iodination

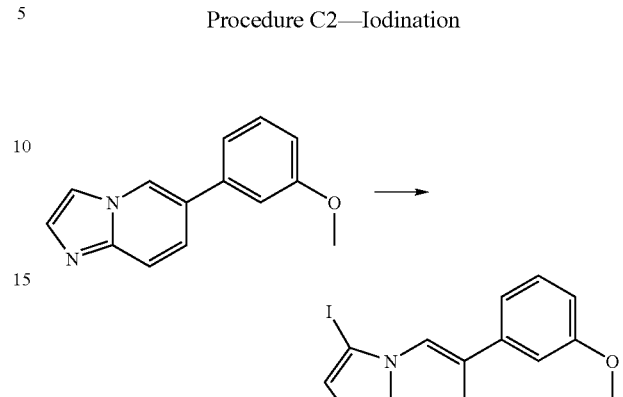

Method as described in General Route A Procedure A2

Procedure C3—General Suzuki at 3 Position

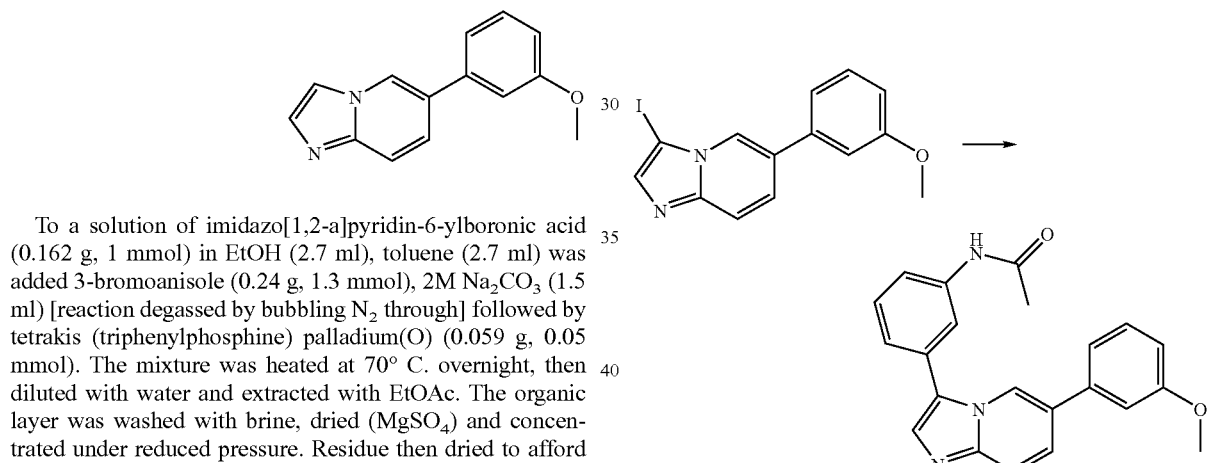

Method as described in General Route A Procedure 3b

General Route C4

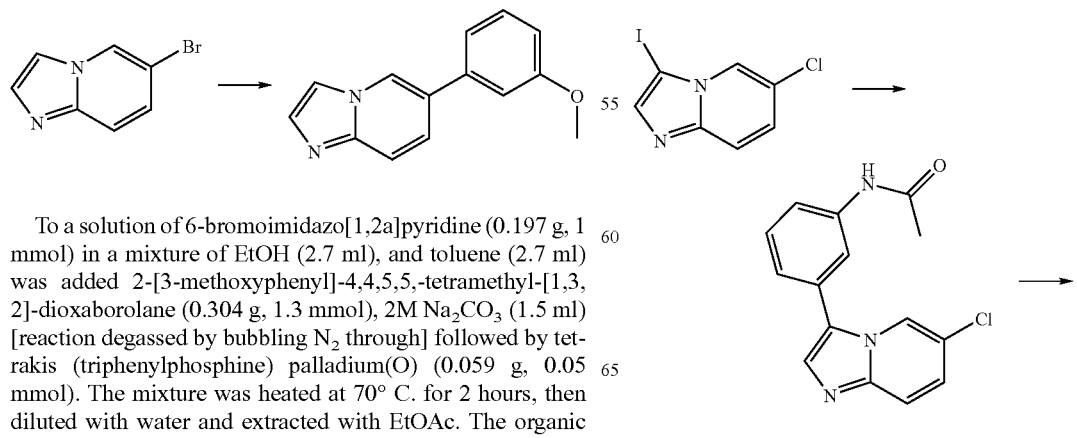

-continued

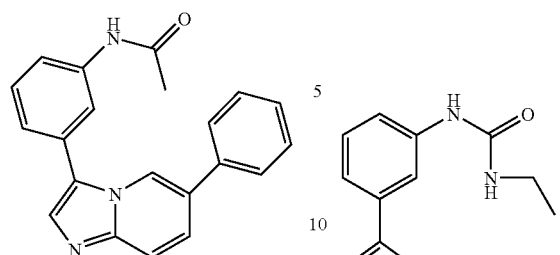

As procedure A3a

To a suspension of 6-Chloro-3-iodo-imidazo[1,2-a]pyridine (0.2 g, 0.71 mmol) in toluene (1 ml) was added (3-acetylaminophenyl)boronic acid (0.11 g, 0.71 mmol), $K_2CO_3$ (0.59 g, 3.55 mmol), MeOH (1 ml), EtOH (1 ml), $H_2O$ (1.5 ml) [reaction degassed by bubbling $N_2$ through] followed by bis(tri-t-butylphosphine)palladium(O) (0.006 g, 0.0116 mmol). The mixture was heated at 100° C. for 2 h then excess boronate (0.06 g) and bis(tri-t-butylphosphine)palladium(O) (0.006 g) was added and the reaction heated for a further 2 hours. The reaction was diluted with water and extracted with EtOAc. The organic layer was washed with brine, dried ($MgSO_4$), filtered and concentrated under reduced pressure to give 0.203 g of product. MS: $[M+H]^+$ 286

To a suspension of 1-[3-(6-Chloro-imidazo[1,2-a]pyridin-3-yl)-phenyl]-ethanone (0.1 g, 0.35 mmol), phenylboronic acid (0.043 g, 0.35 mmol), $K_2CO_3$ (0.29 g, 2.1 mmol), MeOH (0.5 ml), EtOH (0.5 ml), $H_2O$ (0.8 ml) [reaction degassed by bubbling $N_2$ through] was added bis(tri-t-butylphosphine) palladium(O) (0.004 g, 0.0077 mmol). The mixture was heated using microwave radiation in a CEM discover microwave synthesizer (50 W) at 155° C. until the reaction was complete. The reaction was diluted with water and extracted with EtOAc. The organic layer was washed with brine, dried ($MgSO_4$), filtered and concentrated under reduced pressure and purified by preparative HPLC to give 0.0014 g of product. MS: $[M+H]^+$ 328

General Modifications D at the 7-Position

Latent functionality at the 7-position of the imidazo[1,2-a]pyridine can be utilised in order to synthesise alternative motifs

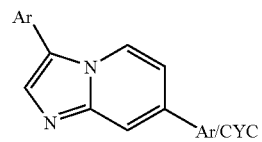

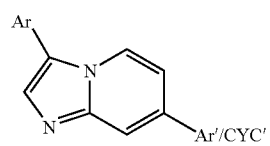

Procedure D1—Hydrogenation

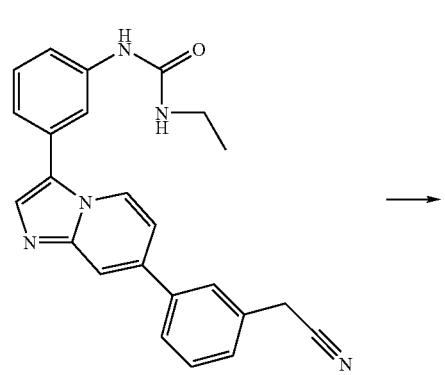

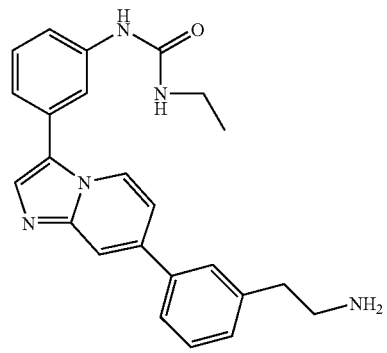

To a solution of 1-{3-[7-(3-Cyanomethyl-phenyl)-imidazo[1,2-a]pyridin-3-yl]-phenyl}-3-ethyl-urea (0.03 g, 0.76 mmol) in 2M methanolic ammonia (10 ml) was added Raney Ni. The mixture was shaken under a hydrogen atmosphere at ambient temperature for 48 h. Catalyst filtered through GF/A paper and filtrate reduced in vacuo, followed by trituration with MeOH and the solid dried to give 12 mgs of product. MS: $[M+H]^+$ 400

Procedure D2—Hydrolysis

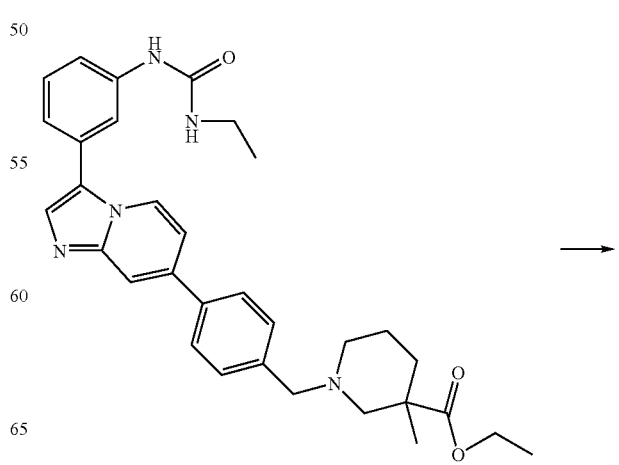

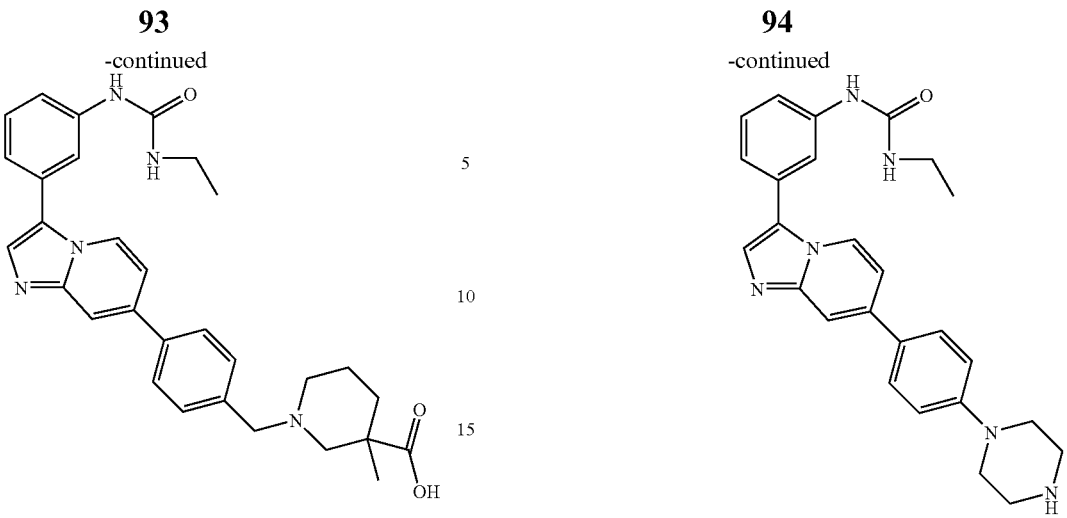

To a suspension of 1-(4-{3-[3-(3-Ethyl-ureido)-phenyl]-imidazo[1,2-a]pyridin-7-yl}-benzyl)-3-methyl-piperidine-3-carboxylic acid ethyl ester (0.020 g, 0.037 mmol) in EtOH (0.4 ml) was added 2M NaOH (0.48 ml). Reaction heated at 50° C. for 24 hours, concentrated under reduced pressure and purified by open access preparative HPLC to give 0.07 g of product. MS: [M+H]$^+$ 512

Procedure D3—Boc Deprotection

Procedure D3a—Boc Deprotection

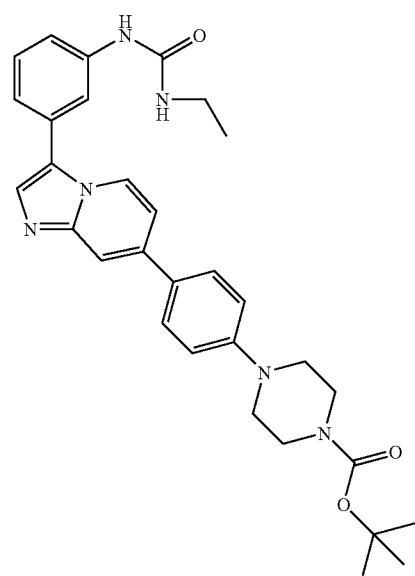

4-(4-{3-[3-(3-Ethyl-ureido)-phenyl]-imidazo[1,2-a]pyridin-7-yl}-phenyl)-piperazine-1-carboxylic acid tert-butyl ester (0.015 g, 0.027 mmol) treated with saturated EtOAc/HCl, stirred at ambient for 3 hours, concentrated under reduced pressure then dried to give (0.010 g) of product. MS: [M+H]$^+$ 441

D3b: Preparation of 1-(2-Amino-ethyl)-3-{3-[6-(4-fluoro-phenyl)-pyrazolo[1,5-a]pyrimidin-3-yl]-phenyl}-urea

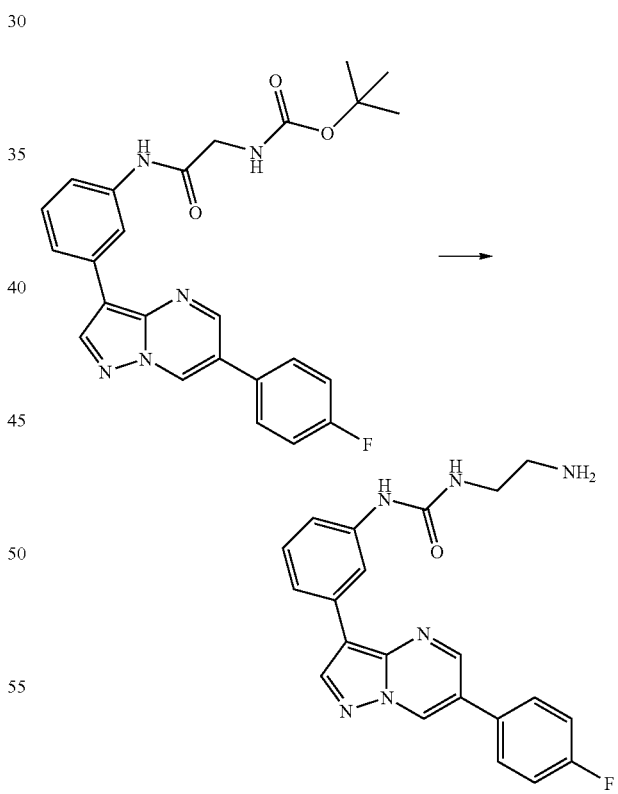

TFA (2 ml) was added slowly to a stirred suspension of [2-(3-{3-[6-(4-Fluoro-phenyl)-pyrazolo[1,5-a]pyrimidin-3-yl]phenyl}ureido)-ethyl]carbamic acid tert-butyl ester (390 mg, 0.80 mmol) in CH$_2$Cl$_2$ (4 ml) at RT. After 1 hour the volatiles were removed in vacuo. The residue was taken up in MeOH and loaded on a SCX cartridge (20 g). Eluting with 2M NH$_3$. MeOH and removal of the solvent in vacuo gave the title compound (155 mg) as a yellow solid.

Procedure D4—Pyridone Formation

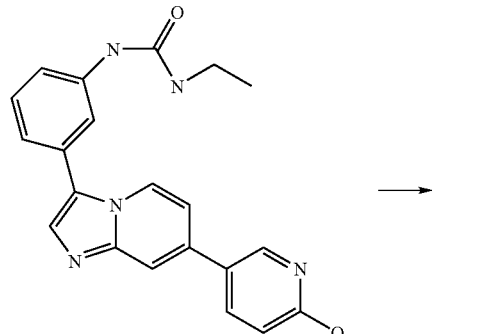

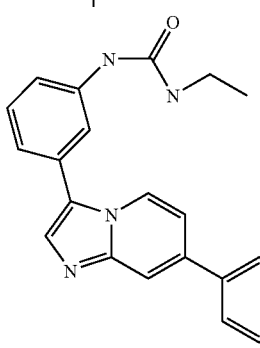

Procedure D4a

To 1-ethyl-3-{3-[7-(6-methoxy-pyridin-3-yl)-imidazo[1,2-a]pyridin-3-yl]-phenyl}-urea (0.1 g, 0.258 mmol) was added pyridine hydrochloride (0.59 g, 5.1 mmol). The mixture was heated at 150° C. for 15 mins, diluted with water, and the resulting precipitated solid filtered. The filtrate was concentrated under reduced pressure, purified by preparative HPLC to give (0.001 g) of product MS: [M+H]+ 374

Procedure D4b

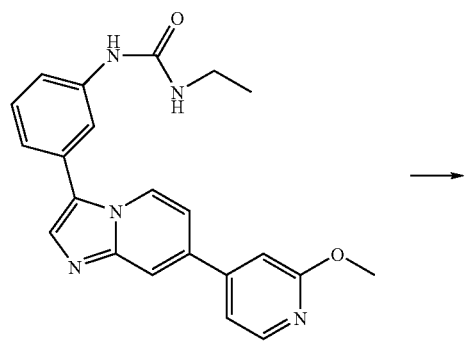

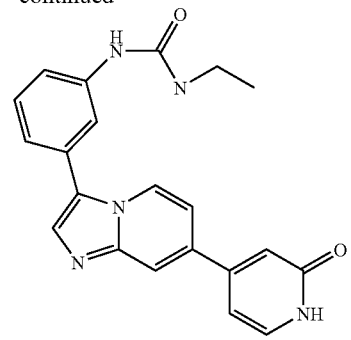

1-Ethyl-3-{3-[7-(2-methoxy-pyridin-4-yl)-imidazo[1,2-a]pyridin-3-yl]-phenyl}-urea (0.03 g, 0.077 mmol) was treated with saturated EtOAc/HCl (5 ml) and EtOH (5 ml) and heated 80° C. overnight. The reaction was concentrated under reduced pressure then triturated with EtOAc to give (0.02 g) of product MS: [M+H]+ 374.

General Modification D5—Pyridine N-Oxidation

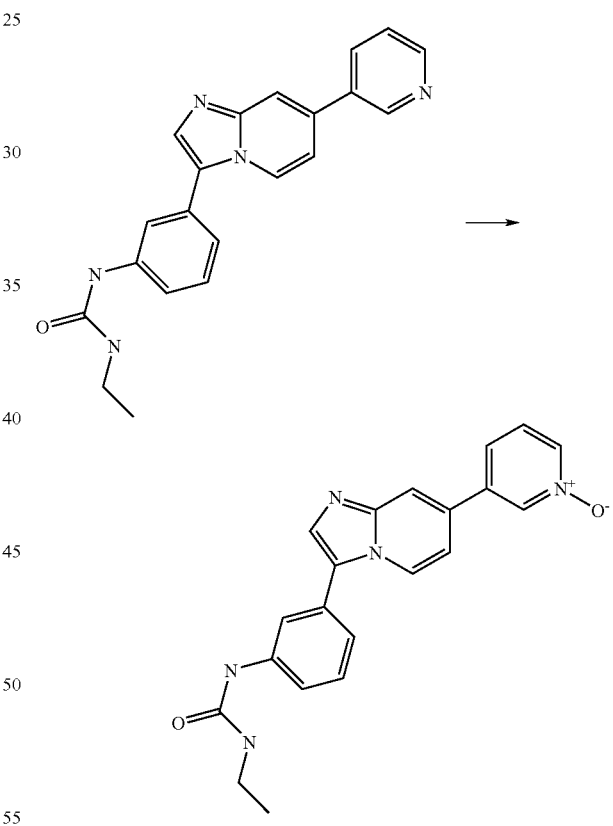

To a solution of 1-ethyl-3-[3-(7-pyridin-3-yl-imidazo[1,2-a]pyridin-3-yl)-phenyl]-urea (50 mg, 0.14 mmol, 1 equiv.) in $CH_2Cl_2$ (5 ml) was added mCPBA (29 mg, 0.17 mmol, 1.2 equiv.) and stirred at RT for 12 h. A further portion of mCPBA (29 mg, 0.17 mmol, 1.2 equiv.) and stirred at RT for 2 h. To the reaction mixture was added 2N NaOH and partitioned between $CH_2Cl_2$ and water. The organic layer was dried ($MgSO_4$), filtered and the solvent removed in vacuo. The resultant oil that separated was purified with by column chromatography ($SiO_2$) eluted with 10% $MeOH:CH_2Cl_2$ to afford the N-oxide as a yellow solid (7 mg, 13%)

97
General Modification D6—Debenzylation

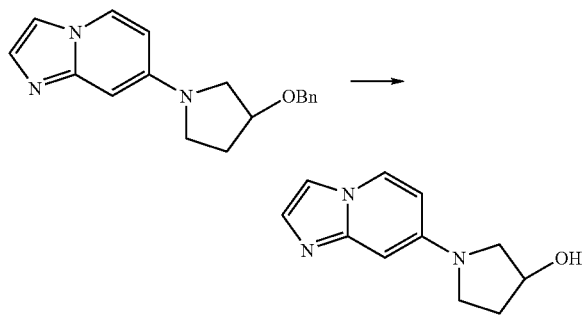

7-(3-Benzyloxypyrrolidin-1-yl)-imidazo[1,2-a]pyridine (68 mg, 0.23 mmol) was dissolved in $CH_2Cl_2$ and cooled to 0° C. Trimethylsilyl iodide (41 µL, 1.3 equiv) was added before the solution was allowed to warm to room temperature and stirred for a further 30 min. MeOH (4 mL, excess) was added and the reaction mixture was concentrated under reduced pressure. The product was purified by column chromatography (0-80% MeOH in $Et_2O$). MS: [M+H]+ 204.

Procedure D7

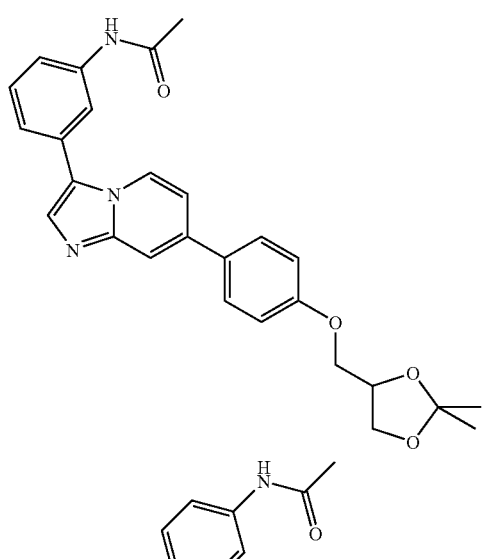

To a solution of N-[(E)-3-{7-[4-(2,2-Dimethyl-[1,3]dioxolan-4-ylmethoxy)-phenyl]-imidazo[1,2-a]pyridin-3-yl}-1-eth-(E)-ylidene-but-2-enyl]-acetamide(0.24 g, 0.52 mmol) in MeOH (3 ml) added 1M HCl (2 ml) stirred ambient for 1 hour, concentrated under reduced pressure and purified by preparative LC to give 0.06 g of product. MS: [M+H]$^+$ 418

98
Procedure D8—Demethylation

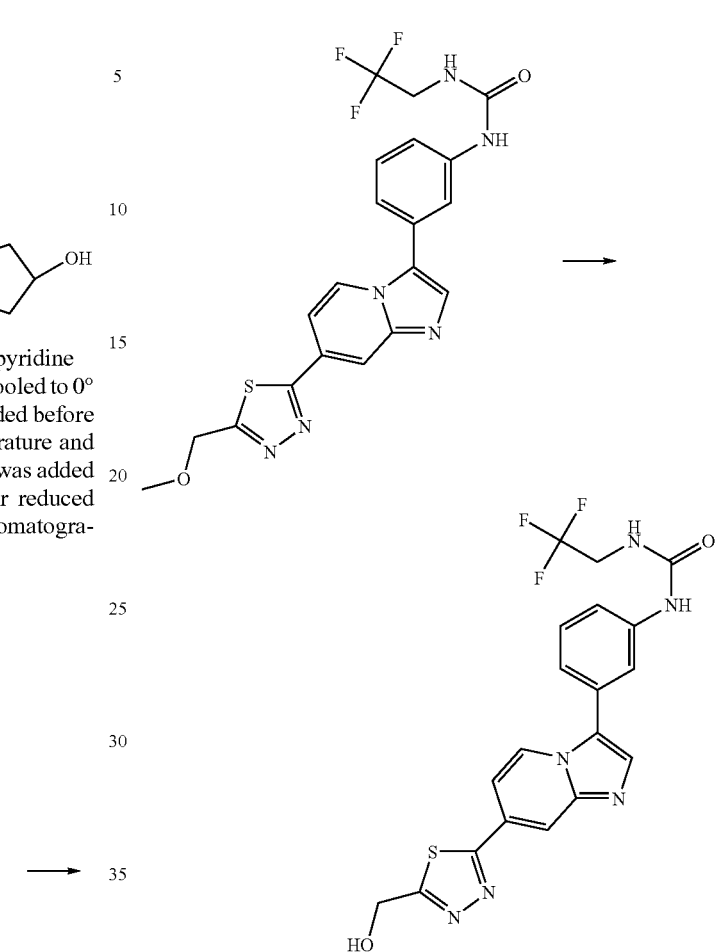

To a solution of 1-{3-[7-(5-methoxymethyl-[1,3,4]thiadiazol-2-yl)-imidazo[1,2-a]pyridin-3-yl]-phenyl}-3-(2,2,2-trifluoro-ethyl)-urea (280 mg, 0.60 mmol) in $CHCl_3$ (1 ml) at −78° C. was added a 1M solution of $BBr_3$ in $CH_2Cl_2$ (1.84 ml). The reaction was stirred for 1 h before being warmed to room temperature and then quenched by pouring in saturated bicarbonate solution. The resulting solid was filtered off and washed with $CH_2Cl_2$ and EtOAc, then purified by preparative HPLC to afford the desired compound (5 mg). MS: [M+H]$^+$ 449.

General Modifications E at the 7-Position

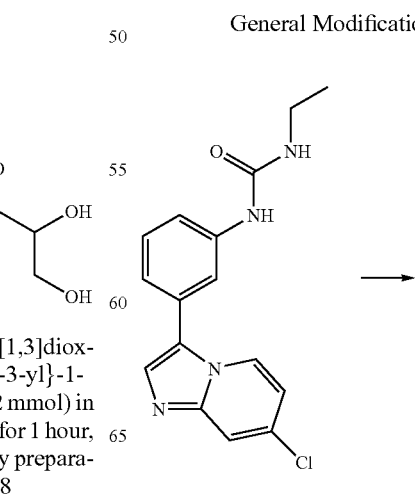

-continued

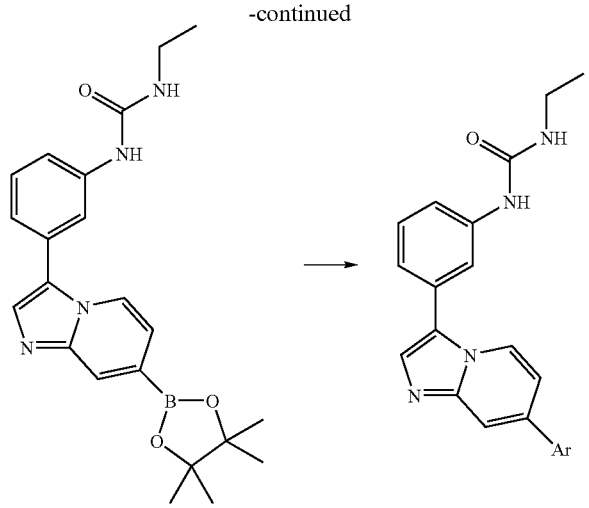

Procedure E1—Synthesis of 1-Bromo-3-(2-methoxy-ethoxy)-benzene

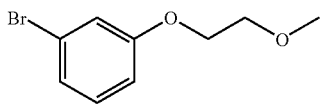

To a solution of 3-bromophenol (0.865 g, 5 mmol) in MeOH (1.5 ml) was added 2-bromoethyl methyl ether (0.56 ml, 6 mmol) followed by K$_2$CO3 (0.68 g, 5 mmol). The mixture was heated using microwave irradiation in a CEM discover microwave synthesizer (50 W) at 100° C. until the reaction was complete. The reaction was diluted with ether and filtered to remove solid which was washed with further ether. Filtrate concentrated under reduced pressure to give (0.8 g) of product.

Procedure E2—Conversion of Halide to Boronic Acid

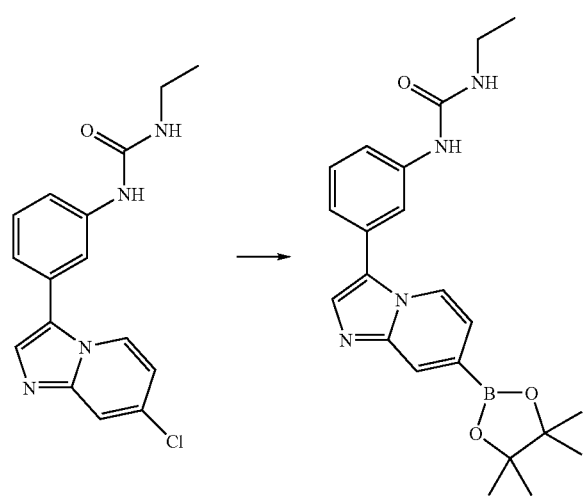 [SMILES: CCNC(=O)Nc1cccc(-c2cnc3cc(Cl)ccn23)c1 ; CCNC(=O)Nc1cccc(-c2cnc3cc(B4OC(C)(C)C(C)(C)O4)ccn23)c1]

To a solution of 1-[3-(7-Chloro-imidazo[1,2-a]pyridin-3-yl)-phenyl]-3-ethyl-urea (0.258 g, 0.82 mmol) in dioxane (5 ml) was added tricyclohexylphosphine (0.028 g, 0.098 mmol), KOAc (0.12 g, 1.23 mmol), bis(pinacolato)boron (0.23 g, 0.9 mmol) [reaction degassed by bubbling N$_2$ through] followed by Pd$_2$(dba)$_3$ (0.038 g). The mixture was heated at 80° C. overnight, then filtered through GFA paper, washed with CH$_2$Cl$_2$ and concentrated under reduced pressure. Reaction mixture used crude assumed quantitative.

Procedure E3—Boronate to Aryl Group Using Suzuki Reaction

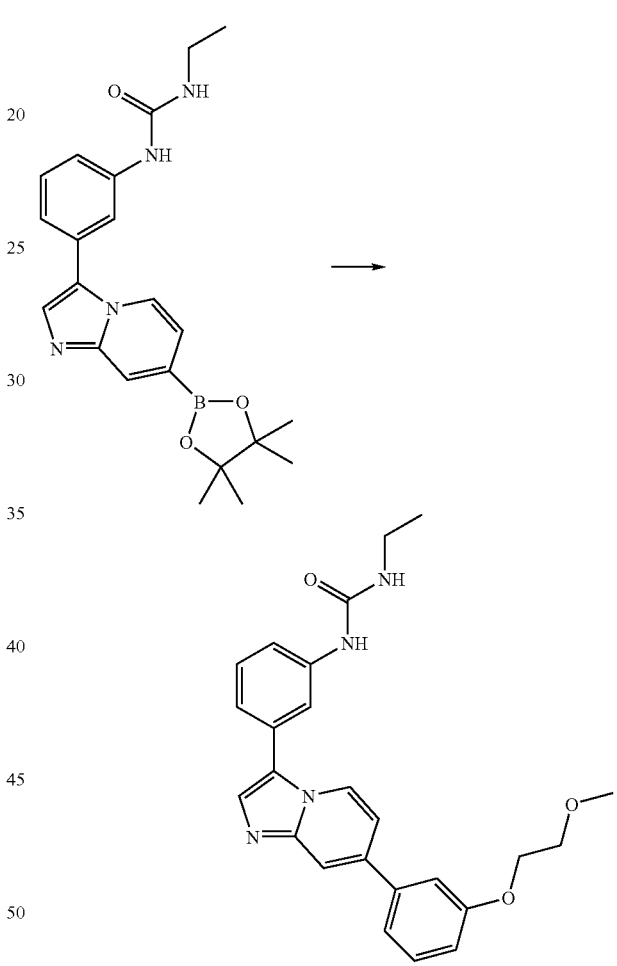

To a solution of 1-Ethyl-3-{3-[7-(4,4,5,5-tetramethyl-[1,3,2]dioxaborolan-2-yl)-imidazo[1,2-a]pyridin-3-yl]-phenyl}-urea (0.333 g, 0.82 mmol) in dioxane (5 ml) and water (2.5 ml) was added Dicyclohexyl-(2',6'-dimethoxy-biphenyl-2-yl)-phosphane [S-PHOS] (0.038 g, 0.0625 mmol), potassium phosphate (0.31 g, 1.6 mmol) [reaction degassed by bubbling N$_2$ through] followed by palladium II acetate (0.008 g, 0.04 mmol). The mixture was heated at 80° C. for 48 h, concentrated under reduced pressure then triturated with CH$_2$Cl$_2$, filtered and solid washed with further CH$_2$Cl$_2$ Filtrate concentrated under reduced pressure purified by preparative HPLC to give impure product. Mixture columned using SCX cartridge to give (0.004 g) of product MS: [M+H]$^+$ 431

Procedure E3b—Suzuki

Using the conditions described in generic Suzuki A4b.

Procedure E3c—{3-[7-(1-Methyl-1H-imidazol-4-yl)-imidazo[1,2-a]pyridin-3-yl]phenyl}-3-(2,2,2-trifluoro-ethyl)-urea Procedure E3c is using the conditions described in generic Suzuki A4e To a stirred mixture of 1-[3-(7-Boronic acid-imidazo[1,2-a]pyridn-3-yl)-phenyl]-3-(2,2,2-trifluoro-ethyl)-urea (0.15 g, 0.39 mmol), in a MW tube was added 4-iodo-1-methyl-1H-imidazole (83 mg, 0.39 mmol), SPHOS (6.5 mg, 0.016 mmol) and Pd$_2$(dba)$_3$ (7 mg, 0.0076 mmol) in dioxane (2 ml) followed by K$_3$PO$_4$ (252 mg, 1.18 mmol) in water (1.2 ml). The reaction mixture was heated in a CEM discover microwave synthesizer (300 W) at 120° C. for hr. The mixture was allowed to cool, then partitioned between EtOAc/H$_2$O, the organic layer was separated, dried (MgSO$_4$), filtered and the solvent removed in vacuo. The residue was purified by prep HPLC to afford the desired product (8 mg) MS: [M+H]$^+$=415.

Procedure E3d—1-{3-[7-(2-Methyl-thiazol-4-yl)-imidazo[1,2-a]pyridin-3-yl]-phenyl}-3-(2,2,2-trifluoro-ethyl)-urea

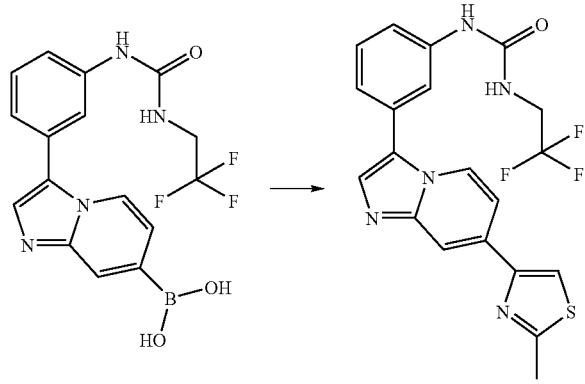 [SMILES: O=C(NCC(F)(F)F)Nc1cccc(-c2cnc3cc(B(O)O)ccn23)c1 ; Cc1nc(-c2ccn3c(-c4cccc(NC(=O)NCC(F)(F)F)c4)cnc3c2)cs1]

To a stirred mixture of 1-[3-(7-Boronic acid-imidazo[1,2-a]pyridn-3-yl)-phenyl]-3-(2,2,2-trifluoro-ethyl)-urea (200 mg, 0.26 mmol), 4-bromo-2-methyl thiazole (61 mg, 0.34 mmol) and K$_3$PO$_4$ (168 mg, 0.79 mmol) in dioxane (4 ml) and water (1 ml) [reaction degassed by bubbling N$_2$ through] was added PdCl$_2$dppf (19 mg, 0.3 mmol). The reaction mixture was then heated at 80° C. for 4 h. The mixture was allowed to cool, then partitioned between EtOAc/H$_2$O, the organic layer was separated, dried (MgSO$_4$), filtered and the solvent removed in vacuo. The residue was purified by prep HPLC to afford the desired product (26 mg). MS: [M+H]$^+$=432.

Procedure E3e

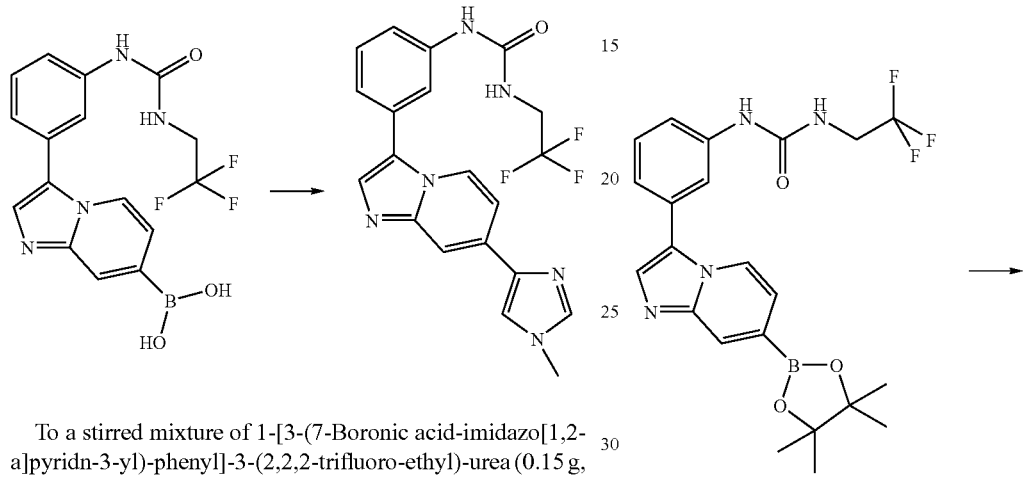

To a solution of 1-{3-[7-(4,4,5,5-tetramethyl-[1,3,2]dioxaborolan-2-yl)-imidazo[1,2-a]pyridin-3-yl]-phenyl}-3-(2,2,2-trifluoro-ethyl)-urea (107 mg, 0.23 mmol) and 2-bromo-[1,3,4]thiadiazole (96 mg, 0.58 mmol) in a mixture of toluene (2 ml), "butanol (2 ml) and water (0.5 ml) was added cesium carbonate (228 mg, 0.7 mmol). The reaction mixture was deoxygenated and tetrakis(triphenylphosphine)palladium (O) (81 mg, 0.07 mmol) added. The reaction mixture was again degassed and heated at 80° C. overnight. The mixture was cooled, partitioned between EtOAc and H$_2$O, the organic layer separated, dried (MgSO$_4$), filtered and the solvent remove in vacuo. The crude product was purified by preparative HPLC to give the 18 mg of product. MS: [M+H]$^+$ 419.

General Modifications F at the 3-Position

Latent functionality at the 3-position of the imidazo[1,2-a]pyridine can be utilised in order to synthesise alternative motifs

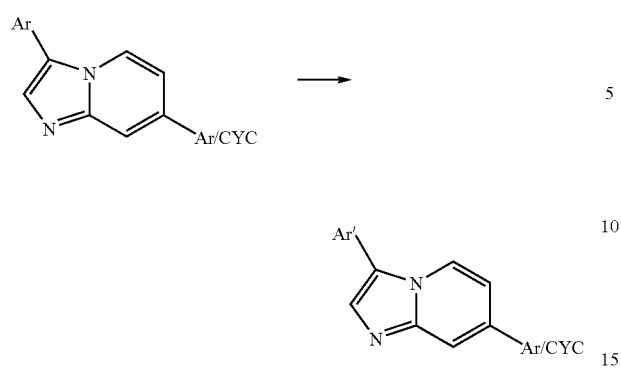

Procedure F1a—Urea Formation

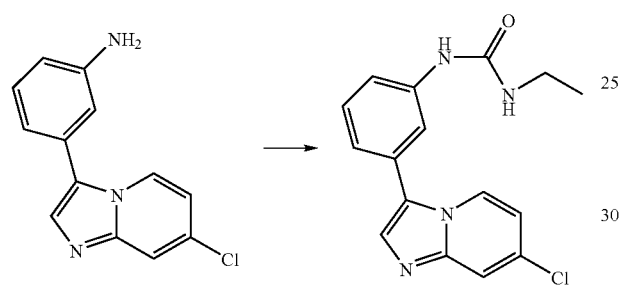

To a solution of 3-(7-Chloro-imidazo[1,2-a]pyridin-3-yl)-phenylamine [Method as described in procedure A3a] (1.9 g, 7.8 mmol) in THF (30 ml) was added triethylamine (3.3 ml, 23.4 mmol) and ethyl isocyanate (0.93 ml, 11.7 mmol) drop wise. The mixture was stirred at 50° C. for 2 h and the mixture was evaporated under reduced pressure. The crude mixture was partitioned between water and EtOAc and the organic layer was washed with water then brine, dried (MgSO$_4$), filtered and concentrated under reduced pressure. The product was purified by Biotage (SiO$_2$, eluted with 50% EtOAC/petrol, EtOAc, 10% MeOH/EtOAC) to afford 1.1 g of product.

Procedure F1b—2 Step Urea Formation

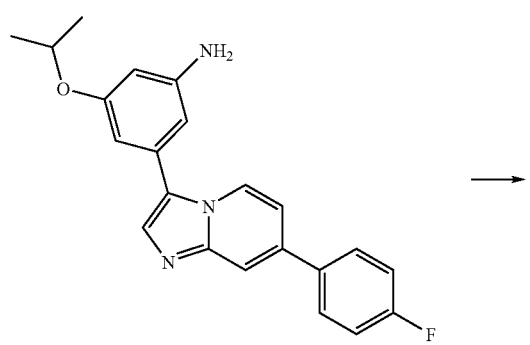

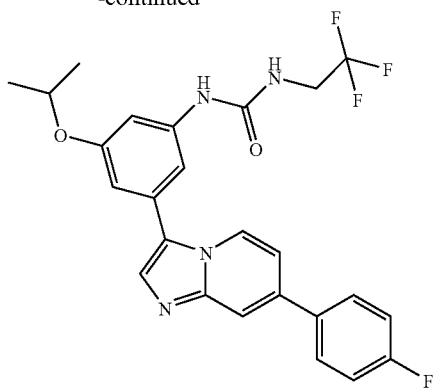

A mixture of 3-[7-(4-Fluoro-phenyl)-imidazo[1,2-a]pyridin-3-yl]-5-isopropoxy-phenylamine (90 mg, 0.25 mmol) and p-nitrophenylchloroformate (50 mg, 0.25 mmol) in DME (1.5 ml) were heated at 60° C. for 2 h. After cooling to room temperature, DIPEA (0.13 ml, 0.75 mmol) and 2,2,2-Trifluoro-ethylamine (0.12 ml, 1.50 mmol) were added and the mixture stirred for 3 days. The solvent was removed in vacuo and the crude residue purified by reverse phase HPLC. The resulting material was subsequently purified using a SCX cartridge to afford the product as a light brown solid. MS: [M+H]$^+$ 487.

Procedure F2—Sulfonyl Urea Formation

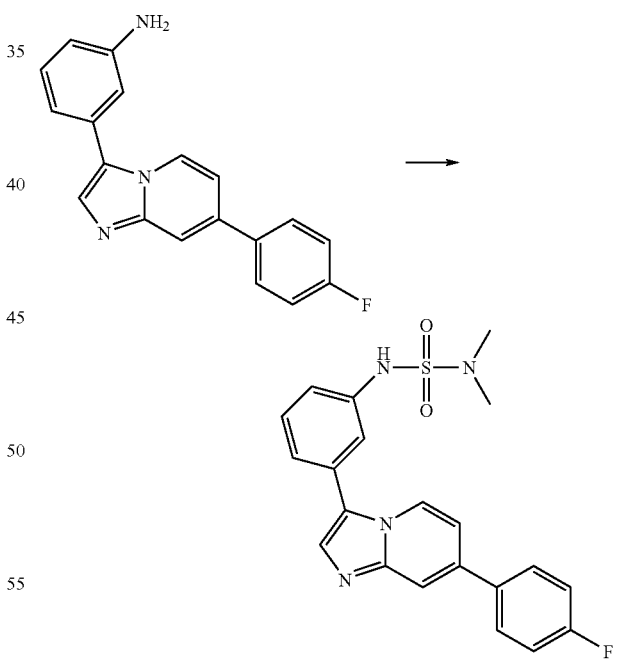

To a solution of 3-[7-(4-Fluoro-phenyl)-imidazo[1,2-a]pyridin-3-yl]-phenylamine (100 mg, 0.33 mmol, 1.0 equiv) in THF (3.3 ml) was added triethylamine (0.14 ml, 1.0 mmol, 3.0 equiv) and dimethylsulfamoyl chloride (0.069 ml, 0.5 mmol, 1.5 equiv) dropwise. The mixture was stirred at 60° C. overnight and the mixture was evaporated under reduced pressure. The crude mixture was partitioned between water and EtOAc and the organic layer was washed with brine, dried

Procedure F3a—Amide Formation

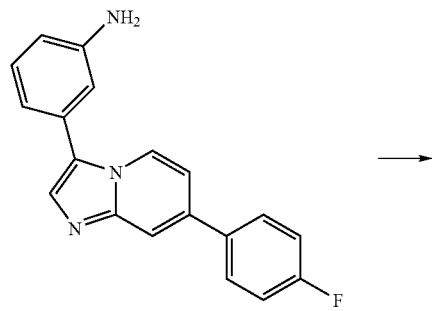

To a solution of 3-[7-(4-Fluoro-phenyl)-imidazo[1,2-a]pyridin-3-yl]-phenylamine (100 mg, 0.33 mmol, 1.0 equiv) and glycolic acid (34 µl, 0.4 mmol, 1.2 equiv) in DMF (2 ml) was added N-(3-dimethylaminopropyl)-N'-ethylcarbodiimide hydrochloride (70 mg, 0.36 mmol, 1.1 equiv) and 1-hydroxybenzotriazole (49 mg, 0.36 mmol, 1.1 equiv). The reaction mixture was stirred at 60° C. overnight. The solvent was removed and water was added to form a gum. Ethyl acetate was added to form a precipitate that was filtered to afford the desired compound (20 mg).

Procedure F3b—Amide Formation

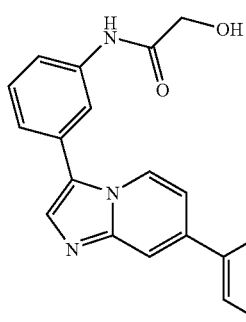

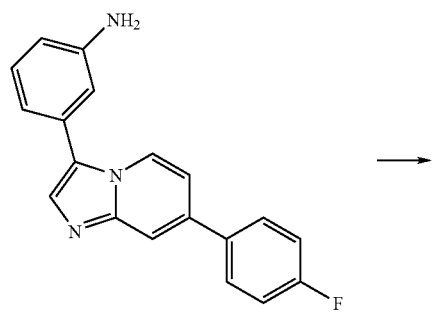

To a solution of 3-[7-(4-Fluoro-phenyl)-imidazo[1,2-a]pyridin-3-yl]-phenylamine (0.1 g, 0.33 mmol) in THF (3 ml) was added triethylamine (0.09 ml, 0.66 mol), followed by dropwise addition of propionyl chloride (28 µl, 0.33 mmol). The reaction was stirred at RT overnight, before the solvent was removed in vacuo. The residue was triturated with EtOAc and the solid filtered off. The filtrate was evaporated down and the resulting residue triturated with MeOH, to afford the desired product. (0.04 g). MS: [M+H]$^+$=360.

Procedure F4—Carbamate Formation

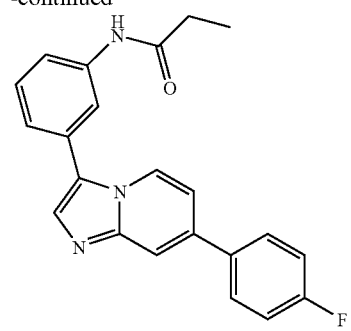

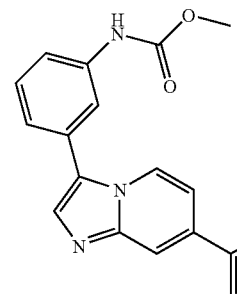

To a solution of 3-[7-(4-Fluoro-phenyl)-imidazo[1,2-a]pyridin-3-yl]-phenylamine (0.1 g, 0.33 mol) in THF (3.3 ml) was added triethylamine (0.138 ml, 0.99 mmol), followed by dropwise addition of methyl chloroformate (38 ml, 0.50 mmol). The reaction mixture was stirred at 60° C. overnight, cooled and the solvent removed in vacuo. The residue was partitioned between EtOAc and H$_2$O, the organic layer separated, dried (MgSO$_4$), filtered and the solvent removed in vacuo. The crude material was purified by reverse phase HPLC to afford the product (33 mg). MS: [M+H]$^+$=362.

Procedure F5—Synthesis of Triazole-3-Thiones

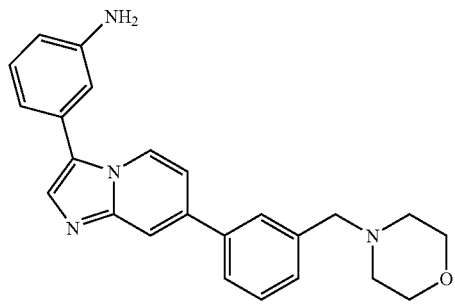

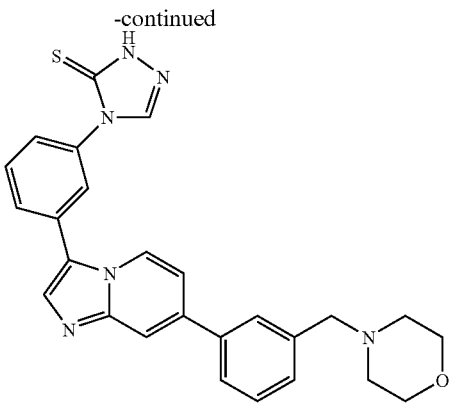

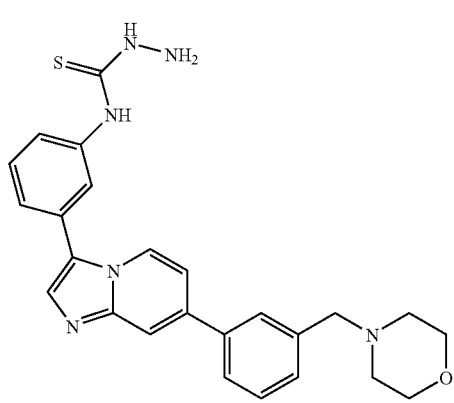

To a suspension of 3-[7-(3-Morpholin-4-ylmethyl-phenyl)-imidazo[1,2-a]pyridin-3-yl]-phenylamine (0.25 g, 0.65 mmol) in anhydrous toluene (20 ml) was added 1,1'-thiocarbonyldi-2(1 h)-pyridone (0.51 g, 0.65 mmol) stirred and heated at 110° C. for 1 h. The reaction was cooled to ambient, diluted $CH_2Cl_2$ washed with water and brine, dried ($Na_2SO_4$) filtered and concentrated under reduced pressure to give a brown oil. Residue taken up in THF (4 ml), cooled in an ice bath and treated with hydrazine hydrate (0.05 ml, 9.7 mmol). After complete addition, the reaction was stirred at this temperature for 15 mins and concentrated under reduced pressure. This material was used without further purification in the step below.

To a solution of thiosemicarbazide (0.305 g, 0.66 mmol) in anhydrous DMF (5 ml) was added diethyl chlorophosphate (0.23 ml, 1.58 mmol) dropwise such that the internal temperature remained <25° C. After 30 mins, further diethyl chlorophosphate added. The reaction mixture was poured in to $H_2O$ and extracted with EtOAc. The aqueous fraction was concentrated under reduced pressure, the residue triturated with hot ethanol, and the solid filtered off. The filtrate was concentrated under reduced pressure and purified by preparative HPLC to give 0.08 g of product. MS: $[M+H]^+$ 469

This reaction can also be used to synthesise the alternative cyclisation product, the amino-thiadiazole.

Procedure F6—Reductive Amination

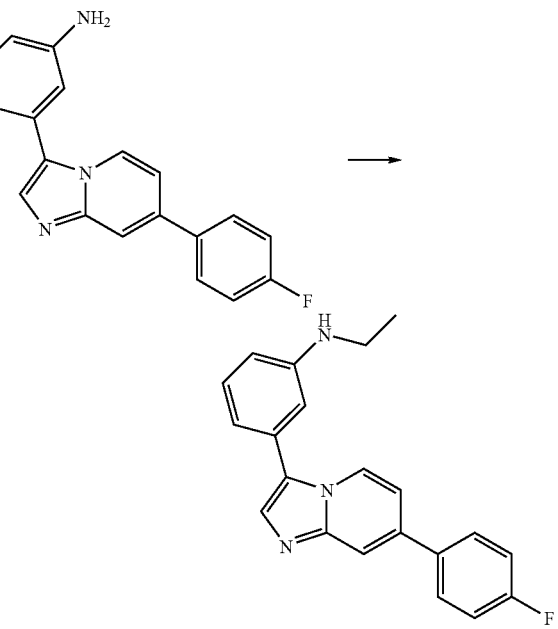

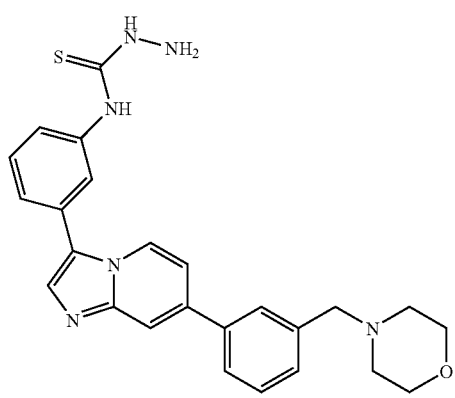

To a solution of 3-[7-(4-Fluoro-phenyl)-imidazo[1,2-a]pyridin-3-yl]-phenylamine (100 mg, 0.33 mmol, 1.0 equiv) in toluene (30 ml) and methanol (10 ml) was added was added acetaldehyde (17 μl, 0.40 mmol, 1.2 equiv). The reaction mixture was stirred at room temperature for 3 h and the solvent was removed under reduced pressure. The resultant crude imine was dissolved in ethanol and methanol (1:1, 30 ml) and sodium borohydride (20 mg, 0.5 mmol, 1.5 equiv) was added portion-wise. The reaction mixture was stirred overnight and solvents were removed in vacuo. The reaction was quenched very slowly by the addition of aqueous 2N NaOH (20 ml). Ethyl acetate was added and the layers were separated. The organic layer was washed with brine, dried ($MgSO_4$), and concentrated under reduced pressure. The compound was purified by preparative HPLC to afford desired compound.

109

Procedure F7—Alkylation

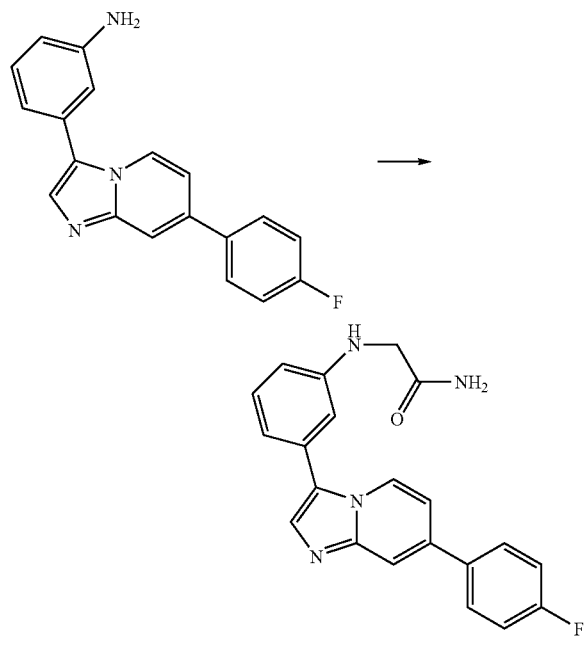

To a solution of 3-[7-(4-fluoro-phenyl)-imidazo[1,2-a]pyridin-3-yl]-phenylamine (100 mg, 0.33 mmol) [Method as described in procedure A3a] in EtOH (0.5 ml) was added 2-chloro-acetamide (30 mg, 0.33 mmol) and anhydrous sodium acetate (54 mg, 0.66 mmol). The reaction was heated at 78° C. for 18 h. The reaction mixture was triturated with MeOH and the resulting solid filtered off. The solid was furthered purified by reverse phase HPLC to afford the desired product (7 mg). MS: [M+H]+ 361.

General Procedure H—Synthesis of Trisubstituted Benzene Analogues at the 3-Position of Imidazo[1,2-a]pyridine Procedure H1: 3-[7-(3-Morpholin-4-ylmethyl-phenyl)-imidazo[1,2-a]pyridin-3-yl]-5-nitro-benzamide

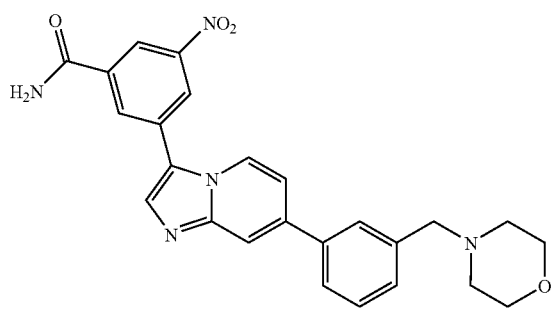 [SMILES: NC(=O)c1cc(-c2cnc3cc(-c4cccc(CN5CCOCC5)c4)ccn23)cc([N+](=O)[O-])c1]

Prepared using general route A procedure A3b, substituting (3-aminocarbonyl-5-nitrophenyl)boronic acid for 3-aminobenzeneboronic acid. MS: [M+H]+ 458.

110

Procedure H2

3-Amino-5-[7-(3-morpholin-4-ylmethyl-phenyl)-imidazo[1,2-a]pyridin-3-yl]-benzamide

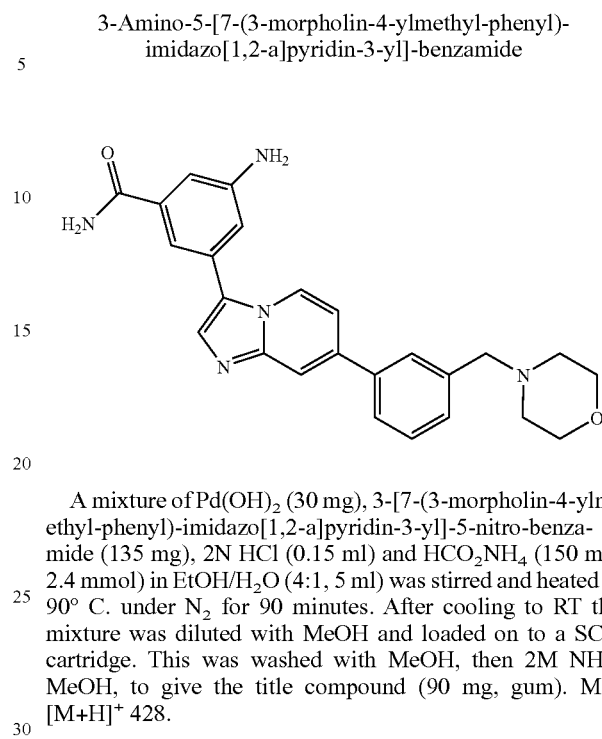

A mixture of Pd(OH)$_2$ (30 mg), 3-[7-(3-morpholin-4-ylmethyl-phenyl)-imidazo[1,2-a]pyridin-3-yl]-5-nitro-benzamide (135 mg), 2N HCl (0.15 ml) and HCO$_2$NH$_4$ (150 mg, 2.4 mmol) in EtOH/H$_2$O (4:1, 5 ml) was stirred and heated at 90° C. under N$_2$ for 90 minutes. After cooling to RT the mixture was diluted with MeOH and loaded on to a SCX cartridge. This was washed with MeOH, then 2M NH$_3$-MeOH, to give the title compound (90 mg, gum). MS: [M+H]+ 428.

Procedure H3

3-Acetylamino-5-[7-(3-morpholin-4-ylmethyl-phenyl)-imidazo[1,2-a]pyridin-3-yl]-benzamide

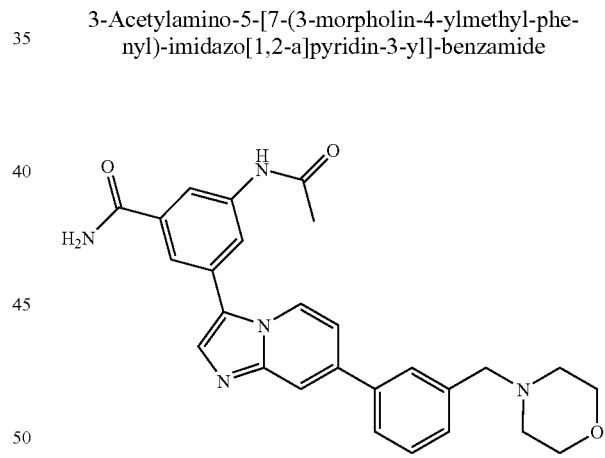

A mixture of 3-Amino-5-[7-(3-morpholin-4-ylmethyl-phenyl)-imidazo[1,2-a]pyridin-3-yl]-benzamide (90 mg), AcOH (29 µL, 0.5 mmol), 1-hydroxybenzotriazole (68 mg, 0.5 mmol) and N-(3-dimethylaminopropyl)-N'-ethylcarbodiimide hydrochloride (96 mg, 0.5 mmol) in dry DMF (2 ml) was stirred at RT under N$_2$ for 24 h. The mixture was partitioned between CH$_2$Cl$_2$/H$_2$O. The layers were separated and the aqueous layer was loaded on to a SCX cartridge. This was washed with MeOH, then 2M NH$_3$-MeOH. The NH$_3$-MeOH fraction was evaporated and the residue was purified by preparative HPLC to give the title compound (40 mg, solid). $^1$H NMR (400 MHz, DMSO-d$_6$): 10.26 (1H, s), 8.68 (1H, d), 8.12 (1H, s), 8.07 (2H, brs), 7.99 (1H, s), 7.87 (1H, s), 7.83 (1H, s), 7.81-7.72 (2H, m), 7.54-7.43 (2H, m), 7.43-7.34 (2H, m), 3.66-3.54 (6H, m), 2.47-2.36 (4H, m), 2.11 (3H, s).

Procedure H4: N-{3-Cyano-5-[7-(3-morpholin-4-ylmethyl-phenyl)-imidazo[1,2-a]pyridin-3-yl]-phenyl}-acetamide This was prepared as described in General Procedure H Steps H1 and H3, substituting 3-amino-5-cyanophenylboronic acid for 3-aminocarbonyl-5-nitrophenylboronic acid in Step 1. $^1$H NMR (400 MHz, DMSO-$d_6$): 10.45 (1H, s), 8.71 (1H, d), 8.12 (1H, t), 8.08 (1H, t), 8.01 (1H, brs), 7.94 (1H, s), 7.88 (1H, t), 7.82-7.72 (2H, m), 7.49 (1H, t), 7.44-7.35 (2H, m), 3.67-3.54 (6H, m), 2.47-2.36 (4H, m), 2.13 (3H, s).

Procedure H5: N-{3-Methoxy-5-[7-(3-morpholin-4-ylmethyl-phenyl)-imidazo[1,2-a]pyridin-3-yl]-phenyl}-acetamide

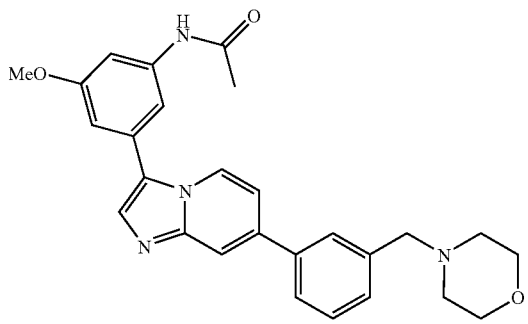 [SMILES: COc1cc(NC(C)=O)cc(-c2cnc3cc(-c4cccc(CN5CCOCC5)c4)ccn23)c1]

This was prepared as described in Example H Steps H1, H2 and H3, substituting 3-methoxy-5-nitro-phenyl boronic acid pinacol ester (18) for 3-aminocarbonyl-5-nitro phenylboronic acid in Step 1. $^1$H NMR (400 MHz, DMSO-$d_6$): 10.11 (1H, s), 8.64 (1H, d), 7.97 (1H, s), 7.82 (1H, s), 7.78-7.73 (2H, m), 7.51-7.45 (2H, m), 7.40-7.36 (2H, m), 7.33 (1H, t), 6.93 (1H, dd), 3.83 (3H, s), 3.63-3.55 (6H, m), 2.41 (4H, s), 2.08 (3H, s).

Procedure I—Synthesis of Boronic Acids and Esters

Boronic Acid I1

2-Methoxy-N-[4-(4,4,5,5-tetramethyl-[1,3,2]dioxaborolan-2-yl)-phenyl]-acetamide

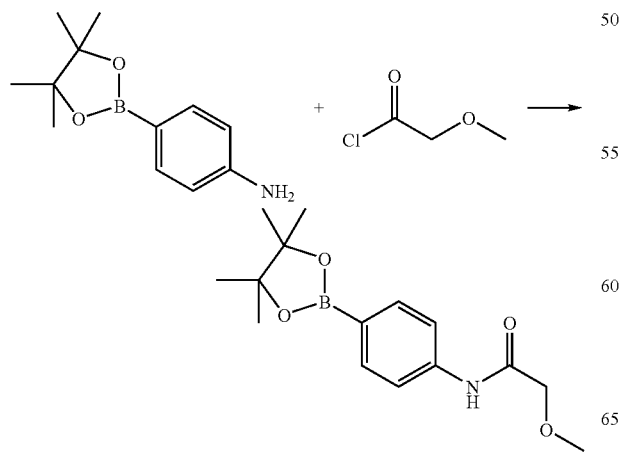

To a solution of 4-(4,4,5,5-Tetramethyl-[1,3,2]dioxaborolan-2-yl)-phenylamine (1 g, 4.56 mmol) in THF (20 ml) was added triethylamine (0.95 ml, 6.84 mmol) and methoxyacetyl chloride (0.417 ml, 4.56 mmol) dropwise, the resulting mixture was stirred for 2 hours at RT. The reaction mixture was diluted with EtOAc and washed with water then brine, dried (Na$_2$SO$_4$) filtered and concentrated in vacuo to give the product (1.2 g) as an orange oil.
MS: M+H]$^+$ 292

Boronic Acid I2

2-Methyl-2-[4-(4,4,5,5-tetramethyl-[1,3,2]dioxaborolan-2-yl)-phenyl]-propionic acid methyl ester

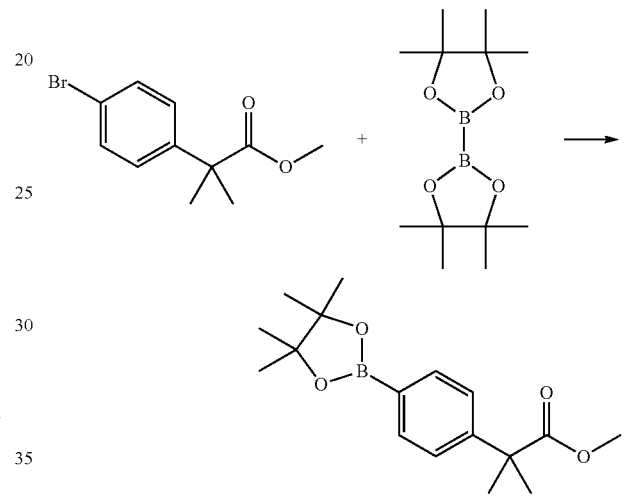

To a solution of 4,4,5,5,4',4',5',5'-Octamethyl-2,2'-bi-1,3,2-dioxaborolane (0.74 g, 2.91 mmol) in dioxane (4 ml) added 2-(4-Bromo-phenyl)-2-methyl-propionic acid methyl ester (0.5 g, 1.94 mmol), [1,1'-bis(diphenylphosphino)ferrocene]dichloropalladium(II) (80 mgs, 0.97 mmol), dppf (40 mgs, 0.07 mmol) and potassium acetate (0.596 g, 6.07 mmol) and heated at 80° C. overnight. The reaction mixture was diluted with EtOAc and washed with water then brine, dried (Na$_2$SO$_4$) filtered and concentrated in vacuo to give the product (0.7 g) as a brown oil MS: [M+H]$^+$ 305.

Boronic Acid I3

1-Methyl-5-(4,4,5,5-tetramethyl-[1,3,2]dioxaborolan-2-yl)-1H-pyridin-2-one

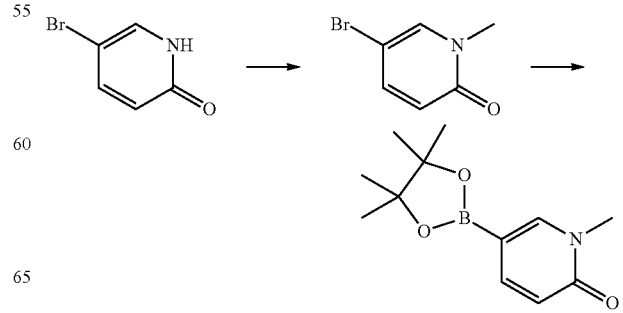

To a solution of 5-Bromo-1H-pyridin-2-one (4 g, 22.9 mmol) in DME (40 ml) was added $K_2CO_3$ (6.36, 45.7 mmol) and MeI (2.84 ml, 45.7 mmol) the resulting mixture was heated at 80° C. for 2 hours allowed to cool overnight. Reaction filtered and the solid washed with DME. Filtrate concentrated in vacuo to give an oil which was partitioned between EtOAc and water, organics washed with brine, dried ($Na_2SO_4$) filtered and concentrated in vacuo to give the product (2.98 g) as an oil that crystallised on standing.

To a solution of 4,4,5,5,4',4',5',5'-Octamethyl-2,2'-bi-1,3,2-dioxaborolane (0.88 g, 3.46 mmol) in dioxane (40 ml) added 5-Bromo-1-methyl-1H-pyridin-2-one (0.5 g, 2.65 mmol), [reaction degassed by bubbling nitrogen through] [1,1'-bis(diphenylphosphino)Ferrocene]dichloropalladium (II) (59 mgs, 0.080 mmol), dppf (88 mgs, 0.16 mmol) and potassium acetate (0.77 g, 7.84 mmol) and heated at 80° C. over the weekend. The reaction mixture was diluted with EtOAc and washed with water then brine, dried ($Na_2SO_4$) filtered and concentrated in vacuo to give the product as a brown oil and can be used without purification otherwise can be purified by column chromatographed using Biotage using EtOAc as eluent to give pure product (0.173 g). MS: $[M+H]^+$ 224

Boronic Acid I6

1-[3-(4,4,5,5-Tetramethyl-[1,3,2]dioxaborolan-2-yl)-phenyl]-3-(2,2,2-trifluoro-ethyl)-urea Step 1: 1-(3-Bromo-phenyl)-3-(2,2,2-trifluoro-ethyl)-urea

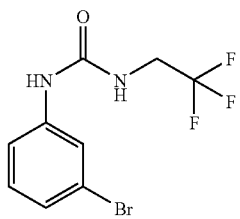 [SMILES: O=C(NCC(F)(F)F)Nc1cccc(Br)c1]

3-Bromophenyl isocyanate (1.0 ml, 8.1 mmol) was added slowly to a stirred solution of 2,2,2-trifluoroethyl amine (3.2 ml, 40 mmol) in THF (10 ml) at 0° C. under $N_2$. After 1 hour the reaction was allowed to warm to RT and kept at this temperature for 16 hours. The volatiles were removed in vacuo to give the title compound (2.5 g, solid). $^1$H NMR (400 MHz, DMSO-d6): 9.00 (1H, s), 7.86 (1H, t), 7.33 (1H, ddd), 7.26 (1H, t), 7.18 (1H, ddd), 6.89 (1H, t), 4.03-3.92 (2H, m).

Step 2: 1-[3-(4,4,5,5-Tetramethyl-[1,3,2]dioxaborolan-2-yl)-phenyl]-3-(2,2,2-trifluoro-ethyl)-urea

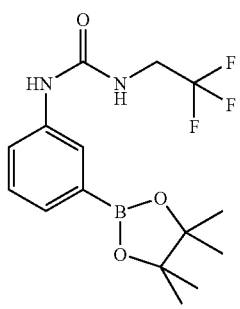 [SMILES: CC1(C)OB(c2cccc(NC(=O)NCC(F)(F)F)c2)OC1(C)C]

A mixture of 1-(3-bromo-phenyl)-3-(2,2,2-trifluoro-ethyl)-urea (2.1 g, 7.1 mmol), bis(pinacolato)diboron (3.6 g, 14 mmol) and KOAc (2.1 g, 21 mmol) in dry DMSO (7 ml) was deoxygenated by evacuation/refill with $N_2$ (×3). $PdCl_2$ddpf (512 mg, 0.7 mmol) was added and the mixture was deoxygenated again (×2) then stirred and heated at 100° C. under $N_2$ for 3 hours. The reaction was allowed to cool to RT and then left to stand at this temperature for 18 hours. The mixture was partitioned between EtOAc/$H_2O$ then filtered through Celite®. The layers were separated and the aqueous layer was extracted with EtOAc (×1). The combined organic extracts were washed with water (×1), brine (×1), then dried ($MgSO_4$), filtered and evaporated. The residue was triturated with petrol to give the title compound (2.6 g, solid). $^1$H NMR (400 MHz, $CDCl_3$): 7.65 (1H, s), 7.60 (1H, d), 7.49 (1H, d), 7.37 (1H, t), 6.64 (1H, brs), 5.20 (1H, brs), 3.99-3.86 (2H, m), 1.35 (12H, s).

Boronic Acid I7

1-Methyl-3-[3-(4,4,5,5-tetramethyl-[1,3,2]dioxaborolan-2-yl)-phenyl]-urea

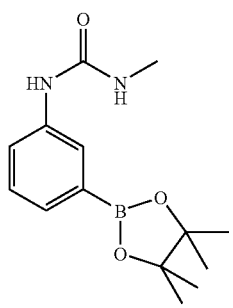 [SMILES: CNC(=O)Nc1cccc(B2OC(C)(C)C(C)(C)O2)c1]

Prepared as described for 1-[3-(4,4,5,5-tetramethyl-[1,3,2]dioxaborolan-2-yl)-phenyl]-3-(2,2,2-trifluoro-ethyl)-urea (I6), substituting methylamine in THF (2M) for 2,2,2-trifluoroethyl amine in Step 1. $^1$H NMR (400 MHz, $CDCl_3$): 7.59-7.53 (2H, m), 7.50 (1H, d), 7.34 (1H, t), 2.83 (3H, s), 1.33 (12H, s).

Boronic Acid I8

3-Methoxy-5-nitro-phenyl boronic acid pinacol ester

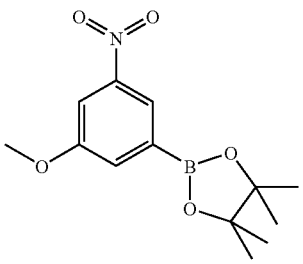

A mixture of 1-bromo-3-methoxy-5-nitro-benzene (387 mg, 1.7 mmol), bis(pinacolato)diboron (850 mg, 3.3 mmol)

and KOAc (490 mg, 5.0 mmol) in dry DMSO (3.5 ml) was deoxygenated by evacuation/refill with $N_2$ (×3). $PdCl_2ddpf$ (61 mg, 0.08 mmol) was added and the mixture was deoxygenated again (×3) then stirred and heated at 100° C. under $N_2$ for 16 hours. After cooling to RT the mixture was partitioned between $EtOAc/H_2O$ then filtered through Celite®. The layers were separated and the aqueous layer was extracted with EtOAc (×1). The combined organic extracts were washed with brine (×1), then dried ($Na_2SO_4$), filtered and evaporated. The residue was purified by chromatography on silica (5→40% EtOAc/petrol) to give the title compound (185 mg, solid—after trituration with petrol). $^1$H NMR (400 MHz, $CDCl_3$): 8.23 (1H, d), 7.79 (1H, t), 7.62 (1H, d), 3.90 (3H, s), 1.36 (12H, s).

Boronic Acid I9

1-Ethyl-3-[3-(4,4,5,5-tetramethyl-[1,3,2]dioxaborolan-2-yl)-phenyl]-urea

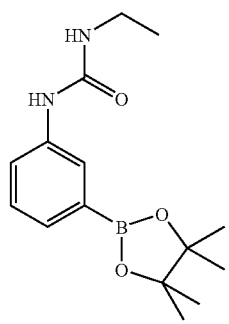 [SMILES: CCNC(=O)Nc1cccc(B2OC(C)(C)C(C)(C)O2)c1]

To a solution of 3-(4,4,5,5-tetramethyl-1,3,2-dioxaborolan-2-yl)aniline (30 g, 137 mmol, 1.0 equiv) in THF (300 ml) was added triethylamine (58 ml, 410 mmol, 3.0 equiv) and ethyl isocyanate (16.3 ml, 205 mmol, 1.5 equiv). The reaction was warmed to 60° C. for 2 hours. The reaction was cooled to room temperature and diluted with diethyl ether (600 ml). The precipitate was filtered and solid was washed with diethylether to afford desired product 34 g.

Boronic Acid I10-I13

1-[4-(4,4,5,5-Tetramethyl-1,3,2-dioxaborolan-2-yl) benzyl]-amines

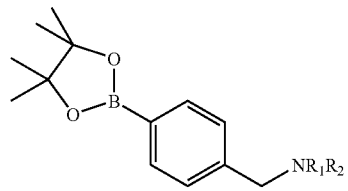

A mixture of $K_2CO_3$ (2 eq), the amine (1.25 eq) and (4-bromomethylphenyl)boronic acid pinacol ester (1 eq) in dry DMF (1 ml/mmol) was stirred at RT for 20 h. The mixture was partitioned between $Et_2O/H_2O$. The organic layer was washed with water (×1), brine (×1), then dried ($Na_2SO_4$), filtered and evaporated to give the title compound.

| | Amine | Product Name | MS: $[M + H]^+$ |
|---|---|---|---|
| I10 | azetidine | 1-[4-(4,4,5,5-Tetramethyl-[1,3,2]dioxaborolan-2-yl)-benzyl]-azetidine | 274 |
| I11 | pyrrolidine | 1-[4-(4,4,5,5-Tetramethyl-[1,3,2]dioxaborolan-2-yl)-benzyl]-pyrrolidine | 288 |
| I12 | N-methylpiperazine | 1-Methyl-4-[4-(4,4,5,5-tetramethyl-[1,3,2]dioxaborolan-2-yl)-benzyl]-piperazine | 317 |
| I13 | 3-methylpiperidine-3-carboxylic acid ethyl ester (±) | (±)-1-[4-(4,4,5,5-Tetramethyl-1,3,2-dioxaborolan-2-yl)benzyl]-3-methyl-piperidine-3-carboxylic acid ethyl ester | 388 |

Boronic Acid I14

4-(2,2-Dimethyl-[1,3]dioxolan-4-ylmethoxy)-phenyl-boronic acid

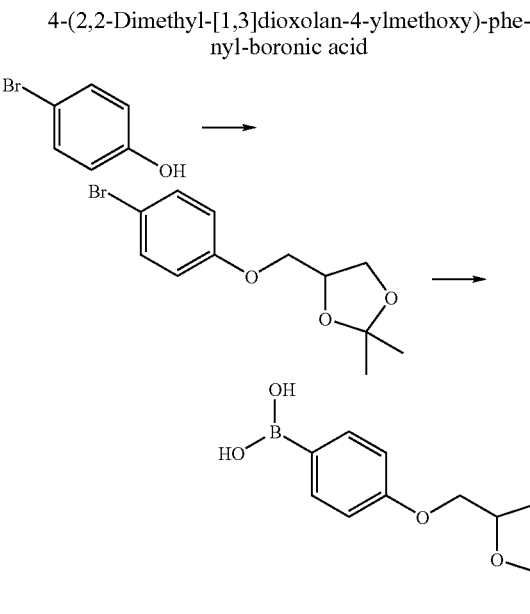

To a solution of 4-bromophenol (865 mg, 5.0 mmol, 1.0 equiv) in DMF (10 ml) was added sodium hydride (200 mg, 5.0 mmol, 1.0 equiv) portion wise. 4-(chloromethyl)-2,2-dimethyl-1,3-dioxolane (0.78 ml, 5.5 mmol, 1.1 equiv) was added dropwise. The reaction mixture was heated to 70° C. overnight. The reaction mixture was cooled to room temperature, methanol (10 ml) was added and the solvents were removed under reduced pressure. The crude mixture was partitioned between ethyl acetate and water and the layers were separated. The organic layer was washed with water, dried (MgSO₄), and concentrated under reduced pressure. The crude mixture was purified by column chromatography (eluting with 4% EtOAc-petrol, scanning at 220 nM) to afford 1.0 g of desired material (71%).

To a solution of arylbromide (1.0 g, 3.6 mmol, 1.0 equiv) in THF (10 ml) under nitrogen at −78° C. was added n-BuLi (2.25 ml of a 1.6M solution in hexanes, 3.6 mmol, 1.0 equiv) drop-wise. After 15 min a solution of trimethylborate (1.3 ml, 12.3 mmol, 3.5 equiv) was added slowly over 15 min. The reaction mixture was warmed to RT overnight. The solvents were removed under vacuum. The mixture was partitioned with diethylether and Sorenson's Buffer (pH 5.5—an aqueous solution of Na₂HPO₄ and KH₂PO₄). The aqueous layer was extracted with diethylether (3×) and the combined organic layers were washed with water, brine, dried (MgSO₄), filtered and concentrated under reduced pressure to give a colourless solid (852 mg, 94%)

Boronic Acid I15

Step 1: 4-(4-Bromo-phenoxy)-piperidine-1-carboxylic acid tert-butyl ester

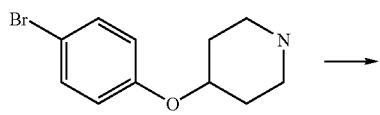

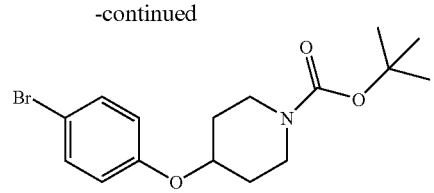

To a solution of 4-(4-Bromo-phenoxy)-piperidine (1 g, 3.9 mmol) in dioxane (20 ml), water (20 ml) added Na₂CO₃ (1.6 g, 18.9 mmol) and (BOC)₂O (1.3 g, 5.9 mmol). Reaction stirred at ambient for 48 hours, solvent was removed under reduced pressure and residue partitioned between EtOAc and water the layers were separated. The organic layer was washed with brine, dried (MgSO₄), and concentrated under reduced pressure to give (1.2 g) of product.

Step 2: 4-[4-(4,4,5,5-Tetramethyl-[1,3,2]dioxaborolan-2-yl)-phenoxy]-piperidine-1-carboxylic acid tert-butyl ester

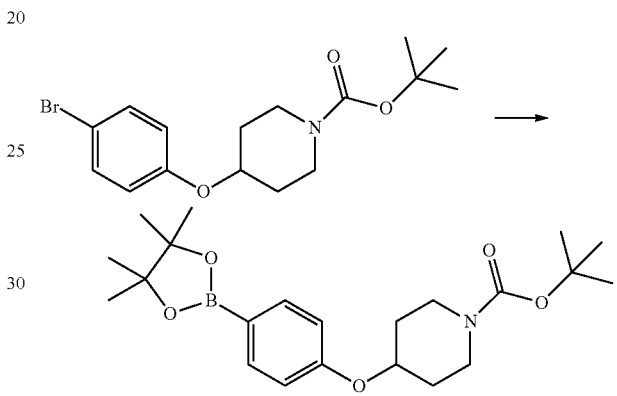

To a solution of 4-(4-Bromo-phenoxy)-piperidine-1-carboxylic acid tert-butyl ester (1 g, 2.8 mmol) in dioxane (25 ml) [reaction degassed by bubbling nitrogen through] was added bis(pinacolato)diboron (0.93 g, 36.5 mmol), KOAc (0.83 g, 84.5 mmol), PdCl₂ddpf (0.061 g, 0.84 mmol) and dppf (0.092 g, 0.16 mmol) and the mixture then stirred and heated at 80° C. for 16 hours. After cooling to RT the mixture was partitioned between EtOAc/H₂O, the organic layer was washed with brine, dried (MgSO₄), filtered and concentrated under reduced pressure to give (1.06 g) of product. MS: [M+H]⁺ no mass ion used crude

Boronic Acid 118

N-Methyl-2-[3-(4,4,5,5-tetramethyl-[1,3,2]dioxaborolan-2-yl)-phenyl-acetamide

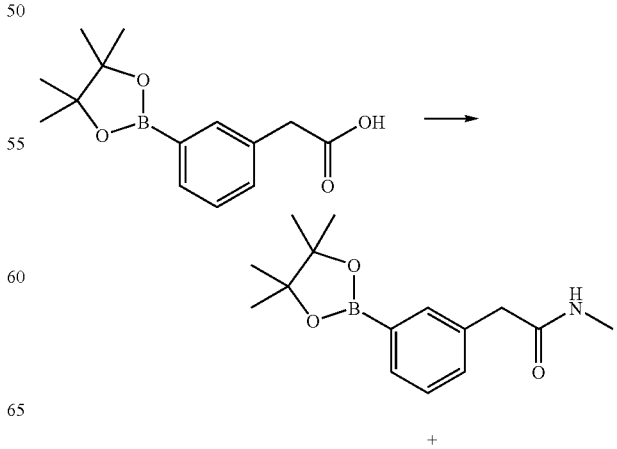

-continued

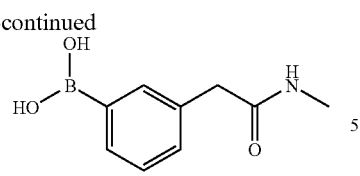

To a solution of [3-(4,4,5,5-Tetramethyl-[1,3,2]dioxaborolan-2-yl)-phenyl]acetic acid (0.60 g, 2.28 mmol) in DMF (15 ml) was added a solution of 1-hydroxybenzotriazole (0.37 g, 2.73 mmol) and TBTU 2-(1H-benzotriazole-1-yl)-1,1,3,3-tetramethyluronium tetrafluoroborate (0.88 g, 2.73 mmol) in DMF (15 ml). Triethylamine (0.95 ml) and methylamine (1.2 ml) was added and the reaction mixture left to stir for 18 h at room temperature. The reaction mixture was concentrated in vacuo and purified using reverse phase chromatography to afford a mixture of the boronic ester/acid, which was used crude. MS: [MH$^+$] 276 (ester), [MH$^+$] 193 (acid).

Boronic Acid I19

(3-methylpiperazinone)phenyl boronic acid

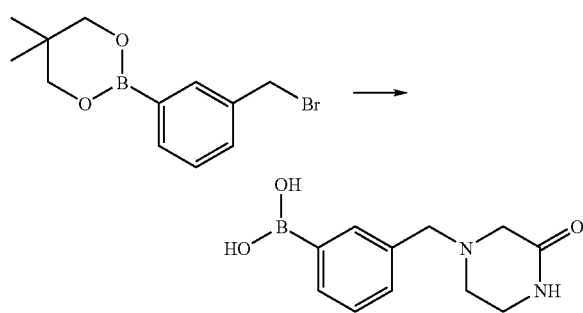

To a solution of piperazine-2-one (0.2 g, 2 mmol) in dry THF/DMSO (10 ml: 2.5 ml) was added (3-bromomethylphenyl)boronic acid, neopentyl glycol ester (0.45 g, 1.6 mmol), NaHCO$_3$ (0.34 g, 4 mmol) and NaI (0.01 g, 0.74 mmol). The reaction mixture was heated at reflux for 12 h, cooled and passed through a C18 reverse phase chromatography column to afford a colourless gum, which was used crude MS: [MH$^+$] 235

Boronic Ester I20

1-(3-Amino-2,2-difluoro-propyl)-3-[3-(4,4,5,5-tetramethyl-[1,3,2]dioxaborolan-2-yl)-phenyl]-urea Step 1

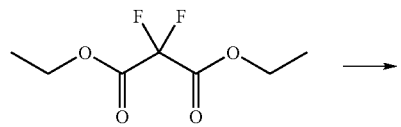

To a solution of diethyl difluoromalonate (5 g, 25.5 mmol, 1 equiv) in methanol (15 ml) under a nitrogen atmosphere was added a solution of 7N ammonia in methanol (14.3 ml, 101.9 mmol, 4 equiv). Upon completion of reaction the mixture was concentrated under reduced pressure. The crude mixture was triturated with petrol to afford 2,2-difluoro-malonamide as a white solid 3.44 g (98%).

Step 2

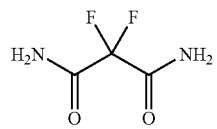

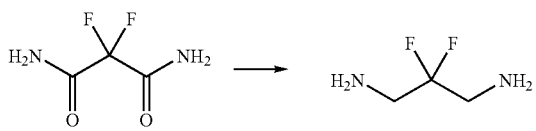 [SMILES: NC(=O)C(F)(F)C(N)=O ; NCC(F)(F)CN]

To 2,2-difluoro-malonamide (1.34 g, 9.7 mmol) in THF (26 ml) added BH3.THF [1M in THF] (58 ml, 58 mmol). Reaction mixture heated at 45° C. with stirring overnight, cooled in an ice bath, treated with 2M HCl (26 ml), stirred 30 mins, concentrated under reduced pressure and re-evaporated with MeOH (3×), triturated with EtOH, filtered and dried to give 2,2-difluoro-propane-1,3-diamine (0.92 g) MS: [M+H]$^+$ 111.

Step 3

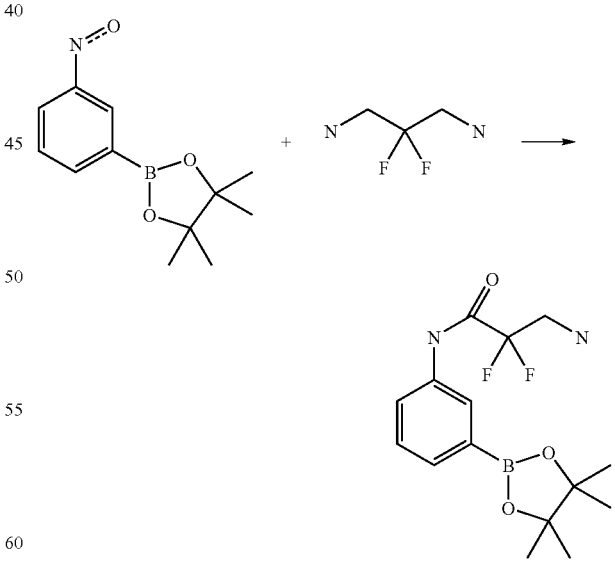

To a suspension of 2-(3-isocyanatophenyl)-4,4,5,5-tetramethyl-[1,3,2]-dioxaborolane, pinacol ester (0.135 g, 0.55 mmol) in THF (15 ml) was added 2,2-Difluoro-propane-1,3-diamine (0.4 g, 2.2 mmol) and triethylamine (1.5 ml, 11 mmol) stirred at ambient until reaction complete. Solid fil-

Boronic Acid I21

2-(tetrahydro-pyran-4-yloxy)-4-pyridinylboronic acid

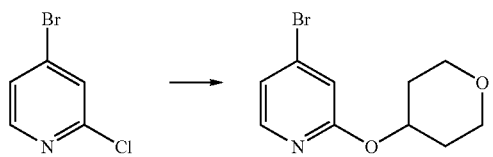 [SMILES: Clc1cc(Br)ccn1 ; Brc1ccnc(OC2CCOCC2)c1]

To a suspension of NaH (0.4 g, 10 mmol) in THF (20 ml) at 0° C. was added 4-hydroxytetrahydropyran (1.02 ml, 10 mmol). The reaction mixture was allowed to warm to room temperature and stirred for 30 mins before 4-bromo-2-chloropyridine (0.89 ml, 8.0 mmol) was added dropwise. The reaction mixture was stirred for 18 h before being quenched with EtOH (1 ml), partitioned between $CH_2Cl_2$ and $H_2O$ and extracted $CH_2Cl_2$ (×2). The organics were combined, dried ($MgSO_4$) and the solvent removed in vacuo. Purified by column chromatography to afford 4-bromo-2-(tetrahydro-pyran-4-yloxy)-pyridine MS: $[MH]^+$ 258, 260

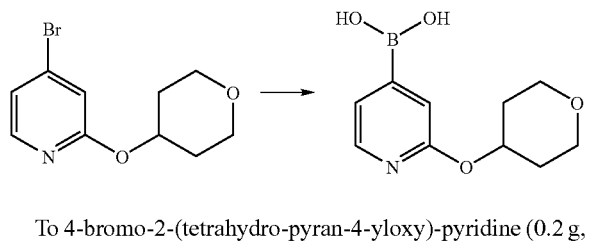

To 4-bromo-2-(tetrahydro-pyran-4-yloxy)-pyridine (0.2 g, 0.77 mmol) in DMSO (5 ml) (degassed by bubbling $N_2$ through) was added 4,4,5,5,4',4',5',5'-octamethyl-2,2'-bi-1,3,2-dioxaborolane (0.39 g, 1.55 mmol) and potassium acetate (0.27 g, 2.31 mmol). $PdCl_2ddpf$ (0.028 g, 0.04 mmol) was added, the reaction mixture again degassed and then heated at 100° C. for 5 h. The compound was passed through a C18 reverse phase chromatography column to afford desired product, used crude. MS: $[MH]^+$ 224.

Boronic Acid I22

4-[3-(4,4,5,5-Tetramethyl-[1,3,2]dioxaborolan-2-yl)-phenoxy]-piperidine-1-carboxylic acid tert-butyl ester

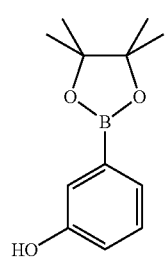 +

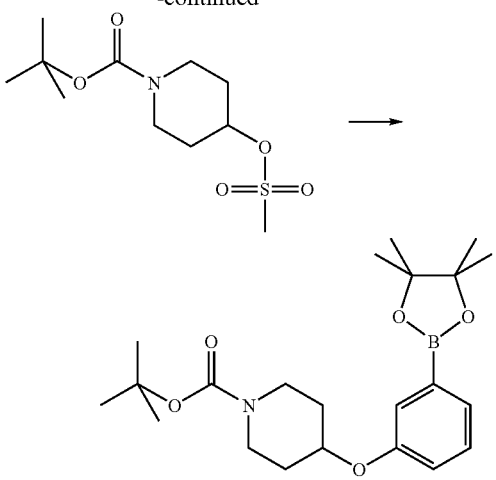

To a solution of 3-(4,4,5,5-tetramethyl-[1,3,2]dioxaborolan-2-yl)-phenol (10.0 g, 45.4 mmol, 1.0 equiv) in NMP (100 ml) was added $Cs_2CO_3$ (44.4 g), 136.3 mmol, 3.0 equiv) and 4-methanesulfonyloxy-piperidine-1-carboxylic acid tert-butyl ester (19.0 g, 68.2 mmol, 1.5 equiv). The reaction mixture was heated to 80° C. and monitored until complete. The reaction mixture was cooled to room temperature, diluted with water and extracted with EtOAc. The organic layer was washed successively with 2N KOH, water, brine, dried ($MgSO_4$), filtered and concentrated under reduced pressure. The target molecule was purified by column chromatography ($SiO_2$), eluted with 5→30% EtOAc-petrol to afford a colourless liquid (9.5 g) that crystallised on standing. 1H NMR (400 MHz, CDCl3): 7.42 (1H, d), 7.37 (1H, d), 7.31 (1H, t), 7.03 (1H, dd), 4.61-4.49 (1H, m), 3.76-3.62 (2H, m), 3.47-3.32 (2H, m), 1.99-1.86 (2H, m), 1.86-1.70 (2H, m), 1.49 (9H, s).

Boronate I24

1-[3-(4,4,5,5-Tetramethyl-[1,3,2]dioxaborolan-2-yl)-phenyl]-3-(2,2,-difluoro-ethyl)-urea

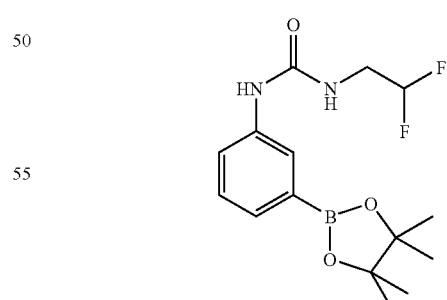

This was prepared as described in procedure I6 substituting 2,2-difluoroethylamine for 2,2,2-trifluoroethyl amine. 1H NMR (400 MHz, $CDCl_3$): 7.64-7.53 (2H, m), 7.48 (1H, d), 7.35 (1H, t), 6.46 (1H, s), 5.88 (1H, tt), 3.61 (2H, td), 1.34 (12H, s).

Previous step: tered off, washed with THF, filtrate concentrated under reduced pressure and dried to give title compound, used crude MS: $[M+H]^+$ 356

Boronate I25

1-(2-Fluoro-ethyl)-3-[3-(4,4,5,5-tetramethyl-[1,3,2]dioxaborolan-2-yl)-phenyl]-urea

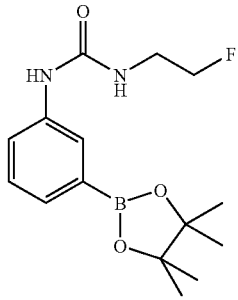 [SMILES: CC1(C)OB(c2cccc(NC(=O)NCCF)c2)OC1(C)C]

This was prepared as described in procedure I6 substituting 2-fluoroethylamine for 2,2,2-trifluoroethyl amine 1H NMR (400 MHz, CDCl$_3$): 7.60 (1H, s), 7.55 (1H, d), 7.50 (1H, d), 7.34 (1H, t), 4.51 (2H, dt), 3.56 (2H, dt), 1.33 (12H, s).

Boronate I26

(2-{3-[3-(4,4,5,5-Tetramethyl-[1,3,2]dioxaborolan-2-yl)-phenyl]-ureido}-ethyl)-carbamic acid tert-butyl ester

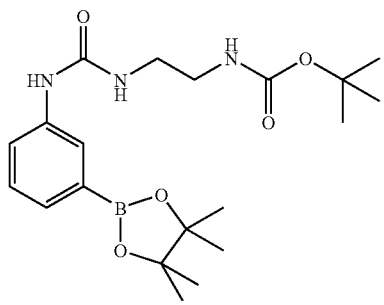 [SMILES: CC(C)(C)OC(=O)NCCNC(=O)Nc1cccc(B2OC(C)(C)C(C)(C)O2)c1]

This was prepared as described in procedure I6 substituting (2-amino-ethyl)-carbamic acid tert-butyl ester for 2,2,2-trifluoroethyl amine 1H NMR (400 MHz, DMSO-d$^6$): 8.59 (1H, s), 7.77 (1H, s), 7.47 (1H, dt), 7.26-7.17 (2H, m), 6.84 (1H, t), 6.16 (1H, t), 3.18-3.07 (2H, m), 3.07-2.95 (2H, m), 1.39 (9H, s), 1.29 (12H, s).

Boronate I27

(3-{3-[3-(4,4,5,5-Tetramethyl-[1,3,2]dioxaborolan-2-yl)-phenyl]-ureido}-propyl)-carbamic acid tert-butyl ester

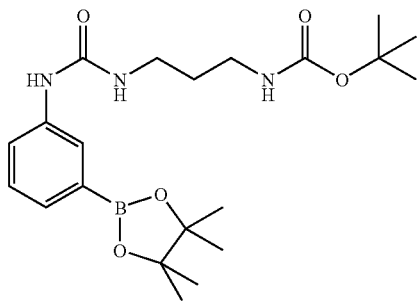 [SMILES: CC(C)(C)OC(=O)NCCCNC(=O)Nc1cccc(B2OC(C)(C)C(C)(C)O2)c1]

(3-Amino-propyl)-carbamic acid tert-butyl ester (0.79 ml, 4.5 mmol) was added slowly to a stirred solution of 2-(3-isocyanato-phenyl)-4,4,5,5-tetramethyl-[1,3,2]dioxaborolane (1 g, 4.1 mmol) in dry THF (8 ml) at RT under N$_2$ After 16 hours the volatiles were removed in vacuo and the residue was partitioned between EtOAc/H$_2$O. The organic layer was washed with brine (×1), then dried (Na$_2$SO$_4$), filtered and evaporated to give the title compound (1.6 g) as a colourless solid. 1H NMR (400 MHz, DMSO-d6): 8.52 (1H, s), 7.77 (1H, s), 7.47 (1H, dt), 7.25-7.17 (2H, m), 6.80 (1H, t), 6.08 (1H, t), 3.13-3.02 (2H, m), 3.02-2.89 (2H, m), 1.57-1.48 (2H, m), 1.39 (9H, s), 1.29 (12H, s).

Boronic ester 128:1-[5-(4,4,5,5-Tetramethyl-[1,3,2]dioxaborolan-2-yl)-pyridin-3-yl]-3-(2,2,2-trifluoro-ethyl)-urea

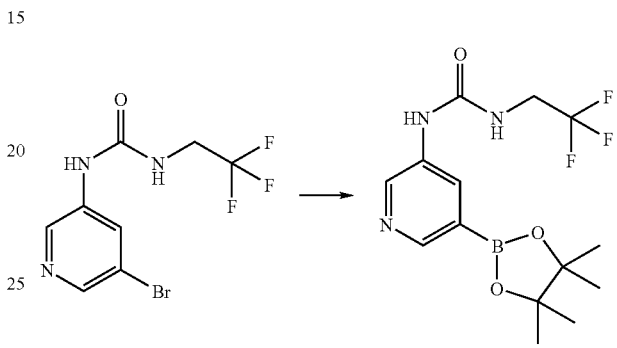

To 1-(5-bromo-pyridin-3-yl)-3-(2,2,2-trifluoro-ethyl)-urea (0.51 g, 1.72 mmol) in anhydrous DMSO (3 mL) was added bis(pinacolato)diboron (0.88 g, 3.45 mmol). The reaction flask was purged with N$_2$ and PdCl$_2$dppf (40 mg, 0.05 mmol) added. The flask was further purged with N$_2$ and the reaction then heated at 100° C. for 22 hours. After cooling to room temperature, H$_2$O (30 mL) and EtOAc (30 mL) were added and the two phases separated. The organic phase was further washed with H$_2$O (2×35 mL). The organic phase was dried over MgSO$_4$, filtered and concentrated in vacuo and used crude in the subsequent reaction.

Boronic ester I29—(Tetrahydro-pyran-4-yl)-[3-(4,4,5,5-tetramethyl-[1,3,2]dioxaborolan-2-yl)-phenyl]-amine Step 1: (3-Bromo-phenyl)-(tetrahydro-pyran-4-yl)-amine

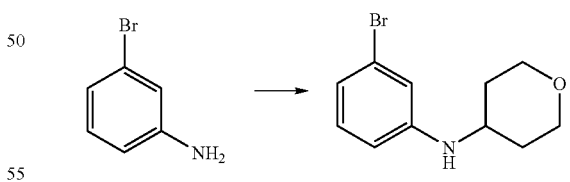

To a solution of 3-Bromo-phenylamine (0.54 ml, 5 mmol) and tetrahydro-4H-pyran-4-one (0.5 g, 5 mmol) in DCE (20 ml) was added sodium triacetoxyborohydride (1.48 g, 7 mmol) and acetic acid (0.3 g). The mixture was stirred for 18 h before being quenched with 1N NaOH (10 ml). The mixture was partitioned between Et$_2$O and H$_2$O, the aqueous layer further extracted with Et$_2$O, the organics combined, dried (MgSO$_4$), filtered and the solvent removed in vacuo to give a colourless liquid. Purification using silica column chromatography (0-80% EtOAc/hexane gradient) afforded the title compound as a white solid (0.81 g). MS: [M+H]$^+$=256,258

Step 2: (Tetrahydro-pyran-4-yl)-[3-(4,4,5,5-tetram-ethyl-[1,3,2]dioxaborolan-2-yl)-phenyl]-amine

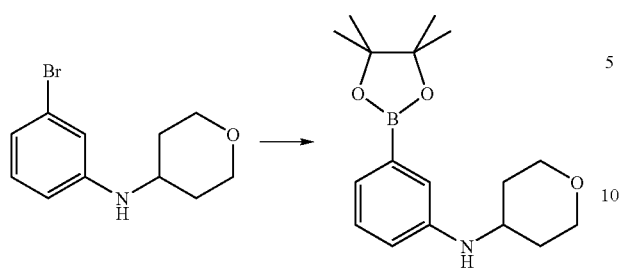

To a solution of (3-Bromo-phenyl)-(tetrahydro-pyran-4-yl)-amine (0.2 g, 0.77 mmol) in DMSO (5 ml) was added bis(pinacolato)diboron (0.4 g, 1.55 mmol) and potassium acetate (0.23 g, 2.31 mmol). The reaction was deoxygenated and PdCl$_2$ddpf (28 mg, 39 µmol) was added and the mixture was deoxygenated again, then stirred and heated at 100° C. under N$_2$ for 18 h. The crude reaction mixture was purified using reverse phase silica chromatography (0-100% MeCN in H$_2$O) to afford the title compound as a pale brown gum (0.24 g). MS: [M+H]$^+$=304

Boronic ester I30—N-ethyl-3-(4,4,5,5-tetramethyl-1,3,2-dioxaborolan-2-yl)benzamide

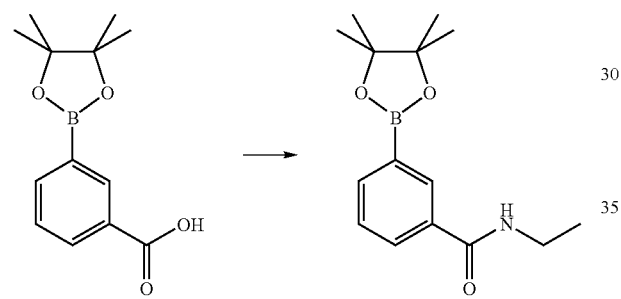

To a solution of 3-(4,4,5,5-Tetramethyl-1,3,2-dioxaborolan-2-yl)benzoic acid (0.2 g, 0.8 mmol) in THF (6 ml) was added EDAC (0.17 g, 0.88 mmol), HOAt (0.12 g, 0.88 mol) and triethylamine (0.1 ml, 0.8 mmol). Ethylamine (0.4 g, 0.8 mmol) was added and the reaction mixture stirred at room temperature for 2 h. The reaction mixture was partitioned between CH$_2$Cl$_2$ and 5% citric acid, the organic layer separated and washed with saturated bicarbonate, brine, dried (MgSO$_4$), filtered and the solvent removed in vacuo. The crude residue was used directly in the next reaction. MS: [M+H]$^+$=276

Boronic ester I31—N-azetidine-3-(4,4,5,5-tetramethyl-1,3,2-dioxaborolan-2-yl)benzamide

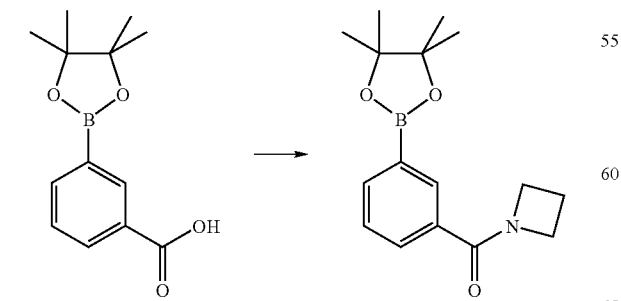

Procedure as for I30 substituting azetidine for ethylamine. MS: [M+H]$^+$=288

Boronic ester I32—{2-[3-(4,4,5,5-Tetramethyl-[1,3,2]dioxaborolan-2-yl)-benzoylamino]-ethyl}-carbamic acid tert-butyl ester

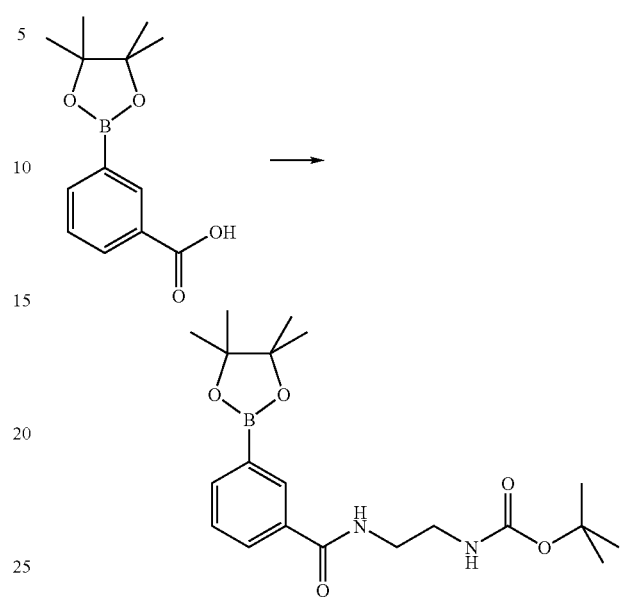

Procedure as for I30 substituting tert-butyl N-(2-aminoethyl)carbamate for ethylamine. MS: [M+H]$^+$=391

Boronic ester I33—N-isopropyl-3-(4,4,5,5-tetramethyl-1,3,2-dioxaborolan-2-yl)benzamide

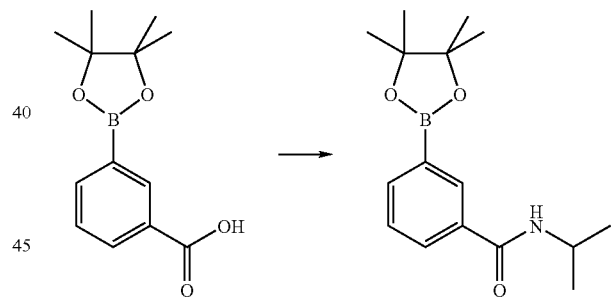

Procedure as for I30 substituting isopropylamine for ethylamine. MS: [M+H]$^+$=290

Boronic ester I34—(4-ethyl-piperazin-1-yl)-{3-(4,4,5,5-tetramethyl-[1,3,2]-dioxaborolan-2-yl)-phenyl]-methanone

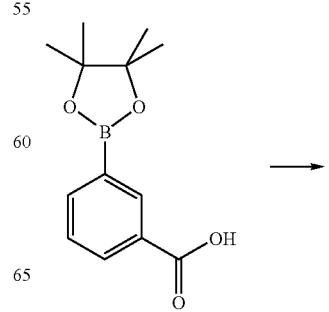

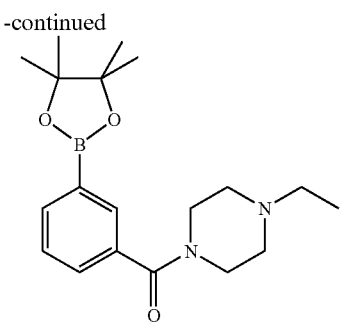

Procedure as for I30 substituting 1-Ethyl-piperazine for ethylamine. MS: [M+H]⁺=345

Boronic ester I35-4-[3-(4,4,5,5-Tetramethyl-[1,3,2]dioxaborolan-2-yl)-benzoyl]-[1,4]diazepane-1-carboxylic acid tert-butylester

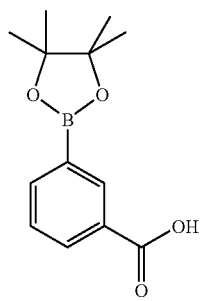

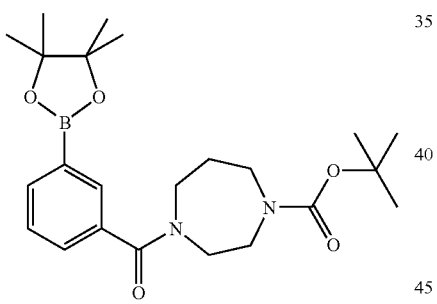

Procedure as for I30 substituting [1,4]Diazepane-1-carboxylic acid tert-butyl ester for ethylamine. MS: [M+H]⁺=431

Boronic ester I36-2-(3-Isopropoxy-5-nitro-phenyl)-4,4,5,5-tetramethyl-[1,3,2]dioxaborolane Step 1

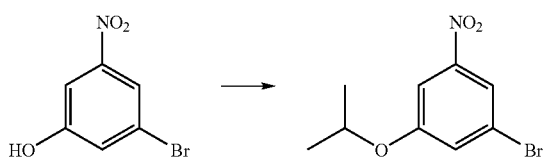

To a mixture of 3-Bromo-5-nitro-phenol (0.40 g, 1.83 mmol) and $K_2CO_3$ (0.51 g, 3.67 mmol) in dry DMF (2 ml) at room temperature was added isopropyl iodide (0.37 ml, 3.70 mmol) and the reaction mixture left to stirred for 18 h. The reaction mixture was partitioned between EtOAc/$H_2O$. The organic layer was washed with water (×1), brine (×1), dried ($Na_2SO_4$), filtered and the solvent removed in vacuo. The residue was purified by silica column chromatography (2-5% EtOAc in petrol) to afford the product as a brown oil. 1H NMR (400 MHz, CDCl3): 7.94 (1H, t), 7.67 (1H, t), 7.36 (1H, t), 4.71-4.57 (1H, m), 1.40 (6H, d).

Step 2

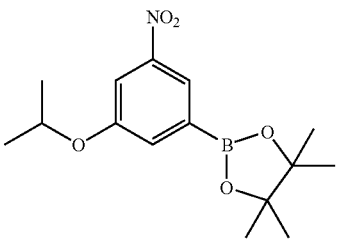

Prepared according to the procedure outlined in I8, no purification was performed and the crude material was used directly in the next step Boronic ester I37—3-Nitro-5-(4,4,5,5-tetramethyl-[1,3,2]dioxaborolan-2-yl)-phenyl]-methanol Step 1

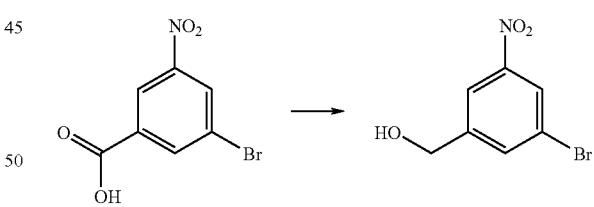

$BH_3$.THF (1.0M in THF, 100 ml) was added dropwise over a 40 min period to a stirred solution of 3-Bromo-5-nitrobenzoic acid (15.0 g, 61 mmol) in dry THF (100 ml) under an atmosphere of nitrogen. The reaction mixture was stirred at room temperature overnight before being poured into saturated $NaHCO_{3(aq)}$. $Et_2O$ was added to the reaction and the resulting mixture stirred for 20 mins, then partitioned. The aqueous layer was extracted with $Et_2O$ (×2), the organic fractions combined then extracted with 1N NaOH (×1), brine (×1), dried ($Na_2SO_4$), filtered and the solvent removed in vacuo. The residue was purified by silica column chromatography (10-30% EtOAc in petrol) to afford a light yellow solid (1.97 g). 1H NMR (400 MHz, CDCl3): 8.31 (1H, s), 8.20 (1H, s), 7.89 (1H, s), 4.84 (2H, s).

Step 2

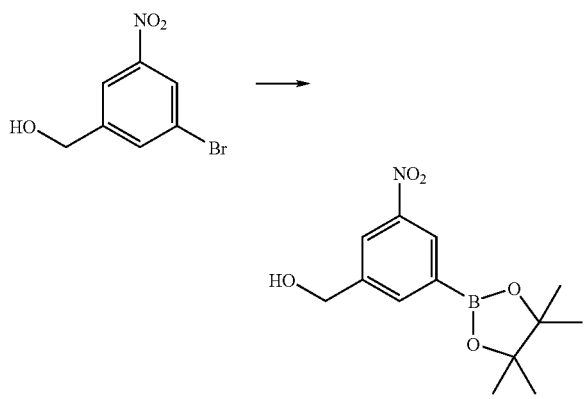

Prepared according to the procedure outlined in I8, no purification was performed and the crude material was used directly in the next step Boronic ester I38—1-[4-Fluoro-3-(4,4,5,5-tetramethyl-[1,3,2]dioxaborolan-2-yl)-phenyl]-3-(2,2,2-trifluoro-ethyl)-urea Step One

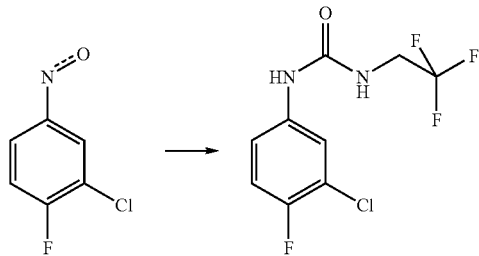

2-Chloro-1-fluoro-4-isocyanato-benzene (5.0 g, 29 mmol) was added slowly to a stirred solution of 2,2,2-trifluoroethylamine (12 ml, 150 mmol) in dry THF (40 ml) at 0° C. under an atmosphere of nitrogen. After 1 h, the reaction mixture was allowed to warm to room temperature and stirred for 18 h. The solvent was removed in vacuo and the residue triturated with Et$_2$O to give a colourless solid (6.2 g). 1H NMR (400 MHz, DMSO-d6): 8.95 (1H, s), 7.75 (1H, dd), 7.36-7.21 (2H, m), 6.85 (1H, s), 3.99-3.84 (2H, m).

Step Two

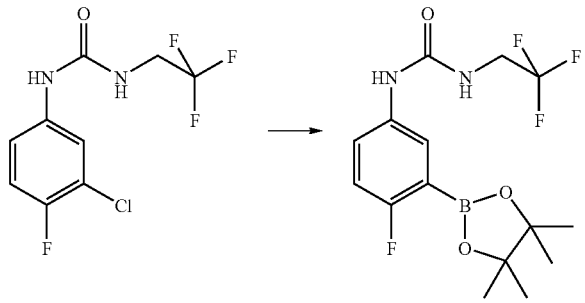 [SMILES: O=C(NCC(F)(F)F)Nc1ccc(F)c(Cl)c1 ; CC1(C)OB(c2cc(NC(=O)NCC(F)(F)F)ccc2F)OC1(C)C]

Prepared according to the procedure outlined in I8 substituting Pd$_2$dba$_3$ and S-Phos for PdCl$_2$ddpf. Product was isolated by trituration with petrol after aqueous work up (1.4 g). 1H NMR (400 MHz, DMSO-d6): 8.82 (1H, s), 7.72 (1H, dd), 7.52 (1H, ddd), 7.05 (1H, t), 6.67 (1H, t), 3.98-3.83 (2H, m), 1.30 (12H, s).

Boronic ester I39-2-Fluoro-5-(4,4,5,5-tetramethyl-[1,3,2]dioxaborolan-2-yl)-phenylamine

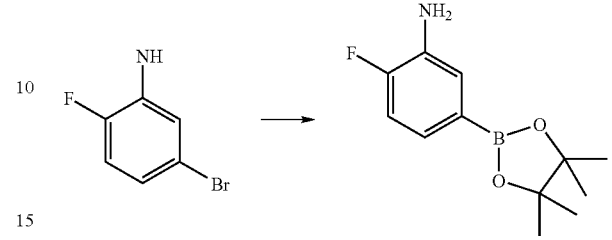

Prepared according to the procedure outlined in I8, no purification was performed and the crude material was used directly in the next step Boronic acid I40—1-Dimethylsulfamoyl-1H-pyrazole-4-boronic acid Step One—4-Bromo-pyrazole-1-sulfonic acid dimethylamide

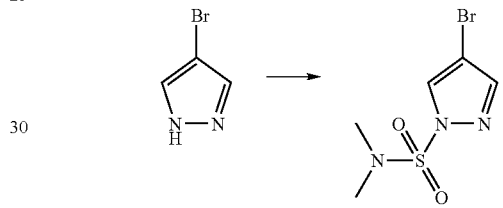

To a solution of 4-bromopyrazole (2.20 g, 15 mmol) and DABCO (1.85 g, 16.5 mmol) in anhydrous MeCN (15 ml) at room temperature was added dimethylsulfamoyl chloride (1.61 ml, 15 mmol). The reaction mixture was stirred for 20 h, then partitioned between 1N HCl$_{(aq)}$ and EtOAc. The aqueous layer was extracted with EtOAc (×2), the organics combined, washed with brine (×1), dried (MgSO$_4$), filtered and the solvent removed in vacuo to afford a colourless liquid. (3.79 g). 1H NMR (400 MHz, CDCl$_3$): 8.00 (1H, s), 7.70 (1H, s), 2.99 (6H, s).

Step Two—1-Dimethylsulfamoyl-1H-pyrazole-4-boronic acid

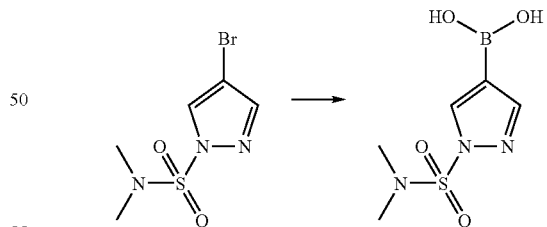

Methyl lithium (1.6M in Et$_2$O, 12.2 ml, 19.5 mmol) was added to a stirred solution of 4-bromo-pyrazole-1-sulfonic acid dimethylamide (3.18 g, 14.9 mmol) and triethyl borate (3.80 ml, 22.3 mmol) in anhydrous THF (40 ml), such that the internal temperature remained >-60° C. After 30 min, the reaction was allowed to warm to room temperature and stirred for 18 h. The reaction was quenched with 2N HCl (25 ml), then extracted with EtOAc (×3). The organic extracts were combined, dried (Na$_2$SO$_4$), filtered and the solvent removed in vacuo. The material was purified by silica column chromatography to afford a colourless gum (2.1 g). MS: [M+H]$^+$= 220

Boronic ester I41-4-(4,4,5,5-Tetramethyl-[1,3,2]dioxaborolan-2-yl)-2-trifluoromethyl-pyridine

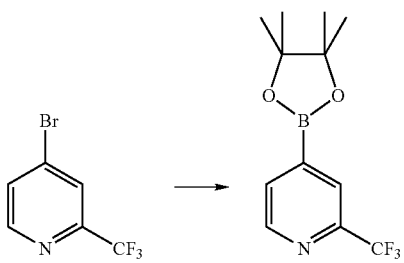 [SMILES: FC(F)(F)c1cc(Br)ccn1 ; CC1(C)OB(c2ccnc(C(F)(F)F)c2)OC1(C)C]

Prepared according to the procedure outlined in I8, no purification was performed and the crude material was used directly in the next step (1.25 g). 1H NMR (400 MHz, DMSO-d$^6$): 8.93 (1H, s), 8.29 (1H, d), 7.91 (1H, d), 1.34 (12H, s).

Boronic ester I42-5-(4,4,5,5-Tetramethyl-[1,3,2]dioxaborolan-2-yl)-pyridine-2-carboxylic acid methyl ester

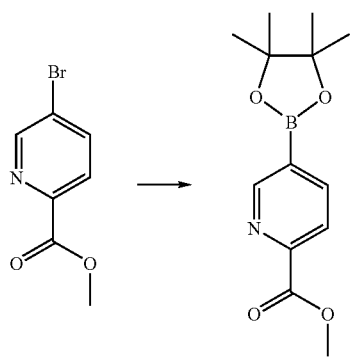

Prepared according to the procedure outlined in I8, no purification was performed and the crude material was used directly in the next step (3.1 g). 1H NMR (400 MHz, DMSO-d$^6$): 8.88 (1H, dd), 8.21 (1H, dd), 8.06 (1H, dd), 3.90 (3H, s), 1.34 (12H, s).

Procedure J1—Formation HCl salt 1-(3-{7-[3-(2-Amino-ethyl)-phenyl]-imidazo[1,2-a]pyridin-3-yl}-phenyl)-3-ethyl-urea dihydrochloride salt

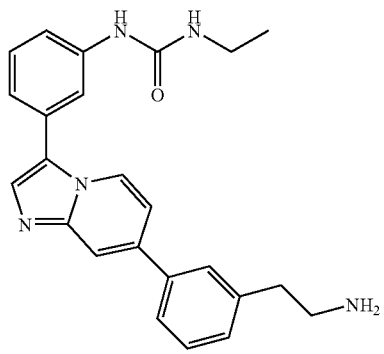 [SMILES: CCNC(=O)Nc1cccc(-c2cnc3cc(-c4cccc(CCN)c4)ccn23)c1]

A suspension of 1-(3-{7-[3-(2-Amino-ethyl)-phenyl]-imidazo[1,2-a]pyridin-3-yl}-phenyl)-3-ethyl-urea (0.01 g) in EtOH (2 ml) was treated with saturated EtOAc/HCl. The reaction was stirred until all in solution, then concentrated under reduced pressure, and the residue triturated with ether and dried to give (0.007 g) of the product MS: [M+H]$^+$ 400

Procedure J2

Step 1: [2-(3-{3-[7-(4-Fluoro-phenyl)-imidazo[1,2-a]pyridin-3-yl]-phenyl}-ureido)-ethyl]-carbamic acid tert-butyl ester

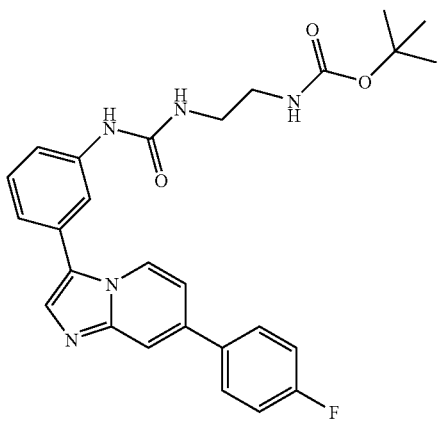 [SMILES: CC(C)(C)OC(=O)NCCNC(=O)Nc1cccc(-c2cnc3cc(-c4ccc(F)cc4)ccn23)c1]

Imidazol-1-yl-(3H-pyrrol-3-yl)-methanone (240 mg, 1.5 mmol) was added to a stirred solution of 3-[7-(4-fluoro-phenyl)-imidazo[1,2-a]pyridin-3-yl]phenylamine (450 mg, 1.5 mmol) in THF (10 ml) at 0° C. under N$_2$. The mixture was stirred at this temperature for 2 hours and then at RT for 3 hours. Half of the reaction mixture was transferred to a separate flask and treated with (2-amino-ethyl)-carbamic acid tert-butyl ester (320 mg, 2 mmol). The mixture was stirred at RT for 16 hours. The volatiles were removed in vacuo and the residue was purified using silica chromatography (2→4% 2M NH$_3$-MeOH/CH$_2$Cl$_2$) to give the title compound (85 mg, foam). MS: [M+H]$^+$ 490.

Step 2: 1-(2-Amino-ethyl)-3-{3-[7-(4-fluoro-phenyl)-imidazo[1,2-a]pyridin-3-yl]-phenyl}-urea

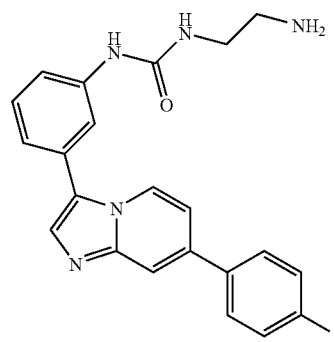

Trifluoroacetic acid (1 ml) was added to a stirred solution of [2-(3-{3-[7-(4-fluoro-phenyl)-imidazo[1,2-a]pyridin-3-yl]-phenyl}-ureido)-ethyl]-carbamic acid tert-butyl ester (85 mg, 0.17 mmol) in CH$_2$Cl$_2$ (2 ml) at 0° C. After 1 h the volatiles were removed in vacuo and the residue was purified by preparative HPLC to give the title compound (10 mg, solid).

General Scheme to synthesise pyrazolo[1,5-a]pyrimidines

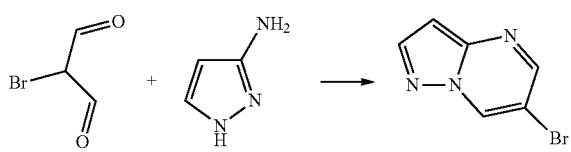

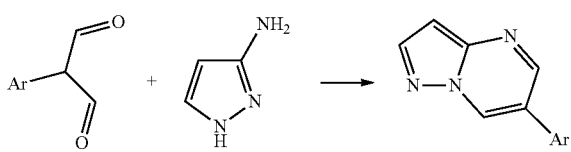

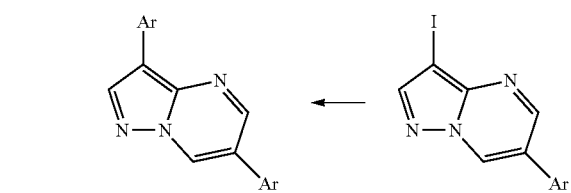

Preparation (or Procedure) K—General Ring Formation

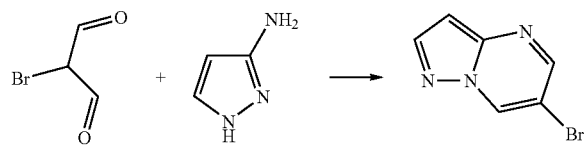

To a solution of 2-Bromo-malonaldehyde(12.8 g, 80 mmol) in EtOH (150 ml) was added 3-aminopyrazole (6 g, 37 mmol) followed by glacial acetic acid (10 ml). The mixture was refluxed for 4 h then allowed to cool, solid was filtered off and the filtrate was evaporated under reduced pressure. The residue was partitioned between 1M NaOH (50 ml) and EtOAc (200 ml) [some insoluble material was filtered off]. The organic layer was washed with brine, dried (MgSO$_4$), filtered and concentrated under reduced pressure. The solid was recrystallised from MeOH, filtered warm and washed with further MeOH and dried to afford 4.5 g of product.

MS: [M+H]$^+$ 198

Preparation (or Procedure) K1

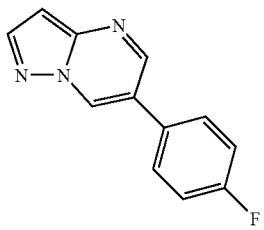 [SMILES: Fc1ccc(-c2cnc3ccnn3c2)cc1]

Same conditions as Preparation K (above) but replacement of 2-bromo-malonaldehyde with 2-(4-fluoro-phenyl)-malonaldehyde.

Preparation (or Procedure) L—Suzuki Reaction

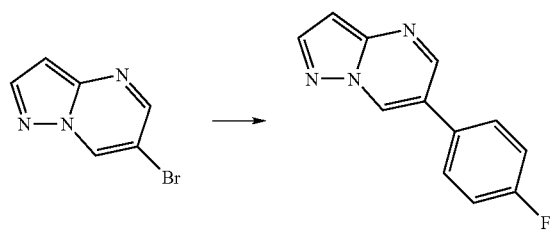 [SMILES: Brc1cnc2ccnn2c1 ; Fc1ccc(-c2cnc3ccnn3c2)cc1]

To a solution of 6-Bromo-pyrazolo[1,5-a]pyrimidine (0.5 g, 2.5 mmol) in DME (10 ml) added 4-fluorophenylboronic acid (0.46 g, 3.25 mmol) and 2M Na$_2$CO$_3$ (10 ml) [reaction degassed by bubbling N$_2$ through] followed by tetrakis(triphenylphosphine) palladium(0) (0.130 g, 0.11 mmol). The mixture was heated at 70° C. overnight, then diluted with water and extracted with EtOAc. The organic layer was washed with brine, dried (MgSO$_4$), filtered and concentrated under reduced pressure. Residue triturated with EtOAc, filtered, and the solid washed with more EtOAc then dried to afford (0.16 g) of the product. The filtrate was concentrated under reduced pressure. The product was purified by column chromatography on the Biotage (SiO$_2$, eluted with 5% EtOAC-petrol—50% EtOAC-petrol) to afford a further 0.223 g of product. MS: [M+H]$^+$ 214

Preparation (or Procedure) M—Iodination

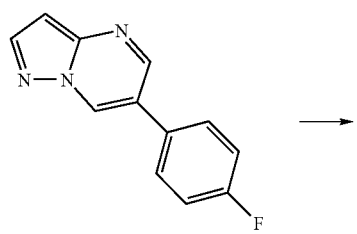

-continued

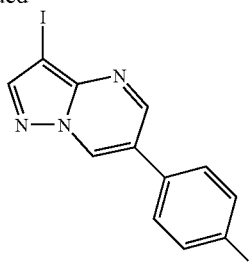

Method as described in General Route A Procedure 2 (A2)

Preparation (or Procedure) N—Suzuki at Position 3

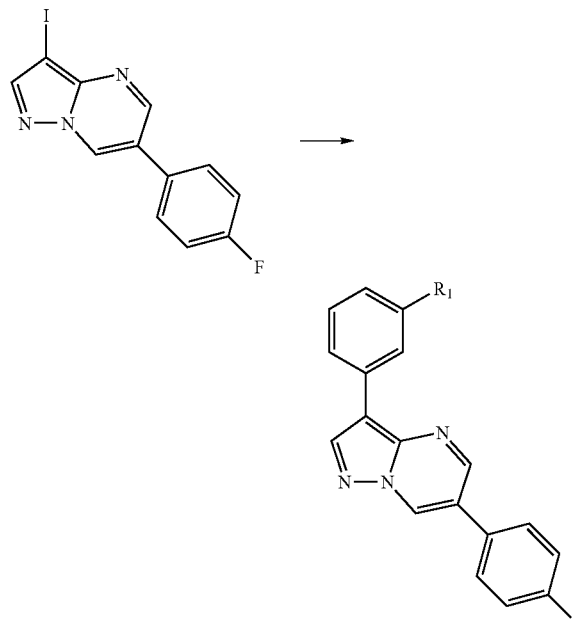

Method as described in General Route A Procedure 3b (A3b)

General Procedure O Benzamidazole Template

Procedure O1:
N-(4-Bromo-2-nitro-phenyl)-benzene-1,3-diamine

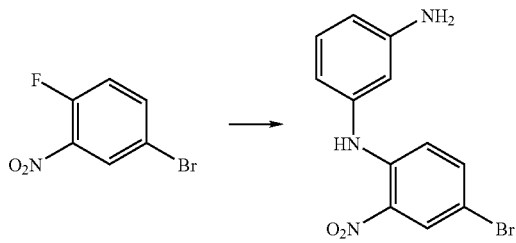 [SMILES: O=[N+]([O-])c1cc(Br)ccc1F ; Nc1cccc(Nc2ccc(Br)cc2[N+](=O)[O-])c1]

A mixture of 4-bromo-1-fluoro-2-nitro-benzene (1.14 ml, 9.25 mmol), benzene-1,3-diamine (1.96 g, 18.1 mmol) and DIPEA (1.93 ml, 11.1 mmol) in dry NMP (5 ml) was deoxygenated by evacuate/fill $N_2$ (×3), then stirred and heated at 120° C. under $N_2$ for 18 hours. After cooling to RT the mixture was partitioned between EtOAc and 0.5N HCl. The organic layer was washed with $H_2O$ (×1), brine (×1) then dried (MgSO$_4$), filtered and evaporated. The residue was purified by chromatography on silica (10→40% EtOAc/petrol) to give the title compound (1.8 g) as a red solid. 1H NMR (400 MHz, DMSO-d6): 9.28 (1H, s), 8.20 (1H, d), 7.63 (1H, dd), 7.14 (1H, d), 7.07 (1H, t), 6.49 (1H, s), 6.48-6.39 (2H, m), 5.24 (2H, s).

Procedure O2: N-(4'-Fluoro-3-nitro-biphenyl-4-yl)-benzene-1,3-diamine

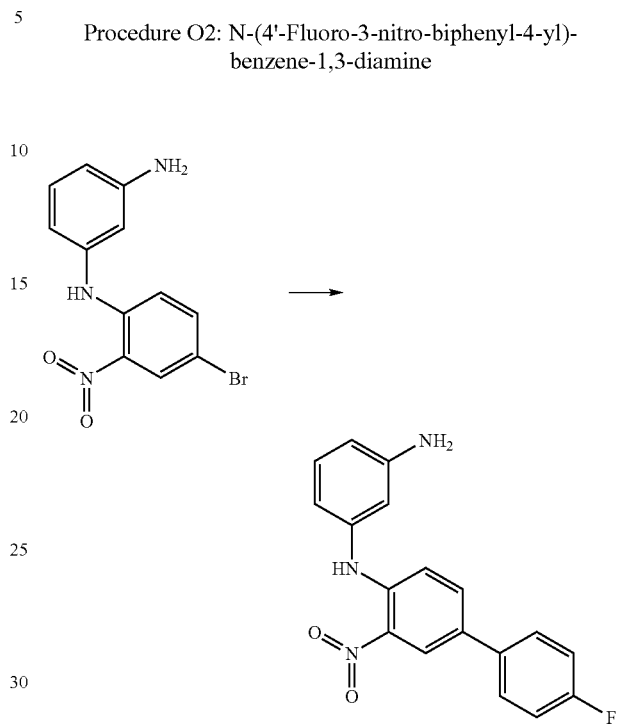

To a mixture of PdCl$_2$dppf (210 mg, 0.29 mmol), N-(4-bromo-2-nitro-phenyl)-benzene-1,3-diamine (Procedure O1, 1.8 g, 5.8 mmol) and 4-fluorophenylboronic acid (975 mg, 7.0 mmol) in DME (10 ml) was added 2N Na$_2$CO$_3$ (10 ml). The reaction was deoxygenated by evacuate/fill $N_2$ (×3), then stirred and heated at 90° C. under $N_2$ for 18 hours. After cooling to RT the mixture was partitioned between EtOAc/ $H_2O$ and then filtered through Celite. The organic layer was washed with $H_2O$ (×1), brine (×1), then dried (MgSO$_4$), filtered and evaporated. The residue was purified by chromatography on silica (10→50% EtOAc/petrol) to give the title compound (1.66 g) as a dark red/brown solid. 1H NMR (400 MHz, DMSO-d6): 9.30 (1H, s), 8.32 (1H, d), 7.85 (1H, dd), 7.72 (2H, dd), 7.35-7.24 (3H, m), 7.08 (1H, t), 6.54 (1H, s), 6.47 (2H, t), 5.25 (2H, s).

Procedure O3: N*4*-(3-Amino-phenyl)-4'-fluoro-biphenyl-3,4-diamine

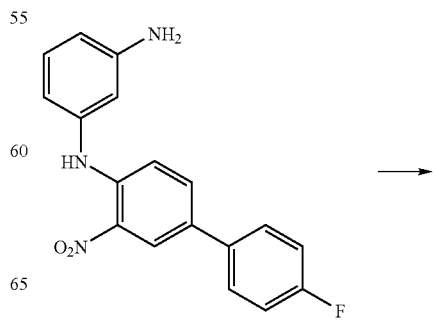

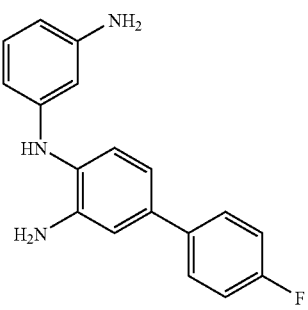

N-(4'-Fluoro-3-nitro-biphenyl-4-yl)-benzene-1,3-diamine (Procedure O2, 1.66 g, 5.1 mmol) was hydrogenated at atmospheric pressure over 10% Pd/C (300 mg) in EtOH/AcOH (3:1, 40 ml) until hydrogen consumption ceased. The catalyst was removed by filtration—washing with EtOH. The volatiles were removed in vacuo and the residue was azeotroped with PhMe to give the title compound. This material was used immediately in the next step.

Procedure O4: 3-[5-(4-Fluoro-phenyl)-benzoimidazol-1-yl]-phenylamine

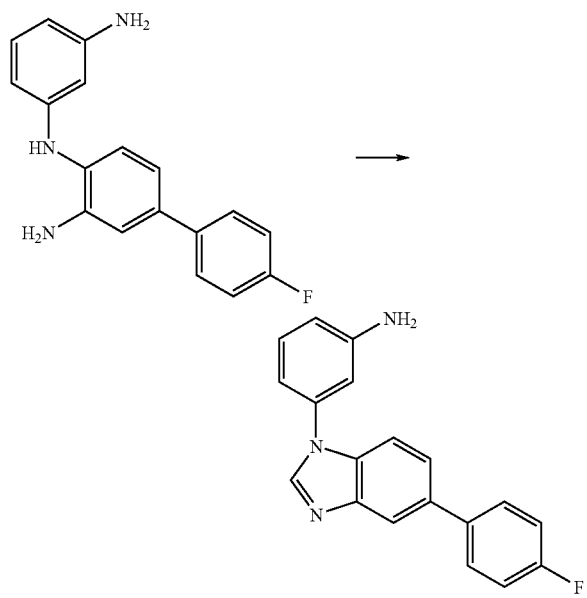

A solution of N*4*-(3-Amino-phenyl)-4'-fluoro-biphenyl-3,4-diamine (Procedure O3, ~5.1 mmol) in trimethylorthoformate (30 ml) was stirred and heated at 120° C. under $N_2$ for 10 hours. The volatiles were removed in vacuo and the residue was taken up in EtOH (30 ml) and treated with c.HCl (2 ml), then stirred and heated at reflux for 3 hours. After cooling to RT, the mixture was concentrated to ~2 ml, then diluted with $H_2O$. NaHCO$_3$ (sat) was added to give ~pH7.5. The solid was taken up in $CH_2Cl_2$. The organic layer was dried and evaporated. The residue was purified by chromatography on silica (0%→1%→>2% 2M NH$_3$-MeOH/ CH$_2$Cl$_2$). The material was then triturated with Et$_2$O to give the title compound (890 mg) as an off-white solid.

Procedure O5: 1-{3-[5-(4-Fluoro-phenyl)-benzoimidazol-1-yl]-phenyl}-3-(2,2,2-trifluoro-ethyl)-urea

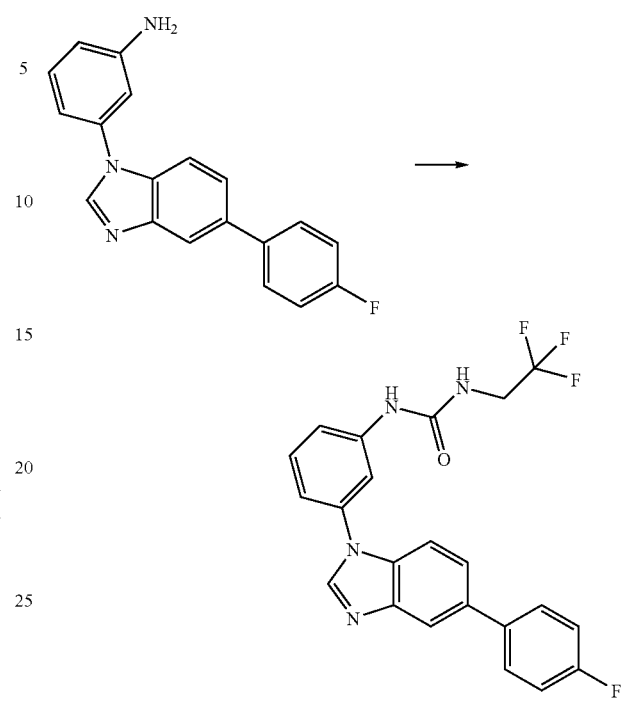

A solution of 3-[5-(4-fluoro-phenyl)-benzoimidazol-1-yl]-phenylamine (150 mg, 0.5 mmol) and 4-nitrophenyl chloroformate (105 mg, 0.52 mmol) in dry THF (5 ml) was stirred and heated at 60° C. under $N_2$ for 3 hours. After cooling to RT, DIPEA (2504 1.5 mmol) and 2,2,2-trifluoroethylamine (804 1.0 mmol) were added and the solution was stirred at RT for 16 hours. The volatiles were removed in vacuo and the residue was taken up in $CH_2Cl_2$ and loaded onto a SCX cartridge. The cartridge was eluted with MeOH to remove the phenol and then 2M NH$_3$-MeOH to give the product. The fractions were evaporated and the residue was triturated with Et$_2$O to give the title compound (180 mg) as a colourless solid.

Procedure O6: Salt formation; 1-{3-[5-(4-Fluoro-phenyl)-benzoimidazol-1-yl]-phenyl}-3-(2,2,2-trifluoro-ethyl)-urea Hydrochloride A suspension of 1-{3-[5-(4-Fluoro-phenyl)-benzoimidazol-1-yl]-phenyl}-3-(2,2,2-trifluoro-ethyl)-urea (Procedure O5) in MeOH was treated with an EtOAc solution of hydrogen chloride. The solid was collected and dried under vacuum.

General Procedure P: Azabenzamidazole Template

Preparation P1: N-(5-Bromo-3-nitro-pyridin-2-yl)-benzene-1,3-diamine

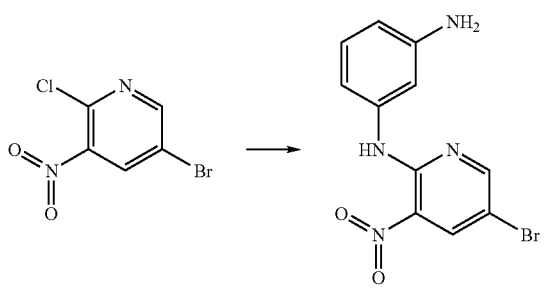 [SMILES: O=[N+]([O-])c1cc(Br)cnc1Cl ; Nc1cccc(Nc2ncc(Br)cc2[N+](=O)[O-])c1]

A mixture of 5-bromo-2-chloro-3-nitro-pyridine (2.4 g, 10.1 mmol), benzene-1,3-diamine (2.7 g, 25 mmol) and DIPEA (5.3 ml, 30 mmol) in dry NMP (20 ml) was stirred and heated at 120° C. under $N_2$ for 2 hours. After cooling to RT the mixture was partitioned between EtOAc and $H_2O$. The organic layer was washed with brine (×1) then dried (MgSO$_4$), filtered and evaporated. The residue was purified by chromatography on silica (10→50% EtOAc/petrol) to give the title compound (2.5 g) as a red solid. 1H NMR (400 MHz, DMSO-d6): 9.78 (1H, s), 8.66 (1H, d), 8.60 (1H, d), 7.00 (1H, t), 6.83-6.71 (2H, m), 6.39 (1H, d), 5.13 (2H, s).

Preparation P2: N-[5-(4-Fluoro-phenyl)-3-nitro-pyridin-2-yl]-benzene-1,3-diamine

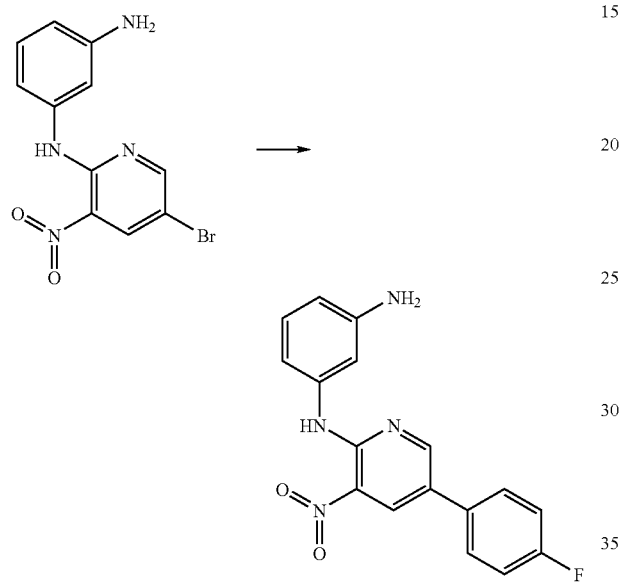

A mixture of PdCl$_2$dppf (300 mg, 0.4 mmol), N-(5-bromo-3-nitro-pyridin-2-yl)-benzene-1,3-diamine (Preparation P1, 2.5 g, 8.2 mmol) and 4-fluorophenylboronic acid (1.4 g, 10 mmol) in DME (16 ml) and 2N Na$_2$CO$_3$ (16 ml) was deoxygenated by evacuate/fill N$_2$ (×3), then stirred and heated at 80° C. under N$_2$ for 4 hours. After cooling to RT the mixture was partitioned between EtOAc/H$_2$O and then filtered through Celite. The organic layer was washed with brine (×1) then dried (MgSO$_4$), filtered and evaporated. The residue was purified by chromatography on silica (10→50% EtOAc/petrol) to give the title compound (1.66 g) as a dark red/brown solid. 1H NMR (400 MHz, DMSO-d6): 9.85 (1H, s), 8.87 (1H, d), 8.70 (1H, d), 7.82 (2H, dd), 7.33 (2H, t), 7.02 (1H, t), 6.92-6.81 (2H, m), 6.40 (1H, d), 5.15 (2H, s).

Preparation P3: 3-[6-(4-Fluoro-phenyl)-imidazo[4,5-b]pyridin-3-yl]-phenylamine

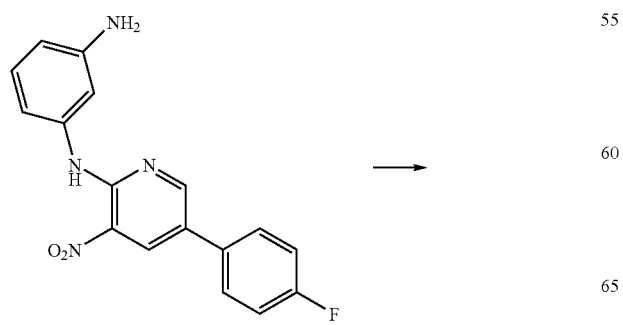

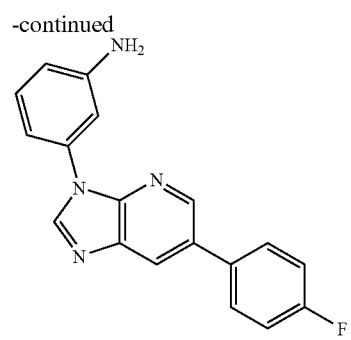

Zinc dust (9.3 g, 142 mmol) was added to a stirred solution of N-[5-(4-fluoro-phenyl)-3-nitro-pyridin-2-yl]-benzene-1,3-diamine (2.3 g, 7.1 mmol) in AcOH (35 ml) at RT. After the exotherm had subsided the reaction was stirred and heated at 60° C. for 3 hours. The mixture was allowed to cool to RT then filtered through Celite—washing with AcOH (~150 ml). The filtrate was evaporated and the residue was azeotroped with toluene (×2). The residue was taken up in trimethylorthoformate (50 ml) and then stirred and heated at reflux under N$_2$ for 1 hour. After cooling to RT, the volatiles were removed in vacuo. The residue was taken up in EtOH (100 ml). c. HCl (4 ml) was added and the mixture was heated at reflux for 2 hours. After cooling, the mixture was concentrated to ~4 ml and basified with saturated aqueous NaHCO$_3$. The aqueous mixture was extracted with CH$_2$Cl$_2$ (×3). The combined extracts were dried (MgSO$_4$), filtered and evaporated. The residue was purified by chromatography on silica (40→100% EtOAc/petrol) to give the title compound (0.86 g).

General Procedure R—Urea Formation

Procedure R1

1-(2,2-Dimethyl-[1,3]dioxolan-4-ylmethyl)-3-{3-[7-(4-fluoro-phenyl)-imidazo[1,2-a]pyridin-3-yl]-phenyl}-urea

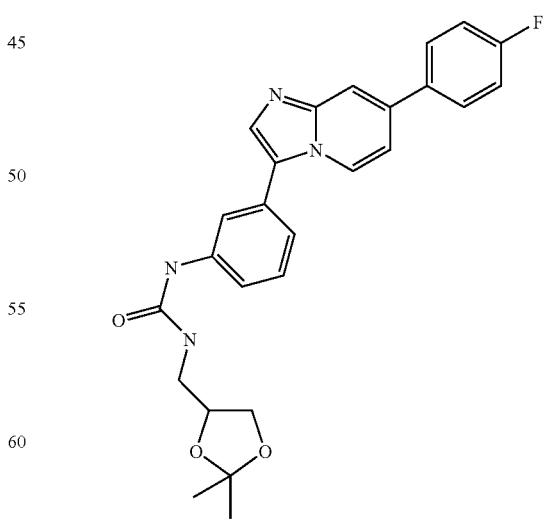

To a solution of 3-[7-(4-Fluoro-phenyl)-imidazo[1,2-a]pyridin-3-yl]-phenylamine (0.1 g, 0.33 mmol) in CH$_2$Cl$_2$ (7 ml) was added CDI (0.054 g, 0.33 mmol) and stirred ambient for 5 hours. To the precipitate, was added (2,2-dimethyl-[1,3]-dioxolan-4-yl)-methylamine (0.04 ml, 0.33 mmol) and reaction heated at 50° C. overnight. The reaction was washed with sat. sodium bicarbonate solution, the organic layer was washed with brine, dried (MgSO₄), and concentrated under reduced pressure and the residue was purified by preparative HPLC to give the title compound (8 mg) MS: [M+H]⁺ 461.

Procedure R2

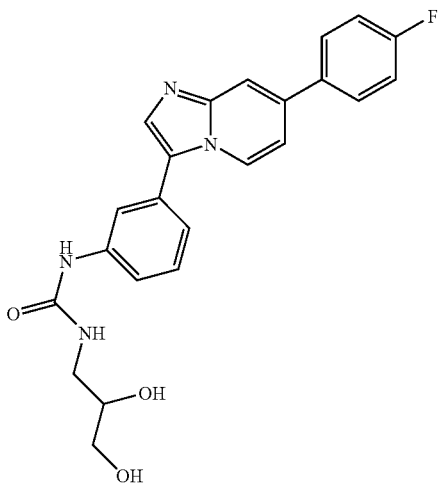 [SMILES: O=C(NCC(O)CO)Nc1cccc(-c2cnc3cc(-c4ccc(F)cc4)ccn23)c1]

1-(2,2-Dimethyl-[1,3]dioxolan-4-ylmethyl)-3-{3-[7-(4-fluoro-phenyl)-imidazo[1,2-a]pyridin-3-yl]-phenyl}-urea (0.02 g) treated with sat EtOAc/HCl (3 ml) and MeOH (0.5 ml) stirred ambient overnight, concentrated under reduced pressure to give the title compound (12 mg) MS: [M+H]⁺ 421

Procedure S 1-(3-{7-[6-Oxo-1-(3-piperidin-1-yl-propyl)-1,6-dihydro-pyridin-3-yl]-imidazo[1,2-a]pyridin-3-yl}-phenyl)-3-(2,2,2-trifluoro-ethyl)-urea hydrochloride

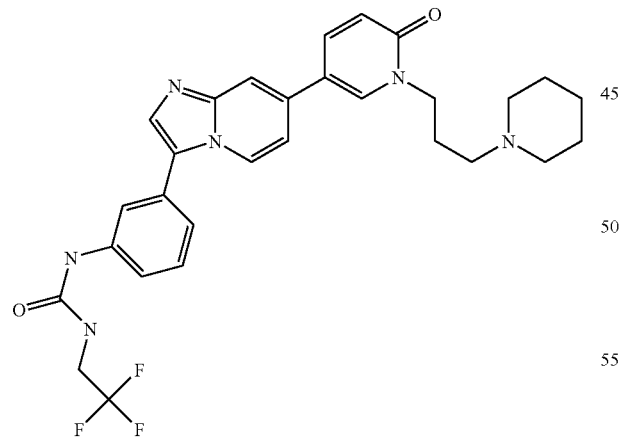

General route A, procedure A3b using 1-[3-(4,4,5,5-Tetramethyl-[1,3,2]dioxaborolan-2-yl)-phenyl]-3-(2,2,2-trifluoro-ethyl)-urea, procedure A4b using 2-methoxy-5-pyridineboronic acid.

To 1-{3-[7-(6-Methoxy-pyridin-3-yl)-imidazo[1,2-a]pyridin-3-yl]-phenyl}-3-(2,2,2-trifluoro-ethyl)-urea (0.187 g, 0.226 mmol) in DCE (10 ml) was added PBr₃ (0.174 ml). The reaction was heated at 80° C. for 3 hours, then partitioned between EtOAc and water, insoluble material filtered off and dried to give 1-{3-[7-(6-Oxo-1,6-dihydro-pyridin-3-yl)-imidazo[1,2-a]pyridin-3-yl]-phenyl}-3-(2,2,2-trifluoro-ethyl)-urea (0.12 g) MS: [M+H]+428

To 1-{3-[7-(6-Oxo-1,6-dihydro-pyridin-3-yl)-imidazo[1,2-a]pyridin-3-yl]-phenyl}-3-(2,2,2-trifluoro-ethyl)-urea (0.12 g, 0.63 mmol) in DMF (1.5 ml) was added N-(3-chloropropyl)piperidine hydrochloride (0.125 g, 0.63 mmol), Cs₂CO₃ (0.32 g, 0.98 mmol) and NaI (0.095 g, 0.63 mmol). The reaction was heated at 80° C. for 48 hours then partitioned between EtOAc and water, the organic layer was washed with brine, dried (MgSO₄), filtered and concentrated under reduced pressure. The residue was purified by preparative HPLC to give the title compound (16 mg) MS: [M+H]+ 553

Procedure T 1-(3-{7-[3-(1-Acetyl-piperidin-4-yloxy)-phenyl]-imidazo[1,2-a]pyridine-3-yl}-phenyl)-3-(2,2,2-trifluoro-ethyl)-urea

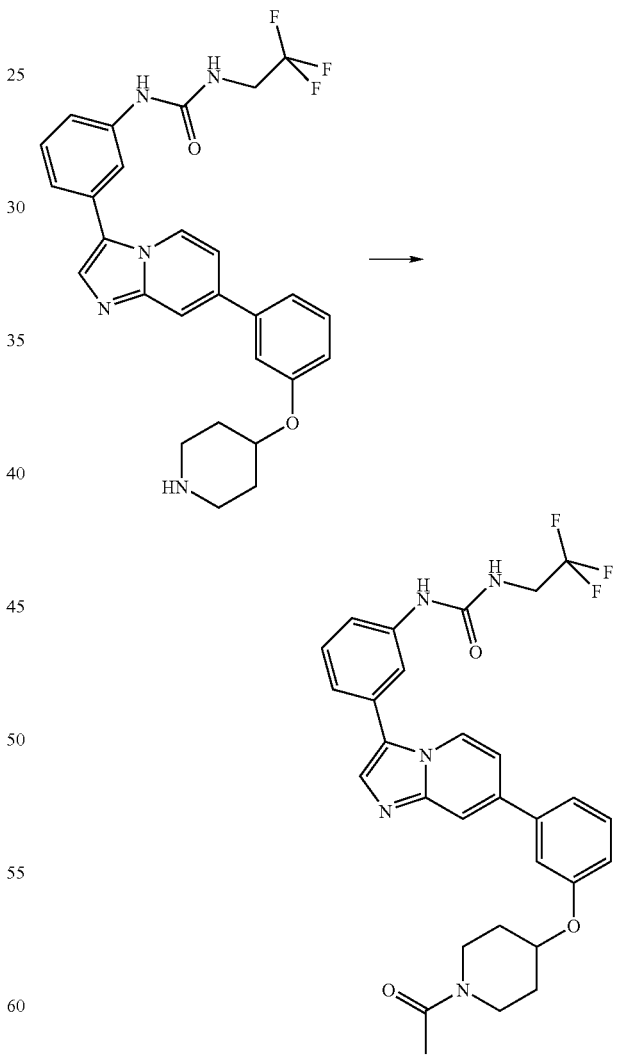

To a solution of 1-(3-{7-[3-(Piperidin-4-yloxy)-phenyl]-imidazo[1,2-a]pyridine-3-yl}-phenyl)-3-(2,2,2-trifluoro-ethyl)-urea (50 mg, 98 μmol in DMF(10 ml) was added acetyl chloride (6.3 μl, 82 μmol) and Et₃N (14 μl). The reaction was stirred at room temperature for 3 h, then partitioned between EtOAc and H₂O. The aqueous layer was again extracted with EtOAc, the organics combined, dried (MgSO₄), filtered and the solvent removed in vacuo. The residue was purified by preparative HPLC to give the title compound (17.5 mg).

Halo-Monomer Formations U

Procedure U2:
1-(5-Bromo-pyridin-3-yl)-3-ethyl-urea

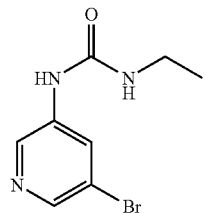

A mixture of EtNCO (1.6 ml, 20 mmol) and 5-bromo-pyridin-3-ylamine (1.73 g, 10 mmol) in DME (10 ml) was stirred and heated at 60° C. under $N_2$. After 2 hours another aliquot of EtNCO (1.6 ml, 20 mmol) was added and the mixture was stirred at 60° C. for a further 16 hours. After cooling to RT the mixture was evaporated. The residue was triturated with EtOAc. The solid was collected by filtration and dried under vacuum to give the title compound (2.2 g) as a colourless solid. 1H NMR (400 MHz, DMSO-d⁶): 8.85 (1H, s), 8.43 (1H, d), 8.27 (1H, t), 8.21 (1H, d), 6.39 (1H, t), 3.19-3.05 (2H, m), 1.06 (3H, t).

Procedure U3: 1-(5-Bromo-pyridin-3-yl)-3-(2,2,2-trifluoro-ethyl)-urea

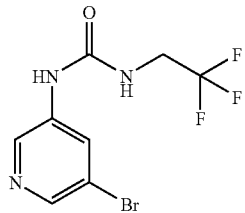 [SMILES: O=C(NCC(F)(F)F)Nc1cncc(Br)c1]

A solution of 5-bromo-pyridin-3-ylamine (1.73 g, 10 mmol) and 4-nitrophenyl chloroformate (2.2 g, 11 mmol) in dry THF (40 ml) was stirred and heated at 60° C. under $N_2$ for 3 hours. After cooling to RT, DIPEA (5.2 ml, 30 mmol) and 2,2,2-trifluoroethylamine (1.6 ml, 20 mmol) were added and the solution was stirred at RT for 16 hours. The volatiles were removed in vacuo and the residue was partitioned between EtOAc and 1N NaOH. The organic layer was washed with H₂O (×1) and brine (×1), then dried (MgSO₄), filtered and evaporated. The residue was triturated with CH₂Cl₂. The solid was collected by filtration, washed with Et₂O and dried under vacuum to give the title compound (1.7 g) as a colourless solid. 1H NMR (400 MHz, DMSO-d⁶): 9.18 (1H, s), 8.49 (1H, d), 8.28 (1H, d), 8.25 (1H, t), 7.06 (1H, t), 3.99-3.88 (2H, m).

Procedure U4: 1-(2-Chloro-pyridin-4-yl)-3-(2,2,2-trifluoro-ethyl)-urea

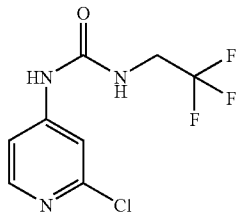 [SMILES: O=C(NCC(F)(F)F)Nc1ccnc(Cl)c1]

To 4-nitrophenyl chloroformate (2.91 g, 14.5 mmol) in THF (35 mL) was added 4-amino-2-chloropyridine (2.08 g, 16.2 mmol) and the reaction stirred at 60° C. for 2 hours. After cooling to room temperature 2,2,2-trifluoroethylamine (1.26 mL, 15.9 mmol) and DIPEA (7.5 mL, 43.4 mmol) were added and the reaction stirred at room temperature for 18 hours. The reaction was concentrated in vacuo and the residue partitioned between 1M NaOH (40 mL) and EtOAc (2×50 mL). The combined organic phases were washed with brine (60 mL), dried over MgSO₄, filtered and concentrated in vacuo. The resulting yellow solid was suspended in CH₂Cl₂, filtered and washed with CH₂Cl₂ to give the product as a pale yellow solid (1.72 g).

Procedure U5:
1-(4-Chloro-pyridin-2-yl)-3-ethyl-urea

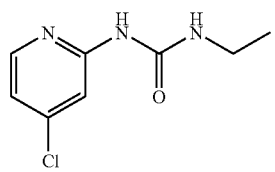

To 2-amino-4-chloropyridine (1.02 g, 7.9 mmol) in THF (20 mL) was added ethyl isocyanate (0.69 ml, 8.69 mmol) and the reaction heated at 55° C. for 18 hours. The reaction was concentrated in vacuo. The resulting white solid was suspended in EtOAc and filtered to give the product as a white solid (0.79 g).

Procedure U6:
2-(4-Bromo-pyridin-2-yl)-propan-2-ol

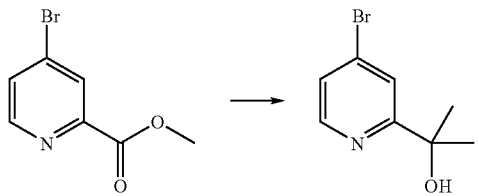

A solution of 4-bromo-pyridine-2-carboxylic acid methyl ester (1.08 g, 5 mmol) in dry THF (10 ml) was added slowly to a stirred solution of MeMgBr (3M in $Et_2O$, 4.2 ml, 12.6 mmol) in dry THF (20 ml) at 0° C. under $N_2$. After 1 hr at this temperature the cooling bath was removed and the mixture was stirred at RT for 2 hours. The reaction was quenched with saturated aqueous $NaHCO_3$, then partitioned between $EtOAc/H_2O$. The aqueous layer was extracted with EtOAc (×2). The combined extracts were washed with $H_2O$ (×1), brine (×1), then dried ($Na_2SO_4$), filtered and evaporated. The residue was purified by chromatography on silica: 5→25% EtOAc/hexanes to give the title compound (518 mg) as a colourless liquid. $^1H$ NMR (400 MHz, $CDCl_3$): 8.36 (1H, d), 7.60 (1H, d), 7.39 (1H, dd), 4.52 (1H, s), 1.56 (6H, s).

Procedure U7-2—Bromo-[1,3,4]thiadiazole

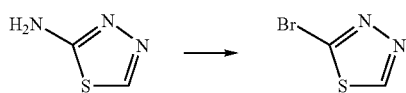

To [1,3,4]thiadiazol-2-ylamine (1 g, 9.89 mmol) was added 48% aqueous HBr (10 ml) and $H_2O$ (10 ml). The reaction mixture was cooled to 0° C. using an icebath, CuBr (142 mg, 0.99 mmol) was added and then a solution of sodium nitrite (0.682 mg, 9.89 mmol) in $H_2O$ (10 ml) was added dropwise and the mixture allowed to stir for 10 mins. The reaction mixture was gradually warmed up to room temperature over 30 min, then a saturated solution of bicarbonate added until the pH of the mixture reached 8.0. The aqueous layer was extracted with EtOAc (×3), the organics combined, dried ($MgSO_4$), filtered and the solvent removed in vacuo to give a pale yellow solid (1 g), which was used directly in the next reaction. 1H NMR (400 MHz, DMSO-d6): 9.63 (1H, s).

Procedure U8-2-Bromo-5-methoxymethyl-[1,3,4]thiadiazole

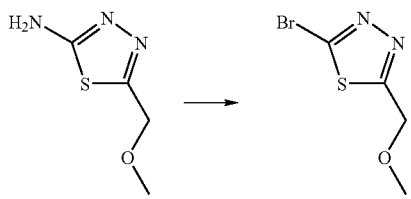

To a stirred mixture of 48% aqueous HBr (2.7 ml) and CuBr (20 mg, 0.14 mmol) cooled to approximately −7° C. using an ice/salt bath was added portionwise over 30 mins a mixture of 5-methoxymethyl-[1,3,4]thiadiazol-2-ylamine (348 mg, 2.4 mmol) and sodium nitrite (0.759 g, 11 mmol). The reaction mixture was stirred for 1 h at −7° C. and then at room temperature for a further 1.5 h. The mixture was then neutralised using 10 M NaOH, treated with a solution of saturated sodium metabisulfite (5 ml), heated to 60° C. for 30 mins, then neutralised. The reaction mixture was extracted with cyclohexane (×2), the organic fractions combined, dried ($MgSO_4$), filtered and the solvent removed in vacuo to give the product (123 mg). MS: $[M+H]^+$ 209, 211.

Procedure U9-2—Bromo-4,5-dimethyl-thiazole

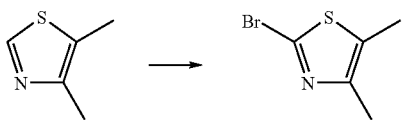

To a solution of 4,5-dimethyl-thiazole (5.00 g, 44.3 mmol) in $CHCl_3$ (125 ml) at 0° C. was added bromine (6.8 ml, 0.132 mol) dropwise. The reaction was allowed to warm to room temperature and stirred for 5 h, before being treated with aqueous sodium thiosulphate. The layers were separated and the aqueous extracted with further $CHCl_3$. The organic fractions were combined, washed with $H_2O$, then brine, dried ($MgSO_4$), filtered and the solvent removed in vacuo. The residue was purified by silica column chromatography running a 2-10% EtOAc in hexane gradient to afford 1.2 g of product. MS: $[M+H]^+$ 192, 194.

Procedure U10—4-Bromo-1,2,5-Trimethyl-1H-Imidazole

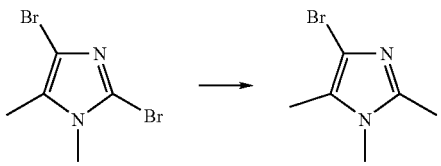

2,4-Dibromo-1,5-dimethyl-1H-imidazole (1.25 g, 4.9 mmol) was dissolved in THF (25 ml) under an argon atmosphere and the solution was cooled to −78° C. n-Butyl lithium (2 ml of a 2.5M solution in hexanes, 5 mmol) was added dropwise, so that the internal temperature remained below −70° C. The resulting solution was stirred for 15 mins before iodomethane (0.62 ml, 10 mmol) was added and the reaction was allowed to warm to 0° C. and stirred for 1 h. 2N HCl (3 ml) was added and the volatiles were removed in vacuo. The residue was partitioned between water and $CH_2Cl_2$ and the aqueous extracts were adjusted to pH 8 with 2N NaOH, then extracted with $CH_2Cl_2$ (×4). The organic extracts were dried by passing through a phase separation cartridge and concentrated in vacuo. The residue was purified by preparative HPLC to generate the product (85 mg) as a pale yellow solid. MS: $[M+H]^+$=189, 191.

Procedure U11—3-Bromo-[1,2,4]-thiadiazole

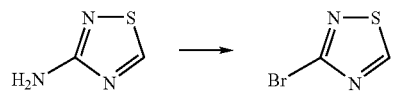

Prepared as described in procedure U7, replacing [1,3,4]thiadiazol-2-ylamine with [1,2,4]thiadiazol-3-ylamine. 1H NMR (400 MHz, DMSO-d6): 8.87 (1H, s).

General Route V

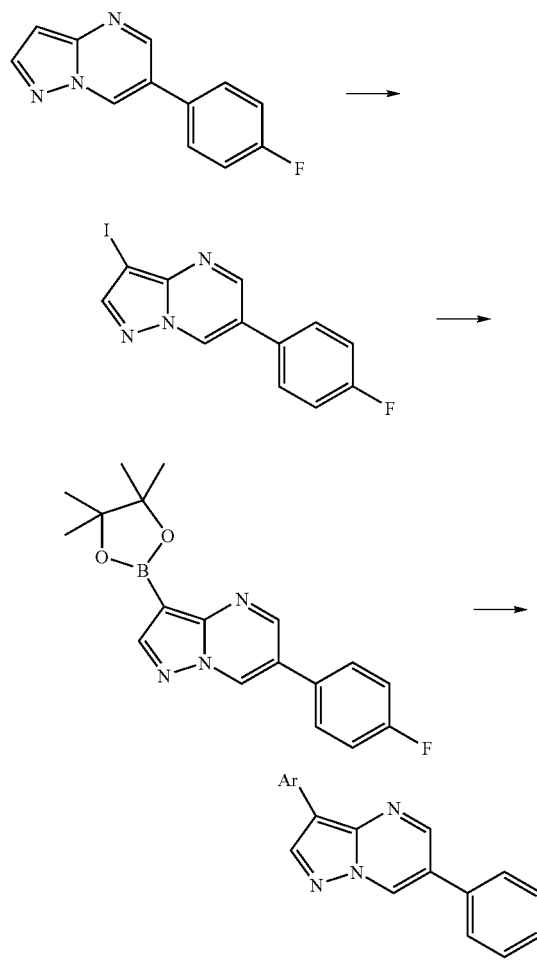

Procedure V1—Iodination

148

Method as described in General Route A Procedure 2 (A2)

Procedure V2—Formation of 6-(4-Fluoro-phenyl)-3-(4,4,5,5-tetramethyl-[1,3,2]dioxaborolan-2-yl)-pyrazolo[1,5-a]pyrimidine To 6-(4-fluoro-phenyl)-3-iodo-pyrazolo[1,5-a]pyrimidine (0.69 g, 2.02 mmol) in anhydrous DMSO (4 mL) was added bis(pinacolato)diboron (1.03 g, 4.07 mmol) and KOAc (0.63 g, 6.38 mmol). The reaction flask was purged with $N_2$ and $PdCl_2dppf$ (82 mg, 0.11 mmol) added. The reaction flask was further purged with $N_2$ and then heated at 100° C. for 3 hrs. After cooling to room temperature, EtOAc (30 mL) and $H_2O$ (30 mL) were added and the insoluble material filtered. The filtrate was retained and the organic and aqueous phases separated. The aqueous phase was re-extracted with EtOAc (25 mL). The combined organic phases were dried over $MgSO_4$, filtered and concentrated in vacuo. The solid was triturated with $Et_2O$ to afford the title compound as a brown solid (0.35 g).

Procedure V3b—Suzuki Reaction

1-Ethyl-3-{2-[6-(4-fluoro-phenyl)-pyrazolo[1,5-a]pyrimidin-3-yl]-pyridin-4-yl}-urea

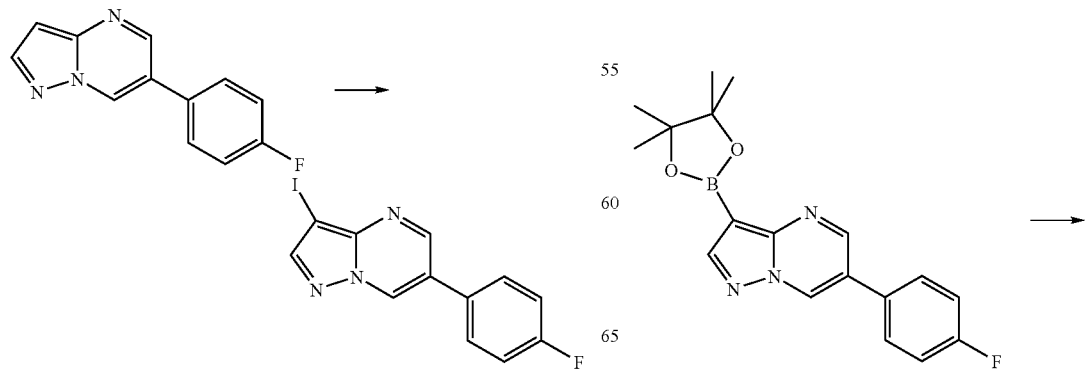

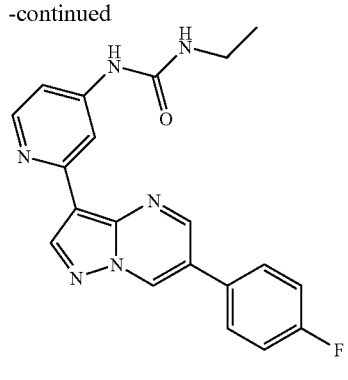

A solution of K₃PO₄ (640 mg, 3 mmol) in H₂O (2 ml) was added to a stirred mixture of 6-(4-fluoro-phenyl)-3-(4,4,5,5-tetramethyl-[1,3,2]dioxaborolan-2-yl)-pyrazolo[1,5-a]pyrimidine (330 mg, 0.97 mmol) and 1-(2-chloro-pyridin-4-yl)-3-ethyl-urea (procedure U4, 420 mg, 2.1 mmol) in dioxane (8 ml) at RT under N₂. The mixture was deoxygenated by evacuate/fill N₂ (×2), PdCl₂dppf (40 mg, 0.05 mmol) was added and the mixture was deoxygenated again (×3). The reaction was stirred and heated at 90° C. for 18 h. After cooling to RT the reaction was partitioned between CH₂Cl₂/H₂O. The aqueous layer was extracted with CH₂Cl₂ (×1). The combined extracts were dried, then evaporated. The residue was purified by preparative HPLC to give the title compound (68 mg) as a yellow solid.

Procedure W: Heck Reaction

5-[7-(4-Fluoro-phenyl)-imidazo[1,2-a]pyridin-3-yl]-pyridin-3-ylamine

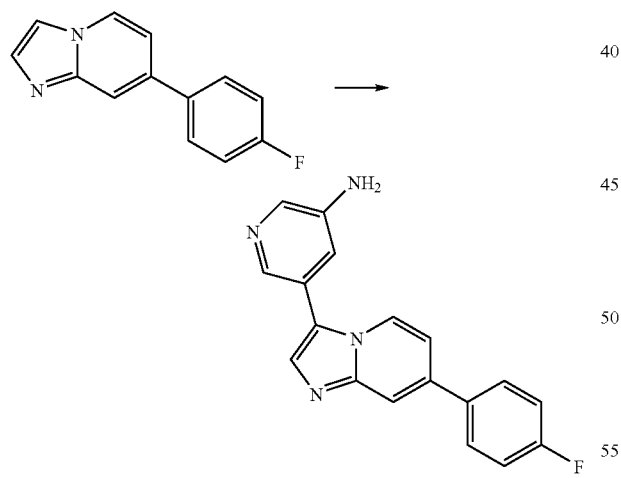

To 7-(4-fluoro-phenyl)-imidazo[1,2-a]pyridine (0.1093 g, 0.52 mmol) and 3-amino-5-bromopyridine (0.181 g, 1.05 mmol) in DMF (2 mL) was added 0.5 M K₂CO₃ (2.06 mL, 1.03 mmol). The reaction vessel was purged with N₂ and Pd(PPh₃)₄ (63 mg, 0.055 mmol) added. The vessel was further purged with N2 and then heated in the microwave at 120° C. for 30 mins. Further 3-amino-5-bromopyridine (0.13 g, 0.75 mmol) and Pd(PPh₃)₄ (43 mg, 0.037 mmol) were added and the reaction heated in the microwave at 140° C. for 1 hour. The solids were filtered and the filtrate was concentrated in vacuo. The residue was partitioned between H₂O (20 ml) and EtOAc (2×20 mL). The combined organic phases were dried over MgSO₄, filtered and concentrated in vacuo and the product used crude in the subsequent reaction.

Procedure XX (2,2,2-Trifluoroethyl)sulfamoyl)chloride

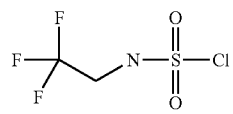

To 2,2,2-trifluoroethylamine (3.9 ml, 4.9 mmol) cooled in an ice bath was added sulfuryl chloride (8 ml) in CH₃CN (15 ml) dropwise slowly. A solid was observed to precipitate from the reaction mixture. Reaction stirred at 42° C. overnight, solid filtered off and filtrate concentrated under reduced pressure, re-evaporated with toluene and used crude.

General Procedure to Synthesise Imidazo[1,2-c]pyrimidine template

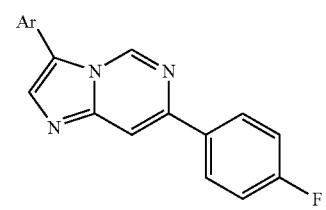

Procedure X—General Route to Imidazo[1,2c]pyrimidine

Preparation X1—Suzuki Coupling

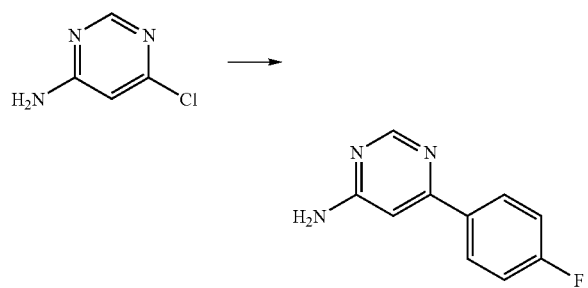

To a solution of 6-Chloro-pyrimidin-4-ylamine (0.5 g, 3.87 mmol) in dioxane (15 ml) was added 4-fluorophenylboronic acid (0.7 g, 5.00 mmol) and a solution of $K_3PO_4$ (2.87 g, 13.55 mmol) in $H_2O$. The reaction mixture was deoxygenated, bis(triphenylphosphine)palladium(II) chloride (54 mg) added and the reaction mixture heated at 50° C. for 4 h. The reaction mixture was partitioned between EtOAc, and $H_2O$, the aqueous layer washed with EtOAc, the organics combined, dried ($MgSO_4$), filtered and the solvent removed in vacuo. The residue was triturated with EtOAc to afford the product (0.47 g). MS: $[M+H]^+$ 190.

Procedure X2—Ring Formation

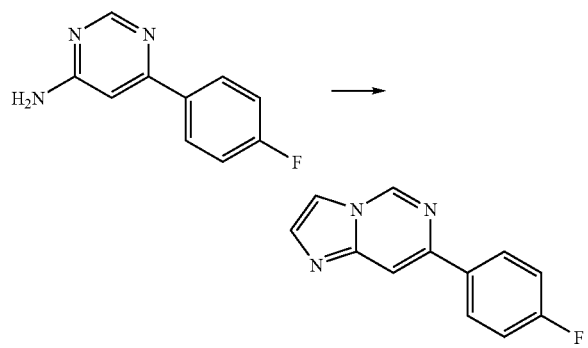

Same conditions as Preparation A1

Procedure X3—Bromination of Heterocylic Ring

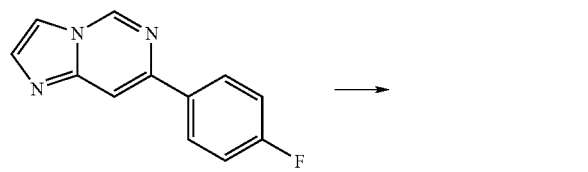

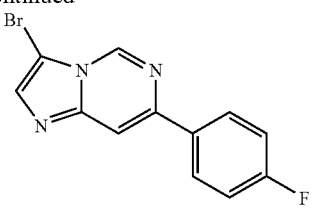

To 7-(4-Fluoro-phenyl)-imidazo[1,2-c]pyrimidine (120 mg, 0.56 mmol) in acetic acid (2 ml) was added sodium acetate (69 mg, 0.84 mmol), then a solution of bromine (29 μl, 0.62 mmol) in acetic acid (0.1 ml) and the reaction mixture was stirred at room temperature for 30 mins. The reaction mixture was partitioned between EtOAc and saturated bicarbonate, the aqueous layer washed with EtOAc, the organics combined, dried ($MgSO_4$) and the solvent removed in vacuo to afford the product (40 mg). MS: $[M+H]^+$ 292,294.

Procedure X4—Suzuki Coupling

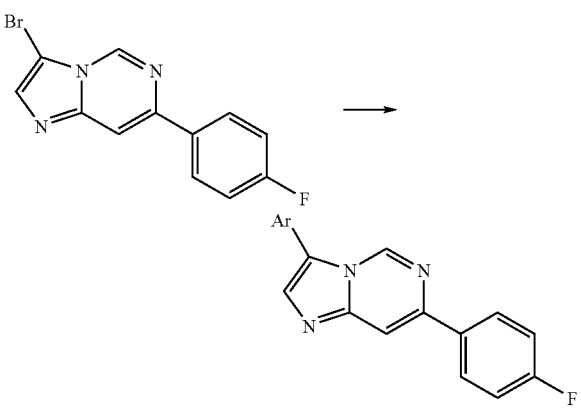

Prepared as in Procedure A3b substituting THF for DME.

Preparation Y—General Procedure to Synthesise Imidazo[1,2-a]pyrazine template

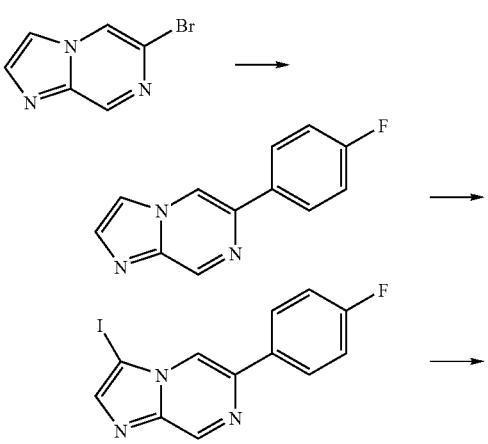

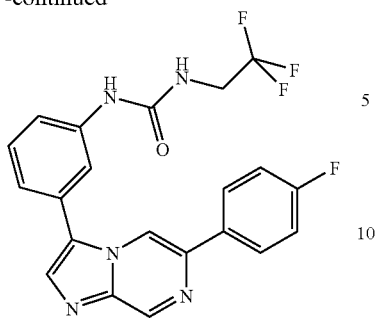

Preparation
Y1-6-(4-Fluoro-phenyl)-imidazo[1,2-a]pyrazine

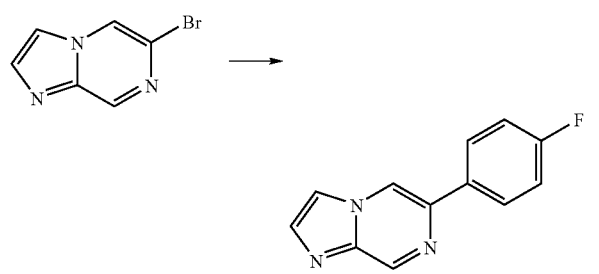

Method as described in General route A Procedure A4b using 4-fluorophenyl boronic acid.

Preparation Y2—6-(4-Fluoro-phenyl)-3-iodo-imidazo[1,2-a]pyrazine

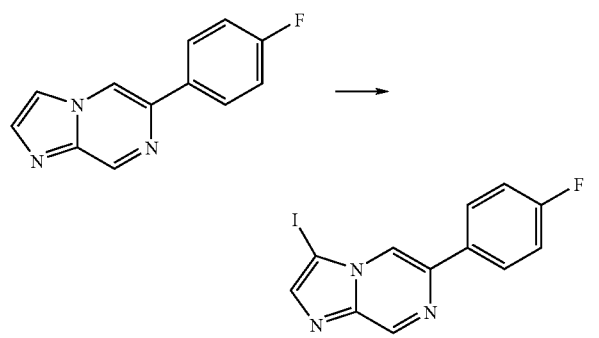

Method as described in General Route A Procedure 2

Preparation Y3—1-{3-[6-(4-Fluoro-phenyl)-imidazo[1,2-a]pyrazin-3-yl]-phenyl}-3-(2,2,2-trifluoro-ethyl)-urea

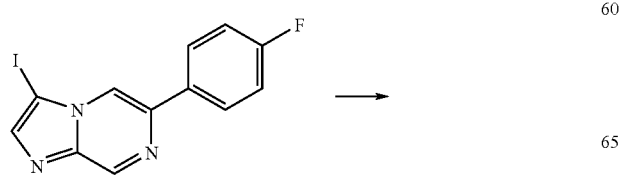

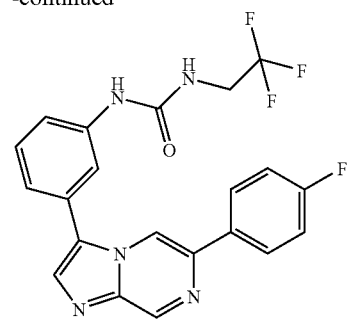

Method as for A4b using I6 1-[3-(4,4,5,5-Tetramethyl-[1,3,2]dioxaborolan-2-yl)-phenyl]-3-(2,2,2-trifluoro-ethyl)-urea and substituting Na$_2$CO$_3$ for K$_3$PO$_4$ Procedure Z—1,1,1-Trifluoro-2-isocyanato-ethane

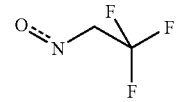

To a solution of 3,3,3-Trifluoro-propionic acid (0.14 ml, 1.56 mmol) in toluene (5 ml) was added DPPA (0.47 g, 1.72 mmol) and the reaction mixture heated at 110° C. for 2.5 h before being cooled to room temperature. Triethylamine (0.24 ml, 1.72 mmol) was added and the mixture heated at 70° C. for 18 h. Reaction solution used crude. MS: [M+H]$^+$ 361.

Procedure AA—1-{3-[7-(4H-[1,2,4]Triazol-3-yl)-imidazo[1,2-a]pyridin-3-yl]-phenyl}-3-(2,2,2-trifluoro-ethyl)-urea

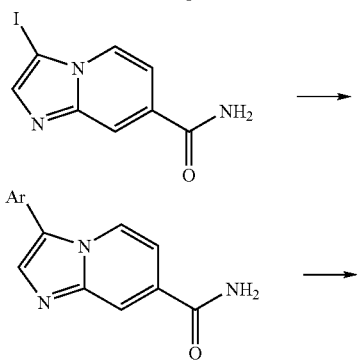

-continued

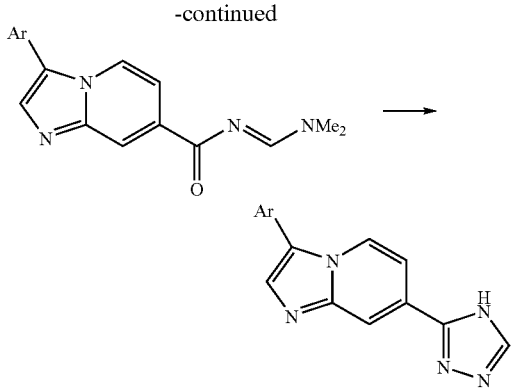

a) 3-[3-[3-(2,2,2-trifluoroethyl)ureido]-phenyl}imidazo[1,2-a]pyridine-7-carboxylic acid amide

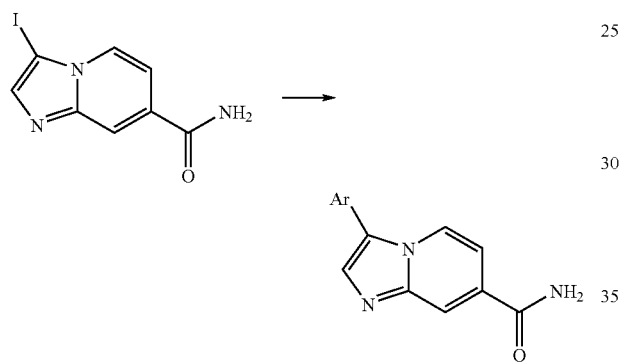

To a solution of 7-amido-3-iodo-imidazo[1,2-a]pyridine (1 equiv) (made in an analogous fashion to Procedures A1 and A2 using 4-amido-pyridin-2-ylamine) in DME was added 1-[3-(4,4,5,5-Tetramethyl-[1,3,2]dioxaborolan-2-yl)-phenyl]-3-(2,2,2-trifluoro-ethyl)-urea (1.2 equiv), 1M Na$_2$CO$_3$ (8 equiv) [reaction degassed by bubbling N$_2$ through] followed by tetrakis(triphenylphosphine)palladium(0) (0.05 equiv). The mixture was heated at 80° C. overnight, then diluted with water and extracted with EtOAc. The organic layer was washed with brine, dried (MgSO$_4$) and concentrated under reduced pressure. The products were purified by trituration with Et$_2$O or by column chromatography on silica (0→50% MeOH/Et$_2$O).

b) 3-{3-[3-(2,2,2-Trifluoro-ethyl)-ureido]-phenyl}-imidazo[1,2-a]pyridine-7-carboxylic acid 1-dimethylamino-meth-(E)-ylideneamide

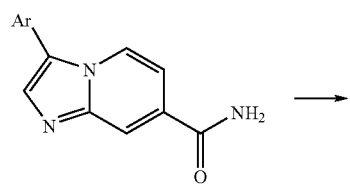

-continued

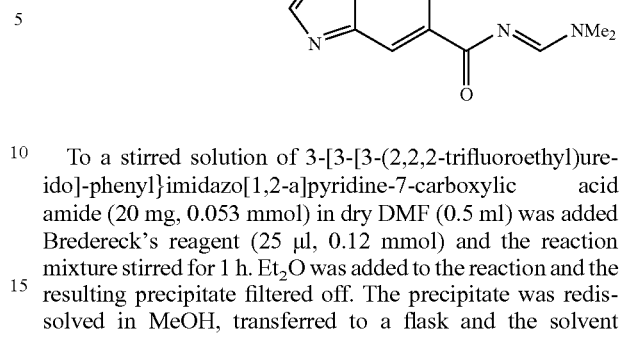

To a stirred solution of 3-[3-[3-(2,2,2-trifluoroethyl)ureido]-phenyl}imidazo[1,2-a]pyridine-7-carboxylic acid amide (20 mg, 0.053 mmol) in dry DMF (0.5 ml) was added Bredereck's reagent (25 µl, 0.12 mmol) and the reaction mixture stirred for 1 h. Et$_2$O was added to the reaction and the resulting precipitate filtered off. The precipitate was redissolved in MeOH, transferred to a flask and the solvent removed in vacuo to afford a pale yellow solid (17 mg). MS: [M+H]$^+$433.

c) 1-{3-[7-(4H-[1,2,4]Triazol-3-yl)-imidazo[1,2-a]pyridin-3-yl]-phenyl}-3-(2,2,2-trifluoro-ethyl)-urea

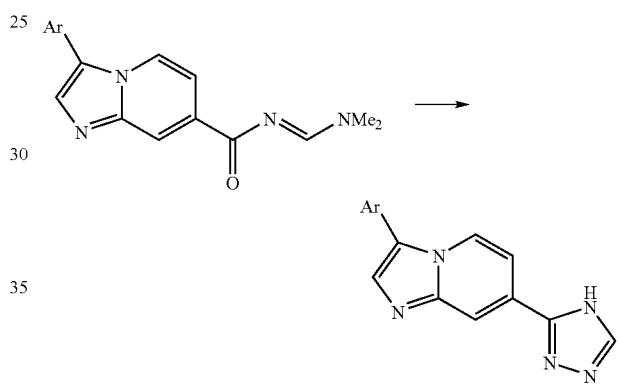

To a stirred solution of 3-{3-[3-(2,2,2-Trifluoro-ethyl)-ureido]-phenyl}-imidazo[1,2-a]pyridine-7-carboxylic acid 1-dimethylamino-meth-(E)-ylideneamide (17 mg, 0.04 mmol) in acetic acid (0.5 ml) was added hydrazine hydrate (5 µl, 0.1 mmol). The reaction mixture was heated at 90° C. for 30 min before being cooled to room temperature. The volatiles were removed in vacuo and the residue azeotroped with toluene. Trituration of the residue with Et$_2$O afforded a pink solid (12 mg). MS: [M+H]$^+$ 402.

Procedure AB—1-[3-(7-Oxazol-5-yl-imidazo[1,2-a]pyridin-3-yl)-phenyl]-3-(2,2,2-trifluoro-ethyl)-urea a) Imidazo[1,2-a]pyridin-7-yl-methanol

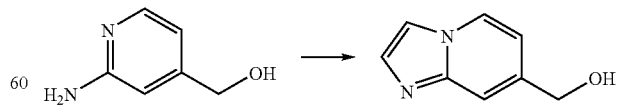

To a solution of (2-amino-pyridin-4-yl)-methanol (0.40 g, 3.3 mmol) in EtOH was added NaHCO$_3$ (0.56 g, 6.67 mmol) followed by chloroacetaldehyde (0.81 ml, 5.0 mmol). The mixture was refluxed for 2 h. Solvents were removed in vacuo and the crude mixture was partitioned between water and EtOAc. The aqueous was further extracted with EtOAc, the organics combined, dried (MgSO₄) and the solvent removed in vacuo. The residue was purified using silica column chromatography (0-50% MeOH/Et₂O) to afford 0.40 g of product MS: [M+H]⁺=149.

b) (3-Iodo-imidazo[1,2-a]pyridin-7-yl)-methanol

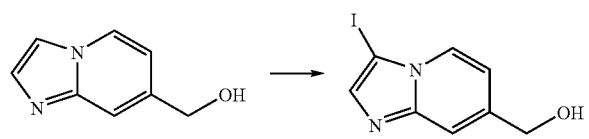 [SMILES: OCc1ccn2ccnc2c1 ; OCc1ccn2c(I)cnc2c1]

Prepared using the method outlined in procedure A2.

c) 1-[3-(7-Hydroxymethyl-imidazo[1,2-a]pyridin-3-yl)-phenyl]-3-(2,2,2-trifluoro-ethyl)-urea

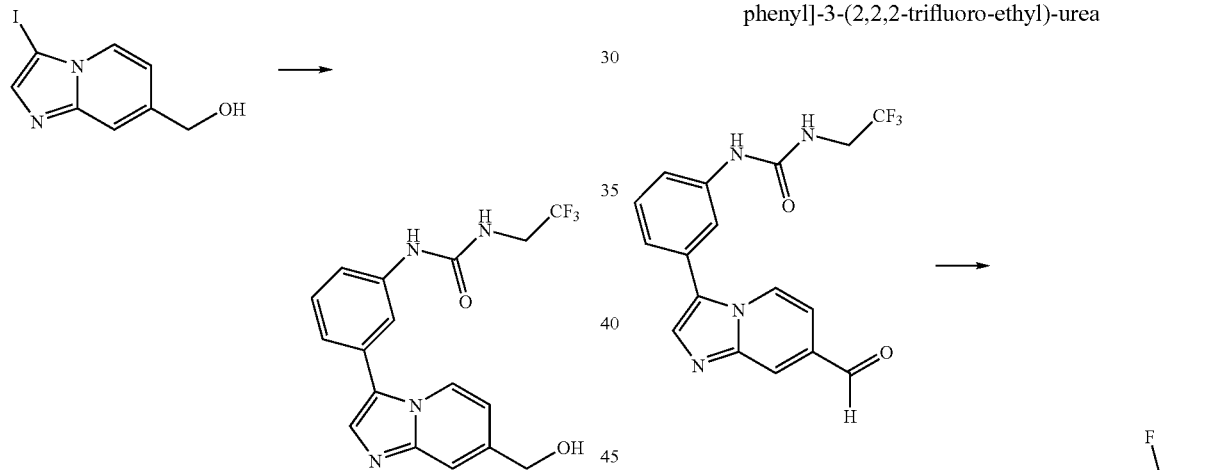

Prepared using the method outlined in A3b.

d) 1-[3-(7-Formyl-imidazo[1,2-a]pyridin-3-yl)-phenyl]-3-(2,2,2-trifluoro-ethyl)-urea

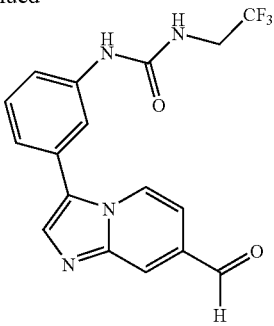

To a solution of 1-[3-(7-Hydroxymethyl-imidazo[1,2-a]pyridin-3-yl)-phenyl]-3-(2,2,2-trifluoro-ethyl)-urea (1.42 g, 3.90 mmol) and NMO (1.38, 11.7 mmol) in CH₂Cl₂ (30 ml) with sieves (3 g) at 0° C. was added TPAP (0.14 g, 0.38 mmol). The reaction mixture was allowed to warm to room temperature and stirred for 18 h, before being filtered to remove the sieves. The organic layer was washed with H₂O (×2), dried (MgSO₄) and the solvent removed in vacuo. The residue was purified by silica column chromatography (0-60% MeOH in Et₂O) to afford the product (0.2 g). MS: [M+H]⁺=363 e) 1-[3-(7-Oxazol-5-yl-imidazo[1,2-a]pyridin-3-yl)-phenyl]-3-(2,2,2-trifluoro-ethyl)-urea

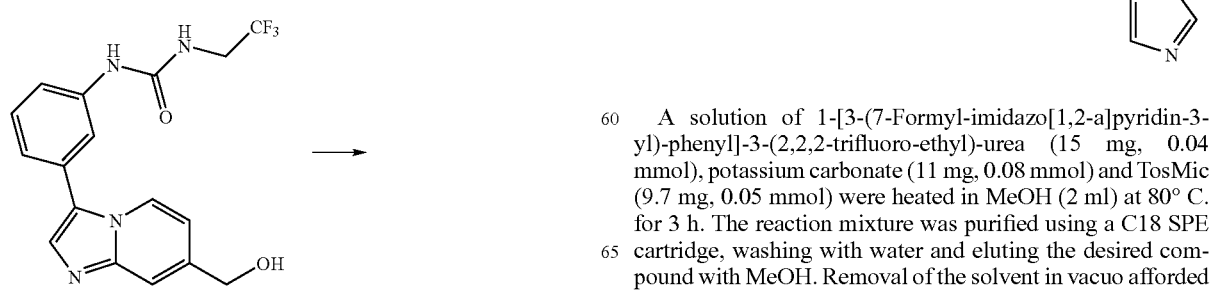

A solution of 1-[3-(7-Formyl-imidazo[1,2-a]pyridin-3-yl)-phenyl]-3-(2,2,2-trifluoro-ethyl)-urea (15 mg, 0.04 mmol), potassium carbonate (11 mg, 0.08 mmol) and TosMic (9.7 mg, 0.05 mmol) were heated in MeOH (2 ml) at 80° C. for 3 h. The reaction mixture was purified using a C18 SPE cartridge, washing with water and eluting the desired compound with MeOH. Removal of the solvent in vacuo afforded the title compound (6 mg). MS: [M+H]⁺=402

Procedure AC—1-{3-[7-(2H-Tetrazol-5-yl)-imidazo[1,2-a]pyridin-3-yl]-phenyl}-3-(2,2,2-trifluoro-ethyl)-urea

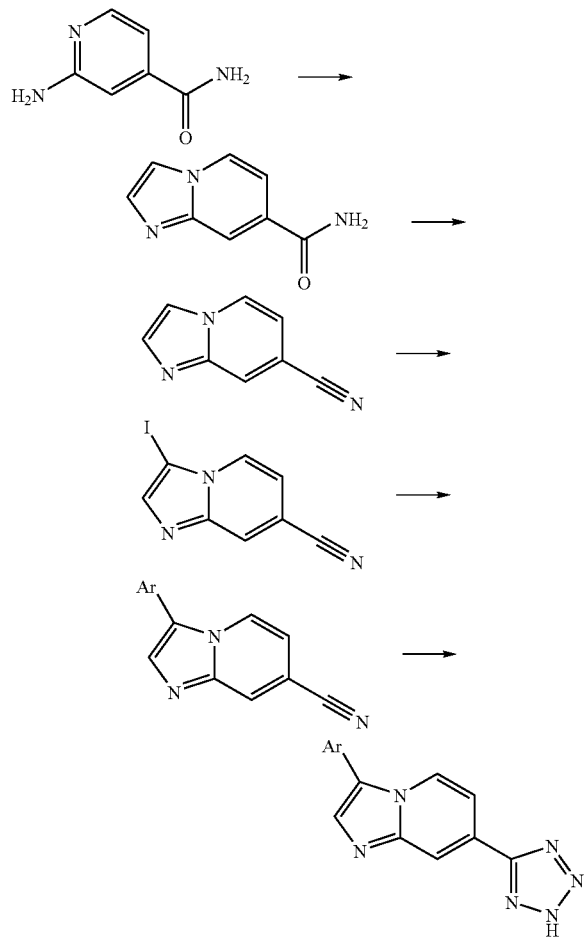

a) Imidazo[1,2-a]pyridine-7-carboxylic acid amide

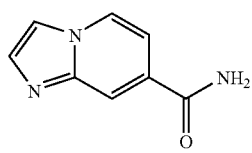 [SMILES: NC(=O)c1ccn2ccnc2c1]

Prepared as described in procedure A1 using 2-aminoisonicotinamide MS: [M+H]+ 162.

b) Imidazo[1,2-a]pyridine-7-carbonitrile

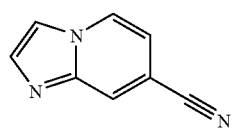 [SMILES: N#Cc1ccn2ccnc2c1]

To a solution of Imidazo[1,2-a]pyridine-7-carboxylic acid amide (38 mg, 0.24 mmol) and triethylamine (0.066 ml, 0.47 mmol) in CH$_2$Cl$_2$ (5 ml) was added trifluoroacetic anhydride (0.39, 2.83 mmol) dropwise. The reaction mixture was stirred at room temperature for 2 h before the crude mixture was loaded onto a SCX SPE cartridge, washing with MeOH and eluting with the product with 2M NH$_3$/MeOH. Removal of solvent in vacuo afforded the title compounds (32 mg). MS: [M+H]+ 143.

c) 3-Iodo-imidazo[1,2-a]pyridine-7-carbonitrile

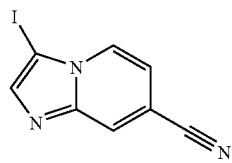

Method as described in procedure A2 using Imidazo[1,2-a]pyridine-7-carbonitrile. MS: [M+H]+ 270.

d) 1-[3-(7-Cyano-imidazo[1,2-a]pyridin-3-yl)-phenyl]-3-(2,2,2-trifluoro-ethyl)-urea

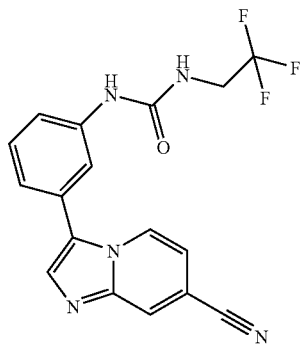 [SMILES: N#Cc1ccn2c(-c3cccc(NC(=O)NCC(F)(F)F)c3)cnc2c1]

Method as described in procedure A3b using 3-Iodo-imidazo[1,2-a]pyridine-7-carbonitrile. Purification via reverse phase HPLC to afforded the product as a white solid. MS: [M+H]+ 360.

e) 1-{3-[7-(2H-Tetrazol-5-yl)-imidazo[1,2-a]pyridin-3-yl]-phenyl}-3-(2,2,2-trifluoro-ethyl)-urea

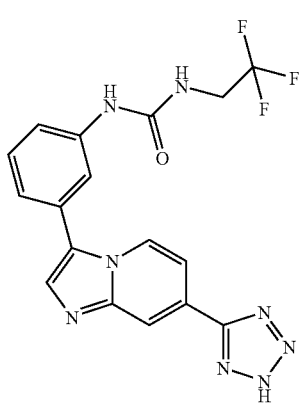 [SMILES: O=C(NCC(F)(F)F)Nc1cccc(-c2cnc3cc(-c4nn[nH]n4)ccn23)c1]

1-[3-(7-Cyano-imidazo[1,2-a]pyridin-3-yl)-phenyl]-3-(2,2,2-trifluoro-ethyl)-urea (65 mg, 0.18 mmol), sodium azide (14 mg, 0.19 mmol) and ammonium chloride (11 mg, 0.20 mmol) were dissolved in DMF (2 ml) and heated at 90° C. for 18 h. The reaction mixture was cooled, the solvent removed in vacuo and the crude reaction mixture purified using reverse phase HPLC. This afforded the title compound as a white solid (14 mg). MS: [M+H]+ 403.

Procedure AE: S-Alkylated Triazole step a) 1-{3-[7-(5-Mercapto-4-methyl-4H-[1,2,4]triazol-3-yl)-imidazo[1,2-a]pyridin-3-yl]-phenyl}-3-(2,2,2-trifluoro-ethyl)-urea

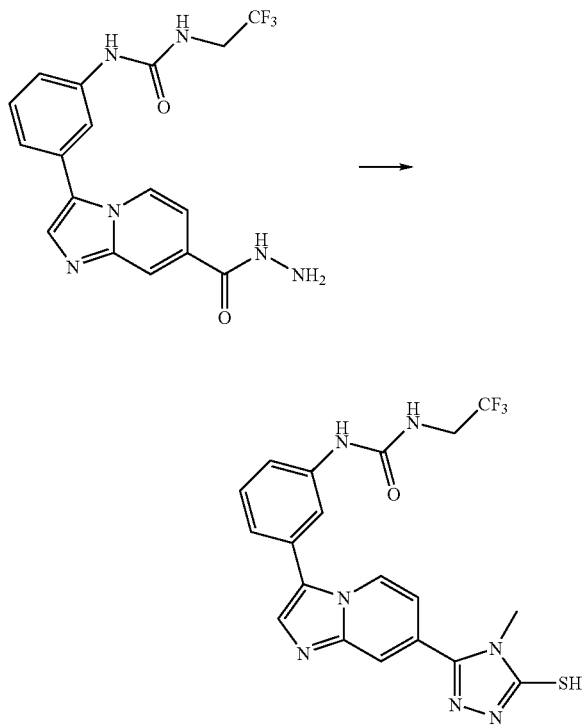 [SMILES: NNC(=O)c1ccn2c(-c3cccc(NC(=O)NCC(F)(F)F)c3)cnc2c1 ; Cn1c(S)nnc1-c1ccn2c(-c3cccc(NC(=O)NCC(F)(F)F)c3)cnc2c1]

To a solution of 1-[3-(7-Hydrazinocarbonyl-imidazo[1,2-a]pyridin-3-yl)-phenyl]-3-(2,2,2-trifluoro-ethyl)-urea (200 mg, 0.51 mmol) and methyl isothiocyanate (37 mg, 0.57 mmol) were dissolved in EtOH (6 ml) and heated at 70° C. overnight. The reaction mixture was allowed to cool, placed in an ice bath upon which a precipitate was formed. The solid was filtered off, washed with EtOAc and Et₂O, then dried to afford the title compound (72 mg). MS: [M+H]⁺=448.

Step b) 1-{3-[7-(4-Methyl-5-methylsulfanyl-4H-[1,2,4]triazol-3-yl)-imidazo[1,2-a]pyridin-3-yl]-phenyl}-3-(2,2,2-trifluoro-ethyl)-urea formate

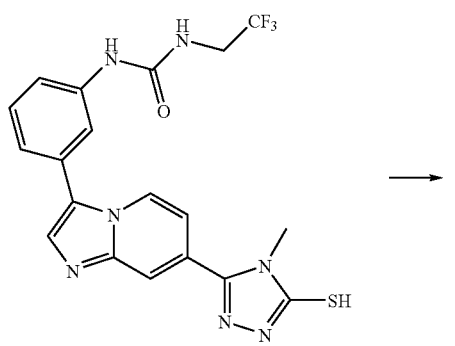

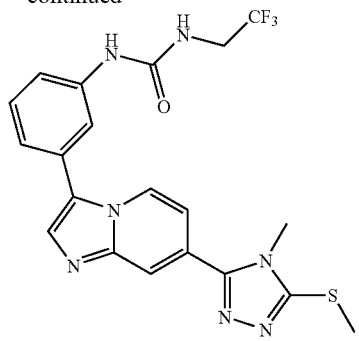

To a solution of 1-{3-[7-(5-Mercapto-4-methyl-4H-[1,2,4]triazol-3-yl)-imidazo[1,2-a]pyridin-3-yl]-phenyl}-3-(2,2,2-trifluoro-ethyl)-urea (72 mg, 0.16 mmol) in EtOH (3 ml) was added KOH (10 mg, 0.18 mmol) and iodomethane (20 μl, 0.16 mmol) and the reaction mixture was stirred at room temperature overnight. The reaction mixture was placed in an ice bath and the precipitate formed filtered off. The precipitate was purified by reverse phase HPLC to afford the title compound (18 mg). MS: [M+H]⁺=462.

Procedure AF: Triazole step a) Imidazo[1,2-a]pyridin-7-yl-methanol

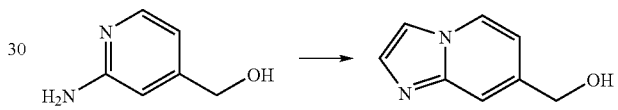

To a solution of a (2-Amino-pyridin-4-yl)-methanol (0.40 g, 3.3 mmol) in EtOH was added NaHCO₃ (0.56 g, 6.67 mmol) followed by chloroacetaldehyde (0.81 ml, 5.0 mmol). The mixture was refluxed for 2 h. Solvents were removed in vacuo and the crude mixture was partitioned between water and EtOAc. The aqueous was further extracted with EtOAc, the organics combined, dried (MgSO₄), filtered and the solvent removed in vacuo. The residue was purified using silica column chromatography (0-50% MeOH/Et₂O) to afford 0.40 g of product MS: [M+H]⁺=149.

Step b) (3-Iodo-imidazo[1,2-a]pyridin-7-yl)-methanol

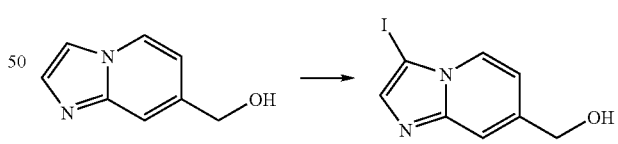

Prepared using the method outlined in procedure A2.

Step c) 3-Iodo-imidazo[1,2-a]pyridine-7-carbaldehyde

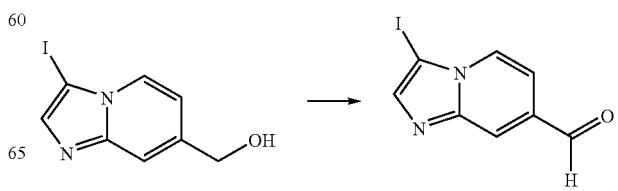

To a solution of (3-Iodo-imidazo[1,2-a]pyridin-7-yl) methanol (1.00 g, 3.65 mmol) and NMO (0.64 g, 5.47 mmol) in CH$_2$Cl$_2$ (30 ml) with sieves (3 g) at 0° C. was added TPAP (0.06 g, 0.18 mmol). The reaction mixture was allowed to warm to room temperature and stirred for 18 h, before being filtered to remove the sieves. The organic layer was washed with H$_2$O (×2), dried (MgSO$_4$), filtered and the solvent removed in vacuo. The residue was purified by silica column chromatography (0-60% MeOH in Et$_2$O) to afford the product (0.15 g). MS: [M+H]$^+$=273

Step d) 1-(3-Iodo-imidazo[1,2-a]pyridin-7-yl)-2-nitro-ethanol

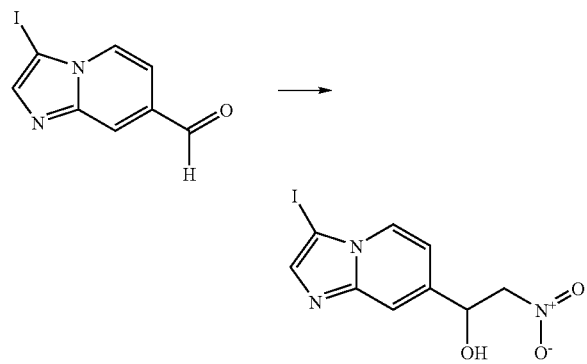

To a solution of 3-Iodo-imidazo[1,2-a]pyridine-7-carbaldehyde (150 mg, 0.54 mmol) in THF (10 ml) was added nitromethane (88 μl, 1.63 mmol), diethylamine (6 μl, 0.05 mmol) and sieves (300 mg). The reaction mixture was heated at 55° C. for 2 hours before being cooled. The sieves were filtered off and the resulting solution partitioned between EtOAc and H$_2$O. The organic layer was separated, dried (MgSO$_4$), filtered and the solvent removed in vacuo to afford a crude product that was used as is (116 mg). MS: [M+H]$^+$=334.

Step e) 3-Iodo-7-((E)-2-nitro-vinyl)-imidazo[1,2-a] pyridine

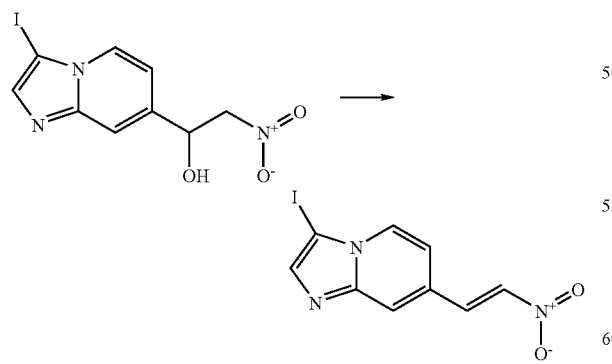

To a solution of 1-(3-Iodo-imidazo[1,2-a]pyridin-7-yl)-2-nitro-ethanol (116 mg, 0.35 mmol) in CH$_2$Cl$_2$ (2 ml) at 0° C. was added triethylamine (121 μl, 0.87 mmol) and methanesulfonyl chloride (38 μl, 0.49 mmol). The reaction mixture was allowed to warm to room temperature and stirred at room temperature for 1 h. The mixture was partitioned between CH$_2$Cl$_2$ and H$_2$O, the organic layer was separated, dried (MgSO$_4$), filtered and the solvent removed in vacuo. The residue was purified by silica column chromatography (0-50% MeOH in Et$_2$O) to afford the product (57 mg). MS: [M+H]$^+$=316.

Step f) 3-Iodo-7-(3H-[1,2,3]triazol-4-yl)-imidazo[1,2-a]pyridine

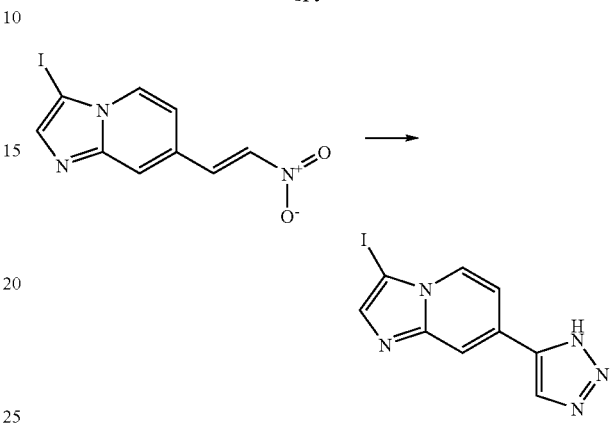

3-Iodo-74(E)-2-nitro-vinyl)-imidazo[1,2-a]pyridine (57 mg, 0.17 mmol) and trimethylsilylazide (33 μl, 0.24 mmol) were dissolved in DMF (3 ml) and the reaction mixture heated at 50° C. for 10 mins. Tetrabutylammonium fluoride solution (0.18 ml, 1.0M solution in THF, 0.18 mmol) was added and the reaction mixture heated at 50° C. for a further 10 mins. The reaction mixture was cooled, partitioned between EtOAc and H$_2$O, the organic layer was separated, dried (MgSO$_4$), filtered and the solvent removed in vacuo. The residue was purified by silica column chromatography (0-20% MeOH in Et$_2$O) to afford the product (34 mg). MS: [M+H]$^+$=312.

Step g) 1-{3-[7-(3H-[1,2,3]Triazol-4-yl)-imidazo[1,2-a]pyridin-3-yl]-phenyl}-3-(2,2,2-trifluoro-ethyl)-urea

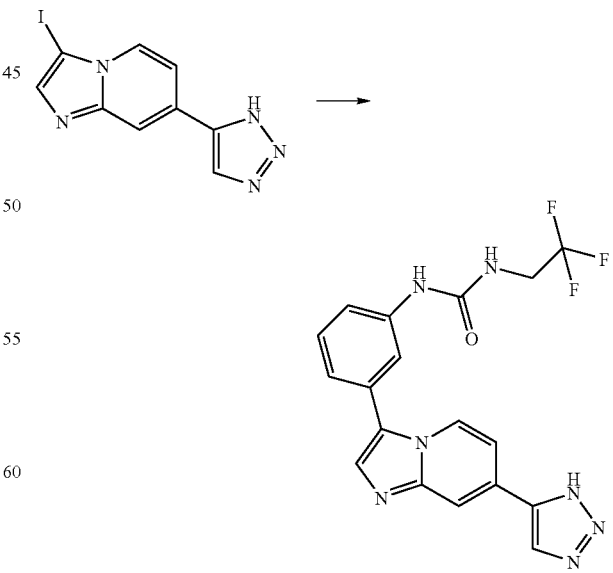

To a solution of 3-Iodo-7-(3H-[1,2,3]triazol-4-yl)-imidazo[1,2-a]pyridine (34 mg, 0.11 mmol) in DME (10 ml) was added I6 (45 mg, 0.13 mmol) and Cs$_2$CO$_3$ (107 mg) [reaction degassed by bubbling N₂ through] followed by tetrakis(triphenylphosphine)palladium(0) (0.013 g, 0.01 mmol). The mixture was heated at 80° C. overnight, then loaded directly onto an SCX cartridge, washing with MeOH and eluting with NH₃/MeOH. The resulting residue, after the solvent was removed in vacuo, was purified by preparative HPLC to give 1.6 mg of product. MS: [M+H]⁺ 402.

Procedure AG: Oxazole

Step a) Imidazo[1,2-a]pyridine-7-carboxylic acid methoxy-methyl-amide

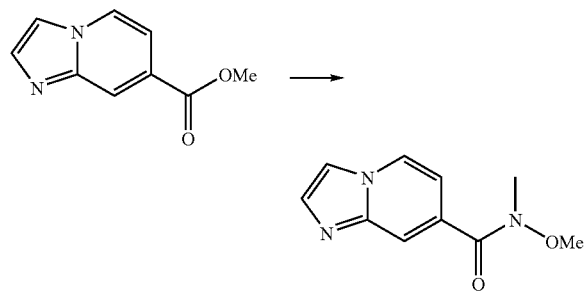

To a solution of Imidazo[1,2-a]pyridine-7-carboxylic acid methyl ester (0.67 g, 3.83 mmol) and dimethylhydroxylamine (0.93 g, 9.57 mmol) in CH₂Cl₂ (40 ml) at 0° C. was added 2M trimethylaluminium solution in hexane (3.8 ml, 9.57 mmol). The reaction mixture was allowed to warm to room temperature and stirred for 1 h, before being cooled back to 0° C. and quenched with ice. The reaction was filtered and liquid fraction partitioned between CH₂Cl₂/H₂O. The organic layer was separated, dried (MgSO₄), filtered and the solvent removed in vacuo to afford the crude product. The residue was purified by silica column chromatography (0-50% MeOH in Et₂O) to afford the product (187 mg). MS: [M+H]⁺=206.

Step b) 1-Imidazo[1,2-a]pyridin-7-yl-but-2-yn-1-one

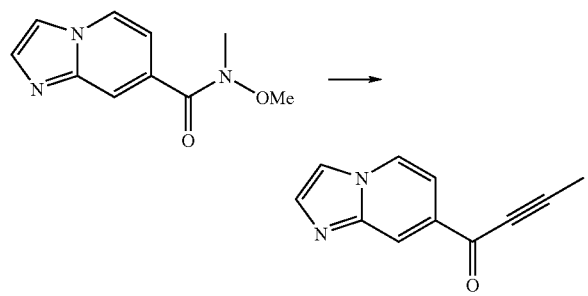

To a solution of Imidazo[1,2-a]pyridine-7-carboxylic acid methoxy-methyl-amide (187 mg, 0.91 mmol) in THF (10 ml) at −78° C. was added 1-propynylmagnesium bromide (0.5M in THF, 2.74 ml). The reaction was allowed to warm to room temperature and stirred for 1.5 h before being quenched with 2M HCl (2 ml) and washed with CH₂Cl₂. The aqueous fraction was basified using Na₂CO₃ and extracted with CH₂Cl₂. The organic fraction was dried (MgSO₄), filtered and the solvent removed in vacuo to afford the product (168 mg). MS: [M+H]⁺=185.

Step c) 7-(5-Methyl-isoxazol-3-yl)-imidazo[1,2-a]pyridine

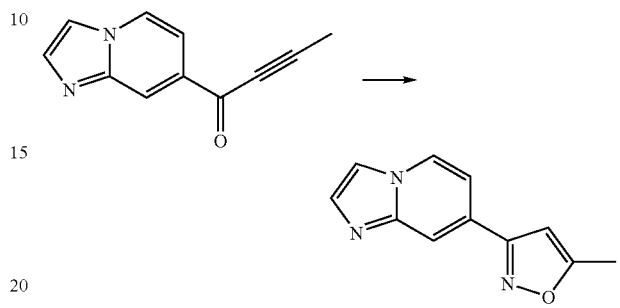

To a solution of 1-Imidazo[1,2-a]pyridin-7-yl-but-2-yn-1-one (168 mg, 0.91 mmol) and hydroxylamine hydrochloride (94 mg, 1.37 mmol) in DMF (10 ml) was added triethylamine (0.21 ml, 1.83 mmol). The reaction mixture was heated at 80° C. for 18 h, then partitioned between EtOAc and H₂O. The organic fraction was separated, dried (MgSO₄), filtered and the solvent removed in vacuo. The crude residue was purified by silica column chromatography (0-50% MeOH in Et₂O) to afford the product (46 mg). MS: [M+H]⁺=200.

Step d) 3-Iodo-7-(5-methyl-isoxazol-3-yl)-imidazo[1,2-a]pyridine

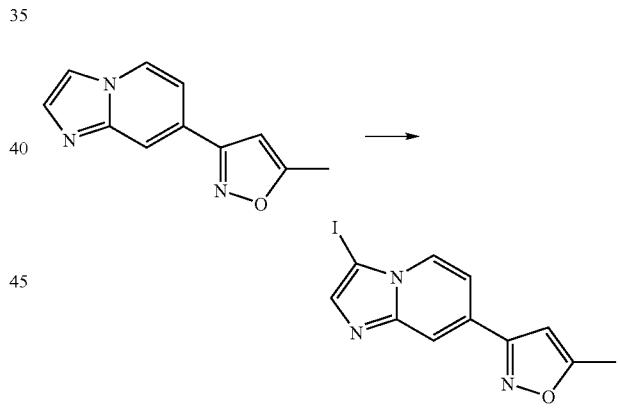

Prepared using the method outlined in procedure A2 (59 mg). MS: [M+H]⁺=326.

Step e) 1-{3-[7-(5-Methyl-isoxazol-3-yl)-imidazo[1,2-a]pyridin-3-yl]-phenyl}-3-(2,2,2-trifluoro-ethyl)-urea

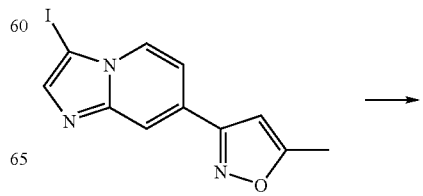

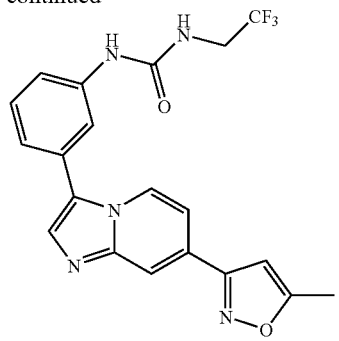

Prepared using the method outlined in procedure A3b (15 mg). MS: [M+H]+=416.

Procedure AH: Alkylated Triazoles

Step a) 1-[3-(7-Ethynyl-imidazo[1,2-a]pyridin-3-yl)-phenyl]-3-(2,2,2-trifluoro-ethyl)-urea

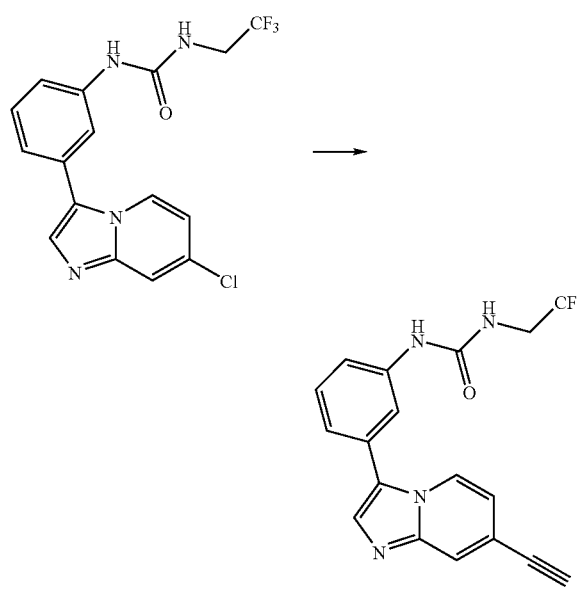

Prepared as described in procedure SGD4a.

Step b) 1-{3-[7-(1-Methyl-1H-[1,2,3]Triazol-4-yl)-imidazo[1,2-a]pyridin-3-yl]-phenyl}-3-(2,2,2-trifluoro-ethyl)-urea

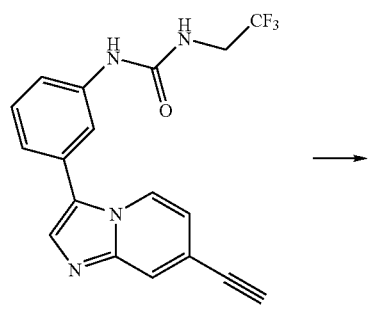

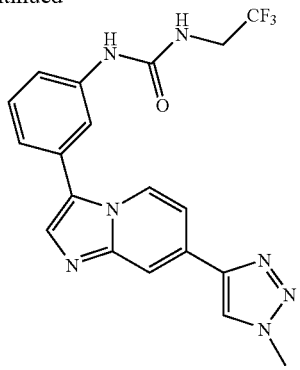

1-[3-(7-Ethynyl-imidazo[1,2-a]pyridin-3-yl)-phenyl]-3-(2,2,2-trifluoro-ethyl)-urea (130 mg, 0.36 mmol) was dissolved in tert-butyl alcohol (2 mL) and water (2 mL). Sodium azide (24 mg, 0.36 mmol) was added, followed by iodomethane (0.18 mL of a 2M solution in THF, 0.36 mmol). The reaction was stirred at room temperature for 5 minutes before the addition of copper (II) sulphate (0.02 mL of a 1M aqueous solution, 0.02 mmol) and sodium ascorbate (7 mg, 0.04 mmol). The reaction was stirred for 2 h at room temperature.

The solution was partitioned between water and dichloromethane, dried through a phase separation cartridge and concentrated in vacuo. The residue was purified by preparative HPLC to give the title compound as an off-white solid (1.8 mg).

Procedure AI: Methyl Tetrazole

Step 1: Imidazo[1,2-a]pyridine-7-carbonitrile

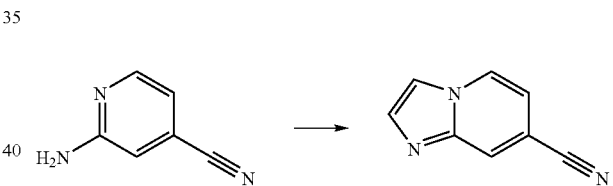

Chloroacetaldehyde (~50% in H$_2$O, 3.24 ml, 26 mmol) was added to a stirred mixture of 2-amino-isonicotinonitrile (1.6 g, 3.4 mmol) and NaHCO$_3$ (2.23 g, 26.5 mmol) in ethanol (20 ml) at RT under N$_2$. The reaction was stirred and heated at 80° C. for 18 hours. After cooling to RT the volatiles were removed in vacuo and the residue was partitioned between EtOAc/H$_2$O. This mixture was filtered to remove some dark insoluble residue. The solid was washed with MeOH. The aqueous layer was extracted with EtOAc (×2). The combined EtOAc extracts were dried (Na$_2$SO$_4$) and filtered. The MeOH washings were added and the volatiles were removed in vacuo. The residue was purified by chromatography on silica: 100% DCM→1% 2M NH3-MeOH/DCM to give the title product. $^1$H NMR (400 MHz, DMSO-d6): 8.74 (1H, dd), 8.35 (1H, s), 8.19 (1H, s), 7.86 (1H, s), 7.21 (1H, dd).

Step 2: 7-(2H-Tetrazol-5-yl)-imidazo[1,2-a]pyridine

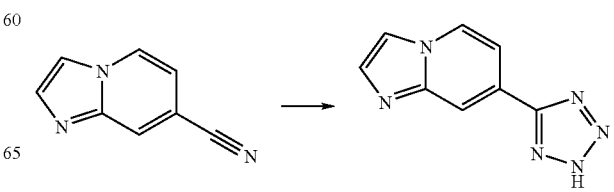

Sodium azide (97 mg, 1.45 mmol) was added to a stirred mixture of NH₄Cl (82 mg, 1.53 mmol) and imidazo[1,2-a]pyridine-7-carbonitrile (200 mg, 1.4 mmol) in dry DMF (5 ml) at RT under N₂. The reaction was stirred and heated at 80° C. in a sealed vial for 10 hours. [3 identical reactions were run in parallel]. After cooling to RT the reaction mixtures were combined and diluted with Et₂O. The solid was collected by filtration and dried to give the title compound (860 mg) as a light brown solid. [presumably contains NaCl] ¹H NMR (400 MHz, DMSO-d6): 8.55 (1H, dd), 8.02 (1H, s), 7.94 (1H, s), 7.57 (1H, d), 7.54 (1H, dd).

Step 3: 7-(2-Methyl-2H-tetrazol-5-yl)-imidazo[1,2-a]pyridine+isomer

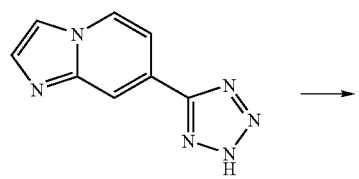

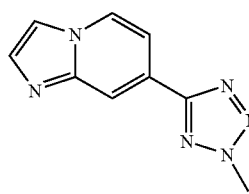

Methyl iodide (530 µl, 8.4 mmol) was added to a stirred mixture of 7-(2H-tetrazol-5-yl)-imidazo[1,2-a]pyridine (~4.2 mmol) and K₂CO₃ (1.16 g, 8.4 mmol) in dry DMF (4 ml) at RT under N₂. After 5 hours, the reaction was partitioned between EtOAc/H₂O. The aqueous layer was extracted with EtOAc (×2). The combined EtOAc extracts were dried (Na₂SO₄) and filtered and evaporated. The residue was purified by chromatography on silica: 100% DCM→4% 2M NH₃-MeOH/DCM to give the two regioisomers [Regiochemistry was assigned using nOe studies]:

7-(2-Methyl-2H-tetrazol-5-yl)-imidazo[1,2-a]pyridine (less polar): ¹H NMR (400 MHz, DMSO-d6): 8.73 (1H, d), 8.19 (1H, s), 8.10 (1H, s), 7.72 (1H, d), 7.50 (1H, dd), 4.46 (3H, s).

7-(1-Methyl-1H-tetrazol-5-yl)-imidazo[1,2-a]pyridine (more polar): ¹H NMR (400 MHz, DMSO-d6): 8.78 (1H, dd), 8.18-8.15 (2H, m), 7.79 (1H, d), 7.35 (1H, dd), 4.28 (3H, s).

Step 4: 3-Iodo-7-(2-methyl-2H-tetrazol-5-yl)-imidazo[1,2-a]pyridine

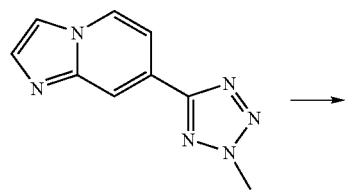

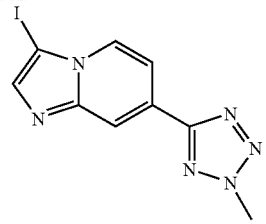

N-Iodo succinimide (300 mg, 1.3 mmol) was added in one portion to a stirred suspension of 7-(2-methyl-2H-tetrazol-5-yl)-imidazo[1,2-a]pyridine (240 mg, 1.2 mmol) in dry DMF (2 ml) at RT under N₂. After 5 hours, the reaction was quenched with saturated aqueous sodium thiosulphate/saturated aqueous NaHCO₃ (1:1, 2 ml). Water (2 ml) was then added and the mixture was stirred at RT for 15 minutes. The solid was collected by filtration and dried in vacuo to give the title compound (360 mg) as a cream solid. ¹H NMR (400 MHz, DMSO-d6): 8.51 (1H, dd), 8.20 (1H, dd), 7.86 (1H, s), 7.65 (1H, dd), 4.47 (3H, s).

Step 5: 1-{3-[7-(2-Methyl-2H-tetrazol-5-yl)-imidazo[1,2-a]pyridin-3-yl]-phenyl}-3-(2,2,2-trifluoroethyl)-urea

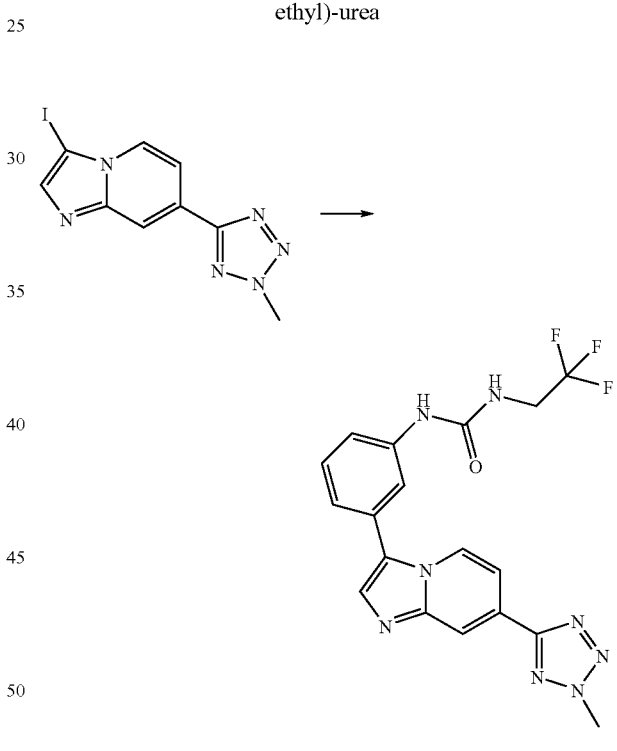

A mixture of 3-iodo-7-(2-methyl-2H-tetrazol-5-yl)-imidazo[1,2-a]pyridine (170 mg, 0.52 mmol), 1-[3-(4,4,5,5-Tetramethyl-[1,3,2]dioxaborolan-2-yl)-phenyl]-3-(2,2,2-trifluoro-ethyl)-urea (16, 225 mg, 0.65 mmol) and Cs₂CO₃ (340 mg, 1.04 mmol) in dry DME (2.5 ml) was deoxygenated by evacuate/fill N₂ (×2). PdCl₂dppf (38 mg, 0.05 mmol) was added, and the mixture was deoxygenated again (×3). The reaction was stirred and heated at 80° C. for 16 hours. After cooling to RT the mixture was partitioned between EtOAc/H₂O. The aqueous layer was extracted with EtOAc (×2). The combined EtOAc extracts were dried (Na₂SO₄) and filtered and evaporated. The residue was purified by preparative HPLC to give the title compound (60 mg) as a solid.

In an alternative arrangement of Procedure AI, step 3 may be performed as described in Step 3b below:

171

Procedure AI, step 3b: 7-[2-(2,2,2-Trifluoro-ethyl)-2H-tetrazol-5-yl]-imidazo[1,2-a]pyridine

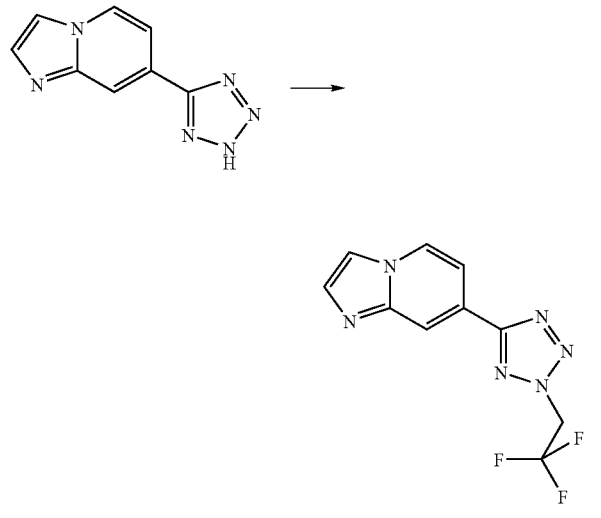

Sodium hydride (60 mg, 1.5 mmol) was added to a stirred suspension of 7-(2H-tetrazol-5-yl)-imidazo[1,2-a]pyridine (250 mg, 1.3 mmol) in dry DMF (4 ml) under a nitrogen atmosphere. After 1 h, Trifluoro-methanesulfonic acid 2,2,2-trifluoro-ethyl ester (1.16 g, 5 mmol) was added, followed by 18-crown-6 (260 mg, 1mmol). The reaction mixture was stirred at room temperature for 18 h then quenched with water and extracted with EtOAc (×2). The combined organic extracts were washed with brine (×1), dried (Na$_2$SO$_4$), filtered and the solvent removed in vacuo. Purification via silica column chromatography (0-2% 2M NH$_3$MeOH/CH$_2$Cl$_2$) afforded the product (138 mg). MS: [M+H]$^+$ 269.

Procedure AJ

Step 1: 5-Chloro-1,3-dimethyl-1H-[1,2,4]triazole+isomers

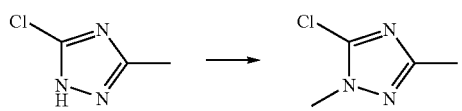

A mixture of 5-chloro-3-methyl-1H-[1,2,4]triazole (1.76 g, 15 mmol), K$_2$CO$_3$ (4.2 g, 30 mmol) and MeI (1.4 ml, 22 mmol) in acetone (15 ml) was stirred at RT for 20 hours. The mixture was filtered. The solid was washed with EtOAc. The solid was partitioned between CH$_2$Cl$_2$/H$_2$O. The CH$_2$Cl$_2$ layer was separated and added to the filtrate from above. The combined organic extracts were evaporated and the residue was taken up in CH$_2$Cl$_2$. This was dried by passing through a phase separating cartridge and then evaporated to give the methylated triazoles (1.6 g, brown liquid) as a mixture of isomers. $^1$H NMR (400 MHz, CDCl$_3$): 3.77 (3H, s), 2.43 (3H, s) [Signals for major isomer only]. This material was used without further purification.

172

Step 2. 1-{3-[7-(2,5-Dimethyl-2H-[1,2,4]triazol-3-yl)-imidazo[1,2-a]pyridin-3-yl]-phenyl}-3-(2,2,2-trifluoro-ethyl)-urea

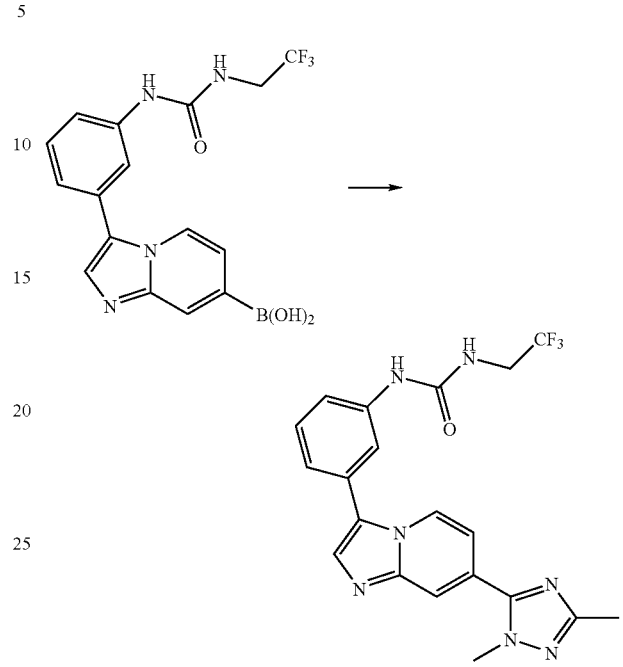

This was prepared as described in procedure E3d, substituting: 5-Chloro-1,3-dimethyl-1H-[1,2,4]triazole (+isomers) for 4-bromo-2-methyl thiazole. The desired isomer was isolated by chromatography on silica: 100% DCM→6% 2M NH$_3$-MeOH/DCM. Regiochemistry was assigned using nOe studies.

Procedure AK

Step 1: 4-Iodo-1,5-dimethyl-1H-imidazole+isomer

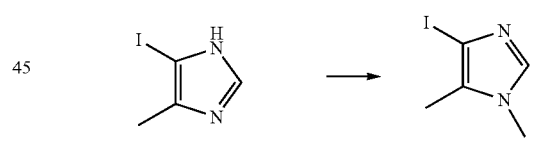

A stirred mixture of 4-iodo-5-methyl-1H-imidazole (2.1 g, 10 mmol) and K$_2$CO$_3$ (2.1 g, 15 mmol) in dry DMF (5 ml) at RT under N$_2$ was treated with methyl iodide (940 μl, 15 mmol). After 5 hours the reaction quenched with H$_2$O, then partitioned between EtOAc/H$_2$O. The aqueous layer was extracted with EtOAc (×2). The combined EtOAc extracts were dried (Na$_2$SO$_4$) and filtered and evaporated. The residue was purified by chromatography on silica: 60% EtOAc/CH$_2$Cl$_2$→80% EtOAc/CH$_2$Cl$_2$→100% EtOAc to give the regioisomers: [Regiochemistry was assigned with the aid of nOe studies]

4-Iodo-1,5-dimethyl-1H-imidazole (less polar): (Contaminated with regioisomer and some unreacted starting material).

1H NMR (400 MHz, DMSO-d6): 7.58 (1H, s), 3.58 (3H, s), 2.13 (3H, s).

5-Iodo-1,4-dimethyl-1H-imidazole (more polar): 1H NMR (400 MHz, DMSO-d6): 7.78 (1H, s), 3.51 (3H, s), 2.07 (3H, s).

Step 2: 1-{3-[7-(1,5-Dimethyl-1H-imidazol-4-yl)-imidazo[1,2-a]pyridin-3-yl]-phenyl}-3-(2,2,2-trifluoro-ethyl)-urea This was prepared as described in procedure E3d, substituting 4-Iodo-1,5-dimethyl-1H-imidazole for 4-bromo-2-methyl thiazole.

Procedure AL

1-{3-[7-(5-Thioxo-4,5-dihydro-[1,3,4]oxadiazol-2-yl)-imidazo[1,2-a]pyridin-3-yl]-phenyl}-3-(2,2,2-trifluoro-ethyl)-urea

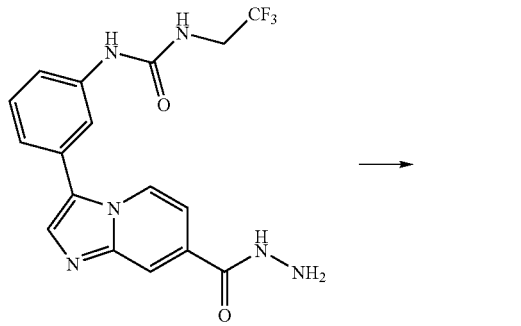

1-[3-(7-Hydrazinocarbonyl-imidazo[1,2-a]pyridin-3-yl)-phenyl]-3-(2,2,2-trifluoro-ethyl)-urea is made as described in Example 332.

To a solution of 1-[3-(7-Hydrazinocarbonyl-imidazo[1,2-a]pyridin-3-yl)-phenyl]-3-(2,2,2-trifluoro-ethyl)-urea (120 mg, 0.30 mmol) and KOH (20 mg, 0.36 mmol) in EtOH (4 ml) was added carbon disulfide (241, 0.36 mmol). The reaction mixture was heated at 65° C. for 3 h, cooled and then placed in an ice bath upon which a precipitate was formed. The solid was filtered off, wash with EtOAc and Et$_2$O, then dried to afford the title compound (69 mg). MS: [M+H]$^+$=435.

Procedure AM

1-{3-[7-(5-Methylsulfanyl-[1,3,4]oxadiazol-2-yl)-imidazo[1,2-a]pyridin-3-yl]-phenyl}-3-(2,2,2-trifluoro-ethyl)-urea

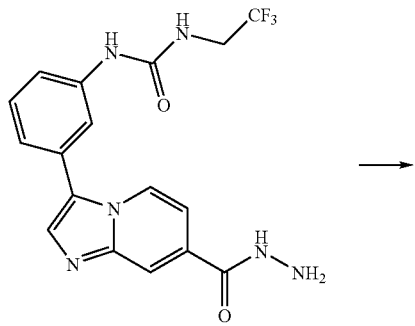

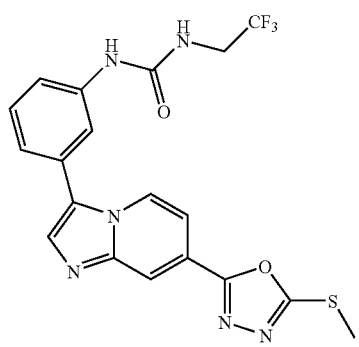

1-[3-(7-Hydrazinocarbonyl-imidazo[1,2-a]pyridin-3-yl)-phenyl]-3-(2,2,2-trifluoro-ethyl)-urea is made as described in Example 332.

To a solution of 1-[3-(7-Hydrazinocarbonyl-imidazo[1,2-a]pyridin-3-yl)-phenyl]-3-(2,2,2-trifluoro-ethyl)-urea (120 mg, 0.30 mmol) and KOH (20 mg, 0.36 mmol) in EtOH (4 ml) was added carbon disulfide (241, 0.36 mmol). The reaction mixture was heated at 65° C. for 3 h. Methyl iodide (200, excess) was added and the reaction mixture heated at 65° C. for 1 h. The mixture was then cooled, placed in an ice bath upon which a precipitate was formed. The solid was filtered off, washed with EtOAc and Et$_2$O, then dried to afford the title compound (89 mg). MS: [M+H]$^+$=449.

Procedure AN

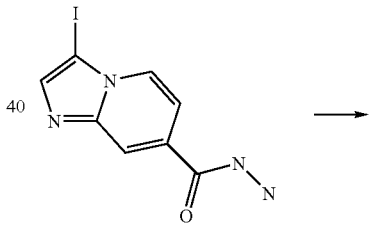

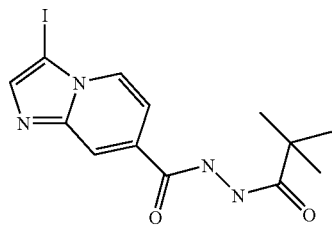

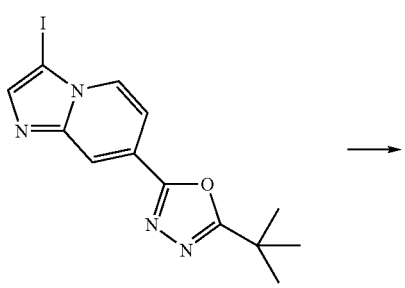

-continued

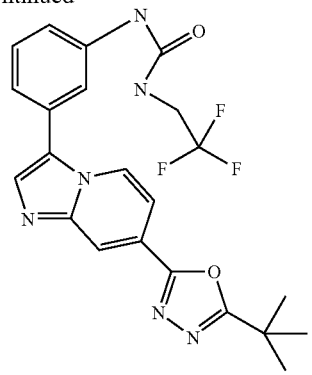

3-Iodo-imidazo[1,2-a]pyridine-7-carboxylic acid hydrazide (906 mg, 3 mmol) (prepared as described in 2 Step preparation of example 329) was suspended in THF (10 mL). Triethylamine (0.42 mL, 3 mmol) was added followed by pivaloyl chloride (0.37 mL, 3 mmol). The reaction was stirred for 2 h at room temperature. Concentrated sulphuric acid (0.5 mL) was added to the mixture and it was stirred 1 h further. The reaction was filtered, the solid washed with EtOAc and Et$_2$O and dried to give 3-Iodo-imidazo[1,2-a]pyridine-7-carboxylic acid N'-(2,2-dimethylpropionyl) hydrazide (875 mg) as an off-white solid.

3-Iodo-imidazo[1,2-a]pyridine-7-carboxylic acid N'-(2,2-di methyl propionyl) hydrazide (875 mg, 2.27 mmol) was suspended in anhydrous THF (15 mL) under a nitrogen atmosphere. Pyridine (0.388 mL, 4.76 mmol) and tosyl chloride (518 mg, 2.72 mmol) were added and the mixture was heated to 70° C. overnight. The reaction was cooled and partitioned between EtOAc and 1M HCl. The aqueous fraction was basified with 2M sodium carbonate solution and extracted with CH$_2$Cl$_2$. The organic phase was dried through a phase separation cartridge and evaporated to give 7-(5-tert-Butyl-[1,3,4]-oxadiazol-2-yl)-3-iodo-imidazo[1,2-a]pyridine (70 mg) as a white solid.

Suzuki coupling as described in example 329 was used to synthesise the final product.

Procedure AO

Mono-Fluoro Oxadiazole Formation

2-Imino-1(1-iodo-vinyl)-1,2-dihydro-pyridine-4-carboxylic acid N'-(2-fluoro-acetyl)-hydrazide

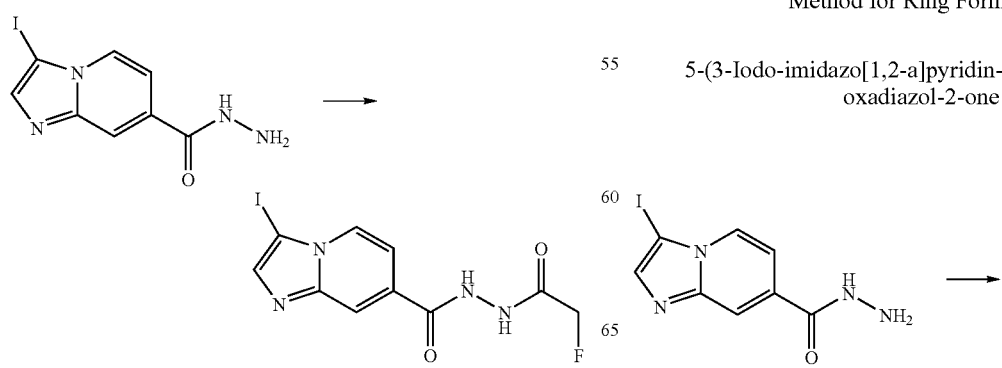

To a solution of fluoroacetic acid (52 mg, 0.66 mmol) in CH$_2$Cl$_2$ (5 ml) was added EDC (127 mg, 0.66 mmol) and DMAP (5 mg, catalytic) and the reaction mixture stirred at room temperature for 15 min. 3-Iodo-imidazo[1,2-a]pyridine-7-carboxylic acid hydrazide (prepared as described in Example 329 steps a-c) (100 mg, 0.33 mmol) was added and the reaction mixture stirred at room temperature for 18 h. The reaction mixture was filtered, the precipitate washed with Et$_2$O and dried to afford a crude product which was used directly in the next reaction (101 mg). MS: [M+H]$^+$=363.

7-(5-Fluoromethyl-[1,3,4]oxadiazol-2-yl)-3-iodo-imidazo[1,2-a]pyridine

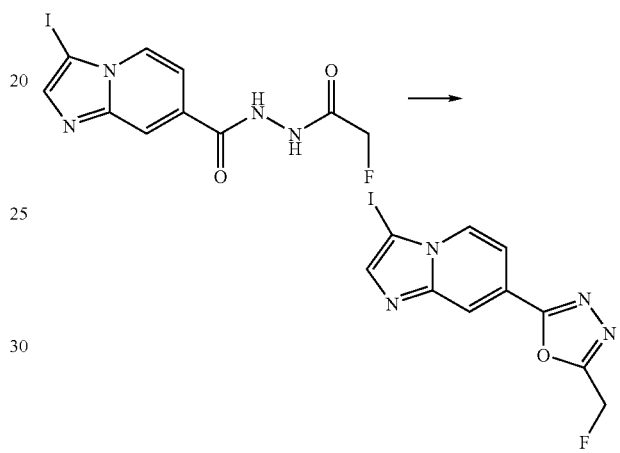

2-Imino-1-(1-iodo-vinyl)-1,2-dihydro-pyridine-4-carboxylic acid N'-(2-fluoro-acetyl)-hydrazide (89 mg, 0.25 mmol), DIPEA (0.24 ml, 1.48 mmol) and triphenylphosphine (129 mg, 0.49 mmol) were stirred in MeCN for 10 min. Hexachloroethane (87 mg, 0.37 mmol) was added and the reaction mixture stirred for 4 h. The precipitate formed during the reaction was filtered off and rinsed with MeCN. The MeCN liquors concentrated in vacuo and the residue purified by silica column chromatography (0-50% MeOH in Diethyl ether) to afford the product (74 mg). MS: [M+H]$^+$=345

7-(5-Fluoromethyl-[1,3,4]oxadiazol-2-yl)-3-iodo-imidazo[1,2-a]pyridine was then used in step e of Example 329.

Procedure AP

Method for Ring Formation 5-(3-Iodo-imidazo[1,2-a]pyridin-7-yl)-3H-[1,3,4]oxadiazol-2-one -continued

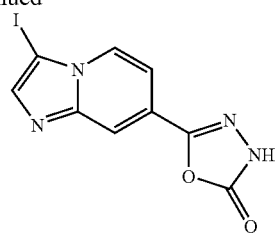

To a solution of 3-Iodo-imidazo[1,2-a]pyridine-7-carboxylic acid hydrazide (196 mg, 0.5 mmol) (prepared as described in Example 329 steps a-c) in THF (10 ml) was added carbonyldiimidazole (243 mg, 1.5 mmol) and triethylamine (0.35 ml, 2.5 mmol) and the reaction mixture left to stir for 3 h. The precipitate formed in the reaction was filtered off, washed with Et$_2$O and dried to afford the desired product (189 mg). MS: [M+H]$^+$=329.

5-(3-Iodo-imidazo[1,2-a]pyridin-7-yl)-3H-[1,3,4]oxadiazol-2-one was then used in Step e of Example 329.

Procedure AQ

Step a) 7-(4,4,5,5-Tetramethyl-[1,3,2]dioxaborolan-2-yl)-imidazo[1,2-a]pyridine

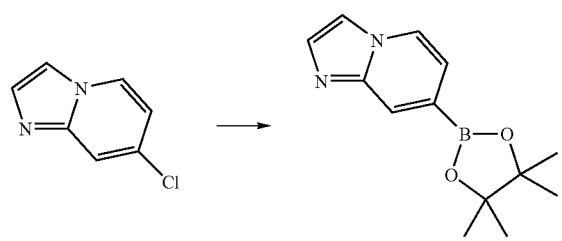 [SMILES: Clc1ccn2ccnc2c1 ; CC1(C)OB(c2ccn3ccnc3c2)OC1(C)C]

To a stirred mixture of 7-Chloro-imidazo[1,2-a]pyridine (2 g, 13.1 mmol), bis pinacolatoboron (4 g, 15.8 mmol), K$_2$CO$_3$ (2.7 g, 19.5 mmol), Pd (OAc)$_2$ (146 mg, 0.63 mmol), tricyclohexylphosphine (360 mg, 1.3 mmol) in diglyme (20 ml) and water (27 μl). The reaction mixture was heated at 100° C. for 24 hr then stirred at ambient overnight. Solid filtered off and washed with diglyme. Residue suspended in water (25 ml) stirred for 1 hr, filtered, solid washed with water and dried on the sinter to afford the desired product (1.48 g). MS: [{M-pinacol}+H]$^+$=163

Step b)
5-Imidazo[1,2-a]pyridin-7-yl-pyridine-2-carboxylic acid methyl ester

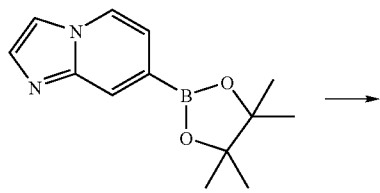

-continued

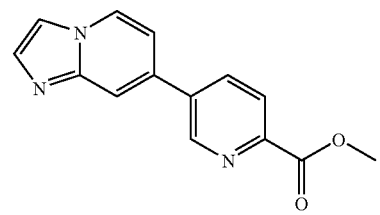

To a stirred mixture of 7-(4,4,5,5-Tetramethyl-[1,3,2]dioxaborolan-2-yl)-imidazo[1,2-a]pyridine (732 mg, 3 mmol), 5-bromopyridine-2-carboxylic acid methyl ester (650 mg, 3 mmol) and cesium carbonate (2.0 g, 6 mmol) in dry DME (15 ml) was added PdCl$_2$dppf (220 mg, 0.3 mmol) and H$_2$O (55 μl, 3 mmol). The reaction mixture was deoxygenated and then heated at 80° C. for 3 h. The mixture was allowed to cool, then partitioned between CH$_2$Cl$_2$/H$_2$O and stirred for 20 min. The solid material was filtered off and washed with MeOH (100 ml). The CH$_2$Cl$_2$ layer was separated, combined with the MeOH washings and the solvent removed in vacuo. The residue was purified by silica column chromatography (0-3% 2M NH$_3$. MeOH/CH$_2$Cl$_2$) to afford a dark yellow solid, which was used directly in the next reaction (492 mg). MS: [M+H]$^+$=254. $^1$H NMR d6 DMSO: 9.21 (1H, d), 8.71 (1H, d), 8.44 (1H, dd), 8.20-8.10 (2H, m), 8.04 (1H, s), 7.69 (1H, s), 7.43 (1H, dd), 3.92 (3H, s).

Step c) 2-(5-Imidazo[1,2-a]pyridin-7-yl-pyridin-2-yl)-propan-2-ol

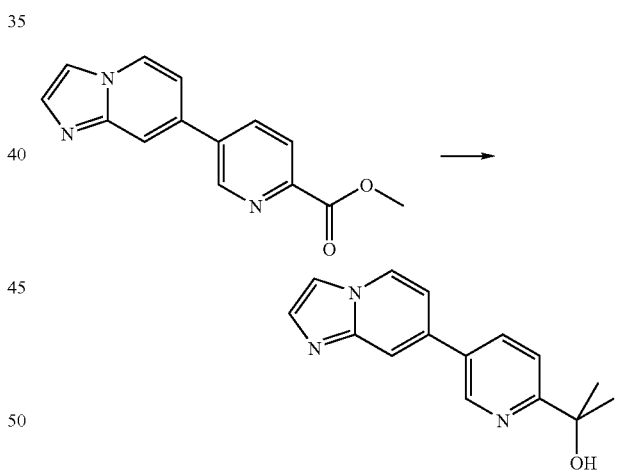

To a stirred solution of 5-Imidazo[1,2-a]pyridin-7-yl-pyridine-2-carboxylic acid methyl ester (135 mg, 0.53 mmol) in dry THF (5 ml) was added methyl magnesium bromide (3M in Et$_2$O, 0.5 ml). After 1 h, a further aliquot of methyl magnesium bromide (3M in Et$_2$O, 0.5 ml) was added and the reaction mixture stirred for a further 1 h, then quenched with saturated NH$_4$Cl (aq). The reaction mixture was then partitioned between EtOAc/H$_2$O, the aqueous layer was extracted with EtOAc (×2), the organics combined, dried (MgSO$_4$), filtered and the solvent removed in vacuo. The residue was purified by silica column chromatography (0-3% 2M NH$_3$. MeOH/CH$_2$Cl$_2$) to afford a yellow gum, which was used directly in the next reaction (44 mg). MS: [M+H]$^+$=254. $^1$H NMR (400 MHz, CDCl3): 8.84 (1H, d), 8.27 (1H, d), 7.99 (1H, dd), 7.90 (1H, s), 7.74 (1H, s), 7.67 (1H, s), 7.53 (1H, d), 7.11 (1H, dd), 1.62 (6H, s).

step d) 2-[5-(3-Iodo-imidazo[1,2-a]pyridin-7-yl)-pyridin-2-yl]-propan-2-ol

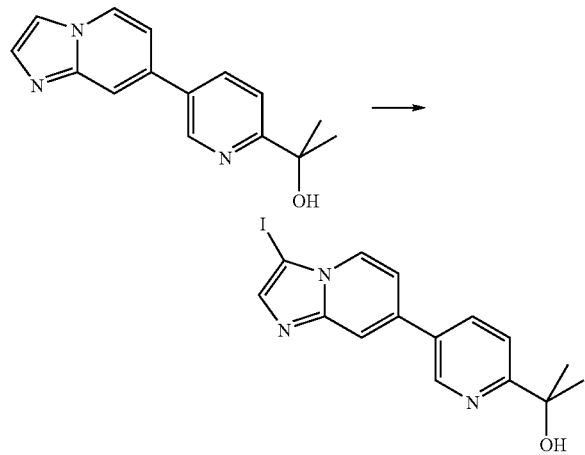

Prepared using the method outlined in procedure A2.

$^1$H NMR (400 MHz, DMSO-d6): 8.97 (1H, d), 8.41 (1H, dd), 8.24 (1H, dd), 8.05 (1H, s), 7.80-7.76 (2H, m), 7.49 (1H, dd), 5.30 (1H, s), 1.49 (6H, s).

step e) 1-(3-{7-[6-(1-Hydroxy-1-methyl-ethyl)-pyridin-3-yl]-imidazo[1,2-a]pyridin-3-yl}-phenyl)-3-(2,2,2-trifluoro-ethyl)-urea

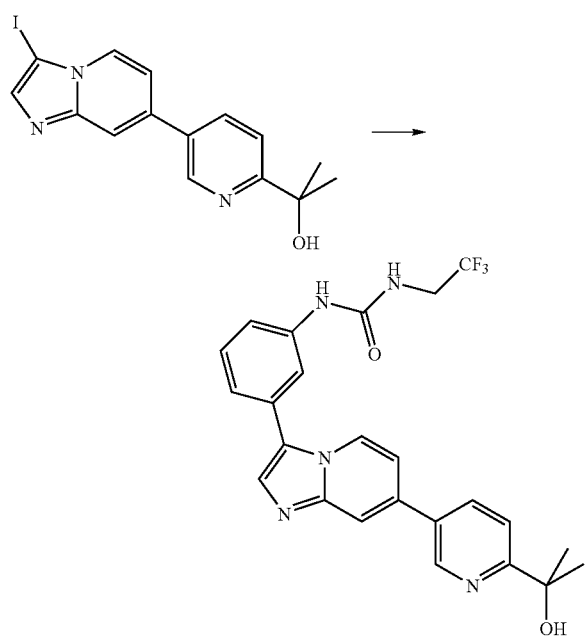

Prepared using the method outlined in procedure B3a, substituting PdCl$_2$dppf for Pd tetrakis.

Procedure AR—1-[3-(7-[1,2,4]Oxadiazol-5-yl-imidazo[1,2-a]pyridin-3-yl)-phenyl]-3-(2,2,2-trifluoro-ethyl)-urea

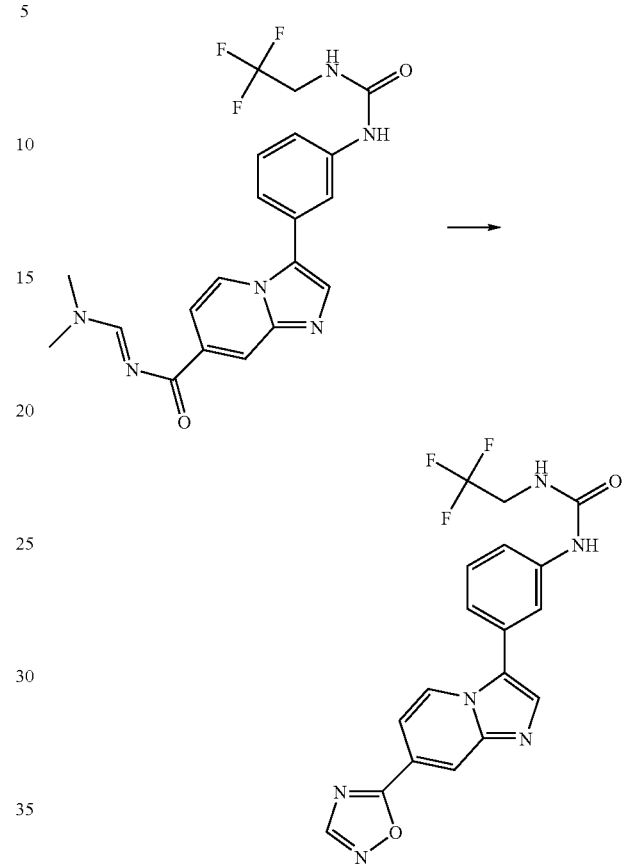

Hydroxylamine. HCl (30 mg, 0.43 mmol) was added to 3-{3-[3-(2,2,2-trifluoro-ethyl)-ureido]-phenyl}-imidazo[1,2-a]pyridine-7-carboxylic acid 1-dimethylamino-meth-(E)-ylideneamide (135 mg, 0.3 mmol) and 5N NaOH (75 μl, 0.38 mmol) in AcOH/H$_2$O (7:3, 1 ml) at RT. The reaction mixture was stirred at room temperature for 2 h before being heated at 60° C. for 7 h. The reaction mixture was allowed to cool then the volatiles removed in vacuo. The residue was purified by preparative HPLC to afford the desired product (35 mg). MS: [M+H]$^+$ 403.

Procedure AS—1-[3-(7-[1,2,4]Triazol-1-yl-imidazo[1,2-a]pyridin-3-yl)-phenyl]-3-(2,2,2-trifluoro-ethyl)-urea Step 1-7-[1,2,4]Triazol-1-yl-imidazo[1,2-a]pyridine

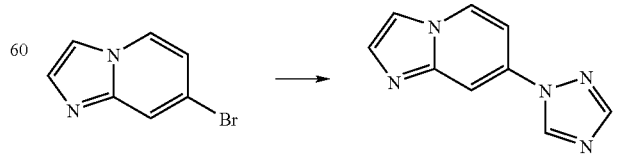

A solution of ferric acetylacetonate (0.94 g, 2.59 mmol), copper(II) oxide (86 mg, 0.86 mmol), 1H-[1,2,4]triazole (0.90 g, 12.9 mmol), cesium carbonate (5.65 g, 17.3 mmol) and 7-bromo-imidazo[1,2-a]pyridine (1.7 g, 8.63 mmol) in anhydrous DMF (43 ml) were heated under nitrogen at 90° C. for 30 h. The reaction mixture was allowed to cool, diluted with CH$_2$Cl$_2$, filtered and the organics washed with H$_2$O (×2). The aqueous fraction was washed with CH$_2$Cl$_2$ and the organic fractions combined, dried (MgSO$_4$) and the solvent removed in vacuo. The residue was triturated with EtOAc to give the product (150 mg). MS: [M+H]$^+$ 185.

Step 2→3-Iodo-7-[1,2,4]triazol-1-yl-imidazo[1,2-a]pyridine

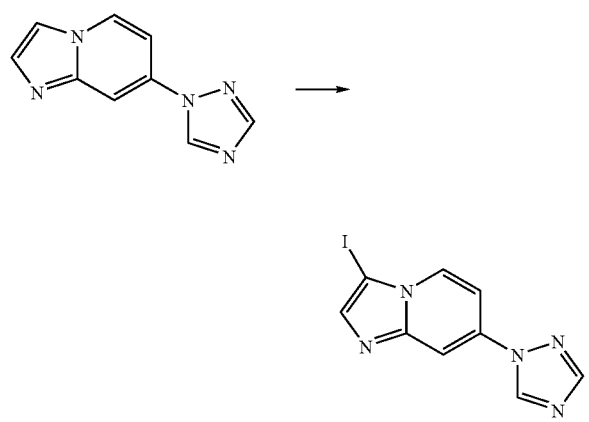

Method as described in general route B procedure B2.

Step 3→1-[3-(7-[1,2,4]Triazol-1-yl-imidazo[1,2-a]pyridin-3-yl)-phenyl]-3-(2,2,2-trifluoro-ethyl)-urea

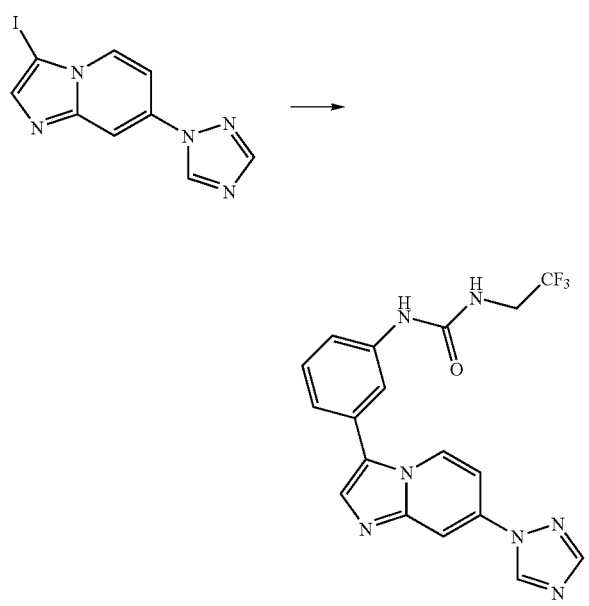

Method as described in general route B, procedure B3a using I6 [3-(4,4,5,5-tetramethyl-[1,3,2]dioxaborolan-2-yl)-phenyl]-3-(2,2,2-trifluoro-ethyl)-urea as coupling partner.

General Route SGA

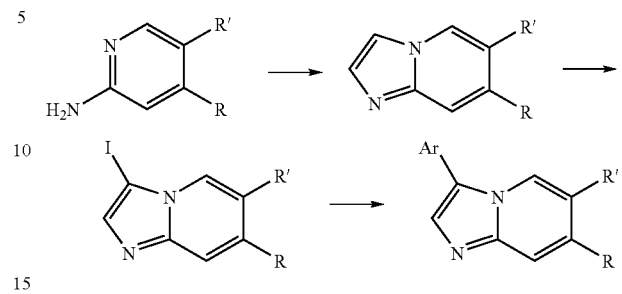

Procedure SGA1—Imidazopyridine Ring Formation

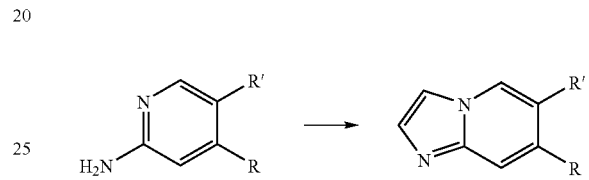

To a solution of a 4-substituted-pyridin-2-ylamine (1.0 equiv) in EtOH was added NaHCO$_3$ (2.0 equiv) followed by chloroacetaldehyde (1.5 equiv). The mixture was refluxed for 2 h. Solvents were removed under reduced pressure and the crude mixture was partitioned between water and EtOAc. The products were purified using column chromatography, trituration or recrystallisation.

| R | R' | Product | MS: [M + H]$^+$ |
|---|---|---|---|
| CH$_2$OH | H | Imidazo[1,2-a]pyridin-7-yl-methanol | 149 |
| CH$_3$ | H | 7-Methyl-imidazo[1,2-a]pyridine | 133 |
| CH$_2$CH$_3$ | H | 7-Ethyl-imidazo[1,2-a]pyridine | 147 |
| CF$_3$ | H | 7-Trifluoromethyl-imidazo[1,2-a]pyridine | 187 |
| OCH$_3$ | H | 7-Methoxy-imidazo[1,2-a]pyridine | 149 |
| OCH$_2$CH$_3$ | H | 7-Ethoxy-imidazo[1,2-a]pyridine | 163 |
| CH$_3$ | Cl | 6-Chloro-7-methyl-imidazo[1,2-a]pyridine | 167 |

Procedure SGA2—Iodination

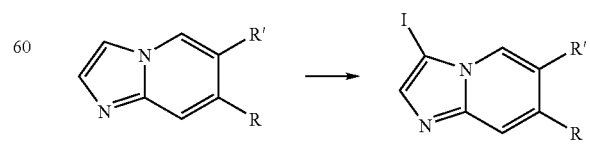

To a solution of 7-substituted Imidazo[1,2-a]pyridine (1.0 equiv) in DMF was added N-iodosuccinimide (1.2 equiv) and the resulting mixture was stirred for 2 h at room temperature. The thin brown slurry was diluted with water, 10% w/v sodium thiosulfate and sodium carbonate (1M) and extracted with $CH_2Cl_2$. The aqueous was further extracted with $CH_2Cl_2$. The combined organic phases were washed with brine, dried ($MgSO_4$) and concentrated in vacuo to give the product. Where necessary, the product was further purified by trituration or column chromatography on silica.

| R | R' | Product | MS: $[M+H]^+$ |
|---|---|---|---|
| $CH_2OH$ | H | (3-Iodo-imidazo[1,2-a]pyridin-7-yl)-methanol | 275 |
| $CH_3$ | H | 3-Iodo-7-methyl-imidazo[1,2-a]pyridine | 259 |
| $CH_2CH_3$ | H | 7-Ethyl-3-iodo-imidazo[1,2-a]pyridine | 273 |
| $CF_3$ | H | 3-Iodo-7-trifluoromethyl-imidazo[1,2-a]pyridine | 313 |
| $OCH_3$ | H | 3-Iodo-7-methoxy-imidazo[1,2-a]pyridine | 275 |
| $OCH_2CH_3$ | H | 7-Ethoxy-3-iodo-imidazo[1,2-a]pyridine | 289 |
| $CH_3$ | Cl | 6-Chloro-3-iodo-7-methyl-imidazo[1,2-a]pyridine | 293 |

Procedure SGA3a—Suzuki Reaction with 1-[3-(4,4,5,5-Tetramethyl-[1,3,2]dioxaborolan-2-yl)-phenyl]-3-(2,2,2-trifluoro-ethyl)-urea To a solution of 7-substituted-3-iodo-imidazo[1,2-a]pyridine (1 equiv) in DME was added 1-[3-(4,4,5,5-Tetramethyl-[1,3,2]dioxaborolan-2-yl)-phenyl]-3-(2,2,2-trifluoro-ethyl)-urea (1.2 equiv), 1M $Na_2CO_3$ (8 equiv) [reaction degassed by bubbling $N_2$ through] followed by tetrakis(triphenylphosphine)palladium(0) (0.05 equiv). The mixture was heated at 80° C. overnight, then diluted with water and extracted with EtOAc. The organic layer was washed with brine, dried ($MgSO_4$) and concentrated under reduced pressure. The products were purified by trituration with $Et_2O$, column chromatography on silica or reverse phase HPLC.

Where appropriate the product was dissolved in HCl/dioxane, the solvent removed and the product recrystallised from MeOH to afford the hydrochloride.

Procedure SGB

Procedure SGB1—(5-Nitro-pyridin-2-yl)-carbamic acid tert-butyl ester

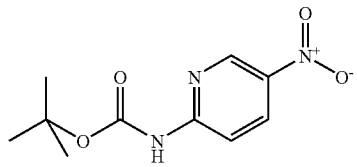 [SMILES: CC(C)(C)OC(=O)Nc1ccc([N+](=O)[O-])cn1]

To a suspension of sodium hydride (0.20 g, 5 mmol) in dry THF (20 ml) at 0° C. was added 2-amino-5-nitropyridine (0.70 g, 5 mmol). The mixture was allowed to warm to room temperature and stirred for 30 mins before a solution of di-tert-butyl dicarbonate (1.274 g, 5 mmol) in THF (40 ml) was added portionwise, whilst venting the flask under an atmosphere of nitrogen. The reaction mixture was stirred for 3 h before being quenched with EtOH (1 ml) and partitioned between $CH_2Cl_2$ and $H_2O$. The aqueous layer was further extracted with $CH_2Cl_2$, the organics combined, dried ($MgSO_4$) and the solvent removed in vacuo. Trituration of the residue with EtOAc afforded the product as a white solid (1.13 g). MS: $[M–H]^-$ 238

Procedure SGB2—(5-Amino-pyridin-2-yl)-carbamic acid tert-butyl ester

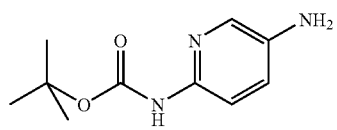

To a solution of (5-Nitro-pyridin-2-yl)-carbamic acid tert-butyl ester (0.80 g, 3.4 mmol) in THF:MeOH (1:1, 80 ml) was added 10% Pd/C (0.08 g) and the reaction placed under a hydrogen atmosphere for 3 h. The catalyst was filtered off and the organic solvent removed in vacuo to afford the title compound as a white solid (0.70 g). MS: $[M+H]^+$ 210

Procedure SGB3—(5-Methanesulfonylamino-pyridin-2-yl)-carbamic acid tert-butyl ester

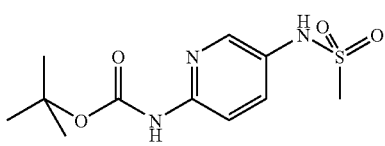 [SMILES: CC(C)(C)OC(=O)Nc1ccc(NS(C)(=O)=O)cn1]

To a solution of (5-Amino-pyridin-2-yl)-carbamic acid tert-butyl ester (0.70 g, 3.36 mmol) in $CH_2Cl_2$ (70 ml) was added pyridine (0.44 ml, 5.68 mmol). The reaction was cooled to 0° C. and methanesulfonyl chloride (0.42 ml, 5.38 mmol) was added dropwise. The reaction mixture was allowed to warm up to room temperature and stirred for 18 h, before being concentrated in vacuo. The crude material was purified using silica column chromatography running a 0-30% MeOH in $Et_2O$ gradient to afford the product as a white solid (0.43 g). MS: $[M+H]^+$ 288

Procedure SGB4—N-(6-Amino-pyridin-3-yl)-methanesulfonamide

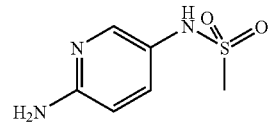

To a solution of (5-Methanesulfonylamino-pyridin-2-yl)-carbamic acid tert-butyl ester (0.43 g, 1.48 mmol) in dioxane (10 ml) was added 4M HCl in dioxane (20 ml) and the reaction heated at 55° C. for 18 h. The solvent was removed in vacuo and the crude material purified using silica column chromatography, running a 0-60% MeOH in $Et_2O$ gradient to afford the product as a white solid (0.28 g). MS: $[M+H]^+$ 188

Procedure SGB5—N-Imidazo[1,2-a]pyridin-6-yl-methanesulfonamide

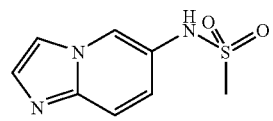

To a solution of N-(6-Amino-pyridin-3-yl)-methanesulfonamide (0.28 g, 1.48 mmol) in EtOH (30 ml) was added chloroacetaldehyde (0.3 ml, 2.25 mmol) and sodium hydrogen carbonate (0.25 g, 3 mmol). The reaction mixture was heated at 80° C. for 4 h, allowed to cool to room temperature and the solvent removed in vacuo. The residue was partitioned between EtOAc and $H_2O$. The aqueous layer was further extracted with EtOAc, the organics combined, dried ($MgSO_4$) and the solvent removed in vacuo. The residue was purified using silica column chromatography running a 0-50% MeOH in $Et_2O$ to afford a white solid (0.15 g). MS: $[M+H]^+$ 212

Procedure SGB6—N-(3-Iodo-imidazo[1,2-a]pyridin-6-yl)-methanesulfonamide

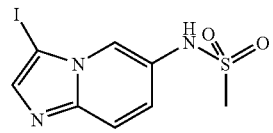

To a solution of N-Imidazo[1,2-a]pyridin-6-yl-methanesulfonamide (61 mg, 0.29 mmol) in DMF (3 ml) was added N-iodosuccinimide (70 mg, 0.31 mmol). The reaction was stirred at room temperature for 2 h before being diluted with water, 10% w/v sodium thiosulfate and sodium carbonate (1M) and extracted with EtOAc. The aqueous was further extracted with EtOAc. The combined organic phases were washed with brine (80 ml), dried ($MgSO_4$) and concentrated in vacuo to give a pale green residue. The residue was purified by chromatography on silica (0→30% MeOH/Et$_2$O) to afford a crude product (72 mg) which was used directly in the next reaction. MS: [M+H]$^+$ 338

Procedure SGB7—N-(3-{3-[3-(2,2,2-Trifluoro-ethyl)-ureido]-phenylamino}-imidazo[1,2-a]pyridin-6-yl)-methanesulfonamide

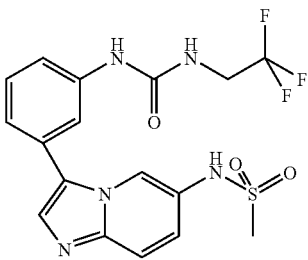 [SMILES: CS(=O)(=O)Nc1ccc2ncc(-c3cccc(NC(=O)NCC(F)(F)F)c3)n2c1]

To a solution of N-(3-Iodo-imidazo[1,2-a]pyridin-6-yl)-methanesulfonamide (72 mg, 0.21 mmol) in DME (5 ml) was added 1-[3-(4,4,5,5-Tetramethyl-[1,3,2]dioxaborolan-2-yl)-phenyl]-3-(2,2,2-trifluoro-ethyl)-urea (87 mg, 0.25 mmol), 1M Na$_2$CO$_3$ (2 ml) [reaction degassed by bubbling N$_2$ through] followed by tetrakis(triphenylphosphine)palladium (0) (12 mg). The mixture was heated at 80° C. overnight, then diluted with water and extracted with EtOAc. The organic layer was washed with brine, dried (MgSO$_4$) and the solvent removed in vacuo. The product was purified by reverse phase HPLC to afford the title compound as a white solid (3.6 mg). MS: [M+H]$^+$ 428

Procedure SGC

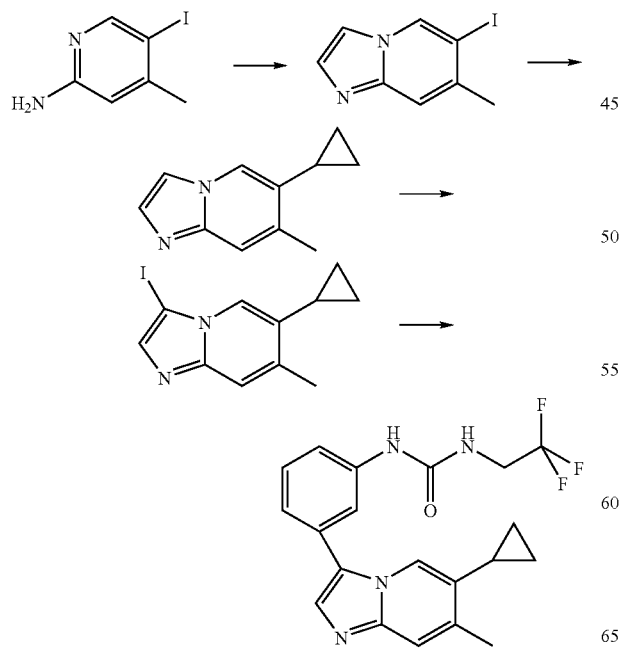

Procedure SGC1—6-Iodo-7-methyl-imidazo[1,2-a]pyridine

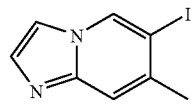

As procedure SGA1 using 5-Iodo-4-methyl-pyridin-2-ylamine

Procedure SGC2—6-Cyclobrobyl-7-methyl-imidazo[1,2-a]pyridine

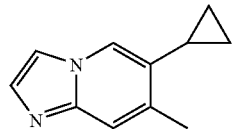

To a solution of 6-Iodo-7-methyl-imidazo[1,2-a]pyridine (50 mg, 019) in DME (5 ml) was added 1-[3-(4,4,5,5-Tetramethyl-[1,3,2]dioxaborolan-2-yl)-phenyl]-3-(2,2,2-trifluoro-ethyl)-urea (33 mg, 0.39 mmol), 1M Na$_2$CO$_3$ (1.6 ml) [reaction degassed by bubbling N$_2$ through] followed by tetrakis(triphenylphosphine)palladium(0) (11 mg). The mixture was heated at using microwave irradiation at 120° C. for 30 min, then diluted with water and extracted with CH$_2$Cl$_2$. The organic layer was washed with brine, dried (MgSO$_4$) and the solvent removed in vacuo. The product was purified using silica column chromatography to afford a crude residue which was used directly in the next reaction (34 mg). MS: [M+H]$^+$ 173

Procedure SGC3—6-Cyclobrobyl-3-iodo-7-methyl-imidazo[1,2-a]pyridine

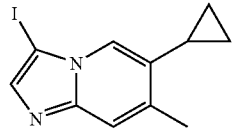

Procedure as SGA2 using 6-Cyclopropyl-7-methyl-imidazo[1,2-a]pyridine (165 mg). MS: [M+H]$^+$ 299

Procedure SGC4—1-[3-(6-Cyclopropyl-7-methyl-imidazo[1,2-a]pyridin-3-ylamino)-phenyl]-3-(2,2,2-trifluoro-ethyl)-urea

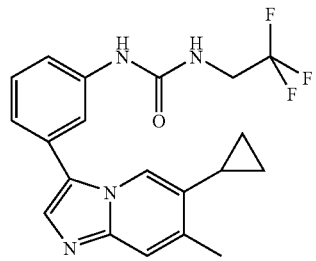 [SMILES: Cc1cc2ncc(-c3cccc(NC(=O)NCC(F)(F)F)c3)n2cc1C1CC1]

Procedure as SGA3a using 6-Cyclopropyl-3-iodo-7-methyl-imidazo[1,2-a]pyridine (7 mg). MS: [M+H]$^+$ 389

General Procedure SGD

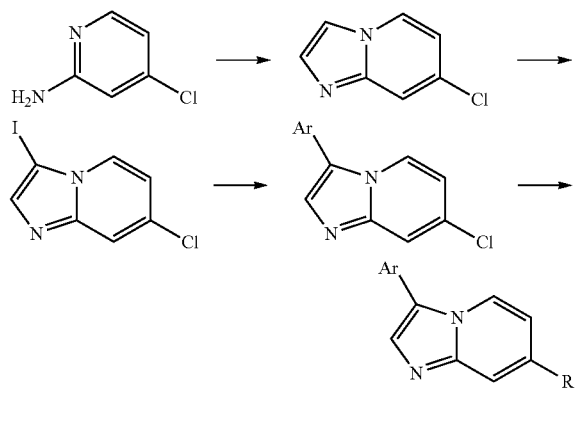

Procedure SGD1—General Imidazopyridine Ring Formation

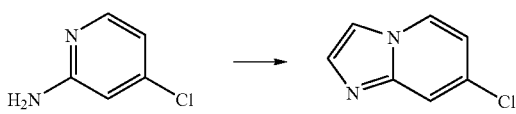

To a solution of 4-Chloro-pyridin-2-ylamine (12.8 g, 100 mmol, 1.0 equiv) in EtOH (170 ml) was added NaHCO$_3$ (16.8 g, 200 mmol, 2.0 equiv) followed by chloroacetaldehyde (19.0 ml, 150 mmol, 1.5 equiv). The mixture was refluxed for 6 h. Solvents removed under reduced pressure and the crude mixture was partitioned between water and EtOAc. The organic layer was washed with brine, dried (MgSO$_4$) and concentrated under reduced pressure. The product was purified by column chromatography (SiO$_2$, eluted with 50% EtOAC-petrol) to afford 13.2 g of product. MS: [M+H]$^+$ 153

Procedure SGD2—General Iodination

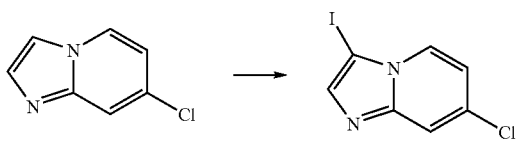 [SMILES: Clc1ccn2ccnc2c1 ; Clc1ccn2c(I)cnc2c1]

As for procedure A2: To a solution of 7-Chloro-imidazo[1,2-a]pyridine (30.9 g, 186 mmol, 1.0 equiv) in DMF (280 ml) was added N-iodosuccinimide (43.6 g, 194 mmol, 1.05 equiv) and the resulting mixture was stirred overnight at RT. The thin brown slurry was diluted with water (840 ml), brine (280 ml) and extracted with EtOAc (560 ml). The aqueous was further extracted with EtOAc (3×280 ml). The combined organic phases were washed with water (2×280 ml), 10% w/v sodium thiosulfate (280 ml), brine (280 ml), dried (MgSO$_4$) and concentrated in vacuo to give a brown residue. The residue was triturated with ether (200 ml), filtered and the solid was washed ether (2×50 ml) and dried on the filter to give 39 g of product. MS: [M+H]$^+$ 279

Procedure SGD3—Suzuki Reaction with 1-[3-(4,4,5,5-Tetramethyl-[1,3,2]dioxaborolan-2-yl)-phenyl]-3-(2,2,2-trifluoro-ethyl)-urea

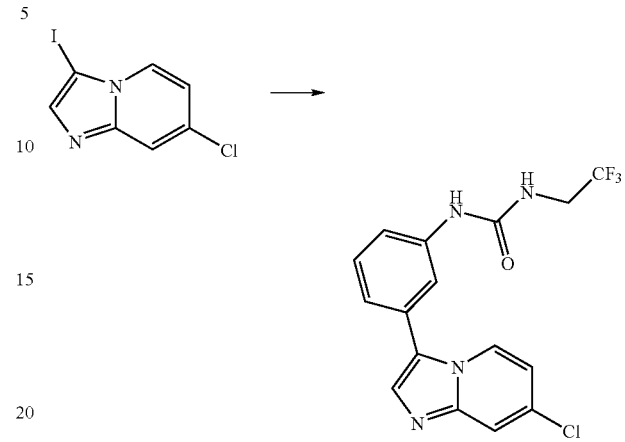

As for procedure A3b: To a solution of 7-chloro-3-iodo-imidazo[1,2-a]pyridine (1 equiv) in DME was added 1-[3-(4,4,5,5-Tetramethyl-[1,3,2]dioxaborolan-2-yl)-phenyl]-3-(2,2,2-trifluoro-ethyl)-urea (1.2 equiv), 1M Na$_2$CO$_3$ (8 equiv) [reaction degassed by bubbling N$_2$ through] followed by tetrakis(triphenylphosphine)palladium(0) (0.05 equiv). The mixture was heated at 80° C. overnight, then diluted with water and extracted with EtOAc. The organic layer was washed with brine, dried (MgSO$_4$) and concentrated under reduced pressure. The crude material was triturated with CH$_2$Cl$_2$ to afford the desired product as a beige solid. MS: [M+H]$^+$ 389

Procedure SGD4a—Sonagshira Reaction

Preparation of 1-[3-(7-Ethynyl-imidazo[1,2-a]pyridin-3-yl)-phenyl]-3-(2,2,2-trifluoro-ethyl)-urea

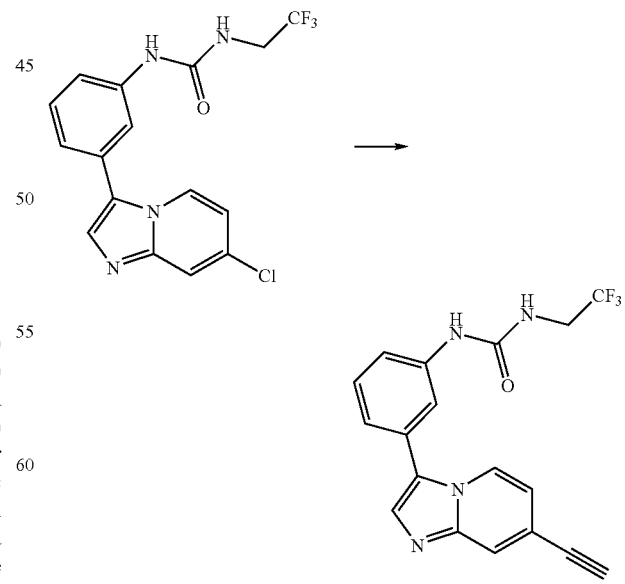

1-[3-(7-Chloro-imidazo[1,2-a]pyridin-3-yl)-phenyl]-3-(2,2,2-trifluoro-ethyl)-urea (0.59 g, 1.6 mmol), trimethylsilylacetylene (0.92 ml, 6.4 mmol), potassium carbonate (0.44 g, 3.2 mmol), palladium acetate (0.07 g, 0.32 mmol) and 2,2'-Bis(diphenylphosphino)-1,1'-binaphthalene (0.4 g, 0.64 mmol) were suspended in toluene (20 ml). The reaction mixture was microwaved (2×90 min) at 120° C., allowed to cool and then partitioned between CH₂Cl₂ and H₂O. The aqueous layer was further extracted with CH₂Cl₂, the organics combined, dried (MgSO₄) and the solvent removed in vacuo. The residue was purified by silica column chromatography (0-60% MeOH in Et₂O) to afford a solid which was used directly in the next reaction.

To a solution of 1-(2,2,2-Trifluoro-ethyl)-3-[3-(7-trimethylsilanylethynyl-imidazo[1,2-a]pyridin-3-yl)-phenyl]-urea (25 mg, 0.06 mmol) in THF (5 ml) at 0° C. was added a 1M tetrabutylammonium fluoride solution (0.09 ml) and the reaction mixture stirred for 1 h at 0° C. The reaction mixture was diluted with water and extracted with CH₂Cl₂. The organic layer was washed with brine, dried (MgSO₄) and the solvent removed in vacuo. The residue was purified by reverse phase HPLC to afford the product as an off-white solid (4.2 mg). MS: [M+H]⁺ 359

Procedure SGE

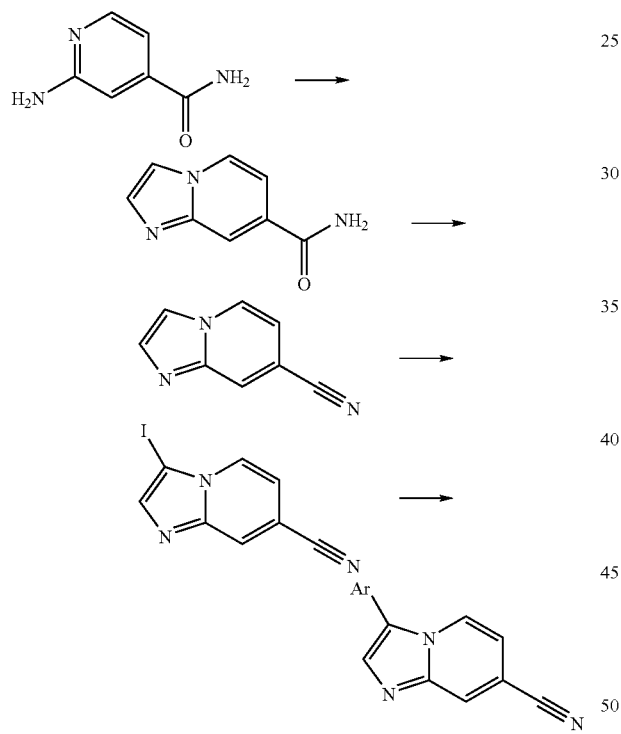

Procedure SGE1—Imidazo[1,2-a]pyridine-7-carboxylic acid amide

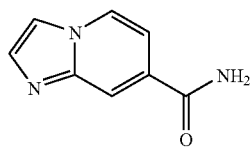 [SMILES: NC(=O)c1ccn2ccnc2c1]

Procedure SGA1 using 2-aminoisonicotinamide MS: [M+H]⁺ 162.

Procedure SGE2—Imidazo[1,2-a]pyridine-7-carbonitrile

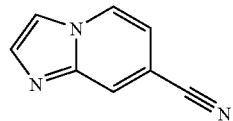

To a solution of Imidazo[1,2-a]pyridine-7-carboxylic acid amide (38 mg, 0.24 mmol) and triethylamine (0.066 ml, 0.47 mmol) in CH₂Cl₂ (5 ml) was added trifluoroacetic anhydride (0.39, 2.83 mmol) dropwise. The reaction mixture was stirred at room temperature for 2 h before the crude mixture was loaded onto a SCX SPE cartridge, washing with MeOH and eluting with the product with 2M NH₃/MeOH. Removal of solvent in vacuo afforded the title compound (32 mg). MS: [M+H]⁺ 144.

Procedure SGE3—3-Iodo-imidazo[1,2-a]pyridine-7-carbonitrile

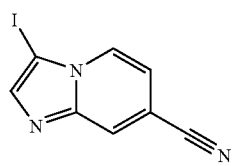 [SMILES: N#Cc1ccn2c(I)cnc2c1]

Procedure SGA2 using Imidazo[1,2-a]pyridine-7-carbonitrile. MS: [M+H]⁺ 270.

Procedure SGE4-1-[3-(7-Cyano-imidazo[1,2-a]pyridin-3-yl)-phenyl]-3-(2,2,2-trifluoro-ethyl)-urea

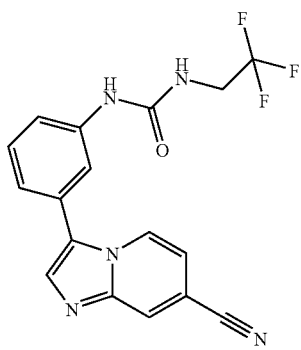 [SMILES: N#Cc1ccn2c(-c3cccc(NC(=O)NCC(F)(F)F)c3)cnc2c1]

Procedure A3a using 3-Iodo-imidazo[1,2-a]pyridine-7-carbonitrile. Purification via reverse phase HPLC to afforded the product as a white solid. MS: [M+H]⁺ 360.

Procedure SGF

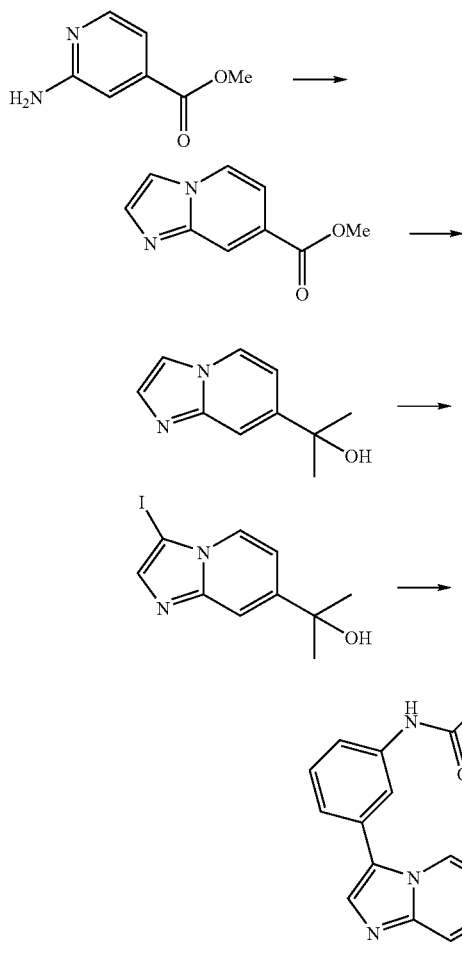

Procedure SGF1—Methyl imidazo[1,2-a]pyridine-7-carboxylate

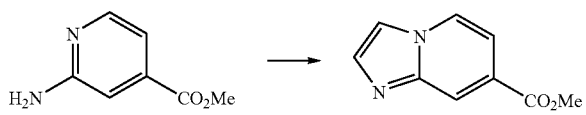

Procedure SGA1 using methyl-2-aminopyridine-4-carboxylate: To a solution of Methyl 2-aminopyridine-4-carboxylate (10.0 g, 66 mmol, 1.0 equiv) in EtOH (150 ml) was added NaHCO$_3$ (11.1 g, 132 mmol, 2.0 equiv) followed by chloroacetaldehyde (13.0 ml, 99 mmol, 1.5 equiv). The mixture was refluxed for 2 h. Solvents were removed under reduced pressure and the crude mixture was partitioned between water and EtOAc. The resulting precipitate was washed with Et$_2$O and recrystallised from MeOH/Et$_2$O to afford 8.4 g of product. MS: [M+H]$^+$ 177.

Procedure SGF2—2-Imidazo[1,2-a]pyridin-7-yl-propan-2-ol

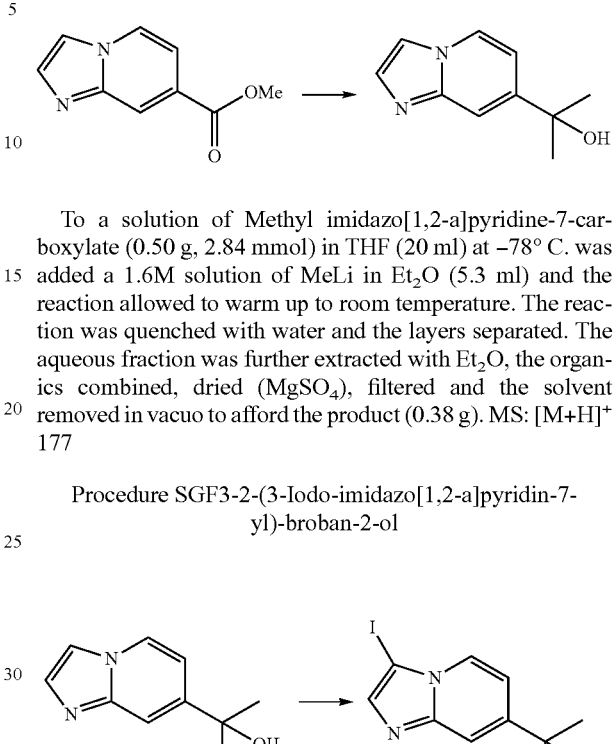

To a solution of Methyl imidazo[1,2-a]pyridine-7-carboxylate (0.50 g, 2.84 mmol) in THF (20 ml) at −78° C. was added a 1.6M solution of MeLi in Et$_2$O (5.3 ml) and the reaction allowed to warm up to room temperature. The reaction was quenched with water and the layers separated. The aqueous fraction was further extracted with Et$_2$O, the organics combined, dried (MgSO$_4$), filtered and the solvent removed in vacuo to afford the product (0.38 g). MS: [M+H]$^+$ 177

Procedure SGF3-2-(3-Iodo-imidazo[1,2-a]pyridin-7-yl)-broban-2-ol

Procedure SGA2 using 2-Imidazo[1,2-a]pyridin-7-yl-propan-2-ol. MS: [M+H]$^+$ 303.

Procedure SGF4—1-{3-[7-(1-Hydroxy-1-methyl-ethyl)-imidazo[1,2-a]pyridin-3-yl]-phenyl}-3-(2,2,2-trifluoro-ethyl)-urea

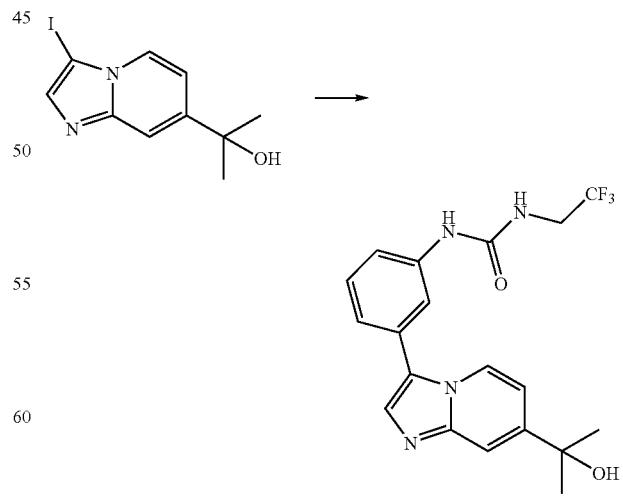

Procedure SGA3a using 2-(3-Iodo-imidazo[1,2-a]pyridin-7-yl)-propan-2-ol. Purification via reverse phase HPLC afforded the product. MS: [M+H]$^+$ 393.

Procedure SGG

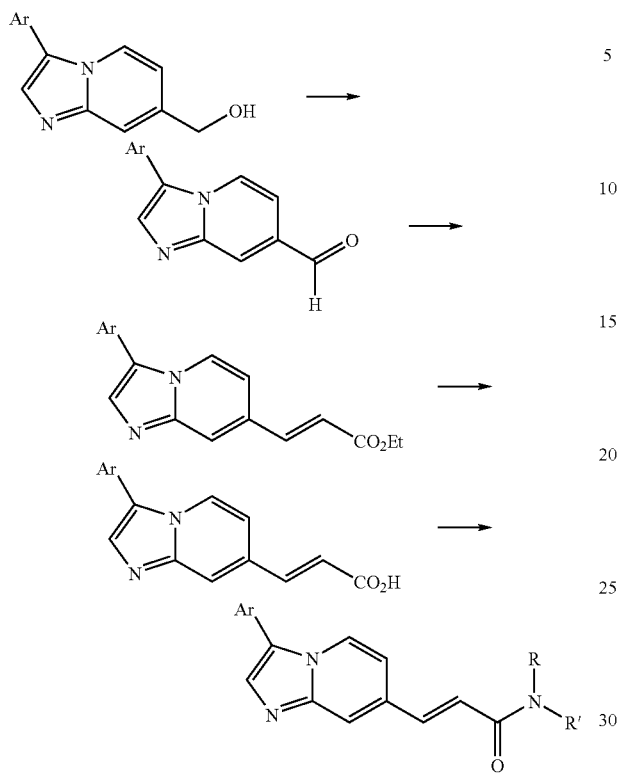

Procedure SGG1: 1-[3-(7-Formyl-imidazo[1,2-a]pyridin-3-yl)-phenyl]-3-(2,2,2-trifluoro-ethyl)-urea

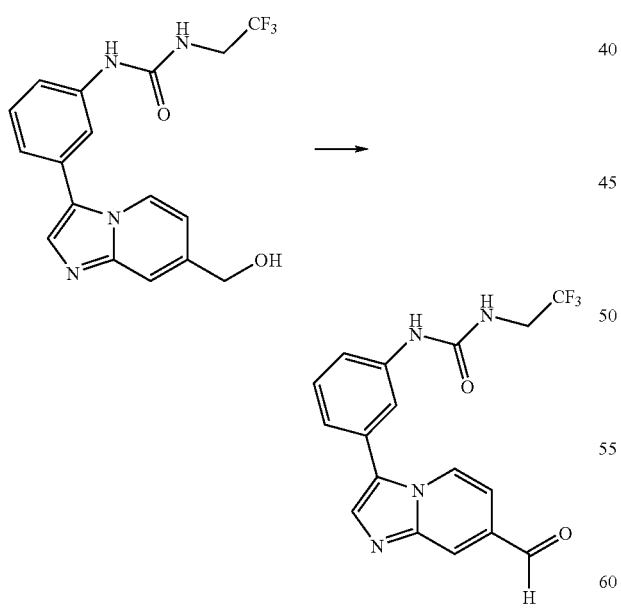

To a solution of 1-[3-(7-Hydroxymethyl-imidazo[1,2-a]pyridin-3-yl)-phenyl]-3-(2,2,2-triluoro-ethyl)-urea (1.42 g, 3.90 mmol) (prepared according to procedure SGA) and NMO (1.38, 11.7 mmol) in $CH_2Cl_2$ (30 ml) with sieves (3 g) at 0° C. was added TPAP (0.14 g, 0.38 mmol). The reaction mixture was allowed to warm to room temperature and stirred for 18 h, before being filtered to remove the sieves. The organic layer was washed with $H_2O$ (×2), dried ($MgSO_4$) and the solvent removed in vacuo. The residue was purified by silica column chromatography (0-60% MeOH in $Et_2O$) to afford the product (0.2 g). MS: $[M+H]^+$ 363.

Procedure SGG2 (E)-3-(3-{3-[3-(2,2,2-Trifluoro-ethyl)-ureido]-phenyl}-imidazo[1,2-a]pyridin-7-yl)-acrylic acid ethyl ester

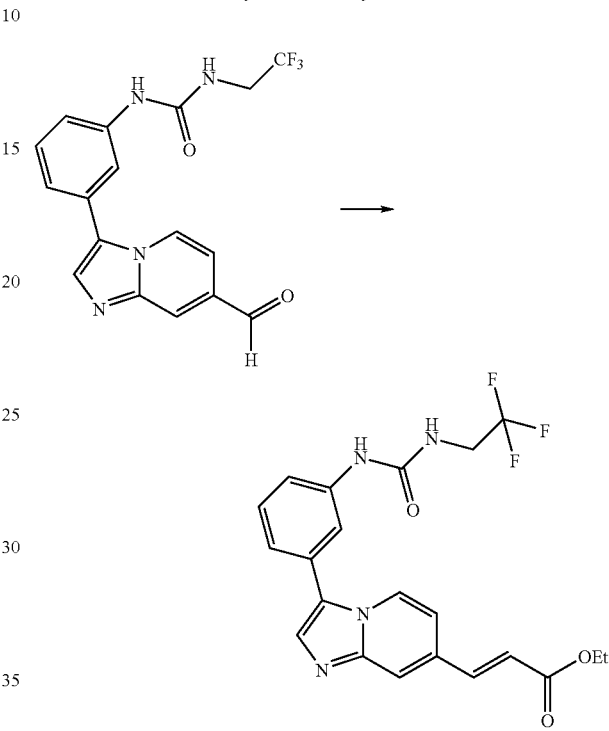

Triethylphosphonoacetate (99 μl, 0.5 mmol) and lithium chloride (21 mg, 0.5 mmol) were stirred in MeCN (5 ml). DBU (62 μl, 0.41 mmol) was added and the reaction mixture left to stir for 15 min before 1-[3-(7-Formyl-imidazo[1,2-a]pyridin-3-yl)-phenyl]-3-(2,2,2-trifluoro-ethyl)-urea was introduced. The mixture was left to stir for 1 h before being partitioned between EtOAc and $H_2O$. The aqueous layer was further extracted with EtOAc, the organics combined, dried ($MgSO_4$) and the solvent removed in vacuo. The residue was triturated with $Et_2O$ to afford the product as a bright yellow solid. MS: $[M+H]^+$ 433.

Procedure SGG3 (E)-3-(3-{3-[3-(2,2,2-Trifluoro-ethyl)-ureido]-phenyl}-imidazo[1,2-a]pyridin-7-yl)-acrylic acid

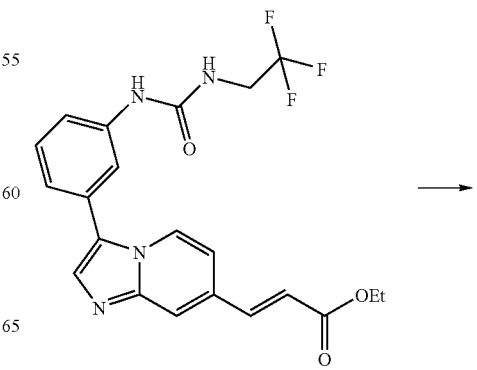

-continued

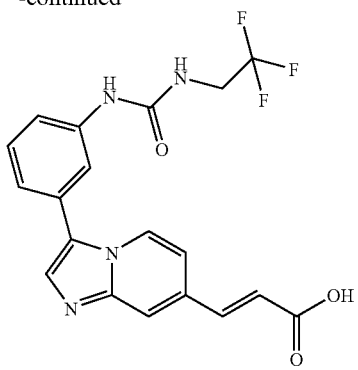

To a solution of (E)-3-(3-{3-[3-(2,2,2-Trifluoro-ethyl)-ureido]-phenyl}-imidazo[1,2-a]pyridin-7-yl)-acrylic acid ethyl ester (83 mg, 0.19 mmol) in EtOH (10 ml) was added 1M Na₂CO₃ (4 ml) and the reaction heated to 80° C. for 1.5 h. The reaction was neutralised using 1M HCl and then concentrated. The residue was taken up in hot EtOH, filtered and the solvent removed in vacuo to afford the product. MS: [M+H]⁺ 405.

Procedure SGG4 (E)-N-alkyl-3-(3-{3-[3-(2,2,2-trifluoro-ethyl)-ureido]-phenyl}imidazo[1,2-a]pyridin-7-yl)-acrylamide

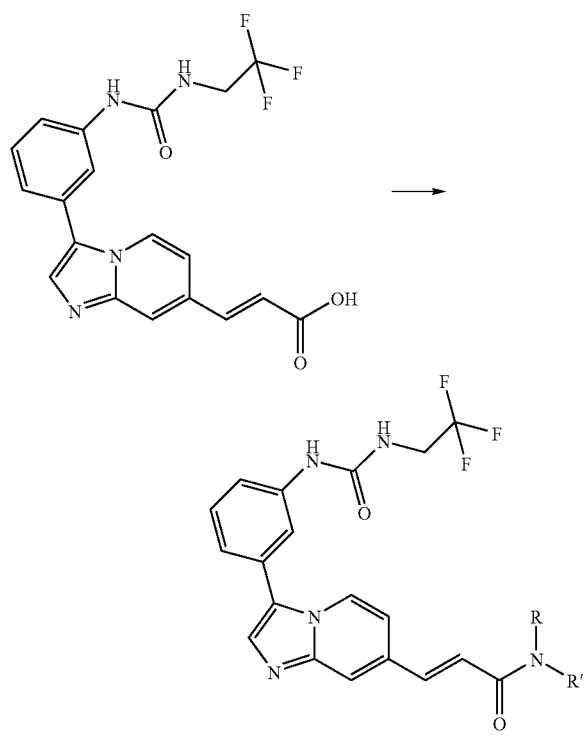

To a solution of (E)-3-(3-{3-[3-(2,2,2-Trifluoro-ethyl)-ureido]-phenyl}-imidazo[1,2-a]pyridin-7-yl)-acrylic acid in DMF was added TBTU (1.5 equiv) and HOBt (1.5 equiv) and the reaction mixture stirred for 15 min. An amine (2 equiv) was added and the reaction mixture stirred for 2 h. The crude material was loaded onto a SCX SPE cartridge, the cartridge washed with MeOH (×2 column volumes) and eluted with 2M NH₃/MeOH (1 column volume). The solvent was removed in vacuo to afford the desired product.

Procedure SGH

Procedure SGH1

7-Bromo-imidazo[1,2-a]pyridine

Preparation as for Procedure A1 using 4-bromo-pyridin-2-ylamine.

Procedure SGH2—7-Cyclobrobyl-imidazo[1,2-a]pyridine

To a mixture of 7-Bromo-imidazo[1,2-a]pyridine (0.5 g, 2.53 mmol), cyclopropylboronic acid (0.29 g, 3.29 mmol), K₃PO₄ (1.79 g, 8.88 mmol), Pcy₃ (0.07 g, 10 mol %) in deoxygenated toluene (11.36 ml) and H₂O (0.57 ml) was added Pd(OAc)₂ (0.03 g). The reaction mixture was heated at 100° C. for 18 h, before being partitioned between EtOAc and H₂O. The aqueous layer was washed with EtOAc, the organics combined, dried (MgSO₄) and the solvent removed in vacuo. The residue was purified by silica column chromatography to afford the product (0.31 g). MS: [M+H]⁺=159

Procedure SGH3-7-Cyclobrobyl-3-iodo-imidazo[1,2-a]pyridine

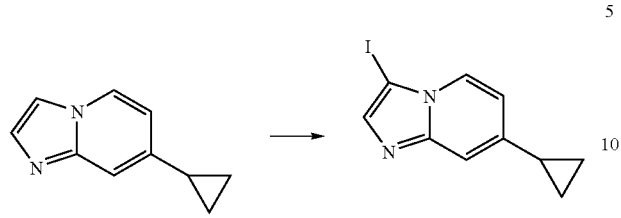

Procedure SGA2 followed to afford the product as a yellow oil. MS: [M+H]$^+$=285

Procedure SGH4—1-[3-(7-Cyclopropyl-imidazo[1,2-a]pyridin-3-yl)-phenyl]-3-(2,2,2-trifluoro-ethyl)-urea

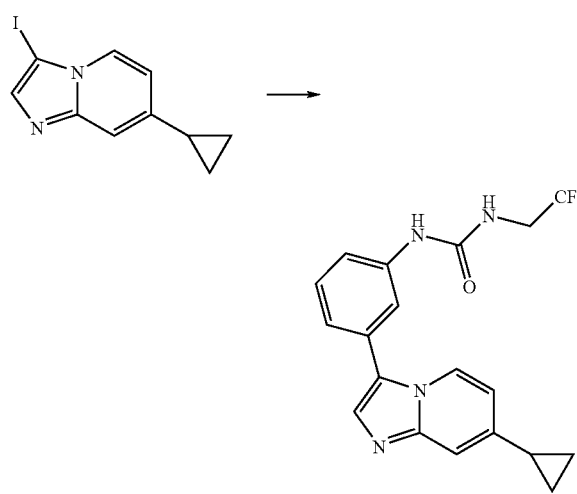

Procedure as for SGA3a to afford the product. MS: [M+H]$^+$=375

Procedure SGI: 1-{3-[7-(Hydroxyimino-methyl)-imidazo[1,2-a]pyridin-3-yl]-phenyl}-3-(2,2,2-trifluoro-ethyl)-urea

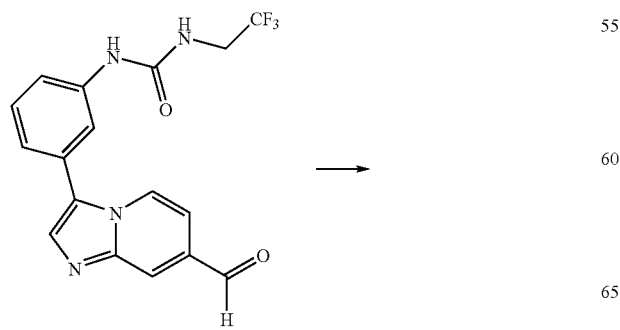

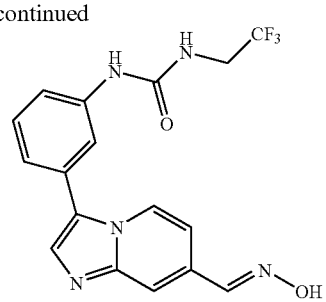

To a suspension of 1-[3-(7-Formyl-imidazo[1,2-a]pyridin-3-yl)-phenyl]-3-(2,2,2-trifluoro-ethyl)-urea (50 mg, 0.14 mmol) in toluene (5 ml) was added hydroxylamine hydrochloride (11 mg, 0.15 mmol) and triethylamine (21 µl, 0.15 mmol). The reaction mixture was stirred for 10 min before tosic acid (3 mg, 0.014 mmol) was added and then stirred for a further 18 h. The resulting precipitate was filtered off and washed with Et$_2$O to give the product (23 mg). MS: [M+H]$^+$ 378.

1-{3-[7-(Methoxyimino-methyl)-imidazo[1,2-a]pyridin-3-yl]-phenyl}-3-(2,2,2-trifluoro-ethyl)-urea

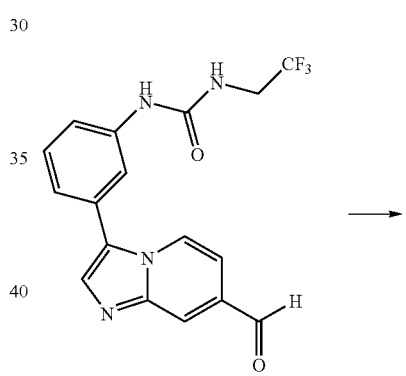

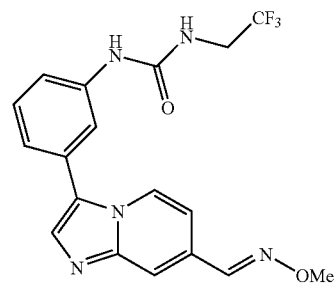

Method as above replacing hydroxylamine hydrochloride with methoxyamine hydrochloride. MS: [M+H]$^+$ 392.

Examples 1 to 59

By following the methods described above, the compounds of Examples 1 to 59 set out in the Table below were prepared.

| Eg. No. | Compound | Chemical Name | Procedure | N.M.R. Data | M.S. |
|---|---|---|---|---|---|
| 1 | | 7-Phenyl-3-(1H-pyrazol-4-yl)-imidazo[1,2-a]pyridine | General route B, procedure B1a using Phenylboronic Acid, procedure B2, procedure B3a using 4-(4,4,5,5-Tetramethyl-1,3,2-Dioxaborolan-2-yl)-Pyrazole-1-Carboxylic Acid Tert-Butyl Ester | $^1$H NMR (400 MHz, Me-d$_3$-OD): 8.49 (1H, d), 8.08 (2H, br s), 7.83 (1H, s), 7.79 (2H, d), 7.71 (1H, s), 7.53 (2H, t), 7.44 (1H, t), 7.37 (1H, dd). | MS: [M + H]$^+$ 261 |
| 2 | | N-[3-(7-Phenyl-imidazo[1,2-a]pyridin-3-yl)-phenyl]-acetamide hydrochloride salt | General route B, procedure B1a using Phenylboronic Acid, procedure B2, procedure B3a using (3-Acetylaminophenyl) Boronic Acid. Procedure J1. | $^1$H NMR (400 MHz, Me-d$_3$-OD): 8.72 (1H, d), 8.03 (2H, d), 7.91 (1H, s), 7.84 (2H, d), 7.61-7.43 (7H, m), 2.19 (3H, s). | MS: [M + H]$^+$ 328 |
| 3 | | 4-{4-[3-(3-Acetylamino-phenyl)-imidazo[1,2-a]pyridin-7-yl]-phenyl}-piperazine-1-carboxylic acid tert-butyl ester | General Route A, procedure A3a using (3-Acetylaminophenyl) Boronic Acid, procedure A4b using Tert-Butyl 4-[4-(4,4,5,5-Tetramethyl-1,3,2-Dioxaborolan-2-yl)Phenyl]Tetrahydro-1(2h)-Pyrazinecarboxylate | $^1$H NMR (400 MHz, Me-d$_3$-OD): 8.59 (1H, d), 7.97 (1H, s), 7.79 (1H, s), 7.76-7.66 (3H, m), 7.62-7.49 (2H, m), 7.45-7.31 (2H, m), 7.13 (2H, d), 3.62 (4H, t), 3.27 (4H, t), 2.19 (3H, s), 1.51 (9H, s). | MS: [M + H]$^+$ 512 |

-continued

| Eg. No. | Compound | Chemical Name | Procedure | N.M.R. Data | M.S. |
|---|---|---|---|---|---|
| 4 | | N-{3-[7-(4-Piperazin-1-yl-phenyl)-imidazo[1,2-a]pyridin-3-yl]-phenyl}-acetamide hydrochloride salt | General Route A, procedure A3a using (3-Acetylaminophenyl) Boronic Acid, procedure A4b using Tert-Butyl 4-[4-(4,4,5,5-Tetramethyl-1,3,2-Dioxaborolan-2-yl)Phenyl]Tetrahydro-1(2h)-Pyrazine-carboxylate, general modification D3a | $^1$H NMR (400 MHz, Me-d$_3$-OD): 8.79 (1H, d), 8.20 (1H, s), 8.15 (1H, s), 8.13 (1H, s), 7.91 (2H, d), 7.87 (1H, dd), 7.66-7.58 (2H, m), 7.52-7.44 (1H, m), 7.25 (2H, d), 3.62 (4H, t), 3.43 (4H, t), 2.20 (3H, s). | MS: [M + H]$^+$ 412 |
| 5 | | N-{3-[7-(4-Morpholin-4-yl-phenyl)-imidazo[1,2-a]pyridin-3-yl]-phenyl}-acetamide | General Route A, procedure A3a using (3-acetylaminophenyl) boronic acid, procedure A4b using 4-(morpholino)-phenylboronic acid | $^1$H NMR (400 MHz, Me-d$_3$-OD): 8.59 (1H, d), 7.99 (1H, s), 7.80 (1H, s), 7.78-7.47 (5H, m), 7.39 (2H, t), 7.10 (2H, d), 3.87 (4H, t), 3.26 (4H, t), 2.19 (3H, s). | MS: [M + H]$^+$ 413 |
| 6 | | N-[3-(7-Pyridin-4-yl-imidazo[1,2-a]pyridin-3-yl)-phenyl]-acetamide | General Route A, procedure A3a using (3-acetylaminophenyl) boronic acid, procedure using A4a 4-(4,4,5,5-tetramethyl-1,3,2-dioxaborolan-2-yl)pyridine | $^1$H NMR (400 MHz, Me-d$_3$-OD): 8.75-8.64 (3H, m), 8.09 (1H, s), 8.01 (1H, t), 7.93-7.85 (2H, m), 7.82 (1H, s), 7.62-7.53 (2H, m), 7.50-7.39 (2H, m), 2.19 (3H, s). | MS: [M + H]$^+$ 329 |

| Eg. No. | Compound | Chemical Name | Procedure | N.M.R. Data | M.S. |
|---|---|---|---|---|---|
| 7 | 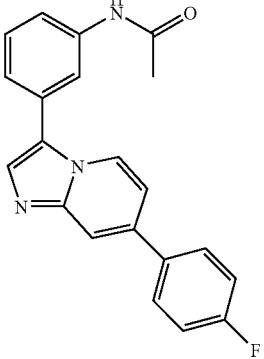 | N-{3-[7-(4-Fluoro-phenyl)-imidazo[1,2-a]pyridin-3-yl]-phenyl}-acetamide | General Route A, procedure A3a using (3-acetylaminophenyl)boronic acid, procedure A4b using 4-fluorophenylboronic acid | $^1$H NMR (400 MHz, Me-d$_3$-OD): 8.64 (1H, d), 7.99 (1H, t), 7.88-7.79 (3H, m), 7.75 (1H, s), 7.59 (1H, d), 7.54 (1H, t), 7.42 (1H, d), 7.35 (1H, dd), 7.31-7.21 (2H, m), 2.19 (3H, s). | MS: [M + H]$^+$ 346 |
| 8 | 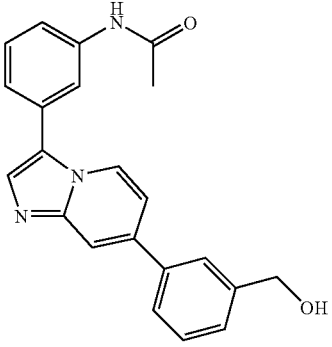 [SMILES: CC(=O)Nc1cccc(-c2cnc3cc(-c4cccc(CO)c4)ccn23)c1] | N-{3-[7-(3-Hydroxymeth-yl-phenyl)-imidazo[1,2-a]pyridin-3-yl]-phenyl}-acetamide | General Route A, procedure A3a using (3-acetylaminophenyl)boronic acid, procedure A4b using (3-hydroxymethylphen-yl)boronic acid | $^1$H NMR (400 MHz, Me-d$_3$-OD): 8.63 (1H, d), 8.28-8.16 (1H, m), 7.99 (1H, t), 7.89 (1H, s), 7.84-7.73 (2H, m), 7.69 (1H, d), 7.58 (1H, d), 7.56-7.48 (2H, m), 7.42 (3H, dd), 4.73 (2H, s), 2.19 (3H, s). | MS: [M + H]$^+$ 358 |
| 9 | 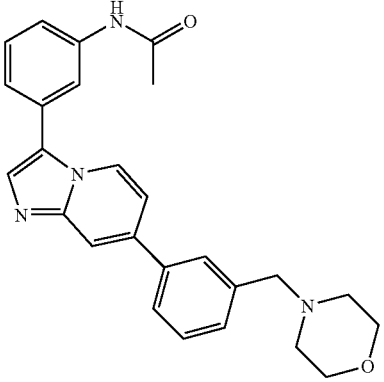 [SMILES: CC(=O)Nc1cccc(-c2cnc3cc(-c4cccc(CN5CCOCC5)c4)ccn23)c1] | N-{3-[7-(3-Morpholin-4-ylmethyl-phenyl)-imidazo[1,2-a]pyridin-3-yl]-phenyl}-acetamide | General Route A, procedure A3a using (3-acetylaminophenyl)boronic acid, procedure A4b using 4-[3-(4,4,5,5-tetramethyl-1,3,2-dioxaborolan-2-yl)benzyl]morpholine | $^1$H NMR (400 MHz, Me-d$_3$-OD): 8.64 (1H, d), 7.99 (1H, t), 7.88 (1H, s), 7.80 (1H, s), 7.74 (1H, s), 7.72 (1H, d), 7.59 (1H, d), 7.57-7.47 (2H, m), 7.43 (2H, t), 7.38 (1H, dd), 3.73 (4H, t), 3.65 (2H, s), 2.54 (4H, t), 2.19 (3H, s). | MS: [M + H]$^+$ 427 |

-continued

| Eg. No. | Compound | Chemical Name | Procedure | N.M.R. Data | M.S. |
|---|---|---|---|---|---|
| 10 | | N-{3-[7-(4-Morpholin-4-ylmethyl-phenyl)-imidazo[1,2-a]pyridin-3-yl]-phenyl}-acetamide hydrochloride salt | General Route A, procedure A3a using (3-acetylaminophenyl) boronic acid, procedure A4b using 4-[4-(4,4,5,5-tetramethyl-1,3,2-dioxaborolan-2-yl)benzyl]morpholine. Procedure J1. | $^1$H NMR (400 MHz, Me-d$_3$-OD): 8.89 (1H, d), 8.27 (1H, s), 8.24 (2H, s), 8.08 (2H, d), 7.90 (1H, dd), 7.83 (2H, d), 7.67-7.56 (2H, m), 7.54-7.46 (1H, m), 4.51 (2H, s), 4.08 (2H, br s), 3.83 (2H, br s), 3.43 (4H, br s), 2.20 (3H, s). | MS: [M + H]$^+$ 427 |
| 11 | | {3-[3-(3-Acetylamino-phenyl)-imidazo[1,2-a]pyridin-7-yl]-phenyl}-acetic acid | General Route A, procedure A3a using (3-acetylaminophenyl) boronic acid, procedure A4b using 2-(3-(4,4,5,5-tetramethyl-1,3,2-dioxaborolan-2-yl)phenyl)acetic acid | $^1$H NMR (400 MHz, Me-d$_3$-OD): 8.65 (1H, d), 7.99 (1H, t), 7.90 (1H, s), 7.80-7.66 (3H, m), 7.60 (1H, d), 7.56-7.48 (2H, m), 7.47-7.35 (3H, m), 3.74 (2H, s), 2.19 (3H, s). | MS: [M + H]$^+$ 386 |
| 12 | | N-{3-[7-(4-Fluoro-phenyl)-imidazo[1,2-a]pyridin-3-yl]-phenyl}-methanesulfon-amide formate salt | General Route B, procedure B1a using 4-fluorophenyl-boronic acid, procedure B2, procedure B3a using 3-aminobenzeneboron-ic acid, general modification F2 using methane sulphonyl chloride | $^1$H NMR (400 MHz Me-d3-OD): 8.61 (1H, d), 8.17 (1H, s), 7.91-7.72 (4H, m), 7.57 (2H, d), 7.46 (1H, d), 7.37 (2H, s), 7.26 (2H, t), 3.06 (3H, s)). | MS: [M + H]$^+$ 382 |
| 13 | | 3-{3-[7-(4-Fluoro-phenyl)-imidazo[1,2-a]pyridin-3-yl]-phenyl}-1,1-dimethyl-urea formate salt | General Route B, procedure B1a using 4-fluorophenyl-boronic acid, procedure B2, procedure B3a using 3-aminobenzeneboron-ic acid, general modification F1a using dimethylcarbamyl chloride | $^1$H NMR (400 MHz, Me-d$_3$-OD): 8.63 (1H, d), 8.21 (0.5H, s), 7.86-7.70 (5H, m), 7.52-7.40 (2H, m), 7.38-7.19 (4H, m), 3.07 (6H, s). | MS: [M + H]$^+$ 375 |

| Eg. No. | Compound | Chemical Name | Procedure | N.M.R. Data | M.S. |
|---|---|---|---|---|---|
| 14 | | N-{3-[7-(4-Fluoro-phenyl)-imidazo[1,2-a]pyridin-3-yl]-phenyl}-2-hydroxy-acetamide | General Route B, procedure B1a using 4-fluorophenyl-boronic acid, procedure B2, procedure B3a using 3-aminobenzeneboronic acid, general modification F3a. | $^1$H NMR (400 MHz, DMSO-$d_6$): 9.97 (1H, s), 8.80 (1H, d), 8.15 (2H, d), 8.00 (3H, dd), 7.89 (1H, d), 7.76-7.67 (1H, m), 7.57 (1H, t), 7.49-7.37 (4H, m), 4.05 (2H, s). | MS: [M + H]$^+$ 362 |
| 15 | | 1-Ethyl-3-{3-[7-(4-fluoro-phenyl)-imidazo[1,2-a]pyridin-3-yl]-phenyl}-urea formate salt | General Route B, procedure B1a using 4-fluorophenyl-boronic acid, procedure B2, procedure B3a using 3-aminobenzeneboronic acid, general modification F1a using ethylisocyanate | $^1$H NMR (400 MHz, Me-$d_3$-OD): 8.59 (1H, d), 8.24 (0.5H, s), 7.88-7.68 (5H, m), 7.43 (1H, t), 7.38-7.17 (5H, m), 3.27 (2H, q), 1.18 (3H, t). | MS: [M + H]$^+$ 375 |
| 16 | | {3-[7-(4-Fluoro-phenyl)-imidazo[1,2-a]pyridin-3-yl]-phenyl}-carbamic acid methyl ester formate salt | General Route B, procedure B1a using 4-fluorophenyl-boronic acid, procedure B2, procedure B3a using 3-aminobenzeneboronic acid, general modification F4 using methyl chloroformate | $^1$H NMR (400 MHz, Me-$d_3$-OD): 8.58 (1H, d), 8.19 (1H, s), 7.88-7.69 (5H, m), 7.47 (2H, d), 7.42-7.17 (4H, m), 3.78 (3H, s). | MS: [M + H]$^+$ 362 |
| 17 | | 1,1-dimethyl-3-{3-[7-(4-fluoro-phenyl)-imidazo[1,2-a]pyridin-3-yl]-phenyl}-sulfonylurea formate salt | General Route B, procedure B1a using 4-fluorophenyl-boronic acid, procedure B2, procedure B3a using 3-aminobenzeneboronic acid, general modification F2 | $^1$H NMR (400 MHz, Me-$d_3$-OD): 8.59 (1H, d), 8.15 (1H, s), 7.93-7.74 (4H, m), 7.58-7.47 (2H, m), 7.45-7.20 (5H, m), 2.85 (6H, s). | MS: [M + H]$^+$ 411 |

-continued

| Eg. No. | Compound | Chemical Name | Procedure | N.M.R. Data | M.S. |
|---|---|---|---|---|---|
| 18 | | Ethyl-{3-[7-(4-fluoro-phenyl)-imidazo[1,2-a]pyridin-3-yl]-phenyl}-amine formate salt | General Route B, procedure B1a using 4-fluorophenyl-boronic acid, procedure B2, procedure B3a using 3-aminobenzeneboron-ic acid, general modification F6 | $^1$H NMR (400 MHz, Me-d$_3$-OD): 8.59 (1H, d), 7.88-7.76 (3H, m), 7.73-7.63 (1H, m), 7.39-7.20 (4H, m), 6.92-6.82 (2H, m), 6.76 (1H, dd), 3.20 (2H, q), 1.34-1.19 (3H, m). | MS: [M + H]$^+$ 332 |
| 19 | | 1-Ethyl-3-{3-[7-(3-morpholin-4-ylmethyl-phenyl)-imidazo[1,2-a]pyridin-3-yl]-phenyl}-urea formate salt | General Route B, procedure B1a using 4-[3-(4,4,5,5-tetramethyl-1,3,2-dioxaborolan-2-yl)benzyl]morpholine, procedure B2, procedure B3a using 3-aminobenzeneboron-ic acid, general modification F1a using ethyl isocyanate | $^1$H NMR (400 MHz, Me-d$_3$-OD): 8.67 (1H, d), 8.33 (1H, s), 7.92-7.80 (3H, m), 7.75 (2H, t), 7.57-7.34 (5H, m), 7.29 (1H, d), 3.81-3.71 (6H, m), 3.28 (2H, q), 2.64 (4H, d), 1.19 (3H, t). | MS: [M + H]$^+$ 456 |
| 20 | | 5-[7-(4-Fluoro-phenyl)-imidazo[1,2-a]pyridin-3-yl]-1H-indazole | As described in General Route B; Procedure B1a using 4-fluorophenyl boronic acid, procedure B2, Procedure 3a using 1H-indazole-5-boronic acid | $^1$H NMR (400 MHz, Me-d$_3$-OD): 8.58 (1H, d), 8.19 (1H, d), 8.10 (1H, s), 7.91-7.73 (5H, m), 7.72-7.62 (1H, m), 7.37 (1H, d), 7.27 (2H, t). | MS: [M + H]$^+$ 329 |
| 21 | | 7-(4-Fluoro-phenyl)-3-(3-pyrazol-1-yl-phenyl)-imidazo[1,2-a]pyridine | As described in General Route B; Procedure B1a using 4-fluorophenyl boronic acid, procedure B2, Procedure 3a using 1-[3-(4,4,5,5-tetramethyl-1,3,2-dioxaborolan-2-yl)phenyl]-1H-pyrazole | $^1$H NMR (400 MHz, Me-d$_3$-OD): 8.65 (1H, d), 8.35 (1H, d), 8.05 (1H, t), 7.88-7.74 (6H, m), 7.74-7.68 (1H, m), 7.62 (1H, d), 7.34 (1H, dd), 7.28-7.20 (2H, m), 6.58 (1H, t). | |

-continued

| Eg. No. | Compound | Chemical Name | Procedure | N.M.R. Data | M.S. |
|---|---|---|---|---|---|
| 22 | | N-{3-[7-(4-Fluoro-phenyl)-imidazo[1,2-a]pyridin-3-yl]-benzyl}-acetamide formate salt | As described in General Route B; Procedure B1a using 4-fluorophenyl boronic acid, procedure B2, Procedure 3a using (3-acetamidomethyl-phenyl)boronic acid | $^1$H NMR (400 MHz, Me-d$_3$-OD): 8.59 (1H, d), 8.17 (1H, s), 7.90-7.72 (4H, m), 7.70-7.51 (3H, m), 7.49-7.33 (2H, m), 7.26 (2H, t), 4.48 (2H, s), 2.03 (3H, s). | MS: [M + H]$^+$ 360 |
| 23 | | 3-[7-(4-Fluoro-phenyl)-imidazo[1,2-a]pyridin-3-yl]-N-methyl-benzamide formate salt | As described in General Route B; Procedure B1a using 4-fluorophenyl boronic acid, procedure B2, Procedure 3a using 3-(N-methylaminocarbonyl)benzeneboronic acid | $^1$H NMR (400 MHz, Me-d$_3$-OD): 8.61 (1H, d), 8.18 (0.5H, s), 8.09 (1H, s), 7.90 (1H, d), 7.87-7.74 (5H, m), 7.67 (1H, t), 7.34 (1H, d), 7.25 (2H, t), 2.98 (3H, s). | MS: [M + H]$^+$ 346 |
| 24 | | N-{3-[7-(3-Morpholin-4-ylmethyl-phenyl)-imidazo[1,2-a]pyridin-3-yl]-phenyl}-methanesulfon-amide | General Route B, procedure B1a using 4-[3-(4,4,5,5-tetramethyl-1,3,2-dioxaborolan-2-yl)benzyl]morpholine, procedure B2, procedure B3a using 3-aminobenzeneboron-ic acid, general modification F2 using methanesulfonyl chloride | $^1$H NMR (400 MHz, Me-d$_3$-OD): 8.62 (1H, d), 7.89 (1H, s), 7.84-7.68 (3H, m), 7.62-7.54 (2H, m), 7.54-7.42 (3H, m), 7.42-7.33 (2H, m), 3.73 (4H, t), 3.65 (2H, s), 3.07 (3H, s), 2.54 (4H, t). | MS: [M + H]$^+$ 463 |
| 25 | | {3-[7-(4-Fluoro-phenyl)-imidazo[1,2-a]pyridin-3-yl]-phenyl}-acetonitrile | As described in General Route B; Procedure B1a using 4-fluorophenyl boronic acid, procedure B2, Procedure 3a using (3-cyanomethylphenyl)boronic acid, pinacol ester | $^1$H NMR (400 MHz, Me-d$_3$-OD): 8.55 (1H, d), 7.86-7.72 (4H, m), 7.72-7.56 (3H, m), 7.50 (1H, d), 7.35-7.19 (3H, m), 4.04 (2H, s). | MS: [M + H]$^+$ 328 |

-continued

| Eg. No. | Compound | Chemical Name | Procedure | N.M.R. Data | M.S. |
|---|---|---|---|---|---|
| 26 | | 3-Acetylamino-5-[7-(3-morpholin-4-ylmethyl-phenyl)-imidazo[1,2-a]pyridin-3-yl]-benzamide | General Route H; Procedure H1, H2 and H3 | $^1$H NMR (400 MHz, DMSO-d$_6$): 10.26 (1H, s), 8.68 (1H, d), 8.12 (1H, s), 8.07 (2H, brs), 7.99 (1H, s), 7.87 (1H, s), 7.83 (1H, s), 7.81-7.72 (2H, m), 7.54-7.43 (2H, m), 7.43-7.34 (2H, m), 3.66-3.54 (6H, m), 2.47-2.36 (4H, m), 2.11 (3H, s). | MS: [M + H]$^+$ 470 |
| 27 | | N-(3-{7-[3-(4-Methyl-piperazin-1-ylmethyl)-phenyl]-imidazo[1,2-a]pyridin-3-yl}-phenyl)-acetamide | General Route B, Procedure B1d, procedure B2, procedure B3a using (3-acetylaminophenyl) boronic acid | $^1$H NMR (400 MHz, Me-d$_3$-OD): 8.63 (1H, d), 7.98 (1H, s), 7.87 (1H, s), 7.78 (1H, s), 7.73 (1H, s), 7.70 (1H, d), 7.58 (1H, d), 7.56-7.46 (2H, m), 7.45-7.39 (2H, m), 7.36 (1H, dd), 3.66 (2H, s), 2.57 (8H, br s), 2.32 (3H, s), 2.19 (3H, s). | |
| 28 | | N-{3-Cyano-5-[7-(3-morpholin-4-ylmethyl-phenyl)-imidazo[1,2-a]pyridin-3-yl]-phenyl}-acetamide | General Route H; Procedure H1 and then procedure H3 using 3-amino-5-cyanophenylboronic acid (Procedure H4) | $^1$H NMR (400 MHz, DMSO-d$_6$): 10.45 (1H, s), 8.71 (1H, d), 8.12 (1H, t), 8.08 (1H, t), 8.01 (1H, brs), 7.94 (1H, s), 7.88 (1H, t), 7.82-7.72 (2H, m), 7.49 (1H, t), 7.44-7.35 (2H, m), 3.67-3.54 (6H, m), 2.47-2.36 (4H, m), 2.13 (3H, s). | MS: [M + H]$^+$ 452 |

| Eg. No. | Compound | Chemical Name | Procedure | N.M.R. Data | M.S. |
|---|---|---|---|---|---|
| 29 | | 1-Ethyl-3-(3-{7-[3-(4-methyl-piperazin-1-ylmethyl)-phenyl]-imidazo[1,2-a]pyridin-3-yl}-phenyl)-thiourea | General Route B, procedures B1d, B2, B3 using 3-aminobenzene boronic acid, then general modification F1a using ethyl thioisocyanate | $^1$H NMR (400 MHz, Me-d$_3$-OD): 8.76 (1H, d), 7.89 (1H, d), 7.85 (1H, s), 7.77 (1H, s), 7.74 (1H, s), 7.70 (1H, d), 7.60-7.38 (4H, m), 7.34 (2H, dd), 3.66 (4H, m), 2.63 (8H, s), 2.38 (3H, s), 1.25 (3H, t). | MS: [M + H]$^+$ 485 |
| 30 | | 1-Ethyl-3-{3-[7-(4-morpholin-4-yl-phenyl)-imidazo[1,2-a]pyridin-3-yl]-phenyl}-urea hydrochloride salt | General Route A, Procedure A1 and A2, Procedure A3b using 3-aminobenzeneboronic acid, general modification F1a, procedure A4b using 4-[4-(4,4,5,5-tetramethyl-1,3,2-dioxaborolan-2-yl)benzyl]morpholine. Procedure J1. | $^1$H NMR (400 MHz, Me-d$_3$-OD): 8.60 (1H, d), 7.83 (1H, t), 7.78 (1H, s), 7.75-7.65 (3H, m), 7.46 (1H, t), 7.43-7.31 (2H, m), 7.28 (1H, d), 7.11 (2H, d), 3.88 (4H, t), 3.31-3.24 (6H, m), 1.19 (3H, t). | MS: [M + H]$^+$ 442 |
| 31 | | 4-(4-{3-[3-(3-Ethyl-ureido)-phenyl]-imidazo[1,2-a]pyridin-7-yl}-phenyl)-piperazine-1-carboxylic acid tert-butyl ester | General Route A, Procedure A1 and A2, Procedure A3b using 3-aminobenzeneboronic acid, general modification F1a, procedure A4b using tert-butyl 4-[4-(4,4,5,5-tetramethyl-1,3,2-dioxaborolan-2-yl)phenyl]tetrahydro-1(2h)-pyrazinecarboxylate | $^1$H NMR (400 MHz, Me-d$_3$-OD): 8.60 (1H, d), 7.83 (1H, t), 7.77 (1H, s), 7.76-7.63 (3H, m), 7.46 (1H, t), 7.40-7.31 (2H, m), 7.27 (1H, d), 7.12 (2H, d), 3.67-3.56 (4H, m), 3.30-3.21 (6H, m), 1.51 (9H, s), 1.19 (3H, t). | MS: [M + H]$^+$ 541 |

| Eg. No. | Compound | Chemical Name | Procedure | N.M.R. Data | M.S. |
|---|---|---|---|---|---|
| 32 | 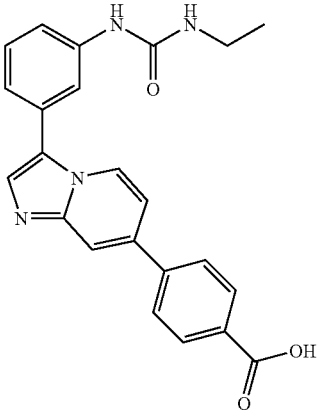 [SMILES: CCNC(=O)Nc1cccc(-c2cnc3cc(-c4ccc(C(=O)O)cc4)ccn23)c1] | 4-{3-[3-(3-Ethyl-ureido)-phenyl]-imidazo[1,2-a]pyridin-7-yl}-benzoic acid | General Route A, Procedure A1 and A2, Procedure A3b using 3-aminobenzeneboronic acid, general modification F1a, procedure A4b using 4-carboxyphenylboronic acid | $^1$H NMR (400 MHz, Me-d$_3$-OD): 8.69 (1H, d), 8.17 (2H, d), 7.96 (1H, s), 7.91 (2H, d), 7.85 (1H, s), 7.77 (1H, s), 7.48 (1H, t), 7.43 (1H, dd), 7.39 (1H, d), 7.30 (1H, d), 3.28 (2H, q), 1.19 (3H, t) | MS: [M + H]$^+$ 401 |
| 33 | 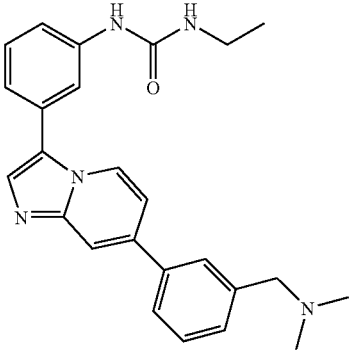 [SMILES: CCNC(=O)Nc1cccc(-c2cnc3cc(-c4cccc(CN(C)C)c4)ccn23)c1] | 1-{3-[7-(3-Dimethylamino-methyl-phenyl)-imidazo[1,2-a]pyridin-3-yl]-phenyl}-3-ethyl-urea | General Route A, Procedure A1 and A2, Procedure A3b using 3-aminobenzeneboronic acid, general modification F1a, procedure A4b using 3-((N,N-dimethylamino)methyl)phenyl boronic acid pinacol ester hydrochloride | $^1$H NMR (400 MHz, Me-d$_3$-OD): 8.69 (1H, d), 8.17 (2H, d), 7.96 (1H, s), 7.91 (2H, d), 7.85 (1H, s), 7.77 (1H, s), 7.48 (1H, t), 7.43 (1H, dd), 7.39 (1H, d), 7.30 (1H, d), 3.28 (2H, q), 1.19 (3H, t) | MS: [M + H]$^+$ 414 |
| 34 | 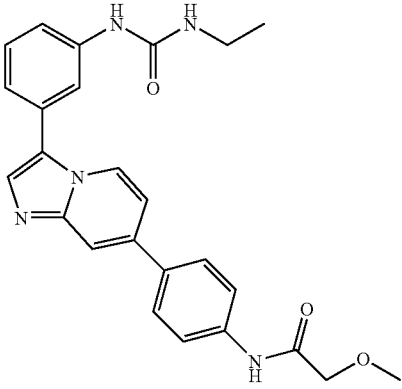 [SMILES: CCNC(=O)Nc1cccc(-c2cnc3cc(-c4ccc(NC(=O)COC)cc4)ccn23)c1] | N-(4-{3-[3-(3-Ethyl-ureido)-phenyl]-imidazo[1,2-a]pyridin-7-yl}-phenyl)-2-methoxy-acetamide | General Route A, Procedure A1 and A2, Procedure A3b using 3-aminobenzeneboronic acid, general modification F1a, procedure A4b using 2-Methoxy-N-[4-(4,4,5,5-tetramethyl-[1,3,2]dioxaborolan-2-yl)-phenyl]-acetamide (I1) | $^1$H NMR (400 MHz, Me-d$_3$-OD): 8.66 (1H, d), 7.87 (1H, s), 7.86-7.83 (1H, m), 7.81 (4H, s), 7.75 (1H, s), 7.47 (1H, t), 7.41 (1H, dd), 7.37 (1H, d), 7.29 (1H, d), 4.09 (2H, s), 3.53 (3H, s), 3.27 (2H, q), 1.19 (3H, t). | MS: [M + H]$^+$ 444 |
| 35 | 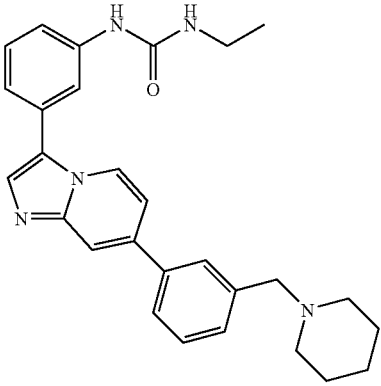 [SMILES: CCNC(=O)Nc1cccc(-c2cnc3cc(-c4cccc(CN5CCCCC5)c4)ccn23)c1] | 1-Ethyl-3-{3-[7-(3-piperidin-1-ylmethyl-phenyl)-imidazo[1,2-a]pyridin-3-yl]-phenyl}-urea | General Route A, Procedure A1 and A2, Procedure A3b using 3-aminobenzeneboronic acid, general modification F1a, procedure A4b using piperidinomethyl-3-phenylboronic acid pinacol ester hydrochloride | $^1$H NMR (400 MHz, Me-d$_3$-OD): 8.66 (1H, d), 7.88 (1H, s), 7.84 (1H, s), 7.79 (1H, s), 7.73 (2H, d), 7.55-7.34 (5H, m), 7.29 (1H, d), 3.64 (2H, s), 3.28 (2H, q), 2.52 (4H, br s), 1.70-1.61 (4H, m), 1.52 (2H, br s), 1.19 (3H, t). | MS: [M + H]$^+$ 454 |

-continued

| Eg. No. | Compound | Chemical Name | Procedure | N.M.R. Data | M.S. |
|---|---|---|---|---|---|
| 36 | | 1-Ethyl-3-(3-{7-[3-(morpholine-4-carbonyl)-phenyl]-imidazo[1,2-a]pyridin-3-yl}-phenyl)-urea | General Route A, Procedure A1 and A2, Procedure A3b using 3-aminobenzeneboronic acid, general modification F1a, procedure A4b using N-morpholinyl 3-boronobenzamide | $^1$H NMR (400 MHz, Me-d$_3$-OD): 8.68 (1H, d), 7.93 (2H, d), 7.89-7.81 (2H, m), 7.76 (1H, s), 7.65 (1H, t), 7.55-7.49 (1H, m), 7.47 (1H, d), 7.43-7.33 (2H, m), 7.30 (1H, d), 3.71 (8H, d), 3.27 (2H, q), 1.19 (3H, t). | MS: [M + H]$^+$ 470 |
| 37 | | 1-Ethyl-3-[3-(7-morpholin-4-yl-imidazo[1,2-a]pyridin-3-yl)-phenyl]-urea | General Route A, Procedure A1 and A2, Procedure A3b using 3-aminobenzeneboronic acid, general modification F1a, procedure A4c using morpholine. | $^1$H NMR (400 MHz, Me-d$_3$-OD): 8.39 (1H, d), 7.75 (1H, t), 7.51-7.37 (2H, m), 7.35-7.26 (1H, m), 7.21 (1H, d), 6.92 (1H, dd), 6.78 (1H, d), 3.88 (4H, t), 3.31 (4H, t), 3.26 (2H, q), 1.18 (3H, t). | MS: [M + H]$^+$ 366 |
| 38 | | 1-Ethyl-3-(3-{7-[3-(1H-tetrazol-5-yl)-phenyl]-imidazo[1,2-a]pyridin-3-yl}-phenyl)-urea formate salt | General Route A, Procedure A1 and A2, Procedure A3b using 3-aminobenzeneboronic acid, general modification F1a, procedure A4b using 3-(2H-tetrazol-5-yl)-phenyl-boronic acid | $^1$H NMR (400 MHz, Me-d$_3$-OD): 8.74 (1H, d), 8.51 (1H, s), 8.17-8.13 (2H, m), 8.05 (1H, s), 7.92 (1H, d), 7.87 (2H, d), 7.69 (1H, t), 7.59 (1H, dd), 7.54-7.45 (1H, m), 7.43 (1H, d), 7.32 (1H, d), 3.28 (2H, q), 1.19 (3H, t). | MS: [M + H]$^+$ 425 |
| 39 | | 2-(4-{3-[3-(3-Ethyl-ureido)-phenyl]-imidazo[1,2-a]pyridin-7-yl}-phenyl)-2-methyl-propionic acid methyl ester | General Route A, Procedure A1 and A2, Procedure A3b using 3-aminobenzeneboronic acid, general modification F1a, procedure A4b using 2-Methyl-2-[4-(4,4,5,5-tetramethyl-[1,3,2]dioxaborolan-2-yl)-phenyl]-propionic acid methyl ester (I2) | $^1$H NMR (400 MHz, Me-d$_3$-OD): 8.65 (1H, d), 7.89-7.81 (2H, m), 7.77 (2H, d), 7.72 (1H, s), 7.55-7.42 (3H, m), 7.41-7.33 (2H, m), 7.29 (1H, d), 3.70 (3H, s), 3.27 (2H, q), 1.64 (6H, s), 1.19 (3H, t). | MS: [M + H]$^+$ 457 |

-continued

| Eg. No. | Compound | Chemical Name | Procedure | N.M.R. Data | M.S. |
|---|---|---|---|---|---|
| 40 | | 1-Ethyl-3-{3-[7-(4-pyrrolidin-1-ylmethyl-phenyl)-imidazo[1,2-a]pyridin-3-yl]-phenyl}-urea | General Route A, Procedure A1 and A2, Procedure A3b using 3-aminobenzeneboronic acid, general modification F1a, procedure A4b using 4-(1-pyrrolidinylmethyl) phenylboronic acid | $^1$H NMR (400 MHz, Me-d$_3$-OD): 8.64 (d, J = 7.3 Hz, 1H), 7.89-7.85 (m, 1H), 7.83 (t, J = 2.1 Hz, 1H), 7.77 (d, J = 7.8 Hz, 2H), 7.72 (s, 1H), 7.51 (d, J = 7.8 Hz, 2H), 7.46 (t, J = 7.9 Hz, 1H), 7.36 (dd, J = 7.5, 2.1 Hz, 2H), 7.28 (d, J = 7.5 Hz, 1H), 3.73 (s, 2H), 3.27 (q, J = 7.3 Hz, 2H), 2.69-2.56 (m, 4H), 1.92-1.80 (m, 4H), 1.19 (t, J = 7.2 Hz, 3H). | MS: [M + H]$^+$ 440 |
| 41 | | 4-{3-[3-(3-Ethyl-ureido)-phenyl]-imidazo[1,2-a]pyridin-7-yl}-benzoic acid methyl ester formate salt | General Route A, Procedure A1 and A2, Procedure A3b using 3-aminobenzeneboronic acid, general modification F1a, procedure A4b using 4-methoxycarbonylphenylboronic acid | $^1$H NMR (400 MHz, Me-d$_3$-OD): 8.66 (1H, d), 8.38 (1H, s), 8.15 (2H, d), 7.98-7.87 (3H, m), 7.84 (1H, t), 7.76 (1H, s), 7.46 (1H, t), 7.42-7.32 (2H, m), 7.28 (1H, d), 3.96 (3H, s), 3.27 (2H, q), 1.19 (3H, t). | MS: [M + H]$^+$ 415 |
| 42 | | 1-(3-{7-[3-(2-Amino-ethyl)-phenyl]-imidazo[1,2-a]pyridin-3-yl}-phenyl)-3-ethyl-urea | General Route A, Procedure A1 and A2, Procedure A3b using 3-aminobenzeneboronic acid, general modification F1a, procedure A4b using (3-cyanomethylphenyl) boronic acid, pinacol ester, General Modification D1 | 1H NMR (400 MHz, Me-d3-OD): 8.55 (1H, d), 7.75 (2H, s), 7.62 (1H, s), 7.56 (2H, d), 7.41-7.33 (2H, m), 7.33-7.14 (4H, m), 3.17 (2H, q), 2.92 (2H, t), 2.82 (2H, t), 1.08 (3H, t). | MS: [M + H]$^+$ 400 |
| 43 | | 1-Ethyl-3-{3-[7-(6-methoxy-pyridin-3-yl)-imidazo[1,2-a]pyridin-3-yl]-phenyl}-urea | General Route A, Procedure A1 and A2, Procedure A3b using 3-aminobenzeneboronic acid, general modification F1a, procedure A4b using 2-methoxy-5-pyridineboronic acid | $^1$H NMR (400 MHz, Me-d$_3$-OD): 8.66 (1H, d), 8.58 (1H, d), 8.12 (1H, dd), 7.84 (2H, s), 7.73 (1H, s), 7.47 (1H, t), 7.41-7.31 (2H, m), 7.29 (1H, d), 6.96 (1H, d), 4.00 (3H, s), 3.28 (2H, q), 1.19 (3H, t). | MS: [M + H]$^+$ 388 |

| Eg. No. | Compound | Chemical Name | Procedure | N.M.R. Data | M.S. |
|---|---|---|---|---|---|
| 44 | | 4-{3-[3-(3-Butyl-ureido)-phenyl]-imidazo[1,2-a]pyridin-7-yl}-benzoic acid | General Route A, Procedure A1 and A2, Procedure A3b using 3-aminobenzeneboronic acid, procedure A3a, general modification F1a using N-butyl isocyanate, procedure A4b using 4-carboxyphenylboronic acid | $^1$H NMR (400 MHz, Me-d$_3$-OD): 8.68 (1H, d), 8.16 (2H, d), 7.96 (1H, s), 7.90 (2H, d), 7.84 (1H, t), 7.77 (1H, s), 7.47 (1H, t), 7.43 (1H, dd), 7.41-7.34 (1H, m), 7.30 (1H, d), 3.24 (2H, t), 1.61-1.50 (2H, m), 1.50-1.37 (2H, m), 0.99 (3H, t). | MS: [M + H]$^+$ 429 |
| 45 | | 1-Ethyl-3-{3-[7-(2-methoxy-pyridin-4-yl)-imidazo[1,2-a]pyridin-3-yl]-phenyl}-urea | General Route A, Procedure A1 and A2, Procedure A3b using 3-aminobenzeneboronic acid, general modification F1a, procedure A4b using 2-methoxy-4-pyridinylboronic acid | $^1$H NMR (400 MHz, Me-d$_3$-OD): 8.69 (1H, d), 8.27 (1H, d), 8.01 (1H, s), 7.86 (1H, t), 7.79 (1H, s), 7.48 (1H, t), 7.44-7.34 (3H, m), 7.29 (1H, d), 7.22 (1H, s), 4.00 (3H, s), 3.27 (2H, q), 1.19 (3H, t). | |
| 46 | | 1-Ethyl-3-{3-[7-(2-oxo-1,2-dihydro-pyridin-4-yl)-imidazo[1,2-a]pyridin-3-yl]-phenyl}-urea | General Route A, Procedure A1 and A2, Procedure A3b using 3-aminobenzeneboronic acid, general modification F1a, procedure A4b using 2-methoxy-4-pyridinylboronic acid, general modification D4b | $^1$H NMR (400 MHz, Me-d$_3$-OD): 8.93 (1H, d), 8.28 (2H, d), 8.05 (1H, t), 7.83 (1H, dd), 7.70 (1H, d), 7.57 (1H, t), 7.41 (1H, dd), 7.36 (1H, d), 7.04 (1H, d), 6.91 (1H, dd), 3.28 (2H, q), 1.19 (3H, t). | MS: [M + H]$^+$ 374 |
| 47 | | 1-Ethyl-3-{3-[7-(4-methyl-piperazin-1-yl)-imidazo[1,2-a]pyridin-3-yl]-phenyl}-urea formate salt | General Route A, Procedure A1 and A2, Procedure A3b using 3-aminobenzeneboronic acid, general modification F1a, procedure A4c using 1-methylpiperazine | $^1$H NMR (400 MHz, Me-d$_3$-OD): 8.44 (2H, d), 7.87 (1H, t), 7.67 (1H, s), 7.46 (1H, t), 7.34 (1H, dd), 7.23 (1H, d), 7.15 (1H, dd), 6.90 (1H, d), 3.58 (4H, t), 3.26 (2H, q), 2.83 (4H, t), 2.52 (3H, s), 1.18 (3H, t). | MS: [M + H]$^+$ 379 |

-continued

| Eg. No. | Compound | Chemical Name | Procedure | N.M.R. Data | M.S. |
|---|---|---|---|---|---|
| 48 | | 1-[3-(7-Chloro-imidazo[1,2-a]pyridin-3-yl)-phenyl]-3-methyl-urea | General Route A; Procedure A3a using 1-Methyl-3-[3-(4,4,5,5-tetramethyl-[1,3,2]dioxaborolan-2-yl)-phenyl]-urea (I7) and $K_3PO_4$ in place of $Na_2CO_3$ | $^1$H NMR (400 MHz, DMSO-$d_6$): 8.70 (1H, s), 8.55 (1H, d), 7.83 (1H, d), 7.81-7.70 (2H, m), 7.42 (2H, d), 7.17 (1H, dt), 7.05 (1H, dd), 6.10 (1H, q), 2.66 (3H, d). | MS: [M + H]$^+$ 301 |
| 49 | | 1-Ethyl-3-{3-[7-(6-morpholin-4-yl-pyridin-3-yl)-imidazo[1,2-a]pyridin-3-yl]-phenyl}-urea formate salt | General Route A, Procedure A1 and A2, Procedure A3b using 3-aminobenzeneboronic acid, general modification F1a, procedure A4b using 4-[5-(4,4,5,5-tetramethyl-[1,3,2]dioxaborolan-2-yl)-pyridin-2-yl]-morpholine | $^1$H NMR (400 MHz, DMSO-$d_6$): 8.71-8.63 (2H, m), 8.57 (1H, d), 8.18 (1H, s), 8.09 (1H, dd), 7.95 (1H, s), 7.80 (1H, s), 7.77-7.70 (1H, m), 7.45-7.33 (3H, m), 7.24-7.15 (1H, m), 6.97 (1H, d), 6.24 (1H, t), 3.73 (4H, t), 3.55 (4H, t), 3.18-3.08 (2H, m), 1.07 (3H, t). | MS: [M + H]$^+$ 379 |
| 50 | | 1-{3-[7-(4-Fluoro-phenyl)-imidazo[1,2-a]pyridin-3-yl]-phenyl}-3-methyl-urea formate salt | General Route A; Procedure A1 and A2, Procedure A3b using 3-aminobenzeneboronic acid, Procedure A3a using 1-Methyl-3-[3-(4,4,5,5-tetramethyl-[1,3,2]dioxaborolan-2-yl)-phenyl]-urea (I7) and $K_3PO_4$ as base Procedure A4a using 4-fluorobenzeneboronic acid and $K_3PO_4$ as base. | $^1$H NMR (400 MHz, DMSO-$d_6$): 8.74 (1H, s), 8.62 (1H, d), 8.17 (1H, s), 7.99 (1H, s), 7.96-7.87 (2H, m), 7.85-7.74 (2H, m), 7.46-7.29 (5H, m), 7.25-7.16 (1H, m), 6.13 (1H, q), 2.67 (3H, d). | MS: [M + H]$^+$ 361 |
| 51 | | 1-{3-[7-(6-Amino-pyridin-3-yl)-imidazo[1,2-a]pyridin-3-yl]-phenyl}-3-ethyl-urea hydrochloride salt | General Route A, Procedure A1 and A2, Procedure A3b using 3-aminobenzeneboronic acid, general modification F1a, procedure A4b using 2-amino-5-(4,4,5,5-tetramethyl-1,3,2-dioxaborolan-2-yl)pyridine. Procedure J1. | $^1$H NMR (400 MHz, Me-$d_3$-OD): 8.91 (1H, d), 8.57-8.47 (2H, m), 8.29 (1H, s), 8.24 (1H, s), 8.06 (1H, t), 7.84 (1H, dd), 7.56 (1H, t), 7.44-7.38 (1H, m), 7.35 (1H, d), 7.26 (1H, d), 3.28 (2H, q), 1.19 (3H, t). | MS: [M + H]$^+$ 373 |

-continued

| Eg. No. | Compound | Chemical Name | Procedure | N.M.R. Data | M.S. |
|---|---|---|---|---|---|
| 52 | | 1-(4-{3-[3-(3-Ethyl-ureido)-phenyl]-imidazo[1,2-a]pyridin-7-yl}-benzyl)-3-methyl-piperidine-3-carboxylic acid ethyl ester | General Route A, Procedure A1 and A2, Procedure A3b using 3-aminobenzeneboronic acid, general modification F1a, procedure A4b using 3-Methyl-1-[4-(4,4,5,5-tetramethyl-[1,3,2]dioxaborolan-2-yl)-benzyl]-piperidine-3-carboxylic acid ethyl ester (I13). | $^1$H NMR (400 MHz, Me-d$_3$-OD): 8.65 (1H, d), 7.89-7.81 (2H, m), 7.80-7.69 (3H, m), 7.48 (3H, t), 7.42-7.33 (2H, m), 7.29 (1H, d), 4.21-4.09 (2H, m), 3.63 (1H, d), 3.47 (1H, d), 3.27 (2H, q), 3.09 (1H, d), 2.78-2.70 (1H, m), 2.21-2.06 (2H, m), 1.94 (1H, d), 1.83-1.74 (1H, m), 1.67-1.60 (1H, m), 1.25-1.17 (6H, m), 1.13 (3H, s). | MS: [M + H]$^+$ 540 |
| 53 | | 1-Ethyl-3-{3-[7-(2-hydroxymethyl-morpholin-4-yl)-imidazo[1,2-a]pyridin-3-yl]-phenyl}-urea hydrochloride salt | General Route A, Procedure A1 and A2, Procedure A3b using 3-aminobenzeneboronic acid, general modification F1a, procedure A4c using 2-hydroxymethylmorpholine, Procedure J1. | $^1$H NMR (400 MHz, Me-d$_3$-OD): 8.40 (1H, d), 7.77 (1H, d), 7.51 (1H, s), 7.48-7.16 (3H, m), 6.97 (1H, dd), 6.80 (1H, d), 4.08 (1H, dd), 3.86-3.60 (6H, m), 3.26 (2H, q), 3.02-2.89 (1H, m), 2.79-2.66 (1H, m), 1.18 (3H, t). | MS: [M + H]$^+$ 396 |
| 54 | | 1-{3-[7-(4-Acetyl-piperazin-1-yl)-imidazo[1,2-a]pyridin-3-yl]-phenyl}-3-ethyl-urea hydrochloride salt | General Route A, Procedure A1 and A2, Procedure A3b using 3-aminobenzeneboronic acid, general modification F1a, procedure A4c using 1-acetylpiperazine, Procedure J1. | $^1$H NMR (400 MHz, Me-d$_3$-OD): 8.38 (1H, d), 7.76 (1H, t), 7.48 (1H, s), 7.41 (1H, t), 7.34-7.25 (1H, m), 7.19 (1H, d), 6.91 (1H, d), 6.78 (1H, s), 3.84-3.68 (4H, m), 3.46-3.36 (2H, m), 3.36-3.34 (2H, m), 3.26 (2H, q), 2.18 (3H, s), 1.18 (3H, t). | MS: [M + H]$^+$ 407 |

| Eg. No. | Compound | Chemical Name | Procedure | N.M.R. Data | M.S. |
|---|---|---|---|---|---|
| 55 | | 1-Ethyl-3-{3-[7-(6-piperazin-1-yl-pyridin-3-yl)-imidazo[1,2-a]pyridin-3-yl]-phenyl}-urea formate salt | General Route A, Procedure A1 and A2, Procedure A3b using 3-aminobenzeneboronic acid, general modification F1a, procedure A4b using 4-(5-(4,4,5,5-tetramethyl-1,3,2-dioxaborolan-2-yl)pyridin-2-yl)-1-boc-piperazine, general modification D3a | $^1$H NMR (400 MHz, Me-d$_3$-OD): 8.69-8.61 (2H, m), 8.46-8.39 (1H, m), 8.09 (1H, dd), 7.88 (1H, t), 7.82 (1H, s), 7.73 (1H, s), 7.47 (1H, t), 7.38-7.26 (3H, m), 7.08 (1H, d), 3.91 (3H, t), 3.27 (2H, q), 1.19 (3H, t). | MS: [M + H]$^+$ 442 |
| 56 | | 1-Ethyl-3-(3-{7-[4-(2-morpholin-4-yl-ethyl)-phenyl]-imidazo[1,2-a]pyridin-3-yl}-phenyl)-urea hydrochloride salt | General Route A, Procedure A1 and A2, Procedure A3b using 3-aminobenzeneboronic acid, general modification F1a, procedure A4b using 4-[2-[4-(4,4,5,5-tetramethyl-[1,3,2]dioxaborolan-2-yl)-phenyl]-ethyl]-morpholine. Procedure J1. | $^1$H NMR (400 MHz, Me-d$_3$-OD): 8.53 (1H, d), 7.72 (2H, s), 7.66-7.56 (3H, m), 7.35 (1H, t), 7.29 (2H, d), 7.24 (2H, dd), 7.17 (1H, d), 3.63 (4H, t), 3.15 (3H, q), 2.84-2.76 (2H, m), 2.61-2.53 (2H, m), 2.48 (4H, t), 1.07 (3H, t). | MS: [M + H]$^+$ 470 |
| 57 | | 1-Ethyl-3-{3-[7-(4-piperazin-1-yl-phenyl)-imidazo[1,2-a]pyridin-3-yl]-phenyl}-urea hydrochloride salt | General Route A, Procedure A1 and A2, Procedure A3b using 3-aminobenzeneboronic acid, general modification F1a, procedure A4b using tert-butyl 4-[4-(4,4,5,5-tetramethyl-1,3,2-dioxaborolan-2-yl)phenyl]tetrahydro-1(2h)-pyrazinecarboxylate, general modification D3a | $^1$H NMR (400 MHz, Me-d$_3$-OD): 8.82 (1H, d), 8.12 (2H, d), 8.05 (1H, t), 7.91 (2H, d), 7.86 (1H, dd), 7.55 (1H, t), 7.42-7.30 (2H, m), 7.25 (2H, d), 3.62 (4H, t), 3.43 (4H, t), 3.28 (2H, q), 1.19 (3H, t). | MS: [M + H]$^+$ 441 |

-continued

| Eg. No. | Compound | Chemical Name | Procedure | N.M.R. Data | M.S. |
|---|---|---|---|---|---|
| 58 | | 1-Ethyl-3-{3-[7-(3,4,5,6-tetrahydro-2H-[1,2']bipyridinyl-5'-yl)-imidazo[1,2-a]pyridin-3-yl]-phenyl}-urea hydrochloride salt | General Route A, Procedure A1 and A2, Procedure A3b using 3-aminobenzeneboronic acid, general modification F1a, procedure A4b using 2-(piperidin-1-yl)pyridine-5-boronic acid pinacol ester. Procedure J1. | $^1$H NMR (400 MHz, Me-d$_3$-OD): 8.62 (1H, d), 8.52 (1H, d), 7.97 (1H, dd), 7.83 (1H, t), 7.77 (1H, s), 7.69 (1H, s), 7.46 (1H, t), 7.40-7.24 (3H, m), 6.94 (1H, d), 3.70-3.61 (4H, m), 3.27 (2H, q), 1.79-1.63 (6H, m), 1.19 (3H, t). | MS: [M + H]$^+$ 441 |
| 59 | | 1-{3-[7-(4-Fluoro-phenyl)-imidazo[1,2-a]pyridin-3-yl]-phenyl}-3-(2,2,2-trifluoro-ethyl)-urea | General Route A; Procedure A3a using 1-[3-(4,4,5,5-Tetramethyl-[1,3,2]dioxaborolan-2-yl)-phenyl]-3-(2,2,2-trifluoro-ethyl)-urea (I6) and K$_3$PO$_4$ as base Procedure A4a using 4-fluorobenzeneboronic acid and K$_3$PO$_4$ as base. | $^1$H NMR (400 MHz, DMSO-d$_6$): 8.97 (1H, s), 8.62 (1H, d), 7.99 (1H, brs), 7.96-7.87 (2H, m), 7.81-7.78 (2H, m), 7.47-7.44 (2H, m), 7.41-7.31 (3H, m), 7.31-7.23 (1H, m), 6.85 (1H, t), 4.01-3.89 (2H, m). | |

Example 59A

1-{3-[7-(4-Fluoro-phenyl)-imidazo[1,2-a]pyridin-3-yl]-phenyl}-3-(2,2,2-trifluoro-ethyl)-urea hydrochloride

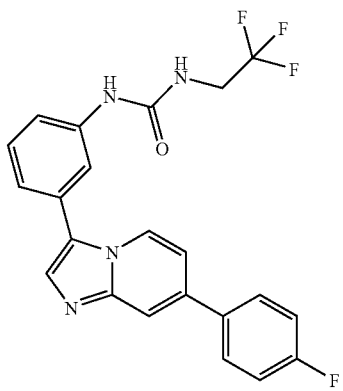 [SMILES: O=C(NCC(F)(F)F)Nc1cccc(-c2cnc3cc(-c4ccc(F)cc4)ccn23)c1]

Step (a): 1-(3-Bromo-phenyl)-3-(2,2,2-trifluoro-ethyl)-urea

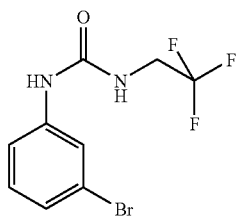 [SMILES: O=C(NCC(F)(F)F)Nc1cccc(Br)c1]

3-Bromophenyl isocyanate (21.12 g, 107 mmol) was added slowly to a stirred solution of 2,2,2-trifluoroethyl amine (40 ml, 0.5 mol) in THF (100 mL) at 0° C. under N$_2$, rinsing with THF (25 mL). The reaction was allowed to warm slowly to RT and kept at this temperature for 16 hours. The volatiles were removed under reduced pressure to give the title compound (31.6 g) as a solid. $^1$H NMR (400 MHz, DMSO-d$_6$) δ 8.94 (1H, s), 7.80 (1H, t), 7.31-7.24 (1H, m), 7.20 (1H, t), 7.16-7.08 (1H, m), 6.83 (1H, bt), 3.98-3.85 (2H, m).

Step (b): 1-[3-(4,4,5,5-Tetramethyl-[1,3,2]dioxaborolan-2-yl)-phenyl]-3-(2,2,2-trifluoro-ethyl)-urea

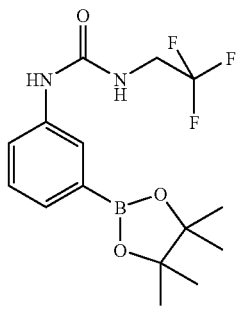 [SMILES: CC1(C)OB(c2cccc(NC(=O)NCC(F)(F)F)c2)OC1(C)C]

A mixture of 1-(3-bromo-phenyl)-3-(2,2,2-trifluoroethyl)-urea (31.6 g, 106 mmol), bis(pinacolato)diboron (54 g, 212 mmol) and KOAc (31.3 g, 319 mmol) in dry DMSO (110 mL) was deoxygenated by evacuation/refill with $N_2$ (×3). $PdCl_2ddpf$ (7.78 g, 10.6 mmol) was added and the mixture was deoxygenated again (×3) then stirred and heated at 100° C. under $N_2$ for 100 mins. The reaction was allowed to cool to RT, diluted with water (320 mL) and extracted with EtOAc (2×320 mL). The combined organic extracts were washed with water (320 mL), brine (320 mL) then dried ($MgSO_4$), filtered and evaporated. The residue was triturated petrol to give the title compound (37.4 g) as a solid. $^1$H NMR (400 MHz, $CDCl_3$) δ 7.63 (1H, s), 7.58 (1H, d), 7.46 (1H, d), 7.34 (1H, t), 6.65 (1H, brs), 5.21 (1H, brs), 3.99-3.86 (2H, m), 1.33 (12H, s).

Step (c): 7-Chloro-imidazo[1,2-a]pyridine

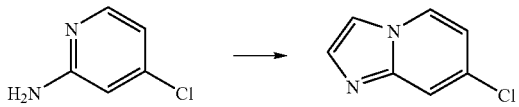

To a solution of 4-chloro-pyridin-2-ylamine (25.0 g, 0.194 mol) in EtOH (250 mL) was added $NaHCO_3$ (32.7 g, 0.389 mol) followed by a 50% solution of chloroacetaldehyde in water (37 mL, 0.292 mol). The mixture was refluxed for 6 h. The solvents were removed under reduced pressure and the crude mixture was diluted with water (250 mL) and extracted with EtOAc (2×125 mL). The combined organic layers were washed with brine (50 mL), dried ($MgSO_4$) and concentrated under reduced pressure to give 7-chloro-imidazo[1,2-a]pyridine (32.7 g). $^1$H NMR (400 MHz, $CDCl_3$) δ 8.06 (1H, d), 7.64 (2H, d), 7.56 (1H, s), 6.79 (1H, dd).

Step (d): 7-(4-fluoro-phenyl)-imidazo[1,2-a]pyridine

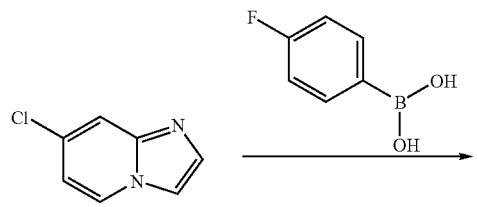

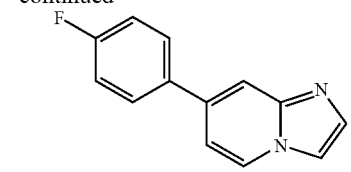

A mixture of 7-chloro-imidazo[1,2-a]pyridine (15.0 g, 98.6 mmol), 4-fluorophenylboronic acid (16.55 g, 118.3 mmol), potassium carbonate (81.5 g, 590 mmol) in toluene-methanol-ethanol-water (1:1:1:1, 800 mL) was degassed with $N_2$ and then bis(tri-tert-butylphosphine)palladium(0) (400 mg) added. The mixture was degassed and then heated to 80° C. for 18 h. The mixture was cooled to ambient, transferred to a separating funnel and the layers separated. The organic portion was reduced under reduced pressure and the residue extracted with dichloromethane. The dichloromethane extracts were washed with water, dried ($MgSO_4$), filtered and concentrated under reduced pressure to afford 17.3 g (83%) of the title compound. $^1$H NMR (400 MHz, $CDCl_3$) δ 8.22 (1H, d), 7.87 (1H, s), 7.71 (1H, s), 7.69-7.58 (3H, m), 7.20 (2H, t), 7.11 (1H, d).

Step (e): 7-(4-fluoro-phenyl)-3-iodo-imidazo[1,2-a]pyridine

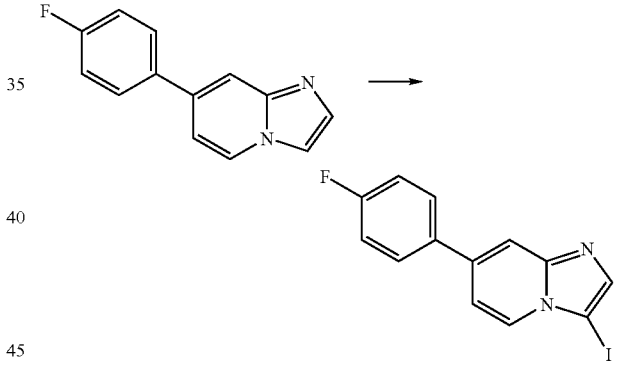

To a solution of 7-(4-fluoro-phenyl)-imidazo[1,2-a]pyridine (13.0 g, 61.3 mmol) in N,N-dimethylformamide (100 mL) stirring under a nitrogen atmosphere at ambient was added N-iodosuccinimide (14.5 g, 64.4 mmol). The reaction mixture was stirred for 2 h and then poured into water (1 L) and stirred for a further 30 min. The solid obtained was collected by filtration, washed with water and air dried on the filter. The solid was triturated with ether, collected by filtration and dried under vacuum at 50° C. The solid obtained was partitioned between water and EtOAc. The organic layer was washed with brine, dried ($MgSO_4$), filtered and concentrated under reduced pressure. The solid thus obtained was partitioned between aqueous sodium thiosulphate solution and EtOAc. The organic layer was washed with brine, dried ($MgSO_4$) and concentrated under reduced pressure. The product was triturated with EtOAc, collected by filtration and air-dried to afford 6.0 g (29%) of the title compound. $^1$H NMR (400 MHz, $CDCl_3$) δ 8.23 (1H, d), 7.91 (1H, s), 7.78 (1H, s), 7.67 (2H, dd), 7.28 (1H, d), 7.22 (2H, t). A further crop of product (11.0 g) containing minor impurities was obtained by evaporating the filtrates under reduced pressure, triturating with petrol/EtOAc and collection by filtration.

Step (f): 1-{3-[7-(4-Fluoro-phenyl)-imidazo[1,2-a]pyridin-3-yl]-phenyl}-3-(2,2,2-trifluoro-ethyl)-urea

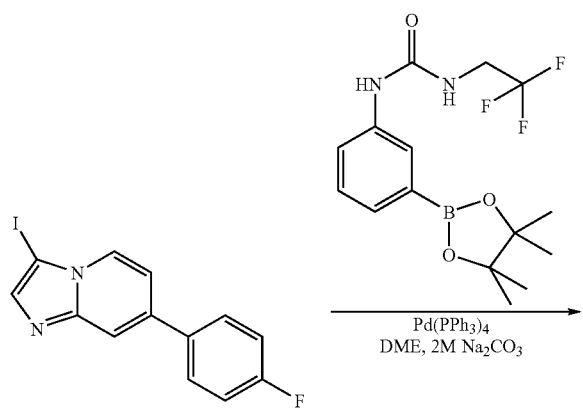

A mixture of 7-(4-fluoro-phenyl)-3-iodo-imidazo[1,2-a]pyridine (10.1 g, 29.8 mmol), 1-(3-bromo-phenyl)-3-(2,2,2-trifluoro-ethyl)-urea (12.3 g, 35.8 mmol) and 2M sodium carbonate (120 mL) in dimethoxyethane (595 mL) was deoxygenated by evacuation/refill with $N_2$ (×3). Tetrakis(triphenylphosphine)palladium (1.72 g, 1.49 mmol) was added, the resulting mixture was deoxygenated again (×3) and then heated at 80° C. under $N_2$ overnight. The reaction was allowed to cool to RT, and solvents were removed under reduced pressure. The crude mixture was diluted with water (100 mL), EtOAc (100 mL) and DCM (100 mL) with stirring. The resulting slurry was filtered, the solid was washed with EtOAc and dried under vacuum to give the title compound (9.8 g). $^1$H NMR (400 MHz, DMSO-$d_6$) δ 8.98 (1H, s), 8.61 (1H, d), 7.99 (1H, s), 7.96-7.87 (2H, m), 7.79 (2H, s), 7.45 (2H, d), 7.41-7.30 (3H, m), 7.30-7.23 (1H, m), 6.87 (1H, bt), 4.00-3.89 (2H, m). MS: [M+H]$^+$ 429

Step (g): 1-{3-[7-(4-Fluoro-phenyl)-imidazo[1,2-a]pyridin-3-yl]-phenyl}-3-(2,2,2-trifluoro-ethyl)-urea hydrochloride salt To a mixture of 1-{3-[7-(4-fluoro-phenyl)-imidazo[1,2-a]pyridin-3-yl]-phenyl}-3-(2,2,2-trifluoro-ethyl)-urea (9.8 g) and methanol (100 mL) was added 4M hydrogen chloride/dioxane (10 mL). The solution was stirred at RT for 90 mins before concentrating under reduced pressure to give the title compound (11.1 g). $^1$H NMR (400 MHz, DMSO-$d_6$) δ 9.47 (1H, s), 8.81 (1H, d), 8.41 (1H, s), 8.24 (1H, s), 8.03 (3H, dd), 7.95-7.82 (2H, m), 7.60-7.51 (2H, m), 7.50-7.39 (3H, m), 7.37-7.28 (1H, m), 7.14 (1H, t), 4.03-3.42 (7H, m), 3.17 (3H, s).

Examples 60 to 110

By following the methods described above, the compounds of Examples 60 to 110 set out in the Table below were prepared.

| Eg. No. | Compound | Chemical Name | Procedure | N.M.R. Data | M.S. |
|---|---|---|---|---|---|
| 60 | 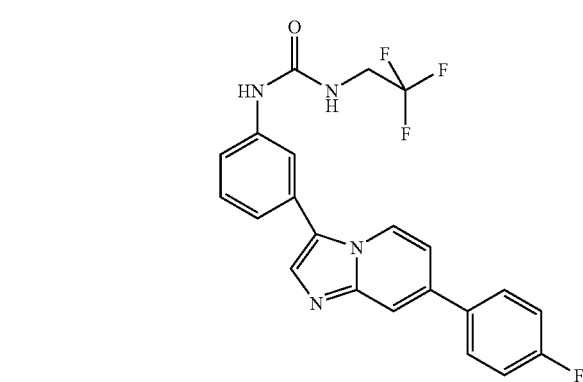 | 1-Ethyl-3-(3-{7-[3-(2-morpholin-4-yl-ethyl)-phenyl]-imidazo[1,2-a]pyridin-3-yl}-phenyl)-urea hydro-chloride salt | General Route A, Procedure A1 and A2, Procedure A3b using 3-amino-benzeneboronic acid, general modification F1a, procedure A4b using 4-[2-[3-(4,4,5,5-tetramethyl-[1,3,2]dioxaborolan-2-yl)-phenyl]-ethyl]-morpholine. Procedure J1. | $^1$H NMR (400 MHz, Dioxane): 9.13 (1H, d), 8.50 (1H, s), 8.44 (1H, s), 8.29 (1H, s), 8.22-8.05 (3H, m), 7.91-7.74 (3H, m), 7.68-7.56 (2H, m), 4.36 (2H, d), 4.10 (2H, t), 3.87 (2H, d), 3.81-3.74 (2H, m), 3.54-3.48 (6H, m), 1.42 (3H, t). | MS: [M + H]$^+$ 470 |

-continued

| Eg. No. | Compound | Chemical Name | Procedure | N.M.R. Data | M.S. |
|---|---|---|---|---|---|
| 61 | | N-{3-[7-(3-Cyanomethyl-phenyl)-imidazo[1,2-a]pyridin-3-yl]-phenyl}-acetamide | General Route A, procedure A3a using (3-acetylamino-phenyl)boronic acid, procedure A4b using (3-cyano-methylphenyl)boronic acid, pinacol ester | $^1$H NMR (400 MHz, Me-d$_3$-OD): 8.64 (1H, d), 7.99 (1H, s), 7.88 (1H, s), 7.82-7.72 (3H, m), 7.62-7.32 (6H, m), 4.03 (2H, s), 2.19 (3H, s). | MS: [M + H]$^+$ 367 |
| 62 | | N-(3-{7-[2-(4-Methyl-piperazin-1-yl)-pyridin-4-yl]-imidazo[1,2-a]pyridin-3-yl}-phenyl)-acetamide | General Route A, procedure A3a using (3-acetylamino-phenyl)boronic acid, procedure A4b using 1-methyl-4-[4-(4,4,5,5-tetramethyl-1,3,2-dioxaborolan-2-yl)pyridin-2-yl]piperazine | $^1$H NMR (400 MHz, Me-d$_3$-OD): 8.64-8.52 (2H, m), 8.05-7.93 (2H, m), 7.79 (1H, s), 7.70 (1H, s), 7.62-7.47 (2H, m), 7.40 (1H, d), 7.32 (1H, dd), 6.97 (1H, d), 3.69 (4H, t), 2.64 (4H, t), 2.41 (3H, s), 2.19 (3H, s). | MS: [M + H]$^+$ 427 |
| 63 | | 3-[7-(4-Fluoro-phenyl)-imidazo[1,2-a]pyridin-3-yl]-phenylamine | General Route B, procedure B1a using 4-fluorophenylboronic acid, procedure B2, procedure B3a using 3-aminobenzene-boronic acid | $^1$H NMR (400 MHz, EtOD): 6.39 (1H, d), 5.68-5.57 (3H, m), 5.46 (1H, s), 5.16-5.01 (4H, m), 4.80 (1H, t), 4.76 (1H, d), 4.68-4.59 (1H, m). | MS: [M + H]$^+$ 304 |
| 64 | | N-{3-[7-(4-Fluoro-phenyl)-imidazo[1,2-a]pyridin-3-yl]-phenyl}-propionamide | General Route B. procedure B1a using 4-fluorophenyl boronic acid. Procedure B2, procedure B3a using 3-aminobenzene boronic acid. General Route F3b using propionyl chloride | $^1$H NMR (400 MHz, Me-d$_3$-OD): 8.64 (1H, d), 8.01 (1H, t), 7.88-7.78 (3H, m), 7.74 (1H, s), 7.59 (1H, d), 7.53 (1H, t), 7.41 (1H, d), 7.35 (1H, dd), 7.31-7.22 (2H, m), 2.46 (2H, q), 1.25 (3H, t). | MS: [M + H]$^+$ 360 |

| Eg. No. | Compound | Chemical Name | Procedure | N.M.R. Data | M.S. |
|---|---|---|---|---|---|
| 65 | | N-(3-{7-[4-(2,3-Dihydroxy-propoxy)-phenyl]-imidazo[1,2-a]pyridin-3-yl}-phenyl)-acetamide | General Route A, procedure A3a using (3-acetylamino-phenyl)boronic acid, procedure using A4b using [4-[(2,2-dimethyl-1,3-dioxolan-4-yl)methoxy]phenyl]-boronic acid (I14), general modification D7 | $^1$H NMR (400 MHz, Me-d$_3$-OD): 8.53 (1H, d), 7.94 (1H, s), 7.79-7.62 (4H, m), 7.62-7.44 (2H, m), 7.36 (1H, d), 7.27 (1H, dd), 7.09 (2H, d), 4.14 (1H, dd), 4.09-3.97 (2H, m), 3.79-3.64 (2H, m), 2.18 (3H, s). | MS: [M + H]$^+$ 418 |
| 66 | | N-{3-[7-(4-Fluoro-phenyl)-imidazo[1,2-a]pyridin-3-yl]-phenyl}-butyramide | General Route B. procedure B1a using 4-fluorophenyl boronic acid. Procedure B2, procedure B3a using 3-aminobenzene boronic acid. As described in General Route F3b using butyryl chloride | $^1$H NMR (400 MHz, DMSO-d$_6$): 10.06 (1H, s), 8.62 (1H, d), 8.04-7.87 (4H, m), 7.80 (1H, s), 7.65 (1H, d), 7.49 (1H, t), 7.43-7.29 (4H, m), 2.33 (2H, t), 1.71-1.58 (2H, m), 0.94 (3H, t). | MS: [M + H]$^+$ 374 |
| 67 | | 2-Amino-N-{3-[7-(4-fluoro-phenyl)-imidazo[1,2-a]pyridin-3-yl]-phenyl}-acetamide formate salt | General Route B. Procedure B1a using 4-fluorophenylboronic acid. Procedure B2, Procedure B3a using 3-aminobenzene boronic acid. General Route F3a using t-butoxycarbonyl-glycine, isolated and treated with HCl dioxan (Procedure D3a) | $^1$H NMR (400 MHz, Me-d$_3$-OD): 8.60 (1H, d), 8.35 (1H, s), 8.00 (1H, s), 7.88-7.67 (4H, m), 7.67-7.51 (2H, m), 7.45 (1H, d), 7.40-7.20 (3H, m), 3.92 (2H, s). | MS: [M + H]$^+$ 361 |

| Eg. No. | Compound | Chemical Name | Procedure | N.M.R. Data | M.S. |
|---|---|---|---|---|---|
| 68 | | {3-[7-(4-Fluoro-phenyl)-imidazo[1,2-a]pyridin-3-yl]-phenyl}-morpholin-4-yl-methanone | General Route B. Procedure B1a using 4-fluorophenylboronic acid. Procedure B2. Procedure B3a using N-morpholinyl 3-boronobenzamide | $^1$H NMR (400 MHz, Me-d$_3$-OD): 8.64 (1H, d), 7.89-7.63 (7H, m), 7.63-7.50 (1H, m), 7.36 (1H, dd), 7.31-7.22 (2H, m), 3.76 (6H, br s), 3.57 (2H, br s). | MS: [M + H]$^+$ 402 |
| 69 | | 3-[7-(4-Fluoro-phenyl)-imidazo[1,2-a]pyridin-3-yl]-4-methyl-phenylamine | General Route B. Procedure B1a using 4-fluorophenylboronic acid. Procedure B2. Procedure B3a using 5-amino-2-methylphenylboronic acid, pinacol ester | $^1$H NMR (400 MHz, Me-d$_3$-OD): 8.30 (1H, s), 8.21 (1H, s), 8.04 (1H, d), 7.88 (1H, s), 7.82-7.76 (2H, m), 7.74 (1H, d), 7.70 (1H, s), 7.62 (1H, dd), 7.43 (1H, d), 7.34 (1H, dd), 7.26 (2H, d), 2.16 (3H, s). | MS: [M + H]$^+$ 318 |
| 70 | | 7-(4-Fluoro-phenyl)-3-(1H-indol-5-yl)-imidazo[1,2-a]pyridine formate salt | General Route B. Procedure B1a using 4-fluorophenylboronic acid. Procedure B2. Procedure B3a using 5-indolylboronic acid | $^1$H NMR (400 MHz, Me-d$_3$-OD): 8.65 (1H, d), 7.96 (1H, s), 7.88 (4H, d), 7.64 (1H, d), 7.50 (1H, d), 7.39 (2H, d), 7.30 (2H, t), 6.61 (1H, s). | MS: [M + H]$^+$ 328 |
| 71 | | 6-[7-(4-Fluoro-phenyl)-imidazo[1,2-a]pyridin-3-yl]-1H-indazole | General Route B. Procedure B1a using 4-fluorophenylboronic acid. Procedure B2. Procedure B3a using 6-Indazolylboronic acid | $^1$H NMR (400 MHz, Me-d$_3$-OD): 8.65 (1H, d), 8.17 (1H, s), 8.00 (1H, d), 7.88 (1H, s), 7.86-7.77 (4H, m), 7.50-7.34 (2H, m), 7.33-7.21 (2H, m). | MS: [M + H]$^+$ 329 |

-continued

| Eg. No. | Compound | Chemical Name | Procedure | N.M.R. Data | M.S. |
|---|---|---|---|---|---|
| 72 | | 7-(4-Fluorophenyl)-3-phenyl-imidazo[1,2-a]pyridine formate salt | General Route B. Procedure B1a using 4-fluorophenylboronic acid. Procedure B2. Procedure B3a using phenylboronic acid | $^1$H NMR (400 MHz, Me-d$_3$-OD): 8.59 (1H, d), 8.16 (1H, s), 7.88 (1H, s), 7.85-7.76 (2H, m), 7.68 (2H, d), 7.60 (2H, t), 7.52 (1H, t), 7.46-7.37 (1H, m), 7.27 (2H, t). | MS: [M + H]$^+$ 289 |
| 73 | | 3-[7-(4-Fluorophenyl)-imidazo[1,2-a]pyridin-3-yl]-benzoic acid methyl ester formate salt | General Route B. Procedure B1a using 4-fluorophenylboronic acid. Procedure B2. Procedure B3a using 3-methoxycarbonyl-phenylboronic acid | $^1$H NMR (400 MHz, Me-d$_3$-OD): 8.49 (1H, d), 8.20 (1H, s), 8.02 (1H, d), 7.84 (1H, s), 7.80-7.52 (5H, m), 7.26 (1H, d), 7.17 (2H, d), 3.89 (3H, s). | MS: [M + H]$^+$ 347 |
| 74 | | 4-{3-[7-(3-Morpholin-4-ylmethyl-phenyl)-imidazo[1,2-a]pyridin-3-yl]-phenyl}-2,4-dihydro-[1,2,4]triazole-3-thione | General route B, procedure B1a using 4-[3-(4,4,5,5-tetramethyl-1,3,2-dioxaborolan-2-yl)benzyl]morpholine, procedure B2, procedure B3a using (3-acetylaminophenyl)boronic acid, general modification F5 | $^1$H NMR (400 MHz, DMSO-d$_6$): 14.08-13.97 (1H, m), 8.88 (1H, d), 8.85 (1H, s), 8.12 (1H, s), 8.01 (1H, s), 7.95 (1H, s), 7.87-7.70 (5H, m), 7.48 (1H, t), 7.39 (2H, d), 3.66-3.53 (6H, m), 2.45-2.34 (4H, m). | MS: [M + H]$^+$ 469 |
| 75 | | N-{4-[7-(4-Fluorophenyl)-imidazo[1,2-a]pyridin-3-yl]-phenyl}-acetamide | General Route B. Procedure B1a using 4-fluorophenylboronic acid. Procedure B2. Procedure B3a using 4'-(4,4,5,5-tetramethyl-1,3,2-dioxaborolan-2-yl)acetanilide | $^1$H NMR (400 MHz, DMSO-d$_6$): 10.16-10.10 (1H, m), 8.59 (1H, d), 7.98 (1H, s), 7.95-7.86 (2H, m), 7.78 (3H, d), 7.63 (2H, d), 7.40-7.29 (3H, m), 2.10 (3H, s). | MS: [M + H]$^+$ 346 |

-continued

| Eg. No. | Compound | Chemical Name | Procedure | N.M.R. Data | M.S. |
|---|---|---|---|---|---|
| 76 | | 7-(4-Fluoro-phenyl)-3-(1H-indol-6-yl)-imidazo[1,2-a]pyridine formate salt | General Route B. Procedure B1a using 4-fluorophenylboronic acid. Procedure B2. Procedure B3a using indole-6-boronic acid | $^1$H NMR (400 MHz, Me-d$_3$-OD): 8.59 (1H, d), 8.30 (1H, s), 7.90-7.79 (3H, m), 7.77 (1H, d), 7.72 (1H, s), 7.66 (1H, s), 7.39 (1H, d), 7.33 (1H, d), 7.31-7.20 (3H, m), 6.57 (1H, d). | MS: [M + H]$^+$ 328 |
| 77 | | N-{3-[7-(4-Fluoro-phenyl)-imidazo[1,2-a]pyridin-3-yl]-phenyl}-succinimic acid formate salt | General Route B. Procedure B1a using 4-fluorophenylboronic acid. Procedure B2. Procedure B3a using 3-succinamido-phenylboronic acid, pinacol ester | $^1$H NMR (400 MHz, Me-d$_3$-OD): 8.65 (1H, d), 8.34 (1H, s), 8.01 (1H, s), 7.88-7.78 (3H, m), 7.75 (1H, s), 7.62-7.49 (2H, m), 7.38 (2H, dd), 7.27 (2H, t), 2.72 (4H, m). | MS: [M + H]$^+$ 404 |
| 78 | | N-{3-Methoxy-5-[7-(3-morpholin-4-ylmethyl-phenyl)-imidazo[1,2-a]pyridin-3-yl]-phenyl}-acetamide | General Route H; Procedure H1 using 3-methoxy-5-nitro-phenyl boronic acid pinacol ester (I8), H2 then general modification F3b using acetylchloride | $^1$H NMR (400 MHz, DMSO-d$_6$): 10.11 (1H, s), 8.64 (1H, d), 7.97 (1H, s), 7.82 (1H, s), 7.78-7.73 (2H, m), 7.51-7.45 (2H, m), 7.40-7.36 (2H, m), 7.33 (1H, t), 6.93 (1H, dd), 3.83 (3H, s), 3.63-3.55 (6H, m), 2.41 (4H, s), 2.08 (3H, s). | MS: [M + H]$^+$ 457 |
| 79 | | 1-Ethyl-3-(3-{7-[3-(4-methyl-piperazine-1-carbonyl)-phenyl]-imidazo[1,2-a]pyridin-3-yl}-phenyl)-urea | General Route A, Procedure A1 and A2, Procedure A3b using 3-aminobenzene-boronic acid, general modification F1a, procedure A4b using 3-(4-methyl-piperazine-1-carbonyl) phenylboronic acid pinacol ester | $^1$H NMR (400 MHz, Me-d$_3$-OD): 8.69 (1H, d), 7.99-7.90 (2H, m), 7.90-7.82 (2H, m), 7.76 (1H, s), 7.65 (1H, t), 7.55-7.25 (5H, m), 4.01-3.52 (2H, m), 3.35-3.30 (2H, m), 3.28 (2H, q), 2.64 (4H, s), 2.44 (3H, s), 1.19 (3H, t). | MS: [M + H]$^+$ 483 |

-continued

| Eg. No. | Compound | Chemical Name | Procedure | N.M.R. Data | M.S. |
|---|---|---|---|---|---|
| 80 | | 1-{3-[7-(6-Dimethylamino-pyridin-3-yl)-imidazo[1,2-a]pyridin-3-yl]-phenyl}-3-ethyl-urea formate salt | General Route A, Procedure A1 and A2, Procedure A3b using 3-aminobenzene-boronic acid, general modification F1a, procedure A4b using Dimethyl-[5-(4,4,5,5-tetramethyl-[1,3,2]dioxaborolan-2-yl)-pyridin-2-yl]-amine | $^1$H NMR (400 MHz, Me-d$_3$-OD): 8.64 (1H, d), 8.53 (1H, d), 8.20 (2H, s), 7.99 (1H, dd), 7.91-7.75 (3H, m), 7.52-7.39 (2H, m), 7.36 (1H, d), 7.27 (1H, d), 6.82 (1H, d), 3.27 (2H, q), 3.18 (6H, s), 1.19 (3H, t). | MS: [M + H]$^+$ 400 |
| 81 | | 1-Ethyl-3-(3-{7-[4-(4-methyl-piperazine-1-carbonyl)-phenyl]-imidazo[1,2-a]pyridin-3-yl}-phenyl)-urea | General Route A, Procedure A1 and A2, Procedure A3b using 3-aminobenzene-boronic acid, general modification F1a, procedure A4b using (4-methyl-piperazine-1-yl)-[4-(4,4,5,5-tetramethyl-[1,3,2]-dioxaborolan-2-yl)-phenyl]-methanone | $^1$H NMR (400 MHz, Me-d$_3$-OD): 8.69 (1H, d), 7.92 (3H, d), 7.86 (1H, t), 7.76 (1H, s), 7.60 (2H, d), 7.53-7.25 (4H, m), 4.01-3.51 (4H, m), 3.28 (2H, q), 2.59 (4H, s), 2.42 (3H, s), 1.19 (3H, t). | MS: [M + H]$^+$ 483 |
| 82 | | 1-{3-[7-(4-Azetidin-1-ylmethyl-phenyl)-imidazo[1,2-a]pyridin-3-yl]-phenyl}-3-ethyl-urea | General Route A, Procedure A1 and A2, Procedure A3b using 3-aminobenzene-boronic acid, general modification F1a, procedure A4b using 1-[4-(4,4,5,5-Tetramethyl-[1,3,2]-dioxaborolan-2-yl)-benzyl]-azetidine (I10) | $^1$H NMR (400 MHz, Me-d$_3$-OD): 8.63 (1H, d), 7.89-7.81 (2H, m), 7.76 (2H, d), 7.72 (1H, s), 7.51-7.40 (3H, m), 7.40-7.23 (3H, m), 3.72 (2H, s), 3.38 (4H, t), 3.27 (2H, q), 2.24-2.11 (2H, m), 1.19 (3H, t). | MS: [M + H]$^+$ 426 |
| 83 | | 1-Ethyl-3-(3-{7-[3-(2-methoxy-ethoxy)-phenyl]-imidazo[1,2-a]pyridin-3-yl}-phenyl)-urea | General Route A, Procedure A1 and A2, Procedure A3b using 3-aminobenzene-boronic acid, general modification F1a, General modification E (E2 & E3). | $^1$H NMR (400 MHz, Me-d$_3$-OD): 8.65 (1H, d), 7.89-7.80 (2H, m), 7.73 (1H, s), 7.52-7.41 (2H, m), 7.41-7.32 (4H, m), 7.29 (1H, d), 7.04 (1H, dd), 4.29-4.20 (2H, m), 3.86-3.77 (2H, m), 3.47 (3H, s), 3.30-3.21 (2H, m), 1.19 (3H, t). | MS: [M + H]$^+$ 431 |

| Eg. No. | Compound | Chemical Name | Procedure | N.M.R. Data | M.S. |
|---|---|---|---|---|---|
| 84 | 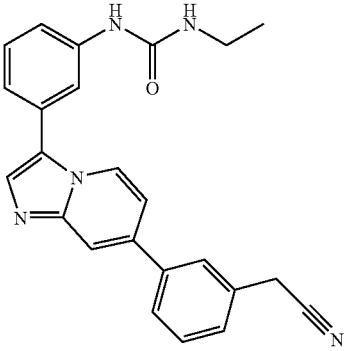 [SMILES: CCNC(=O)Nc1cccc(-c2cnc3cc(-c4cccc(CC#N)c4)ccn23)c1] | 1-{3-[7-(3-Cyanomethyl-phenyl)-imidazo[1,2-a]pyridin-3-yl]-phenyl}-3-ethyl-urea | General Route A, Procedure A1 and A2, Procedure A3b using 3-aminobenzene-boronic acid, general modification F1a, procedure A4b using (3-cyanomethyl-phenyl)boronic acid, | $^{1}$H NMR (400 MHz, Me-d$_{3}$-OD): 8.67 (1H, d), 7.89 (1H, s), 7.85 (1H, t), 7.82-7.76 (2H, m), 7.74 (1H, s), 7.57 (1H, t), 7.52-7.42 (2H, m), 7.42-7.33 (2H, m), 7.29 (1H, d), 4.04 (2H, s), 3.27 (2H, q), 1.19 (3H, t). | MS: [M + H]$^{+}$ 396 |
| 85 | 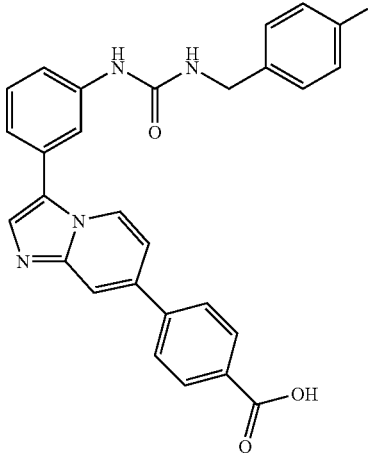 | 4-(3-{3-[3-(4-Fluoro-benzyl)-ureido]-phenyl}-imidazo[1,2-a]pyridin-7-yl)-benzoic acid | General Route A, Procedure A1 and A2, procedure A3a using 3-aminobenzene-boronic acid, general modification F1a using 4-fluorobenzyl isocyanate procedure A4b using 4-carboxyphenylboronic acid | $^{1}$H NMR (400 MHz, Me-d$_{3}$-OD): 8.67 (1H, d), 8.14 (2H, d), 7.94 (1H, s), 7.91-7.80 (3H, m), 7.76 (1H, s), 7.48 (1H, t), 7.45-7.35 (4H, m), 7.32 (1H, d), 7.13-7.03 (2H, m), 4.42 (2H, s). | MS: [M + H]$^{+}$ 481 |
| 86 | 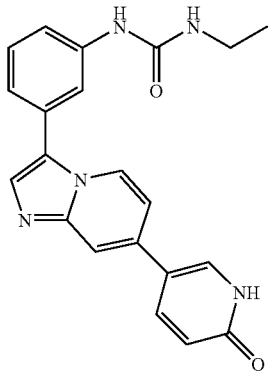 [SMILES: CCNC(=O)Nc1cccc(-c2cnc3cc(-c4ccc(=O)[nH]c4)ccn23)c1] | 1-Ethyl-3-{3-[7-(6-oxo-1,6-dihydro-pyridin-3-yl)-imidazo[1,2-a]pyridin-3-yl]-phenyl}-urea | General Route A, Procedure A1 and A2, Procedure A3b using 3-aminobenzene-boronic acid, general modification F1a, procedure A4b using 2-methoxy-5-pyridine-boronic acid, procedure modification D4b | $^{1}$H NMR (400 MHz, Me-d$_{3}$-OD): 8.64 (1H, d), 8.12 (1H, dd), 7.95 (1H, d), 7.85 (1H, t), 7.80 (1H, s), 7.73 (1H, s), 7.47 (1H, t), 7.39-7.32 (1H, m), 7.28 (2H, d), 6.71 (1H, d), 3.28 (2H, q), 1.19 (3H, t). | MS: [M + H]$^{+}$ 374 |

-continued

| Eg. No. | Compound | Chemical Name | Procedure | N.M.R. Data | M.S. |
|---|---|---|---|---|---|
| 87 | 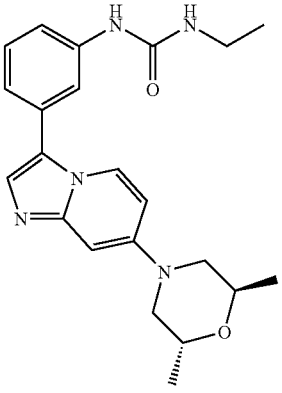 [SMILES: CCNC(=O)Nc1cccc(-c2cnc3cc(N4C[C@@H](C)O[C@H](C)C4)ccn23)c1] | 1-{3-[7-((2R,6R)-2,6-Dimethyl-morpholin-4-yl)-imidazo[1,2-a]pyridin-3-yl]-phenyl}-3-ethyl-urea formate salt | General Route A, Procedure A1 and A2, Procedure A3b using 3-aminobenzene-boronic acid, general modification F1a, procedure A4c using (2R, 6R) 2,6-dimethylmorpholine | $^1$H NMR (400 MHz, Me-d$_3$-OD): 8.52 (1H, s), 8.41 (1H, d), 7.82 (1H, t), 7.56 (1H, s), 7.44 (1H, t), 7.31 (1H, d), 7.22 (1H, d), 7.01 (1H, dd), 6.78 (1H, d), 4.26-4.16 (2H, m), 3.49 (2H, dd), 3.27 (2H, q), 3.17 (2H, dd), 1.32 (6H, d), 1.18 (3H, t). | MS: [M + H]$^+$ 394 |
| 88 | 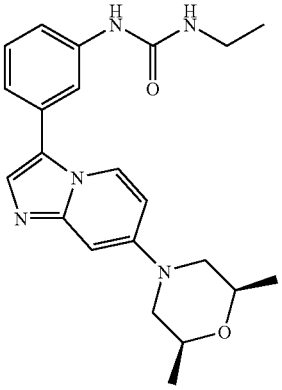 [SMILES: CCNC(=O)Nc1cccc(-c2cnc3cc(N4C[C@@H](C)O[C@@H](C)C4)ccn23)c1] | 1-{3-[7-((2R,6S)-2,6-Dimethyl-morpholin-4-yl)-imidazo[1,2-a]pyridine-3-yl]-phenyl}-3-ethyl-urea formate salt | General Route A, Procedure A1 and A2, Procedure A3b using 3-aminobenzene-boronic acid, general modification F1a, procedure A4c using (2R, 6S) 2,6-dimethylmorpholine | $^1$H NMR (400 MHz, Me-d$_3$-OD): 8.40 (1H, d), 7.81 (1H, t), 7.56 (1H, s), 7.44 (1H, t), 7.31 (1H, d), 7.22 (1H, d), 7.04 (1H, dd), 6.80 (1H, d), 3.87-3.72 (4H, m), 3.26 (2H, q), 2.55 (2H, t), 1.29 (6H, d), 1.19 (3H, t). | MS: [M + H]$^+$ 394 |
| 89 | 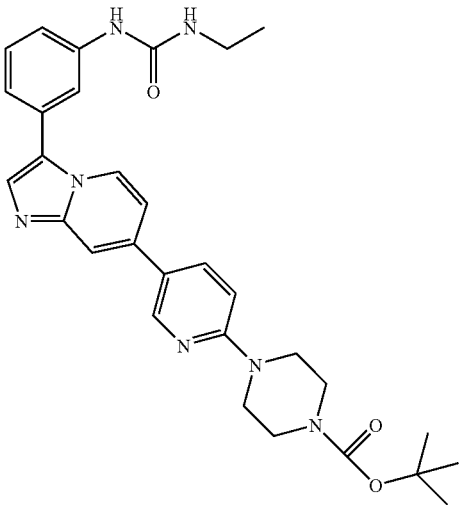 [SMILES: CCNC(=O)Nc1cccc(-c2cnc3cc(-c4ccc(N5CCN(C(=O)OC(C)(C)C)CC5)nc4)ccn23)c1] | 4-(5-{3-[3-(3-Ethyl-ureido)-phenyl]-imidazo[1,2-a]pyridin-7-yl}-pyridin-2-yl)-piperazine-1-carboxylic acid tert-butyl ester hydro-chloride salt | General Route A, Procedure A1 and A2, Procedure A3b using 3-aminobenzene-boronic acid, general modification F1a, procedure A4b using 4-(5-(4,4,5,5-tetramethyl-[1,3,2]-dioxaborolan-2-yl)pyridin-2-yl)-piperazine-1-carboxylic acid tert butyl ester. Procedure J1., | 1H NMR (400 MHz, Me-d3-OD): 8.88 (1H, d), 8.63 (1H, d), 8.41 (1H, dd), 8.22 (2H, d), 8.10-8.04 (1H, m), 7.87 (1H, dd), 7.56 (1H, t), 7.42-7.33 (3H, m), 3.88-3.79 (4H, m), 3.73-3.65 (4H, m), 3.28 (2H, q), 1.52 (9H, s), 1.19 (3H, t). | MS: [M + H]$^+$ 542 |

| Eg. No. | Compound | Chemical Name | Procedure | N.M.R. Data | M.S. |
|---|---|---|---|---|---|
| 90 | | 1-Methyl-3-(3-{7-[3-(morpholine-4-carbonyl)-phenyl]-imidazo[1,2-a]pyridin-3-yl}-phenyl)-urea formate salt | General Route A; Procedure A3a using 1-Methyl-3-[3-(4,4,5,5-tetramethyl-[1,3,2]dioxaborolan-2-yl)-phenyl]-urea (I7) and $K_3PO_4$ as base Procedure A4a using N-morpholinyl 3-boronbenzamide and $K_3PO_4$ as base. | $^1$H NMR (400 MHz, DMSO-$d_6$): 8.74 (1H, s), 8.63 (1H, d), 8.17 (0.5H, s), 8.06 (1H, brs), 7.96 (1H, d), 7.88 (1H, s), 7.84-7.79 (2H, m), 7.60 (1H, t), 7.48-7.40 (4H, m), 7.25-7.19 (1H, m), 6.13 (1H, q), 3.64 (4H, brs), 3.32 (4H, brs), 2.67 (3H, d). | MS: [M + H]$^+$ 456 |
| 91 | | 2-[4-(3-{3-[3-(4-Fluoro-benzyl)-ureido]-phenyl}-imidazo[1,2-a]pyridin-7-yl)-phenyl]-2-methyl-propionic acid methyl ester formate salt | General Route A, procedure A3a using 3-aminobenzene-boronic acid, general modification F1a using 4-fluorobenzyl isocyanate procedure A4b using 2-Methyl-2-[4-(4,4,5,5-tetramethyl-[1,3,2]dioxaborolan-2-yl)-phenyl]-propionic acid methyl ester (I2) | $^1$H NMR (400 MHz, Me-$d_3$-OD): 8.65 (1H, d), 8.32 (1H, s), 7.86 (2H, s), 7.83-7.71 (3H, m), 7.59-7.44 (3H, m), 7.44-7.32 (4H, m), 7.30 (1H, d), 7.08 (2H, t), 4.41 (2H, s), 3.69 (3H, s), 1.63 (6H, s). | MS: [M + H]$^+$ 537 |
| 92 | | 1-(4-{3-[3-(3-Ethyl-ureido)-phenyl]-imidazo[1,2-a]pyridin-7-yl}-benzyl)-3-methyl-piperidine-3-carboxylic acid formate salt | Procedure D2 on Example 52 | $^1$H NMR (400 MHz, Me-$d_3$-OD): 8.67 (1H, d), 8.27 (2H, s), 7.90 (3H, d), 7.86 (1H, t), 7.76 (1H, s), 7.68 (2H, d), 7.47 (1H, t), 7.43-7.32 (2H, m), 7.28 (1H, d), 4.43 (1H, d), 4.20 (1H, d), 3.57-3.42 (2H, m), 3.27 (2H, q), 3.01-2.87 (1H, m), 2.13-1.84 (4H, m), 1.49-1.34 (1H, m), 1.25-1.10 (6H, m). | MS: [M + H]$^+$ 512 |

| Eg. No. | Compound | Chemical Name | Procedure | N.M.R. Data | M.S. |
|---|---|---|---|---|---|
| 93 | | 2-[4-(3-{3-[3-(4-Fluoro-benzyl)-ureido]-phenyl}-imidazo[1,2-a]pyridin-7-yl)-phenyl]-2-methyl-propionic acid | General Route A, procedure A3a using 3-aminobenzene-boronic acid, general modification F1a using 4-fluorobenzyl isocyanate procedure A4b using 2-Methyl-2-[4-(4,4,5,5-tetramethyl-[1,3,2]dioxaborolan-2-yl)-phenyl]-propionic acid methyl ester (I2), general modification D2 (i.e. Procedure D2 on Example 91) | $^1$H NMR (400 MHz, Me-d$_3$-OD): 8.65 (1H, d), 7.90-7.82 (2H, m), 7.77 (2H, d), 7.73 (1H, s), 7.57 (2H, d), 7.54-7.44 (1H, m), 7.39 (4H, dd), 7.31 (1H, d), 7.13-7.02 (2H, m), 4.42 (2H, s), 1.62 (6H, s). | MS: [M + H]$^+$ 523 |
| 94 | | 1-Ethyl-3-{3-[7-(1-methyl-1H-pyrazol-4-yl)-imidazo[1,2-a]pyridin-3-yl]-phenyl}-urea | General route A, Procedure A1 and A2, Procedure A3b using 3-aminobenzene-boronic acid, procedure A4d using 1-methylpyrazole-4-boronic acid pinacol ester (commercially available) and 1-[3-(7-chloro-imidazo[1,2,a]pyridine-3-yl)-phenyl]3-ethyl urea (made using procedure F1a) | 1H NMR (400 MHz, DMSO-d6): 8.66-8.50 (2H, m), 8.35 (1H, s), 8.07 (1H, s), 7.86 (1H, s), 7.81-7.73 (1H, m), 7.68 (1H, s), 7.45-7.33 (2H, m), 7.29-7.15 (2H, m), 6.19 (1H, d), 3.90 (3H, s), 3.18-3.08 (2H, m), 1.19-1.02 (3H, m). | MS: [M + H]$^+$ 361 |
| 95 | | 1-Ethyl-3-{3-[7-(1-methyl-6-oxo-1,6-dihydro-pyridin-3-yl)-imidazo[1,2-a]pyridin-3-yl]-phenyl}-urea | General Route A, Procedure A1 and A2, Procedure A3b using 3-aminobenzene-boronic acid, general modification F1a, procedure A3b using 1-Methyl-5-(4,4,5,5-tetramethyl-[1,3,2]dioxaborolan-2-yl)-1H-pyridin-2-one (I3) | $^1$H NMR (400 MHz, Me-d$_3$-OD): 8.62 (1H, d), 8.24 (1H, d), 8.05 (1H, dd), 7.84 (1H, t), 7.79 (1H, s), 7.71 (1H, s), 7.46 (1H, t), 7.39-7.31 (1H, m), 7.27 (2H, dd), 6.71 (1H, d), 3.70 (3H, s), 3.27 (2H, q), 1.19 (3H, t). | MS: [M + H]$^+$ 388 |

-continued

| Eg. No. | Compound | Chemical Name | Procedure | N.M.R. Data | M.S. |
|---|---|---|---|---|---|
| 96 | | 1-Ethyl-3-(3-{7-[3-(3-morpholin-4-yl-propyl)-phenyl]-imidazo[1,2-a]pyridin-3-yl}-phenyl)-urea formate salt | General Route A, Procedure A1 and A2, Procedure A3b using 3-aminobenzene-boronic acid, general modification F1a, procedure A3b using 4-[3-(4,4,5,5-tetramethyl-[1,3,2]dioxaborolan-2-yl)-phenyl]-propyl]-morpholine | $^1$H NMR (400 MHz, Me-d$_3$-OD): 8.66 (1H, d), 7.92-7.83 (2H, m), 7.75 (3H, d), 7.52-7.31 (5H, m), 7.27 (1H, d), 3.88 (4H, t), 3.27 (2H, q), 3.14 (4H, s), 3.08-2.98 (2H, m), 2.79 (2H, t), 2.16-2.03 (2H, m), 1.19 (3H, t). | MS: [M + H]$^+$ 484 |
| 97 | | N-{3-[6-(3-Methoxy-phenyl)-imidazo[1,2-a]pyridin-3-yl]-phenyl}-acetamide | General Route C, procedure C1 using 3-methoxyphenylboronic acid, procedure C2, procedure C3 using (3-acetylamino-phenyl)boronic acid | 1H NMR (400 MHz, Me-d3-OD): 8.71 (1H, s), 8.10 (1H, s), 7.77-7.67 (3H, m), 7.58-7.50 (2H, m), 7.46-7.35 (2H, m), 7.29-7.18 (2H, m), 6.98 (1H, dd), 3.88 (3H, s), 2.17 (3H, s). | MS: [M + H]$^+$ 358 |
| 98 | | 6-(3-Methoxy-phenyl)-3-(1H-pyrazol-4-yl)-imidazo[1,2-a]pyridine | General Route C, procedure C1 procedure C2, procedure C3 using 4-(4,4,5,5-tetramethyl-[1,3,2]-dioxaborolan-2-yl)-1H-pyrazole | 1H NMR (400 MHz, Me-d3-OD): 8.47 (1H, s), 8.28-7.92 (2H, m), 7.73-7.63 (3H, m), 7.41 (1H, t), 7.28-7.17 (2H, m), 6.99 (1H, dd), 3.88 (3H, s). | MS: [M + H]$^+$ 291 |
| 99 | | 6-(3-Benzyloxy-phenyl)-3-(1H-pyrazol-4-yl)-imidazo[1,2-a]pyridine | General Route C, procedure C1 using 3-benzyloxyphenylboronic acid, procedure C2, procedure C3 using 4-(4,4,5,5-tetramethyl-[1,3,2]-dioxaborolan-2-yl)-1H-pyrazole | 1H NMR (400 MHz, Me-d3-OD): 8.43 (1H, s), 8.19 (1H, br s), 7.98 (1H, br s), 7.71-7.62 (3H, m), 7.48 (2H, d), 7.44-7.21 (6H, m), 7.06 (1H, dd), 5.19 (2H, s). | MS: [M + H]$^+$ 367 |

| Eg. No. | Compound | Chemical Name | Procedure | N.M.R. Data | M.S. |
|---|---|---|---|---|---|
| 100 | | N-{3-[6-(4-Methoxy-phenyl)-imidazo[1,2-a]pyridin-3-yl]-phenyl}-acetamide formate salt | General Route C, procedure C1 using 2-(4-methoxylphenyl)-4,4,5,5-tetramethyl-[1,3,2]-dioxamorolane, procedure C2, procedure C3 using (3-acetylamino-phenyl)boronic acid | 1H NMR (400 MHz, DMSO-d6): 10.12 (1H, s), 8.64 (1H, s), 8.14 (1H, s), 7.99 (1H, s), 7.81-7.71 (2H, m), 7.71-7.65 (2H, m), 7.65-7.56 (2H, m), 7.49 (1H, t), 7.40 (1H, d), 7.10-7.01 (2H, m), 3.81 (3H, s), 2.09 (3H, s). | MS: [M + H]+ 358 |
| 101 | | N-{3-[6-(5-Methoxy-pyridin-3-yl)-imidazo[1,2-a]pyridin-3-yl]-phenyl}-acetamide | General Route C, procedure C1 using 3-methoxy-5-pyridineboronic acid pinacol ester, procedure C2, procedure C3 using (3-acetylamino-phenyl)boronic acid | 1H NMR (400 MHz, DMSO-d6): 10.14 (1H, s), 8.85 (1H, s), 8.57 (1H, d), 8.33 (1H, d), 8.09 (1H, s), 7.87-7.68 (4H, m), 7.56 (1H, d), 7.49 (1H, t), 7.43 (1H, d), 3.94 (3H, s), 2.08 (3H, s). | MS: [M + H]+ 359 |
| 102 | | N-{3-[6-(3-Trifluoromethoxy-phenyl)-imidazo[1,2-a]pyridin-3-yl]-phenyl}-acetamide | General Route C, procedure C1 using 3-(trifluoromethoxy)phenylboronic acid, procedure C2, procedure C3 using (3-acetylamino-phenyl)boronic acid | 1H NMR (400 MHz, Me-d3-OD): 8.78 (1H, s), 8.12 (1H, s), 7.80-7.67 (4H, m), 7.67-7.49 (4H, m), 7.47-7.40 (1H, m), 7.34 (1H, dt), 2.18 (3H, s). | MS: [M + H]+ 412 |
| 103 | | N-[3-(6-Benzo[b]thiophen-3-yl-imidazo[1,2-a]pyridin-3-yl)-phenyl]-acetamide | General Route C, procedure C1 using benzothiophene-3-boronic acid, procedure C2, procedure C3 using (3-acetylamino-phenyl)boronic acid | 1H NMR (400 MHz, Me-d3-OD): 8.71 (1H, s), 8.09 (1H, s), 8.00-7.91 (2H, m), 7.81-7.76 (3H, m), 7.67 (1H, dd), 7.56-7.49 (2H, m), 7.47-7.41 (3H, m), 2.16 (3H, s). | MS: [M + H]+ 384 |
| 104 | | N-[3-(6-Furan-3-yl-imidazo[1,2-a]pyridin-3-yl)-phenyl]-acetamide | General Route C, procedure C1 using furan-3-boronic acid, procedure C2, procedure C3 using (3-acetylamino-phenyl)boronic acid | 1H NMR (400 MHz, Me-d3-OD): 8.72 (1H, s), 8.05 (2H, d), 7.70 (1H, s), 7.68-7.46 (5H, m), 7.40 (1H, dt), 6.94-6.86 (1H, m), 2.19 (3H, s). | MS: [M + H]+ 318 |

-continued

| Eg. No. | Compound | Chemical Name | Procedure | N.M.R. Data | M.S. |
|---|---|---|---|---|---|
| 105 | | N-[3-(6-Phenyl-imidazo[1,2-a]pyridin-3-yl)-phenyl]-acetamide | General Route C4 | 1H NMR (400 MHz, Me-d3-OD): 8.76-8.69 (1H, m), 8.07 (1H, s), 7.79-7.65 (5H, m), 7.61-7.38 (6H, m), 2.18 (3H, s). | MS: [M + H]$^+$ 328 |
| 106 | | N-{3-[6-(3-Benzyloxy-phenyl)-imidazo[1,2-a]pyridin-3-yl]-phenyl}-acetamide | General Route C, procedure C1 using 3-benzyloxyphenylboronic acid, procedure C2, procedure C3 using (3-acetylamino-phenyl)boronic acid | 1H NMR (400 MHz, Me-d3-OD): 8.68 (1H, s), 8.16 (1H, s), 7.73 (3H, d), 7.52 (2H, d), 7.46 (2H, d), 7.40-7.27 (6H, m), 7.23 (1H, d), 7.03 (1H, dd), 5.16 (2H, s), 2.13 (3H, s). | MS: [M + H]$^+$ 434 |
| 107 | | 1-Ethyl-3-{3-[7-(2-methyl-2H-pyrazol-3-yl)-imidazo[1,2-a]pyridin-3-yl]-phenyl}-urea | General route B, procedure B1c using 1-methyl-5-(4,4,5,5-tetramethyl)-[1,3,2]-dioxaborolan-2-yl)-1H-pyrazole followed by B2 and then B3b using 1-ethyl-3-[3-(4,4,5,5-tetramethyl-[1,3,2]dioxaborolan-2-yl)-phenyl]-urea (I9) and 3-iodo-7-(2-methyl-2H-pyrazol-3-yl)-imidazo[1,2,a]pyridine | 1H NMR (400 MHz, DMSO-d6): 8.66-8.58 (2H, m), 7.90-7.77 (3H, m), 7.56-7.49 (1H, m), 7.45-7.37 (2H, m), 7.24-7.14 (2H, m), 6.64-6.58 (1H, m), 6.19 (1H, t), 4.00 (3H, s), 3.18-3.08 (2H, m), 1.14-1.02 (3H, m) | MS: [M + H]$^+$ 361 |
| 108 | | 1-[3-(7-Morpholin-4-yl-imidazo[1,2-a]pyridin-3-yl)-phenyl]-3-(2,2,2-trifluoro-ethyl)-urea hydrochloride salt | General Route B, procedure B1b using morpholine, procedure B2, procedure B3a using 1-[3-(4,4,5,5-Tetramethyl-[1,3,2]dioxaborolan-2-yl)-phenyl]-3-(2,2,2-trifluoro-ethyl)-urea (I6). Procedure J1. | 1H NMR (400 MHz, Me-d3-OD): 8.39 (1H, d), 7.75 (1H, t), 7.51-7.39 (2H, m), 7.34 (1H, dd), 7.25 (1H, d), 6.91 (1H, dd), 6.78 (1H, d), 3.95 (2H, q), 3.88 (4H, t), 3.30 (4H, t). | MS: [M + H]$^+$ 420 |

-continued

| Eg. No. | Compound | Chemical Name | Procedure | N.M.R. Data | M.S. |
|---|---|---|---|---|---|
| 109 | | 1-Ethyl-3-(3-{7-[6-(2-morpholin-4-yl-ethylamino)-pyridin-3-yl]-imidazo[1,2-a]pyridin-3-yl}-phenyl)-urea hydro-chloride salt | General Route A, Procedure A1 and A2, Procedure A3b using 3-aminobenzene-boronic acid, general modification F1a, procedure A4b using 2-(2-morpholin-4-ylethylamino)pyridine-5-boronic acid, pinacol ester. Procedure J1. | 1H NMR (400 MHz, DMSO-d6): 9.54-9.30 (1H, m), 8.58-8.48 (2H, m), 7.93-7.80 (3H, m), 7.70 (1H, s), 7.44-7.29 (3H, m), 7.15 (1H, d), 7.09-6.92 (1H, m), 6.72 (1H, t), 6.62 (1H, d), 3.60 (4H, t), 3.44 (2H, t), 3.16-3.06 (2H, m), 2.43 (4H, s), 1.06 (3H, t). | MS: [M + H]$^+$ 486 |
| 110 | | 3-(2-Chloro-pyridin-4-yl)-7-(4-fluoro-phenyl)-imidazo[1,2-a]pyridine | General Route B. Procedure B1 using 4-fluorophenylboronic acid. Procedure B3 using 2-chloropyridine-4-boronic acid | $^1$H NMR (400 MHz, CDCl$_3$): 8.57 (1H, d), 8.52 (1H, d), 8.02 (1H, s), 7.97 (1H, s), 7.75-7.63 (2H, m), 7.60 (1H, d), 7.49 (1H, dd), 7.31 (1H, d), 7.27-7.18 (2H, m). | MS: [M]$^+$ 323 |

Examples 111 to 116

By following the methods described above, the pyrazolo[1,5-a]pyrimidine compounds of Examples 111 to 114 set out in the Table below were prepared.

| Eg. No. | Compound | Chemical Name | Method | N.M.R. Data | M.S. |
|---|---|---|---|---|---|
| 111 | | 1-Ethyl-3-{3-[6-(4-fluoro-phenyl)-pyrazolo[1,5-a]pyrimidin-3-yl]-phenyl}-urea | Procedure K1, Procedure M, then procedure N using 1-ethyl-3-[3-(4,4,5,5-tetramethyl-[1,3,2]dioxaborolan-2-yl)-phenyl]-urea (I9) | 1H NMR (400 MHz, Me-d3-OD): 9.15 (1H, d), 8.92 (1H, d), 8.57 (1H, s), 8.16 (1H, t), 7.86-7.75 (3H, m), 7.38-7.26 (4H, m), 3.28 (2H, q), 1.20 (3H, t). | MS: [M + H]$^+$ 376 |

| Eg. No. | Compound | Chemical Name | Method | N.M.R. Data | M.S. |
|---|---|---|---|---|---|
| 112 | | N-{3-[6-(4-Fluoro-phenyl)-pyrazolo[1,5-a]pyrimidin-3-yl]-phenyl}-methanesulfonamide | Procedure K1, Procedure M, then procedure N using N-3-(4,4,5,5-tetramethyl-1,3,2-dioxaborolan-2-yl)phenyl-methane-sulfonamide | 1H NMR (400 MHz, Me-d3-OD): 9.18 (1H, d), 8.95 (1H, d), 8.59 (1H, s), 8.09 (1H, t), 7.92 (1H, d), 7.87-7.78 (2H, m), 7.43 (1H, t), 7.35-7.28 (2H, m), 7.23-7.18 (1H, m), 3.05 (3H, s). | MS: [M + H]$^+$ 383 |
| 113 | | 1-{3-[6-(6-Amino-pyridin-3-yl)-pyrazolo[1,5-a]pyrimidin-3-yl]-phenyl}-3-(2,2,2-trifluoro-ethyl)-urea hydrochloride salt | Procedure K, Procedure L using 2-amino-5-(4,4,5,5-tetramethyl-[1,3,2]-dioxaborolan-2-yl)pyridine, procedure M then procedure N using 1-[3-(4,4,5,5-tetramethyl-[1,3,2]dioxaborolan-2-yl)-phenyl]-3-(2,2,2-trifluoro-ethyl)-urea (Ib). Procedure J1. | 1H NMR (400 MHz, DMSO-d6): 9.55 (1H, d), 8.99 (1H, d), 8.89 (1H, s), 8.73 (1H, s), 8.49 (1H, d), 8.40 (1H, d), 8.19 (1H, t), 7.99 (1H, br s), 7.69 (1H, dt), 7.43-7.31 (2H, m), 7.09 (1H, d), 6.80 (1H, t), 4.02-3.90 (2H, m). | MS: [M + H]$^+$ 428 |
| 114 | | 1-{3-[6-(6-Amino-pyridin-3-yl)-pyrazolo[1,5-a]pyrimidin-3-yl]-phenyl}-3-ethyl-urea hydrochloride salt | Procedure K, Procedure L using 2-amino-5-(4,4,5,5-tetramethyl-[1,3,2]-dioxaborolan-2-yl)pyridine, procedure M then procedure N using 1-ethyl-3-[3-(4,4,5,5-tetramethyl-[1,3,2]dioxaborolan-2-yl)-phenyl]-urea (I9). Procedure J1. | 1H NMR (400 MHz, Me-d3-OD): 8.97 (1H, d), 8.76 (1H, d), 8.42 (1H, s), 8.21 (1H, d), 8.02 (1H, s), 7.77 (1H, dd), 7.66-7.62 (1H, m), 7.27-7.16 (2H, m), 6.64 (1H, d), 3.15 (2H, q), 1.08 (3H, t). | MS: [M + H]$^+$ 374 |
| 115 | | 1-Ethyl-3-[3-(7-thiophen-3-yl-imidazo[1,2-a]pyridin-3-yl)-phenyl]-urea formate salt | General Route A. Procedure A1 and A2, Procedure A3b using 3-aminobenzeneboronic acid, Procedure F1a, Procedure A4d using 3-thiophene boronic acid | 1H NMR (400 MHz, Me-d3-OD): 8.64 (1H, d), 8.16 (1H, s), 7.98 (1H, dd), 7.94 (1H, s), 7.87 (1H, t), 7.80 (1H, s), 7.66 (1H, dd), 7.61 (1H, dd), 7.57-7.49 (1H, m), 7.47 (1H, d), 7.41-7.33 (1H, m), 7.29 (1H, d), 3.27 (3H, q), 1.19 (3H, t) | MS: [M + H]$^+$ 363 |

| Eg. No. | Compound | Chemical Name | Method | N.M.R. Data | M.S. |
|---|---|---|---|---|---|
| 116 | | 7-(4-Fluoro-phenyl)-3-pyridin-3-yl-imidazo[1,2-a]pyridine | General Route B. Procedure B1c using 4-fluorophenyl-boronic acid Procedure B2, Procedure B3a used 3-(4,4,5,5-tetramethyl-[1,3,2]-dioxaborolan-2-yl)pyridine | 1H NMR (400 MHz, DMSO-d6): 8.93 (1H, d), 8.71-8.61 (2H, m), 8.17 (1H, d), 8.03 (1H, s), 8.00-7.87 (3H, m), 7.60 (1H, dd), 7.39-7.32 (3H, m) | MS: [M + H]+ 290 |

Example 117

N-{3-[6-(4-Fluoro-phenyl)-pyrazolo[1,5-a]pyrazin-3-yl]-phenyl}-acetamide

Step 1: 2-Bromo-5-trimethylsilanylethynyl-pyrazine

A mixture of 2-bromo-5-iodo-pyrazine (1.14 g, 4.0 mmol) and copper (I) iodide (80 mg, 0.42 mmol) in DMF/Et₃N (2:1, 24 ml) was deoxygenated by evacuate/refill with nitrogen (×3). Ethynyl-trimethyl-silane (680 µl, 4.8 mmol) followed by Pd(PPh₃)₄ (230 mg, 0.2 mmol) were added and the mixture was deoxygenated again (×1). The reaction was stirred at RT for 16 hours, then partitioned between Et₂O/H₂O. The organic layer was washed with water (×1), brine (×1), then dried (MgSO₄), filtered and evaporated. The residue was purified by chromatography on silica (2∝34% Et₂O/Petrol) to give the title compound (850 mg, waxy solid) as ~3:1 mixture of mono coupled product to bis coupled. ¹H NMR (400 MHz, CDCl₃): 8.63 (1H, d), 8.43 (1H, d), 0.25 (9H, s), [Bis coupled product: 8.60 (s), 0.25 (s)] This material was used without further purification.

Step 2: 6-Bromo-2-trimethylsilanyl-pyrazolo[1,5-a]pyrazine

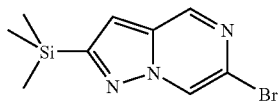

O-(Mesitylenesulfonyl)hydroxylamine (680 mg, 3.2 mmol) was added in one portion to a stirred solution of 2-bromo-5-trimethylsilanylethynyl-pyrazine (Step 1, 3 mmol) in CH₂Cl₂ (3 ml) at 0° C. The mixture was stirred at 0° C. for 30 minutes, at RT for 4 hours, then evaporated. The N-amino adduct was used without further manipulation. K₂CO₃ (410 mg, 3 mmol) was added to a stirred solution of the N-aminopyrazine from above in dry DMF (5 ml) at RT under nitrogen. After 6 hours the mixture was partitioned between EtOAc/H₂O. The organic layer was washed with brine (×2), then evaporated. The residue was taken up in CH₂Cl₂ and passed through a phase separating cartridge. The filtrate was evaporated and the residue was purified by chromatography on silica (2→4% EtOAc/Petrol) to give the title compound (62 mg, oil) MS: [M+H]+ 270/272.

Step 3: 6-(4-Fluoro-phenyl)-pyrazolo[1,5-a]pyrazine

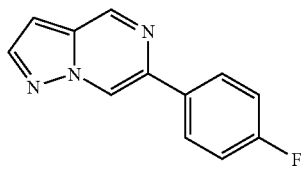 [SMILES: Fc1ccc(-c2cn3nccc3cn2)cc1]

A mixture of 6-bromo-2-trimethylsilanyl-pyrazolo[1,5-a]pyrazine (60 mg, 0.23 mmol), 4-fluorophenylboronic acid (40 mg, 0.29 mmol) and PdCl₂dppf (10 mg, 0.014 mmol) in CH₃CN (1 ml) and 2N Na₂CO₃ (aq, 1 ml) in a microwave vial was deoxygenated by bubbling N₂ through for 20 seconds. The vial was sealed and then stirred and heated at 150° C. in the microwave for 20 minutes. After cooling the reaction mixture was partitioned between CH₂Cl₂/H₂O. The mixture was passed through a phase separating cartridge. The organic layer was evaporated and the residue was purified by chromatography on silica (5→20% EtOAc/Petrol) to give the title compound (14 mg, oil) ¹H NMR (400 MHz, CDCl₃): 9.15 (1H, d), 8.75 (1H, s), 8.06 (1H, d), 7.98-7.92 (2H, m), 7.24-7.14 (2H, m), 6.84 (1H, d).

Step 4: 6-(4-Fluoro-phenyl)-3-iodo-pyrazolo[1,5-a]pyrazine

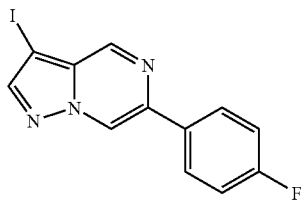 [SMILES: Fc1ccc(-c2cn3ncc(I)c3cn2)cc1]

N-iodosuccinimide (13 mg, 0.06 mmol) was added in one portion to a stirred solution of 6-(4-fluoro-phenyl)-pyrazolo[1,5-a]pyrazine (11 mg, 0.05 mmol) in dry DMF (0.5 ml) at RT under N₂. After 30 minutes, a further portion of N-iodosuccinimide (13 mg, 0.06 mmol) in DMF (0.2 mmol) was added. After a further 30 minutes at RT the mixture was heated to 50° C. for 90 minutes. After cooling to RT, the reaction was quenched with saturated aqueous sodium thiosulphate/saturated NaHCO₃ (1:1, 1 ml). The mixture was stirred at RT for 1 hour then partitioned between CH₂Cl₂/H₂O. The mixture was passed through a phase separating cartridge. The organic layer was evaporated to give the title compound (13 mg, solid). $^1$H NMR (400 MHz, CDCl₃): 9.01 (1H, d), 8.69 (1H, d), 8.05 (1H, s), 8.00-7.90 (2H, m), 7.24-7.14 (2H, m).

Step 5: N-{3-[6-Fluoro-phenyl)-pyrazolo[1,5-a]pyrazin-3-yl]-phenyl}-acetamide

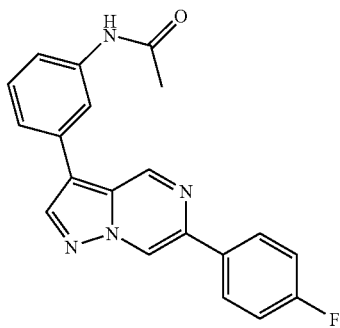 [SMILES: CC(=O)Nc1cccc(-c2cnn3cc(-c4ccc(F)cc4)ncc23)c1]

A mixture of 6-(4-fluoro-phenyl)-3-iodo-pyrazolo[1,5-a]pyrazine (13 mg, 0.04 mmol) 3-acetamidophenyl boronic acid (14 mg, 0.08 mmol) and PdCl₂dppf (3 mg) in CH₃CN (1 ml) and 2N Na₂CO₃ (aq, 1 ml) in a microwave vial was deoxygenated by bubbling N₂ through for 20 seconds. The vial was sealed and then stirred and heated at 150° C. in the microwave for 30 minutes. After cooling the reaction mixture was partitioned between CH₂Cl₂/H₂O. The mixture was passed through a phase separating cartridge. The organic layer was evaporated and the residue was purified by preparative HPLC to give the title compound (6 mg, solid). $^1$H NMR (400 MHz, Me-d₃-OD): 9.46 (1H, d), 9.08 (1H, d), 8.38 (1H, s), 8.15-8.09 (3H, m), 7.56-7.44 (3H, m), 7.31-7.21 (2H, m), 2.20 (3H, s).

Example 118

3-[6(4-Fluoro-phenyl)-pyrazolo[1,5-a]pyridin-3-yl]-phenylamine

Step 1: 3-(4-Fluoro-phenyl)-pyridine

A solution of 3-bromopyridine (2.5 g, 15.8 mmol) and 4-fluorophenylboronic acid (2.8 g, 20.0 mmol) in DME (20 ml) and 2N Na₂CO₃ (aq, 20 ml) was deoxygenated by evacuation/refill with N₂ (×2). PdCl₂dppf (600 mg, 0.8 mmol) was added and the mixture was deoxygenated again (×3). The reaction was stirred and heated at 80° C. under N₂ for 16 hours. After cooling to RT the mixture was partitioned between EtOAc/H₂O. The aqueous layer was extracted with EtOAc (×2).The combined extracts were washed with brine (×1), dried (Na₂SO₄), filtered and evaporated. The residue was purified by chromatography on silica (10→40% EtOAc/Petrol) to give the title compound (3.0 g, oil). $^1$H NMR (400 MHz, CDCl₃): 8.83 (1H, brs), 8.61 (1H, brs), 7.85 (1H, d), 7.54 (2H, dd), 7.39 (1H, brs), 7.18 (2H, t).

Step 2: 6-(4-Fluoro-phenyl)-pyrazolo[1,5-a]pyridine-3-carboxylic acid methyl ester

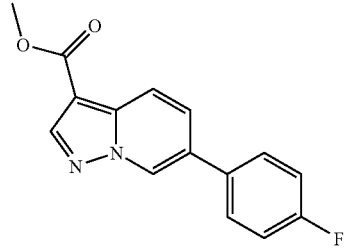 [SMILES: COC(=O)c1cnn2cc(-c3ccc(F)cc3)ccc12]

O-(Mesitylenesulfonyl)hydroxylamine (3.5 g, 16.2 mmol) was added in one portion to a stirred solution of 3-(4-fluoro-phenyl)-pyridine (2.8 g, 16 mmol) in dry CH₂Cl₂ at 0° C. under N₂. After 30 minutes the ice bath was removed and the reaction was stirred at RT for 16 hours. The volatiles were removed in vacuo and the N-aminopyridine was used without further purification.

K₂CO₃ (4.4 g, 32 mmol) was added to a stirred solution of the N-aminopyridine from above (~16 mmol) and 2-benzenesulfonyl-3-dimethylamino-acrylic acid methyl ester (4.3 g,

| Eg. No. | Compound | Chemical Name | Method | N.M.R. Data | M.S. |
|---------|----------|---------------|--------|-------------|------|
| 117 |  | N-{3-[6-(4-Fluoro-phenyl)-pyrazolo[1,5-a]pyrazin-3-yl]-phenyl}-acetamide | Single example as described above | $^1$H NMR (400 MHz, Me-d₃-OD): 9.46 (1H, d), 9.08 (1H, d), 8.38 (1H, s), 8.15-8.09 (3H, m), 7.56-7.44 (3H, m), 7.31-7.21 (2H, m), 2.20 (3H, s). | MS: [M + H]⁺ 347 |

16 mmol) in dry DMF (48 ml) at RT under N₂. After 3 hours at RT the reaction was heated at 100° C. for 2 hours. After cooling to RT the mixture was partitioned between EtOAc/H₂O. The aqueous layer was extracted with EtOAc (×2). The combined extracts were washed with water (×1), brine (×1), then dried (MgSO₄), filtered and evaporated. The residue was purified by trituration with CH₂Cl₂/petrol to give the title compound (2.7 g, solid). ¹H NMR (400 MHz, CDCl₃): 8.68 (1H, s), 8.42 (1H, s), 8.22 (1H, d), 7.63 (1H, dd), 7.60-7.51 (2H, m), 7.23-7.14 (2H, m), 3.94 (3H, s).

Step 3: 6-(4-Fluoro-phenyl)-pyrazolo[1,5-a]pyridine

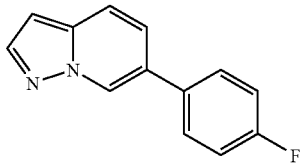 [SMILES: Fc1ccc(-c2ccc3ccnn3c2)cc1]

A mixture 6-(4-fluoro-phenyl)-pyrazolo[1,5-a]pyridine-3-carboxylic acid methyl ester (1.08 g, 4 mmol) and aqueous NaOH (2N, 4 ml) and EtOH (16 ml) was stirred and heated at 85° C. under N₂ for 30 minutes. The reaction was allowed to cool to RT, then placed in an ice bath. 2N Hydrochloric acid (5 ml) was added slowly. The solid was collected by filtration, washed with Et₂O then dried under vacuum. The acid was used without further manipulation.

A suspension of the acid from above in polyphosphoric acid (~15 ml) was stirred and heated at 150° C. under N₂. After 3 hours the reaction was allowed to cool to RT then poured cautiously on to ice water. The solid was isolated by filtration then dissolved in CH₂Cl₂. This solution was passed through a phase separating cartridge then evaporated to give the title compound (582 mg, solid). ¹H NMR (400 MHz, CDCl₃): 8.66 (1H, s), 7.98 (1H, s), 7.63-7.51 (3H, m), 7.34 (1H, d), 7.17 (2H, t), 6.55 (1H, s).

Step 4: 6-(4-Fluoro-phenyl)-3-iodo-pyrazolo[1,5-a]pyridine

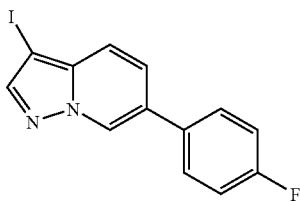 [SMILES: Fc1ccc(-c2ccc3c(I)cnn3c2)cc1]

N-iodosuccinimide (630 mg, 2.8 mmol) was added in one portion to a stirred solution of 6-(4-fluoro-phenyl)-pyrazolo[1,5-a]pyridine (500 mg, 2.4 mmol) in dry DMF (6 ml) at RT under N₂. After 45 minutes, the reaction was quenched with saturated aqueous sodium thiosulphate/saturated NaHCO₃ (1:1, 40 ml). The mixture was stirred at RT for 15 minutes then partitioned between EtOAc/H₂O. The organic layer was washed with water (×1), brine (×1), then dried (MgSO₄), filtered and evaporated. The residue was purified trituration with petrol to give the title compound (635 mg, solid). ¹H NMR (400 MHz, CDCl₃): 8.61 (1H, s), 7.98 (1H, s), 7.57-7.51 (3H, m), 7.42 (1H, dd), 7.22-7.13 (2H, m).

Step 5: 3-[6-(4-Fluoro-phenyl)-pyrazolo[1,5-a]pyridin-3-yl]phenylamine

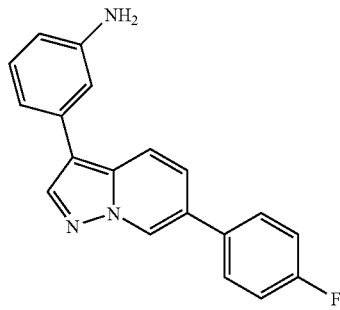 [SMILES: Nc1cccc(-c2cnn3cc(-c4ccc(F)cc4)ccc23)c1]

A mixture of 6-(4-fluoro-phenyl)-3-iodo-pyrazolo[1,5-a]pyridine (140 mg, 0.41 mmol) and 3-aminophenylboronic acid pinacol ester (120 mg, 0.5 mmol) in DME (2 ml) and 2N Na₂CO₃ (aq, 2 ml) was deoxygenated by evacuation/refill with N₂ (×3). PdCl₂ddpf (15 mg, 0.02 mmol) was added and the mixture was deoxygenated again (×2). The reaction was stirred and heated at 90° C. under N₂ for 24 hours. After cooling to RT the mixture was partitioned between CH₂Cl₂/H₂O. The layers were separated using a phase separating cartridge. The organic layer was evaporated and the residue was purified by chromatography on silica (25→65% EtOAc/Petrol) to give the title compound (55 mg, solid).

Example 119

1-Ethyl-3-{3-[6-(4-fluoro-phenyl)-pyrazolo[1,5-a]pyridin-3-yl]-phenyl}-urea

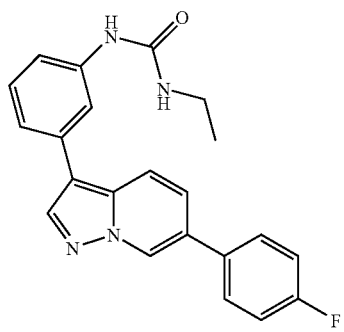 [SMILES: CCNC(=O)Nc1cccc(-c2cnn3cc(-c4ccc(F)cc4)ccc23)c1]

A solution of 3-[6-(4-fluoro-phenyl)-pyrazolo[1,5-a]pyridin-3-yl]-phenylamine (Example 118, 50 mg, 0.16 mmol), Et₃N (45 μL, 0.32 mmol) and ethyl isocyanate (26 μL, 0.32 mmol) in dry DME (2 ml) was stirred and heated at 60° C. under N₂ for 24 hours [Further ethyl isocyanate (30 μL) was added after 7 hours]. The reaction mixture was evaporated and dried under vacuum to give the title compound (55 mg, solid). ¹H NMR (400 MHz, DMSO-d6): 9.09 (1H, s), 8.53 (1H, s), 8.36 (1H, s), 8.02 (1H, d), 7.93-7.83 (3H, m), 7.72 (1H, dd), 7.38-7.29 (3H, m), 7.27-7.22 (2H, m), 6.15 (1H, t), 3.19-3.09 (2H, m), 1.08 (3H, t).

| Eg. No. | Compound | Chemical Name | Method | NMR Data (400 MHz, DMSO-d$_6$) | M.S. |
|---|---|---|---|---|---|
| 118 | | 3-[6-(4-Fluoro-phenyl)-pyrazolo[1,5-a]pyridin-3-yl]-phenylamine | Single example described above | $^1$H NMR: 9.06 (1H, s), 8.28 (1H, s), 7.99 (1H, d), 7.93-7.81 (2H, m), 7.66 (1H, dd), 7.40-7.29 (2H, m), 7.11 (1H, t), 6.95 (1H, t), 6.85 (1H, d), 6.51 (1H, dd), 5.14 (2H, s). | MS: [M + H]$^+$ 304 |
| 119 | | 1-Ethyl-3-{3-[6-(4-fluoro-phenyl)-pyrazolo[1,5-a]pyridin-3-yl]-phenyl}-urea | Single example described above | $^1$H NMR: 9.09 (1H, s), 8.53 (1H, s), 8.36 (1H, s), 8.02 (1H, d), 7.93-7.83 (3H, m), 7.72 (1H, dd), 7.38-7.29 (3H, m), 7.27-7.22 (2H, m), 6.15 (1H, t), 3.19-3.09 (2H, m), 1.08 (3H, t). | MS: [M + H]$^+$ 375 |

Examples 120 to 328

By following the methods described above, the compounds of Examples 120 to 328 set out in the Table below were prepared.

| Eg. No. | Compound | Chemical Name | Procedure | $^1$H NMR Data | M.S. |
|---|---|---|---|---|---|
| 120 | | 1-Ethyl-3-(3-{7-[4-(piperidin-4-yloxy)-phenyl]-imidazo[1,2-a]pyridin-3-yl}-phenyl)-urea | General Route A, general modification F1a, procedure A4b using 4-[4-(4,4,5,5-Tetramethyl-[1,3,2] dioxaborolan-2-yl)-phenoxy]-piperidine-1-carboxylic acid tert-butyl ester (I15), general modification D3a | (400 MHz, Me-d$_3$-OD): 8.62 (1H, d), 7.86 (1H, t), 7.83-7.67 (4H, m), 7.46 (1H, t), 7.38-7.31 (2H, m), 7.28 (1H, d), 7.13 (2H, d), 4.76-4.65 (1H, m), 3.34-3.31 (2H, m), 3.28 (2H, q), 3.09-2.96 (2H, m), 2.22-2.08 (2H, m), 1.98-1.84 (2H, m), 1.19 (3H, t). | MS: [M + H]$^+$ 456 |

-continued

| Eg. No. | Compound | Chemical Name | Procedure | ¹H NMR Data | M.S. |
|---|---|---|---|---|---|
| 121 | | 1-(2-Amino-ethyl)-3-{3-[7-(4-fluoro-phenyl)-imidazo[1,2-a]pyridin-3-yl]-phenyl}-urea | General route A, procedure A3a using 3-aminobenzeneboronic acid, then procedure A4b using 4-fluorophenyl benzene boronic acid then Procedure J2 | (400 MHz, Me-d3-OD): 8.62 (1H, d), 7.90-7.75 (4H, m), 7.71 (1H, s), 7.46 (1H, t), 7.37 (1H, ddd), 7.33-7.22 (4H, m), 3.35-3.32 (2H, m), 2.82 (2H, t). | MS: [M + H]⁺ 390 |
| 122 | | 1-(3-Amino-propyl)-3-{3-[7-(4-fluoro-phenyl)-imidazo[1,2-a]pyridin-3-yl]-phenyl}-urea | General route A, procedure A3a using 3-aminobenzeneboronic acid, then procedure A4b using 4-fluorophenyl benzene boronic acid then Procedure J2 using (3-Amino-propyl)-carbamic acid tert-butyl ester in Step 1. | (400 MHz, Me-d3-OD): 8.61 (1H, d), 7.85-7.77 (4H, m), 7.71 (1H, s), 7.46 (1H, t), 7.36 (1H, ddd), 7.33-7.19 (4H, m), 3.34-3.32 (2H, m), 2.78 (2H, t), 1.79-1.70 (2H, m). | MS: [M + H]⁺ 404 |
| 123 | | 1-{3-[6-(4-Fluoro-phenyl)-pyrazolo[1,5-a]pyrimidin-3-yl]-phenyl}-3-(2,2,2-trifluoro-ethyl)-urea | Procedure K, then Procedure M, then Preparation N using 1-[3-(4,4,5,5-Tetramethyl-[1,3,2]dioxaborolan-2-yl)-phenyl]-3-(2,2,2-trifluoro-ethyl)-urea (I6) and using K₃PO₄ as base | (400 MHz, DMSO-d6): 9.51 (1H, s), 9.02 (1H, s), 8.85 (1H, s), 8.71 (1H, s), 8.14 (1H, s), 8.01-7.90 (2H, m), 7.70 (1H, d), 7.50-7.29 (4H, m), 6.75 (1H, t), 4.03-3.90 (2H, m). | MS: [M + H]⁺ 430 |
| 124 | | 1-Ethyl-3-[3-(6-pyridin-4-yl-pyrazolo[1,5-a]pyrimidin-3-yl)-phenyl]-urea | Preparation K using 2-(4-pyridyl) malondialdehyde, procedure M, procedure N using 1-Ethyl-3-[3-(4,4,5,5-tetramethyl-[1,3,2]-dioxaborolan-2-yl)-phenyl]-urea (I9) | (400 MHz, DMSO-d6): 9.75 (1H, d), 9.13 (1H, d), 8.76 (1H, s), 8.74-8.68 (2H, m), 8.54 (1H, s), 8.10 (1H, s), 8.01-7.93 (2H, m), 7.64 (1H, d), 7.46 (1H, d), 7.31 (1H, t), 6.15 (1H, t), 3.19-3.09 (2H, m), 1.08 (3H, t). | MS: [M + H]⁺ 359 |

| Eg. No. | Compound | Chemical Name | Procedure | ¹H NMR Data | M.S. |
|---|---|---|---|---|---|
| 125 | | 1-Ethyl-3-[3-(6-pyrazin-2-yl-pyrazolo[1,5-a]pyrimidin-3-yl)-phenyl]-urea | Preparation K using, 2-(2-pyrazinyl)malondialdehyde procedure M, procedure N using 1-Ethyl-3-[3-(4,4,5,5-tetramethyl-[1,3,2]-dioxaborolan-2-yl)-phenyl]-urea (I9). | (400 MHz, DMSO-d6): 9.90 (1H, d), 9.48 (1H, d), 9.35 (1H, d), 8.84-8.75 (2H, m), 8.72 (1H, d), 8.54 (1H, s), 8.08 (1H, t), 7.64 (1H, d), 7.49 (1H, d), 7.32 (1H, t), 6.14 (1H, t), 3.18-3.09 (2H, m), 1.08 (3H, t). | MS: [M + H]⁺ 360 |
| 126 | | 1-Ethyl-3-[3-(6-pyrimidin-4-yl-pyrazolo[1,5-a]pyrimidin-3-yl)-phenyl]-urea | Preparation K using 2-(4-pyrimidyl)malondialdehyde, procedure M, procedure N using 1-Ethyl-3-[3-(4,4,5,5-tetramethyl-[1,3,2]-dioxaborolan-2-yl)-phenyl]-urea (I9), | (400 MHz, DMSO-d6): 9.96 (1H, d), 9.41 (1H, d), 9.33 (1H, d), 8.96 (1H, d), 8.81 (1H, s), 8.55 (1H, s), 8.34 (1H, dd), 8.08 (1H, t), 7.64 (1H, d), 7.48 (1H, d), 7.32 (1H, t), 6.15 (1H, t), 3.19-3.09 (2H, m), 1.08 (3H, t). | MS: [M + H]⁺ 360 |
| 127 | | 1-{3-[6-(1-Methyl-1H-pyrazol-4-yl)-pyrazolo[1,5-a]pyrimidin-3-yl]-phenyl}-3-(2,2,2-trifluoro-ethyl)-urea | Procedures K, Precedure L using 1-methyl-4-(4,4,5,5)-tetramethyl-[1,3,2]-dioxaborolan-2-yl)-1H-pyrazole (commercially available), M and N using 1-[3-(4,4,5,5-tetramethyl-[1,3,2]dioxaborolan-1-yl)-phenyl]-3-(2,2,2-trifluoro-ethyl)-urea (I6). | 1H NMR (400 MHz, DMSO-d6): 9.44 (1H, m), 9.87 (1H, m), 8.89 (1H, m), 8.61 (1H, s), 8.38 (1H, s), 8.11 (2H, s), 7.67 (1H, dd), 7.43 (1H, dd), 7.33 (1H, t), 6.80 (1H, t), 3.97 (2H, m), 3.93 (3H, s) | [M + H]+ 416 |
| 128 | | 1-{3-[7-(1-Methyl-1H-pyrazol-4-yl)-imidazo[1,2-a]pyridin-3-yl]-phenyl}-3-(2,2,2-trifluoro-ethyl)-urea formate | Procedures B1c using 1-methyl-4-(4,4,5,5)-tetramethyl-[1,3,2]-dioxaborolan-2-yl)-1H-pyrazole (commercially available), B2 and B3b using 1-[3-(4,4,5,5-tetramethyl-[1,3,2]dioxaborolan-2-yl)-phenyl]-3-(2,2,2-trifluoro-ethyl)-urea (I6). | 1H NMR (400 MHz Me-d3-OD): 8.58 (1H, d), 8.21 (2H, m), 8.02 (1H, s), 7.85 (1H, s), 7.80 (1H, s), 7.76 (1H, s), 7.50 (1H, t), 7.40 (1H, dd), 7.36 (1H, dd), 7.30 (1H, dd), 3.98 (3H, s), 3.96 (2H, m). | [M + H]+ 415 |

-continued

| Eg. No. | Compound | Chemical Name | Procedure | ¹H NMR Data | M.S. |
|---|---|---|---|---|---|
| 129 | 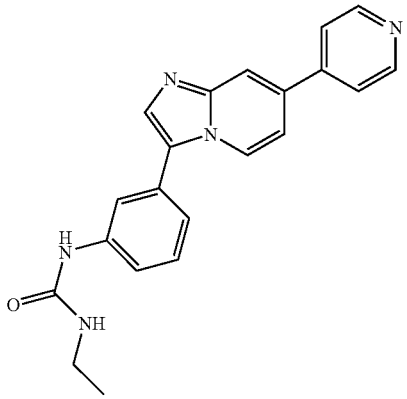 [SMILES: CCNC(=O)Nc1cccc(-c2cnc3cc(-c4ccncc4)ccn23)c1] | 1-Ethyl-3-[3-(7-pyridin-4-yl-imidazo[1,2-a]pyridin-3-yl)-phenyl]-urea | General Route A, Procedure A1 and A2, Procedure A3b using 3-aminobenzeneboronic acid, general modification F1a, procedure A4b using pyridine-4-boronic acid | 1H NMR (400 MHz, CDCl3): 8.68 (1H, d), 8.67 (1H, d), 8.46 (1H, d), 8.28 (1H, s), 7.90 (1H, s), 7.76 (1H, s), 7.69 (1H, s), 7.51 (1H, d), 7.50 (1H, d), 7.34 (2H, d), 7.14-7.11 (1H, m), 7.08 (1H, dd), 5.86 (1H, s), 3.33 (2H, qt), 1.18 (3H, t) | [M + H]+ 358 |
| 130 | 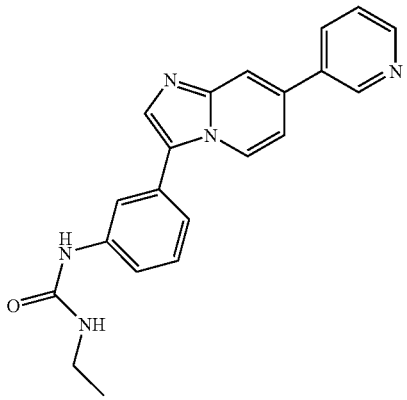 [SMILES: CCNC(=O)Nc1cccc(-c2cnc3cc(-c4cccnc4)ccn23)c1] | 1-Ethyl-3-[3-(7-pyridin-3-yl-imidazo[1,2-a]pyridin-3-yl)-phenyl]-urea | General Route A, Procedure A1 and A2, Procedure A3b using 3-aminobenzeneboronic acid, general modification F1a, procedure A4b using pyridine-3-boronic acid | 1H NMR (400 MHz, CDCl3): 8.87 (1H, d), 8.63 (1H, dd), 8.46 (1H, d), 8.12 (1H, s), 7.96-7.88 (1H, m), 7.84 (1H, s), 7.67 (1H, t), 7.65 (1H, s), 7.45-7.31 (3H, m), 7.11 (1H, d), 7.08 (1H, dd), 5.77 (1H, s), 3.32 (2H, qt), 1.18 (3H, t) | [M + H]+ 358 |
| 131 | 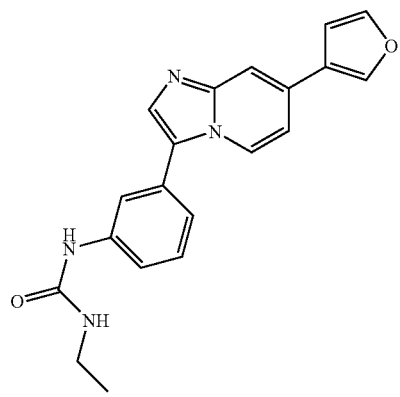 [SMILES: CCNC(=O)Nc1cccc(-c2cnc3cc(-c4ccoc4)ccn23)c1] | 1-Ethyl-3-[3-(7-furan-3-yl-imidazo[1,2-a]pyridin-3-yl)-phenyl]-urea | General Route A, general modification F1a, procedure A4b using 3-(4,4,5,5-tetramethyl-[1,3,2]-dioxaborolan-2-yl)-foran | 1H NMR (400 MHz, Me-d3-OD): 8.55 (1H, d), 8.12 (1H, s), 7.80 (1H, t), 7.74 (1H, s), 7.67 (1H, s), 7.65 (1H, t), 7.45 (1H, t), 7.36 (1H, d), 7.26 (2H, dd), 7.01-6.93 (1H, m), 3.27 (2H, q), 1.19 (3H, t). | [M + H]+ 347 |
| 132 | 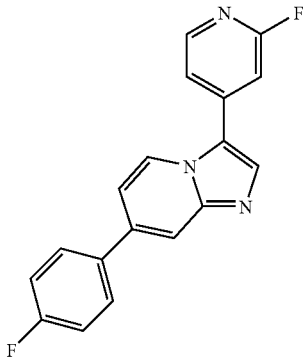 [SMILES: Fc1ccc(-c2ccn3c(-c4ccnc(F)c4)cnc3c2)cc1] | 7-(4-Fluoro-phenyl)-3-(2-fluoro-pyridin-4-yl)-imidazo[1,2-a]pyridine | General route B. Procedures B1a using 4-fluorophenyl boronic acid, procedure B2, procedure B3b using 2-fluoropyridine-4-boronic acid | 1H NMR (400 MHz, Me-d3-OD): 8.82 (1H, d), 8.36 (1H, d), 8.08 (1H, s), 7.91 (1H, s), 7.89-7.81 (2H, m), 7.70 (1H, dt), 7.49 (1H, s), 7.46 (1H, dd), 7.34-7.23 (2H, m). | [M + H]+ 308 |

| Eg. No. | Compound | Chemical Name | Procedure | ¹H NMR Data | M.S. |
|---|---|---|---|---|---|
| 133 | | 1-Ethyl-3-{3-[7-(1-oxy-pyridin-4-yl)-imidazo[1,2-a]pyridin-3-yl]-phenyl}-urea | General Route A, Procedure A1 and A2, Procedure A3b using 3-aminobenzeneboronic acid, general modification F1a, procedure A4b using pyridine-4-boronic acid. Followed by general modification D5 | 1H NMR (400 MHz, Me-d3-OD): 8.72 (1H, d), 8.44 (2H, d), 8.10 (1H, s), 8.04 (2H, d), 7.87 (1H, t), 7.82 (1H, s), 7.52-7.42 (2H, m), 7.36 (1H, dd), 7.30 (1H, d), 3.27 (2H, q), 1.19 (3H, t). | [M + H]+ 374 |
| 134 | | 1-(2-Fluoro-ethyl)-3-{3-[7-(4-fluoro-phenyl)-imidazo[1,2-a]pyridin-3-yl]-phenyl}-urea Hydrochloride | General route B. Procedures B1a using 4-fluorophenyl boronic acid, procedure B2, procedure B3b using 1-(2-Fluoro-ethyl)-3-[3-(4,4,5,5-tetramethyl-[1,3,2]-dioxaborolan-2-yl)-phenyl]-urea [boronate I25]. Procedure J1. | 1H NMR (400 MHz, DMSO-d6): 9.12 (1H, s), 8.80 (1H, d), 8.38 (1H, s), 8.23 (1H, s), 8.06-8.00 (2H, m), 7.92 (1H, s), 7.85 (1H, dd), 7.53-7.50 (2H, m), 7.46 (2H, t), 7.31-7.27 (1H, m), 6.65 (1H, t), 4.47 (2H, dt), 3.42 (2H, dq). | [M + H]+ 393 |
| 135 | | 1-Ethyl-3-{3-[6-(1-methyl-1H-pyrazol-4-yl)-pyrazolo[1,5-a]pyrimidin-3-yl]-phenyl}-urea | Procedures K, Procedure L using 1-methyl-4-(4,4,5,5)-tetramethyl-[1,3,2]-dioxaborolan-2-yl)-1H-pyrazole (commercially available), M and N using 1-ethyl-3-[3-(4,4,5,5-tetramethyl-[1,3,2]-dioxaborolan-2-yl)-phenyl]-urea (I9). | 1H NMR (400 MHz, DMSO-d6): 9.44 (1H, dd), 8.95 (1H, dd), 8.60 (1H, s), 8.50 (1H, s), 8.38 (1H, s), 8.12 (1H, s), 8.06 (1H, t), 7.60 (1H, dd), 7.45 (1H, dd), 7.29 (1H, t), 6.11 (1H, t), 3.92 (3H, s), 3.13 (2H, m), 1.08 (3H, t) | [M + H]+ 362 |

-continued

| Eg. No. | Compound | Chemical Name | Procedure | ¹H NMR Data | M.S. |
|---|---|---|---|---|---|
| 136 | | 1-Ethyl-3-{3-[7-(1-oxy-pyridin-3-yl)-imidazo[1,2-a]pyridin-3-yl]-phenyl}-urea | General Route A, Procedure A1 and A2, Procedure A3b using 3-aminobenzeneboronic acid, general modification F1a, procedure A4b using pyridine-3-boronic acid. Followed by general modification D5 | 1H NMR (400 MHz, Me-d3-OD): 8.81 (1H, s), 8.70 (1H, d), 8.39 (1H, d), 8.09-8.01 (2H, m), 7.85 (1H, t), 7.80 (1H, s), 7.69 (1H, dd), 7.47 (1H, t), 7.41-7.31 (2H, m), 7.28 (1H, d), 3.27 (2H, q), 1.19 (3H, t). | [M + H]+ 374 |
| 137 | | 1-{3-[7-(1-Methyl-6-oxo-1,6-dihydro-pyridin-3-yl)-imidazo[1,2-a]pyridin-3-yl]-phenyl}-3-(2,2,2-trifluoro-ethyl)-urea | General route A, Procedure A1 and A2, procedure A3b using 1-[3-(4,4,5,5-Tetramethyl-[1,3,2]dioxaborolan-2-yl)-phenyl]-3-(2,2,2-trifluoro-ethyl)-urea (I6), procedure A4b using 1-methyl-5-(4,4,5,5-tetramethyl-[1,3,2]-dioxaborolan-2-yl)-1H-pyridin-2-one (I3) | 1H NMR (400 MHz, DMSO-d6): 8.96 (1H, s), 8.59 (1H, d), 8.41 (1H, d), 8.05 (1H, dd), 7.91 (1H, s), 7.78 (2H, d), 7.48-7.38 (2H, m), 7.35-7.22 (2H, m), 6.85 (1H, t), 6.52 (1H, d), 4.01-3.89 (2H, m), 3.55 (3H, s). | [M + H]+ 442 |
| 138 | | 1-(2,2-Difluoro-ethyl)-3-{3-[6-(4-fluoro-phenyl)-pyrazolo[1,5-a]pyrimidin-3-yl]-phenyl}-urea | Preparation K, L using 4-fluorophenyl boronic acid, M and N using 1-[3-(4,4,5,5-tetramethyl-[1,3,2]dioxaborolan-2-yl)-phenyl]-3-(2,2,-difluoro-ethyl)-urea [Boronate I24] | 1H NMR (400 MHz, DMSO-d6): 9.51 (1H, s), 9.02 (1H, s), 8.79 (1H, s), 8.71 (1H, s), 8.12 (1H, s), 8.00-7.90 (2H, m), 7.68 (1H, d), 7.50-7.29 (4H, m), 6.50 (1H, t), 6.08 (1H, t), 3.63-3.49 (2H, m). | [M + H]+ 412 |

| Eg. No. | Compound | Chemical Name | Procedure | ¹H NMR Data | M.S. |
|---|---|---|---|---|---|
| 139 | | 1-[3-(6-Chloro-pyrazolo[1,5-a]pyrimidin-3-yl)-phenyl]-3-(2,2,2-trifluoro-ethyl)-urea | Preparation K using 2-chloro-malonaldehyde; Preparation M; Preparation N using boronic ester I6 | 1H NMR (400 MHz, DMSO-d6): 9.60 (1H, d), 8.88-8.82 (1H, m), 8.71 (2H, s), 8.06 (1H, s), 7.64 (1H, d), 7.46 (1H, d), 7.34 (1H, t), 6.74 (1H, t), 4.01-3.89 (2H, m). | [M + H]+ 370 |
| 140 | | 1-(2-Fluoro-ethyl)-3-{3-[6-(4-fluoro-phenyl)-pyrazolo[1,5-a]pyrimidin-3-yl]-phenyl}-urea | Preparation K, L using 4-fluorophenyl boronic acid, M and N using 1-(2-Fluoro-ethyl)-3-[3-(4,4,5,5-tetramethyl-[1,3,2]dioxaborolan-2-yl)-phenyl]-urea [boronate I25] | 1H NMR (400 MHz, DMSO-d6): 9.51 (1H, s), 9.02 (1H, s), 8.74-8.64 (2H, m), 8.10 (1H, s), 8.01-7.90 (2H, m), 7.66 (1H, d), 7.50-7.35 (3H, m), 7.32 (1H, t), 6.41 (1H, t), 4.48 (2H, dt), 3.43 (2H, dq). | [M + H]+ 394.12 |
| 141 | | 1-[3-(7-Benzo[1,3]dioxol-5-yl-imidazo[1,2-a]pyridin-3-yl)-phenyl]-3-(1,2,2-trifluoro-ethyl)-urea Hydrochloride | General route A, Procedure A1 and A2, procedure A3b using 1-[3-(4,4,5,5-Tetramethyl-[1,3,2]dioxaborolan-2-yl)-phenyl]-3-(2,2,2-trifluoro-ethyl)-urea (I6), procedure A4b using 3,4-methylenedioxyphenyl boronic acid, pinacol ester. Procedure J1. | 1H NMR (400 MHz, Me-d3-OD): 8.81 (1H, d), 8.15 (1H, s), 8.13-8.01 (2H, m), 7.82 (1H, dd), 7.58 (1H, t), 7.52-7.35 (4H, m), 7.06 (1H, d), 6.11 (2H, s), 3.96 (2H, q). | [M + H]+ 455 |

-continued

| Eg. No. | Compound | Chemical Name | Procedure | ¹H NMR Data | M.S. |
|---|---|---|---|---|---|
| 142 | 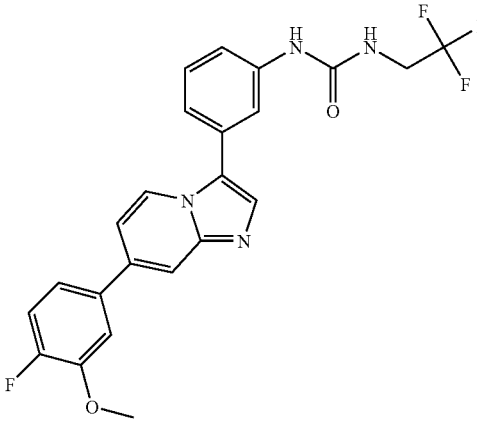 | 1-{3-[7-(4-Fluoro-3-methoxy-phenyl)-imidazo[1,2-a]pyridin-3-yl]-phenyl}-3-(2,2,2-trifluoro-ethyl)-urea Hydrochloride | General route A, Procedure A1 and A2, procedure A3b using 1-[3-(4,4,5,5-Tetramethyl-[1,3,2]dioxaborolan-2-yl)-phenyl]-3-(2,2,2-trifluoro-ethyl)-urea (I6), procedure A4b using (4-fluoro-3-methoxyphenyl)boronic acid. Procedure J1. | 1H NMR (400 MHz, Me-d3-OD): 8.86 (1H, d), 8.19 (2H, d), 8.07 (1H, t), 7.87 (1H, dd), 7.66-7.55 (2H, m), 7.55-7.28 (4H, m), 4.04 (3H, s), 3.96 (2H, q). | [M + H]+ 459 |
| 143 | 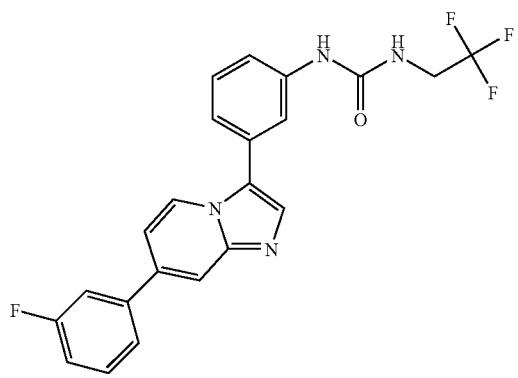 [SMILES: O=C(NCC(F)(F)F)Nc1cccc(-c2cnc3cc(-c4cccc(F)c4)ccn23)c1] | 1-{3-[7-(3-Fluoro-phenyl)-imidazo[1,2-a]pyridin-3-yl]-phenyl}-3-(2,2,2-trifluoro-ethyl)-urea Hydrochloride | General route A, Procedure A1 and A2, procedure A3b using 1-[3-(4,4,5,5-Tetramethyl-[1,3,2]dioxaborolan-2-yl)-phenyl]-3-(2,2,2-trifluoro-ethyl)-urea (I6), procedure A4b using 3-fluorophenylboronic acid. Procedure J1. | 1H NMR (400 MHz, Me-d3-OD): 8.87 (1H, d), 8.21 (1H, s), 8.20-8.16 (1H, m), 8.09-8.01 (1H, m), 7.85 (1H, dd), 7.79-7.53 (4H, m), 7.49-7.38 (2H, m), 7.38-7.28 (1H, m), 4.03-3.89 (2H, m). | [M + H]+ 429 |
| 144 | 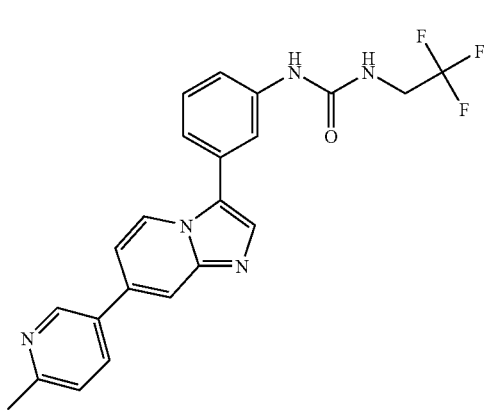 [SMILES: Cc1ccc(-c2ccn3c(-c4cccc(NC(=O)NCC(F)(F)F)c4)cnc3c2)cn1] | 1-{3-[7-(6-Methyl-pyridin-3-yl)-imidazo[1,2-a]pyridin-3-yl]-phenyl}-3-(2,2,2-trifluoro-ethyl)-urea Formate | General route A, Procedure A1 and A2, procedure A3b using 1-[3-(4,4,5,5-Tetramethyl-[1,3,2]dioxaborolan-2-yl)-phenyl]-3-(2,2,2-trifluoro-ethyl)-urea (I6), procedure A4b using 2-picoline-5-boronic acid | 1H NMR (400 MHz, Me-d3-OD): 8.85 (1H, d), 8.69 (1H, d), 8.19-8.13 (3H, m), 7.95 (1H, s), 7.91-7.75 (2H, m), 7.56-7.44 (2H, m), 7.41 (2H, dd), 7.33 (1H, d), 3.96 (2H, q), 2.62 (3H, s). | [M + H]+ 426 |

| Eg. No. | Compound | Chemical Name | Procedure | ¹H NMR Data | M.S. |
|---|---|---|---|---|---|
| 145 | | 1-(3-Amino-propyl)-3-{3-[6-(4-fluoro-phenyl)-pyrazolo[1,5-a]pyrimidin-3-yl]-phenyl}-urea | Preparation K, L using 4-fluorophenylboronic acid, M and N using (3-{3-[3-(4,4,5,5-Tetramethyl-[1,3,2]dioxaborolan-2-yl)-phenyl]-ureido}-propyl)-carbamic acid tert-butyl ester (I27), then procedure D3b | 1H NMR (400 MHz, DMSO-d6): 9.51 (1H, d), 9.01 (1H, d), 8.69 (1H, s), 8.57 (1H, s), 8.08 (1H, s), 7.95 (2H, dd), 7.64 (1H, d), 7.46 (1H, d), 7.40 (2H, t), 7.30 (1H, t), 6.20 (1H, t), 3.23-3.10 (2H, m), 2.61 (2H, t), 1.58-1.48 (2H, m). | [M + H]+ 405 |
| 146 | | [2-(3-{3-[6-(4-Fluoro-phenyl)-pyrazolo[1,5-a]pyrimidin-3-yl]-phenyl}-ureido)-ethyl]-carbamic acid tert-butyl ester | Preparation K, L using 4-fluorophenylboronic acid, M and N using (2-{3-[3-(4,4,5,5-Tetramethyl-[1,3,2]dioxaborolan-2-yl)-phenyl]-ureido}-ethyl)-carbamic acid tert-butyl ester I26 | 1H NMR (400 MHz, DMSO-d6): 9.51 (1H, d), 9.02 (1H, d), 8.69 (1H, s), 8.64 (1H, s), 8.10 (1H, s), 7.95 (2H, dd), 7.64 (1H, d), 7.49-7.35 (3H, m), 7.31 (1H, t), 6.87 (1H, t), 6.27-6.18 (1H, m), 3.21-3.10 (2H, m), 3.08-2.98 (2H, m), 1.40 (9H, s). | [M + H]+ 491.16 |
| 147 | | 1-Ethyl-3-{3-[7-(1H-pyrazol-4-yl)-imidazo[1,2-a]pyridin-3-yl]-phenyl}-urea Hydrochloride | General Route A, Procedure A1 and A2, Procedure A3b using 3-aminobenzeneboronic acid, general modification F1a, procedure A4b using 4-(4,4,5,5-tetramethyl-1,3,2-dioxaborolan-2-yl)-pyrazole-1-carboxylic acid tert-butyl ester, procedure J1 | 1H NMR (400 MHz, DMSO-d6): 8.90 (1H, s), 8.72 (1H, d), 8.51 (2H, s), 8.31 (1H, s), 8.09 (1H, s), 7.92 (1H, s), 7.83 (1H, d), 7.48 (2H, d), 7.25 (1H, d), 6.36 (1H, s), 3.13 (2H, d), 1.07 (3H, t). | [M + H]+ 347 |

| Eg. No. | Compound | Chemical Name | Procedure | ¹H NMR Data | M.S. |
|---|---|---|---|---|---|
| 148 | | 1-(2-Amino-ethyl)-3-{3-[6-(4-fluoro-phenyl)-pyrazolo[1,5-a]pyrimidin-3-yl]-phenyl}-urea | Preparation K, L using 4-fluorophenylboronic acid, M and N using (2-{3-[3-(4,4,5,5,-Tetramethyl-[1,3,2]dioxaborolan-2-yl)-phenyl]-ureido}-ethyl)-carbamic acid tert-butyl ester, then preparation D3b | 1H NMR (400 MHz, DMSO-d6): 9.50 (1H, d), 9.00 (1H, d), 8.77 (1H, s), 8.67 (1H, s), 8.11 (1H, s), 7.94 (2H, dd), 7.65 (1H, d), 7.49-7.34 (3H, m), 7.30 (1H, t), 6.38 (1H, s), 3.26-3.15 (2H, m), 2.80-2.69 (2H, m). | [M + H]+ 391.13 |
| 149 | | 1-[3-(7-Phenyl-imidazo[1,2-a]pyridin-3-yl)-phenyl]-3-(2,2,2-trifluoro-ethyl)-urea Hydrochloride | General route A, Procedure A1 and A2, procedure A3b using 1-[3-(4,4,5,5-Tetramethyl-[1,3,2]dioxaborolan-2-yl)-phenyl]-3-(2,2,2-trifluoro-ethyl)-urea (I6), procedure A4b using phenylboronic acid. Procedure J1. | 1H NMR (400 MHz, Me-d3-OD): 8.91-8.83 (1H, m), 8.19 (2H, s), 8.06 (1H, s), 7.91 (3H, dd), 7.68-7.54 (4H, m), 7.50-7.37 (2H, m), 4.02-3.91 (2H, m). | [M + H]+ 411 |
| 150 | | 1-(3-{7-[3-(Morpholine-4-carbonyl)-phenyl]-imidazo[1,2-a]pyridin-3-yl}-phenyl)-3-(2,2,2-trifluoro-ethyl)-urea Hydrochloride | General route A, Procedure A1 and A2, procedure A3b using 1-[3-(4,4,5,5-Tetramethyl-[1,3,2]dioxaborolan-2-yl)-phenyl]-3-(2,2,2-trifluoro-ethyl)-urea (I6), procedure A4b using N-morpholinyl 3-borono-benzamide. Procedure J1. | 1H NMR (400 MHz, Me-d3-OD): 8.90 (1H, d), 8.23 (2H, d), 8.11-7.95 (3H, m), 7.90 (1H, dd), 7.78-7.70 (1H, m), 7.70-7.54 (2H, m), 7.50-7.37 (2H, m), 3.96 (2H, q), 3.77 (6H, s), 3.60-3.49 (2H, m). | [M + H]+ 524 |

| Eg. No. | Compound | Chemical Name | Procedure | ¹H NMR Data | M.S. |
|---|---|---|---|---|---|
| 151 | | 1-{3-[6-(2-Methoxy-pyrimidin-5-yl)-pyrazolo[1,5-a]pyrimidin-3-yl]-phenyl}-3-(2,2,2-trifluoro-ethyl)-urea | Preparation K using 2-chloro-malonaldehyde; Preparation M; Preparation N using boronic ester I6. Procedure A4b using 5-methoxypyrimidine-2-boronic acid | 1H NMR (400 MHz, DMSO-d6): 9.65 (1H, d), 9.14 (2H, s), 9.06 (1H, d), 8.86 (1H, s), 8.74 (1H, s), 8.16 (1H, s), 7.69 (1H, d), 7.45 (1H, d), 7.35 (1H, t), 6.74 (1H, t), 4.01 (3H, s), 4.00-3.91 (2H, m). | [M + H]+ 444 |
| 152 | | 1-{3-[6-(2-Methyl-pyridin-4-yl)-pyrazolo[1,5-a]pyrimidin-3-yl]-phenyl}-3-(2,2,2-trifluoro-ethyl)-urea Hydrochloride | Preparation K using 2-chloro-malonaldehyde; Preparation M; Preparation N using boronic ester I6, procedure A4b using 2-methylpyridine-4-boronic acid pinacol ester, Procedure J1 | 1H NMR (400 MHz, DMSO-d6): 9.99 (1H, d), 9.26 (1H, d), 9.04 (1H, s), 8.91-8.82 (2H, m), 8.48 (1H, s), 8.38 (1H, d), 8.22 (1H, s), 7.70 (1H, d), 7.45-7.31 (2H, m), 6.92 (1H, t), 4.03-3.89 (2H, m), 2.78 (3H, s). | [M + H]+ 427 |
| 153 | | 1-[3-(6-Phenyl-pyrazolo[1,5-a]pyrimidin-3-yl)-phenyl]-3-(2,2,2-trifluoro-ethyl)-urea | Preparation K using 2-chloro-malonaldehyde; Preparation M; Preparation N using boronic ester I6, procedure A4b using phenylboronic acid | 1H NMR (400 MHz, Me-d3-OD): 9.28-9.21 (1H, m), 9.03-8.96 (1H, m), 8.62 (1H, s), 8.22 (1H, s), 7.83 (3H, d), 7.64-7.47 (3H, m), 7.40 (2H, d), 3.99 (2H, q). | [M + H]+ 412 |

-continued

| Eg. No. | Compound | Chemical Name | Procedure | ¹H NMR Data | M.S. |
|---|---|---|---|---|---|
| 154 | | 1-[3-(6-Pyrimidin-5-yl-pyrazolo[1,5-a]pyrimidin-3-yl)-phenyl]-3-(2,2,2-trifluoro-ethyl)-urea | Preparation K using 2-chloro-malonaldehyde; Preparation M; Preparation N using boronic ester I6. Procedure A4b using pyrimidin-5-boronic acid | 1H NMR (400 MHz, DMSO-d6): 9.76 (1H, d), 9.36 (2H, s), 9.28 (1H, s), 9.13 (1H, d), 8.91 (1H, s), 8.78 (1H, s), 8.17 (1H, s), 7.70 (1H, d), 7.46 (1H, d), 7.35 (1H, t), 6.79 (1H, t), 4.01-3.91 (2H, m). | [M + H]+ 414 |
| 155 | | 1-{3-[6-(1H-Pyrazol-4-yl)-pyrazolo[1,5-a]pyrimidin-3-yl]-phenyl}-3-(2,2,2-trifluoro-ethyl)-urea Hydrochloride | Preparation K using 2-chloro-malonaldehyde; Preparation M; Preparation N using boronic ester I6. Procedure A4e using 4-(4,4,5,5-tetramethyl-1,3,2-dioxaborolan-2-yl)-1h-pyrazole. Procedure J1. | 1H NMR (400 MHz, DMSO-d6): 9.48 (1H, d), 9.02 (1H, d), 8.91 (1H, s), 8.69-8.59 (1H, m), 8.33 (2H, s), 8.17-8.09 (1H, m), 7.67 (1H, d), 7.47-7.38 (1H, m), 7.33 (1H, t), 6.85-6.75 (1H, m), 4.02-3.90 (2H, m). | [M + H]+ 402 |
| 156 | | 1-{3-[6-(2-Amino-pyrimidin-5-yl)-pyrazolo]1,5-a]pyrimidin-3-yl]-phenyl}-3-(2,2,2-trifluoro-ethyl)-urea Hydrochloride | Preparation K using 2-chloro-malonaldehyde; Preparation M; Preparation N using boronic ester I6, procedure A4b using 2-aminopyrimidine-5-boronic acid, Procedure J1 | 1H NMR (400 MHz, DMSO-d6): 9.49 (1H, d), 8.98 (1H, d), 8.88 (1H, s), 8.78 (2H, s), 8.68 (1H, m), 8.13 (1H, s), 7.68 (1H, d), 7.44 (1H, d), 7.34 (1H, t), 7.10 (2H, br), 6.77 (1H, t), 3.98 (2H, m). | [M + H]+ 429 |
| 157 | | 3-[5-(4-Fluoro-phenyl)-benzoimidazol-1-yl]-phenylamine | General procedure O using Procedure O1, then O2, Then O3 and then O4 | 1H NMR (400 MHz, DMSO-d6): 8.52 (1H, s), 8.01 (1H, s), 7.78 (2H, dd), 7.68 (1H, d), 7.62 (1H, d), 7.37-7.20 (3H, m), 6.84 (1H, s), 6.76 (1H, d), 6.68 (1H, d), 5.52 (2H, s). | [M + H]+ 304.08 |

-continued

| Eg. No. | Compound | Chemical Name | Procedure | ¹H NMR Data | M.S. |
|---|---|---|---|---|---|
| 158 | | 1-{3-[6-(1-Methyl-6-oxo-1,6-dihydro-pyridin-3-yl)-pyrazolo[1,5-a]pyrimidin-3-yl]-phenyl}-3-(2,2,2-trifluoro-ethyl)-urea | Preparation K using 2-chloro-malonaldehyde; Preparation M; Preparation N using boronic ester I6, procedure A4b using boronic acid I3 | 1H NMR (400 MHz, DMSO-d6): 9.41 (1H, s), 8.95 (1H, s), 8.84 (1H, s), 8.68 (1H, s), 8.39 (1H, s), 8.15 (1H, s), 8.00 (1H, d), 7.68 (1H, d), 7.42 (1H, d), 7.34 (1H, t), 6.80-6.70 (1H, m), 6.56 (1H, d), 4.04-3.89 (2H, m), 3.55 (3H, s). | [M + H]+ 443 |
| 159 | | 1-Ethyl-3-{3-[5-(4-fluoro-phenyl)-benzoimidazol-1-yl]-phenyl}-urea Hydrochloride | General procedure O using Procedure O1, then O2, Then O3 and then O4, Preparation F1a, Procedure O6 | 1H NMR (400 MHz, DMSO-d6): 9.26 (1H, s), 9.03 (1H, s), 8.09 (1H, s), 8.07-7.99 (1H, m), 7.87-7.76 (4H, m), 7.52 (1H, t), 7.43 (1H, d), 7.34 (2H, t), 7.27 (1H, d), 6.39 (1H, s), 3.13 (2H, q), 1.07 (3H, t). | [M + H]+ 375.12 |
| 160 | | 4-[3-(3-{3-[3-(2,2,2-Trifluoro-ethyl)-ureido]-phenyl}-pyrazolo[1,5-a]pyrimidin-6-yl)-phenoxy]-piperidine-1-carboxylic acid tert-butyl ester | Preparation K using 2-chloro-malonaldehyde; Preparation M; Preparation N using boronic ester I6, procedure A4b using I22 and 2'-(dimethylamino)-2-biphenylyl-palladium(ii) chloride dinorbornyl-phosphone complex as catalyst | 1H NMR (400 MHz, DMSO-d6): 9.54 (1H, d), 9.04 (1H, d), 8.85 (1H, s), 8.72 (1H, s), 8.15 (1H, s), 7.70 (1H, d), 7.53-7.40 (4H, m), 7.34 (1H, t), 7.07 (1H, d), 6.76 (1H, t), 4.79-4.71 (1H, m), 4.02-3.91 (2H, m), 3.77-3.66 (2H, m), 3.22 (2H, t), 1.98 (2H, d), 1.63-1.51 (2H, m), 1.42 (9H, s). | [M + H]+ 611 |

| Eg. No. | Compound | Chemical Name | Procedure | $^1$H NMR Data | M.S. |
|---|---|---|---|---|---|
| 161 | | 1-Ethyl-3-[3-(6-pyridin-2-yl-pyrazolo[1,5-a]pyrimidin-3-yl)-phenyl]-urea | Preparation K using 2-(2-pyridyl)malondialdehyde, Preparation M; Preparation N using boronic ester I9 | 1H NMR (400 MHz, DMSO-d6): 9.77 (1H, d), 9.38 (1H, d), 8.79-8.70 (2H, m), 8.52 (1H, s), 8.22 (1H, d), 8.07 (1H, s), 7.99 (1H, t), 7.65 (1H, d), 7.53-7.42 (2H, m), 7.31 (1H, t), 6.13 (1H, t), 3.20-3.08 (2H, m), 1.08 (3H, t). | [M + H]+ 359 |
| 162 | | 1-Ethyl-3-{3-[7-(5-methyl-furan-2-yl)-imidazo[1,2-a]pyridin-3-yl]-phenyl}-urea | General Route A, Procedure A1 an A2, Procedure A3b using 3-aminobenzeneboronic acid, general modification F1a, procedure A4b using 5-methylfuran-2-boronic acid | 1H NMR (400 MHz, DMSO-d6): 8.88 (1H, s), 8.71 (1H, d), 8.31 (1H, s), 7.95 (1H, s), 7.90 (1H, s), 7.75 (1H, d), 7.53-7.41 (3H, m), 7.28-7.20 (1H, m), 6.43 (1H, d), 6.34 (1H, d), 3.18-3.08 (2H, m), 2.44 (3H, s), 1.07 (3H, t). | [M + H]+ 361 |
| 163 | | 1-(3-{6-[3-(Piperidin-4-yloxy)-phenyl]-pyrazolo[1,5-a]pyrimidin-3-yl}-phenyl)-3-(2,2,2-trifluoro-ethyl)-urea hydrochloride salt | Preparation K using 2-chloro-malonaldehyde; Preparation M; Preparation N using boronic ester I6, procedure A4b using I22 and 2'-(dimethyl-amino)-2-biphenylyl-palladium(ii) chloride dinorbornylphosphine complex as catalyst, procedure D3a | 1H NMR (400 MHz, DMSO-d6): 9.54 (1H, d), 9.09-9.02 (1H, m), 8.89 (1H, s), 8.75-8.69 (1H, m), 8.65-8.55 (2H, m), 8.18 (1H, s), 7.71 (1H, d), 7.56-7.44 (3H, m), 7.41-7.31 (2H, m), 7.10 (1H, d), 6.80 (1H, t), 4.86-4.80 (1H, m), 4.01-3.91 (2H, m), 3.31 (2H, br m), 3.17-3.07 (2H, m), 2.22-2.12 (2H, m), 1.94-1.83 (2H, m). | [M + H]+ 511 |

-continued

| Eg. No. | Compound | Chemical Name | Procedure | ¹H NMR Data | M.S. |
|---|---|---|---|---|---|
| 164 | | 1-{3-[7-(4-Acetyl-piperazin-1-yl)-imidazo[1,2-a]pyridin-3-yl]-phenyl}-3-(2,2,2-trifluoro-ethyl)-urea hydrochloride salt | General route B, procedure B1b using N-acylpiperazine, procedure B2, procedure B3a using I6 1-[3-(4,4,5,5-Tetramethyl-[1,3,2]dioxaborolan-2-yl)-phenyl]-3-(2,2,2-trifluoro-ethyl)-urea. Procedure J1. | 1H NMR (400 MHz, DMSO-d6): 13.55 (1H, s), 9.41 (1H, s), 8.45 (1H, d), 8.02 (1H, s), 7.84 (1H, s), 7.49 (2H, m), 7.35-7.20 (2H, m), 7.11 (1H, t), 6.88 (1H, d), 3.95 (2H, q), 3.84-3.69 (4H, m), 3.50-3.27 (4H, m), 2.18 (3H, s) | [M + H]+ 461 |
| 165 | | 1-(3-{6-[3-(Morpholine-4-carbonyl)-phenyl]-pyrazolo[1,5-a]pyrimidin-3-yl}-phenyl)-3-(2,2,2-trifluoro-ethyl)-urea | Preparation K - using 2-chloro-malonaldehyde; Preparation M; Preparation N using boronic ester I6, procedure A4b using N-morpholinyl 3-boronobenzamide | 1H NMR (400 MHz, DMSO-d6): 9.58 (1H, d), 9.06 (1H, d), 8.89-8.82 (1H, m), 8.73 (1H, s), 8.14 (1H, s), 8.03-7.90 (2H, m), 7.75-7.58 (2H, m), 7.47 (2H, dd), 7.35 (1H, t), 6.75 (1H, t), 4.03-3.90 (2H, m), 3.59 (8H, br s). | [M + H]+ 525 |
| 166 | | 4-[4-(3-{3-[3-(2,2,2-Trifluoro-ethyl)-ureido]-phenyl}-pyrazolo[1,5-a]pyrimidin-6-yl)-phenoxy]-piperidine-1-carboxylic acid tert-butyl ester | Preparation K - using 2-chloro-malonaldehyde; Preparation M; Preparation N using boronic ester I6, procedure A4b using I15 and 2'-(dimethylamino)-2-biphenylyl-palladium(II) chloride dinorbornyl-phosphine complex as catalyst | 1H NMR (400 MHz, DMSO-d6): 9.44 (1H, d), 9.01 (1H, d), 8.90 (1H, s), 8.68 (1H, s), 8.13 (1H, s), 7.82 (2H, d), 7.69 (1H, d), 7.45 (1H, d), 7.34 (1H, t), 7.15 (2H, d), 6.81 (1H, t), 4.71-4.65 (1H, m), 4.01-3.91 (2H, m), 3.74-3.64 (2H, m), 3.28-3.16 (2H, m), 1.95 (2H, s), 1.62-1.51 (2H, m), 1.42 (9H, s). | [M + H]+ 611 |

-continued

| Eg. No. | Compound | Chemical Name | Procedure | ¹H NMR Data | M.S. |
|---|---|---|---|---|---|
| 167 | | 3-[6-(4-Fluoro-phenyl)-imidazo[4,5-b]pyridin-3-yl]-phenylamine | Preparation P3, | 1H NMR (400 MHz, DMSO-d6): 8.82 (1H, s), 8.71 (1H, d), 8.45 (1H, d), 7.85 (2H, dd), 7.35 (2H, t), 7.23 (1H, t), 7.14 (1H, t), 6.97 (1H, d), 6.66 (1H, d), 5.47 (2H, s). | [M + H]+ 305.03 |
| 168 | | 1-{3-[6-(3-Fluoro-phenyl)-pyrazolo[1,5-a]pyrimidin-3-yl]-phenyl}-3-(2,2,2-trifluoro-ethyl)-urea | Preparation K, preparation L using 3-fluorophenylboronic acid, preparation M, Preparation N using boronic ester I6 | 1H NMR (400 MHz, Me-d3-OD): 10.41 (1H, d), 9.88 (1H, d), 9.72 (1H, s), 9.55 (1H, s), 8.95 (1H, s), 8.69-8.55 (2H, m), 8.51 (1H, d), 8.41 (1H, q), 8.27 (1H, d), 8.21-8.08 (2H, m), 7.62 (1H, t), 4.81-4.71 (2H, m). | [M + H]+ 430 |
| 169 | | 1-Ethyl-3-{3-[6-(4-fluoro-phenyl)-imidazo[4,5-b]pyridin-3-yl]-phenyl}-urea | Preparation P3, Preparation F1a, Procedure O6 | 1H NMR (400 MHz, DMSO-d6): 8.96 (1H, s), 8.86 (1H, s), 8.74 (1H, d), 8.48 (1H, d), 8.06 (1H, s), 7.86 (2H, dd), 7.54-7.42 (2H, m), 7.42-7.31 (3H, m), 6.28 (1H, brs), 3.13 (2H, q), 1.08 (3H, t). | [M + H]+ 376.11 |
| 170 | | 1-[3-(6-Pyridin-2-yl-pyrazolo[1,5-a]pyrimidin-3-yl)-phenyl]-3-(2,2,2-trifluoro-ethyl)-urea | Preparation K - using 2-(2-pyridyl)malondi-aldehyde, Preparation M; Preparation N using boronic ester I6 | 1H NMR (400 MHz, DMSO-d6): 9.77 (1H, d), 9.39 (1H, d), 8.88 (1H, s), 8.76 (2H, d), 8.23 (1H, d), 8.12 (1H, s), 8.02-7.96 (1H, m), 7.71 (1H, d), 7.51-7.44 (2H, m), 7.36 (1H, t), 6.77 (1H, t), 4.01-3.92 (2H, m). | [M + H]+ 413 |

-continued

| Eg. No. | Compound | Chemical Name | Procedure | ¹H NMR Data | M.S. |
|---|---|---|---|---|---|
| 171 | | 1-{3-[7-(6-Amino-pyridin-3-yl)-imidazo[1,2-a]pyridin-3-yl]-phenyl}-3-(2,2,2-trifluoro-ethyl)-urea hydrochloride salt | general route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 2-amino-5-(4,4,5,5-tetramethyl-1,3,2-dioxaborolan-2-yl) pyridine, Procedure J1 | 1H NMR (400 MHz, DMSO-d6): 9.49 (1H, s), 8.82 (1H, d), 8.69 (1H, d), 8.51 (1H, dd), 8.39 (1H, s), 8.25 (3H, m), 7.92 (1H, s), 7.82 (1H, d), 7.54 (2H, d), 7.31 (1H, t), 7.20-7.08 (2H, m), 3.95 (2H, m). | [M + H]+ 427 |
| 172 | | 1-(3-{6-[4-(Piperidin-4-yloxy)-phenyl]-pyrazolo[1,5-a]pyrimidin-3-yl}-phenyl)-3-(2,2,2-trifluoro-ethyl)-urea | Preparation K - using 2-chloro-malonaldehyde; Preparation M; Preparation N using boronic ester I6, procedure A4b using I15 and 2'-(dimethyl-amino)-2-biphenylyl-palladium(II) chloride dinorbornylphosphine complex as catalyst, procedure D3a | 1H NMR (400 MHz, DMSO-d6): 9.45 (1H, s), 9.02 (1H, s), 8.89-8.73 (3H, m), 8.68 (1H, d), 8.15 (1H, s), 7.85 (2H, d), 7.70 (1H, d), 7.46-7.28 (2H, m), 7.18 (2H, d), 6.86 (1H, m), 4.77 (1H, m), 4.04-3.89 (2H, m), 3.27 (2H, m), 3.11 (2H, m), 2.15 (2H, m), 1.89 (2H, m). | [M + H]+ 511 |
| 173 | | 1-Ethyl-3-{2-[6-(4-fluoro-phenyl)-pyrazolo[1,5-a]pyrimidin-3-yl]-pyridin-4-yl}-urea | Procedure V3b | 1H NMR (400 MHz, DMSO-d6): 9.56 (1H, d), 9.13-9.03 (2H, m), 8.81 (1H, s), 8.34 (1H, d), 8.31 (1H, d), 7.97 (2H, dd), 7.51 (1H, dd), 7.41 (2H, t), 6.29 (1H, t), 3.23-3.09 (2H, m), 1.09 (3H, t). | [M + H]+ 377.12 |

| Eg. No. | Compound | Chemical Name | Procedure | ¹H NMR Data | M.S. |
|---|---|---|---|---|---|
| 174 | | 1-{3-[7-(6-Fluoro-pyridin-3-yl)-imidazo[1,2-a]pyridin-3-yl]-phenyl}-3-(2,2,2-trifluoro-ethyl)-urea | general route A, procedure A3b using 1-[3-(4,4,5,5-Tetramethyl-[1,3,2]dioxaborolan-2-yl)-phenyl]-3-(2,2,2-trifluoro-ethyl)-urea (I6), procedure A4b using 2-fluoropyridine-5-boronic acid | 1H NMR (400 MHz, Me-d3-OD): 8.74-8.62 (2H, m), 8.44-8.33 (1H, m), 7.97-7.83 (2H, m), 7.78 (1H, s), 7.50 (1H, t), 7.46-7.20 (4H, m), 3.96 (2H, q) | [M + H]+ 430 |
| 175 | | 1-{3-[5-(4-Fluoro-phenyl)-benzoimidazol-1-yl]-phenyl}-3-(2,2,2-trifluoro-ethyl)-urea | Procedure O5 | 1H NMR (400 MHz, DMSO-d6): 9.12 (1H, s), 8.61 (1H, s), 8.04 (1H, s), 7.91 (1H, t), 7.85-7.76 (2H, m), 7.72 (1H, d), 7.65 (1H, dd), 7.52 (1H, t), 7.44 (1H, d), 7.37-7.24 (3H, m), 6.91 (1H, t), 4.03-3.89 (2H, m). | [M + H]+ 429.08 |
| 176 | | 1-{3-[7-(4-Ethanesulfonyl-piperazin-1-yl)-imidazo[1,2-a]pyridin-3-yl]-phenyl}-3-ethyl-urea hydrochloride salt | General route B, procedure B1b using 1-ethanesulfonylpiperazine, procedure B2, procedure B3a using 1-Ethyl-3-[3-(4,4,5,5-tetramethyl-[1,3,2]dioxaborolan-2-yl)-phenyl]urea. Procedure J1. | 1H NMR (400 MHz, DMSO-d6): 9.03 (1H, s), 8.47 (1H, d), 8.03 (1H, s), 7.86 (1H, s), 7.44 (2H, m), 7.34 (1H, dd), 7.21-7.13 (1H, m), 6.95 (1H, d), 6.44 (1H, t), 3.64 (4H, s), 3.37 (4H, m), 3.16-3.06 (4H, m), 1.25 (3H, t), 1.06 (3H, t). | [M + H]+ 457 |

-continued

| Eg. No. | Compound | Chemical Name | Procedure | ¹H NMR Data | M.S. |
|---|---|---|---|---|---|
| 177 | | 1-{3-[7-(4-Ethanesulfonyl-piperazin-1-yl)-imidazo[1,2-a]pyridin-3-yl]-phenyl}-3-(2,2,2-trifluoro-ethyl)-urea hydrochloride salt | General route B, procedure B1b using 1-ethanesulfonylpiperazine, procedure B2, procedure B3a using I6 1-[3-(4,4,5,5-Tetramethyl-[1,3,2]dioxaborolan-2-yl)-phenyl]-3-(2,2,2-trifluoro-ethyl)-urea. Procedure J1. | 1H NMR (400 MHz, DMSO-d6): 9.37 (1H, s), 8.47 (1H, d), 8.04 (1H, s), 7.85 (1H, s), 7.49 (2H, d), 7.33 (1H, dd), 7.24 (1H, d), 7.08 (1H, t), 6.95 (1H, d), 4.01-3.87 (2H, m), 3.64 (5H, s), 3.38 (4H, s), 3.14 (2H, q), 1.25 (3H, t). | [M + H]+ 511 |
| 178 | | 1-{3-[6-(1H-Imidazol-2-yl)-pyrazolo[1,5-a]pyrimidin-3-yl]-phenyl}-3-(2,2,2-trifluoro-ethyl)-urea Hydrochloride | Preparation K - using 2-(1H-imidazol-2-yl)-malonaldehyde and 3-amino-4-bromopyrazole, Preparation N; using boronic ester I6. Procedure J1. | 1H NMR (400 MHz, DMSO-d6): 12.79 (1H, br s), 9.50 (1H, d), 9.21 (1H, d), 8.89 (1H, s), 8.71 (1H, s), 8.09 (1H, s), 7.68 (1H, d), 7.53-7.38 (2H, m), 7.35 (1H, t), 7.19-7.11 (1H, m), 6.77 (1H, t), 4.02-3.91 (2H, m). | [M + H]+ 402 |
| 179 | | 1-{3-[6-(4-Fluoro-imidazo[4,5-b]pyridin-3-yl]-phenyl}-3-(2,2,2-trifluoro-ethyl)-urea | Preparation P3 then procedures from Preparations O5 and O6 | 1H NMR (400 MHz, DMSO-d6): 9.11 (1H, s), 8.90 (1H, s), 8.73 (1H, d), 8.48 (1H, d), 8.09 (1H, s), 7.86 (2H, dd), 7.57-7.43 (3H, m), 7.36 (2H, t), 6.86 (1H, t), 4.02-3.89 (2H, m). | [M + H]+ 430.05 |

-continued

| Eg. No. | Compound | Chemical Name | Procedure | ¹H NMR Data | M.S. |
|---|---|---|---|---|---|
| 180 | | 1-{3-[6-(5-Methyl-furan-2-yl)-pyrazolo[1,5-a]pyrimidin-3-yl]-phenyl}-3-(2,2,2-trifluoro-ethyl)-urea | Preparation K - using 2-chloro-malonaldehyde; Preparation M; Preparation N using boronic ester I6, procedure A4d using 5-methylfuran-2-boronic acid | 1H NMR (400 MHz, DMSO-d6): 9.30 (1H, d), 9.00 (1H, d), 8.85 (1H, s), 8.67 (1H, s), 8.10 (1H, s), 7.67 (1H, d), 7.44 (1H, d), 7.34 (1H, t), 7.12 (1H, d), 6.75 (1H, t), 6.32 (1H, d), 4.02-3.90 (2H, m), 2.40 (3H, s). | [M + H]+ 416 |
| 181 | | {3-[7-(4-Fluoro-phenyl)-imidazo[1,2-a]pyridin-3-yl]-phenyl}-carbamic acid ethyl ester Hydrochloride | General route B procedure B1a using 4-fluorophenyl-boronic acid, procedure B2, procedure B3a using 3-aminobenzeneboronic acid, general modification F4 using ethyl chloroformate | 1H NMR (400 MHz, DMSO-d6): 9.80 (1H, s), 8.61 (1H, d), 8.03-7.97 (1H, m), 7.93 (2H, dd), 7.81 (2H, d), 7.56-7.44 (2H, m), 7.42-7.28 (4H, m), 4.16 (2H, q), 1.27 (3H, t). | [M + H]+ 376 |
| 182 | | 1-[3-(6-d5-Phenyl-pyrazolo[1,5-a]pyrimidin-3-yl)-phenyl]-3-(2,2,2-trifluoro-ethyl)-urea | Preparation K using 2-chloro-malonaldehyde; Preparation M; Preparation N using boronic ester I6, procedure A4b using phenyl-d5-boronic acid | 1H NMR (400 MHz, DMSO-d6): 9.52 (1H, d), 9.05 (1H, d), 8.85 (1H, s), 8.72 (1H, s), 8.14 (1H, s), 7.70 (1H, d), 7.46 (1H, d), 7.35 (1H, t), 6.75 (1H, t), 4.02-3.91 (2H, m). | [M + H]+ 417 |

-continued

| Eg. No. | Compound | Chemical Name | Procedure | ¹H NMR Data | M.S. |
|---|---|---|---|---|---|
| 183 | | 4-(3-{3-[3-(2,2,2-Trifluoro-ethyl)-ureido]-phenyl}-imidazo[1,2-a]pyridin-7-yl)-piperazine-1-carboxylic acid ethyl ester | General route B, procedure B1b using Ethyl piperazine-1-carboxylate, procedure B2, procedure B3a using I6 1-[3-(4,4,5,5-Tetramethyl-[1,3,2]dioxaborolan-2-yl)-phenyl]-3-(2,2,2-trifluoro-ethyl)-urea. | 1H NMR (400 MHz, Me-d3-OD): 8.39 (1H, d), 7.76 (1H, s), 7.49 (1H, s), 7.44 (1H, t), 7.39-7.30 (1H, m), 7.25 (1H, d), 6.93 (1H, dd), 6.80 (1H, d), 4.19 (2H, q), 3.95 (2H, q), 3.68 (4H, s), 3.54-3.36 (4H, m), 1.31 (3H, t). | [M + H]+ 491 |
| 184 | | 1-{3-[7-(3-Morpholin-4-ylmethyl-phenyl)-imidazo[1,2-a]pyridin-3-yl]-phenyl}-3-(2,2,2-trifluoro-ethyl)-urea Hydrochloride | general route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-[3-(4,4,5,5-tetramethyl-1,3,2-dioxaborolan-2-yl)benzyl]morpholine, Procedure J1 | 1H NMR (400 MHz, DMSO-d6): 11.9 (1H, brs) 9.52 (1H, s), 8.86 (1H, d), 8.44-8.30 (3H, m), 8.03 (1H, d), 7.92 (2H, d), 7.75 (1H, d), 7.69 (1H, t), 7.60-7.50 (2H, m), 7.33 (1H, d), 7.17 (1H, t), 4.47 (2H, s), 4.03-3.83 (6H, m), 3.26 (2H, s), 3.16 (2H, s). | [M + H]+ 510 |
| 185 | | 1-Ethyl-3-{5-[7-(4-fluoro-phenyl)-imidazo[1,2-a]pyridin-3-yl]-pyridin-3-yl}-urea Hydrochloride | General route B, procedure B1a using 4-fluorophenyl-boronic acid, procedure W using 3-amino-5-bromopyridine, procedure F1a. Procedure J1 | 1H NMR (400 MHz, Me-d3-OD): 8.65 (1H, d), 8.54 (1H, d), 8.46 (1H, d), 8.39 (1H, t), 7.91-7.79 (4H, m), 7.39 (1H, dd), 7.28 (2H, t), 3.29 (2H, q), 1.20 (3H, t). | [M + H]+ 376 |

| Eg. No. | Compound | Chemical Name | Procedure | ¹H NMR Data | M.S. |
|---|---|---|---|---|---|
| 186 | | 1-(2,2-Dimethyl-[1,3]dioxolan-4-ylmethyl)-3-{3-[7-(4-fluoro-phenyl)-imidazo[1,2-a]pyridin-3-yl]-phenyl}-urea | General route B procedure B1a using 4-fluorophenyl-boronic acid, procedure B2, procedure B3a using 3-aminobenzeneboronic acid, procedure R1 | 1H NMR (400 MHz, Me-d3-OD): 8.65 (1H, d), 7.88-7.80 (4H, m), 7.73 (1H, s), 7.48 (1H, t), 7.40-7.23 (5H, m), 4.31-4.24 (1H, m), 4.09 (1H, dd), 3.74 (1H, dd), 3.52-3.42 (2H, m), 1.45 (3H, s), 1.39-1.33 (3H, m). | [M+H]+ 461 |
| 187 | | 1-(2,3-Dihydroxy-propyl)-3-{3-[7-(4-fluoro-phenyl)-imidazo[1,2-a]pyridin-3-yl]-phenyl}-urea Hydrochloride | General route B procedure B1a using 4-fluorophenyl-boronic acid, procedure B2, procedure B3a using 3-aminobenzeneboronic acid, procedure R1 then R2 | 1H NMR (400 MHz, Me-d3-OD): 8.65 (1H, d), 7.88-7.78 (4H, m), 7.73 (1H, s), 7.47 (1H, t), 7.42-7.22 (5H, m), 3.80-3.71 (1H, m), 3.57 (2H, d), 3.49-3.42 (2H, m). | [M+H]+ 421 |
| 188 | | 1-{3-[7-(4-Fluoro-phenyl)-imidazo[1,2-a]pyridin-3-yl]-phenyl}-3-isobutyl-urea Hydrochloride | General route B procedure B1a using 4-fluorophenyl-boronic acid, procedure B2, procedure B3a using 3-aminobenzeneboronic acid, procedure R1 using isobutylamine | 1H NMR (400 MHz, Me-d3-OD): 8.65 (1H, d), 7.88-7.77 (4H, m), 7.73 (1H, s), 7.47 (1H, t), 7.40-7.21 (5H, m), 3.07 (2H, d), 1.88-1.77 (1H, m), 0.98 (6H, d). | [M+H]+ 403 |

| Eg. No. | Compound | Chemical Name | Procedure | ¹H NMR Data | M.S. |
|---|---|---|---|---|---|
| 189 | | 1-{3-[6-(3-Morpholin-4-ylmethyl-phenyl)-pyrazolo[1,5-a]pyrimidin-3-yl]-phenyl}-3-(2,2,2-trifluoro-ethyl)-urea Hydrochloride | Preparation K - using 2-chloro-malonaldehyde; Preparation M; Preparation N using boronic ester I6, procedure A4b using 4-[3-(4,4,5,5-tetramethyl-1,3,2-dioxaborolan-2-yl)benzyl]morpholine and 2'-(dimethylamino)-2-biphenylyl-palladium(II) chloride dinorbornylphosphine complex as catalyst, Procedure J1 | 1H NMR (400 MHz, DMSO-d6): 11.12 (1H, s), 9.59 (1H, d), 9.14 (1H, d), 8.96 (1H, s), 8.74 (1H, s), 8.20 (2H, d), 8.01 (1H, d), 7.74-7.59 (3H, m), 7.44 (1H, d), 7.35 (1H, t), 6.82 (1H, t), 4.44 (2H, s), 4.04-3.90 (4H, m), 3.83 (2H, t), 3.32 (2H, m), 3.17 (2H, m). | [M + H]+ 511 |
| 190 | | (±)-1-{3-[7-(4-Fluoro-phenyl)-imidazo[1,2-a]pyridin-3-yl]-phenyl}-3-(tetrahydro-furan-2-ylmethyl)-urea Hydrochloride | General route B procedure B1a using 4-fluorophenyl-boronic acid, procedure B2, procedure B3a using 3-aminobenzeneboronic acid, procedure R1 using tetrahydrofurfurylamine. Procedure J1. | 1H NMR (400 MHz, Me-d3-OD): 8.65 (1H, d), 7.89-7.78 (4H, m), 7.74 (1H, s), 7.47 (1H, t), 7.36 (2H, d), 7.32-7.21 (3H, m), 4.08-3.98 (1H, m), 3.98-3.86 (1H, m), 3.79 (1H, q), 3.42 (2H, dd), 2.09-1.90 (3H, m), 1.72-1.62 (1H, m). | [M + H]+ 431 |
| 191 | | 1-(3-Amino-2,2-dimethyl-propyl)-3-{3-[7-(4-fluoro-phenyl)-imidazo[1,2-a]pyridin-3-yl]-phenyl}-urea Hydrochloride | General route B procedure B1a using 4-fluorophenyl-boronic acid, procedure B2, procedure B3a using 3-aminobenzeneboronic acid, procedure R1 using 2,2-dimethyl-1,3-propanediamine. Procedure J1. | 1H NMR (400 MHz, DMSO-d6): 9.67-9.59 (1H, m), 8.61 (1H, d), 8.29 (2H, s), 7.99 (1H, s), 7.92 (2H, dd), 7.84 (1H, s), 7.78 (1H, s), 7.51-7.30 (6H, m), 7.22 (1H, d), 3.03 (2H, d), 2.59 (2H, s), 0.92 (6H, s). | [M + H]+ 432 |

| Eg. No. | Compound | Chemical Name | Procedure | ¹H NMR Data | M.S. |
|---|---|---|---|---|---|
| 192 | | {3-[7-(4-Fluoro-phenyl)-imidazo[1,2-a]pyridin-3-yl]-phenyl}-carbamic acid 2,2,2-trifluoro-ethyl ester | General route B procedure B1a using 4-fluorophenyl-boronic acid, procedure B2, procedure B3a using 3-aminobenzeneboronic acid, procedure R1 using trifluoroethanol | 1H NMR (400 MHz, Me-d3-OD): 8.63 (1H, d), 7.88-7.80 (4H, m), 7.74 (1H, s), 7.54 (2H, d), 7.41-7.33 (2H, m), 7.30-7.24 (2H, m), 4.72 (2H, q). | [M + H]+ 430 |
| 193 | | 1-(3-{7-[3-(1-Acetyl-piperidin-4-yloxy)-phenyl]-imidazo[1,2-a]pyridin-3-yl}-phenyl)-3-(2,2,2-trifluoro-ethyl)-urea Formate | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using I22, procedure D3, procedure T | 1H NMR (400 MHz, DMSO-d6): 12.85-12.59 (1H, m), 8.97 (1H, s), 8.61 (1H, d), 8.14 (1H, s), 8.03 (1H, s), 7.80 (2H, s), 7.50-7.35 (5H, m), 7.32-7.24 (1H, m), 7.09-7.01 (1H, m), 6.86 (1H, t), 4.85-4.77 (1H, m), 4.01-3.83 (3H, m), 3.76-3.66 (1H, m), 3.43-3.22 (2H, m), 2.08-1.98 (4H, m), 1.94 (1H, s), 1.71-1.50 (2H, m). | [M + H]+ 552 |
| 194 | | 1-{3-[7-(4-Fluoro-phenyl)-imidazo[1,2-a]pyridin-3-yl]-phenyl}-3-(2,2,2-trifluoro-ethyl)-sulfamoylurea | General route B procedure B1a using 4-fluorophenyl-boronic acid, procedure B2, procedure B3a using 3-aminobenzeneboronic acid, procedure R1 using (2,2,2-Trifluoroethyl)sulfamoyl)chloride (Procedure XX) | 1H NMR (400 MHz, Me-d3-OD): 8.59 (1H, d), 7.90-7.72 (4H, m), 7.60-7.47 (2H, m), 7.37 (2H, t), 7.32-7.20 (3H, m), 3.71 (2H, q). | [M + H]+ 465 |

-continued

| Eg. No. | Compound | Chemical Name | Procedure | ¹H NMR Data | M.S. |
|---|---|---|---|---|---|
| 195 | | (±)-1-{3-[7-(4-Fluorophenyl)-imidazo[1,2-a]pyridin-3-yl]-phenyl}-3-(2-methoxypropyl)-urea Hydrochloride | General route B procedure B1a using 4-fluorophenyl-boronic acid, procedure B2, procedure B3a using 3-aminobenzeneboronic acid, procedure R1 using 2-methoxy-1-propanamine hydrochloride. Procedure J1. | 1H NMR (400 MHz, Me-d3-OD): 8.85 (1H, d), 8.16 (2H, s), 8.03 (1H, s), 8.01-7.91 (2H, m), 7.83 (1H, dd), 7.69-7.51 (1H, m), 7.45-7.30 (4H, m), 3.56-3.47 (1H, m), 3.44-3.37 (4H, m), 3.26-3.11 (1H, m), 1.19 (3H, d). | [M + H]+ 419 |
| 196 | | (±)-1-{3-[7-(4-Fluorophenyl)-imidazo[1,2-a]pyridin-3-yl]-phenyl}-3-piperidin-2-ylmethyl-urea Hydrochloride | General route B procedure B1a using 4-fluorophenyl-boronic acid, procedure B2, procedure B3a using 3-aminobenzeneboronic acid, procedure R1 using 2-(aminomethyl)-1-N-BOC-piperidine, procedure D3a | 1H NMR (400 MHz, Me-d3-OD): 8.85 (1H, dd), 8.16 (2H, s), 8.01-7.88 (3H, m), 7.82 (1H, d), 7.68-7.54 (2H, m), 7.47-7.31 (3H, m), 4.78-4.69 (1H, m), 4.04 (1H, d), 3.52-3.36 (3H, m), 3.17-2.92 (1H, m), 2.03-1.52 (6H, m). | [M + H]+ 444 |
| 197 | | 1-Ethyl-3-{5-[6-(4-fluorophenyl)-pyrazolo[1,5-a]pyrimidin-3-yl]-pyridin-3-yl}-urea | Procedure K1, general route V, procedure V1, procedure V2, procedure V3b using 1-(5-bromopyridin-3-yl)-3-ethyl urea from procedure U2. | 1H NMR (400 MHz, Me-d3-OD): 9.23 (1H, s), 9.03-8.99 (1H, m), 8.98 (1H, s), 8.74 (1H, s), 8.69 (1H, s), 8.55 (1H, br s), 7.88-7.78 (2H, m), 7.37-7.26 (2H, m), 3.30 (2H, q), 1.21 (3H, t). | [M + H]+ 377.17 |

| Eg. No. | Compound | Chemical Name | Procedure | ¹H NMR Data | M.S. |
|---|---|---|---|---|---|
| 198 | | 1-{5-[6-(4-Fluoro-phenyl)-pyrazolo[1,5-a]pyrimidin-3-yl]-pyridin-3-yl}-3-(2,2,2-trifluoro-ethyl)-urea | Procedure K1, general route V, procedure V1, procedure V2, procedure V3b using 1-(5-bromo-pyridin-3-yl)-3-(2,2,2-trifluoroethyl)-urea from procedure U3. | 1H NMR (400 MHz, DMSO-d6): 9.56 (1H, d), 9.07 (2H, d), 8.91 (1H, d), 8.85 (1H, s), 8.64 (1H, t), 8.54 (1H, d), 8.00-7.92 (2H, m), 7.44-7.36 (2H, m), 6.91 (1H, t), 4.02-3.93 (2H, m). | [M + H]+ 431 |
| 199 | | 1-{2-[6-(4-Fluoro-phenyl)-pyrazolo[1,5-a]pyrimidin-3-yl]-pyridin-4-yl}-3-(2,2,2-trifluoro-ethyl)-urea | Procedure K1, general route V, procedure V1, procedure V2, procedure V3 using 1-(2-chloro-pyridin-4-yl)-3-(2,2,2-trifluoroethyl)urea from procedure U4. | 1H NMR (400 MHz, DMSO-d6): 9.57 (1H, s), 9.42 (1H, s), 9.08 (1H, s), 8.82 (1H, s), 8.45-8.35 (2H, m), 8.00-7.93 (2H, m), 7.49-7.46 (1H, m), 7.41 (2H, t), 6.91 (1H, s), 3.99 (2H, d). | [M + h]+ 431 |
| 200 | | 1-(3-{7-[3-(Piperidin-4-yloxy)-phenyl]-imidazo[1,2-a]pyridin-3-yl}-phenyl)-3-(2,2,2-trifluoro-ethyl)-urea | general route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using I22, procedure D3a | 1H NMR (400 MHz, Me-d3-OD): 8.67 (1H, d), 7.90 (2H, d), 7.79 (1H, s), 7.56-7.26 (7H, m), 7.12 (1H, d), 4.92 (1H, m), 3.96 (2H, q), 3.54-3.40 (2H, m), 3.30-3.22 (2H, m), 2.31-2.17 (2H, m), 2.17-2.05 (2H, m). | [M + H]+ 510 |

| Eg. No. | Compound | Chemical Name | Procedure | ¹H NMR Data | M.S. |
|---|---|---|---|---|---|
| 201 | | 1-[3-(7-Pyrrolidin-1-yl-imidazo[1,2-a]pyridin-3-yl)-phenyl]-3-(2,2,2-trifluoro-ethyl)-urea Hydrochloride | General route B, procedure B1b using Pyrrolidine, procedure B2, procedure B3a using I6 1-[3-(4,4,5,5-Tetramethyl-[1,3,2]dioxaborolan-2-yl)-phenyl]-3-(2,2,2-trifluoro-ethyl)-urea. Procedure J1. | 1H NMR (400 MHz, Me-d3-OD): 8.34 (1H, d), 7.78-7.70 (1H, m), 7.44 (1H, d), 7.40 (1H, d), 7.33 (1H, d), 7.26-7.21 (1H, m), 6.71-6.63 (1H, m), 6.37 (1H, s), 4.00-3.88 (2H, m), 3.48-3.40 (4H, m), 2.15-2.04 (4H, m). | [M + H]+ 404 |
| 202 | | 1-[3-(7-Azetidin-1-yl-imidazo[1,2-a]pyridin-3-yl)-phenyl]-3-(2,2,2-trifluoro-ethyl)-urea | General route B, procedure B1b using Azetidine, procedure B2, procedure B3a using I6 1-[3-(4,4,5,5-Tetramethyl-[1,3,2]dioxaborolan-2-yl)-phenyl]-3-(2,2,2-trifluoro-ethyl)-urea. | 1H NMR (400 MHz, Me-d3-OD): 8.31 (1H, d), 7.74-7.68 (1H, m), 7.46-7.37 (2H, m), 7.37-7.25 (1H, m), 7.25-7.10 (1H, m), 6.43-6.34 (1H, m), 6.24 (1H, s), 4.01 (4H, t), 3.94 (3H, q), 2.51-2.37 (2H, m). | [M + H]+ 390 |
| 203 | | (±)-1-{3-[7-(3-Methoxy-piperidin-1-yl)-imidazo[1,2-a]pyridin-3-yl]-phenyl}-3-(2,2,2-trifluoro-ethyl)-urea | General route B, procedure B1b using 3-Methoxypiperidine, procedure B2, procedure B3a using I6 1-[3-(4,4,5,5-Tetramethyl-[1,3,2]dioxaborolan-2-yl)-phenyl]-3-(2,2,2-trifluoro-ethyl)-urea. | 1H NMR (400 MHz, Me-d3-OD): 8.47 (1H, s), 8.39 (1H, d), 7.88 (1H, s), 7.66 (1H, s), 7.50 (1H, t), 7.39 (1H, d), 7.27 (1H, d), 7.17 (1H, d), 6.84 (1H, s), 3.95 (2H, q), 3.74 (1H, d), 3.52 (4H, m), 3.41 (3H, s), 2.09-1.86 (2H, m), 1.71 (2H, d). | [M + H]+ 448 |

| Eg. No. | Compound | Chemical Name | Procedure | ¹H NMR Data | M.S. |
|---|---|---|---|---|---|
| 204 | | 1-Ethyl-3-{4-[6-(4-fluoro-phenyl)-pyrazolo[1,5-a]pyrimidin-3-yl]-pyridin-2-yl}-urea | Procedure K1, general route V, procedure V1, procedure V2, procedure V3 using 1-(4-chloro-pyridin-2-yl)-3-ethyl-urea from procedure U5. | 1H NMR (400 MHz, DMSO-d6): 9.59 (1H, d), 9.16 (1H, s), 9.12 (1H, d), 8.80 (1H, s), 8.22 (2H, d), 8.17-8.11 (1H, m), 8.02-7.92 (2H, m), 7.68 (1H, dd), 7.41 (2H, t), 3.24-3.21 (2H, m), 1.12 (3H, t). | [M + H]+ 377 |
| 205 | | 1-{3-[7-(3-Hydroxy-pyrrolidin-1-yl)-imidazo[1,2-a]pyridin-3-yl]-phenyl}-3-(2,2,2-trifluoro-ethyl)-urea | General route B, procedure B1b using 3-benzyloxypyrrolidine, modification D6, procedure B2, procedure B3a using I6 1-[3-(4,4,5,5-Tetramethyl-[1,3,2]dioxaborolan-2-yl)-phenyl]-3-(2,2,2-trifluoro-ethyl)-urea. | 1H NMR (400 MHz, Me-d3-OD): 8.45 (1H, s), 8.41 (1H, d), 7.89 (1H, s), 7.66 (1H, s), 7.50 (1H, t), 7.41 (1H, d), 7.27 (1H, d), 6.94 (1H, d), 6.53 (1H, s), 4.62 (1H, s), 3.94 (2H, q), 3.73-3.52 (3H, m), 3.45 (1H, d), 2.31-2.08 (2H, m). | [M + H]+ 420 |
| 206 | | 1-(3-{7-[3-(3-Oxo-piperazin-1-ylmethyl)-phenyl]-imidazo[1,2-a]pyridin-3-yl}-phenyl)-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using I19 | 1H NMR (400 MHz, DMSO-d6): 9.01 (1H, s), 8.63 (1H, d), 7.99 (1H, s), 7.84-7.71 (5H, m), 7.54-7.43 (3H, m), 7.39 (2H, dd), 7.28 (1H, m), 6.90 (1H, t), 3.95 (2H, m), 3.65 (2H, s), 3.18 (2H, m), 2.97 (2H, s), 2.62 (2H, m). | [M + H]+ 523 |

| Eg. No. | Compound | Chemical Name | Procedure | ¹H NMR Data | M.S. |
|---|---|---|---|---|---|
| 207 | | 1-[3-(7-Furan-2-yl-imidazo[1,2-a]pyridin-3-yl)-phenyl]-3-(2,2,2-trifluoro-ethyl)-urea | General route A, procedure A3b using - I6 1-[3-(4,4,5,5-Tetramethyl-[1,3,2] dioxaborolan-2-yl)-phenyl]-3-(2,2,2-trifluoro-ethyl)-urea, procedure A4b using 2-furylboronic acid. | 1H NMR (400 MHz, Me-d3-OD): 8.57 (1H, d), 7.86 (1H, s), 7.81 (1H, s), 7.71 (1H, s), 7.70-7.65 (1H, m), 7.49 (1H, t), 7.41 (1H, d), 7.36 (1H, dd), 7.31 (1H, d), 7.01 (1H, d), 6.62 (1H, dd), 3.95 (2H, q). | [M + H]+ 401 |
| 208 | | 1-(3-{7-[6-Oxo-1-(3-piperidin-1-yl-propyl)-1,6-dihydro-pyridin-3-yl]-imidazo[1,2-a]pyridin-3-yl}-phenyl)-3-(2,2,2-trifluoro-ethyl)-urea Hydrochloride | Procedure S | 1H NMR (400 MHz, Me-d3-OD): 8.63 (1H, d), 8.27 (1H, d), 8.05 (1H, dd), 7.86 (1H, s), 7.80 (1H, s), 7.73 (1H, s), 7.49 (1H, t), 7.39 (1H, d), 7.35-7.25 (2H, m), 6.71 (1H, d), 4.17 (2H, t), 3.95 (2H, q), 2.53-2.38 (6H, m), 2.11-2.01 (2H, m), 1.67-1.56 (4H, m), 1.48 (2H, s). | [M + H]+ 553 |
| 209 | | N-Methyl-2-[3-(3-{3-[3-(2,2,2-trifluoro-ethyl)-ureido]-phenyl}-imidazo[1,2-a]pyridin-7-yl)-phenyl]-acetamide Hydrochloride | General route A, procedure A3b using I6 3-(4,4,5,5-Tetramethyl-[1,3,2]dioxaborolan-2-yl)-phenyl]-3-(2,2,2-trifluoro-ethyl)-urea, procedure A4b using I18, Procedure J1 | 1H NMR (400 MHz, DMSO-d6): 9.32 (1H, s), 8.83 (1H, d), 8.41 (1H, s), 8.21 (1H, s), 8.07 (1H, d), 7.92 (1H, s), 7.88-7.77 (3H, m), 7.60-7.49 (3H, m), 7.45 (1H, d), 7.38-7.30 (1H, m), 7.05 (1H, t), 3.95 (2H, m), 3.54 (2H, s), 2.64 (3H, d). | [M + H]+ 482 |

| Eg. No. | Compound | Chemical Name | Procedure | ¹H NMR Data | M.S. |
|---|---|---|---|---|---|
| 210 | | 1-{3-[7-(3-Hydroxy-piperidin-1-yl)-imidazo[1,2-a]pyridin-3-yl]-phenyl}-3-(2,2,2-trifluoro-ethyl)-urea formate | General route B, procedure B1b using 3-Hydroxypiperidine, procedure B2, procedure B3a using I6 1-[3-(4,4,5,5-Tetramethyl-[1,3,2]dioxaborolan-2-yl)-phenyl-3-(2,2,2,-trifluoro-ethyl)-urea. | 1H NMR (400 MHz, DMSO-d6): 8.98 (1H, s), 8.32 (1H, d), 8.17 (2H, s), 7.69 (1H, s), 7.52-7.45 (1H, m), 7.44-7.33 (2H, m), 7.21-7.12 (1H, m), 6.96-6.83 (2H, m), 6.71 (1H, d), 3.94 (2H, dd), 3.72-3.54 (3H, m), 2.94-2.81 (1H, m), 2.77-2.65 (1H, m), 1.90 (1H, d), 1.84-1.72 (1H, m), 1.61-1.46 (1H, m), 1.44-1.31 (1H, m). | [M + H]+ 434 |
| 211 | | 1-{3-[7-(2-Fluoro-pyridin-4-yl)-imidazo[1,2-a]pyridin-3-yl]-phenyl}-3-(2,2,2-trifluoro-ethyl)-urea Hydrochloride | General route B, procedure B1b using 2-fluoropyridine-4-boronic acid, procedure B2, procedure B3a using I6 1-[3-(4,4,5,5-Tetramethyl-[1,3,2]dioxaborolan-2-yl)-phenyl]-3-(2,2,2-trifluoro-ethyl)-urea, Procedure J1 | 1H NMR (400 MHz, Me-d3-OD): 8.68 (1H, d), 8.32 (1H, d), 8.19 (1H, s), 8.08 (1H, s), 7.86 (1H, s), 7.82 (1H, s), 7.74 (1H, d), 7.57-7.45 (2H, m), 7.45-7.35 (2H, m), 7.32 (1H, d), 3.96 (2H, q). | [M + H]+ 430 |
| 212 | | 1-(3-{7-[2-(Tetrahydro-pyran-4-yloxy)-pyridin-4-yl]-imidazo[1,2-a]pyridin-3-yl}-phenyl)-3-(2,2,2-trifluoro-ethyl)-urea | General route A, procedure A3b using I6 1-[3-(4,4,5,5-Tetramethyl-[1,3,2]dioxaborolan-2-yl)-phenyl]-2-(2,2,2-trifluoro-ethyl)-urea, procedure A4b using I21 | 1H NMR (400 MHz, Me-d3-OD): 8.68 (1H, d), 8.24 (1H, d), 8.06-7.96 (1H, m), 7.86 (1H, s), 7.80 (1H, s), 7.50 (1H, t), 7.46-7.29 (4H, m), 7.20 (1H, s), 5.30 (1H, m), 4.05-3.91 (4H, m), 3.71-3.56 (2H, m), 2.18-2.04 (2H, m), 1.88-1.74 (2H, m). | [M + H]+ 512 |

| Eg. No. | Compound | Chemical Name | Procedure | ¹H NMR Data | M.S. |
|---|---|---|---|---|---|
| 213 | | 1-{3-[7-(4-Methyl-3-oxo-piperazin-1-yl)-imidazo[1,2-a]pyridin-3-yl]-phenyl}-3-(2,2,2-trifluoro-ethyl)-urea Formate | General route B, procedure B1b using 1-methylpiperazin-2-one, procedure B2, procedure B3a using I6 1-[3-(4,4,5,5-Tetramethyl-[1,3,2]dioxaborolan-2-yl)-phenyl]-3-(2,2,2-trifluoro-ethyl)-urea. | 1H NMR (400 MHz, Me-d3-OD): 8.41 (1H, d), 7.78 (1H, s), 7.55 (1H, s), 7.49-7.39 (1H, m), 7.35 (1H, d), 7.24 (1H, d), 6.94 (1H, d), 6.76 (1H, s), 4.00 (2H, s), 3.99-3.91 (2H, q), 3.80-3.62 (2H, m), 3.58 (2H, d), 3.06 (3H, s). | [M + H]+ 447 |
| 214 | | 1-{3-Cyano-5-[7-(4-fluoro-phenyl)-imidazo[1,2-a]pyridin-3-yl]-phenyl}-3-(2,2,2-trifluoro-ethyl)-urea | General route B. Procedure B1a using 4-fluorophenyl boronic acid, procedure B2, procedure B3b using 3-amino-5-(4,4,5,5-tetramethyl-[1,3,2]dioxaborolan-2-yl)-benzonitrile then procedure O5 | 1H NMR (400 MHz, DMSO-d6): 9.29 (1H, s), 8.71 (1H, d), 8.02 (1H, d), 8.00-7.89 (5H, m), 7.78 (1H, t), 7.44-7.31 (3H, m), 7.10 (1H, t), 4.02-3.91 (2H, m). | [M + H]+ 454.1 |
| 215 | | 1-{3-Cyano-5-[7-(4-fluoro-phenyl)-imidazo[1,2-a]pyridin-3-yl]-phenyl}-3-ethyl-urea | General route B. Procedure B1a using 4-fluorophenyl boronic acid, procedure B2, procedure B3b using 3-amino-5-(4,4,5,5-tetramethyl-[1,3,2]dioxaborolan-2-yl)-benzonitrile then procedure F1a. | 1H NMR (400 MHz, Me-d3-OD): 8.61 (1H, d), 8.01 (1H, s), 7.85-7.75 (5H, m), 7.59 (1H, s), 7.35 (1H, d), 7.25 (2H, t), 3.28 (2H, q), 1.20 (3H, t). | [M + H]+ 400 |

-continued

| Eg. No. | Compound | Chemical Name | Procedure | ¹H NMR Data | M.S. |
|---|---|---|---|---|---|
| 216 | | 1-Ethyl-3-{3-[7-(4-fluoro-phenyl)-imidazo[1,2-a]pyridin-3-yl]-5-methoxy-phenyl}-urea | General route B. Procedure B1a using 4-fluorophenyl boronic acid, procedure B2, procedure B3b using boronate I8, then procedures H2 and F1a | 1H NMR (400 MHz, DMSO-d6): 8.68-8.58 (2H, m), 7.98 (1H, d), 7.92 (2H, dd), 7.80 (1H, s), 7.39-7.31 (3H, m), 7.28 (1H, s), 7.16 (1H, t), 6.77 (1H, dd), 6.18 (1H, t), 3.81 (3H, s), 3.19-3.06 (2H, m), 1.07 (3H, t). | [Molecular ion]+ 405 |
| 217 | | 1-{3-[7-(4-Fluoro-phenyl)-imidazo[1,2-a]pyridin-3-yl]-5-methoxy-phenyl}-3-(2,2,2-trifluoro-ethyl)-urea | General route B. Procedure B1a using 4-fluorophenyl boronic acid, procedure B2, procedure B3b using boronate I8, then procedures H2 and O5 | 1H NMR (400 MHz, DMSO-d6): 8.97 (1H, s), 8.64 (1H, d), 7.99 (1H, s), 7.92 (2H, dd), 7.81 (1H, s), 7.42-7.31 (3H, m), 7.29 (1H, s), 7.18 (1H, s), 6.90-6.79 (2H, m), 4.02-3.88 (2H, m), 3.82 (3H, s). | [M + H]+ 459 |
| 218 | | 1-{5-[7-(4-Fluoro-phenyl)-imidazo[1,2-a]pyridin-3-yl]-pyridin-3-yl}-3-(2,2,2-trifluoro-ethyl)-urea | General route B, procedure B1a using 4-fluorophenyl-boronic acid, procedure B2, procedure B3b using 1-[5-(4,4,5,5-tetramethyl-[1,3,2]dioxaborolan-2-yl)-pyridin-3-yl]-3-(2,2,2-trifluoro-ethyl)-urea (I28). | 1H NMR (400 MHz, DMSO-d6): 9.18 (1H, s), 8.68-8.59 (2H, m), 8.51 (1H, d), 8.24 (1H, t), 8.03 (1H, s), 7.97-7.91 (3H, m), 7.40 (1H, dd), 7.35 (2H, t), 7.08 (1H, t), 4.02-3.91 (2H, m). | [M + H]+ 430 |

-continued

| Eg. No. | Compound | Chemical Name | Procedure | ¹H NMR Data | M.S. |
|---|---|---|---|---|---|
| 219 | | 1-{3-[7-(3-Hydroxy-methyl-phenyl)-imidazo[1,2-a]pyridin-3-yl]-phenyl}-3-(2,2,2-trifluoro-ethyl)-urea | general route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using (3-hydroxymethylphenyl) boronic acid | 1H NMR (400 MHz, Me-d3-OD): 8.63 (1H, d), 7.84 (2H, d), 7.78 (1H, s), 7.72 (1H, s), 7.68 (1H, d), 7.61-7.27 (6H, m), 4.73 (2H, s), 3.96 (2H, q). | [M + H]+ 441 |
| 220 | | 1-(3-{7-[3-(4-Methyl-piperazine-1-carbonyl)-phenyl]-imidazo[1,2-a]pyridin-3-yl}-phenyl)-3-(2,2,2-trifluoro-ethyl)-urea | General route A, procedure A3b using 1-[3-(4,4,5,5-Tetramethyl-[1,3,2]dioxaborolan-2-yl)-phenyl]-3-(2,2,2-trifluoro-ethyl)-urea (I6), procedure A4b using 3-(4,4,5,5-tetramethyl-1,3,2-dioxaborolan-2-yl)benzoic acid, 4-methylpiperazine | 1H NMR (400 MHz, Me-d3-OD): 8.67 (1H, d), 7.92 (2H, d), 7.85 (2H, d), 7.76 (1H, s), 7.64 (1H, t), 7.50 (2H, t), 7.45-7.36 (2H, m), 7.34 (1H, d), 3.96 (2H, q), 3.83 (2H, s), 3.57 (2H, s), 2.53 (4H, d), 2.36 (3H, s). | [M + H]+ 537 |
| 221 | | 1-(3-Amino-2,2-difluoro-propyl)-3-{3-[7-(4-fluoro-phenyl)-imidazo[1,2-a]pyridin-3-yl]-phenyl}-urea | General route A, procedure A3b using 1-(3-Amino-2,2-difluoro-propyl)-3-[3-(4,4,5,5-tetramethyl-[1,3,2]dioxaborolan-2-yl)-phenyl]-urea (I20), procedure A4b using 4-fluorophenyl boronic acid | 1H NMR (400 MHz, DMSO-d6): 8.88 (1H, s), 8.62 (1H, d), 7.99 (1H, s), 7.95-7.90 (2H, m), 7.79 (2H, d), 7.48-7.42 (2H, m), 7.39-7.32 (3H, m), 7.30-7.21 (1H, m), 6.67-6.59 (1H, m), 3.71-3.57 (2H, m), 2.87 (2H, t). | [M + H]+ 440 |
| 222 | | 1-{3-[7-(4-Fluoro-phenyl)-imidazo[1,2-a]pyridin-3-yl]-phenyl}-3-isopropyl-urea | General route B. Procedures B1a using 4-fluorophenyl boronic acid, procedure B2, procedure B3b using 3-aminophenyl boronic acid then procedure F1a using 2-isocyanato-propane | 1H NMR (400 MHz, DMSO-d6): 8.61 (1H, d), 8.49 (1H, s), 7.99 (1H, d), 7.93 (2H, dd), 7.79 (2H, s), 7.46-7.29 (5H, m), 7.21 (1H, dt), 6.09 (1H, d), 3.84-3.73 (1H, m), 1.12 (6H, d). | [M + H]+ 389 |

-continued

| Eg. No. | Compound | Chemical Name | Procedure | ¹H NMR Data | M.S. |
|---|---|---|---|---|---|
| 223 | | 1-(2,2,2-Trifluoro-ethyl)-3-[3-(7-trifluoro-methyl-imidazo[1,2-a]pyridin-3-yl)-phenyl]-urea Hydrochloride | General Route A. Procedure A1 using 2-amino-4-(trifluoro-methyl)-pyridine, procedure A2, procedure A3b using I6 1-[3-(4,4,5,5-Tetramethyl-[1,3,2]dioxaborolan-2-yl)-phenyl]-3-(2,2,2-trifluoro-ethyl)-urea. Procedure J1. | 1H NMR (400 MHz, DMSO-d6): 9.24 (1H, s), 8.83 (1H, d), 8.32 (1H, s), 8.27 (1H, s), 7.85 (1H, s), 7.54-7.50 (2H, m), 7.47 (1H, d), 7.35-7.25 (1H, m), 7.01 (1H, t), 4.02-3.87 (2H, m). | [M + H]+ 403 |
| 224 | | 1-tert-Butyl-3-{3-[7-(4-fluoro-phenyl)-imidazo[1,2-a]pyridin-3-yl]-phenyl}-urea | General route B. Procedure B1a using 4-fluorophenyl boronic acid, procedure B2, procedure B3b using 3-aminophenyl boronic acid then procedure F1 using 2-Isocyanato-2-methyl-propane | 1H NMR (400 MHz, DMSO-d6): 8.60 (1H, d), 8.44 (1H, s), 7.99 (1H, s), 7.92 (2H, dd), 7.78 (1H, s), 7.73 (1H, s), 7.45-7.29 (5H, m), 7.19 (1H, dt), 6.07 (1H, s), 1.31 (9H, s). | [M + H]+ 403.15 |
| 225 | | 1-[3-(7-Methyl- | General Route A. Procedure A1 using 2-amino-4-methylpyridine, procedure A2, procedure A3b using I6 1-[3-(4,4,5,5-Tetramethyl-[1,3,2]dioxaborolan-2-yl)-phenyl]-3-(2,2,2-trifluoro-ethyl)-urea. Procedure J1. | 1H NMR (400 MHz, Me-d3-OD): 8.38 (1H, d), 7.73 (1H, s), 7.56 (1H, s), 7.41 (1H, d), 7.35 (2H, d), 7.21 (1H, d), 6.78 (1H, dd), 3.94 (2H, q), 2.41 (3H, s). | [M + H]+ 349 |
| 226 | | 1-Ethyl-3-[3-(7-methyl-imidazo[1,2-a]pyridin-2-yl)-phenyl]-urea Hydrochloride | General Route A. Procedure A1 using 2-amino-4-methylpyridine, procedure A2, procedure A3b using 1-Ethyl-3-[3-(4,4,5,5-tetramethyl-[1,3,2]dioxaborolan-2-yl)-phenyl]urea. Procedure J1. | 1H NMR (400 MHz, Me-d3-OD): 8.46 (1H, d), 7.80-7.72 (1H, m), 7.59 (1H, s), 7.49-7.41 (1H, m), 7.39 (1H, s), 7.34 (1H, d), 7.23 (1H, d), 6.87 (1H, d), 3.26 (2H, q), 2.46 (3H, s), 1.18 (3H, t). | [M + H]+ 295 |

-continued

| Eg. No. | Compound | Chemical Name | Procedure | ¹H NMR Data | M.S. |
|---|---|---|---|---|---|
| 227 | | 1-Ethyl-3-(3-{7-[3-(4-methyl- | General Route B procedure B1d, B2, B3a using 3-aminobenzene boronic acid, F1a using ethyl isocyanate | 1H NMR (400 MHz, Me-d3-OD): 8.63 (1H, d), 7.84 (2H, s), 7.77 (1H, s), 7.74-7.64 (2H, m), 7.54-7.38 (3H, m), 7.38-7.31 (2H, m), 7.27 (1H, d), 3.66 (2H, s), 3.27 (2H, q), 2.63 (8H, br s), 2.39 (3H, s), 1.19 (3H, t). | [M + H]+ 469 |
| 228 | | 1-[3-(7-Chloro-imidazo[1,2-a]pyridin-3-yl)-phenyl-3-(2,2,2-trifluoroethyl)-urea | General route A, Procedure A1, A2, procedure A3b using Ib 1-[3-(4,4,5,5-Tetramethyl-[1,3,2]dioxaborolan-2-yl)-phenyl]-3-(2,2,2-trifluoro-ethyl)-urea | 1H NMR (400 MHz, DMSO-d6): 8.95 (1H, s), 8.55 (1H, d), 7.84 (1H, dd), 7.77 (1H, s), 7.73-7.71 (1H, m), 7.52-7.40 (2H, m), 7.24 (1H, dt), 7.05 (1H, dd), 6.85 (1H, t), 4.00-3.88 (2H, m). | [M + H]+ 369 |
| 229 | | 1-(2,2-Difluoro-ethyl)-3-{3-[7-(4-fluoro-phenyl)-imidazo[1,2-a]pyridin-3-yl]-phenyl}-urea Hydrochloride | General route B. Procedures B1a using 4-fluorophenyl boronic acid, procedure B2, procedure B3b using 1-[3-(4,4,5,5-tetramethyl-[1,3,2]dioxaborolan-2-yl)-phenyl]-3-(2,2-difluoro-ethyl)-urea [Boronate I24] | 1H NMR (400 MHz, DMSO-d6): 9.28 (1H, s), 8.80 (1H, d), 8.38 (1H, s), 8.23 (1H, s), 8.08-7.98 (2H, m), 7.91 (1H, s), 7.84 (1H, dd), 7.56-7.50 (2H, m), 7.45 (2H, t), 7.35-7.26 (1H, m), 6.78 (1H, t), 6.06 (1H, tt), 3.62-3.47 (2H, m). | [M + H]+ 411 |
| 230 | | 1-{3-[7-(3-Methyl-3H-[1,2,3]triazol-4-yl)-imidazo[1,2-a]pyridin-3-yl]-phenyl}-3-(2,2,2-trifluoro-ethyl)-urea | Procedure AH | 1H NMR (400 MHz, DMSO-d6): 8.99 (1H, s), 8.74 (1H, s), 8.65 (1H, d), 8.09 (1H, s), 7.81 (1H, s), 7.76 (1H, s), 7.51 (1H, d), 7.48-7.42 (2H, m), 7.27 (1H, d), 6.89 (1H, t), 4.14 (3H, s), 4.00-3.89 (2H, m). | [M + H]+ 416 |

| Eg. No. | Compound | Chemical Name | Procedure | ¹H NMR Data | M.S. |
|---|---|---|---|---|---|
| 231 | | 2-{3-[7-(4-Fluoro-phenyl)-imidazo[1,2-a]pyridin-3-yl]-phenylamino}-acetamide | General Route B procedure B1d using 4-fluorophenylboronic acid, B2, B3a using 3-aminobenzene boronic acid, modification F7 using 2-chloro-acetamide | 1H NMR (400 MHz, DMSO-d6): 8.60 (1H, d), 7.97 (1H, s), 7.95-7.84 (2H, m), 7.73 (1H, s), 7.45-7.23 (5H, m), 7.12 (1H, s), 6.88 (1H, d), 6.83 (1H, s), 6.64 (1H, dd), 6.13 (1H, t), 3.68 (2H, d). | [M + H]+ 361 |
| 232 | | 4-[4-(3-{3-[3-(2,2,2-Trifluoroethyl)-ureido]-phenyl}-imidazo[1,2-a]pyridin-7-yl)-phenyl] piperazine-1-carboxylic acid tert-butyl ester | General route A, procedure A3b using I6 1-[3-(4,4,5,5-Tetramethyl-[1,3,2] dioxaborolan-2-yl)-phenyl]-3-(2,2,2-trifluoro-ethyl)-urea, procedure A4b using tert-butyl 4-[4-(4,4,5,5-tetramethyl-1,3,2-dioxaborolan-1-yl) phenyl]tetrahydro-1(2H)-pyrazine carboxylate | 1H NMR (400 MHz, Me-d3-OD): 8.60 (1H, d), 7.83 (1H, s), 7.78 (1H, s), 7.75-7.66 (3H, m), 7.49 (1H, t), 7.40 (1H, d), 7.37-7.30 (2H, m), 7.13 (2H, d), 3.96 (2H, q), 3.62 (4H, s), 3.26 (4H, t), 1.51 (9H, s). | [M + H]+ 595 |
| 233 | | 1-{3-[7-(4-Piperazin-1-yl-phenyl)-imidazo[1,2-a]pyridin-3-yl]-phenyl}-3-(2,2,2-trifluoro-ethyl)-urea Hydrochloride | General route A, procedure A3b using I6 1-[3-(4,4,5,5-Tetramethyl-[1,3,2] dioxaborolan-2-yl)-phenyl]-3-(2,2,2-trifluoro-ethyl)-urea, procedure A4b using tert-butyl 4-[4-(4,4,5,5-tetramethyl-1,3,2-dioxaborolan-2-yl) phenyl]tetrahydro-1(2H)-pyrazinecarboxylate, procedure D3a | 1H NMR (400 MHz, Me-d3-OD): 8.81 (1H, d), 8.14 (1H, s), 8.12 (1H, s), 8.07 (1H, t), 7.91 (2H, d), 7.87 (1H, dd), 7.58 (1H, t), 7.45-7.37 (2H, m), 7.25 (2H, d), 3.96 (2H, q), 3.64-3.60 (4H, m), 3.43 (4H, t). | [M + H]+ 495 |

| Eg. No. | Compound | Chemical Name | Procedure | ¹H NMR Data | M.S. |
|---|---|---|---|---|---|
| 234 | | 1-(2,2,2-Trifluoro-ethyl)-3-{3-[7-(1,3,5-trimethyl-1H-pyrazol-4-yl)-imidazo[1,2-a]pyridin-3-yl]-phenyl}-urea | General route A, procedure A3b using I6 [3-(4,4,5,5-Tetramethyl-[1,3,2]diox-aborolan-2-yl)-phenyl]-3-(2,2,2-trifluoro-ethyl)-urea, procedure A4a using 1,3,5-trimethyl-4-(4,4,5,5-tetramethyl-1,3,2-dioxaborolan-2-yl)-1H-pyrazole | 1H NMR (400 MHz, Me-d3-OD): 8.59 (1H, d), 7.84 (1H, t), 7.70 (1H, s), 7.48 (1H, t), 7.44 (1H, s), 7.38 (1H, d), 7.31 (1H, d), 6.98 (1H, dd), 3.95 (2H, q), 3.81 (3H, s), 2.36 (3H, s), 2.29 (3H, s). | [M + H]+ 443 |
| 235 | | 4-[7-(4-Fluoro-phenyl)-imidazo[1,2-a]pyridin-3-yl]-pyridin-2-ylamine | General route B, procedure B1 using 4-fluorophenyl-boronic acid, procedure W using (4-Iodo-pyridin-2-yl)-carbamic acid tert-butyl ester | 1H NMR (400 MHz, DMSO-d6): 8.70 (1H, d), 8.05 (1H, d), 8.02 (1H, s), 7.94 (3H, dd), 7.41 (1H, dd), 7.36 (2H, t), 6.83 (1H, d), 6.77 (1H, s), 6.08 (2H, s). | [M + H]+ 305 |
| 236 | | 2-{3-[7-(4-Fluoro-phenyl)-imidazo[1,2-a]pyridin-3-yl]-phenylamino}-N-methyl-acetamide | General Route B procedure B1d using 4-fluorophenylboronic acid, B2, B3 used 3-aminobenzene boronic acid, modification F7 using 2-Bromo-N-methyl-acetamide | 1H NMR (400 MHz, Me-d3-OD): 8.57 (1H, d), 7.87-7.77 (3H, m), 7.66 (1H, s), 7.36 (1H, t), 7.33-7.21 (3H, m), 6.99 (1H, d), 6.84 (1H, s), 6.71 (1H, dd), 3.83 (2H, s), 2.79 (3H, s). | [M + H]+ 375 |
| 237 | | 1-Ethyl-3-{3-[7-(4-fluoro-phenyl)-imidazo[1,2-a]pyridin-3-yl]-5-isopropoxy-phenyl}-urea | General Route H; Procedure H1 using 3-isopropoxy-5-nitro-phenyl boronic acid pinacol ester (I36), H2 then general modification F1 using ethyl isocyanate | 1H NMR (400 MHz, DMSO-d6): 8.66-8.57 (2H, m), 8.00 (1H, s), 7.97-7.88 (2H, m), 7.82 (1H, s), 7.41 (1H, dd), 7.39-7.30 (2H, m), 7.24 (1H, t), 7.15 (1H, t), 6.73 (1H, s), 6.19 (1H, t), 4.69-4.59 (1H, m), 3.19-3.06 (2H, m), 1.31 (6H, d), 1.07 (3H, t). | [M + H]+ 433.13 |

| Eg. No. | Compound | Chemical Name | Procedure | ¹H NMR Data | M.S. |
|---|---|---|---|---|---|
| 238 | | 1-{3-[7-(4-Fluoro-phenyl)-imidazo[1,2-a]pyridin-3-yl]-5-isopropoxy-phenyl}-3-(2,2,2-trifluoro-ethyl)-urea | General Route H; Procedure H1 using 3-isopropoxy-5-nitro-phenyl boronic acid pinacol ester (I36), H2 then general modification F1b using ethyl isocyanate using a 2 step procedure | 1H NMR (400 MHz, DMSO-d6): 8.93 (1H, s), 8.61 (1H, d), 7.98 (1H, d), 7.96-7.86 (2H, m), 7.80 (1H, s), 7.42-7.28 (3H, m), 7.24 (1H, t), 7.17 (1H, t), 6.84 (1H, t), 6.81-6.75 (1H, m), 4.72-4.60 (1H, m), 4.02-3.87 (2H, m), 1.32 (6H, d). | [M + H]+ 487.15 |
| 239 | | N-[3-(3-{3-[3-(2,2,2-Trifluoro-ethyl)-ureido]-phenyl}-imidazo[1,2-a]pyridin-7-yl)-benzyl]-methane-sulfonamide | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using (3-methanesulfonylamino methyl)benzene-boronic acid | 1H NMR (400 MHz, Me-d3-OD): 8.67 (1H, d), 8.16 (2H, s), 7.97-7.63 (5H, m), 7.60-7.36 (5H, m), 7.32 (1H, d), 4.37 (2H, s), 3.96 (2H, q), 2.94 (3H, s). | [M + H]+ 552 |
| 240 | | 1-[3-(7-Oxazol-5-yl-imidazo[1,2-a]pyridin-3-yl)-phenyl]-3-(2,2,2-trifluoro-ethyl)-urea | Procedure AB | 1H NMR (400 MHz, Me-d3-OD): 8.61 (1H, d), 8.35 (1H, s), 7.92 (1H, s), 7.82 (1H, s), 7.74 (2H, d), 7.48 (1H, t), 7.40 (1H, d), 7.35 (1H, d), 7.30 (1H, d), 3.95 (2H, q). | [M + H]+ 402 |

| Eg. No. | Compound | Chemical Name | Procedure | ¹H NMR Data | M.S. |
|---|---|---|---|---|---|
| 241 | | 1-Ethyl-3-{4-[7-(4-fluoro-phenyl)-imidazo[1,2-a]pyridin-3-yl]-pyridin-2-yl}-urea | Procedure B1 using 4-fluorophenylboronic acid, procedure W using (4-Iodo-pyridin-2-yl)-carbamic acid tert-butyl ester, modification F1 using ethyl isocyanate | 1H NMR (400 MHz, DMSO-d6): 9.22 (1H, s), 8.75 (1H, d), 8.30 (1H, d), 8.06 (1H, s), 8.04 (2H, s), 8.00-7.91 (2H, m), 7.79 (1H, s), 7.48 (1H, dd), 7.36 (2H, t), 7.29 (1H, dd), 3.27-3.16 (2H, m), 1.12 (3H, t). | [M + H]+ 375 |
| 242 | | 4-[5-(3-{3-[3-(2,2,2-Trifluoro-ethyl)-ureido]-phenyl}-imidazo[1,2-a]pyridin-7-yl)-pyridin-2-yl]-piperazine-1-carboxylic acid tert-butyl ester | General route A, procedure A3b using I6 1-[3-(4,4,5,5-Tetramethyl-[1.3.2]dioxaborolan-2-yl)-phenyl]-3-(2,2,2-trifluoro-ethyl)-urea, procedure A4b using 4-(5-(4,4,5,5-tetramethyl-1,3,2-dioxaborolan-2-yl)pyridin-2-yl)-1-boc-piperazine | 1H NMR (400 MHz, Me-d3-OD): 8.62 (1H, d), 8.58 (1H, d), 8.01 (1H, dd), 7.84 (1H, s), 7.79 (1H, s), 7.72 (1H, s), 7.49 (1H, t), 7.40 (1H, d), 7.36-7.27 (2H, m), 6.98 (1H, d), 3.96 (2H, q), 3.72-3.55 (8H, m), 1.51 (9H, s). | [M + H]+ 596 |
| 243 | | 1-{3-[7-(6-Piperazin-1-yl-pyridin-3-yl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-(5-(4,4,5,5-tetramethyl-1,3,2-dioxaborolan-2-yl)pyridin-2-yl)-1-boc-piperazine, procedure D3a | 1H NMR (400 MHz, Me-d3-OD): 8.62 (1H, d), 8.57 (1H, d), 8.01 (1H, dd), 7.83 (1H, s), 7.79 (1H, s), 7.71 (1H, s), 7.49 (1H, t), 7.40 (1H, d), 7.33 (2H, dd), 6.97 (1H, d), 3.96 (2H, q), 3.64 (4H, t), 2.99 (4H, t). | [M + H]+ 496 |

| Eg. No. | Compound | Chemical Name | Procedure | ¹H NMR Data | M.S. |
|---|---|---|---|---|---|
| 244 | | 1-(3-{7-[3-(Tetrahydro-pyran-4-ylamino)-phenyl]-imidazo[1,2-a]pyridin-3-yl}-phenyl)-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using I29 3-(Tetrahydro-pyran-4-ylamino)-phenylboronic acid pinacol ester | 1H NMR (400 MHz, Me-d3-OD): 8.61 (1H, d), 7.84 (1H, s), 7.79 (1H, s), 7.77-7.68 (1H, m), 7.49 (1H, t), 7.40 (1H, d), 7.36-7.29 (2H, m), 7.26 (1H, t), 7.09-6.98 (2H, m), 6.76 (1H, dd), 4.07-3.89 (4H, m), 3.69-3.48 (3H, m), 2.11-2.00 (2H, m), 1.62-1.47 (2H, m). | [M + H]+ 510 |
| 245 | | 1-(3-{7-[4-(4-Methyl-piperazin-1-yl)-phenyl]-imidazo[1,2-a]pyridin-3-yl}-phenyl)-3-(2,2,2-trifluoro-ethyl)-urea Acetic acid | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 1-methyl-4-[4-(4,4,5,5-tetramethyl-1,3,2-dioxaborolan-2-yl)phenyl]piperazine | 1H NMR (400 MHz, DMSO-d6): 9.24 (1H, s), 8.56 (1H, d), 7.87 (1H, s), 7.79 (1H, s), 7.77-7.69 (3H, m), 7.49-7.39 (2H, m), 7.39-7.30 (1H, m), 7.29-7.21 (1H, m), 7.21-7.12 (1H, m), 7.06 (2H, d), 4.00-3.88 (2H, m), 3.27-3.19 (4H, m), 2.49-2.45 (4H, m), 2.24 (3H, s). | [M + H]+ 509 |
| 246 | | 1-{3-[7-(4-Fluoro-phenyl)-imidazo[1,2-a]pyridin-3-yl]-phenyl}-3-(2,2,2-trifluoro-1-methyl-ethyl)-urea | General route B. Procedures B1a using 4-fluorophenyl boronic acid, procedure B2, procedure B3b using 3-aminobenzeneboronic acid, and K₃PO₄ in place of Na₂CO₃, general modification F1b using 1,1,1-trifluoro-isopropylamine | 1H NMR (400 MHz, DMSO-d6): 8.70 (1H, s), 8.62 (1H, d), 7.99 (1H, s), 7.96-7.87 (2H, m), 7.83-7.74 (2H, m), 7.51-7.41 (2H, m), 7.41-7.31 (3H, m), 7.31-7.23 (1H, m), 6.86 (1H, d), 4.61-4.48 (1H, m), 1.30 (3H, d). | [M + H]+ 443.14 |

| Eg. No. | Compound | Chemical Name | Procedure | ¹H NMR Data | M.S. |
|---|---|---|---|---|---|
| 247 | | N-Methyl-3-(3-{3-[3-(2,2,2-trifluoro-ethyl)-ureido]-phenyl}-imidazo[1,2-a]pyridin-7-yl)-benzemide Formate | General route A, procedure A3b using I6 1-[3-(4,4,5,5-Tetramethyl-[1,3,2]diox-aborolan-2-yl)-phenyl]-3-(2,2,2-trifluoro-ethyl)-urea, procedure A4b using 3-(N-methylamino-carbonyl)benzene-boronic acid | 1H NMR (400 MHz, Me-d3-OD): 8.72-8.57 (1H, m), 8.19 (3H, s), 8.01-7.70 (5H, m), 7.61 (1H, t), 7.54-7.42 (2H, m), 7.39 (1H, d), 7.30 (1H, d), 3.96 (2H, q), 2.98 (3H, s). | [M + H]+ 468 |
| 248 | | 1-Ethyl-3-{3-[7-(4-fluoro-phenyl)-imidazo[1,2-a]pyridin-3-yl]-5-hydroxy-methyl-phenyl}-urea | General Route H; Procedure H1 using I37 (3-Nitro-5-(4,4,5,5-tetramethyl-[1,3,2]dioxaborolan-2-yl)-phenyl]-methanol), H2 then general modification F1 using ethyl isocyanate | 1H NMR (400 MHz, DMSO-d6): 8.66-8.57 (2H, m), 8.00-7.89 (3H, m), 7.76 (1H, s), 7.69 (1H, s), 7.40-7.31 (4H, m), 7.14 (1H, s), 6.17 (1H, t), 5.25 (1H, t), 4.55 (2H, d), 3.17-3.09 (2H, m), 1.07 (3H, t). | [M + H]+ 405.16 |
| 249 | | 3-(3-{3-[3-(2,2,2-Trifluoro-ethyl)-ureido]-phenyl}-imidazo[1,2-a]pyridin-7-yl)-benzene-sulfonamide formate | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using (3-methylsulfonylamino-phenyl)boronic acid | 1H NMR (400 MHz, DMSO-d6): 8.99 (1H, s), 8.70 (1H, d), 8.30 (1H, s), 8.18-8.05 (3H, m), 7.90-7.77 (3H, m), 7.72 (1H, t), 7.51-7.43 (4H, m), 7.41 (1H, dd), 7.34-7.25 (1H, m), 6.88 (1H, t), 4.02-3.89 (2H, m). | [M + H]+ 490 |
| 250 | | 1-(3-{7-[3-(Piperazine-1-carbonyl)-phenyl]-imidazo[1,2-a]pyridin-3-yl}-phenyl)-3-(2,2,2-trifluoro-ethyl)-urea hydrochloride | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using Tert-butyl 4-[3-(5,5-dimethyl-1,3,2-dioxa-borinan-2-yl)benzoyl]piperazine-1-carboxylate, procedure D3a | 1H NMR (400 MHz, Me-d3-OD): 8.68 (1H, d), 7.98-7.89 (2H, m), 7.86 (2H, d), 7.76 (1H, s), 7.65 (1H, t), 7.55-7.45 (2H, m), 7.45-7.37 (2H, m), 7.34 (1H, d), 3.96 (2H, q), 3.90-3.49 (4H, m), 2.94 (4H, s). | [M + H]+ 523 |

| Eg. No. | Compound | Chemical Name | Procedure | ¹H NMR Data | M.S. |
|---|---|---|---|---|---|
| 251 | | 1-{3-[7-(3-Methane-sulfonyl-phenyl)-imidazo[1,2-a]pyridin-3-yl]-phenyl}-3-(2,2,2-trifluoro-ethyl)-urea formate | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3-(methanesulfonyl) phenylboronic acid | 1H NMR (400 MHz, Me-d3-OD): 8.67 (1H, d), 8.33 (1H, s), 8.26-7.92 (5H, m), 7.92-7.71 (3H, m), 7.54-7.41 (2H, m), 7.38 (1H, d), 7.31 (1H, d), 3.96 (2H, q), 3.23 (3H, s). | [M + H]+ 489 |
| 252 | | 1-[3-(7-Chloro-imidazo[1,2-a]pyridin-3-yl)-4-fluoro-phenyl]-3-(2,2,2-trifluoro-ethyl)-urea | General route A, procedure A3b using I38 - 1-[4-Fluoro-3-(4,4,5,5-tetramethyl-[1,3,2]dioxaborolan-2-yl)-phenyl]-3-(2,2,2-trifluoro-ethyl)-urea and substituting Pd(PPh₃)₄ for PdCl₂dppf | 1H NMR (400 MHz, DMSO-d6): 8.98 (1H, s), 8.26 (1H, dd), 7.87 (1H, d), 7.79 (1H, s), 7.66 (1H, dd), 7.55 (1H, ddd), 7.35 (1H, t), 7.06 (1H, dd), 6.87 (1H, t), 4.00-3.86 (2H, m). | [M + H]+ 387 |
| 253 | | 1-{4-Fluoro-3-[7-(4-fluoro-phenyl)-imidazo[1,2-a]pyridin-3-yl]-phenyl}-3-(2,2,2-trifluoro-ethyl)-urea | General route B. Procedures B1a using 4-fluorophenyl boronic acid, procedure B2, procedure B3b using I38 - 1-[4-Fluoro-3-(4,4,5,5-tetramethyl-[1,3,2]dioxaborolan-2-yl)-phenyl]-3-(2,2,2-trifluoro-ethyl)-urea and K₃PO₄ in place of Na₂CO₃, | 1H NMR (400 MHz, DMSO-d6): 8.97 (1H, s), 8.31 (1H, dd), 8.01 (1H, s), 7.97-7.88 (2H, m), 7.81 (1H, s), 7.71 (1H, dd), 7.54 (1H, ddd), 7.42-7.30 (4H, m), 6.85 (1H, t), 4.00-3.87 (2H, m). | [M + H]+ 447.1 |
| 254 | | 1-{3-[7-(3,5-Difluoro-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3,5-difluorophenylboronic acid | 1H NMR (400 MHz, DMSO-d6): 8.97 (1H, s), 8.62 (1H, d), 8.18 (1H, s), 7.85 (1H, s), 7.81 (1H, s), 7.74-7.64 (2H, m), 7.51-7.41 (3H, m), 7.35-7.24 (2H, m), 6.85 (1H, t), 4.02-3.89 (2H, m). | [M + H]+ 447 |

| Eg. No. | Compound | Chemical Name | Procedure | ¹H NMR Data | M.S. |
|---|---|---|---|---|---|
| 255 | | 1-Ethyl-3-{5-[7-(4-fluoro-phenyl)-imidazo[1,2-a]pyridin-3-yl]-2-methyl-phenyl}-urea | General route B. Procedures B1a using 4-fluorophenyl boronic acid, procedure B2, procedure A3b (substituting tetrakis for PdCl$_2$dppf) using 3-amino-4-methylbenzene boronic acid, modification F1 using ethylisocyanate | 1H NMR (400 MHz, DMSO-d6): 8.60 (1H, d), 8.23 (1H, s), 7.98 (1H, s), 7.93 (2H, dd), 7.79 (1H, s), 7.74 (1H, s), 7.43-7.27 (4H, m), 7.18 (1H, dd), 6.63 (1H, t), 3.21-3.08 (2H, m), 2.27 (3H, s), 1.09 (3H, t). | [M + H]+ 389.16 |
| 256 | | 1-{3-[7-(1-Propyl-1H-pyrazol-4-yl)-imidazo[1,2-a]pyridin-3-yl]-phenyl}-3-(2,2,2-trifluoro-ethyl)-urea formate | General route B, procedure B1 using 1-propyl-4-(4,4,5,5-tetramethyl-1,3,2-dioxaborolan-2-yl)-1H-pyrazole (commercially available), procedure B3 using I6 1-[3-(4,4,5,5-Tetramethyl-[1,3,2]dioxaborolan-2-yl)-phenyl]-3-(2,2,2-trifluoro-ethyl)-urea | 1H NMR (400 MHz, DMSO-d6): 8.98 (1H, s), 8.53 (1H, d), 8.40 (1H, s), 8.18 (0.5H, s), 8.09 (1H, s), 7.87 (1H, s), 7.77 (1H, s), 7.70 (1H, s), 7.48-7.39 (2H, m), 7.30-7.20 (2H, m), 6.89 (1H, t), 4.10 (2H, t), 4.02-3.88 (2H, m), 1.91-1.79 (2H, m), 0.88 (3H, t). | [M + H]+ 443 |
| 257 | | 1-{3-[7-(4-Fluoro-phenyl)-imidazo[1,2-c]pyrimidin-3-yl]-phenyl}-3-(2,2,2-trifluoro-ethyl)-urea | General route X, procedure X1 using 4-fluorophenylboronic acid, procedure X4 using 1-[3-(4,4,5,5-Tetramethyl-[1,3,2]dioxaborolan-2-yl)-phenyl]-3-(2,2,2-trifluoro-ethyl)-urea as the coupling partner. | 1H NMR (400 MHz, Me-d3-OD): 9.48 (1H, d), 8.28-8.18 (2H, m), 8.02 (1H, s), 7.90 (1H, d), 7.79 (1H, s), 7.52 (1H, t), 7.47-7.36 (2H, m), 7.26 (2H, t), 3.96 (2H, q). | [M + H]+ 430 |
| 258 | | 1-{3-[7-(4-Fluoro-phenyl)-imidazo[1,2-a]pyridin-3-yl]-5-hydroxymethyl-phenyl}-3-(2,2,2-trifluoro-ethyl)-urea | General Route H; Procedure H1 using I37 (3-Nitro-5-(4,4,5,5-tetramethyl-[1,3,2]dioxaborolan-2-yl)-phenyl]-methanol), H2 then general modification F1b using 1,1,1-trifluoro-isopropylamine | 1H NMR (400 MHz, DMSO-d6): 8.96 (1H, s), 8.62 (1H, d), 7.99 (1H, s), 7.97-7.87 (2H, m), 7.78 (1H, s), 7.67 (1H, s), 7.42 (1H, s), 7.40-7.32 (3H, m), 7.21 (1H, s), 6.82 (1H, t), 5.28 (1H, t), 4.56 (2H, d), 4.03-3.88 (2H, m). | [M + H]+ 459.16 |

| Eg. No. | Compound | Chemical Name | Procedure | ¹H NMR Data | M.S. |
|---|---|---|---|---|---|
| 259 | | 1-{5-[7-(4-Fluoro-phenyl)-imidazo[1,2-a]pyridin-3-yl]-2-methyl-phenyl}-3-(2,2,2-trifluoro-ethyl)-urea | General route B. Procedures B1a using 4-fluorophenyl boronic acid, procedure B2, procedure A3b (substituting tetrakis for PdCl₂dppf) using 3-amino-4-methyl benzene boronic acid, general modification using 1,1,1-trifluoro-ethylamine in two step procedure F1b | 1H NMR (400 MHz, DMSO-d6): 8.59 (1H, d), 8.19-8.08 (2H, m), 7.98 (1H, s), 7.97-7.88 (2H, m), 7.76 (1H, s), 7.43-7.30 (4H, m), 7.30-7.20 (2H, m), 4.04-3.93 (2H, m), 2.29 (3H, s). | [M + H]+ 443.13 |
| 260 | | 1-{3-[7-(5-Ethyl-[1,3,4]thiadiazol-2-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using 2-Bromo-5-ethyl-1,3,4-thiadiazole | 1H NMR (400 MHz, Me-d3-OD): 8.71 (1H, d), 8.19 (1H, s), 7.86 (2H, d), 7.67 (1H, dd), 7.51 (1H, t), 7.44 (1H, d), 7.35 (1H, d), 3.96 (2H, q), 3.25 (2H, q), 1.50 (3H, t). | [M + H]+ 447 |
| 261 | | N-Ethyl-3-(3-{3-[3-(2,2,2-trifluoro-ethyl)-ureido]-phenyl}-imidazo[1,2-a]pyridin-7-yl)-benzamide Formate | General route A, procedure A3b using Ib 1-[3-(4,4,5,5-Tetramethyl-[1,3,2]dioxaborolan-2-yl)-phenyl]-3-(2,2,2-trifluoro-ethyl)-urea, procedure A4b using I30 N-ethyl-3-(4,4,5,5-tetra-methyl-1,3,2-dioxa-borolan-2-yl)benzamide | 1H NMR (400 MHz, Me-d3-OD): 8.66 (1H, d), 8.20 (2H, d), 8.02-7.72 (5H, m), 7.61 (1H, t), 7.54-7.42 (2H, m), 7.39 (1H, d), 7.31 (1H, d), 3.96 (2H, q), 3.54-3.41 (2H, m), 1.28 (3H, t). | [M + H]+ 482 |

| Eg. No. | Compound | Chemical Name | Procedure | ¹H NMR Data | M.S. |
|---|---|---|---|---|---|
| 262 | | 4-(3-{3-[3-(2,2,2-Trifluoro-ethyl)-ureido]-phenyl}-imidazo[1,2-a]pyridin-7-yl)-pyrazole-1-sulfonic acid dimethylamide | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4e using I40 (1-Dimethylsulfamoyl-1H-pyrazole-4-boronic acid) | 1H NMR (400 MHz, DMSO-d6): 9.01-8.96 (2H, m), 8.62 (1H, s), 8.57 (1H, d), 8.16 (1H, s), 7.79 (1H, s), 7.77 (1H, s), 7.49-7.41 (3H, m), 7.31-7.22 (1H, m), 6.87 (1H, t), 4.02-3.88 (2H, m), 2.92 (6H, s). | [M + H]+ 508.09 |
| 263 | | N-(2-Methoxy-ethyl)-3-(3-{3-[3-(2,2,2-trifluoro-ethyl)-ureido]-phenyl}-imidazo[1,2-a]pyridin-7-yl)-benzamide | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3-(2-methoxyethylamino-carbonyl)benzene-boronic acid | 1H NMR (400 MHz, Me-d3-OD): 8.67 (1H, d), 8.26 (1H, s), 8.02-7.88 (3H, m), 7.85 (1H, s), 7.76 (1H, s), 7.63 (1H, t), 7.50 (1H, t), 7.46-7.37 (2H, m), 7.34 (1H, d), 3.96 (2H, q), 3.63 (4H, s), 3.42 (3H, s). | [M + H]+ 512 |
| 264 | | 1-(3-{7-[3-(Azetidine 1-carbonyl)-phenyl]-imidazo[1,2-a]pyridin-3-yl}-phenyl)-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using I31 N-azetidine-3-(4,4,5,5-tetramethyl-1,3,2-dioxa-borolan-2-yl)benzamide | 1H NMR (400 MHz, Me-d3-OD): 8.68 (1H, d), 8.05 (1H, s), 7.99-7.93 (1H, m), 7.92 (1H, s), 7.86 (1H, t), 7.77 (1H, s), 7.74-7.67 (1H, m), 7.64 (1H, t), 7.50 (1H, t), 7.46-7.37 (2H, m), 7.35 (1H, d), 4.47 (2H, t), 4.27 (2H, t), 3.96 (2H, q), 2.48-2.38 (2H, m). | [M + H]+ 494 |

-continued

| Eg. No. | Compound | Chemical Name | Procedure | ¹H NMR Data | M.S. |
|---|---|---|---|---|---|
| 265 | | N-(2-Amino-ethyl)-3-(3-{3-[3-(2,2,2-trifluoro-ethyl)-ureido]-phenyl}-imidazo[1,2-a]pyridin-7-yl)-benzamide hydrochloride | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using I32 {2-[3-(4,4,5,5-Tetramethyl-[1,3,2]dioxaborolan-2-yl)-benzoylamino]-ethyl}-carbamic acid tert-butyl ester, procedure D3a | 1H NMR (400 MHz, Me-d3-OD): 8.93 (1H, d), 8.48 (1H, s), 8.33 (1H, s), 8.24 (1H, s), 8.14 (1H, d), 8.09 (2H, d), 7.95 (1H, d), 7.76 (1H, t), 7.60 (1H, t), 7.49-7.38 (2H, m), 3.96 (2H, q), 3.80-3.71 (2H, m), 3.25 (2H, t). | [M + H]+ 497 |
| 266 | | 1-Ethyl-3-{2-fluoro-5-[7-(4-fluoro-phenyl)-imidazo[1,2-a]pyridin-3-yl]-phenyl}-urea | General route B. Procedures B1a using 4-fluorophenyl boronic acid, procedure B2, procedure B3b using I39 - 2-Fluoro-5-(4,4,5,5-tetramethyl-[1,3,2]dioxaborolan-2-yl)-phenylamine and using K₃PO₄ in place of Na₂CO₃, modification F1 using ethylisocyanate | 1H NMR (400 MHz, DMSO-d6): 8.55 (1H, d), 8.51-8.42 (2H, m), 7.99 (1H, s), 7.93 (2H, dd), 7.76 (1H, s), 7.44-7.29 (4H, m), 7.27-7.19 (1H, m), 6.67 (1H, t), 3.20-3.09 (2H, m), 1.08 (3H, t). | [M + H]+ 393.13 |
| 267 | | N-Isopropyl-3-(3-{3-[3-(2,2,2-trifluoro-ethyl)-ureido]-phenyl}-imidazo[1,2-a]pyridin-7-yl)-benzamide | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using I33 N-isopropyl-3-(4,4,5,5-tetramethyl-1,3,2-dioxaborolan-2-yl)benzamide | 1H NMR (400 MHz, Me-d3-OD): 8.68 (1H, d), 8.24 (1H, s), 7.96 (2H, d), 7.89 (1H, d), 7.86 (1H, s), 7.76 (1H, s), 7.63 (1H, t), 7.56-7.47 (1H, m), 7.47-7.38 (2H, m), 7.34 (1H, d), 4.32-4.23 (1H, m), 3.96 (2H, q), 1.31 (6H, d). | [M + H]+ 496 |

| Eg. No. | Compound | Chemical Name | Procedure | ¹H NMR Data | M.S. |
|---|---|---|---|---|---|
| 268 | | 3-(3-{3-[3-(2,2,2-Trifluoro-ethyl)-ureido]-phenyl}-imidazo[1,2-a]pyridin-7-yl)-benzamide | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3-aminocarbonylphenyl-boronic acid | 1H NMR (400 MHz, Me-d3-OD): 8.69 (1H, d), 8.32 (1H, s), 8.04-7.92 (3H, m), 7.86 (1H, s), 7.76 (1H, s), 7.65 (1H, t), 7.50 (1H, t), 7.46-7.38 (2H, m), 7.35 (1H, d), 3.96 (2H, q). | [M + H]+ 454 |
| 269 | | 1-{3-[7-(2,4-Difluoro-phenyl)-imidazo[1,2-a]pyridin-3-yl]-phenyl}-3-(2,2,2-trifluoro-ethyl)-urea | general route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 2,4-difluorophenylboronic acid | 1H NMR (400 MHz, DMSO-d6): 8.97 (1H, s), 8.64 (1H, d), 7.88-7.73 (4H, m), 7.51-7.38 (3H, m), 7.33-7.23 (2H, m), 7.20 (1H, d), 6.86 (1H, t), 3.95 (2H, m). | [M + H]+ 447 |
| 270 | | 1-{3-[7-(5-Methyl-thiophen-2-yl)-imidazo[1,2-a]pyridin-3-yl]-phenyl}-3-(2,2,2-trifluoro-ethyl)-urea formate | General route A: procedure A1, procedure A2, procedure A3b using I6 [3-(4,4,5,5-Tetramethyl-[1,3,2]dioxaborolan-2-yl)-phenyl]-3-(2,2,2-trifluoro-ethyl)-urea, procedure A4e using 5-(2-methylthiophene)-4,4,5,5-tetramethyl-1,3,2-dioxaborolane. | ¹H NMR (400 MHz, DMSO-d₆): 9.11 (1H, s), 8.54 (1H, d), 8.22 (1H, s), 7.78 (2H, s), 7.75 (1H, s), 7.55 (1H, d), 7.49-7.40 (2H, m), 7.31-7.21 (2H, m), 7.02 (1H, t), 6.93-6.86 (1H, m), 4.01-3.87 (2H, m). | [Molecular ion]+ 431 |
| 271 | | 1-{3-[7-(4-Methoxy-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 2-(4-methoxyphenyl)-4,4,5,5-tetramethyl-1,3,2-dioxaborolane | 1H NMR (400 MHz, DMSO-d6): 8.95 (1H, s), 8.59 (1H, d), 7.92 (1H, s), 7.82 (2H, d), 7.78 (1H, s), 7.76 (1H, s), 7.45 (2H, d), 7.36 (1H, dd), 7.32-7.23 (1H, m), 7.08 (2H, d), 6.85 (1H, t), 3.95 (2H, m), 3.83 (3H, s). | [Fragment]+ 441 |

| Eg. No. | Compound | Chemical Name | Procedure | ¹H NMR Data | M.S. |
|---|---|---|---|---|---|
| 272 | | 1-{3-[7-(3,4-Difluoro-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3,4-difluorophenyl-boronic acid | 1H NMR (400 MHz, DMSO-d6): 8.97 (1H, s), 8.62 (1H, d), 8.12-7.99 (2H, m), 7.85-7.71 (3H, m), 7.62-7.53 (1H, m), 7.49-7.37 (3H, m), 7.32-7.24 (1H, m), 6.86 (1H, t), 4.01-3.90 (2H, m). | [M + H]+ 447 |
| 273 | | 1-{3-[7-(4-Chloro-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-chlorophenylboronic acid | 1H NMR (400 MHz, DMSO-d6): 8.96 (1H, s), 8.63 (1H, d), 8.04 (1H, s), 7.91 (2H, d), 7.80 (2H, d), 7.57 (2H, d), 7.46 (2H, d), 7.39 (1H, dd), 7.31-7.24 (1H, m), 6.85 (1H, t), 3.95 (2H, m). | [M + H]+ 445 |
| 274 | | 1-{3-[7-(2-Amino-pyrimidin-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using 2-Amino-4-chloropyrimidine | 1H NMR (400 MHz, Me-d3-OD): 8.66 (1H, d), 8.41 (1H, s), 8.37 (1H, d), 7.85 (1H, s), 7.83 (1H, s), 7.74 (1H, dd), 7.50 (1H, t), 7.46-7.38 (1H, m), 7.38-7.31 (1H, m), 7.28 (1H, d), 3.96 (2H, q). | [M + H]+ 428 |

-continued

| Eg. No. | Compound | Chemical Name | Procedure | ¹H NMR Data | M.S. |
|---|---|---|---|---|---|
| 275 | | 1-{4-[7-(4-Fluoro-phenyl)-imidazo[1,2-a]pyridin-3-yl]-pyridin-2-yl}-3-(2,2,2-trifluoro-ethyl)-urea | Procedure B1 using 4-fluorophenyl-boronic acid, procedure W using (4-Iodo-pyridin-2-yl)-carbamic acid tert-butyl ester, modification F1 using 1,1,1-Trifluoro-2-isocyanato-ethane (preparation Z) heating in the microwave at 120° C. for 30 mins | 1H NMR (400 MHz, DMSO-d6): 9.57 (1H, s), 8.76 (1H, d), 8.63-8.57 (1H, m), 8.35 (1H, d), 8.07 (2H, s), 7.97 (2H, dd), 7.80 (1H, s), 7.49 (1H, dd), 7.42-7.31 (3H, m), 4.14-4.03 (2H, m). | [M + H]+ 430.06 |
| 276 | | 1-{3-[7-(2-Methyl-5-trifluoro-methyl-2H-pyrazol-3-yl)-imidazo[1,2-a]pyridin-3-yl]-phenyl}-3-(2,2,2-trifluoro-ethyl)-urea | General route A: procedure A1, procedure A2, procedure A3b using I6 [3-(4,4,5,5-Tetramethyl-[1,3,2]dioxaborolan-2-yl)-phenyl]-3-(2,2,2-trifluoro-ethyl)-urea, procedure A4e using 1-methyl-3-trifluoromethylpyrazole-5-boronic acid and conditions described in procedure E3c. | 1H NMR (400 MHz, Me-d3-OD): 8.70 (1H, d), 8.41 (2H, s), 7.92-7.86 (1H, m), 7.86-7.79 (2H, m), 7.51 (1H, t), 7.47-7.37 (1H, m), 7.34 (1H, d), 7.20 (1H, dd), 6.91 (1H, s), 4.08 (3H, s), 4.02-3.88 (2H, m). | [M + H]+ 483 |
| 277 | | 1-(3-{7-[3-(4-Ethyl-piperazine-1-carbonyl)-phenyl]-imidazo[1,2-a]pyridin-3-yl}-phenyl)-3-(2,2,2-trifluoro-ethyl)-urea Hydrochloride | General route A, procedure A3b using I6 1-[3-(4,4,5,5-Tetramethyl-[1,3,2] dioxaborolan-2-yl)-phenyl]-3-(2,2,2-trifluoro-ethyl)-urea, procedure A4b using I34 3-(4,4,5,5-tetra-methyl-1,3,2-dioxa-borolan-2-yl)benzoic acid, 4-ethylpiperazine. Procedure J1. | 1H NMR (400 MHz, Me-d3-OD): 8.91 (1H, d), 8.29 (1H, s), 8.22 (1H, s), 8.13-8.04 (3H, m), 7.90 (1H, dd), 7.80-7.67 (2H, m), 7.64-7.54 (1H, m), 7.49-7.37 (2H, m), 4.01-3.91 (2H, m), 3.73-3.64 (8H, m), 1.42 (3H, t). | [M + H]+ 551 |

-continued

| Eg. No. | Compound | Chemical Name | Procedure | $^1$H NMR Data | M.S. |
|---|---|---|---|---|---|
| 278 | | 1-{3-[7-(3-Chloro-phenyl)-imidazo]1,2-a]pyridin-3-yl]-phenyl}-3-(2,2,2-trifluoro-ethyl)-urea | General route A, procedure A3b using I6 1-[3-(4,4,5,5-Tetramethyl-[1,3,2] dioxaborolan-2-yl)-phenyl]-3-(2,2,2-trifluoro-ethyl)-urea, procedure A4b using 3-chlorophenylboronic acid | 1H NMR (400 MHz, DMSO-d$^6$): 8.97 (1H, s), 8.62 (1H, d), 8.09 (1H, s), 7.95 (1H, s), 7.89-7.75 (3H, m), 7.60-7.37 (5H, m), 7.28 (1H, m), 6.86 (1H, t), 4.02-3.88 (2H, m). | [M + H]+ 445 |
| 279 | | 1-{3-[7-(3-Methoxy-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2] dioxaborolan-2-yl)-phenyl]-3-(2,2,2-trifluoro-ethyl)-urea, procedure A4b using 3-methoxyphenylboronic acid | 1H NMR (400 MHz, DMSO-d$^6$): 8.96 (1H, s), 8.61 (1H, d), 8.03 (1H, s), 7.84-7.76 (2H, m), 7.50-7.35 (6H, m), 7.32-7.24 (1H, m), 7.05-6.96 (1H, m), 6.85 (1H, t), 3.95 (2H, m), 3.87 (3H, s). | [M + H]+ 441 |
| 280 | | 1-{3-[7-(4-Chloro-3-fluoro-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2] dioxaborolan-2-yl)-phenyl]-3-(2,2,2-trifluoro-ethyl)-urea, procedure A4b using 4-chloro-3-fluorophenyl-boronic acid | 1H NMR (400 MHz, DMSO-d6): 8.97 (1H, s), 8.63 (1H, d), 8.14 (1H, s), 8.01 (1H, dd), 7.87-7.67 (4H, m), 7.50-7.39 (3H, m), 7.28 (1H, m), 6.85 (1H, t), 4.01-3.89 (2H, m). | [M + H]+ 463 |

-continued

| Eg. No. | Compound | Chemical Name | Procedure | ¹H NMR Data | M.S. |
|---|---|---|---|---|---|
| 281 | | N-Methyl-4-(3-{3-[3-(2,2,2-trifluoro-ethyl)-ureido]-phenyl}-imidazo[1,2-a]pyridin-7-yl)-benzamide | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-N-methylcarboxamido-phenylboronic acid, pinacol ester | 1H NMR (400 MHz, DMSO-d6): 9.12 (1H, s), 8.64 (1H, d), 8.55-8.50 (1H, m), 8.10 (1H, s), 7.98 (4H, s), 7.86-7.78 (2H, m), 7.50-7.41 (3H, m), 7.31-7.25 (1H, m), 7.05-6.99 (1H, m), 4.00-3.90 (2H, m), 2.82 (3H, d). | [M + H]+ 468 |
| 282 | | 1-{2-Fluoro-5-[7-(4-fluoro-phenyl)-imidazo[1,2-a]pyridin-3-yl]-phenyl}-3-(2,2,2-trifluoro-ethyl)-urea | General route B. Procedure B1a using 4-fluorophenyl boronic acid, procedure B2, procedure B3b using I39 - 2-Fluoro-5-(4,4,5,5-tetramethyl-[1,3,2]dioxaborolan-2-yl)-phenylamine and K₃PO₄ in place of Na₂CO₃, general modification F1b using 2,2,2-trifluoro-ethyl amine | 1H NMR (400 MHz, DMSO-d6): 8.80 (1H, d), 8.55 (1H, d), 8.41 (1H, dd), 7.99 (1H, d), 7.97-7.88 (2H, m), 7.77 (1H, s), 7.46-7.24 (6H, m), 4.06-3.93 (2H, m). | [M + H]+ 447.09 |
| 283 | | 1-(3-{7-[3-([1,4]Diazepane-1-carbonyl)-phenyl]-imidazo[1,2-a]pyridin-3-yl}-phenyl)-3-(2,2,2-trifluoro-ethyl)-urea Hydrochloride | General route A, procedure A3b using I6 1-[3-(4,4,5,5-Tetramethyl-[1,3,2]dioxaborolan-2-yl)-benzoyl]-[1,4]diazepane-1-carboxylic acid tert-butylester. Procedure D3a. | 1H NMR (400 MHz, Me-d3-OD): 8.69 (1H, d), 7.98-8.74 (4H, m), 7.77 (1H, s), 7.65 (1H, t), 7.58-7.45 (2H, m), 7.45-7.30 (3H, m), 4.02-3.82 (4H, m), 3.70-3.59 (2H, m), 3.28-2.98 (4H, m), 2.10-1.92 (2H, m). | [M + H]+ 537 |

-continued

| Eg. No. | Compound | Chemical Name | Procedure | ¹H NMR Data | M.S. |
|---|---|---|---|---|---|
| 284 | | 1-{3-[7-(3-Chloro-4-fluoro-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3-chloro-4-fluorophenyl-boronic acid | 1H NMR (400 MHz, DMSO-d6): 8.96 (1H, s), 8.62 (1H, d), 8.13 (1H, dd), 8.09 (1H, s), 7.91 (1H, m), 7.82 (1H, s), 7.80 (1H, s), 7.56 (1H, t), 7.51-7.37 (3H, m), 7.28 (1H, m), 6.85 (1H, t), 4.02-3.89 (2H, m). | [M + H]+ 463 |
| 285 | | 1-{3-[7-(2-Methoxy-pyridin-4-yl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 2-methoxy-4-pyridinyl-boronic acid | 1H NMR (400 MHz, DMSO-d6): 8.97 (1H, s), 8.64 (1H, d), 8.28 (1H, d), 8.22 (1H, s), 7.86 (1H, s), 7.80 (1H, s), 7.52 (1H, dd), 7.49-7.42 (3H, m), 7.35-7.24 (2H, m), 6.85 (1H, t), 4.02-3.88 (5H, m). | [M + H]+ 442 |
| 286 | | 1-(2,2,2-Trifluoro-ethyl)-3-{3-[7-(4-trifluoro-methyl-phenyl)-imidazo[1,2-a]pyridin-3-yl]-phenyl}-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-(trifluoromethyl)phenyl-boronic acid | 1H NMR (400 MHz, DMSO-d6): 8.98 (1H, s), 8.67 (1H, d), 8.18-8.06 (3H, m), 7.86 (3H, d), 7.81 (1H, s), 7.51-7.40 (3H, m), 7.33-7.25 (1H, m), 6.87 (1H, t), 4.02-3.89 (2H, m). | [M + H]+ 479 |

| Eg. No. | Compound | Chemical Name | Procedure | ¹H NMR Data | M.S. |
|---|---|---|---|---|---|
| 287 | | 1-{3-[7-(4-Morpholin-4-yl-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-(morpholino)phenyl-boronic acid | 1H NMR (400 MHz, DMSO-d6): 9.01 (1H, s), 8.57 (1H, d), 7.88 (1H, s), 7.82-7.71 (4H, m), 7.44 (2H, d), 7.35 (1H, dd), 7.31-7.22 (1H, m), 7.07 (2H, d), 6.91 (1H, t), 4.02-3.89 (2H, m), 3.82-3.72 (4H, m), 3.24-3.15 (4H, m). | [M + H]+ 496 |
| 288 | | 1-{3-[7-(3,4-Dimethoxy-phenyl)-imidazo[1,2-a]pyridin-3-yl]-phenyl}-3-(2,2,2-trifluoro-ethyl)-urea Formate | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3,4-dimethoxyphenyl-boronic acid | 1H NMR (400 MHz, DMSO-d6): 9.02 (1H, s), 8.58 (1H, d), 8.18 (0.5H, s, formate), 8.00 (1H, s), 7.81 (1H, s), 7.77 (1H, s), 7.50-7.35 (5H, m), 7.27 (1H, m), 7.08 (1H, d), 6.92 (1H, t), 4.03-3.86 (5H, m), 3.82 (3H, s). | [M + H]+ 471 |
| 289 | | 1-{3-[7-(4-Methane-sulfonyl-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-(methanesulphonyl)benzeneboronic acid | 1H NMR (400 MHz, DMSO-d6): 8.97 (1H, s), 8.68 (1H, d), 8.21-8.11 (3H, m), 8.04 (2H, d), 7.86 (1H, s), 7.81 (1H, s), 7.51-7.42 (3H, m), 7.34-7.25 (1H, m), 6.86 (1H, t), 4.02-3.89 (2H, m). | [M + H]+ 489 |

-continued

| Eg. No. | Compound | Chemical Name | Procedure | ¹H NMR Data | M.S. |
|---|---|---|---|---|---|
| 290 | | 1-{3-[7-Thiazol-4-yl)-imidazo[1,2-a]pyridin-3-yl]-phenyl}-3-(2,2,2-trifluoro-ethyl)-urea | General route A steps A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 4-bromothiazole | 1H NMR (400 MHz, DMSO-d6): 9.28 (1H, d), 8.96 (1H, s), 8.63 (1H, d), 8.45 (1H, d), 8.27 (1H, s), 7.80 (1H, s), 7.78 (1H, s), 7.64 (1H, dd), 7.50-7.42 (2H, m), 7.32-7.24 (1H, m), 6.86 (1H, t), 4.01-3.90 (2H, m). | [M + H]+ 418 |
| 291 | | 1-(2,2,2-Trifluoro-ethyl)-3-{3-[7-(3-trifluoro-methyl-phenyl)-imidazo[1,2-a]pyridin-3-yl]-phenyl}-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3-(trifluoromethyl)phenyl-boronic acid | 1H NMR (400 MHz, DMSO-d6): 8.98 (1H, s), 8.65 (1H, d), 8.24-8.13 (3H, m), 7.87-7.71 (4H, m), 7.52-7.42 (3H, m), 7.33-7.24 (1H, m), 6.86 (1H, t), 4.02-3.89 (2H, m). | [M + H]+ 479 |
| 292 | | 1-(2,2,2-Trifluoro-ethyl)-3-{3-[7-(4-trifluoro-methoxy-phenyl)-imidazo[1,2-a]pyridin-3-yl]-phenyl}-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-(trifluoromethoxy) phenylboronic acid | 1H NMR (400 MHz, DMSO-d6): 8.97 (1H, s), 8.64 (1H, d), 8.05 (1H, s), 8.03-7.96 (2H, m), 7.82 (1H, s), 7.80 (1H, s), 7.55-7.42 (4H, m), 7.40 (1H, dd), 7.33-7.24 (1H, m), 6.85 (1H, t), 4.02-3.89 (2H, m). | [M + H]+ 495 |

| Eg. No. | Compound | Chemical Name | Procedure | $^1$H NMR Data | M.S. |
|---|---|---|---|---|---|
| 293 | | 1-(2,2,2-Trifluoro-ethyl)-3-{3-[7-(6-trifluoro-methyl-pyridin-3-yl)-imidazo[1,2-a]pyridin-3-yl]-phenyl}-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4e using I41 - 4-(4,4,5,5-Tetramethyl-[1,3,2]dioxaborolan-2-yl)-2-trifluoromethyl-pyridine | 1H NMR (400 MHz, DMSO-d6): 9.30 (1H, d), 8.98 (1H, s), 8.70 (1H, d), 8.57 (1H, dd), 8.30 (1H, d), 8.03 (1H, d), 7.88 (1H, s), 7.83 (1H, s), 7.52 (1H, dd), 7.50-7.42 (2H, m), 7.34-7.25 (1H, m), 6.87 (1H, t), 4.03-3.88 (2H, m). | [M + H]+ 480.11 |
| 294 | | N-[3-(3-{3-[3-(2,2,2-Trifluoro-ethyl)-ureido]-phenyl}-imidazo[1,2-a]pyridin-7-yl)-phenyl]-methane-sulfonamide | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using (3-methanesulfonylamino-phenyl)boronic acid | 1H NMR (400 MHz, DMSO-d6): 9.89 (1H, s), 8.98 (1H, s), 8.66 (1H, d), 7.92 (1H, s), 7.81 (1H, s), 7.79 (1H, s), 7.65-7.55 (2H, m), 7.54-7.41 (3H, m), 7.34-7.23 (3H, m), 6.87 (1H, t), 4.02-3.89 (2H, m), 3.08 (3H, s). | [M + H]+ 504 |
| 295 | | 1-{3-[7-(3-[N,N-dimethyl-sulfamoyl-amino]phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using [3-(N,N-dimethyl-sulfamoylamino)phenyl]boronic acid | 1H NMR (400 MHz, Me-d3-OD): 8.65 (1H, d), 7.89-7.80 (2H, m), 7.74 (1H, s), 7.63 (1H, s), 7.55-7.37 (4H, m), 7.37-7.27 (3H, m), 3.96 (2H, q), 2.85 (6H, s). | [M + H]+ 533 |

-continued

| Eg. No. | Compound | Chemical Name | Procedure | ¹H NMR Data | M.S. |
|---|---|---|---|---|---|
| 296 | | 1-{3-[7-(4-Piperazin-2-yl-phenyl)-imidazo[1,2-a]pyridin-3-yl]-phenyl}-3-(2,2,2-trifluoro-ethyl)-urea hydrochloride | General route A steps A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 3-(4-chlorophenyl)-piperazine-1-carboxylic acid tert-butyl ester, Procedure D3a | 1H NMR (400 MHz, Me-d3-OD): 8.67 (1H, d), 8.50 (1H, s), 7.92-7.83 (4H, m), 7.79-7.72 (1H, m), 7.61 (2H, d), 7.50 (1H, t), 7.43-7.29 (3H, m), 4.12 (1H, dd), 3.96 (2H, q), 3.53-3.25 (3H, m), 3.25-2.98 (3H, m). | [M + H]+ 495 |
| 297 | | 1-(2,2,2-Trifluoro-ethyl)-3-{3-[7-(3-trifluoro-methoxy-phenyl)-imidazo[1,2-a]pyridin-3-yl]-phenyl}-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3-(trifluoromethoxy)phenylboronic acid | 1H NMR (400 MHz, DMSO-d6): 8.98 (1H, s), 8.64 (1H, d), 8.12 (1H, d), 7.94 (1H, d), 7.88 (1H, s), 7.83 (1H, s), 7.81 (1H, s), 7.65 (1H, t), 7.51-7.39 (4H, m), 7.33-7.24 (1H, m), 6.87 (1H, t), 4.03-3.88 (2H, m). | [M + H]+ 495 |
| 298 | | 1-{3-[7-(3-Isopropyl-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3-isopropylphenylboronic acid | 1H NMR (400 MHz, DMSO-d6): 8.98 (1H, s), 8.62 (1H, d), 7.99 (1H, s), 7.84-7.76 (2H, m), 7.72 (1H, s), 7.66 (1H, d), 7.50-7.36 (4H, m), 7.36-7.24 (2H, m), 6.86 (1H, t), 4.02-3.89 (2H, m), 3.06-2.96 (1H, m), 1.29 (6H, d). | [M + H]+ 453 |

| Eg. No. | Compound | Chemical Name | Procedure | ¹H NMR Data | M.S. |
|---|---|---|---|---|---|
| 299 | | 2-Fluoro-N-methyl-5-(3-{3-[3-(2,2,2-trifluoro-ethyl)-ureido]-phenyl}-imidazo[1,2-a]pyridin-7-yl)-benzamide | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-fluoro-3-(methyl-carbamoyl)benzene-boronic acid | 1H NMR (400 MHz, DMSO-d6): 8.98 (1H, s), 8.63 (1H, d), 8.41 (1H, d), 8.08-7.97 (3H, m), 7.81 (1H, s), 7.80 (1H, s), 7.50-7.36 (4H, m), 7.32-7.24 (1H, m), 6.87 (1H, t), 4.01-3.89 (2H, m), 2.83 (3H, d). | [M + H]+ 486 |
| 300 | | 1-{3-[7-(2-Methyl-pyridin-4-yl)-imidazo[1,2-a]pyridin-3-yl]-phenyl}-3-(2,2,2-trifluoro-ethyl)-urea Formate | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 2-methylpyridine-4-boronic acid | 1H NMR (400 MHz, DMSO-d6): 9.31 (1H, s), 8.64 (1H, d), 8.55 (1H, d), 8.31 (1H, s), 8.17 (1H, s), 7.84 (2H, s), 7.77 (1H, s), 7.67 (1H, d), 7.52-7.40 (3H, m), 7.27 (2H, d), 3.82 (2H, m), 2.58 (3H, s). | [M + H]+ 426 |
| 301 | | 1-{3-[7-(3,4-Dichloro-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 3,4-dichlorophenyl-boronic acid | 1H NMR (400 MHz, DMSO-d6): 8.98 (1H, s), 8.63 (1H, d), 8.18 (1H, d), 8.14 (1H, s), 7.89 (1H, dd), 7.84 (1H, s), 7.80 (1H, s), 7.76 (1H, d), 7.50-7.39 (3H, m), 7.32-7.24 (1H, m), 6.86 ((1H, t), 4.02-3.89 (2H, m). | [M + H]+ 479 |

-continued

| Eg. No. | Compound | Chemical Name | Procedure | ¹H NMR Data | M.S. |
|---|---|---|---|---|---|
| 302 | | 1-{3-[7-(4-Cyano-3-fluoro-phenyl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-cyano-3-fluorophenyl-boronic acid | 1H NMR (400 MHz, DMSO-d6): 8.97 (1H, s), 8.66 (1H, d), 8.28 (1H, s), 8.14 (1H, d), 8.10-8.01 (1H, m), 7.98 (1H, d), 7.89 (1H, s), 7.82 (1H, s), 7.55-7.41 (3H, m), 7.34-7.25 (1H, m), 6.86 (1H, t), 4.02-3.88 (2H, m). | [M + H]+ 454 |
| 303 | | 1-{3-[7-(4-Cyano-phenyl)-imidazo[1,2-a]pyridin-3-yl]-phenyl}-3-(2,2,2-trifluoro-ethyl)-urea formate | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 4-cyanophenylboronic acid | 1H NMR (400 MHz, DMSO-d6): 8.97 (1H, s), 8.66 (1H, d), 8.18 (1H, s), 8.10 (2H, d), 8.02-7.93 (3H, m), 7.86 (1H, s), 7.80 (1H, s), 7.46 (3H, d), 7.33-7.25 (1H, m), 6.86 (1H, t), 4.01-3.89 (2H, m). | [M + H]+ 436 |
| 304 | | 1-{3-[7-(1-Methyl-1H-imidazol-2-yl)-imidazo[1,2-a]pyridin-3-yl]-phenyl}-3-(2,2,2-trifluoro-ethyl)-urea formate | General route A steps A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 2-Bromo-1-methyl-1H-imidazole | 1H NMR (400 MHz, Me-d3-OD): 8.68 (1H, d), 8.39 (1H, s), 7.91 (1H, s), 7.84 (1H, s), 7.81 (1H, s), 7.51 (1H, t), 7.43 (1H, d), 7.35 (2H, t), 7.30 (1H, s), 7.15 (1H, s), 4.02-3.89 (5H, m). | [M + H]+ 415 |

| Eg. No. | Compound | Chemical Name | Procedure | ¹H NMR Data | M.S. |
|---|---|---|---|---|---|
| 305 | | 4-(3-{3-[3-(2,2,2-Trifluoro-ethyl)-ureido]-phenyl}-imidazo[1,2-a]pyridin-7-yl)-benzene-sulfonamide | General route A, procedure A3b using I6 1-[3-(4,4,5,5-Tetramethyl-[1,3,2] dioxaborolan-2-yl)-phenyl]-3-(2,2,2-trifluoro-ethyl)-urea, procedure A4b using 4-Sulfamoylphenylboronic acid, pinacol ester | 1H NMR (400 MHz, DMSO-d6): 8.97 (1H, s), 8.67 (1H, d), 8.13 (1H, s), 8.08 (2H, d), 7.94 (2H, d), 7.85 (1H, s), 7.81 (1H, s), 7.51-7.40 (5H, m), 7.33-7.25 (1H, m), 6.85 (1H, t), 4.02-3.89 (2H, m). | [M + H]+ 490 |
| 306 | | 1-{3-[7-(6-Methoxy-pyridin-3-yl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2] dioxaborolan-2-yl)-phenyl]-3-(2,2,2-trifluoro-ethyl)-urea, procedure A4b using 2-methoxy-5-pyridine-boronic acid | 1H NMR (400 MHz, DMSO-d6): 8.97 (1H, s), 8.70 (1H, d), 8.62 (1H, d), 8.23 (1H, dd), 8.03 (1H, s), 7.79 (2H, s), 7.49-7.42 (2H, m), 7.40 (1H, dd), 7.32-7.23 (1H, m), 6.96 (1H, d), 6.86 (1H, t), 4.02-3.88 (5H, m). | [M + H]+ 442 |
| 307 | | 1-{3-[7-(1-Methyl-1H-pyrazol-3-yl)-imidazo[1,2-a]pyridin-3-yl]-phenyl}-3-(2,2,2-trifluoro-ethyl)-urea | General route A steps A1-A3,procedure A3b using I6 1-[3-(4,4,5,5-Tetramethyl-[1,3,2] dioxaborolan-2-yl)-phenyl]-3-(2,2,2-trifluoro-ethyl)-urea, procedure E2 and procedure E3 using 3-Iodo-1-methyl-1H-pyrazole | 1H NMR (400 MHz, Me-d3-OD): 8.60 (1H, d), 7.98 (1H, s), 7.81 (1H, s), 7.73 (1H, s), 7.69 (1H, d), 7.57-7.46 (2H, m), 7.43 (1H, d), 7.32 (1H, d), 6.82 (1H, d), 4.03-3.89 (5H, m). | [M + H]+ 415 |

-continued

| Eg. No. | Compound | Chemical Name | Procedure | ¹H NMR Data | M.S. |
|---|---|---|---|---|---|
| 308 | | 1-{3-[7-(3-Pyrazol-1-yl-phenyl)-imidazo[1,2-a]pyridin-3-yl]-phenyl}-3-(2,2,2-trifluoro-ethyl)-urea formate | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 1[3-(4,4,5,5-tetramethyl-[1,3,2]-dioxaborolan-2-yl)phenyl]-1H-pyrazole | 1H NMR (400 MHz, DMSO-d6): 9.19 (1H, s), 8.75 (1H, d), 8.66 (1H, d), 8.29 (2H, s), 8.18 (1H, s), 7.97-7.88 (1H, m), 7.87-7.76 (4H, m), 7.64 (1H, t), 7.49 (1H, dd), 7.48-7.42 (2H, m), 7.33-7.24 (1H, m), 7.10 (1H, t), 6.60 (1H, t), 4.02-3.87 (2H, m). | [M + H]+ 477 |
| 309 | | 1-{3-[7-(6-Oxo-1,6-dihydro-pyridin-3-yl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 2-methoxy-5-pyridine-boronic acid, procedure S, step 1 | 1H NMR (400 MHz, DMSO-d6): 11.97 (1H, s), 8.95 (1H, s), 8.54 (1H, d), 8.05 (1H, dd), 7.97 (1H, d), 7.90 (1H, s), 7.78 (1H, s), 7.75 (1H, s), 7.49-7.39 (2H, m), 7.31 (1H, dd), 7.28-7.21 (1H, m), 6.84 (1H, t), 6.47 (1H, d), 4.02-3.88 (2H, m). | [M + H]+ 428 |
| 310 | | 1-{3-[7-(5-Methyl-[1,3,4]-thiadiazol-2-yl)-imidazo[1,2-a]pyridin-3-yl]-phenyl}-3-(2,2,2-trifluoro-ethyl)-urea | General route A steps A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 2-bromo-5-methyl-[1,3,4]-thiadiazole | 1H NMR (400 MHz, DMSO-d6): 8.98 (1H, s), 8.68 (1H, d), 8.23 (1H, s), 7.91 (1H, s), 7.77 (1H, s), 7.60 (1H, dd), 7.56-7.42 (2H, m), 7.30 (1H, d), 6.86 (1H, t), 4.02-3.88 (2H, m), 2.82 (3H, s). | [M + H]+ 433 |

| Eg. No. | Compound | Chemical Name | Procedure | ¹H NMR Data | M.S. |
|---|---|---|---|---|---|
| 311 | 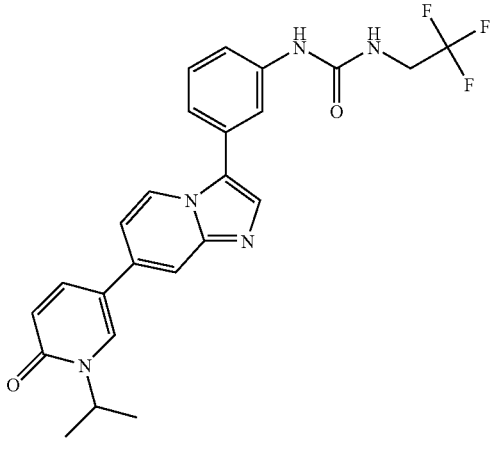 [SMILES: CC(C)n1cc(-c2ccn3c(-c4cccc(NC(=O)NCC(F)(F)F)c4)cnc3c2)ccc1=O] | 1-{3-[7-(1-Isopropyl-6-oxo-1,6-dihydro-pyridin-3-yl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 2-methoxy-5-pyridine-boronic acid, procedure S using 2-bromopropane in Step 2 | 1H NMR (400 MHz, DMSO-d6): 8.98 (1H, s), 8.57 (1H, d), 8.22 (1H, d), 8.04-7.94 (2H, m), 7.84 (1H, s), 7.77 (1H, s), 7.50-7.35 (3H, m), 7.26 (1H, d), 6.88 (1H, t), 6.52 (1H, d), 5.18-5.08 (1H, m), 4.02-3.89 (2H, m), 1.42 (6H, d). | [M + H]+ 470 |
| 312 | 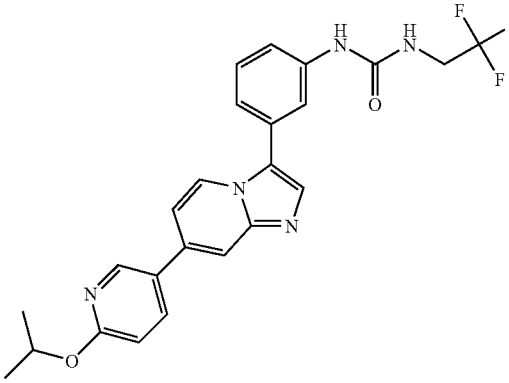 | 1-{3-[7-(6-Isopropoxy-pyridin-3-yl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 2-methoxy-5-pyridine-boronic acid, procedure S using 2-bromopropane in Step 2 | 1H NMR (400 MHz, DMSO-d6): 8.97 (1H, s), 8.68 (1H, d), 8.61 (1H, d), 8.20 (1H, dd), 8.01 (1H, s), 7.79 (2H, s), 7.45 (2H, d), 7.39 (1H, dd), 7.31-7.23 (1H, m), 6.92-6.81 (2H, m), 5.38-5.28 (1H, m), 4.01-3.89 (2H, m), 1.34 (6H, d). | [M + H]+ 470 |
| 313 | 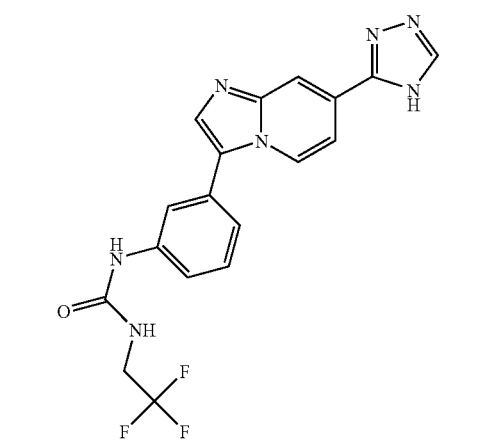 [SMILES: O=C(NCC(F)(F)F)Nc1cccc(-c2cnc3cc(-c4nnc[nH]4)ccn23)c1] | 1-{3-[7-(4H-[1,3,4]Triazol-3-yl)-imidazo[1,2-a]pyridin-3-yl]-phenyl}-3-(2,2,2-trifluoro-ethyl)-urea | Procedure AA | 1H NMR (400 MHz, Me-d3-OD): 8.67 (1H, d), 8.54 (1H, s), 8.32 (1H, s), 7.82 (1H, s), 7.79 (1H, s), 7.70 (1H, d), 7.53-7.48 (1H, m), 7.44 (1H, d), 7.34 (1H, d), 3.96 (2H, q). | [M + H]+ 402 |

-continued

| Eg. No. | Compound | Chemical Name | Procedure | ¹H NMR Data | M.S. |
|---|---|---|---|---|---|
| 314 | | 1-{3-[7-(1H-Tetrazol-5-yl)-imidazo[1,2-a]pyridin-3-yl]-phenyl}-3-(2,2,2-trifluoro-ethyl)-urea | Procedure AC | 1H NMR (400 MHz, DMSO-d6): 8.96 (1H, s), 8.69 (1H, d), 8.22 (1H, s), 7.86 (1H, s), 7.74 (1H, s), 7.63 (1H, d), 7.52 (1H, d), 7.47 (1H, t), 7.29 (1H, d), 6.85 (1H, t), 4.01-3.90 (2H, m). | [M + H]+ 403 |
| 315 | | 1-{5-[7-(1-Methyl-1H-pyrazol-4-yl)-imidazo[1,2-a]pyridin-3-yl]-pyridin-3-yl}-3-(2,2,2-trifluoro-ethyl)-urea | General route B, Procedure B1c using 1-methyl-4-(4,4,5,5-tetramethyl-[1,3,2]-dioxaborolan-2-yl)-1H-pyrazole, B2, B3a using I28 1-[5-(4,4,5,5-Tetramethyl-[1,3,2]dioxaborolan-2-yl)-pyridin-3-yl]-3-(2,2,2-trifluoro-ethyl)-urea | 1H NMR (400 MHz, Me-d3-OD): 8.60-8.50 (2H, m), 8.47 (1H, s), 8.37 (1H, s), 8.30-8.20 (1H, m), 8.20-8.14 (1H, m), 8.04-7.96 (1H, m), 7.81 (1H, s), 7.78 (1H, s), 7.32 (1H, d), 4.04-3.90 (5H, m). | [M + H]+ 416 |
| 316 | | 1-{3-[7-(Methoxy-imino-methyl)-imidazo[1,2-a]pyridin-3-yl]-phenyl}-3-(2,2,2-trifluoro-ethyl)-urea | Procedure SGI using methoxyamine hydrochloride | 1H NMR (400 MHz, Me-d3-OD): 8.54 (1H, d), 8.21 (1H, s), 7.80 (1H, s), 7.74 (1H, s), 7.70 (1H, s), 7.49 (1H, t), 7.42 (2H, d), 7.31 (1H, d), 4.00 (3H, s), 3.95 (2H, q). | [M + H]+ 392 |
| 317 | | 1-{3-[7-(Hydroxy-imino-methyl)-imidazo[1,2-a]pyridin-3-yl]-phenyl}-3-(2,2,2-trifluoro-ethyl)-urea | Procedure SGI using hydroxylamine hydrochloride | 1H NMR (400 MHz, Me-d3-OD): 8.55 (1H, d), 8.20 (1H, s), 7.84-7.79 (1H, m), 7.77 (1H, s), 7.71 (1H, s), 7.55-7.45 (2H, m), 7.43 (1H, d), 7.32 (1H, d), 3.95 (2H, q). | [M + H]+ 378 |

-continued

| Eg. No. | Compound | Chemical Name | Procedure | ¹H NMR Data | M.S. |
|---|---|---|---|---|---|
| 318 | 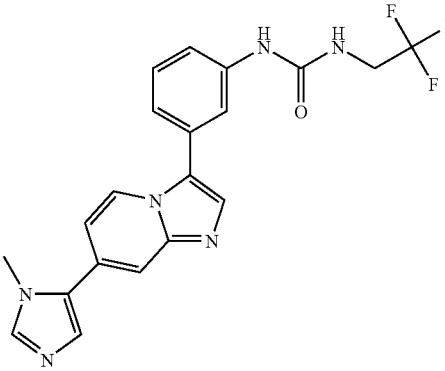 | 1-{3-[7-(3-Methyl-3H-imidazol-4-yl)-imidazo[1,2-a]pyridin-3-yl]-phenyl}-3-(2,2,2-trifluoro-ethyl)-urea | General route A steps A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 5-Bromo-1-methyl-1H-imidazole | 1H NMR (400 MHz, Me-d3-OD): 8.65 (1H, d), 7.91-7.85 (1H, m), 7.83 (1H, s), 7.77 (1H, s), 7.74 (1H, s), 7.50 (1H, t), 7.40 (1H, d), 7.37-7.29 (2H, m), 7.20 (1H, dd), 4.02-3.86 (5H, m). | [M + H]+ 415 |
| 319 | 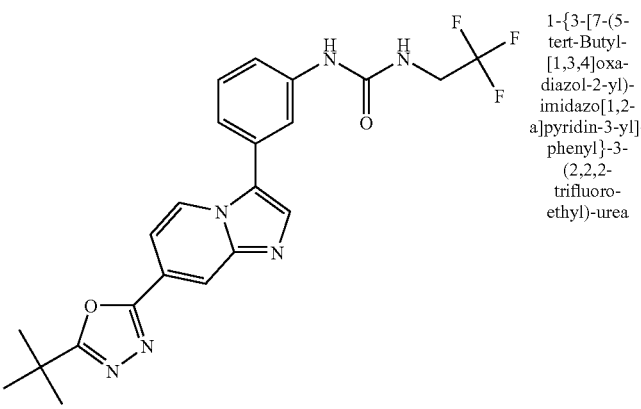 | 1-{3-[7-(5-tert-Butyl-[1,3,4]oxadiazol-2-yl)-imidazo[1,2-a]pyridin-3-yl]-phenyl}-3-(2,2,2-trifluoro-ethyl)-urea | Synthesised in an analogous manner as described in Example 329 except using pyridine and tosyl chloride to close the oxadiazole ring (Procedure AN). | 1H NMR (400 MHz, Me-d3-OD): 8.74 (1H, d), 8.28 (1H, s), 7.93-7.88 (1H, m), 7.88-7.82 (1H, m), 7.63 (1H, d), 7.52 (1H, t), 7.44 (1H, d), 7.35 (1H, d), 3.96 (2H, q), 1.55 (9H, s). | [M + H]+ 459 |
| 320 | 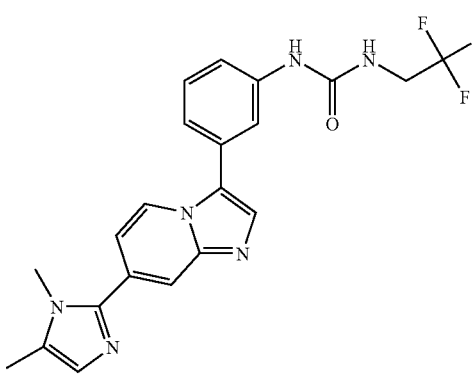 | 1-{3-[7-(1,5-Dimethyl-1H-imidazol-2-yl)-imidazo[1,2-a]pyridin-3-yl]-phenyl}-3-(2,2,2-trifluoro-ethyl)-urea | General route A steps A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 2-Bromo-1,5-dimethyl-1H-imidazole | 1H NMR (400 MHz, Me-d3-OD): 8.68 (1H, d), 7.85 (2H, d), 7.80 (1H, s), 7.51 (1H, t), 7.43 (1H, d), 7.38-7.28 (2H, m), 6.92 (1H, s), 3.95 (2H, q), 3.79 (3H, s), 2.36 (3H, s). | [M + H]+ 429 |
| 321 | 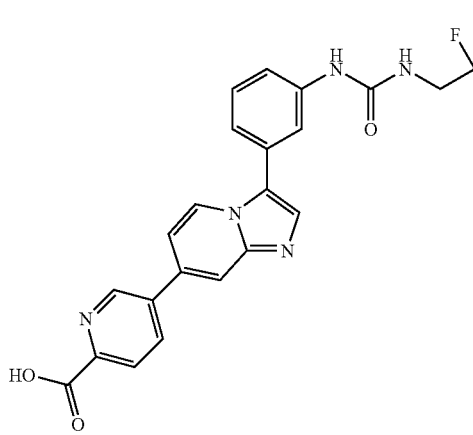 | 5-(3-{3-[3-(2,2,2-Trifluoro-ethyl)-ureido]-phenyl}-imidazo[1,2-a]pyridin-7-yl)-pyridine-2-carboxylic acid | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4e using I42 5-(4,4,5,5-Tetramethyl-[1,3,2]dioxaborolan-2-yl)-pyridine-2-carboxylic acid methyl ester | 1H NMR (400 MHz, DMSO-d6): 9.23 (1H, d), 9.07 (1H, s), 8.70 (1H, d), 8.46 (1H, dd), 8.26 (1H, s), 8.15 (1H, d), 7.88 (1H, s), 7.83 (1H, s), 7.52 (1H, dd), 7.50-7.42 (2H, m), 7.34-7.25 (1H, m), 6.95 (1H, s), 4.02-3.89 (2H, m). | [M + H]+ 456.1 |

-continued

| Eg. No. | Compound | Chemical Name | Procedure | ¹H NMR Data | M.S. |
|---|---|---|---|---|---|
| 322 | | 1-{3-[7-(1,4-Dimethyl-1H-imidazol-2-yl)-imidazo[1,2-a]pyridin-3-yl]-phenyl}-3-(2,2,2-trifluoro-ethyl)-urea | General route A steps A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 2-bromo-1,4-dimethyl-1H-imidazole replacing Pd(OAc)$_2$ and SPHOS with PdCl$_2$(dppf) | 1H NMR (400 MHz, Me-d3-OD): 8.66 (1H, d), 7.90-7.76 (3H, m), 7.50 (1H, t), 7.43 (1H, d), 7.33 (2H, d), 7.02-6.95 (1H, m), 3.95 (2H, q), 3.86 (3H, s), 2.26 (3H, s). | [M + H]+ 429 |
| 323 | | 1-{3-[7-(1,2-Dimethyl-1H-imidazol-4-yl)-imidazo[1,2-a]pyridin-3-yl]-phenyl}-3-(2,2,2-trifluoro-ethyl)-urea | General route A steps A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 4-bromo-1,2-dimethyl-1H-imidazole, replacing Pd(OAc)$_2$ and SPHOS with PdCl$_2$(dppf) | 1H NMR (400 MHz, Me-d3-OD): 8.54 (1H, d), 7.93 (1H, s), 7.80 (1H, s), 7.67 (1H, s), 7.60 (1H, s), 7.48 (1H, t), 7.41 (1H, d), 7.36 (1H, d), 7.31 (1H, d), 3.95 (2H, q), 3.71 (3H, s), 2.46 (3H, s). | [M + H]+ 429 |
| 324 | | 1-{3-[7-(2-Methyl-2H-pyrazol-3-yl)-imidazo[1,2-a]pyridin-3-yl]-phenyl}-3-(2,2,2-trifluoro-ethyl)-urea | General route A, procedure A3b using I6 1-[3-(4,4,5,5-Tetramethyl-[1,3,2]dioxaborolan-2-yl)-phenyl]-3-(2,2,2-trifluoro-ethyl)-urea, procedure A4b using 1-methyl-5-(4,4,5,5-tetramethyl-[1,3,2]dioxaborolan-2-yl)-1H-pyrazole | 1H NMR (400 MHz, DMSO-d6): 7.87 (1H, d), 7.06 (1H, s), 7.03-7.02 (1H, m), 6.98 (2H, d), 6.77 (1H, d), 6.69 (1H, t), 6.64-6.49 (2H, m), 6.37 (1H, dd), 5.78 (1H, d), 3.22 (3H, s), 3.15 (2H, q). | [M + H]+ 415 |

| Eg. No. | Compound | Chemical Name | Procedure | ¹H NMR Data | M.S. |
|---|---|---|---|---|---|
| 325 | | 1-{3-[7-(5-Cyclopropyl-[1,3,4]thiadiazol-2-yl)-imidazo[1,2-a]pyridin-3-yl]-phenyl}-3-(2,2,2-trifluoro-ethyl)-urea | general route A steps A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 2-bromo-5-cyclopropyl-[1,3,4]-thiadiazole replacing Pd(OAc)$_2$ and SPHOS with PdCl$_2$(dppf) | 1H NMR (400 MHz, Me-d3-OD): 8.69 (1H, d), 8.13 (1H, s), 7.85 (2H, s), 7.64 (1H, dd), 7.51 (1H, t), 7.44 (1H, d), 7.34 (1H, d), 3.96 (2H, q), 2.62-2.53 (1H, m), 1.42-1.31 (2H, m), 1.26-1.17 (2H, m). | [M + H]+ 459 |
| 326 | | 1-{3-[7-(3-Methyl-isothiazol-5-yl)-imidazo[1,2-a]pyridin-3-yl]-phenyl}-3-(2,2,2-trifluoro-ethyl)-urea | general route A stpes A1-A3, procedure A3b using I6 1-[3-(4,4,5,5-Tetramethyl-[1,3,2]dioxaborolan-2-yl)-phenyl]-3-(2,2,2-trifluoro-ethyl)-urea, procedure E2 and procedure E3 using 5-Bromo-3-methyl-isothiazole replacing Pd(OAc)$_2$ and SPHOS with PdCl$_2$(dppf) | 1H NMR (400 MHz, Me-d3-OD): 8.66 (1H, d), 7.95 (1H, s), 7.85 (1H, s), 7.80 (1H, s), 7.62 (1H, s), 7.50 (1H, t), 7.41 (1H, d), 7.37-7.27 (2H, m), 3.96 (2H, q), 2.55 (3H, s). | [M + H]+ 432 |
| 327 | | 1-{3-[7-(5-Isopropyl-[1,3,4]oxadiazol-2-yl)-imidazo[1,2-a]pyridin-3-yl]-phenyl}-3-(2,2,2-trifluoro-ethyl)-urea | Synthesised in an analogous manner to Example 329 using triethylorthopropionate in step D. | 1H NMR (400 MHz, Me-d3-OD): 8.73 (1H, d), 8.26 (1H, s), 7.89 (1H, s), 7.85 (1H, s), 7.64-7.54 (2H, m), 7.51 (1H, t), 7.44 (1H, d), 7.33 (1H, d), 3.96 (2H, q), 3.44-3.35 (1H, m), 1.50 (6H, d). | [M + H]+ 445 |

| Eg. No. | Compound | Chemical Name | Procedure | ¹H NMR Data | M.S. |
|---|---|---|---|---|---|
| 328 | | 1-{3-[7-(3,5-Dimethyl-1H-pyrazol-4-yl)-imidazo[1,2-a]pyridin-3-yl]-phenyl}-3-(2,2,2-trifluoro-ethyl)-urea | General route A procedure A3b using I6 1-[3-(4,4,5,5-Tetramethyl-[1,3,2]dioxaborolan-2-yl)-phenyl]-3-(2,2,2-trifluoro-ethyl)-urea, procedure A4d using 3,5-dimethyl-4-(4,4,5,5-tetramethyl-1,3,2-dioxaborolan-2-yl)-1H-pyrazole using Fu's catalyst | 1H NMR (400 MHz, Me-d3-OD): 8.64 (1H, d), 8.21 (1H, s), 7.88 (1H, s), 7.79 (1H, s), 7.56 (1H, s), 7.49 (1H, t), 7.40 (1H, d), 7.32 (1H, d), 7.15 (1H, d), 3.95 (2H, q), 2.39 (6H, s). | [M + H]+ 429 |

Example 329

1-{3-[7-(5-Methyl-[1,3,4]oxadiazol-2-yl)-imidazo[1,2-a]pyridin-3-yl]-phenyl}-3-(2,2,2-trifluoro-ethyl)-urea

Step (a): Methyl imidazo[1,2-a]pyridine-7-carboxylate

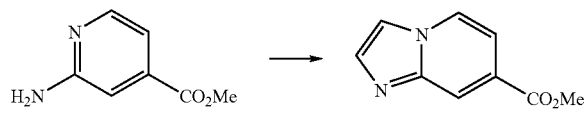

To a solution of Methyl 2-aminopyridine-4-carboxylate (10.0 g, 66 mmol, 1.0 equiv) in EtOH (150 ml) was added NaHCO₃ (11.1 g, 132 mmol, 2.0 equiv) followed by chloroacetaldehyde (13.0 ml, 99 mmol, 1.5 equiv). The mixture was refluxed for 2 h. Solvents were removed under reduced pressure and the crude mixture was partitioned between water and EtOAc. The resulting precipitate was washed with Et₂O and recrystallised from MeOH/Et₂O to afford 8.4 g of product. 1H NMR (400 MHz, DMSO-d⁶): 8.66 (1H, d), 8.16 (2H, s), 7.80 (1H, s), 7.33 (1H, d), 3.90 (3H, s). MS: [M+H]⁺ 177.

Step (b) Methyl 3-iodo-imidazo[1,2-a]pyridine-7-carboxylate

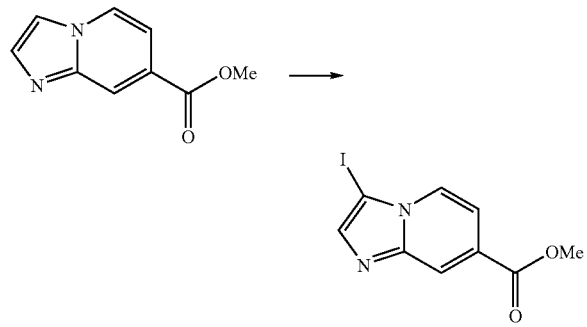

To a solution of Methyl imidazo[1,2-a]pyridine-7-carboxylate (3.8 g, 21.6 mmol, 1.0 equiv) in DMF (20 ml) was added N-iodosuccinimide (5.8 g, 26 mmol, 1.2 equiv) and the resulting mixture was stirred for 2 h at room temperature. The brown slurry was diluted with water, 10% w/v sodium thiosulfate and sodium carbonate (1M) and the resulting white solid was removed by filtration, washed with ether and dried to afford 4.7 g of product. MS: [M+H]⁺ 303; 1H NMR (400 MHz, Me-d³-OD): 8.44 (1H, d), 8.25 (1H, s), 7.88 (1H, s), 7.61 (1H, dd), 3.95 (3H, s).

Step (c) 3-Iodo-imidazo[1,2-a]pyridine-7-carboxylic acid hydrazide

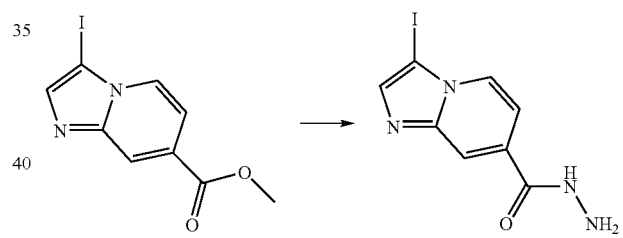

To a suspension of Methyl-3-Iodo-imidazo[1,2-a]pyridine-7-carboxylate (0.4 g, 1.32 mmol) in MeOH (6 ml) was added hydrazine hydrate (0.25 ml, 5.28 mmol). The mixture was refluxed for 4 h then further hydrazine hydrate (0.25 ml, 5.28 mmol) was added, the mixture heated o/n, allowed to cool, solid was filtered off and washed with MeOH and dried to afford 0.36 g of product. MS: [M+H]⁺ 303.

Step (d) 3-Iodo-7-(5-methyl-[1,3,4]oxadiazol-2-yl)-imidazo[1,2-a]pyridine

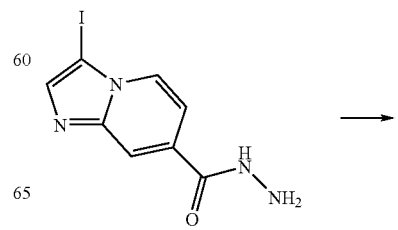

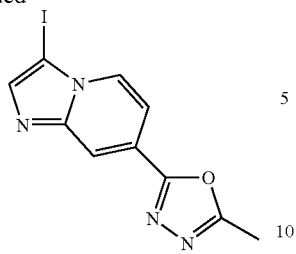

3-Iodo-imidazo[1,2-a]pyridine-7-carboxylic acid hydrazide (0.18 g, 0.59 mmol) was treated with triethylorthoacetate (3 ml) and concentrated $H_2SO_4$ (1 drop). The mixture was heated at 80° C. o/n, allowed to cool, solid was filtered off and washed with EtOH and dried to afford 0.165 g of product. MS: $[M+H]^+$ 327

Step (e) 1-{3-[7-(5-Methyl-[1,3,4]oxadiazol-2-yl)-imidazo[1,2-a]pyridin-3-yl]-phenyl}-(2,2,2-trifluoro-ethyl)-urea

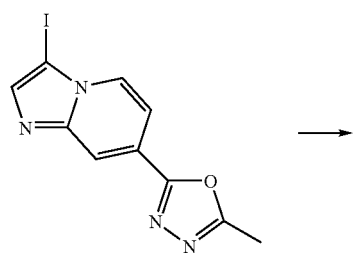

To a solution of 3-Iodo-7-(5-methyl-[1,3,4]oxadiazol-2-yl)-imidazo[1,2-a]pyridine (0.165 g, 0.5 mmol) in DME (10 ml) was added 1-[3-(4,4,5,5-Tetramethyl-[1,3,2]-dioxaborolan-2-yl)-phenyl]-3-(2,2,2-trifluoro-ethyl)-urea (16) (0.226 g, 0.65 mmol) and 2M $Na_2CO_3$ (3.4 ml) [reaction degassed by bubbling $N_2$ through] followed by tetrakis(triphenylphosphine)palladium(0) (45 mg, 0.039 mmol). The mixture was heated at 80° C. overnight, then diluted with water and extracted with EtOAc. The organic layer was washed with brine, dried and concentrated under reduced pressure. The residue was triturated with MeOH, filtered, the solid washed with MeOH, EtOAc then Ether and dried to afford 24 mg of the product. MS: $[M+H]^+$ 417

1H NMR (400 MHz, Me-$d^3$-OD): 8.74 (1H, d), 8.27 (1H, s), 7.87 (2H, d), 7.62 (1H, d), 7.52 (1H, t), 7.48-7.39 (1H, m), 7.39-7.31 (1H, m), 3.96 (2H, q), 2.69 (3H, s).

Example 330

1-[3-(7-[1,3,4]Oxadiazol-2-yl-imidazo[1,2-a]pyridin-3-yl)-phenyl]-3-(2,2,2-trifluoro-ethyl)-urea

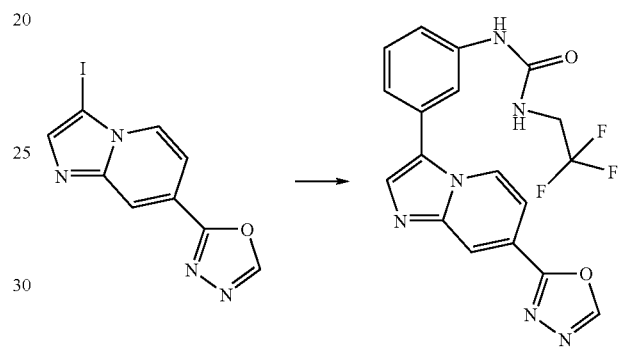

1-[3-(7-[1,3,4]Oxadiazol-2-yl-imidazo[1,2-a]pyridin-3-yl)-phenyl]-3-(2,2,2-trifluoro-ethyl)-urea was made as described above in Example 329 using triethylorthoformate in step d.

MS: $[M+H]^+$ 403

1H NMR (400 MHz, Me-$d^3$-OD): 9.11 (1H, s), 8.76 (1H, d), 8.34 (1H, s), 7.89 (2H, d), 7.67 (1H, dd), 7.52 (1H, t), 7.45 (1H, d), 7.36 (1H, d), 3.96 (2H, q).

Example 331

1-{3-[7-(5-Ethyl-[1,3,4]oxadiazol-2-yl)-imidazo[1,2-a]pyridin-3-yl]-phenyl}-3-(2,2,2-trifluoro-ethyl)-urea

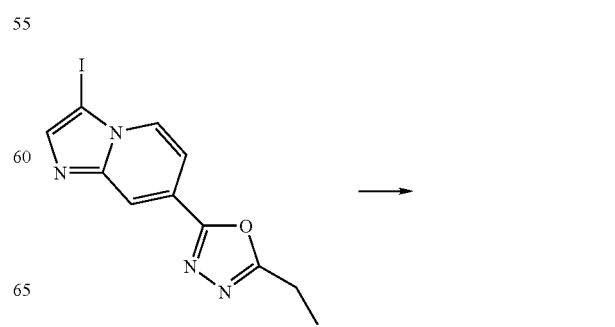

-continued

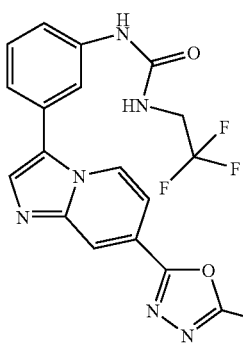

1-{3-[7-(5-Ethyl-[1,3,4]oxadiazol-2-yl)-imidazo[1,2-a]pyridin-3-yl]-phenyl}-3-(2,2,2-trifluoro-ethyl)-urea was made as described above in Example 329 using triethylorthopropionate in step d.

MS: [M+H]$^+$ 431

1H NMR (400 MHz, DMSO-d$^6$): 8.98 (1H, s), 8.72 (1H, d), 8.21 (1H, s), 7.95 (1H, s), 7.77 (1H, s), 7.57-7.43 (3H, m), 7.30 (1H, d), 6.86 (1H, t), 4.03-3.88 (2H, m), 2.99 (2H, q), 1.37 (3H, t).

Example 332

1-{3-[7-(4-Methyl-5-thioxo-4,5-dihydro-1H-[1,2,4]triazol-3-yl)-imidazo[1,2-a]pyridin-3-yl]-phenyl}-3-(2,2,2-trifluoro-ethyl)-urea Step (a) 1-[3-(7-Hydrazinocarbonyl-imidazo[1,2-a]pyridin-3-yl)-phenyl]-3-(2,2,2-trifluoro-ethyl)-urea

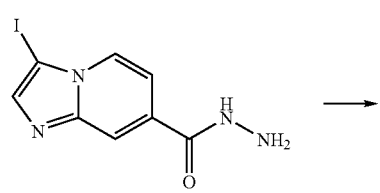

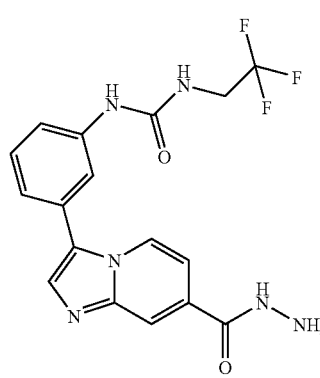

Procedure as described in B3a

Step (b) 1-{3-[7-(4-Methyl-5-thioxo-4,5-dihydro-1H-[1,2,4]triazol-3-yl)-imidazo[1,2-a]pyridin-3-yl]-phenyl}-3-(2,2,2-trifluoro-ethyl)-urea

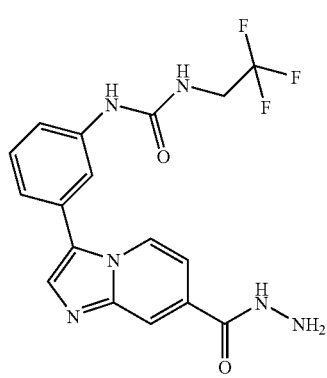

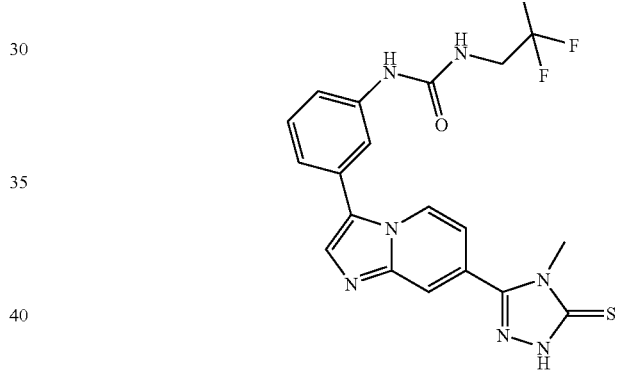

A mixture of 1-[3-(7-hydrazinocarbonyl-imidazo[1,2-a]pyridin-3-yl)-phenyl]-3-(2,2,2-trifluoro-ethyl)-urea (90 mg, 0.23 mmol) and methyl isothiocyanate (17 mg, 0.23 mmol) were heated in EtOH (3 ml) at 70° C. for 18 h. The reaction mixture was allowed to cool and the precipitate formed filtered off to give the product (34 mg). MS: [M+H]$^+$ 447

1H NMR (400 MHz, DMSO-d$^6$): 14.04 (1H, s), 9.00 (1H, s), 8.68 (1H, d), 8.14 (1H, s), 7.92 (1H, s), 7.78 (1H, s), 7.56-7.40 (2H, m), 7.36-7.24 (2H, m), 6.88 (1H, t), 4.02-3.88 (2H, m), 3.70 (3H, s).

Examples 333 to 384

By following the methods described above, the compounds of Examples 333 to 384 set out in the Table below were prepared.

| Eg. No. | Structure | Chemical Name | Method | NMR Data | MS Data |
|---|---|---|---|---|---|
| 333 | 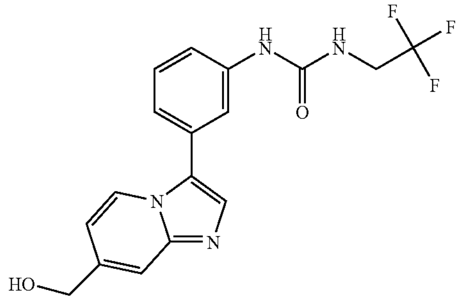 [SMILES: O=C(NCC(F)(F)F)Nc1cccc(-c2cnc3cc(CO)ccn23)c1] | 1-[3-(7-Hydroxymethyl-imidazo[1,2-a]pyridin-3-yl)-phenyl]-3-(2,2,2-trifluoro-ethyl)-urea Hydrochloride | Procedure SGA, procedure SGA3a using 1-[3-(4,4,5,5-Tetramethyl-[1,3,2]dioxaborolan-2-yl)-phenyl]-3-(2,2,2-trifluoro-ethyl)-urea (I6). Procedure J1. | 1H NMR (400 MHz, Me-d3-OD): 8.74 (1H, d), 8.11 (1H, s), 8.00 (1H, s), 7.95 (1H, s), 7.56 (1H, t), 7.49-7.40 (2H, m), 7.36 (1H, d), 3.95 (2H, q), 3.68 (2H, s). | [M + H] + 365 |
| 334 | 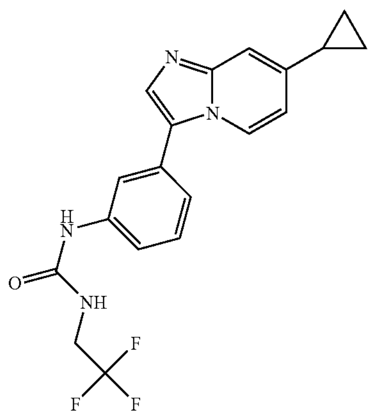 [SMILES: O=C(NCC(F)(F)F)Nc1cccc(-c2cnc3cc(C4CC4)ccn23)c1] | 1-[3-(7-Cyclopropyl-imidazo[1,2-a]pyridin-3-yl)-phenyl]-3-(2,2,2-trifluoro-ethyl)-urea Formate | Procedure SGH | 1H NMR (400 MHz, Me-d3-OD): 8.50 (1H, d), 8.28 (1H, s), 7.83 (1H, s), 7.74 (1H, s), 7.54-7.32 (3H, m), 7.28 (1H, d), 6.88 (1H, d), 3.94 (2H, q), 3.38-3.26 (6H, m), 2.18-2.06 (1H, m), 1.25-1.11 (2H, m), 0.98-0.86 (2H, m). | [M + H] + 375 |
| 335 | 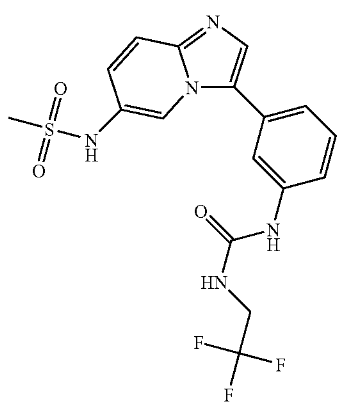 [SMILES: CS(=O)(=O)Nc1ccc2ncc(-c3cccc(NC(=O)NCC(F)(F)F)c3)n2c1] | N-(3-{3-[3-(2,2,2-Trifluoro-ethyl)-ureido]-phenyl}-imidazo[1,2-a]pyridin-6-yl)-methanesulfon-amide | Procedure SGB | 1H NMR (400 MHz, Me-d3-OD): 8.57 (1H, s), 8.19 (1H, s), 7.86 (1H, t), 7.74 (1H, s), 7.66 (1H, d), 7.49 (1H, t), 7.45-7.34 (2H, m), 7.30 (1H, d), 3.95 (2H, q), 3.03 (3H, s), 2.67 (1H, s). | [M + H] + 428 |
| 336 | 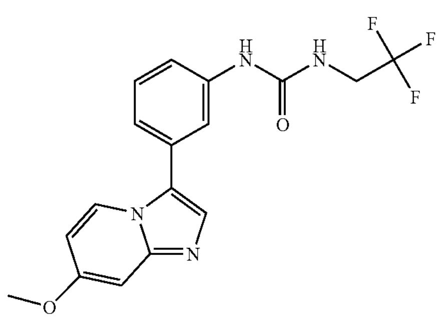 [SMILES: COc1ccn2c(-c3cccc(NC(=O)NCC(F)(F)F)c3)cnc2c1] | 1-[3-(7-Methoxy-imidazo[1,2-a]pyridin-3-yl)-phenyl]-3-(2,2,2-trifluoro-ethyl)-urea Formate | Procedure SGA, procedure SGA3a using 1-[3-(4,4,5,5-Tetramethyl-[1,3,2]dioxaborolan-2-yl)-phenyl]-3-(2,2,2-trifluoro-ethyl)-urea (I6) | 1H NMR (400 MHz, Me-d3-OD): 8.43 (1H, d), 8.39 (1H, s), 7.79 (1H, s), 7.63 (1H, s), 7.45 (1H, t), 7.38 (1H, d), 7.24 (1H, d), 7.03 (1H, d), 6.83 (1H, dd), 4.03-3.87 (5H, m). | [M + H] + 365 |

| Eg. No. | Structure | Chemical Name | Method | NMR Data | MS Data |
|---|---|---|---|---|---|
| 337 | 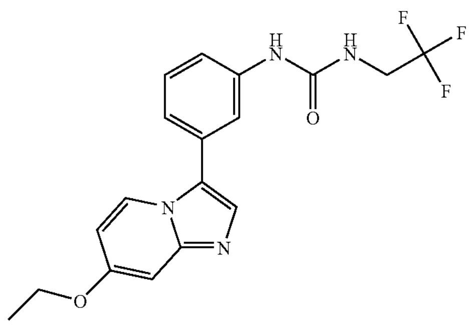 [SMILES: CCOc1ccn2c(-c3cccc(NC(=O)NCC(F)(F)F)c3)cnc2c1] | 1-[3-(7-Ethoxy-imidazo[1,2-a]pyridin-3-yl)-phenyl]-3-(2,2,2-trifluoro-ethyl)-urea Formate | Procedure SGA, procedure SGA3a using 1-[3-(4,4,5,5-Tetramethyl-[1,3,2]dioxaborolan-2-yl)-phenyl]-3-(2,2,2-trifluoro-ethyl)-urea (I6) | 1H NMR (400 MHz, DMSO-d6): 8.92 (1H, s), 8.39 (1H, d), 7.67 (1H, s), 7.55 (1H, s), 7.45-7.37 (2H, m), 7.22-7.15 (1H, m), 6.99 (1H, d), 6.83 (1H, t), 6.68 (1H, dd), 4.13 (2H, q), 3.98-3.88 (2H, m), 1.38 (3H, t). | [M + H] + 379 |
| 338 | 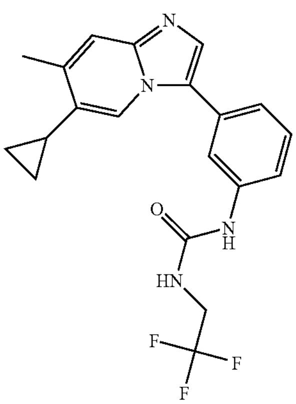 [SMILES: Cc1cc2ncc(-c3cccc(NC(=O)NCC(F)(F)F)c3)n2cc1C1CC1] | 1-[3-(6-Cyclopropyl-7-methyl-imidazo[1,2-a]pyridin-3-yl)-phenyl]-3-(2,2,2-trifluoro-ethyl)-urea | Procedure SGC | 1H NMR (400 MHz, Me-d3-OD): 8.24 (1H, s), 7.86 (1H, s), 7.66 (1H, s), 7.47 (2H, d), 7.35 (1H, d), 7.33-7.22 (2H, m), 4.02-3.87 (2H, m), 1.99-1.90 (1H, m), 1.05-0.96 (2H, m), 0.75-0.66 (2H, m). | [M + H] + 389 |
| 339 | 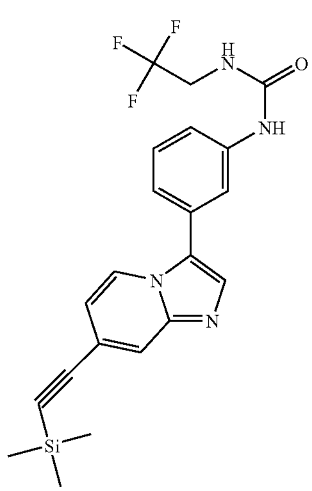 [SMILES: C[Si](C)(C)C#Cc1ccn2c(-c3cccc(NC(=O)NCC(F)(F)F)c3)cnc2c1] | 1-(2,2,2-Trifluoro-ethyl)-3-[3-(7-trimethylsilan-ylethynyl-imidazo[1,2-a]pyridin-3-yl)-phenyl]-urea | General procedure SGD, Procedure SGD4a using trimethylsilylacetylene | 1H NMR (400 MHz, Me-d3-OD): 8.52 (1H, d), 7.79 (1H, s), 7.77 (1H, s), 7.70 (1H, s), 7.48 (1H, t), 7.42 (1H, d), 7.29 (1H, d), 6.98 (1H, d), 3.95 (2H, q), 0.28 (9H, s). | [M + H] + 431 |

-continued

| Eg. No. | Structure | Chemical Name | Method | NMR Data | MS Data |
|---|---|---|---|---|---|
| 340 | 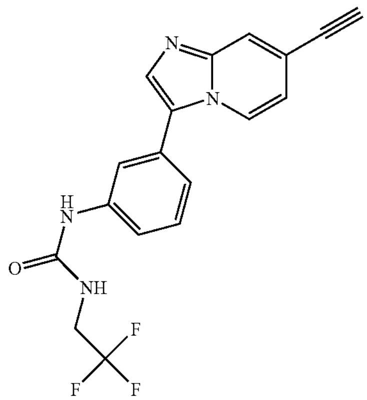 [SMILES: C#Cc1ccn2c(-c3cccc(NC(=O)NCC(F)(F)F)c3)cnc2c1] | 1-[3-(7-Ethynyl-imidazo[1,2-a]pyridin-3-yl)-phenyl]-3-(2,2,2-trifluoro-ethyl)-urea | General procedure SGD, Procedure SGD4a using trimethylsilylacetylene | 1H NMR (400 MHz, Me-d3-OD): 8.53 (1H, d), 7.79 (1H, s), 7.77 (1H, s), 7.74 (1H, s), 7.48 (1H, t), 7.41 (1H, d), 7.29 (1H, d), 7.01 (1H, dd), 3.95 (2H, q), 3.83 (1H, s). | [M + H]+ 359 |
| 341 | 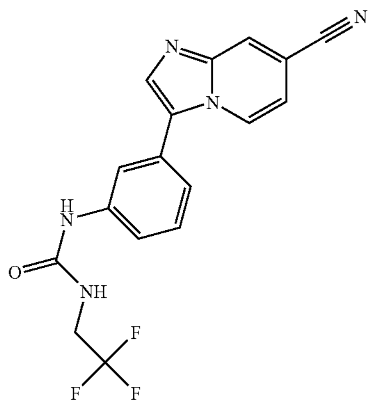 [SMILES: N#Cc1ccn2c(-c3cccc(NC(=O)NCC(F)(F)F)c3)cnc2c1] | 1-[3-(7-Cyano-imidazo[1,2-a]pyridin-3-yl)-phenyl]-3-(2,2,2-trifluoro-ethyl)-urea | Procedure SGE | 1H NMR (400 MHz, Me-d3-OD): 8.70 (1H, d), 8.18 (1H, s), 7.96 (1H, s), 7.84 (1H, t), 7.51 (1H, t), 7.47-7.38 (1H, m), 7.37-7.28 (1H, m), 7.19 (1H, dd), 3.95 (2H, q). | [M + H]+ 360 |
| 342 | 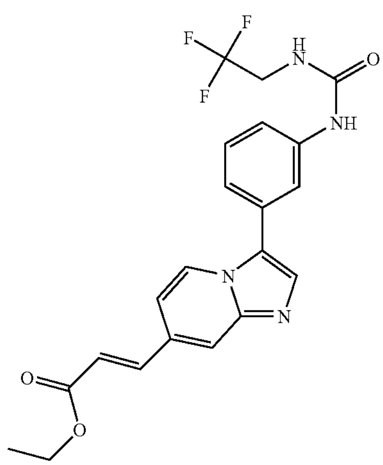 [SMILES: CCOC(=O)/C=C/c1ccn2c(-c3cccc(NC(=O)NCC(F)(F)F)c3)cnc2c1] | (E)-3-(3-{3-[3-(2,2,2-Trifluoro-ethyl)-ureido]-phenyl}-imidazo[1,2-a]pyridin-7-yl)-acrylic acid ethyl ester | Procedure SGG, steps G1 and G2 | 1H NMR (400 MHz, Me-d3-OD): 8.57 (1H, d), 7.86-7.71 (4H, m), 7.49 (1H, t), 7.42 (1H, d), 7.37-7.27 (2H, m), 6.67 (1H, d), 4.29 (2H, q), 3.95 (2H, q), 1.36 (3H, t). | [M + H]+ 433 |
| 343 | 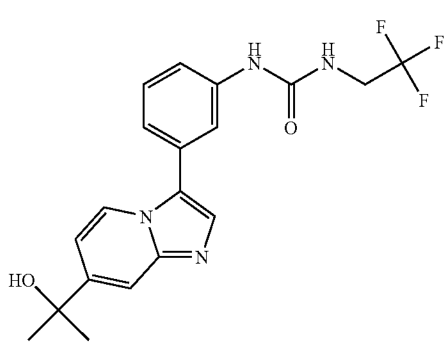 [SMILES: CC(C)(O)c1ccn2c(-c3cccc(NC(=O)NCC(F)(F)F)c3)cnc2c1] | 1-{3-[7-(1-Hydroxy-1-methyl-ethyl)-imidazo[1,2-a]pyridin-3-yl]-phenyl}-3-(2,2,2-trifluoro-ethyl)-urea Formate | Procedure SGF | 1H NMR (400 MHz, Me-d3-OD): 8.57 (1H, d), 8.22 (1H, s), 7.85 (1H, s), 7.77 (2H, d), 7.49 (1H, t), 7.39 (1H, d), 7.30 (1H, d), 7.25 (1H, dd), 3.95 (2H, q), 1.61 (6H, s). | [M + H]+ 393 |

-continued

| Eg. No. | Structure | Chemical Name | Method | NMR Data | MS Data |
|---|---|---|---|---|---|
| 344 | 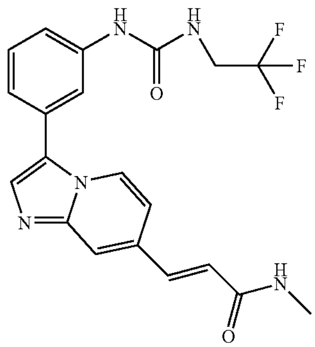 [SMILES: CNC(=O)/C=C/c1ccn2c(-c3cccc(NC(=O)NCC(F)(F)F)c3)cnc2c1] | (E)-N-Methyl-3-(3-{3-[3-(2,2,2-trifluoro-ethyl)-ureido]-phenyl}-imidazo[1,2-a]pyridin-7-yl)-acrylamide | Procedure SGG, step SGG4 using methylamine | 1H NMR (400 MHz, Me-d3-OD): 8.55 (1H, d), 7.82 (1H, s), 7.79-7.75 (1H, m), 7.73 (1H, s), 7.58 (1H, d), 7.48 (1H, t), 7.40 (1H, d), 7.30 (1H, d), 7.24 (1H, d), 6.71 (1H, d), 3.95 (2H, q), 2.89 (3H, s). | [M + H] + 418 |
| 345 | 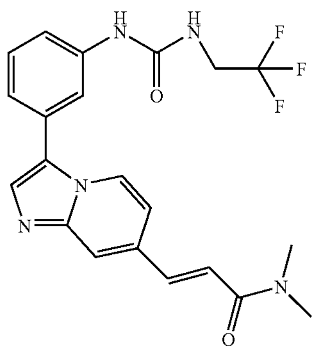 [SMILES: CN(C)C(=O)/C=C/c1ccn2c(-c3cccc(NC(=O)NCC(F)(F)F)c3)cnc2c1] | (E)-N,N-Dimethyl-3-(3-{3-[3-(2,2,2-trifluoro-ethyl)-ureido]-phenyl}-imidazo[1,2-a]pyridin-7-yl)-acrylamide | Procedure SGG, step SGG4 using dimethylamine | 1H NMR (400 MHz, Me-d3-OD): 8.55 (1H, d), 7.83 (1H, s), 7.81-7.76 (1H, m), 7.75 (1H, s), 7.61 (1H, d), 7.48 (1H, t), 7.45-7.35 (2H, m), 7.32-7.21 (2H, m), 3.95 (2H, q), 3.28 (3H, s), 3.09 (3H, s). | [M + H] + 432 |
| 346 | 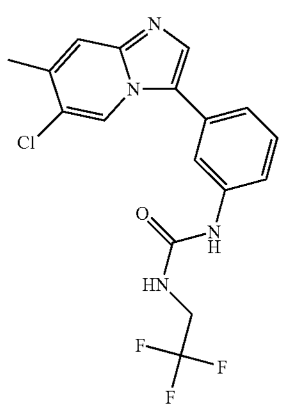 [SMILES: Cc1cc2ncc(-c3cccc(NC(=O)NCC(F)(F)F)c3)n2cc1Cl] | 1-[3-(6-Chloro-7-methyl-imidazo[1,2-a]pyridin-3-yl)-phenyl]-3-(2,2,2-trifluoro-ethyl)-urea | Procedure SGA, procedure SGA3a using 1-[3-(4,4,5,5-Tetramethyl-[1,3,2]dioxaborolan-2-yl)-phenyl]-3-(2,2,2-trifluoro-ethyl)-urea (I6) | 1H NMR (400 MHz, Me-d3-OD): 8.59 (1H, s), 7.74 (1H, s), 7.66 (1H, s), 7.55 (1H, s), 7.52-7.43 (2H, m), 7.36 (1H, s), 7.28 (1H, d), 4.02-3.87 (2H, m), 2.50 (3H, s). | [M + H] + 383 |
| 347 | 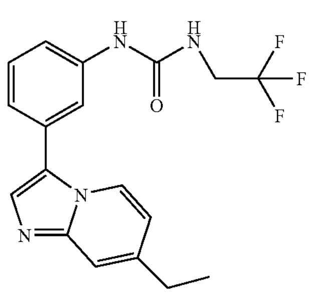 [SMILES: CCc1ccn2c(-c3cccc(NC(=O)NCC(F)(F)F)c3)cnc2c1] | 1-[3-(7-Ethyl-imidazo[1,2-a]pyridin-3-yl)-phenyl]-3-(2,2,2-trifluoro-ethyl)-urea Hydrochloride | Procedure SGA, procedure SGA3a using 1-[3-(4,4,5,5-Tetramethyl-[1,3,2]dioxaborolan-2-yl)-phenyl]-3-(2,2,2-trifluoro-ethyl)-urea (I6). Procedure J1. | 1H NMR (400 MHz, DMSO-d6): 9.43 (1H, s), 8.69 (1H, d), 8.33 (1H, s), 7.87 (1H, s), 7.81 (1H, s), 7.59-7.47 (2H, m), 7.43 (1H, dd), 7.33-7.24 (1H, m), 7.12 (1H, t), 4.02-3.87 (2H, m), 2.88 (2H, q), 1.29 (3H, t). | [M + H] + 363 |

| Eg. No. | Structure | Chemical Name | Method | NMR Data | MS Data |
|---|---|---|---|---|---|
| 348 | 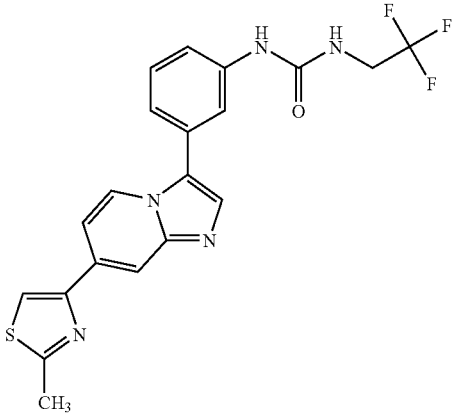 [SMILES: Cc1nc(-c2ccn3c(-c4cccc(NC(=O)NCC(F)(F)F)c4)cnc3c2)cs1] | 1-{3-[7-(2-Methyl-thiazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using 4-Bromo-2-methylthiazole | 1H NMR (400 MHz, Me-d3-OD): 8.60 (1H, d), 8.20 (1H, s), 7.90 (1H, s), 7.82 (1H, s), 7.73 (1H, s), 7.60-7.45 (2H, m), 7.42 (1H, d), 7.32 (1H, d), 3.95 (2H, q), 2.80 (3H, s). | [M + H] + 432 |
| 349 | 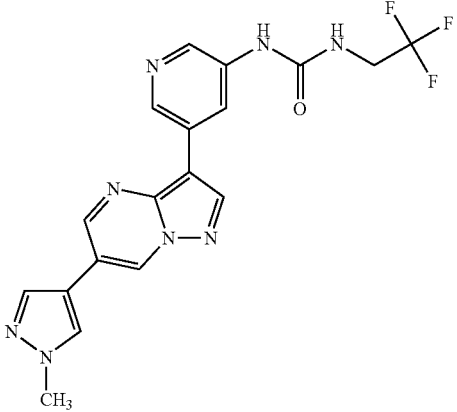 [SMILES: Cn1cc(-c2cnc3c(-c4cncc(NC(=O)NCC(F)(F)F)c4)cnn3c2)cn1] | 1-{5-[6-(1-Methyl-1H-pyrazol-4-yl)-pyrazolo[1,5-a]pyrimidin-3-yl]-pyridin-3-yl}-3-(2,2,2-trifluoro-ethyl)-urea | Preparation K, preparation L using 1-methyl-4-(4,4,5,5-tetramethyl-[1,3,2]dioxaborolan-2-yl)-1H-pyrazole and conditions described in A3b substituting PdCl₂dppf, K₃PO₄, dioxane:H₂O (4:1 v/v) for tetrakis(triphenylphosphine)palladium(0), 2 M Na₂CO₃ and DME respectively, preparation M, preparation N using I28 and conditions described in A3a. | 1H NMR (400 MHz, DMSO-d6): 9.48 (1H, s), 9.10 (1H, s), 9.01 (1H, s), 8.87 (1H, s), 8.75 (1H, s), 8.62 (1H, s), 8.52 (1H, s), 8.38 (1H, s), 8.12 (1H, s), 6.94 (1H, s), 3.93 (5H, s). | [M + H] + 417 |
| 350 | 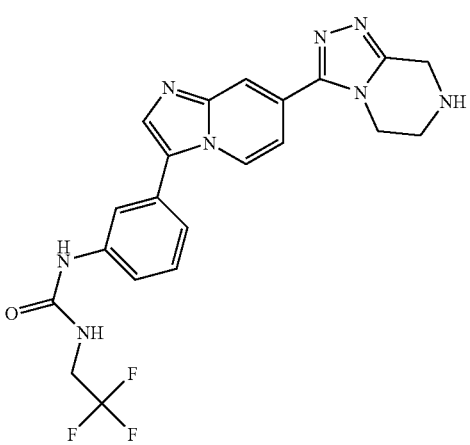 [SMILES: O=C(NCC(F)(F)F)Nc1cccc(-c2cnc3cc(-c4nnc5n4CCNC5)ccn23)c1] | 1-{3-[7-(5,6,7,8-Tetrahydro-[1,2,4]triazolo[4,3-a]pyrazin-3-yl)-imidazo[1,2-a]pyridin-3-yl]-phenyl}-3-(2,2,2-trifluoro-ethyl)-urea hydrochloride | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using Tert-butyl 3-bromo-5,6-dihydro-[1,2,4]triazolo[4,3-A]pyrazine-7(8H)-carboxylate, procedure D3a | 1H NMR (400 MHz, Me-d3-OD): 9.02 (1H, d), 8.44 (1H, s), 8.35 (1H, s), 8.11 (1H, s), 7.97 (1H, d), 7.64-7.56 (1H, m), 7.48-7.38 (2H, m), 4.85-4.83 (2H, m), 4.76-4.71 (2H, m), 3.96 (2H, q), 3.87 (2H, t). | [M + H] + 457 |

-continued

| Eg. No. | Structure | Chemical Name | Method | NMR Data | MS Data |
|---|---|---|---|---|---|
| 351 | 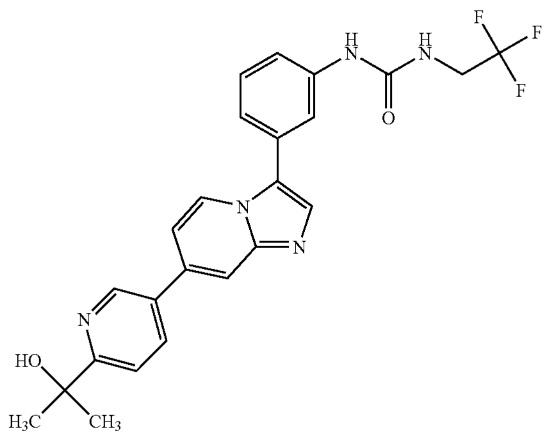 [SMILES: CC(C)(O)c1ccc(-c2ccn3c(-c4cccc(NC(=O)NCC(F)(F)F)c4)cnc3c2)cn1] | 1-(3-{7-[6-(1-Hydroxy-1-methyl-ethyl)-pyridin-3-yl]-imidazo[1,2-a]pyridin-3-yl}-phenyl)-3-(2,2,2-trifluoro-ethyl)-urea | Procedure AQ | 1H NMR (400 MHz, DMSO-d6): 9.03-8.94 (2H, m), 8.65 (1H, d), 8.25 (1H, dd), 8.10 (1H, s), 7.86-7.74 (3H, m), 7.50-7.39 (3H, m), 7.33-7.24 (1H, m), 6.86 (1H, t), 5.29 (1H, s), 4.03-3.89 (2H, m), 1.50 (6H, s). | [M + H] + 470 |
| 352 | 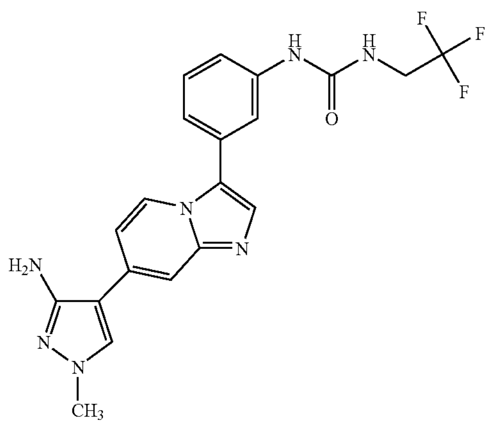 | 1-{3-[7-(3-Amino-1-methyl-1H-pyrazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3b using 3-amino-4-bromo-1-methylpyrazole | 1H NMR (400 MHz, Me-d3-OD): 8.53 (1H, d), 7.81 (1H, s), 7.80 (1H, s), 7.71 (1H, s), 7.64 (1H, s), 7.48 (1H, t), 7.38 (1H, d), 7.30 (1H, d), 7.24-7.16 (1H, m), 3.95 (2H, q), 3.77 (3H, s). | [M + H] + 430 |
| 353 | 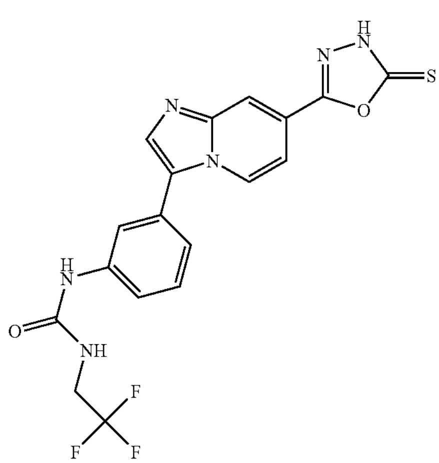 [SMILES: O=C(NCC(F)(F)F)Nc1cccc(-c2cnc3cc(-c4n[nH]c(=S)o4)ccn23)c1] | 1-{3-[7-(5-Thioxo-4,5-dihydro-[1,3,4]oxadiazol-2-yl)-imidazo[1,2-a]pyridin-3-yl]-phenyl}-3-(2,2,2-trifluoro-ethyl)-urea | Example 332 step A, Procedure AL. | 1H NMR (400 MHz, DMSO-d6): 9.04 (1H, s), 8.62 (1H, d), 7.82 (2H, s), 7.70 (1H, s), 7.55 (1H, d), 7.52-7.42 (1H, m), 7.42-7.34 (1H, m), 7.27 (1H, d), 6.93 (1H, t), 4.02-3.88 (2H, m). | [M + H] + 435 |

-continued

| Eg. No. | Structure | Chemical Name | Method | NMR Data | MS Data |
|---|---|---|---|---|---|
| 354 | 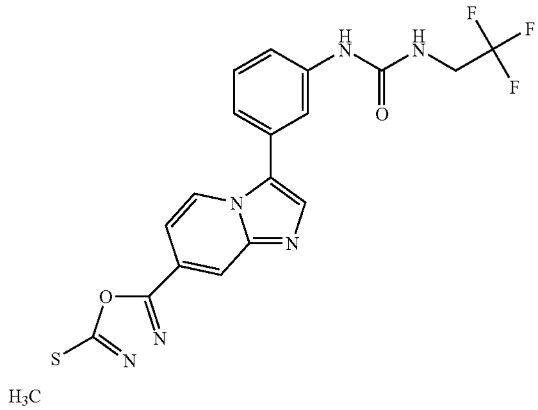 | 1-{3-[7-(5-Methylsulfanyl-[1,3,4]oxadiazol-2-yl)-imidazo[1,2-a]pyridin-3-yl]-phenyl}-3-(2,2,2-trifluoro-ethyl)-urea | Example 332 step A, procedure AM | 1H NMR (400 MHz, DMSO-d6): 8.98 (1H, s), 8.71 (1H, d), 8.24 (1H, s), 7.99-7.93 (1H, m), 7.78 (1H, s), 7.56-7.43 (3H, m), 7.30 (1H, d), 6.86 (1H, t), 4.01-3.89 (2H, m), 2.82 (3H, s). | [M + H] + 449 |
| 355 | 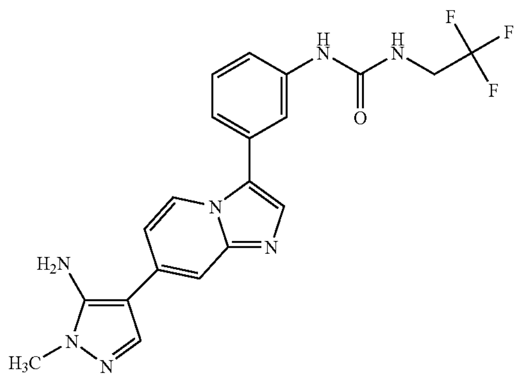 [SMILES: Cn1ncc(-c2ccn3c(-c4cccc(NC(=O)NCC(F)(F)F)c4)cnc3c2)c1N] | 1-{3-[7-(5-Amino-1-methyl-1H-pyrazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3c using 3-amino-4-bromo-2-methylpyrazole | 1H NMR (400 MHz, Me-d3-OD): 8.53 (1H, d), 7.83 (1H, s), 7.67 (1H, s), 7.64 (1H, s), 7.63 (1H, s), 7.48 (1H, t), 7.38 (1H, d), 7.30 (1H, d), 7.24 (1H, dd), 3.95 (2H, q), 3.71 (3H, s). | [M + H] + 430 |
| 356 | 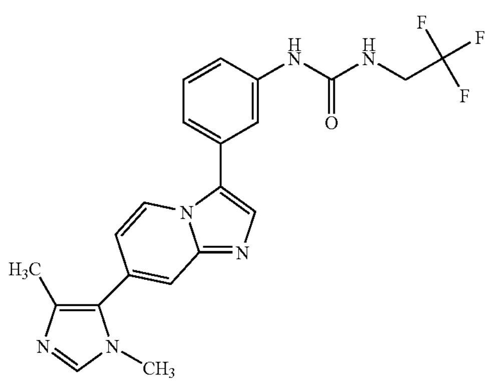 [SMILES: Cc1ncn(C)c1-c1ccn2c(-c3cccc(NC(=O)NCC(F)(F)F)c3)cnc2c1] | 1-{3-[7-(3,5-Dimethyl-3H-imidazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3a using 5-Iodo-1,4-dimethyl-1H-imidazole and substituting PdCl2dppf for Pd(OAc)2 and S-PHOS. | 1H NMR (400 MHz, DMSO-d6): 8.99 (1H, s), 8.60 (1H, d), 7.81 (1H, s), 7.78 (1H, s), 7.65 (2H, s), 7.50-7.41 (2H, m), 7.31-7.23 (1H, m), 7.04 (1H, dd), 6.86 (1H, t), 4.01-3.89 (2H, m), 3.64 (3H, s), 2.20 (3H, s). | [M + H] + 429 |
| 357 | 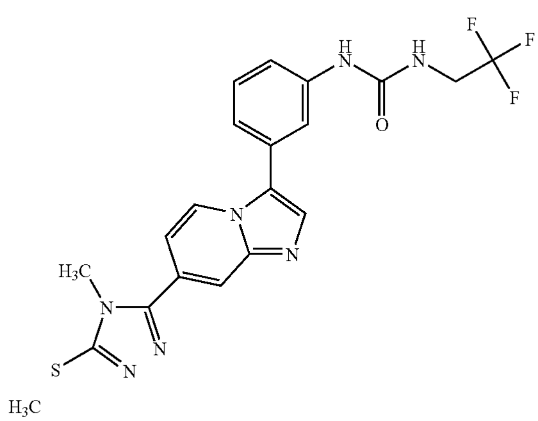 | 1-{3-[7-(4-Methyl-5-methylsulfanyl-4H-[1,2,4]triazol-3-yl)-imidazo[1,2-a]pyridin-3-yl]-phenyl}-3-(2,2,2-trifluoro-ethyl)-urea formate | Procedure AE | 1H NMR (400 MHz, DMSO-d6): 9.06 (1H, s), 8.69 (1H, d), 8.19 (1H, s), 8.05 (1H, s), 7.89 (1H, s), 7.78 (1H, s), 7.54-7.42 (2H, m), 7.37 (1H, dd), 7.29 (1H, d), 6.95 (1H, t), 4.02-3.88 (2H, m), 3.74 (3H, s), 2.69 (3H, s). | [M + H] + 462 |

-continued

| Eg. No. | Structure | Chemical Name | Method | NMR Data | MS Data |
|---|---|---|---|---|---|
| 358 | 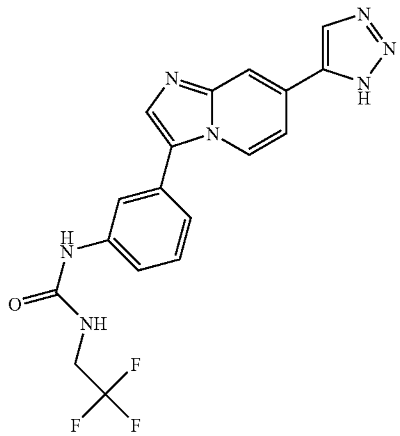 [SMILES: O=C(NCC(F)(F)F)Nc1cccc(-c2cnc3cc(-c4cnn[nH]4)ccn23)c1] | 1-{3-[7-(3H-[1,2,3]Triazol-4-yl)-imidazo[1,2-a]pyridin-3-yl]-phenyl}-3-(2,2,2-trifluoro-ethyl)-urea | Procedure AF | 1H NMR (400 MHz, Me-d3-OD): 8.66 (1H, d), 8.43-8.32 (1H, m), 8.12 (1H, s), 7.83 (1H, s), 7.76 (1H, s), 7.57 (1H, d), 7.50 (1H, t), 7.43 (1H, d), 7.33 (1H, d), 3.96 (2H, q). | [M + H]+ 402 |
| 359 | 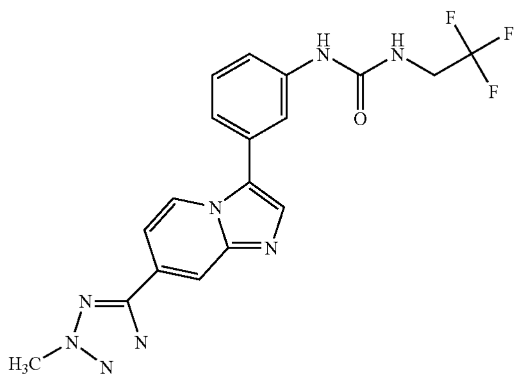 | 1-{3-[7-(2-Methyl-2H-tetrazol-5-yl)-imidazo[1,2-a]pyridin-3-yl]-phenyl}-3-(2,2,2-trifluoro-ethyl)-urea | Procedure AI | 1H NMR (400 MHz, DMSO-d6): 8.98 (1H, s), 8.73 (1H, d), 8.27 (1H, s), 7.89 (1H, s), 7.76 (1H, s), 7.58 (1H, dd), 7.55-7.42 (2H, m), 7.30 (1H, d), 6.86 (1H, t), 4.48 (3H, s), 4.02-3.89 (2H, m). | [M + H]+ 417 |
| 360 | 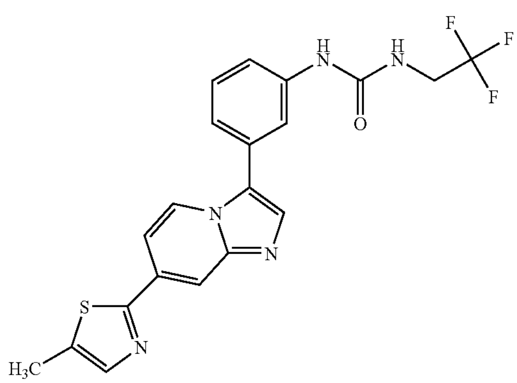 | 1-{3-[7-(5-Methyl-thiazol-2-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using 2-Chloro-5-methyl-thiazole | 1H NMR (400 MHz, Me-d3-OD): 8.63 (1H, d), 8.09 (1H, s), 7.88-7.80 (1H, m), 7.79 (1H, s), 7.67-7.59 (1H, m), 7.55 (1H, dd), 7.49 (1H, t), 7.45-7.38 (1H, m), 7.37-7.28 (1H, m), 3.96 (2H, q), 2.58 (3H, s). | [M + H]+ 432 |
| 361 | 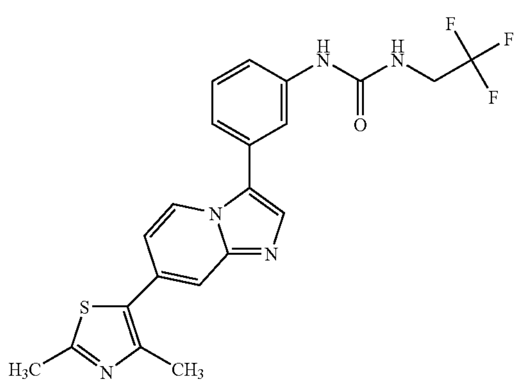 [SMILES: Cc1nc(C)c(-c2ccn3c(-c4cccc(NC(=O)NCC(F)(F)F)c4)cnc3c2)s1] | 1-{3-[7-(2,4-Dimethyl-thiazol-5-yl)-imidazo[1,2-a]pyridin-3-yl]-phenyl}-3-(2,2,2-trifluoro-ethyl)-urea formate | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using 5-Bromo-2,4-dimethyl-1,3-thiazole | 1H NMR (400 MHz, Me-d3-OD): 8.63 (1H, d), 8.21 (2H, s), 7.85 (1H, s), 7.78 (1H, s), 7.69 (1H, s), 7.49 (1H, t), 7.40 (1H, d), 7.32 (1H, d), 7.14 (1H, d), 3.95 (2H, q), 2.72 (3H, s), 2.55 (3H, s). | [M + H]+ 446 |

| Eg. No. | Structure | Chemical Name | Method | NMR Data | MS Data |
|---|---|---|---|---|---|
| 362 | 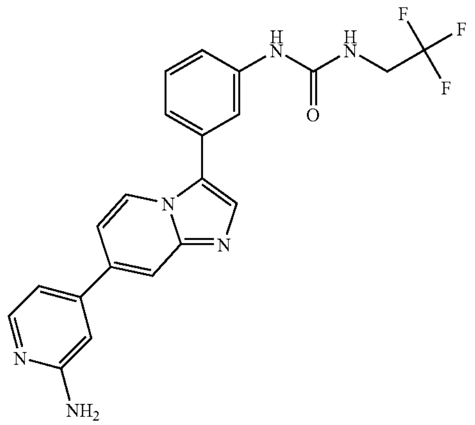 [SMILES: Nc1cc(-c2ccn3c(-c4cccc(NC(=O)NCC(F)(F)F)c4)cnc3c2)ccn1] | 1-{3-[7-(2-Amino-pyridin-4-yl)-imidazo[1,2-a]pyridin-3-yl]-phenyl}-3-(2,2,2-trifluoro-ethyl)-urea formate | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using (4-Iodo-pyridin-2-yl)-carbamic acid tert-butyl ester, procedure D3a. | 1H NMR (400 MHz, Me-d3-OD): 8.70 (1H, d), 8.23 (1H, s), 8.05-7.96 (2H, m), 7.92-7.86 (1H, m), 7.82 (1H, s), 7.51 (1H, t), 7.43-7.30 (3H, m), 7.11 (1H, dd), 7.08 (1H, s), 3.96 (2H, q). | [M + H]+ 427 |
| 363 | 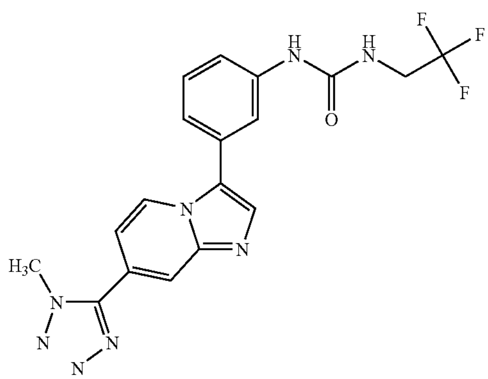 | 1-{3-[7-(1-Methyl-1H-tetrazol-5-yl)-imidazo[1,2-a]pyridin-3-yl]-phenyl}-3-(2,2,2-trifluoro-ethyl)-urea | Prepared as described in procedure AI steps 4 and 5, but substituting 7-(1-Methyl-1H-tetrazol-5-yl)-imidazo[1,2-a]pyridine (Procedure AI, Step 3) for 7-(2-Methyl-2H-tetrazol-5-yl)-imidazo[1,2-a]pyridine. | 1H NMR (400 MHz, Me-d3-OD): 8.79 (1H, d), 8.19 (1H, s), 7.95-7.85 (2H, m), 7.58-7.46 (2H, m), 7.43 (1H, d), 7.40-7.32 (1H, m), 4.35 (3H, s), 4.00-3.90 (2H, m). | [M + H]+ 417 |
| 364 | 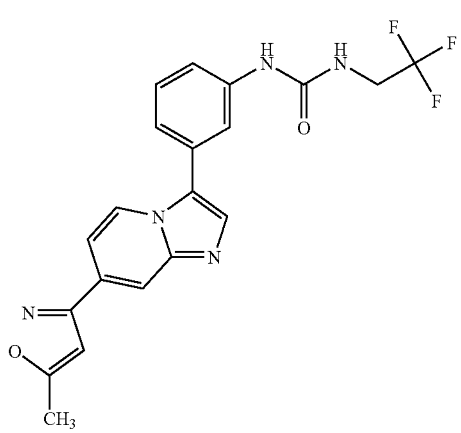 [SMILES: C/C(O)=C/C(=N)c1ccn2c(-c3cccc(NC(=O)NCC(F)(F)F)c3)cnc2c1] | 1-{3-[7-(5-Methyl-isoxazol-3-yl)-imidazo[1,2-a]pyridin-3-yl]-phenyl}-3-(2,2,2-trifluoro-ethyl)-urea | Procedure AG | 1H NMR (400 MHz, Me-d3-OD): 8.68 (1H, d), 8.08 (1H, s), 7.84 (2H, d), 7.54-7.46 (1H, m), 7.42 (2H, d), 7.34 (1H, d), 6.88 (1H, s), 3.96 (2H, q), 2.39 (3H, s). | [M + H]+ 416 |

-continued

| Eg. No. | Structure | Chemical Name | Method | NMR Data | MS Data |
|---|---|---|---|---|---|
| 365 | 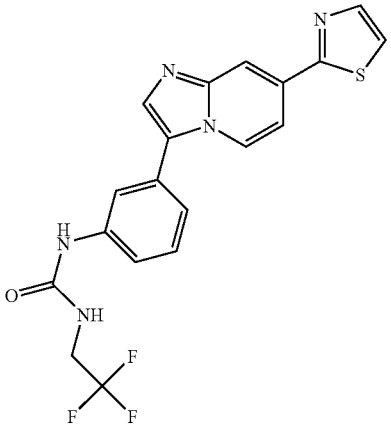 | 1-[3-(7-Thiazol-2-yl-imidazo[1,2-a]pyridin-3-yl)-phenyl]-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using 2-Bromothiazole | 1H NMR (400 MHz, Me-d3-OD): 8.68 (1H, d), 8.22 (1H, s), 7.97 (1H, d), 7.87-7.83 (1H, m), 7.82 (1H, s), 7.73 (1H, d), 7.64 (1H, dd), 7.51 (1H, t), 7.44 (1H, d), 7.35 (1H, d), 3.96 (2H, q). | [M+H]+ 418 |
| 366 | 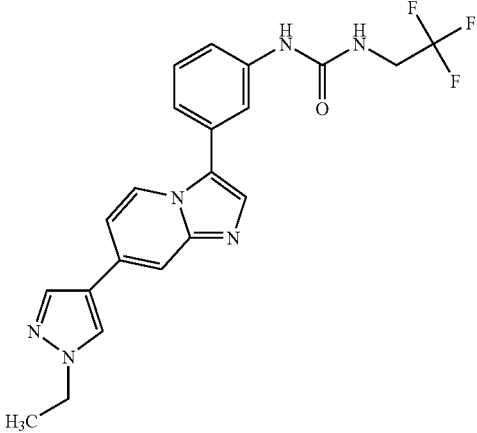 [SMILES: CCn1cc(-c2ccn3c(-c4cccc(NC(=O)NCC(F)(F)F)c4)cnc3c2)cn1] | 1-{3-[7-(1-Ethyl-1H-pyrazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure A4b using 1-Ethyl-4-(4,4,5,5-tetramethyl-[1,3,2]dioxaborolan-2-yl)-1H-pyrazole | 1H NMR (400 MHz, Me-d3-OD): 8.55 (1H, d), 8.23 (1H, s), 8.01 (1H, s), 7.81 (1H, s), 7.76 (1H, s), 7.66 (1H, s), 7.48 (1H, t), 7.39 (1H, d), 7.35-7.23 (2H, m), 4.27 (2H, q), 3.95 (2H, q), 1.53 (3H, t). | [M+H]+ 429 |
| 367 | 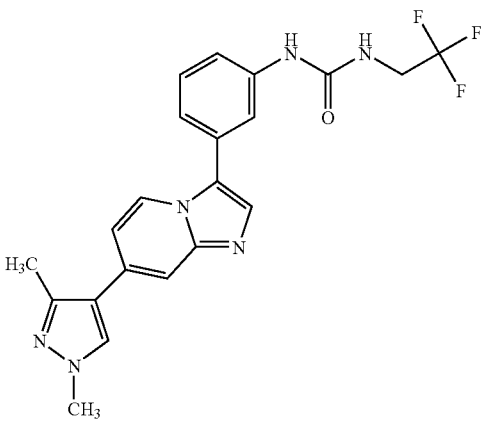 [SMILES: Cc1nn(C)cc1-c1ccn2c(-c3cccc(NC(=O)NCC(F)(F)F)c3)cnc2c1] | 1-{3-[7-(1,3-Dimethyl-1H-pyrazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure A4b using 1,3,5-trimethyl-4-(4,4,5,5-tetramethyl-1,3,2-dioxaborolan-2-yl)-1H-pyrazole | 1H NMR (400 MHz, Me-d3-OD): 8.57 (1H, d), 7.96 (1H, s), 7.82 (1H, s), 7.68 (1H, s), 7.63 (1H, s), 7.48 (1H, t), 7.39 (1H, d), 7.31 (1H, d), 7.16 (1H, dd), 4.02-3.86 (5H, m), 2.49 (3H, s). | [M+H]+ 429 |

| Eg. No. | Structure | Chemical Name | Method | NMR Data | MS Data |
|---|---|---|---|---|---|
| 368 | 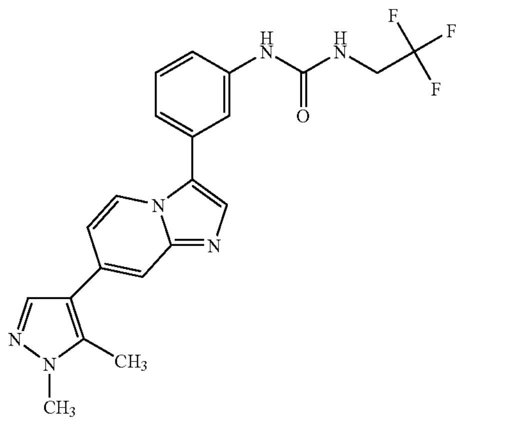 [SMILES: Cc1c(-c2ccn3c(-c4cccc(NC(=O)NCC(F)(F)F)c4)cnc3c2)cnn1C] | 1-{3-[7-(1,5-Dimethyl-1H-pyrazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure A4b using 1,5-Dimethyl-4-(4,4,5,5-tetramethyl-[1,3,2]dioxaborolan-2-yl)-1H-pyrazole | 1H NMR (400 MHz, Me-d3-OD): 8.59 (1H, d), 7.86-7.79 (1H, m), 7.75 (1H, s), 7.69 (1H, s), 7.59 (1H, s), 7.48 (1H, t), 7.39 (1H, d), 7.32 (1H, d), 7.15 (1H, dd), 4.02-3.86 (5H, m), 2.54 (3H, s). | [M + H] + 429 |
| 369 | 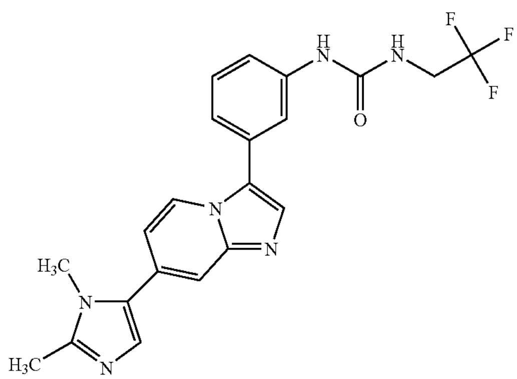 [SMILES: Cc1ncc(-c2ccn3c(-c4cccc(NC(=O)NCC(F)(F)F)c4)cnc3c2)n1C] | 1-{3-[7-(2,3-Dimethyl-3H-imidazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using 5-Bromo-1,2-dimethyl-1H-imidazole | 1H NMR (400 MHz, Me-d3-OD): 8.64 (1H, d), 7.85 (1H, s), 7.75 (1H, s), 7.67 (1H, s), 7.50 (1H, t), 7.40 (1H, d), 7.33 (1H, d), 7.18-7.10 (2H, m), 3.95 (2H, q), 3.74 (3H, s), 2.49 (3H, s). | [M + H] + 429 |
| 370 | 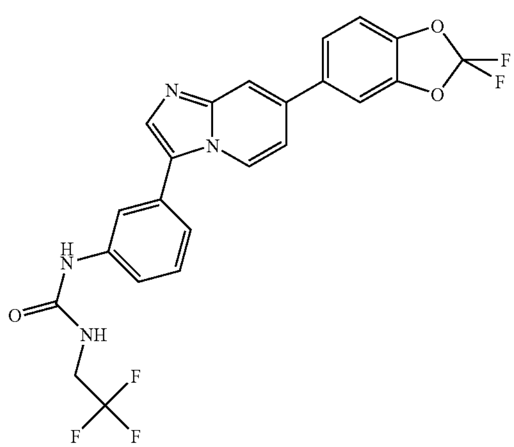 [SMILES: O=C(NCC(F)(F)F)Nc1cccc(-c2cnc3cc(-c4ccc5c(c4)OC(F)(F)O5)ccn23)c1] | 1-{3-[7-(2,2-Difluoro-benzo[1,3]dioxol-5-yl)-imidazo[1,2-a]pyridin-3-yl]-phenyl}-3-(2,2,2-trifluoro-ethyl)-urea | General route A, procedure A3b using I6 [3-(4,4,5,5-Tetramethyl-[1,3,2]dioxaborolan-2-yl)-phenyl]-3-(2,2,2-trifluoro-ethyl)-urea, procedure A4b using 2,2-Difluoro-benzo[1,3]dioxole-5-boronic acid | 1H NMR (400 MHz, DMSO-d6): 9.08 (1H, s), 8.62 (1H, d), 8.05 (1H, s), 7.99 (1H, d), 7.86-7.78 (2H, m), 7.73 (1H, dd), 7.54 (1H, d), 7.45 (2H, d), 7.39 (1H, dd), 7.31-7.23 (1H, m), 6.98 (1H, s), 4.01-3.88 (2H, m). | [M + H] + 491 |

-continued

| Eg. No. | Structure | Chemical Name | Method | NMR Data | MS Data |
|---|---|---|---|---|---|
| 371 | 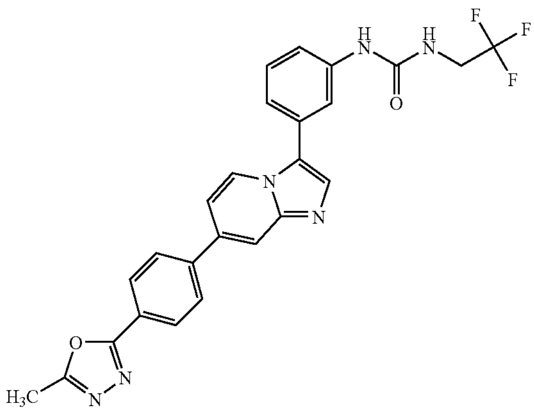 [SMILES: Cc1nnc(-c2ccc(-c3ccn4c(-c5cccc(NC(=O)NCC(F)(F)F)c5)cnc4c3)cc2)o1] | 1-(3-{7-[4-(5-Methyl-[1,3,4]oxadiazol-2-yl)-phenyl]-imidazo[1,2-a]pyridin-3-yl}-phenyl)-3-(2,2,2-trifluoro-ethyl)-urea | General route A, procedure A3b using I6 [3-(4,4,5,5-Tetramethyl-[1,3,2]dioxaborolan-2-yl)-phenyl]-3-(2,2,2-trifluoro-ethyl)-urea, procedure A4b using 4-(5-methyl-1,3,4-oxadiazol-2-yl)phenylboronic acid | 1H NMR (400 MHz, DMSO-d6): 9.12 (1H, s), 8.67 (1H, d), 8.18-8.05 (5H, m), 7.84 (1H, s), 7.81 (1H, s), 7.51-7.42 (3H, m), 7.32-7.25 (1H, m), 7.02 (1H, s), 4.01-3.90 (2H, m), 2.62 (3H, s). | [M + H] + 493 |
| 372 | 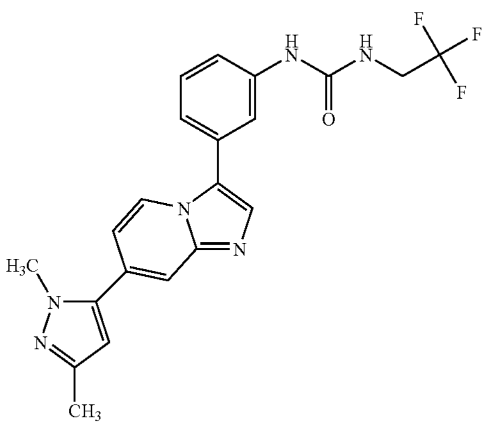 [SMILES: Cc1cc(-c2ccn3c(-c4cccc(NC(=O)NCC(F)(F)F)c4)cnc3c2)n(C)n1] | 1-{3-[7-(2,5-Dimethyl-2H-pyrazol-3-yl)-imidazo[1,2-a]pyridin-3-yl]-phenyl}-3-(2,2,2-trifluoro-ethyl)-urea formate | General route A: procedure A1, procedure A2, procedure A3b using I6 [3-(4,4,5,5-Tetramethyl-[1,3,2]dioxaborolan-2-yl)-phenyl]-3-(2,2,2-trifluoro-ethyl)-urea, procedure E2, procedure E3c using 5-chloro-1,3-dimethylpyrazole. | $^1$H NMR (400 MHz, DMSO-d$_6$): 9.01 (1H, s), 8.61 (1H, d), 8.16 (2H, s), 7.83 (1H, s), 7.81 (1H, s), 7.78 (1H, s), 7.50-7.42 (2H, m), 7.31-7.23 (1H, m), 7.14 (1H, dd), 6.90 (1H, t), 6.38 (1H, s), 4.02-3.92 (2H, m), 3.90 (3H, s), 2.20 (3H, s). | [M + H] + 429 |
| 373 | 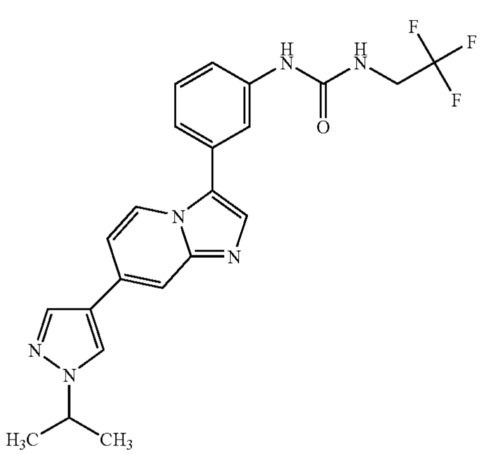 [SMILES: CC(C)n1cc(-c2ccn3c(-c4cccc(NC(=O)NCC(F)(F)F)c4)cnc3c2)cn1] | 1-{3-[7-(1-Isopropyl-1H-pyrazol-4-yl)-imidazo[1,2-a]pyridin-3-yl]-phenyl}-3-(2,2,2-trifluoro-ethyl)-urea formate | General route A: procedure A1, procedure A2, procedure A3b using I6 [3-(4,4,5,5-Tetramethyl-[1,3,2]dioxaborolan-2-yl)-phenyl]-3-(2,2,2-trifluoro-ethyl)-urea, procedure A4 using 4-(4,4,5,5-tetramethyl-1,3,2-dioxaborolan-2-yl)-1H-pyrazole and conditions described in procedure E3c, procedure S step 2 (no NaI addition) using 2-iodopropane. | $^1$H NMR (400 MHz, Me-d$_3$-OD): 8.57 (1H, d), 8.30 (1H, s), 8.26 (1H, s), 8.03 (1H, s), 7.84 (1H, s), 7.81 (1H, s), 7.72 (1H, s), 7.49 (1H, t), 7.44-7.33 (2H, m), 7.31 (1H, d), 4.61 (1H, septet), 3.95 (2H, dd), 1.57 (6H, d). | [M + H] + 443 |

-continued

| Eg. No. | Structure | Chemical Name | Method | NMR Data | MS Data |
|---|---|---|---|---|---|
| 374 | 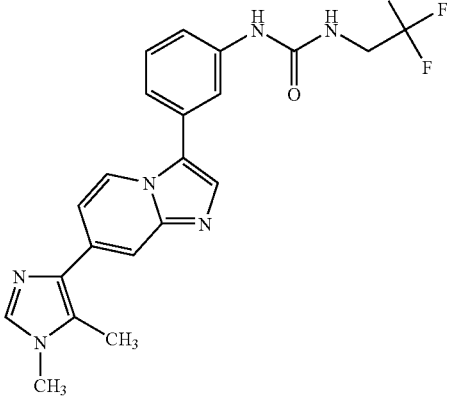 | 1-{3-[7-(1,5-Dimethyl-1H-imidazol-4-yl)-imidazo[1,2-a]pyridin-3-yl]-phenyl}-3-(2,2,2-trifluoro-ethyl)-urea | Procedure AK | 1H NMR (400 MHz, DMSO-d6): 8.97 (1H, s), 8.57 (1H, d), 7.77-7.71 (4H, m), 7.47-7.42 (3H, m), 7.26 (1H, dt), 6.85 (1H, t), 4.01-3.89 (2H, m), 3.63 (3H, s), 2.48 (3H, s). | [M + H] + 429 |
| 375 | 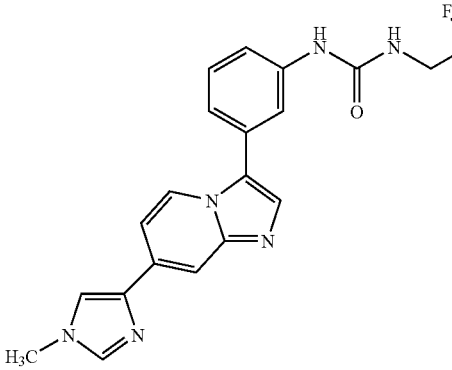 | 1-{3-[7-(1-Methyl-1H-imidazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3c using 4-Iodo-1-methyl-1H-imidazole | 1H NMR (400 MHz, Me-d3-OD): 8.56 (1H, d), 7.96 (1H, s), 7.80 (1H, s), 7.75 (1H, s), 7.70 (1H, s), 7.68 (1H, s), 7.49 (1H, t), 7.45-7.36 (2H, m), 7.31 (1H, d), 3.95 (2H, q), 3.83 (3H, s). | [M + H] + 415 |
| 376 | 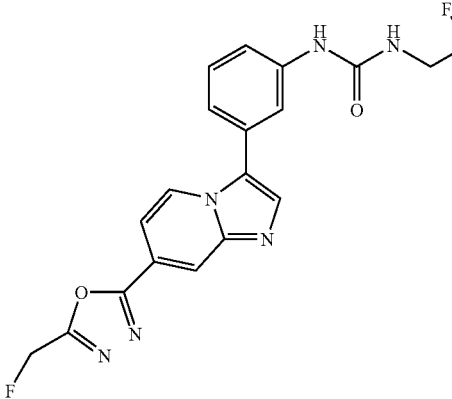 | 1-{3-[7-(5-Fluoromethyl-[1,3,4]oxadia-zol-2-yl)-imidazo[1,2-a]pyridin-3-yl]-phenyl}-3-(2,2,2-trifluoro-ethyl)-urea | Procedure AO | 1H NMR (400 MHz, Me-d3-OD): 8.77 (1H, d), 8.36 (1H, s), 7.92 (1H, s), 7.87 (1H, s), 7.67 (1H, d), 7.52 (1H, t), 7.49-7.47 (1H, m), 7.45 (1H, d), 7.37 (1H, t), 4.00-3.89 (4H, m). | [M + H] + 435 |

| Eg. No. | Structure | Chemical Name | Method | NMR Data | MS Data |
|---|---|---|---|---|---|
| 377 | 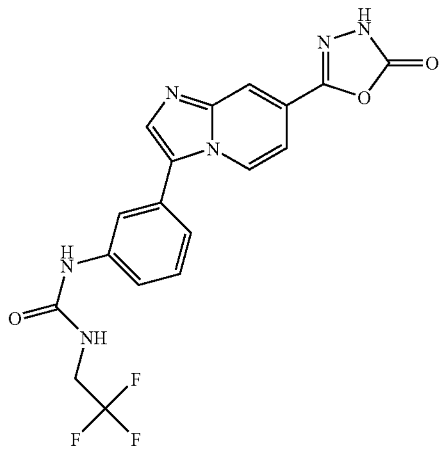 [SMILES: O=C(NCC(F)(F)F)Nc1cccc(-c2cnc3cc(-c4n[nH]c(=O)o4)ccn23)c1] | 1-{3-[7-(5-Oxo-4,5-dihydro-[1,3,4]oxadiazol-2-yl)-imidazo[1,2-a]pyridin-3-yl]-phenyl}-3-(2,2,2-trifluoro-ethyl)-urea | Procedure AP | 1H NMR (400 MHz, DMSO-d6): 12.80-12.73 (1H, m), 8.97 (1H, s), 8.66 (1H, d), 7.98 (1H, s), 7.92 (1H, s), 7.75 (1H, s), 7.54-7.44 (2H, m), 7.32 (1H, dd), 7.28 (1H, d), 6.85 (1H, t), 4.01-3.89 (2H, m). | [M + H] + 419 |
| 378 | 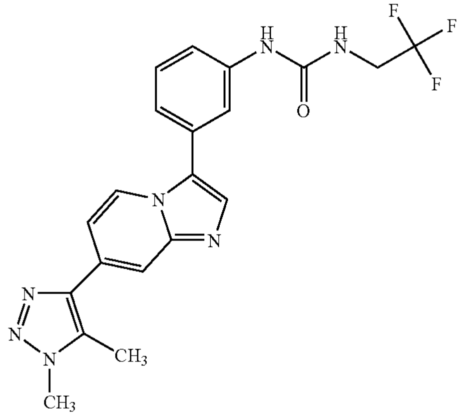 [SMILES: Cc1c(-c2ccn3c(-c4cccc(NC(=O)NCC(F)(F)F)c4)cnc3c2)nnn1C] | 1-{3-[7-(1,5-Dimethyl-1H-[1,2,3]triazol-4-yl)-imidazo[1,2-a]pyridin-3-yl]-phenyl}-3-(2,2,2-trifluoro-ethyl)-urea formate | general route A: procedure A1, procedure A2, procedure A3b using I6 [3-(4,4,5,5-Tetramethyl-[1,3,2]dioxaborolan-2-yl)-phenyl]-3-(2,2,2-trifluoro-ethyl)-urea, procedure E2, procedure E3c using 4-bromo-1,5-dimethyl-1H-[1,2,3]triazole. | 1H NMR (400 MHz, DMSO-d6): 9.03 (1H, s), 8.64 (1H, d), 8.17 (1H, s), 7.84 (1H, s), 7.78 (1H, s), 7.76 (1H, s), 7.53-7.40 (3H, m), 7.31-7.23 (1H, m), 6.93 (1H, t), 4.03 (3H, s), 4.00-3.90 (2H, m), 2.57 (3H, s). | [M + H] + 430 |
| 379 | 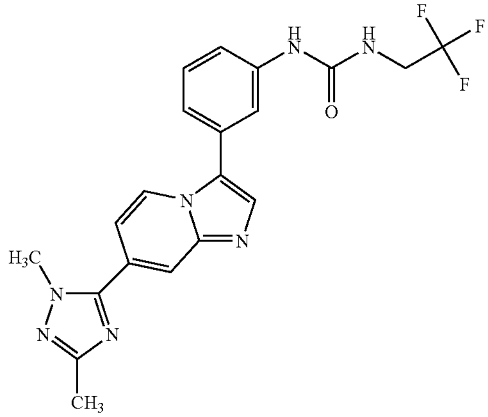 [SMILES: Cc1nc(-c2ccn3c(-c4cccc(NC(=O)NCC(F)(F)F)c4)cnc3c2)n(C)n1] | 1-{3-[7-(2,5-Dimethyl-2H-[1,2,4]triazol-3-yl)-imidazo[1,2-a]pyridin-3-yl]-phenyl}-3-(2,2,2-trifluoro-ethyl)-urea | Procedure AJ | 1H NMR (400 MHz, Me-d3-OD): 8.73 (1H, d), 8.03 (1H, s), 7.90-7.82 (2H, m), 7.51 (1H, t), 7.46-7.39 (1H, m), 7.39-7.30 (2H, m), 4.06 (3H, s), 3.95 (2H, q), 2.41 (3H, s). | [M + H] + 430 |

| Eg. No. | Structure | Chemical Name | Method | NMR Data | MS Data |
|---|---|---|---|---|---|
| 380 | 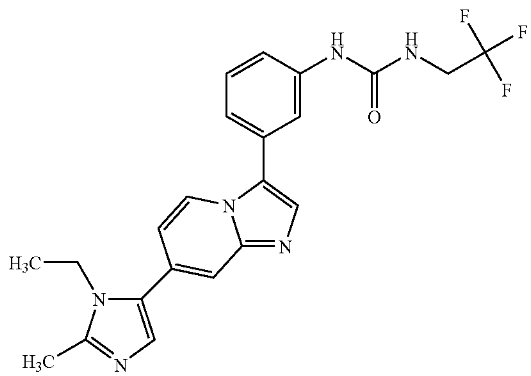 [SMILES: CCn1c(-c2ccn3c(-c4cccc(NC(=O)NCC(F)(F)F)c4)cnc3c2)cnc1C] | 1-{3-[7-(3-Ethyl-2-methyl-3H-imidazol-4-yl)-imidazo[1,2-a]pyridin-3-yl]-phenyl}-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3c using 5-Chloro-1-ethyl-2-methylimidazole | 1H NMR (400 MHz, Me-d3-OD): 8.65 (1H, d), 7.86 (1H, s), 7.77 (1H, s), 7.66 (1H, s), 7.50 (1H, t), 7.40 (1H, d), 7.36-7.29 (1H, m), 7.17-7.08 (2H, m), 4.19 (2H, q), 3.95 (2H, q), 2.52 (3H, s), 1.33 (3H, t). | [M + H]+ 443 |
| 381 | 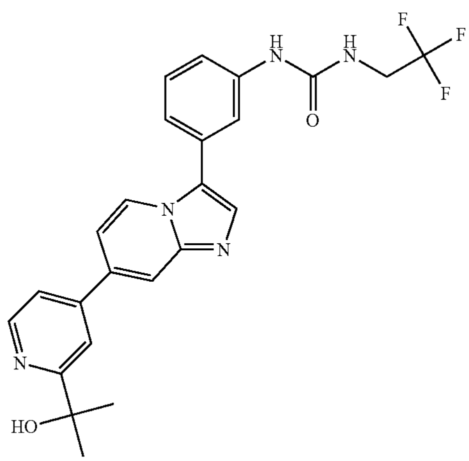 [SMILES: CC(C)(O)c1cc(-c2ccn3c(-c4cccc(NC(=O)NCC(F)(F)F)c4)cnc3c2)ccn1] | 1-(3-{7-[2-(1-Hydroxy-1-methyl-ethyl)-pyridin-4-yl]-imidazo[1,2-a]pyridin-3-yl}-phenyl)-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d, using 2-(4-bromo-pyridin-2-yl)-propan-2-ol (U6) | 1H NMR (400 MHz, DMSO-d6): 9.02 (1H, s), 8.69 (1H, d), 8.60 (1H, d), 8.18 (1H, d), 8.08 (1H, d), 7.87 (1H, s), 7.81 (1H, s), 7.74 (1H, dd), 7.51-7.40 (3H, m), 7.34-7.25 (1H, m), 6.90 (1H, t), 5.33 (1H, s), 4.02-3.89 (2H, m), 1.51 (6H, s). | [M + H]+ 470 |
| 382 | 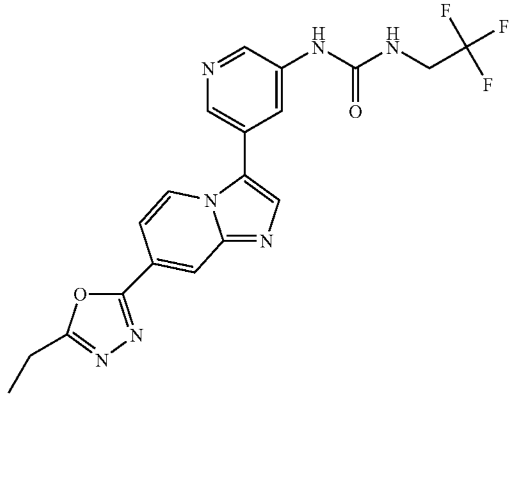 [SMILES: CCc1nnc(-c2ccn3c(-c4cncc(NC(=O)NCC(F)(F)F)c4)cnc3c2)o1] | 1-{5-[7-(5-Ethyl-[1,3,4]oxadia-zol-2-yl)-imidazo[1,2-a]pyridin-3-yl]-pyridin-3-yl}-3-(2,2,2-trifluoro-ethyl)-urea | Procedure as for example 329 steps a-d using triethylorthopropionate in step d. Step e using I28 1-[5-(4,4,5,5-Tetramethyl-[1,3,2]dioxaborolan-2-yl)-pyridin-3-yl]-3-(2,2,2-trifluoro-ethyl)-urea | 1H NMR (400 MHz, Me-d3-OD): 8.75 (1H, d), 8.62 (1H, d), 8.53 (1H, d), 8.41 (1H, t), 8.31 (1H, s), 8.01 (1H, s), 7.67 (1H, dd), 3.97 (2H, q), 3.06 (2H, q), 1.48 (3H, t). | MS: [M + H]+ 432 |

| Eg. No. | Structure | Chemical Name | Method | NMR Data | MS Data |
|---|---|---|---|---|---|
| 383 | 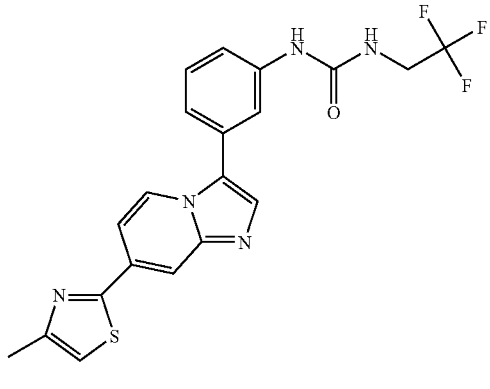 [SMILES: Cc1csc(-c2ccn3c(-c4cccc(NC(=O)NCC(F)(F)F)c4)cnc3c2)n1] | 1-{3-[7-(4-Methyl-thiazol-2-yl)-imidazo[1,2-a]pyridin-3-yl]-phenyl}-3-(2,2,2-trifluoro-ethyl)-urea | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using 2-Bromo-4-methyl-thiazole | 1H NMR (400 MHz, Me-d3-OD): 8.66 (1H, d), 8.18 (1H, s), 7.83 (1H, t), 7.81 (1H, s), 7.60 (1H, dd), 7.51 (1H, t), 7.47-7.41 (1H, m), 7.34 (1H, d), 7.27 (1H, s), 3.96 (2H, q), 2.53 (3H, s). | MS: [M + H]1+ 432 |
| 384 | 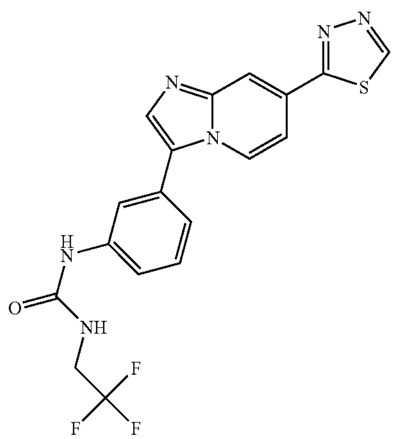 [SMILES: O=C(NCC(F)(F)F)Nc1cccc(-c2cnc3cc(-c4nncs4)ccn23)c1] | 1-[3-(7-[1,3,4]Thiadia-zol-2-yl-imidazo[1,2-a]pyridin-3-yl)-phenyl]-3-(2,2,2-trifluoro-ethyl)-urea | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3e using U7 2-Bromo-[1,3,4]thiadiazole | 1H NMR (400 MHz, DMSO-d6): 9.70 (1H, s), 8.98 (1H, s), 8.70 (1H, d), 8.35 (1H, s), 7.93 (1H, s), 7.78 (1H, s), 7.66 (1H, dd), 7.54-7.45 (2H, m), 7.33-7.28 (1H, m), 6.86 (1H, t), 4.00-3.91 (2H, m). | MS: [M + H]1+ 419 |

Example 384A

1-[3-(7-[1,3,4]-Thiadiazol-2-yl)-imidazo[1,2-a]pyridin-3-yl)-phenyl]-3-(2,2,2-trifluoro-ethyl)-urea hydrochloride salt Step (a): 7-Chloro-imidazo[1,2-a]pyridine

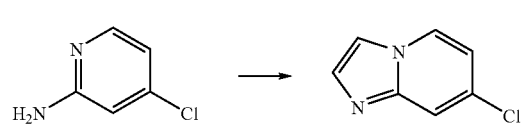

To a solution of 4-chloro-pyridin-2-ylamine (25.0 g, 0.194 mol) in EtOH (250 ml) was added NaHCO$_3$ (32.7 g, 0.389 mol) followed by a 50% solution of chloroacetaldehyde in water (37 mL, 0.292 mol). The mixture was refluxed for 6 h. The solvents were removed under reduced pressure and the crude mixture was diluted with water (250 ml) and extracted with EtOAc (2×125 ml). The combined organic layers were washed with brine (50 ml), dried (MgSO$_4$), filtered and concentrated under reduced pressure to give 7-chloro-imidazo[1,2-a]pyridine (32.7 g). 1H NMR (400 MHz, CDCl$_3$) δ 8.06 (1H, d), 7.64 (2H, d), 7.56 (1H, s), 6.79 (1H, dd).

Step (b): 7-Chloro-3-iodo-imidazo[1,2-a]pyridine

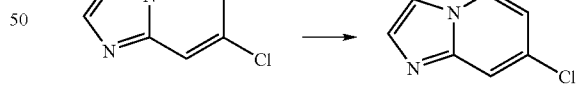

To a solution of 7-Chloro-imidazo[1,2-a]pyridine (30.9 g, 186 mmol, 1.0 equiv) in DMF (280 ml) was added N-iodosuccinimide (43.6 g, 194 mmol, 1.05 equiv) and the resulting mixture was stirred overnight at RT. The thin brown slurry was diluted with water (840 ml), brine (280 ml) and extracted with EtOAc (560 ml). The aqueous was further extracted with EtOAc (3×280 ml). The combined organic phases were washed with water (2×280 ml), 10% w/v sodium thiosulfate (280 ml), brine (280 ml), dried (MgSO$_4$), filtered and concentrated in vacuo to give a brown residue. The residue was triturated with ether (200 ml), filtered and the solid was washed ether (2×50 ml) and dried on the filter to give 39 g of product. MS: [M+H]$^+$ 279

Step (c): 1-(3-Bromo-phenyl)-3-(2,2,2-trifluoro-ethyl)-urea

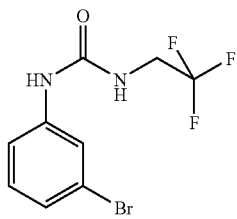 [SMILES: O=C(NCC(F)(F)F)Nc1cccc(Br)c1]

3-Bromophenyl isocyanate (21.12 g, 107 mmol) was added slowly to a stirred solution of 2,2,2-trifluoroethyl amine (40 ml, 0.5 mol) in THF (100 mL) at 0° C. under $N_2$, rinsing with THF (25 mL). The reaction was allowed to warm slowly to RT and kept at this temperature for 16 hours. The volatiles were removed under reduced pressure to give the title compound (31.6 g) as a solid. $^1$H NMR (400 MHz, DMSO-$d_6$) δ 8.94 (1H, s), 7.80 (1H, t), 7.31-7.24 (1H, m), 7.20 (1H, t), 7.16-7.08 (1H, m), 6.83 (1H, bt), 3.98-3.85 (2H, m).

Step (d): 1-[3-(4,4,5,5-Tetramethyl-[1,3,2]dioxaborolan-2-yl)-phenyl]-3-(2,2,2-trifluoro-ethyl)-urea

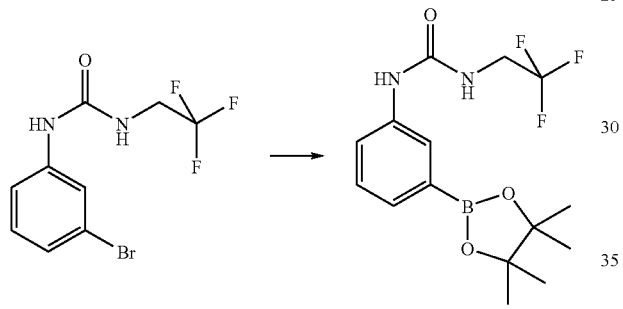

A mixture of 1-(3-bromo-phenyl)-3-(2,2,2-trifluoro-ethyl)-urea (31.6 g, 106 mmol), bis(pinacolato)diboron (54 g, 212 mmol) and KOAc (31.3 g, 319 mmol) in dry DMSO (110 ml) was deoxygenated by evacuation/refill with $N_2$ (×3). PdCl$_2$ddpf (7.78 g, 10.6 mmol) was added and the mixture was deoxygenated again (×3) then stirred and heated at 100° C. under $N_2$ for 100 mins. The reaction was allowed to cool to RT, diluted with water (320 ml) and extracted with EtOAc (2×320 ml). The combined organic extracts were washed with water (320 ml), brine (320 ml) then dried (MgSO$_4$), filtered and evaporated. The residue was triturated petrol to give the title compound (37.4 g) as a solid. $^1$H NMR (400 MHz, CDCl$_3$) δ 7.63 (1H, s), 7.58 (1H, d), 7.46 (1H, d), 7.34 (1H, t), 6.65 (1H, brs), 5.21 (1H, brs), 3.99-3.86 (2H, m), 1.33 (12H, s).

Step (e): 1-[3-(7-Chloro-imidazo[1,2-a]pyridin-3-yl)-phenyl]-3-(2,2,2-trifluoro-ethyl)-urea

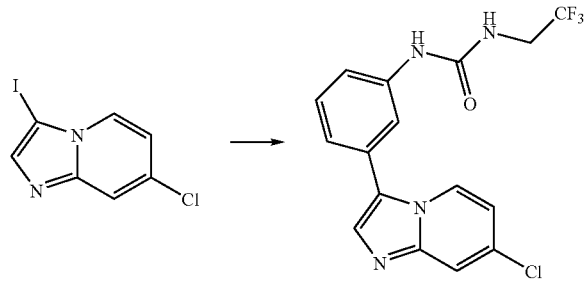 [SMILES: Clc1ccn2c(I)cnc2c1 ; O=C(NCC(F)(F)F)Nc1cccc(-c2cnc3cc(Cl)ccn23)c1]

To a solution of 7-chloro-3-iodo-imidazo[1,2-a]pyridine (5.0 g, 17.8 mmol) in DME (350 ml) was added 1-[3-(4,4,5,5-Tetramethyl-[1,3,2]dioxaborolan-2-yl)-phenyl]-3-(2,2,2-trifluoro-ethyl)-urea (7.36 g, 21.4 mmol), 2M Na$_2$CO$_3$ (71.6 ml, 35.8 mmol) [reaction degassed by bubbling N$_2$ through] followed by tetrakis(triphenylphosphine)palladium(0) (1.03 g, 0.89 mmol). The mixture was heated at 80° C. overnight, then diluted with water and extracted with EtOAc. The organic layer was washed with brine, dried (MgSO$_4$), filtered and concentrated under reduced pressure. The crude material was triturated with CH$_2$Cl$_2$ to afford the desired product as a beige solid. MS: [M+H]$^+$ 389

Step (f): 1-{3-[7-(4,4,5,5-Tetramethyl-[1,3,2]dioxaborolan-2-yl)-imidazo[1,2-a]pyridin-3-yl]-phenyl}-3-(2,2,2-trifluoro-ethyl)-urea

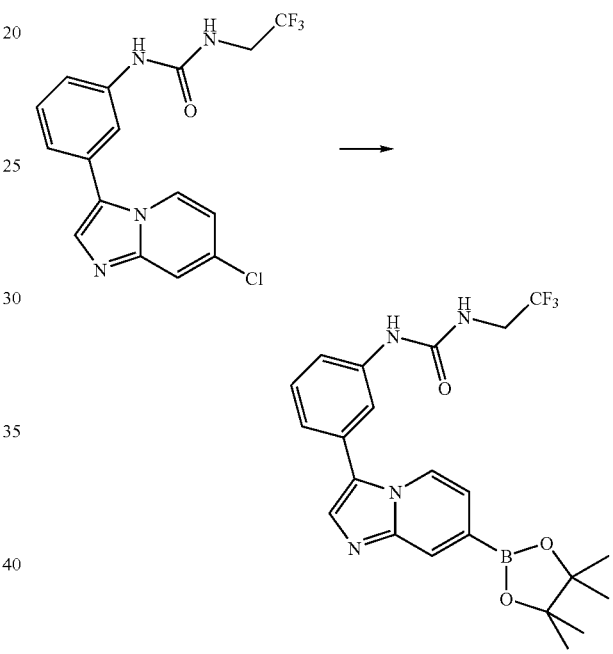

To a solution of 1-[3-(7-Chloro-imidazo[1,2-a]pyridin-3-yl)-phenyl]-3-(2,2,2-trifluoro-ethyl)-urea (10.0 g, 27.1 mmol) in dioxane (160 ml) was added tricyclohexylphosphine (3.73 g, 13.3 mmol), KOAc (12 g, 123 mmol), bis(pinacolato)boron (22.7 g, 89.5 mmol) [reaction degassed by bubbling N$_2$ through] followed by Pd$_2$(dba)$_3$ (3.72 g, 4 mmol). The mixture was heated at reflux for 2 h, then cooled, filtered and concentrated under reduced pressure. The residue was partitioned between ethyl acetate and water and the organic fraction was dried (MgSO$_4$) and concentrated in vacuo. The residue was dissolved in ethyl acetate (150 ml) and petrol (500 ml) was added. The resulting suspension was filtered and the solid washed with petrol and dried to give the title compound (8.9 g) as a beige solid, which was used without further purification.

Step (g): 2-Bromo-[1,3,4]thiadiazole

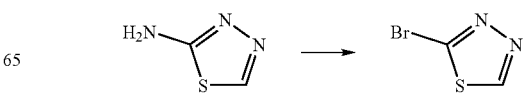

To [1,3,4]thiadiazol-2-ylamine (1 g, 9.89 mmol) was added 48% aqueous HBr (10 ml) and $H_2O$ (10 ml). The reaction mixture was cooled to 0° C. using an icebath, CuBr (142 mg, 0.99 mmol) was added and then a solution of sodium nitrite (0.682 mg, 9.89 mmol) in $H_2O$ (10 ml) was added dropwise and the mixture allowed to stir for 10 mins. The reaction mixture was gradually warmed up to room temperature over 30 min, then a saturated solution of bicarbonate added until the pH of the mixture reached 8.0. The aqueous layer was extracted with EtOAc (×3), the organics combined, dried ($MgSO_4$), filtered and the solvent removed in vacuo to give a pale yellow solid (1 g), which was used directly in the next reaction. 1H NMR (400 MHz, DMSO-$d_6$): 9.63 (1H, s).

Step (h): 1-[3-(7-[1,3,4]-Thiadiazol-2-yl)-imidazo[1,2-a]pyridin-3-yl)-phenyl]-3-(2,2,2-trifluoro-ethyl)-urea hydrochloride salt

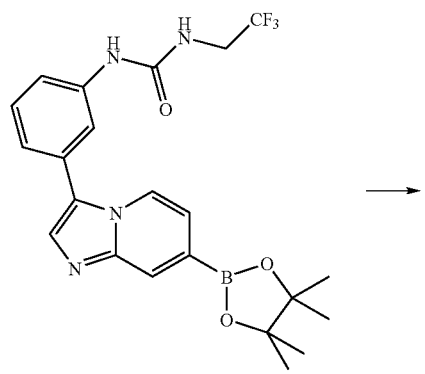

→

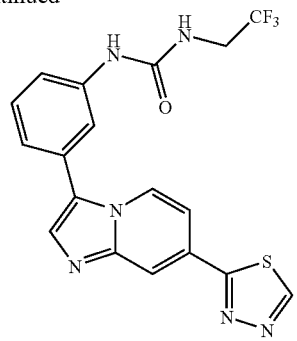

Cesium carbonate (10.27 g, 31.66 mmol) was added to a solution of 1-{3-[7-(4,4,5,5-Tetramethyl-[1,3,2]dioxaborolan-2-yl)-imidazo[1,2-a]pyridin-3-yl]-phenyl}-3-(2,2,2-trifluoro-ethyl)-urea (4.84 mg, 10.52 mmol) and 2-bromo-[1,3,4]thiadiazole (4.43 g, 26.3 mmol) in toluene (87 ml), n-butanol (87 ml) and water (22 ml) [reaction degassed by bubbling $N_2$ through], followed by tetrakis(triphenylphosphine)palladium (3.5 g, 3 mmol). The reaction was heated to 80° C. overnight. The solution was diluted with ethyl acetate and water and the layers separated. The organic fraction was washed with water, dried ($MgSO_4$) and concentrated in vacuo. The residue was triturated with ethyl acetate and further purified by preparative HPLC.

The product was dissolved in saturated HCl/EtOAc, then concentrated under reduced pressure to give the title compound (0.39 g) as a white solid. MS: $[M+H]^+=419$. 1H NMR (400 MHz, DMSO-$d_6$): 9.70 (1H, s), 8.98 (1H, s), 8.70 (1H, d), 8.35 (1H, s), 7.93 (1H, s), 7.78 (1H, s), 7.66 (1H, dd), 7.54-7.45 (2H, m), 7.33-7.28 (1H, m), 6.86 (1H, t), 4.00-3.91 (2H, m).

Examples 385 to 400

By following the methods described above, the compounds of Examples 385 to 400 set out in the Table below were prepared.

| Eg. No. | Structure | Chemical Name | Method | NMR Data | MS Data |
|---|---|---|---|---|---|
| 385 | 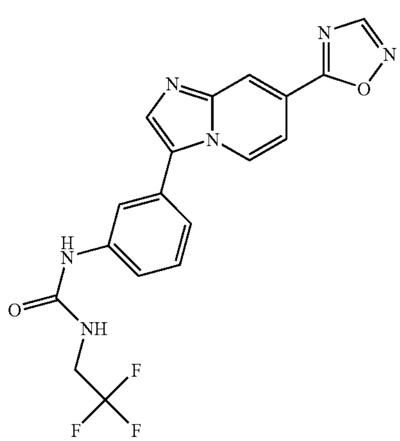 [SMILES: O=C(NCC(F)(F)F)Nc1cccc(-c2cnc3cc(-c4ncno4)ccn23)c1] | 1-[3-(7-[1,2,4]Oxadiazol-5-yl-imidazo[1,2-a]pyridin-3-yl)-phenyl]-3-(2,2,2-trifluoro-ethyl)-urea | Procedure AA steps a-b. Procedure AR. | 1H NMR (400 MHz, DMSO-d6): 9.19 (1H, s), 8.99 (1H, s), 8.76 (1H, dd), 8.46 (1H, dd), 8.03 (1H, s), 7.79 (1H, t), 7.58 (1H, dd), 7.55-7.46 (2H, m), 7.31 (1H, dt), 6.87 (1H, t), 4.02-3.89 (2H, m). | MS: $[M + H]^{1+}$ 403 |

-continued

| Eg. No. | Structure | Chemical Name | Method | NMR Data | MS Data |
|---|---|---|---|---|---|
| 386 | 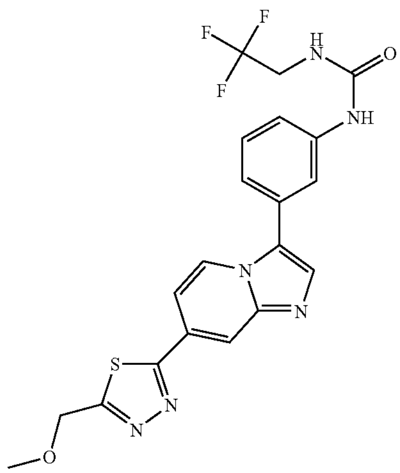 [SMILES: COCc1nnc(-c2ccn3c(-c4cccc(NC(=O)NCC(F)(F)F)c4)cnc3c2)s1] | 1-{3-[7-(5-Methoxy-methyl-[1,3,4]thia-diazol-2-yl)-imidazo[1,2-a]pyridin-3-yl]-phenyl}-3-(2,2,2-trifluoro-ethyl)-urea | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3e using U8 2-Bromo-5-methoxymethyl-[1,3,4]thiadiazole | 1H NMR (400 MHz, Me-d3-OD): 8.72 (1H, d), 8.24 (1H, S), 7.87 (2H, d), 7.73-7.64 (1H, m), 7.57-7.41 (2H, m), 7.36 (1H, d), 4.95 (2H, s), 3.96 (2H, q), 3.55 (3H, s). | MS: [M + H]+ 463 |
| 387 | 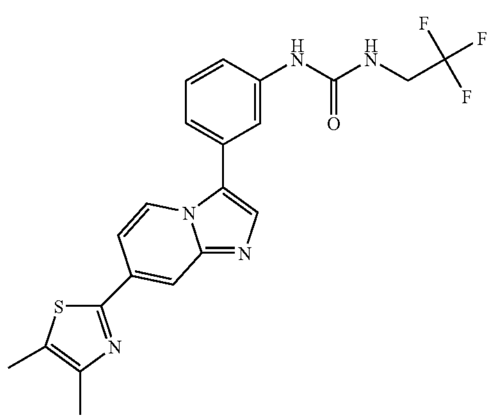 [SMILES: Cc1nc(-c2ccn3c(-c4cccc(NC(=O)NCC(F)(F)F)c4)cnc3c2)sc1C] | 1-{3-[7-(4,5-Dimethyl-thiazol-2-yl)-imidazo[1,2-a]pyridin-3-yl]-phenyl}-3-(2,2,2-trifluoro-ethyl)-urea | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3e using U9 2-Bromo-4,5-dimethyl-thiazole | 1H NMR (400 MHz, Me-d3-OD): 8.63 (1H, d), 8.08 (1H, s), 7.82 (1H, s), 7.78 (1H, s), 7.58-7.51 (1H, m), 7.49 (1H, d), 7.43 (1H, d), 7.33 (1H, d), 3.95 (2H, q), 2.48 (3H, s), 2.42 (3H, s). | MS: [M + H]+ 446 |
| 388 | 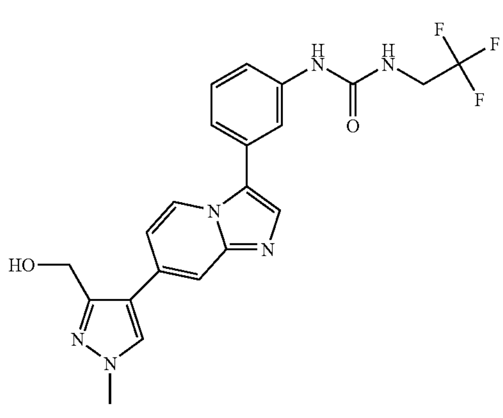 [SMILES: Cn1cc(-c2ccn3c(-c4cccc(NC(=O)NCC(F)(F)F)c4)cnc3c2)c(CO)n1] | 1-{3-[7-(3-Hydroxy-methyl-1-methyl-1H-pyrazol-4-yl)-imidazo[1,2-a]pyridin-3-yl]-phenyl}-3-(2,2,2-trifluoro-ethyl)-urea | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3b using (4-Bromo-1-methyl-1H-pyrazol-3-yl)-methanol | 1H NMR (400 MHz, Me-d3-OD): 8.57 (1H, d), 8.04 (1H, s), 7.93 (1H, s), 7.82 (1H, s), 7.68 (1H, s), 7.48 (1H, t), 7.43-7.35 (1H, m), 7.35-7.26 (2H, m), 4.75 (2H, s), 4.02-3.89 (5H, m). | MS: [M + H]+ 445 |

-continued

| Eg. No. | Structure | Chemical Name | Method | NMR Data | MS Data |
|---|---|---|---|---|---|
| 389 | 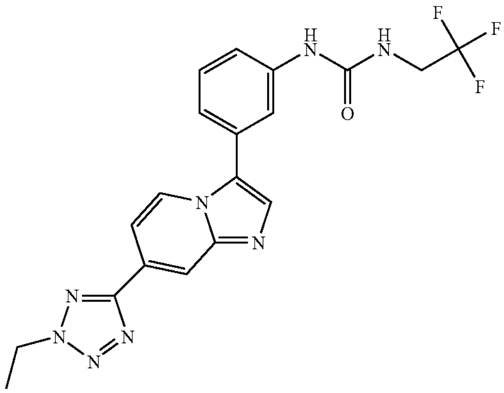 [SMILES: CCn1nnc(-c2ccn3c(-c4cccc(NC(=O)NCC(F)(F)F)c4)cnc3c2)n1] | 1-{3-[7-(2-Ethyl-2H-tetrazol-5-yl)-imidazo[1,2-a]pyridin-3-yl]-phenyl}-3-(2,2,2-trifluoro-ethyl)-urea | Procedure AI steps 1-2. Step 3 performed substituting ethyl iodide for methyl iodide and DMSO for DMF. Steps 4-5. | 1H NMR (400 MHz, DMSO-d6): 9.35 (1H, s), 8.90 (1H, d), 8.53 (1H, s), 8.41 (1H, s), 7.95 (1H, dd), 7.88 (1H, s), 7.61-7.52 (2H, m), 7.33 (1H, dt), 7.07 (1H, t), 4.86 (2H, q), 4.00-3.90 (2H, m), 1.63 (3H, t). | MS: [M + H]$^{1+}$ 431 |
| 390 | 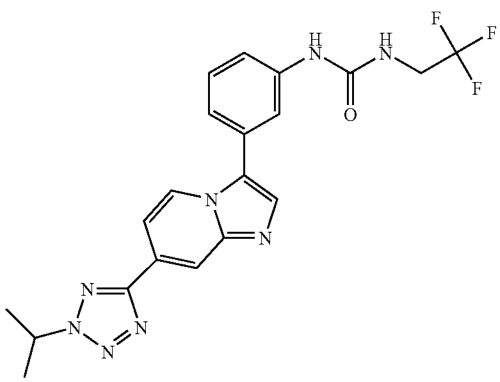 [SMILES: CC(C)n1nnc(-c2ccn3c(-c4cccc(NC(=O)NCC(F)(F)F)c4)cnc3c2)n1] | 1-{3-[7-(2-Isopropyl-2H-tetrazol-5-yl)-imidazo[1,2-a]pyridin-3-yl]-phenyl}-3-(2,2,2-trifluoro-ethyl)-urea | Procedure AI steps 1-2. Step 3 performed substituting 2-iodopropane for methyl iodide and DMSO for DMF. Steps 4-5. | 1H NMR (400 MHz, DMSO-d6): 9.37 (1H, s), 8.96 (1H, br s), 8.47 (1H, br s), 7.94 (1H, d), 7.89 (1H, s), 7.62-7.51 (2H, m), 7.34 (1H, d), 7.07 (1H, t), 5.33-5.22 (1H, m), 4.00-3.90 (2H, m), 1.67 (6H, d). | MS: [M + H]$^{1+}$ 445 |
| 391 | 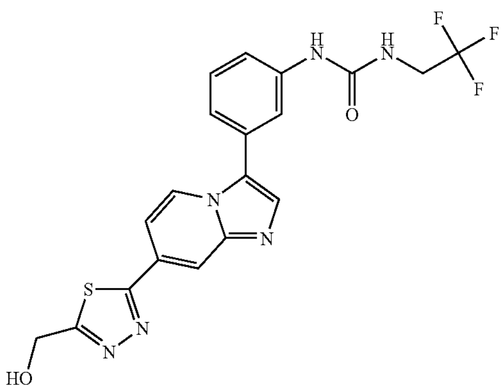 [SMILES: O=C(NCC(F)(F)F)Nc1cccc(-c2cnc3cc(-c4nnc(CO)s4)ccn23)c1] | 1-{3-[7-(5-Hydroxymethyl-[1,3,4]thia-diazol-2-yl)-imidazo[1,2-a]pyridin-3-yl]-phenyl}-3-(2,2,2-trifluoro-ethyl)-urea hydrochloride | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2, procedure E3e using U8 2-Bromo-5-methoxymethyl-[1,3,4]thiadiazole, procedure D8, procedure J1 | 1H NMR (400 MHz, Me-d3-OD): 8.95 (1H, d), 8.61 (1H, s), 8.32 (1H, s), 8.21-8.11 (1H, m), 8.02 (1H, s), 7.60 (1H, t), 7.54 (1H, d), 7.42 (1H, d), 5.09 (2H, s), 3.96 (2H, q). | MS: [M + H]$^{1+}$ 449 |

-continued

| Eg. No. | Structure | Chemical Name | Method | NMR Data | MS Data |
|---|---|---|---|---|---|
| 392 | 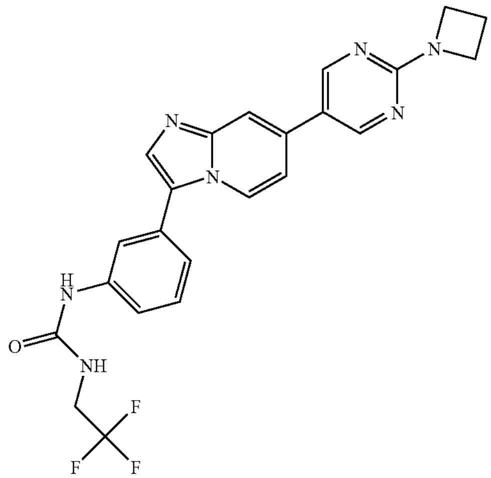 [SMILES: O=C(NCC(F)(F)F)Nc1cccc(-c2cnc3cc(-c4cnc(N5CCC5)nc4)ccn23)c1] | 1-{3-[7-(2-Azetidin-1-yl-pyrimidin-5-yl)-imidazo[1,2-a]pyridin-3-yl]-phenyl}-3-(2,2,2-trifluoro-ethyl)-urea formate | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3d using 2-Azetidin-1-yl-5-bromo-pyrimidine | 1H NMR (400 MHz, DMSO-d6): 9.06 (1H, s), 8.88 (2H, s), 8.60 (1H, d), 8.17 (2H, s), 8.00 (1H, s), 7.80 (1H, s), 7.77 (1H, s), 7.43 (2H, d), 7.37 (1H, dd), 7.26 (1H, d), 6.96 (1H, t), 4.12 (4H, t), 4.02-3.88 (2H, m), 2.42-2.30 (2H, m). | MS: [M + H]¹⁺ 468 |
| 393 | 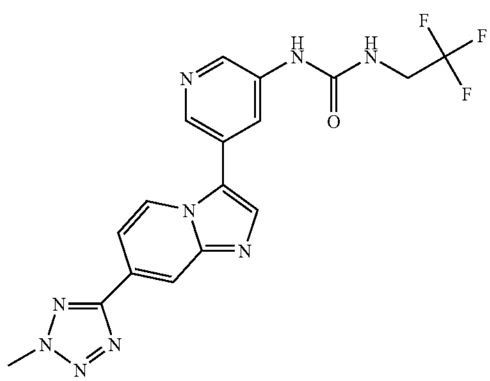 [SMILES: Cn1nnc(-c2ccn3c(-c4cncc(NC(=O)NCC(F)(F)F)c4)cnc3c2)n1] | 1-{5-[7-(2-Methyl-2H-tetrazol-5-yl)-imidazo[1,2-a]pyridin-3-yl]-pyridin-3-yl}-3-(2,2,2-trifluoro-ethyl)-urea | procedure AI steps 1-4. Step 5 using I28 1-[5-(4,4,5,5-Tetramethyl-[1,3,2]dioxaborolan-2-yl)-pyridin-3-yl]-3-(2,2,2-trifluoro-ethyl)-urea | 1H NMR (400 MHz, DMSO-d6): 9.19 (1H, s), 8.76 (1H, d), 8.69 (1H, s), 8.52 (1H, s), 8.29 (1H, s), 8.21 (1H, s), 8.00 (1H, s), 7.60 (1H, d), 7.09 (1H, s), 4.48 (3H, s), 4.05-3.89 (2H, m). | MS: [M + H]¹⁺ 418 |
| 394 | 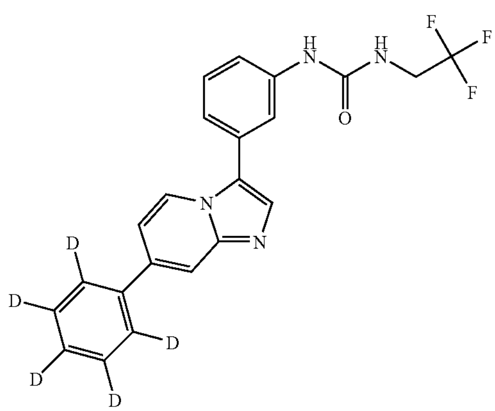 [SMILES: [2H]c1c([2H])c([2H])c(-c2ccn3c(-c4cccc(NC(=O)NCC(F)(F)F)c4)cnc3c2)c([2H])c1[2H]] | 1-[3-(7-Phenyl-d5-imidazo[1,2-a]pyridin-3-yl)-phenyl]-3-(2,2,2-trifluoro-ethyl)-urea | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure A4b using Phenyl-d5-boronic acid, substituting 2-(Dimethylamino)ferrocen-1-yl-palladium(II) chloride dinorbornylphosphine complex for tetrakis(triphenylphosphine)palladium (0) | 1H NMR (400 MHz, Me-d3-OD): 8.66 (1H, d), 7.90-7.81 (2H, m), 7.74 (1H, s), 7.50 (1H, t), 7.46-7.36 (2H, m), 7.34 (1H, d), 3.96 (2H, q). | MS: [M + H]¹⁺ 416 |

-continued

| Eg. No. | Structure | Chemical Name | Method | NMR Data | MS Data |
|---|---|---|---|---|---|
| 395 | 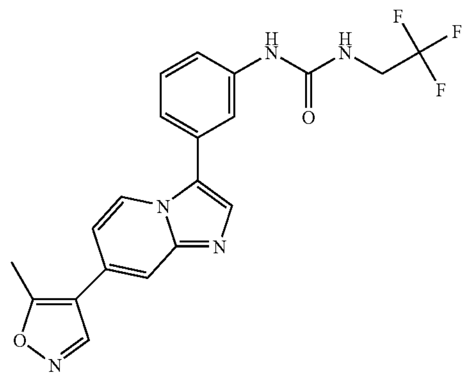 [SMILES: Cc1oncc1-c1ccn2c(-c3cccc(NC(=O)NCC(F)(F)F)c3)cnc2c1] | 1-{3-[7-(5-Methyl-isoxazol-4-yl)-imidazo[1,2-a]pyridin-3-yl]-phenyl}-3-(2,2,2-trifluoro-ethyl)-urea | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3b using 4-Iodo-5-methyl-isoxazole substituting Bis(triphenylphosphine)palladium(II) chloride for tetrakis(triphenyl-phosphine)palladium (0) | 1H NMR (400 MHz, DMSO-d6): 8.99 (1H, s), 8.35 (1H, d), 7.94 (1H, s), 7.73 (1H, s), 7.59-7.42 (3H, m), 7.24 (1H, d), 6.87 (1H, t), 4.01-3.89 (2H, m), 2.15 (3H, s). | MS: [M + H]⁺ 416 |
| 396 | 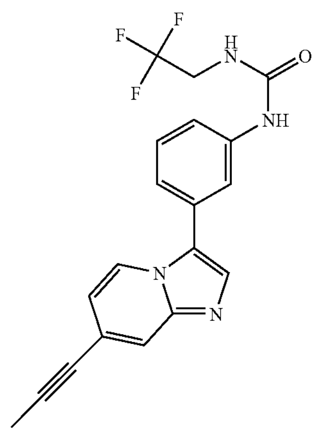 [SMILES: CC#Cc1ccn2c(-c3cccc(NC(=O)NCC(F)(F)F)c3)cnc2c1] | 1-[3-(7-Prop-1-ynyl-imidazo[1,2-a]pyridin-3-yl)-phenyl]-3-(2,2,2-trifluoro-ethyl)-urea | general procedure SGD, steps SGD1-SGD3. SGD4a using 1-Propynylmagnesium bromide (stage 1 only) | 1H NMR (400 MHz, DMSO-d6): 8.94 (1H, s), 8.49 (1H, d), 7.80 (1H, s), 7.70 (2H, d), 7.52-7.39 (2H, m), 7.24 (1H, d), 6.91 (1H, dd), 6.84 (1H, t), 4.01-3.88 (2H, m), 2.11 (3H, s). | MS: [M + H]⁺ 373 |
| 397 | 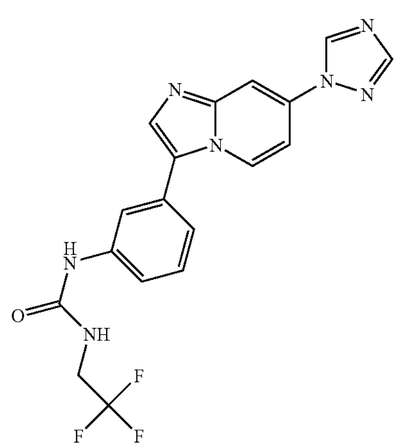 [SMILES: O=C(NCC(F)(F)F)Nc1cccc(-c2cnc3cc(-n4cncn4)ccn23)c1] | 1-[3-(7-[1,2,4]Triazol-1-yl-imidazo[1,2-a]pyridin-3-yl)-phenyl]-3-(2,2,2-trifluoro-ethyl)-urea | Procedure AS | 1H NMR (400 MHz, DMSO-d6): 9.51 (1H, s), 8.97 (1H, s), 8.73 (1H, d), 8.33 (1H, s), 8.21 (1H, d), 7.84 (1H, s), 7.77 (1H, s), 7.60 (1H, dd), 7.53-7.42 (2H, m), 7.32-7.24 (1H, m), 6.86 (1H, t), 4.02-3.88 (2H, m). | MS: [M + H]⁺ 402 |

| Eg. No. | Structure | Chemical Name | Method | NMR Data | MS Data |
|---|---|---|---|---|---|
| 398 | 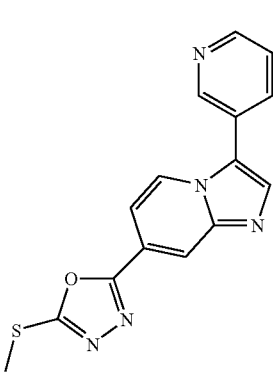 | 1-{5-[7-(5-Methylsulfanyl-[1,3,4]oxa-diazol-2-yl)-imidazo[1,2-a]pyridin-3-yl]-pyridin-3-yl}-3-(2,2,2-trifluoro-ethyl)-urea | Example 332 step A using I28 1-[5-(4,4,5,5-Tetramethyl-[1,3,2]dioxaborolan-2-yl)-pyridin-3-yl]-3-(2,2,2-trifluoro-ethyl)-urea. Procedure AM | 1H NMR (400 MHz, DMSO-d6): 9.25 (1H, s), 8.74 (1H, dd), 8.69 (1H, d), 8.52 (1H, d), 8.30-8.24 (1H, m), 8.22 (1H, t), 8.06 (1H, s), 7.51 (1H, dd), 7.14 (1H, t), 4.03-3.90 (2H, m), 2.82 (3H, s). | MS: [M + H]+ 450 |
| 399 | 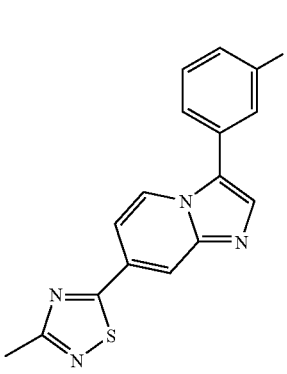 | 1-{3-[7-(3-Methyl-[1,2,4]thia-diazol-5-yl)-imidazo[1,2-a]pyridin-3-yl]-phenyl}-3-(2,2,2-trifluoro-ethyl)-urea | general route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3c using 5-Chloro-3-methyl-[1,2,4]thiadiazole | 1H NMR (400 MHz, DMSO-d6): 9.06 (1H, s), 8.69 (1H, dd), 8.40 (1H, dd), 7.96 (1H, s), 7.80-7.78 (1H, m), 7.58-7.43 (3H, m), 7.30 (1H, dt), 6.95 (1H, t), 4.02-3.88 (2H, m), 2.69 (3H, s). | MS: [M + H]+ 433 |
| 400 | 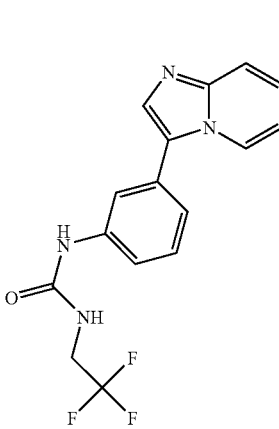 | 1-(2,2,2-Trifluoro-ethyl)-3-(3-{7-[2-(2,2,2-trifluoro-ethyl)-2H-tetrazol-5-yl]-imidazo[1,2-a]pyridin-3-yl}-phenyl)-urea hydro-chloride | Procedure AI steps 1-2. Step 3b. Steps 4-5. Procedure J1 | 1H NMR (400 MHz, Me-d3-OD): 9.00 (1H, d), 8.74 (1H, s), 8.32 (1H, s), 8.22 (1H, dd), 8.06 (1H, t), 7.60 (1H, t), 7.49 (1H, d), 7.42 (1H, d), 5.86 (2H, q), 3.96 (2H, q) | MS: [M + H]+ 485 |

Examples 401-418

Examples 401-418 may be prepared in accordance with the following procedures:

Example 401A 1-(3-{7-[1-(2-Hydroxy-ethyl)-1H-pyrazol-4-yl]-imidazo[1,2-a]pyridin-3-yl}-phenyl)-3-(2,2,2-trifluoro-ethyl)-urea

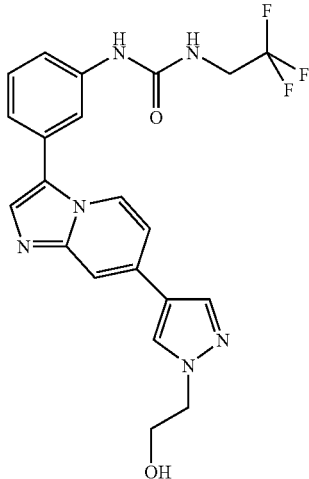 [SMILES: O=C(NCC(F)(F)F)Nc1cccc(-c2cnc3cc(-c4cnn(CCO)c4)ccn23)c1]

The title compound could be prepared by general route A steps A1-A3, procedure A3b using I6 [3-(4,4,5,5-tetramethyl-[1,3,2]dioxaborolan-2-yl)-phenyl]-3-(2,2,2-trifluoro-ethyl)-urea, procedure E2 and procedure E3 using 2-(4-bromo-1H-pyrazol-1-yl)ethanol.

Example 401 B

Example 401 B was prepared in accordance with the procedure set out in the Table below.

Example 402A 1-(3-{7-[1-(2-Amino-ethyl)-1H-pyrazol-4-yl]imidazo[1,2-a]pyridin-3-yl}-phenyl)-3-(2,2,2-trifluoro-ethyl)-urea

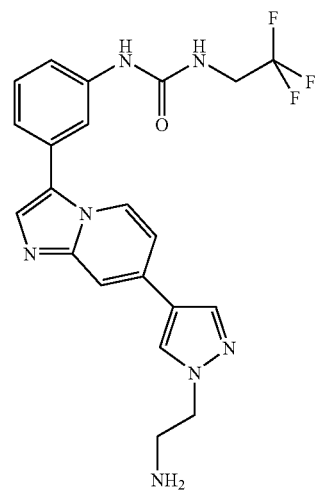 [SMILES: NCCn1cc(-c2ccn3c(-c4cccc(NC(=O)NCC(F)(F)F)c4)cnc3c2)cn1]

The title compound could be prepared by general route A steps A1-A3, procedure A3b using I6 [3-(4,4,5,5-tetramethyl-[1,3,2]dioxaborolan-2-yl)-phenyl]-3-(2,2,2-trifluoro-ethyl)-urea, procedure E2 and procedure E3 using 2-(4-bromo-pyrazol-1-yl)-ethylamine.

Example 402B

Example 402B was prepared in accordance with the procedure set out in the Table below.

| Eg. No. | Structure | Chemical Name | Method | NMR Data | MS Data |
|---|---|---|---|---|---|
| 401B | 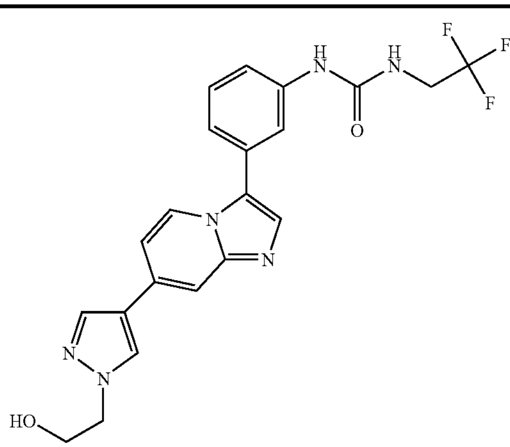 | 1-(3-{7-[1-(2-Hydroxy-ethyl)-1H-pyrazol-4-yl]-imidazo[1,2-a]pyridin-3-yl}-phenyl)-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3c using 2-(4-bromopyrazol-1-yl)-ethanol | 1H NMR (400 MHz, Me-d3-OD): 8.55 (1H, d), 8.23 (1H, s), 8.04 (1H, s), 7.81 (1H, s), 7.76 (1H, s), 7.66 (1H, s), 7.48 (1H, t), 7.39 (1H, d), 7.34-7.23 (2H, m), 4.31 (2H, t), 4.02-3.89 (4H, m). | [M + H]+ 445 |

| Eg. No. | Structure | Chemical Name | Method | NMR Data | MS Data |
|---|---|---|---|---|---|
| 402B | 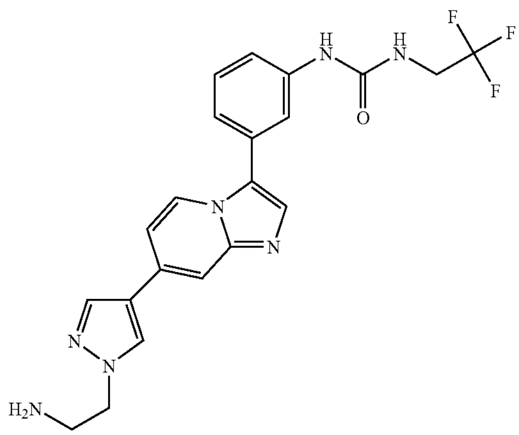 [SMILES: NCCn1cc(-c2ccn3c(-c4cccc(NC(=O)NCC(F)(F)F)c4)cnc3c2)cn1] | 1-(3-{7-[1-(2-Amino-ethyl)-1H-pyrazol-4-yl]-imidazo[1,2-a]pyridin-3-yl}-phenyl)-3-(2,2,2-trifluoro-ethyl)-urea | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3c using 2-(4-bromopyrazol-1-yl)-ethylamine hydrochloride. | 1H NMR (400 MHz, Me-d3-OD): 8.61-8.52 (1H, m), 8.24 (1H, s), 8.08 (1H, s), 7.88-7.80 (1H, m), 7.76 (1H, s), 7.67 (1H, s), 7.48 (1H, t), 7.36 (1H, d), 7.33-7.22 (2H, m), 4.40 (2H, t), 3.96 (2H, q), 3.35-3.30 (2H, m). | [M + H]+ 444 |

Example 403

1-{3-[7-(4,5-Dimethyl-4H-[1,2,4]triazol-3-yl)-imidazo[1,2-a]pyridin-3-yl]-phenyl}-3-(2,2,2-trifluoro-ethyl)-urea

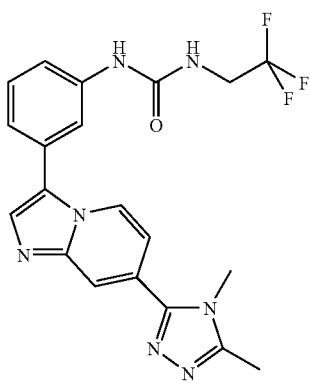 [SMILES: Cc1nnc(-c2ccn3c(-c4cccc(NC(=O)NCC(F)(F)F)c4)cnc3c2)n1C]

The title compound could be prepared by general route A steps A1-A3, procedure A3b using I6 [3-(4,4,5,5-tetramethyl-[1,3,2]dioxaborolan-2-yl)-phenyl]-3-(2,2,2-trifluoro-ethyl)-urea, procedure E2 and procedure E3 using 3-halo-4,5-dimethyl-4H-[1,2,4]triazole.

3-Halo-4,5-dimethyl-4H-[1,2,4]triazole maybe prepared from the commercially available 3-chloro-5-methyl-4H-[1,2,4]triazole.

Alternatively the title compound could be prepared through reaction of 1-{3-[7-(5-methyl-[1,3,4]oxadiazol-2-yl)-imidazo[1,2-a]pyridin-3-yl]-phenyl}-3-(2,2,2-trifluoro-ethyl)-urea with methylamine.

Example 404

1-{3-[7-(5-Methyl-oxazol-2-yl)-imidazo[1,2-a]pyridin-3-yl]-phenyl}-3-(2,2,2-urea

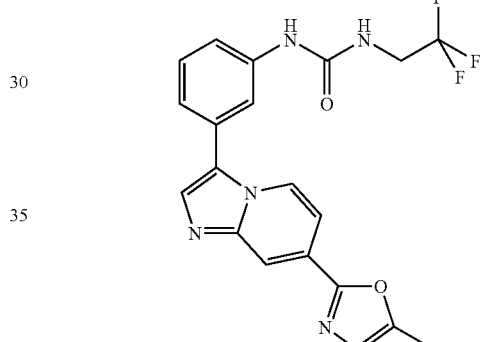

The title compound could be prepared by general route A steps A1-A3, procedure A3b using 16 [3-(4,4,5,5-tetramethyl-[1,3,2]dioxaborolan-2-yl)-phenyl]-3-(2,2,2-trifluoro-ethyl)-urea, procedure E2 and procedure E3 using 2-chloro-5-methyl-oxazole.

Example 405

1-{3-[7-(4-Methyl-oxazol-5-yl)-imidazo[1,2-a]pyridin-3-yl]-phenyl}-3-(2,2,2-trifluoro-ethyl)-urea

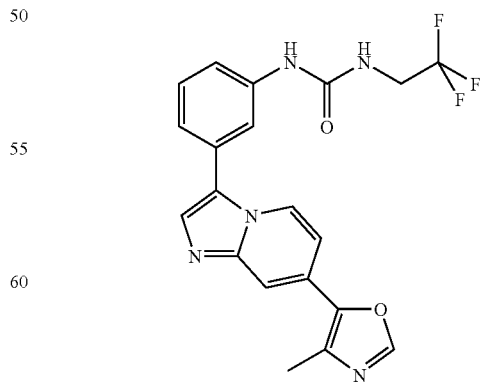

The title compound could be prepared by the route AB replacing TosMIC with Me-TosMIC as described in Bioorg. Med. Chem. Lett. 12 2002 1323.

Example 406

1-{3-[7-(4-Methyl-oxazol-2-yl)-imidazo[1,2-a]pyridin-3-yl]-phenyl}-3-(2,2,2-trifluoro-ethyl)-urea

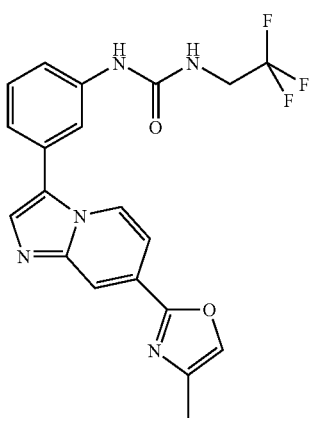 [SMILES: Cc1coc(-c2ccn3c(-c4cccc(NC(=O)NCC(F)(F)F)c4)cnc3c2)n1]

The title compound maybe prepared by reacting imidazo[1,2-a]pyridine-7-carboxylic acid amide, prepared as described in procedure ACa, with chloroacetone as outlined in J. Med. Chem. 1990, 33, 492. Following general route B, steps B2 and B3 would afford the desired compound as illustrated in the scheme below.

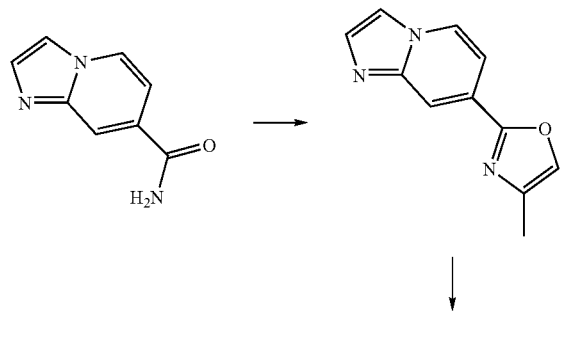

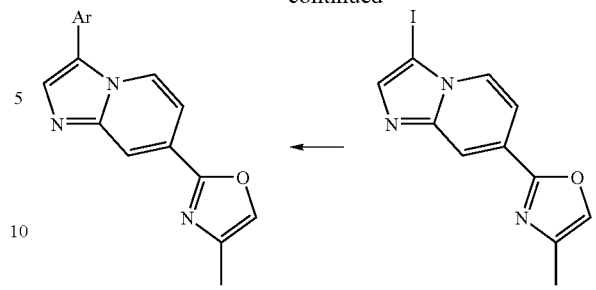

Alternatively the title compound could be prepared by a Stille Type coupling as described in Synthesis 1987, 8, 693.

Example 407A

1-{5-[7-(5-Methyl-[1,3,4]oxadiazol-2-yl)-imidazo[1,2-a]pyridin-3-yl]-pyridin-3-yl}-3-(2,2,2-trifluoro-ethyl-urea

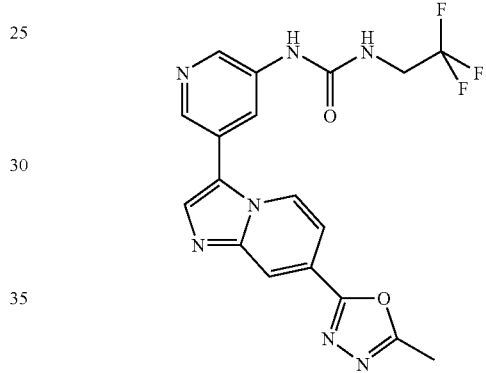

The title compound could be prepared as described in Example 329, substituting I28 1-[5-(4,4,5,5-tetramethyl-[1,3,2]dioxaborolan-2-yl)-pyridin-3-yl]-3-(2,2,2-trifluoro-ethyl)-urea in step e.

Example 407B

Example 407B was prepared in accordance with the procedure set out in the Table below.

| Eg. No. | Structure | Chemical Name | Method | NMR Data | MS Data |
|---|---|---|---|---|---|
| 407B | 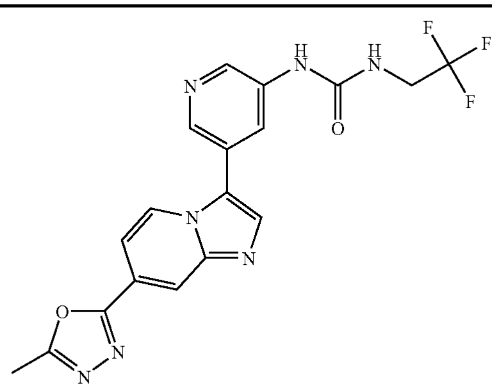 | 1-{5-[7-(5-Methyl-[1,3,4]oxadiazol-2-yl)-imidazo[1,2-a]pyridin-3-yl]-pyridin-3-yl}-3-(2,2,2-trifluoro-ethyl)-urea | Procedure as for example 329 steps a-d. Step e using I28 1-[5-(4,4,5,5-Tetramethyl-[1,3,2]dioxaborolan-2-yl)-pyridin-3-yl]-3-(2,2,2-trifluoro-ethyl)-urea | 1H NMR (400 MHz, DMSO-d6): 9.21 (1H, s), 8.76 (1H, d), 8.69 (1H, d), 8.53 (1H, d), 8.26-8.18 (2H, m), 8.06 (1H, s), 7.52 (1H, dd), 7.09 (1H, t), 4.03-3.91 (2H, m), 2.64 (3H, s). | [M + H]+ 418 |

Example 408A

1-[3-(7-Cyclopropylethynyl)-imidazo[1,2-a]pyridin-3-yl]phenyl-3-(2,2,2-trifluoro-ethyl)-urea

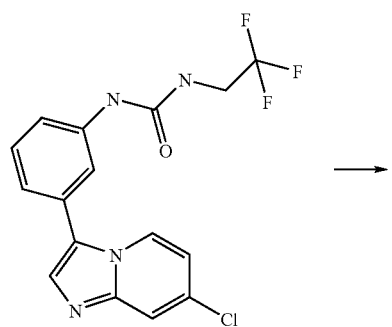

→

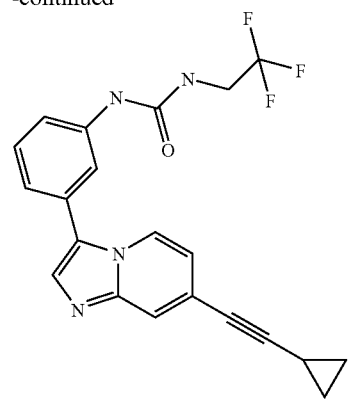

The title compound could be prepared by General Route SGD using commercially available ethynylcyclopropane in step SGD4a.

Example 408B

Example 408B was prepared in accordance with the procedure set out in the Table below.

| Eg. No. | Structure | Chemical Name | Method | NMR Data | MS Data |
|---|---|---|---|---|---|
| 408B | (see structure) | 1-{3-[7-(2-Cyclopropyl-eth-1-ynyl)-imidazo[1,2-a]pyridin-3-yl]-phenyl}-3-(2,2,2-trifluoro-ethyl)-urea | General procedure SGD, steps SGD1-SGD3. SGD4a using Ethynyl-cyclopropane (stage 1 only) | 1H NMR (400 MHz, Me-d3-OD): 8.48 (1H, d), 7.82-7.75 (1H, m), 7.72 (1H, s), 7.57 (1H, s), 7.53-7.44 (1H, m), 7.41 (1H, d), 7.29 (1H, d), 6.91 (1H, dd), 3.95 (2H, q), 1.61-1.50 (1H, m), 1.02-0.89 (2H, m), 0.89-0.77 (2H, m). | [M + H]+ 399 |

Example 409

1-{3-[7-(4,5-Dimethyl-isoxazol-3-yl)-imidazo[1,2-a]pyridin-3-yl]-phenyl}-3-(2,2,2-trifluoro-ethyl)-urea

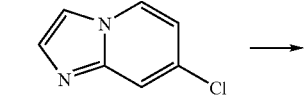

→

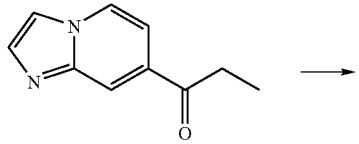

→

-continued

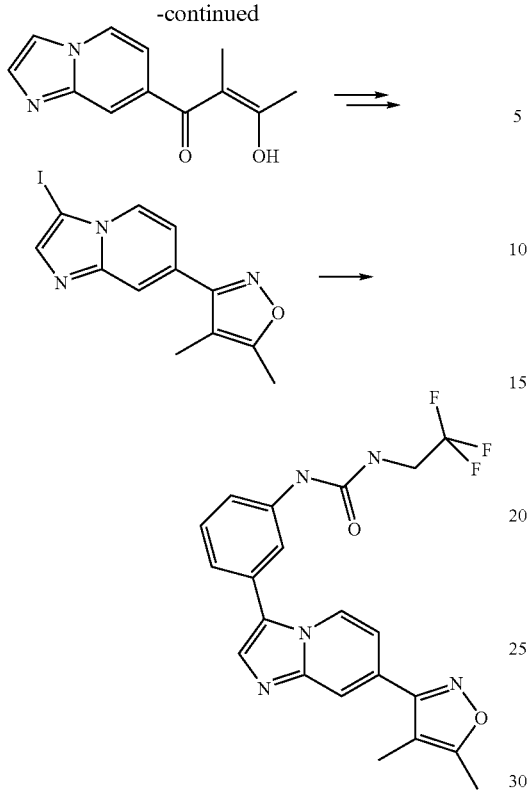

The ethyl ketone could be prepared by a Stille coupling with tributyl(1-ethoxy-1-propenyl) stannane (Synthesis, 2001, (10), 1551) as described in J. Med. Chem., 2007, 50(4), 794. This could be further reacted with base and 2-oxo-propionitrile as described in J. Med. Chem., 2004, 47(4), 792 to prepare the corresponding 1,3-dicarbonyl. Reaction with hydroxylamine as in Tetrahedron, 2006, 62(18), 4430 should generate an oxazole which could be iodinated and reacted under Suzuki coupling conditions as described in General Route B, steps 2 and 3.

Example 410

1-{3-[7-(2,4-Dimethyl-isoxazol-5-yl)-imidazo[1,2-a]pyridin-3-yl]-phenyl}-3-(2,2,2-trifluoro-ethyl)-urea

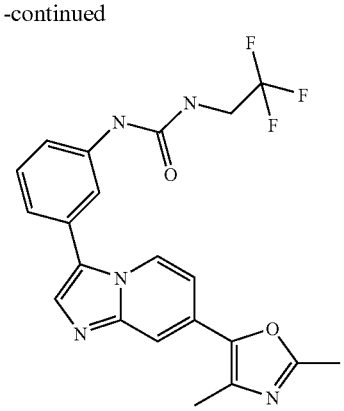

-continued

The aldehyde prepared by Procedure AB could be treated with 2-acetamidoacrylic acid as described in Bioorg. Med. Chem. Lett., 2003, 13, 2059, followed by lithium aluminium hydride reduction to generate the dimethyloxadiazole.

Example 411

1-{3-[7-(2-Methyl-isoxazol-5-yl)-imidazo[1,2-a]pyridin-3-yl]phenyl}-3-(2,2,2-trifluoro-ethyl)-urea

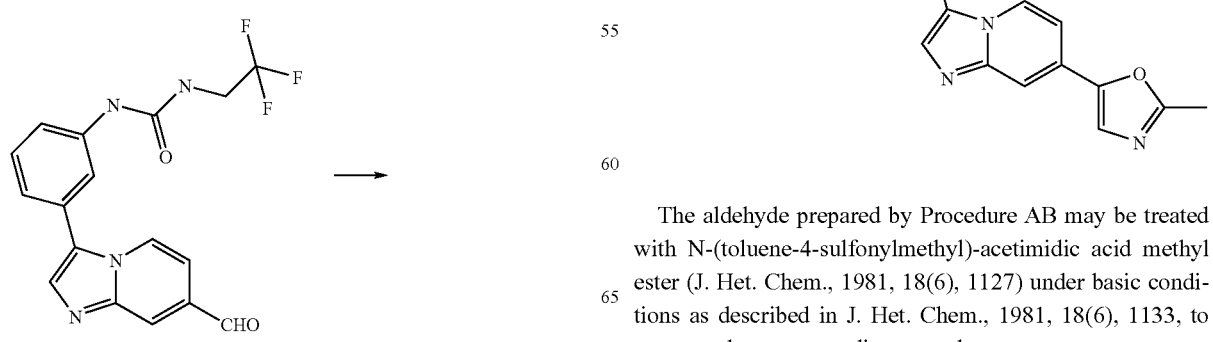

The aldehyde prepared by Procedure AB may be treated with N-(toluene-4-sulfonylmethyl)-acetimidic acid methyl ester (J. Het. Chem., 1981, 18(6), 1127) under basic conditions as described in J. Het. Chem., 1981, 18(6), 1133, to generate the corresponding oxazole.

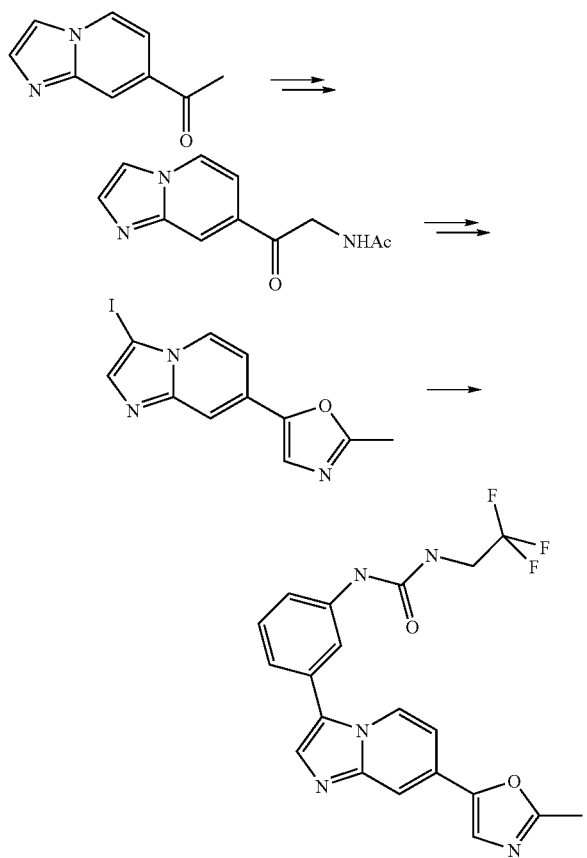

Alternatively, the methyl ketone described above could be brominated under photochemical conditions as described in J. Org. Chem., 2005, 70(7), 2720. The bromide could then be displaced under basic conditions to generate the corresponding acetamide. This may be reacted with Burgess reagent under microwave conditions as exemplified in Synlett, 1999, 1642 to form the oxazole. The compound could then be iodinated and coupled under Suzuki conditions as described in General Route B, steps 2 and 3.

Example 412A 1-(2,2,2-Trifluoro-ethyl)-3-{3-[7-(1,2,5-trimethyl-1H-imidazol-4-yl)-imidazo[1,2,a]pyridine-3-yl]-phenyl}-urea

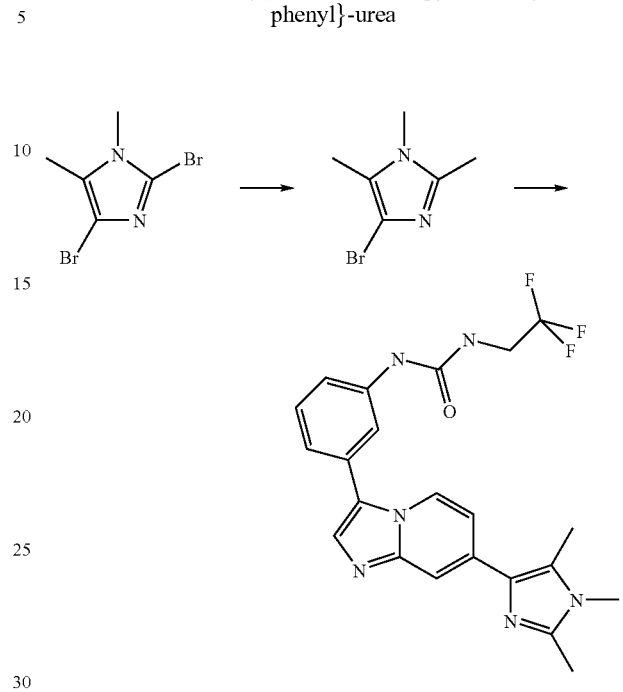

4-Bromo-1,2,5-trimethyl-1H-imidazole may be prepared from 2,4-dibromo-1,5-dimethyl-1H-imidazole by treatment with n-butyl lithium and methyl iodide as described in J. Org. Chem., 1994, 59, 5524. This may be coupled with 1-[3-(7-boronic acid-imidazo[1,2-a]pyridin-3-yl)-phenyl]-3-(2,2,2-trifluoro-ethyl)-urea or 1-{3-[7-(4,4,5,5-tetramethyl-[1,3,2]dioxaborolan-2-yl)-imidazo[1,2-a]pyridin-3-yl]-phenyl}-3-(2,2,2-trifluoro-ethyl)-urea according to procedure E3.

Example 412B

Example 412B was prepared in accordance with the procedure set out in the Table below.

| Eg. No. | Structure | Chemical Name | Method | NMR Data | MS Data |
|---|---|---|---|---|---|
| 412B | 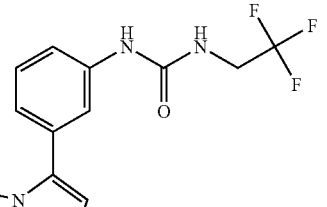 | 1-(2,2,2-Trifluoro-ethyl)-3-{3-[7-(1,2,5-trimethyl-1H-imidazol-4-yl)-imidazo[1,2-a]pyridin-3-yl]-phenyl}-urea hydrochloride | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3c using U10 4-Bromo-1,2,5-trimethyl-1H-imidazole. Procedure J1 | 1H NMR (400 MHz, DMSO-d6): 9.50 (1H, s), 8.84 (1H, d), 8.38 (1H, s), 8.21 (1H, s), 7.90 (1H, s), 7.69 (1H, d), 7.58-7.49 (2H, m), 7.32-7.29 (1H, m), 7.15 (1H, t), 4.00-3.90 (2H, m), 3.71 (3H, s), 2.69 (3H, s), 2.55 (3H, s). | [M + H]+ 443 |

Example 413

1-{3-[7-(4-Methyl-5-oxo-4,5-dihydro-[1,3,4]oxadiazol-2-yl)-imidazo[1,2-a]pyridin-3-yl]-phenyl}-3-(2,2,2-trifluoro-ethyl)-urea

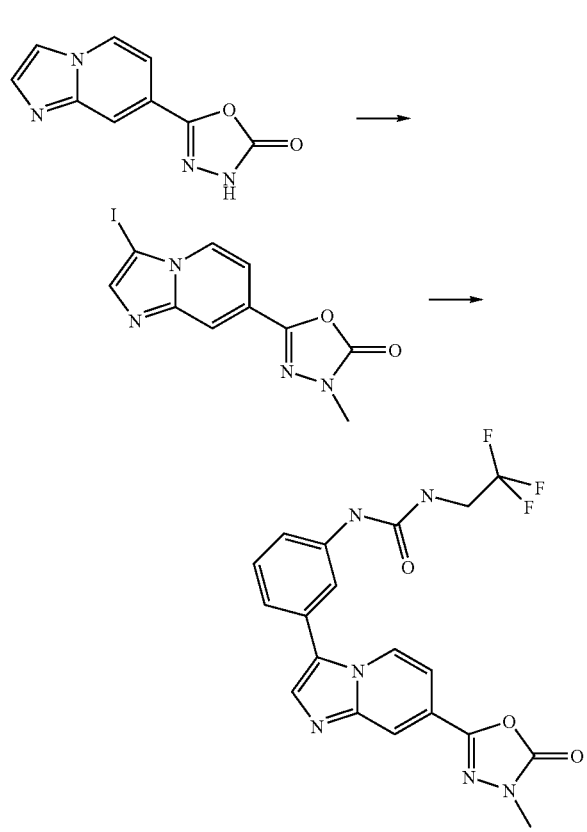

The oxadiazolone may be prepared as described in Procedure AP (Example 377) and could be methylated under Mitsunobu conditions. Iodination and Suzuki coupling using the procedures described in General Route B, steps 2 and 3, should generate the desired product.

Example 414A

1-{3-[7-(3,5-Dimethyl-[1,2,4]triazol-1-yl)-imidazo[1,2-a]pyridin-3-yl]-phenyl}-3-(2,2,2-trifluoro-ethyl)-urea

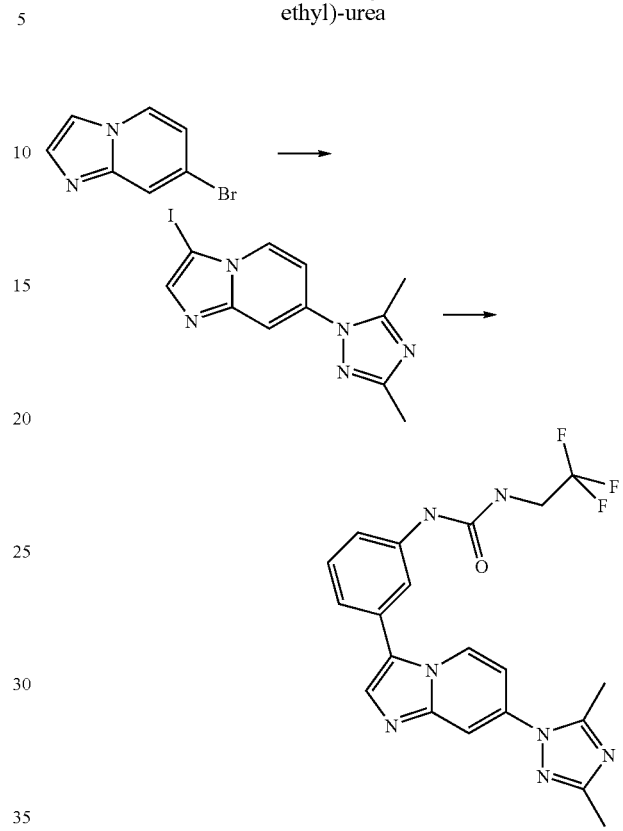

7-Bromo-imidazo[1,2-a]pyridine can be coupled with 3,5-dimethyl-[1,2,4]-triazole using catalytic copper (WO 02085838). The product can then be iodinated and coupled under Suzuki conditions as described in General Route B, steps 2 and 3.

Example 414B

Example 414B was prepared in accordance with the procedure set out in the Table below.

| Eg. No. | Structure | Chemical Name | Method | NMR Data | MS Data |
|---|---|---|---|---|---|
| 414B | 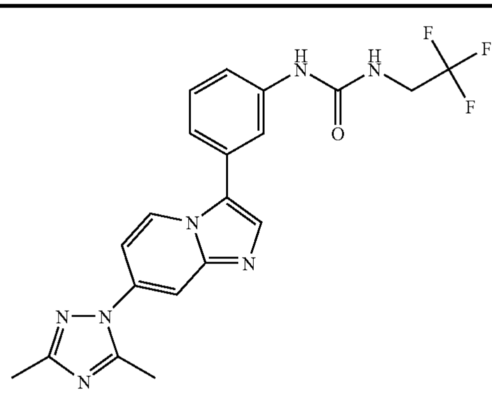 | 1-{3-[7-(3,5-Dimethyl-[1,2,4]triazol-1-yl)-imidazo[1,2-a]pyridin-3-yl]-phenyl}-3-(2,2,2-trifluoro-ethyl)-urea | General Route AS. Step 1 using 3,5-Dimethyl-1H-[1,2,4]triazole. Step 2. Step 3 using I6 [3-(4,4,5,5-Tetramethyl-[1,3,2]dioxaborolan-2-yl)-phenyl]-3-(2,2,2-trifluoro-ethyl)-urea. | 1H NMR (400 MHz, DMSO-d6): 8.97 (1H, s), 8.66 (1H, d), 7.91 (1H, d), 7.85 (1H, s), 7.76 (1H, s), 7.53-7.43 (2H, m), 7.32-7.26 (1H, m), 7.24 (1H, dd), 6.86 (1H, t), 4.01-3.89 (2H, m), 2.57 (3H, s), 2.31 (3H, s). | [M + H]+ 430 |

Example 415

1-{3-[7-(3-Methyl-[1,2,4]triazol-1-yl)-imidazo[1,2-a]pyridin-3-yl]-phenyl}-3-(2,2,2-trifluoro-ethyl)-urea

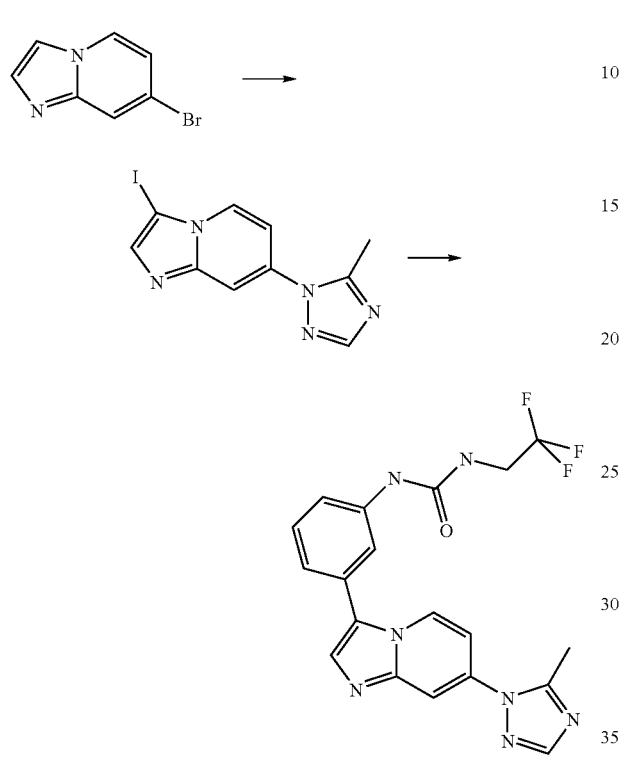

7-Bromo-imidazo[1,2-a]pyridine can be coupled with 3-methyl-[1,2,4]-triazole using catalytic copper (WO 02085838). The product can then be iodinated and coupled under Suzuki conditions as described in General Route B, steps 2 and 3. Regioisomers may be separated by column chromatography.

Example 416A

1-{3-[7-(4-Methyl-imidazol-1-yl)-imidazo[1,2-a]pyridin-3-yl]-phenyl}-3-(2,2,2-trifluoro-ethyl)-urea

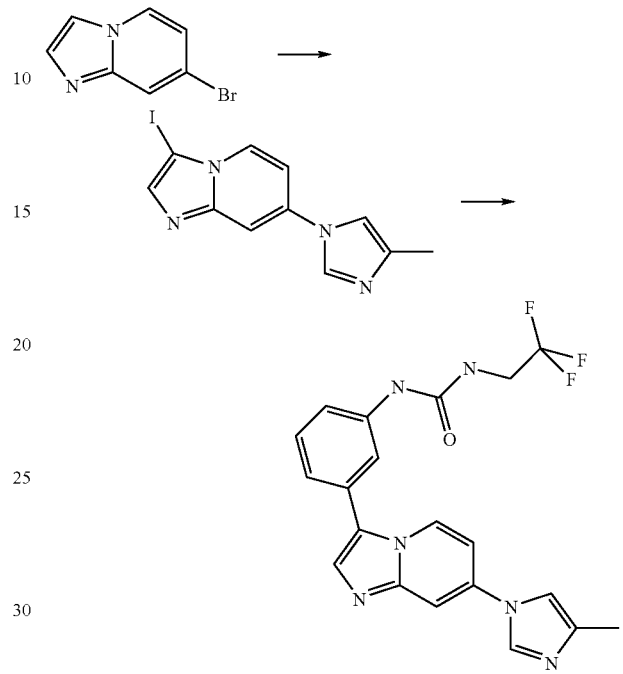

7-Bromo-imidazo[1,2-a]pyridine can be coupled with 4-methyl-1H-imidazole using catalytic copper (WO 02085838). The product can then be iodinated and coupled under Suzuki conditions as described in General Route B, steps 2 and 3. Regioisomers may be separated by column chromatography.

Example 416B

Example 416B was prepared in accordance with the procedure set out in the Table below.

| Eg. No. | Structure | Chemical Name | Method | NMR Data | MS Data |
|---|---|---|---|---|---|
| 416B | 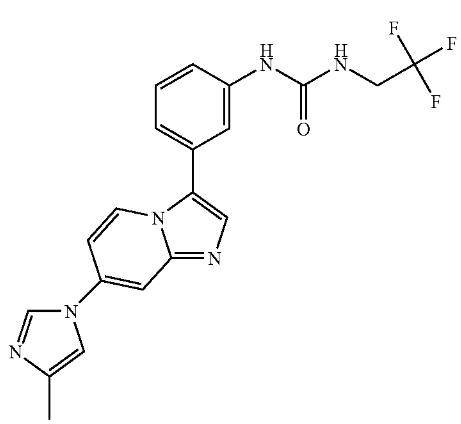 [SMILES: Cc1cn(-c2ccn3c(-c4cccc(NC(=O)NCC(F)(F)F)c4)cnc3c2)cn1] | 1-{3-[7-(4-Methyl-imidazol-1-yl)-imidazo[1,2-a]pyridin-3-yl]-phenyl}-3-(2,2,2-trifluoro-ethyl)-urea. | General Route AS. Step 1 using 4-methylimidazole. Step 2. Step 3 using I6 [3-(4,4,5,5-Tetramethyl-[1,3,2]dioxaborolan-2-yl)-phenyl]-3-(2,2,2-trifluoro-ethyl)-urea. | 1H NMR (400 MHz, DMSO-d6): 8.95 (1H, s), 8.64 (1H, d), 8.38 (1H, d), 7.97 (1H, d), (1H, s), 7.49-7.37 (3H, m), 7.30-7.22 (1H, m), 6.85 (1H, t), 4.01-3.89 (2H, m), 2.19 (3H, s). | [M + H]+ 415 |

Example 417

1-{3-[7-(3,5-Dimethylpyrazol-1-yl)-imidazo[1,2-a]pyridin-3-yl]-phenyl}-3-(2,2,2-trifluoro-ethyl)-urea

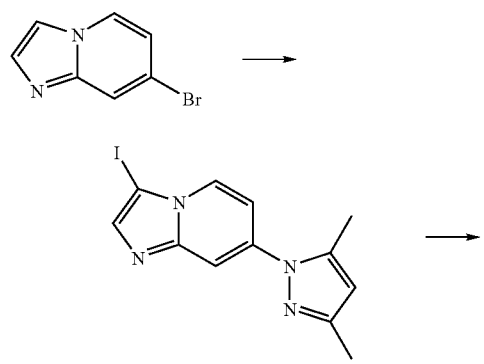

7-Bromo-imidazo[1,2-a]pyridine can be coupled with 3,5-dimethyl-[1,2,4]-triazole using catalytic copper (WO 02085838). The product can then be iodinated and coupled under Suzuki conditions as described in General Route B, steps 2 and 3.

Example 418

1-{3-[7-(5-Methyl-pyrazol-1-yl)-imidazo[1,2-a]pyridin-3-yl]-phenyl}-3-(2,2,2-trifluoro-ethyl)-urea

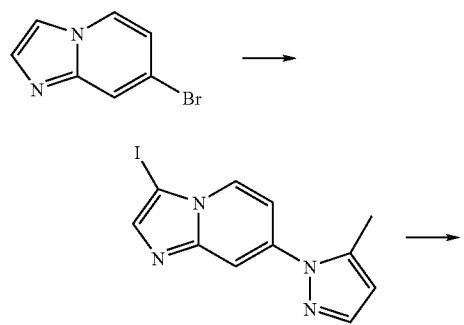

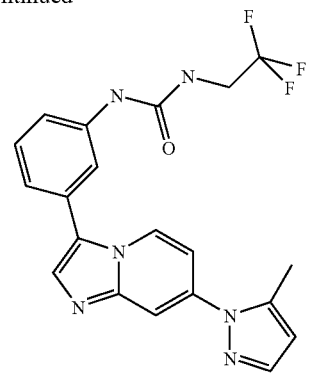

7-Bromo-imidazo[1,2-a]pyridine can be coupled with 3-methyl-[1,2,4]-triazole using catalytic copper (WO 02085838). The product can then be iodinated and coupled under Suzuki conditions as described in General Route B, steps 2 and 3. Regioisomers may be separated by column chromatography.

Example 419

1-(2,2,2-Trifluoro-ethyl)-3-{3-[7-(1,4,5-trimethyl-1H-pyrazol-3-yl)-imidazo[1,2-a]pyridin-3-yl]-phenyl}-urea

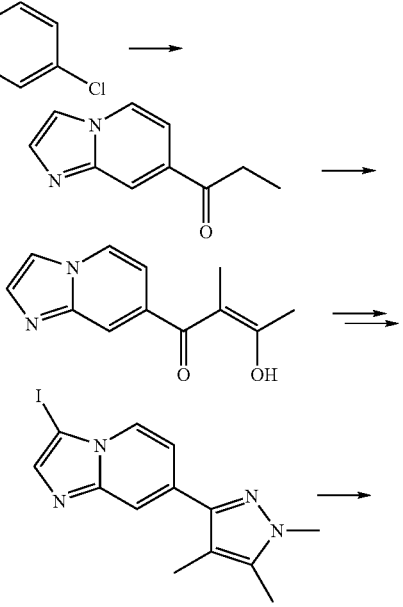

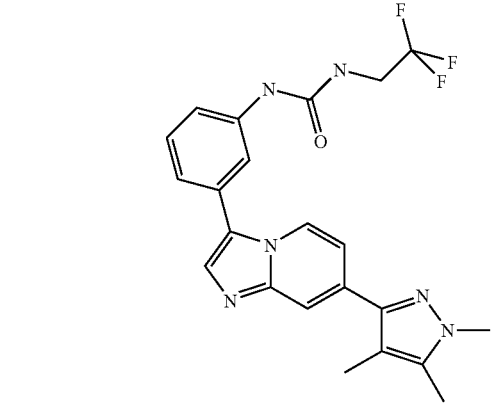

The ethyl ketone could be prepared by a Stille coupling with tributyl(1-ethoxy-1-propenyl) stannane (Synthesis, 2001, (10), 1551) as described in J. Med. Chem., 2007, 50(4), 794. This could be further reacted with base and 2-oxo-propionitrile as described in J. Med. Chem., 2004, 47(4), 792 to prepare the corresponding 1,3-dicarbonyl compound. Reaction with hydrazine as in Org. Proc. Res. Dev., 2004, 28 should generate an pyrazole which could be methylated as described in Tetrahedron, 1982, 38(19), 2933. The compound could then be iodinated and reacted under Suzuki coupling conditions as described in General Route B, steps 2 and 3.

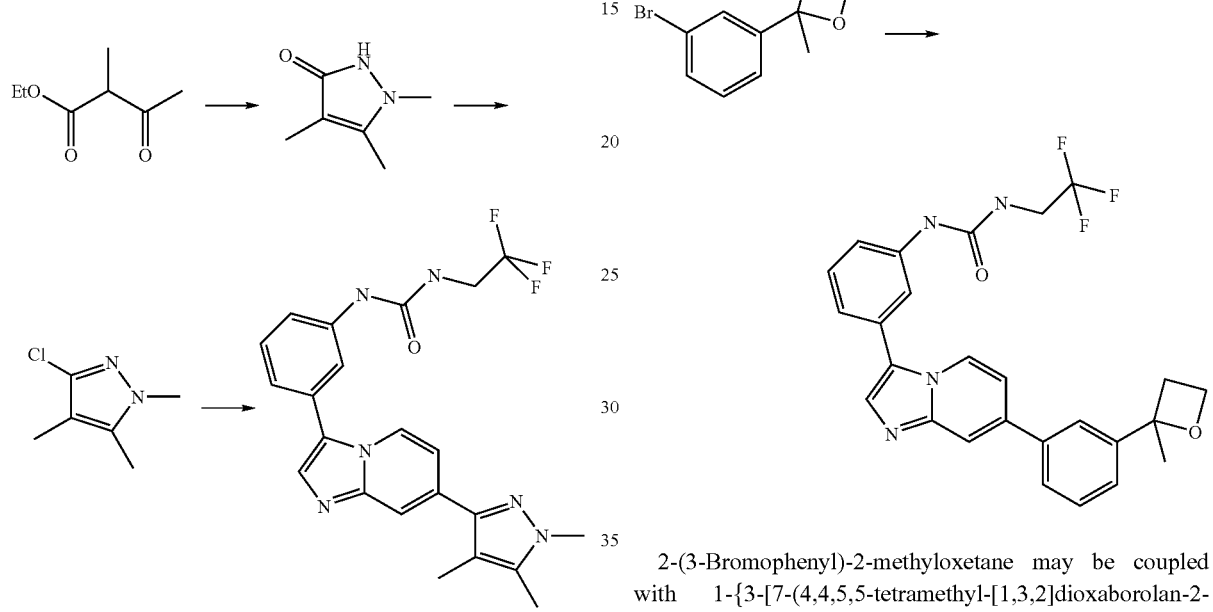

Alternatively, 1,4,5-trimethyl-1,2-dihydro-pyrazol-3-one could be synthesized as described in Organometallics, 2004, 6084. This could then be converted to the corresponding chloride using phosphorus oxychloride and finally may be coupled with 1-[-{3-(-[7-boronic acid-(4,4,5,5-tetramethyl-[1,3,2]dioxaborolan-2-yl)-imidazo[1,2-a]pyridin-3-yl)-]-phenyl]-}-3-(2,2,2-trifluoro-ethyl)-urea according to procedure E3. Regioisomers may be separated by column chromatography.

Example 420

1-(3-{7-[3-(2-Methyl-oxetan-2-yl)-phenyl]-imidazo[1,2-a]pyridin-3-yl}-phenyl)-3-(2,2,2-trifluoro-ethyl)-urea

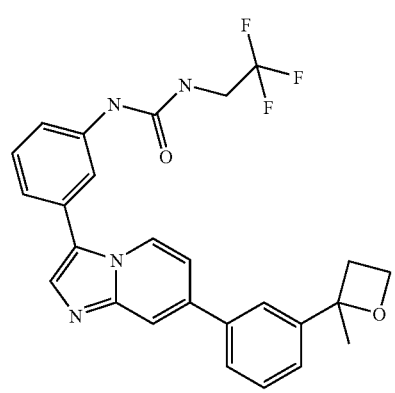

2-(3-Bromophenyl)-2-methyloxetane may be coupled with 1-{3-[7-(4,4,5,5-tetramethyl-[1,3,2]dioxaborolan-2-yl)-imidazo[1,2-a]pyridin-3-yl]-phenyl}-3-(2,2,2-trifluoro-ethyl)-urea according to procedure E3.

Examples 421 to 422

By following the methods described above, the compounds of Examples 421 to 422 set out in the Table below were prepared.

| Eg. No. | Structure | Chemical Name | Method | NMR Data | MS Data |
|---|---|---|---|---|---|
| 421 | 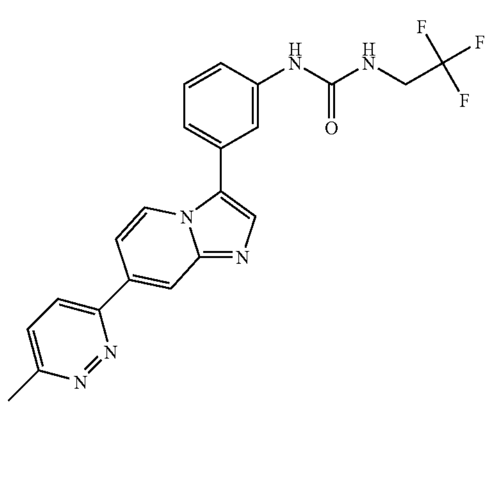 [SMILES: Cc1ccc(-c2ccn3c(-c4cccc(NC(=O)NCC(F)(F)F)c4)cnc3c2)nn1] | 1-{3-[7-(6-Methyl-pyridazin-3-yl)-imidazo[1,2-a]pyridin-3-yl]-phenyl}-3-(2,2,2-trifluoro-ethyl)-urea hydrochloride | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3b using 3-chloro-6-methylpyridazine. Procedure J1. | 1H NMR (400 MHz, DMSO-d6): 9.34 (1H, s), 8.93 (1H, d), 8.72 (1H, s), 8.51 (1H, d), 8.47 (1H, s), 8.26 (1H, dd), 7.93 (1H, s), 7.85 (1H, d), 7.61-7.51 (2H, m), 7.39-7.31 (1H, m), 7.11-7.02 (1H, m), 4.02-3.90 (2H, m), 2.75 (3H, s). | [M + H]+ 427 |

-continued

| Eg. No. | Structure | Chemical Name | Method | NMR Data | MS Data |
|---|---|---|---|---|---|
| 422 | 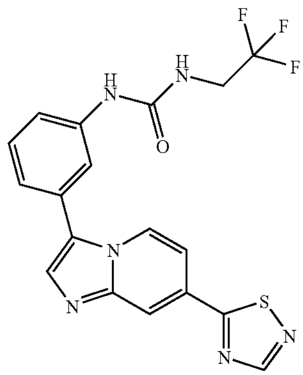 [SMILES: O=C(NCC(F)(F)F)Nc1cccc(-c2cnc3cc(-c4ncns4)ccn23)c1] | 1-[3-(7-[1,2,4]Thia-diazol-5-yl-imidazo[1,2-a]pyridin-3-yl)-phenyl]-3-(2,2,2-trifluoro-ethyl)-urea hydrochloride | General route A steps A1-A3, procedure A3b using I6 [3-(4,4,5,5-Tetramethyl-[1,3,2]dioxaborolan-2-yl)-phenyl]-3-(2,2,2-trifluoro-ethyl)-urea, procedure E2 and procedure E3c using U11 3-Bromo-[1,2,4]-thiadiazole. Procedure J1 | 1H NMR (400 MHz, DMSO-d6): 9.26 (1H, s), 9.13 (1H, s), 8.85 (1H, d), 8.62 (1H, s), 8.33 (1H, s), 7.87 (2H, d), 7.59-7.48 (2H, m), 7.37-7.28 (1H, m), 7.01 (1H, t), 4.01-3.90 (2H, m). | [M + H]+ 419 |

Biological Assays

FGFR3 and PDGFR In Vitro Kinase Inhibitory Activity Assays

Enzymes (from Upstate) were prepared at 2× final concentration in 1× kinase assay buffer (as described below). Enzymes were then incubated with test compounds, biotinylated Flt3 substrate (biotin—DNEYFYV) (Cell Signalling Technology Inc.) and ATP. The reaction was allowed to proceed for 3 hours (FGFR3) or 2.5 hrs (PDGFR-beta) at room temperature on a plate shaker at 900 rpm before being stopped with 20 μl of 35 mM EDTA, pH 8 (FGFR3) or 55 mM EDTA, pH 8 (PDGFR-beta). Twenty μl of 5× detection mix (50 mM HEPES pH 7.5, 0.1% BSA, 2 nM Eu-anti-pY (PY20) (PerkinElmer) 15 nM SA-XL665 (Cisbio) for FGFR3 and 50 mM HEPES, pH 7.5, 0.5 M KF, 0.1% BSA, 11.34 nM Eu-anti-pY (PT66) (PerkinElmer), 94 nM SA-XL665 (Cisbio) for PDGFR-beta) was then added to each well and the plate sealed and incubated at room temperature for one hour on a plate shaker at 900 rpm. The plate was then read on a Packard Fusion plate reader in TRF mode.

| Enzyme | 1 × Assay Buffer | Flt3 substrate concentration | ATP concentration |
|---|---|---|---|
| FGFR3 | A | 0.125 μM | 8 μM |
| PDGFR-beta | B | 0.15 μM | 30 μM |

Kinase Assay buffers were:

A: 50 mM HEPES pH 7.5, 6 mM MnCl$_2$, 1 mM DTT, 0.1% TritonX-100

B: 20 mM MOPS pH 7.0, 10 mM MnCl$_2$, 0.01% Triton X-100, 1 mM DTT, 0.1 mM Sodium orthovanadate Examples 1-74, 76-191, 193-401, 407, 412, 414, and 416 have IC50 values less than 10 μM or provide at least 50% inhibition of the FGFR3 activity at a concentration of 10 μM. Preferred compounds of the invention (for example Examples 1-25, 27-29, 31-67, 70, 72-74, 77-97, 100, 101, 103-105, 107-109, 111-115, 117-131, 133-156, 158-166, 168-172, 174-191, 193-254, 256-342, 344-402, 407, 412, 414, 416 and 421-422) have IC50 values of less than 1 μM or provide at least 50% inhibition of the FGFR3 activity at a concentration of 1 μM in the FGFR3 assay.

VEGFR2 In Vitro Kinase Inhibitory Activity Assay

Assay reactions containing VEGFR2 enzyme (purchased from Upstate), and 250 μM Poly (Glu,Tyr) 4:1 substrate (Cis-Bio) in 50 mM HEPES, pH 7.5, 6 mM MnCl2, 1 mM DTT, 0.01% TritonX-100, 5 μM ATP (2.8 Ci/mmol) were set up in the presence of compound. Reactions were stopped after 15 minutes by adding an excess of phosphoric acid. The reaction mixture was then transferred to a Millipore MAPH filter plate where the peptide binds and the unused ATP is washed away. After washing, scintillant was added and the incorporated activity measured by scintillation counting on a Packard Topcount.

FGFR1, FGFR2, FGFR4, VEGFR1 and VEGFR3 In Vitro Kinase Inhibitory Activity Assays The inhibitory activity against FGFR1, FGFR2, FGFR4, VEGFR1 and VEGFR3 can be determined at Upstate Discovery Ltd. Enzymes were prepared at 10× final concentration in enzyme buffer (20 mM MOPS, pH 7.0, 1 mM EDTA, 0.1% B-mercaptoethanol, 0.01% Brij-35, 5% glycerol, 1 mg/ml BSA). Enzymes were then incubated in assay buffer with various substrates and $^{33}$P-ATP (~500 cpm/pmol) as described in the table.

The reaction was initiated by the addition of Mg/ATP. The reaction was allowed to proceed for 40 minutes at room temperature before being stopped with 5 μl of a 3% phosphoric acid solution. Ten μl of the reaction mix was transferred to either a filtermatA or P30 filtermat and washed three times in 75 mM phosphoric acid and once in methanol before being dried for scintillation counting.

Compounds were tested at the concentrations detailed below in duplicate against all kinases and the percent activity compared to control was calculated. Where inhibition was high an IC$_{50}$ was determined.

| Enzyme | Assay Buffer | Substrate | ATP Concentration (μM) |
|---|---|---|---|
| FGFR1 | A | 250 μM KKKSPGEYVNIEFG | 200 μM |
| FGFR2 | B | 0.1 mg/ml poly(Glu, Tyr) 4:1 | 90 μM |
| FGFR4 | C | 0.1 mg/ml poly(Glu, Tyr) 4:1 | 155 μM |
| VEGFR1 | A | 250 μM KKKSPGEYVNIEFG | 200 μM |
| VEGFR3 | A | 500 μM GGEEEEYFELVKKKK | 200 μM |

Enzyme buffer A: 8 mM MOPS, pH 7.0, 0.2 mM EDTA, 10 mM MgAcetate
Enzyme buffer B: 8 mM MOPS, pH 7.0, 0.2 mM EDTA, 2.5 mM MnCl2, 10 mM MgAcetate
Enzyme buffer C: 8 mM Mops, pH 7.0, 0.2 mM EDTA, 10 mM MnCl2, 10 mM MgAcetate.

Cell-Based pERK ELISA Method

LP-1 or JIM-1 multiple myeloma cells were seeded in 96 well plates at 1×10$^6$ cells/ml in 200 ul per well in serum free media. HUVEC cells were seeded at 2.5×10$^5$ cells/ml and allowed to recover for 24 h prior to transfer to serum free media. Cells were incubated for 16 h at 37° C. prior to the addition of a test compound for 30 minutes. Test compounds were administered at a 0.1% final DMSO concentration. Following this 30 minute incubation a FGF-1/Heparin (FGF-1 at 100 ng/ml final and Heparin at 100 ug/ml) mixture or VEGF$^{165}$ (100 ug/ml) was added to each of the wells for a further 5 minutes. The media was removed and 50 ul ERK ELISA lysis buffer (R and D Systems DuoSet ELISA for pERK and Total ERK #DYC-1940E, DYC-1018E) added. ELISA plates and standards were prepared according o the standard DuoSet protocols and the relative amounts of pERK to total ERK in each sample calculated according to the standard curve.

In particular, compounds of the invention were tested against the LP-1 cell line (DSMZ no.: ACC 41) derived from human multiple myeloma. Many compounds of the invention were found to have IC50 values of less than 20 µM in this assay and some compounds (for example Examples 2, 5, 6, 7, 8, 9, 10, 11, 15, 16, 28, 29, 35, 36, 39, 43, 45, 49, 51, 56, 57, 58, 59, 62, 64, 65, 66, 67, 78, 79, 80, 81, 82, 83, 94, 95, 103, 104, 107, 108, 109, 111, 113, 114, 115, 123, 127, 128, 134, 135, 137, 140, 141, 142, 143, 144, 149, 150, 151, 155, 158, 159, 164, 165, 169, 174, 175, 177, 179, 180, 183, 184, 189, 193, 197, 200, 201, 202, 203, 204, 206, 208, 211, 212, 214, 216, 217, 218, 219, 220, 221, 225, 227, 228, 229, 230, 233, 234, 238, 239, 240, 243, 244, 245, 246, 247, 249, 250, 251, 252, 253, 254, 256, 257, 258, 260, 261, 262, 263, 264, 266, 267, 268, 269, 270, 271, 273, 274, 276, 278, 279, 280, 281, 283, 284, 285-294, 296, 298-305, 307, 309-312, 315-320, 322-327, 329, 330, 331, 332, 334, 336, 337, 340, 341, 344, 345, 346, 348, 349, 351, 352, 354-375, 378-381, 383-394, 396-402, 412, 414, 416 and 421) have IC50 values of less than 1 µM or provide at least 50% inhibition at a concentration of 1 µM.

HUVEC Cell Based Selectivity Assays

HUVEC cells were seeded in 6 well plates at 1×10$^6$ cells/well and allowed to recover for 24 h. They were transferred to serum free media for 16 hours prior to treatment with test compound for 30 minutes in 0.1% DMSO final. Following compound incubation FGF-1 (100 ng/ml) and Heparin (100 ug/ml) or VEGF$^{165}$ (100 ng/ml) were added for 5 minutes. Media was removed, cells washed with ice-cold PBS and lysed in 100 ul TG lysis buffer (20 mM Tris, 130 nM NaCl, 1% Triton-X-100, 10% Glycerol, protease and phosphatase inhibitors, pH 7.5). Samples containing equivalent amounts of protein were made up with LDS sample buffer and run on SDS PAGE followed by western blotting for a number of downstream VEGFR and FGFR pathway targets including phospho-FGFR3, phospho-VEGFR2 and phospho-ERK1/2.

In Vivo Models of Hypertension

A number of animal models exist to measure the potential hypertensive effects of small molecule inhibitors. They can be classified into two main types; indirect and direct measurements. The most common indirect method is the cuff technique. Such methods have the advantages of being non-invasive and as such can be applied to a larger group of experimental animals however the process allows only intermittent sampling of blood pressure and requires the animal to be restrained in some way. Application of restraint can stress the animal and means that changes in blood pressure attributable to a specific drug effect can be hard to pick up.

Direct methodologies include those that make use of radio telemetry technology or via indwelling catheters connected to externally mounted transducers. Such methods require a high level of technical expertise for the initial surgery involved in implantation and costs involved are high. However a key advantage is that they allow continuous monitoring of blood pressure without restraint over the time period of the experiment. These methods are reviewed in Kurz et al (2005), Hypertension. 45, 299-310.

Results

Biological data from the FGFR3 in vitro kinase inhibitory activity assay and cell-based pERK ELISA method described above for the examples identified, is shown below.

| Example Number | FGFR3 IC50 or % inhibition (µM) | LP-1 pERK ELISA (µM) |
|---|---|---|
| 59 | 0.0033 | 0.0021 |
| 329 | 0.0158 | 0.143 |
| 310 | 0.000780 | 0.00420 |
| 354 | 0.0222 | 0.0157 |
| 359 | 0.0164 | 0.0330 |
| 374 | 64% at 0.001 µM | 0.00840 |
| 375 | 0.000490 | 0.0220 |
| 378 | 0.000790 | 0.0160 |
| 384 | 0.00190 | 0.0190 |
| 396 | 0.0183 | 0.0650 |
| 399 | 0.00474 | 0.0220 |
| 416 | 0.00218 | 0.0720 |
| 401 | 0.000704 | 0.100 |
| 412 | 0.00124 | 0.0780 |
| 402 | 0.00160 | 0.940 |
| 421 | 0.00260 | 0.0450 |
| 422 | 0.00330 | |
| 407 | 0.0310 | |

The invention claimed is:

1. A compound of formula (Id):

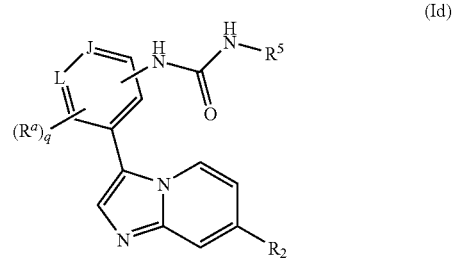

wherein

J and L are independently selected from carbon and nitrogen;

R$^5$ represents hydrogen, C$_{1-6}$ alkyl, C$_{2-6}$ alkenyl, C$_{2-6}$ alkynyl, alkanol, C$_{1-6}$ alkanol, haloC$_{1-6}$ alkyl, —(CH$_2$)$_n$—NR$^x$R$^y$, —(CH$_2$)$_s$—COOR$^z$, or —(CH$_2$)$_n$—O—(CH$_2$)$_m$—OH, wherein said C$_{1-6}$ alkyl, C$_{2-6}$ alkenyl, and C$_{2-6}$ alkynyl groups may be optionally substituted by one or more R$^a$ groups;

R$^x$, R$^y$ and R$^z$ independently represent hydrogen, C$_{1-6}$ alkyl, C$_{2-6}$ alkenyl, C$_{2-6}$ alkynyl, C$_{1-6}$ alkanol, —COOC$_{1-6}$ alkyl, hydroxy, C$_{1-6}$ alkoxy, haloC$_{1-6}$ alkyl, —CO—(CH$_2$)$_n$—C$_{1-6}$ alkoxy, C$_{1-6}$ alkylamino, C$_{3-8}$ cycloalkyl or C$_{3-8}$ cycloalkenyl;

R$^2$ and R$^6$ independently represent halogen, hydrogen, C$_{1-6}$ alkyl, C$_{1-6}$ alkoxy, C$_{2-6}$ alkenyl, C$_{2-6}$ alkynyl, —C≡N, C$_{3-8}$ cycloalkyl, C$_{3-8}$ cycloalkenyl, —NHSO$_2$R$^w$, —CH=N—OR$^w$, an aryl or heterocyclyl group wherein said aryl and heterocyclyl groups may be optionally substituted by one or more R$^b$ groups, and said C$_{1-6}$ alkyl, C$_{2-6}$ alkenyl, and C$_{2-6}$ alkynyl may be optionally substituted by one or more $R^{b'}$ groups, provided that $R^2$ and $R^6$ do not both represent hydrogen;

$R^w$ represents hydrogen or $C_{1-6}$ alkyl;

$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —SO—$R^x$, —$SO_2$—$R^x$, —$COR^x$, —$(CR^xR^y)_s$—$COOR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups;

q represents an integer from 0 to 3;

$R^b$ represents an $R^a$ group or a —Y-carbocyclyl or —Z-heterocyclyl group wherein said carbocyclyl and heterocyclyl groups may be optionally substituted by one or more $R^a$ groups;

Y and Z independently represent a bond, —CO—$(CH_2)_s$—, —COO—, —$(CH_2)_n$—, —$NR^x$—$(CH_2)_n$—, —$(CH_2)_n$—$NR^x$—, —$CONR^x$—, —$NR^xCO$—, —$SO_2NR^x$—, —$NR^xSO_2$—, —$NR^xCONR^y$—, —$NR^xCSNR^y$—, —O—$(CH_2)_s$—, —$(CH_2)_s$—O—, S—, —SO— or —$(CH_2)_s$—$SO_2$—;

$R^{b'}$ represents an $R^{a'}$ group or a —Y-carbocyclyl or —Z-heterocyclyl group wherein said carbocyclyl and heterocyclyl groups may be optionally substituted by one or more $R^a$ groups;

$R^{a'}$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups;

m and n independently represent an integer from 1-4;

s and t independently represent an integer from 0-4;

or a pharmaceutically acceptable salt or solvate thereof, with the proviso that the compound of formula (Id) is not:

N-{2-fluoro-4-[6-(1-trityl-1H-4-pyrazolyl)imidazo[1,2-a]pyridine-3-yl]phenyl}-N'-isopropyl urea; or N-{2-fluoro-4-[6-(1H-4-pyrazolyl)imidazo[1,2-a]pyridin-3-yl]phenyl}-N'-isopropylurea.

2. A compound as defined in claim 1, wherein $R^5$ represents hydrogen, $C_{1-6}$ alkyl, $C_{1-6}$ alkanol, —$(CH_2)_n$—$NR^xR^y$, or halo$C_{1-6}$ alkyl;

$R^x$, $R^y$ and $R^z$ independently represent hydrogen, $C_{1-6}$ alkyl, $C_{1-6}$ alkanol, hydroxy, $C_{1-6}$ alkoxy, halo$C_{1-6}$ alkyl or —CO—$(CH_2)_n$—$C_{1-6}$ alkoxy;

$R^2$ represents an aryl or heterocyclyl group optionally substituted by one or more $R^b$ groups;

$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —O—$(CH_2)_n$—$OR^x$, halo$C_{1-6}$ alkyl, halo$C_{1-6}$ alkoxy, $C_{1-6}$ alkanol, =O, =S, nitro, —$(CH_2)_s$—CN, —S—$R^x$, —SO—$R^x$, —$SO_2$—$R^x$, —$COR^x$, —$(CR^xR^y)_s$—$COOR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups;

$R^b$ represents a —Y-aryl or —Z-heterocyclyl group wherein said aryl and heterocyclyl groups may be optionally substituted by one or more $R^a$ groups;

Y and Z independently represent a bond, CO, —$(CH_2)_n$—, —$NR^x$—$(CH_2)_n$—, —O— or —O—$(CH_2)_s$—;

aryl represents a carbocyclic ring; and heterocyclyl represents a heterocyclic ring, or a pharmaceutically acceptable salt or solvate thereof.

3. A compound as defined in claim 1 wherein A represents a phenyl or pyridyl group optionally substituted by one or more $R^a$ groups, or a pharmaceutically acceptable salt or solvate thereof.

4. A compound as defined in claim 1 wherein A represents phenyl or pyridyl substituted by the —$NHCONHR^5$ group at the 5-position and further optionally substituted by a single $R^a$ group at the 3-position, or a pharmaceutically acceptable salt or solvate thereof.

5. A compound as defined in claim 1 wherein $R^5$ represents —$CH_2CF_3$ or —$CH_2CH_3$, or a pharmaceutically acceptable salt or solvate thereof.

6. A compound as defined in claim 1 wherein $R^2$ represents an aryl or heterocyclyl group optionally substituted by one or more $R^a$ groups, or a pharmaceutically acceptable salt or solvate thereof.

7. A compound as defined in claim 1 wherein $R^2$ represents an aryl group optionally substituted by a halogen, —Z-heterocyclyl group or —$(CR^xR^y)_s$—$COOR^z$ wherein said heterocyclyl group may be optionally substituted by a $C_{1-6}$ alkyl or —$(CR^xR^y)_s$—$COOR^z$ group, or $R^2$ represents a heterocyclyl group optionally substituted by a =O, =S, halogen, $C_{1-6}$ alkyl, halo$C_{1-6}$ alkyl, $C_{3-8}$ cycloalkyl, —$(CH_2)_s$—$NR^xR^y$, —$OR^x$, —$(CH_2)_n$—O—$C_{1-6}$ alkyl, —$COR^x$, —$(CR^xR^y)_s$—$COOR^z$, —S—$R^x$, —$SO_2$—$R^x$, —$(CH_2)_s$—$NR^xR^y$, —$(CH_2)_s$—$SO_2NR^xR^y$ or $C_{1-6}$ alkanol groups, or a pharmaceutically acceptable salt or solvate thereof.

8. A compound as defined in claim 1 wherein $R^2$ represents oxazole, oxadiazole, triazole, tetrazole, thiadiazole or oxathiadiazole optionally substituted by one or more methyl, ethyl or —S-methyl groups, or a pharmaceutically acceptable salt or solvate thereof.

9. A compound as defined in claim 1 wherein Y and Z independently represent a bond, CO, —$CH_2$—, —$(CH_2)_2$—, —$(CH_2)_3$ or —O—, or a pharmaceutically acceptable salt or solvate thereof.

10. A compound as defined in claim 1 which is a compound selected from:

1-{3-[7-(4-Fluoro-phenyl)-imidazo[1,2-a]pyridin-3-yl]-phenyl}-3-(2,2,2-trifluoro-ethyl)-urea, 1-{3-[7-(5-Methyl-[1,3,4]-thiadiazol-2-yl)-imidazo[1,2-a]pyridin-3-yl]-phenyl}-3-(2,2,2-trifluoro-ethyl)-urea, 1-{3-[7-(5-Methyl-[1,3,4]oxadiazol-2-yl)-imidazo[1,2-a]pyridin-3-yl]-phenyl}-3-(2,2,2-trifluoro-ethyl)-urea, 1-{3-[7-(5-Methylsulfanyl-[1,3,4] oxadiazol-2-yl)-imidazo[1,2-a]pyridin-3-yl]-phenyl}-3-(2,2,2-trifluoro-ethyl)-urea, 1-{3-[7-(2-Methyl-2H-tetrazol-5-yl)-imidazo[1,2-a]pyridin-3-yl]-phenyl}-3-(2,2,2-trifluoro-ethyl)-urea, 1-{3-[7-(1,5-Dimethyl-1H-imidazol-4-yl)-imidazo[1,2-a]pyridin-3-yl]-phenyl}-3-(2,2,2-trifluoro-ethyl)-urea, 1-{3-[7-(1-Methyl-1H-imidazol-4-yl)-imidazo[1,2-a]pyridin-3-yl]-phenyl}-3-(2,2,2-trifluoro-ethyl)-urea, 1-{3-[7-(1,5-Dimethyl-1H-[1,2,3]triazol-4-yl)-imidazo[1,2-a]pyridin-3-yl]-phenyl}-3-(2,2,2-trifluoro-ethyl)-urea, 1-[3-(7-[1,3,4]Thiadiazol-2-yl-imidazo[1,2-a]pyridin-3-yl)-phenyl]-3-(2,2,2-trifluoro-ethyl)-urea, 1-[3-(7-Prop-1-ynyl-imidazo[1,2-a]pyridin-3-yl)-phenyl]-3-(2,2,2-trifluoro-ethyl)-urea,
1-{3-[7-(3-Methyl-[1,2,4]thiadiazol-5-yl)-imidazo[1,2-a]pyridin-3-yl]-phenyl}-3-(2,2,2-trifluoro-ethyl)-urea,
1-(3-{7-[1-(2-Hydroxy-ethyl)-1H-pyrazol-4-yl]-imidazo[1,2-a]pyridin-3-yl}-phenyl)-3-(2,2,2-trifluoro-ethyl)-urea,
1-(3-{7-[1-(2-Amino-ethyl)-1H-pyrazol-4-yl]-imidazo[1,2-a]pyridin-3-yl}-phenyl)-3-(2,2,2-trifluoro-ethyl)-urea,
1-{5-[7-(5-Methyl-[1,3,4]oxadiazol-2-yl)-imidazo[1,2-a]pyridin-3-yl]-pyridin-3-yl}-3-(2,2,2-trifluoro-ethyl)-urea,
1-(2,2,2-Trifluoro-ethyl)-3-{3-[7-(1,2,5-trimethyl-1H-imidazol-4-yl)-imidazo[1,2,a]pyridine-3-yl]-phenyl}-urea,
1-{3-[7-(4-Methyl-imidazol-1-yl)-imidazo[1,2-a]pyridin-3-yl]-phenyl}-3-(2,2,2-trifluoro-ethyl)-urea,
1-{3-[7-(6-Methyl-pyridazin-3-yl)-imidazo[1,2-a]pyridin-3-yl]-phenyl}-3-(2,2,2-trifluoro-ethyl)-urea,
and
1-[3-(7-[1,2,4]Thiadiazol-5-yl-imidazo[1,2-a]pyridin-3-yl)-phenyl]-3-(2,2,2-trifluoro-ethyl)-urea,
or a pharmaceutically acceptable salt or solvate thereof.

11. A compound according to claim 10 wherein the compound is 1-{3-[7-(4-Fluoro-phenyl)-imidazo[1,2-a]pyridin-3-yl]-phenyl}-3-(2,2,2-trifluoro-ethyl)-urea or a pharmaceutically acceptable salt or solvate thereof, or 1-[3-(7-[1,3,4]Thiadiazol-2-yl-imidazo[1,2-a]pyridin-3-yl)-phenyl]-3-(2,2,2-trifluoro-ethyl)-urea or a pharmaceutically acceptable salt or solvate thereof.

12. A compound as defined in claim 7 wherein $R^2$ represents a 5-membered heterocyclyl group optionally substituted by a =O, =S, halogen, $C_{1-6}$ alkyl, halo$C_{1-6}$ alkyl, $C_{3-8}$ cycloalkyl, —$(CH_2)_s$—$NR^xR^y$, —$OR^x$, —$(CH_2)_n$—O—$C_{1-6}$ alkyl, —$COR^x$, —$(CR^xR^y)_s$—$COOR^z$, —S—$R^x$, —$SO_2$—$R^x$, —$(CH_2)_s$—$NR^xR^y$, —$(CH_2)_s$—$SO_2NR^xR^y$ or $C_{1-6}$ alkanol groups, or a pharmaceutically acceptable salt or solvate thereof.

13. A process for the preparation of a compound of formula (Id) as defined in claim 1, which process comprises:
(i) the reaction of a compound of the formula:

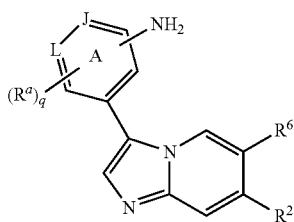

or a protected form thereof, with an appropriately substituted isocyanate or an appropriately substituted amine in the presence of carbonyl diimidazole (CDI); or (ii) reacting a compound of formula (V) and (VI):

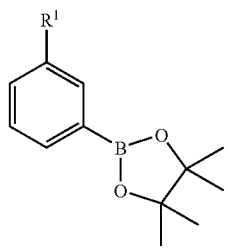

(V)

and

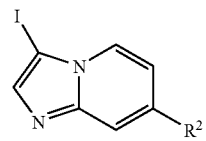

(VI)

wherein $R^1$ is —$NHCONHR^5$,
and thereafter removing any protecting group present;
and optionally thereafter converting one compound of the formula (Id) into another compound of the formula (Id).

14. A pharmaceutical composition comprising a compound of formula (Id) as defined in claim 1, or a pharmaceutically acceptable salt or solvate thereof.

15. A method of inhibiting a FGFR kinase, which method comprises contacting the kinase with a compound of formula (Id) as defined in claim 1, or a pharmaceutically acceptable salt or solvate thereof.

16. A compound as defined in claim 1 wherein $R^5$ is halo$C_{1-6}$ alkyl, or a pharmaceutically acceptable salt or solvate thereof.

17. A compound as defined in claim 3 wherein $R^5$ is halo$C_{1-6}$ alkyl, or a pharmaceutically acceptable salt or solvate thereof.

18. A compound as defined in claim 1 wherein $R^6$ is hydrogen and $R^2$ is selected from halogen, $C_{1-6}$ alkyl, $C_{1-6}$ alkoxy, $C_{2-6}$ alkenyl, $C_{2-6}$ alkynyl, —C≡N, $C_{3-8}$ cycloalkyl, $C_{3-8}$ cycloalkenyl, —$NHSO_2R^w$, —CH=N—$OR^w$, or an aryl or heterocyclyl group, wherein said aryl and heterocyclyl groups may be optionally substituted by one or more $R^b$ groups, and said $C_{1-6}$ alkyl, $C_{2-6}$ alkenyl, and $C_{2-6}$ alkynyl may be optionally substituted by one or more $R^{b'}$ groups, or a pharmaceutically acceptable salt or solvate thereof.

19. A compound according to claim 1 wherein the compound is 1-{3-[7-(4-Fluoro-phenyl)-imidazo[1,2-a]pyridin-3-yl]-5-isopropoxy-phenyl}-3-(2,2,2-trifluoro-ethyl)-urea, or a pharmaceutically acceptable salt or solvate thereof.

20. A compound according to claim 1 wherein the compound is 1-{3-[7-(5-methyl-[1,3,4]oxadiazol-2-yl)-imidazo[1,2-a]pyridin-3-yl]-phenyl}-3-(2,2,2-trifluoro-ethyl)-urea, or a pharmaceutically acceptable salt or solvate thereof.

* * * * *

UNITED STATES PATENT AND TRADEMARK OFFICE
CERTIFICATE OF CORRECTION

PATENT NO. : 8,895,745 B2
APPLICATION NO. : 12/520481
DATED : November 25, 2014
INVENTOR(S) : Berdini et al.

Page 1 of 1

It is certified that error appears in the above-identified patent and that said Letters Patent is hereby corrected as shown below:

In the Claims

Column 481, Line 8: Claim 1, Delete "-CN, -SO-R$^x$" and insert -- -CN, -S-R$^x$, -SO-R$^x$ --

Signed and Sealed this
Fourteenth Day of April, 2015

Michelle K. Lee
*Director of the United States Patent and Trademark Office*